(12) United States Patent
Yu et al.

(10) Patent No.: US 11,654,147 B2
(45) Date of Patent: *May 23, 2023

(54) ALK2 INHIBITORS AND METHODS FOR INHIBITING BMP SIGNALING

(71) Applicants: The Brigham and Women's Hospital, Inc., Boston, MA (US); The United States of America, as Represented by the Secretary, Department of Health and Human Services, Bethesda, MD (US)

(72) Inventors: Paul B. Yu, Boston, MA (US); Wenwei Huang, Rockville, MD (US); Philip Edward Sanderson, Bethesda, MD (US); Jian-Kang Jiang, Columbia, MD (US); Khalida Shamim, Gaithersburg, MD (US); Wei Zheng, Potomac, MD (US); Xiuli Huang, Potomac, MD (US); Gregory Tawa, Doylestown, PA (US); Arthur Lee, San Jose, CA (US); Asaf Alimardanov, North Bethesda, MD (US); Junfeng Huang, Woodstock, MD (US)

(73) Assignees: The Brigham and Women's Hospital, Inc., Boston, MA (US); The United States of America, as Represented by the Secretary, Dept. of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/340,589

(22) Filed: Jun. 7, 2021

(65) Prior Publication Data

US 2023/0000869 A1 Jan. 5, 2023

Related U.S. Application Data

(63) Continuation of application No. 16/608,489, filed as application No. PCT/US2018/029626 on Apr. 26, 2018, now Pat. No. 11,026,947.

(60) Provisional application No. 62/490,772, filed on Apr. 27, 2017.

(51) Int. Cl.
| | | |
|---|---|---|
| *A61K 31/519* | (2006.01) | |
| *A61P 19/08* | (2006.01) | |
| *A61K 31/5377* | (2006.01) | |
| *A61K 31/551* | (2006.01) | |
| *A61K 31/675* | (2006.01) | |
| *A61K 45/06* | (2006.01) | |
| *C07D 487/04* | (2006.01) | |
| *C07D 519/00* | (2006.01) | |
| *C07F 9/6561* | (2006.01) | |

(52) U.S. Cl.
CPC ........ *A61K 31/519* (2013.01); *A61K 31/5377* (2013.01); *A61K 31/551* (2013.01); *A61K 31/675* (2013.01); *A61K 45/06* (2013.01); *A61P 19/08* (2018.01); *C07D 487/04* (2013.01); *C07D 519/00* (2013.01); *C07F 9/6561* (2013.01)

(58) Field of Classification Search
None
See application file for complete search history.

(56) References Cited

U.S. PATENT DOCUMENTS

| | | |
|---|---|---|
| 11,026,947 B2 | 6/2021 | Yu et al. |
| 2016/0046633 A1 | 2/2016 | Alimardanov et al. |
| 2016/0115167 A1 | 4/2016 | Yu et al. |
| 2020/0179389 A1 | 6/2020 | Yu et al. |

FOREIGN PATENT DOCUMENTS

| | | |
|---|---|---|
| WO | WO-02/18382 A1 | 3/2002 |
| WO | WO-2006/052913 A1 | 5/2006 |
| WO | WO-2009/114180 A1 | 9/2009 |
| WO | WO-2010/0091150 A1 | 8/2010 |
| WO | WO-2013/016452 A2 | 1/2013 |
| WO | WO-2013/187416 A1 | 12/2013 |
| WO | WO-2014/138088 A1 | 9/2014 |
| WO | WO-2014/160203 A2 | 10/2014 |
| WO | WO-2015/148654 A1 | 10/2015 |
| WO | WO-2016/011019 A1 | 1/2016 |
| WO | WO-2016/054406 A1 | 4/2016 |
| WO | WO-2016/130897 A1 | 8/2016 |
| WO | WO-2016/165808 A1 | 10/2016 |
| WO | WO-2018/200855 A1 | 11/2018 |

OTHER PUBLICATIONS

Boergermann et al., "Dorsomorphin and LDN-193189 inhibit BMP-mediated Smad, p38 and Akt signalling in C2C12 cells." The International Journal of Biochemistry & Cell Biology, 42(11): 1802-1807 (2010).
CAS Registry No. 890818-46-9; CA Index Name: Pyrazolo[1,5-a]pyrimidin-7-ol, 3-(3,4-diethoxyphenyl)-2,5-dimethyl-6-(4-methyl-1-piperidinyl)-; Entered STN: Jul. 6, 2006.
Extended European Search Report for EP Application No. EP 18790880 dated Dec. 10, 2020.

(Continued)

*Primary Examiner* — Samantha L Shterengarts
(74) *Attorney, Agent, or Firm* — Foley Hoag LLP; David P. Halstead

(57) ABSTRACT

The present invention provides small-molecule inhibitors of BMP signaling and compositions and methods for inhibiting BMP signaling. These compounds and compositions may be used to modulate cell growth, differentiation, proliferation, and apoptosis, and thus may be useful for treating diseases or conditions associated with BMP signaling, including inflammation, cardiovascular disease, hematological disease, cancer, and bone disorders, as well as for modulating cellular differentiation and/or proliferation. These compounds and compositions may also be used to treat subjects with Sjögren's syndrome, or diffuse intrinsic pontine glioma (DIPG).

13 Claims, 4 Drawing Sheets

(56) References Cited

OTHER PUBLICATIONS

Hong et al., "Applications of Small Molecule BMP Inhibitors in Physiology and Disease," Cytokine and Growth Factor Reviews, 20(5-6): 409-418 (2009).
Hopkins et al., "Inhibitors of the bone morphogenetic protein (BMP) signaling pathway: a patent review (2008-2015)," Expert Opinion on Therapeutic Patents, 26(10): 1115-1128 (2016).
International Preliminary Report on Patentability for International Application No. PCT/US2018/029626 dated Oct. 29, 2019.
International Search Report and Written Opinion for International Application No. PCT/US2018/029626 dated Aug. 7, 2018.
Sanvitale et al., "A new class of small molecule inhibitor of BMP signaling," PloS One, 8(4):e62721 (2013).

ALK2 INHIBITORS AND METHODS FOR INHIBITING BMP SIGNALING

RELATED APPLICATIONS

This application is a continuation of U.S. patent application Ser. No. 16/608,489, filed Oct. 25, 2019, which is the U.S. national phase of International Application No. PCT/US2018/029626, filed Apr. 26, 2018, which claims the benefit of priority to U.S. Provisional Patent Application No. 62/490,772, filed Apr. 27, 2017, which are hereby incorporated by reference in their entirety.

STATEMENT REGARDING FEDERALLY SPONSORED RESEARCH OR DEVELOPMENT

This invention was made with government support under Grant No. AR057374 awarded by National Institutes of Health and Grant No. MR140072 awarded by Department of Defense. The government has certain rights in the invention.

FIELD OF THE INVENTION

The present disclosure relates to compounds that inhibit the BMP signaling pathway, as well as methods to treat or prevent a disease or condition in a subject that would benefit by inhibition of BMP signaling.

BACKGROUND

Signaling involving the Transforming Growth Factor (TGF-β) superfamily of ligands is central to a wide range of cellular processes, including cell growth, differentiation, and apoptosis. TGF-β signaling involves binding of a TGF-β ligand to a type II receptor (a serine/threonine kinase), which recruits and phosphorylates a type I receptor. The type I receptor then phosphorylates a receptor-regulated SMAD (R-SMAD; e.g., SMAD1, SMAD2, SMAD3, SMAD5, SMAD8 or SMAD9), which binds to SMAD4, and the SMAD complex then enters the nucleus where it plays a role in transcriptional regulation. The TGF superfamily of ligands includes two major branches, characterized by TGF-β/activin/nodal and Bone Morphogenetic Proteins (BMPs).

Signals mediated by bone morphogenetic protein (BMP) ligands serve diverse roles throughout the life of vertebrates. During embryogenesis, the dorsoventral axis is established by BMP signaling gradients formed by the coordinated expression of ligands, receptors, co-receptors, and soluble inhibitors. Excess BMP signaling causes ventralization, an expansion of ventral at the expense of dorsal structures, while diminished BMP signaling causes dorsalization, an expansion of dorsal at the expense of ventral structures. BMPs are key regulators of gastrulation, mesoderm induction, organogenesis, and endochondral bone formation, and regulate the fates of multipotent cell populations. BMP signals also play critical roles in physiology and disease, and are implicated in primary pulmonary hypertension, hereditary hemorrhagic telangiectasia syndrome, fibrodysplasia ossificans progressiva, and juvenile polyposis syndrome.

The BMP signaling family is a diverse subset of the TGF-β superfamily. Over twenty known BMP ligands are recognized by three distinct type II (BMPRII, ActRIIa, and ActRIIb) and at least four type I (ALK1, ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner. Soluble BMP inhibitors, such as noggin, chordin, gremlin, and follistatin, limit BMP signaling by ligand sequestration.

A role for BMP signals in regulating expression of hepcidin, a peptide hormone and central regulator of systemic iron balance, has also been suggested. Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes. The link between BMP signaling and iron metabolism represents a potential target for therapeutics.

Given the tremendous structural diversity of the BMP and TGF-β superfamily at the level of ligands (>25 distinct ligands at present) and receptors (four type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas receptors heterotetramers exhibit more specificity for particular ligands. Neutralizing antibodies which are specific for particular ligands or receptors have been previously described, and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY OF THE INVENTION

The following embodiments and aspects thereof are described and illustrated in conjunction with compositions and methods which are meant to be exemplary and illustrative, not limiting in scope.

Disclosed herein are compounds of Formula I.

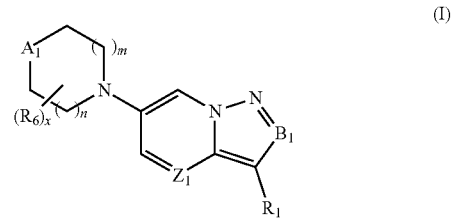

(I)

or a pharmaceutically acceptable salt and/or prodrug thereof, wherein $A_1$ is $NR_{4a}$ or $CR_{4b}R_5$;
$B_1$ is N or $CR_2$;
$Z_1$ is N or $CR_3$;
$R_1$ is selected from cycloalkyl, aryl, heteroaryl, and heterocyclyl;
$R_2$ is H, CN, $NO_2$, alkyl, or amino;
$R_3$ is selected from H, CN, $NO_2$, alkyl, alkoxy, heterocyclyloxy, heteroaryloxy, aryloxy, cycloalkyloxy, carbonyl, amino, amido, sulfonyl, sulfonamido, cycloalkyl, aryl, heterocyclyl, and heteroaryl;

$R_{4a}$ is selected from alkyl, alkenyl, alkynyl, carbonyl, O⁻, alkoxycarbonyl, cycloalkyl, aryl, heterocyclyl, and heteroaryl;

$R_{4b}$ is selected from halo, CN, NO$_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl;

$R_5$ is selected from H, halo, hydroxy and alkyl, or $R_{4b}$ and $R_5$ together with $A_1$ form a ring selected from cycloalkyl and heterocyclyl;

each $R_6$ is independently selected from H, halo, CN, NO$_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl and oxo;

n is 0 or 1;

m is 0 or 1; and x is 0, 1, 2, 3, or 4.

Also disclosed herein are compounds of Formula I.

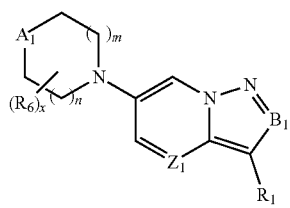

or a pharmaceutically acceptable salt and/or prodrug thereof, wherein $A_1$ is $NR_{4a}$ or $CR_{4b}R_5$;

$B_1$ is N or $CR_2$;

$Z_1$ is N or $CR_3$;

$R_1$ is selected from aryl, heteroaryl, and heterocyclyl;

$R_2$ is H or amino;

$R_3$ is H or heterocyclyloxy; $R_{4a}$ is selected from alkyl, O⁻, aryl, heterocyclyl, and heteroaryl;

$R_{4b}$ is selected from alkyl, alkoxy, amino, aryl, heterocyclyl, and heteroaryl;

$R_5$ is selected from H and alkyl, or $R_{4b}$ and $R_5$ together with $A_1$ form a ring selected from cycloalkyl and heterocyclyl;

each $R_6$ is independently selected from H, halo, alkyl and oxo;

n is 0 or 1;

m is 0 or 1; and x is 0, 1, 2, 3, or 4.

In some embodiments of the compound of Formula I, $R_{4a}$ is selected from alkyl, O⁻, heterocyclyl, and heteroaryl;

$R_{4b}$ is selected from alkyl, alkoxy, amino, amido, heterocyclyl, and heteroaryl;

$R_5$ is selected from H and alkyl, or $R_{4b}$ and $R_5$ together with $A_1$ form a heterocyclyl; and each $R_6$ is independently selected from H, halo, and alkyl; and x is 0 or 1.

In various embodiments, the present invention provides a compound of Formula I:

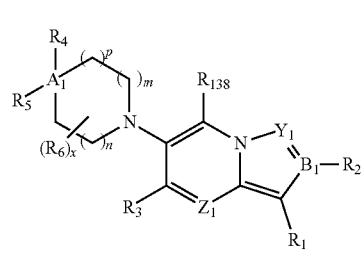

or a pharmaceutically acceptable salt, ester or prodrug thereof, wherein: $R_1$ is hydrogen or an optionally substituted substituent; $R_2$ is optionally absent, or hydrogen or an optionally substituted substituent; $R_3$ is hydrogen or an optionally substituted substituent; $R_4$ is optionally absent, hydrogen, or an optionally substituted substituent; $R_5$ is optionally absent, hydrogen, or an optionally substituted substituent; $R_{138}$ is hydrogen, or an optionally substituted substituent; $R_6$ is independently one or more of hydrogen or an optionally substituted substituent; $B_1$ is C or N; $Y_1$ is N or $CR_{139}$, where $R_{139}$ is hydrogen or an optionally substituted substituent; $Z_1$ is N or $CR_{140}$, where $R_{140}$ is hydrogen or an optionally substituted substituent; $A_1$ is C, N, O, C(O), S, SO, or SO$_2$; m is 0, 1, 2, or 3; n is 0, 1, 2, or 3; and p is 0 or 1; wherein optionally any two or more of $R_4$, $R_5$, or $R_6$ may be joined together to form one or more rings.

In some embodiments, the compound of Formula I has a structure of Formula I-a:

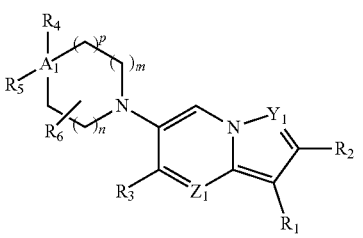

or a pharmaceutically acceptable salt, ester or prodrug thereof, wherein: $R_1$ is hydrogen or an optionally substituted substituent; $R_2$ is hydrogen or an optionally substituted substituent; $R_3$ is hydrogen or an optionally substituted substituent; $R_4$ is optionally absent, hydrogen, or an optionally substituted substituent; $R_5$ is optionally absent, hydrogen, or an optionally substituted substituent; $R_6$ is independently one or more of hydrogen or an optionally substituted substituent; $Y_1$ is CH or N; $Z_1$ is CH or N; $A_1$ is C, N, O, C(O), S, SO, or SO$_2$; m is 0, 1, 2, or 3; n is 0, 1, 2, or 3; and p is 0 or 1; wherein optionally any two or more of $R_4$, $R_5$, or $R_6$ may be joined together to form one or more rings.

In some embodiments of the compound of Formula I or Formula I-a, or a pharmaceutically acceptable salt, ester or prodrug thereof, $R_6$ is independently one or more of hydrogen, oxo, or an optionally substituted substituent.

In some embodiments the compound of Formula I is selected from:

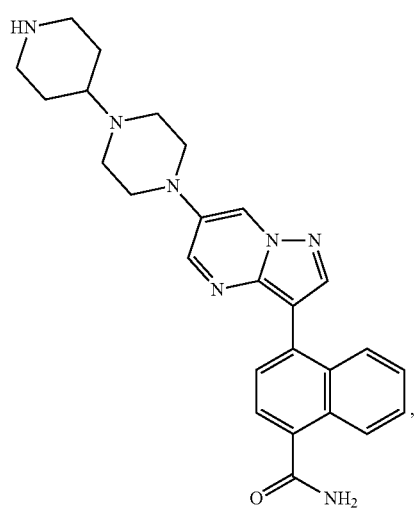
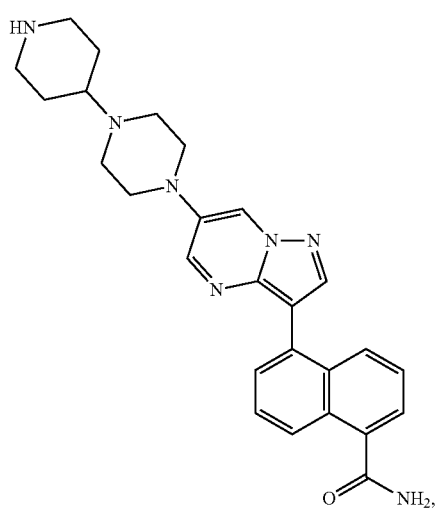
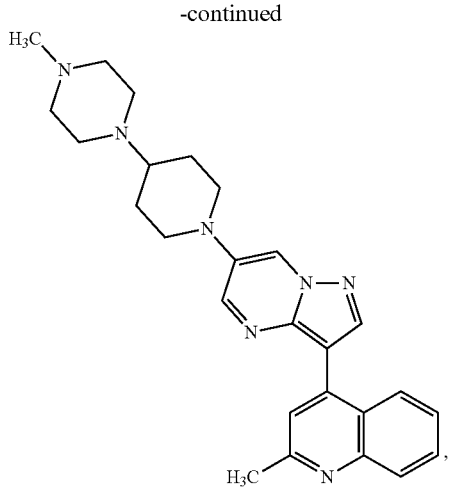
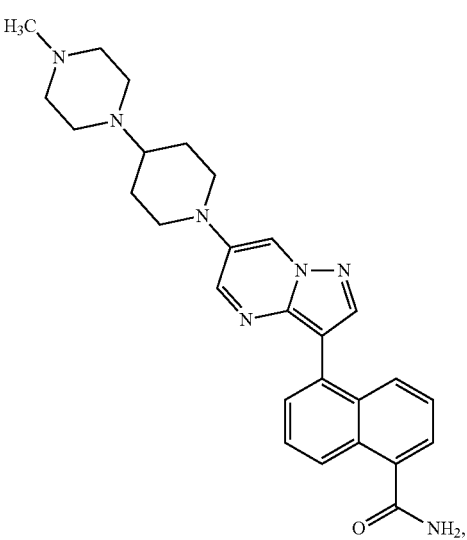

-continued
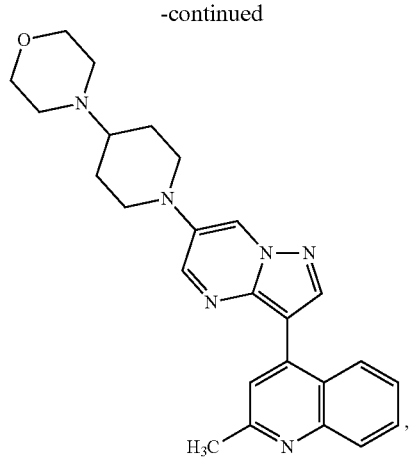
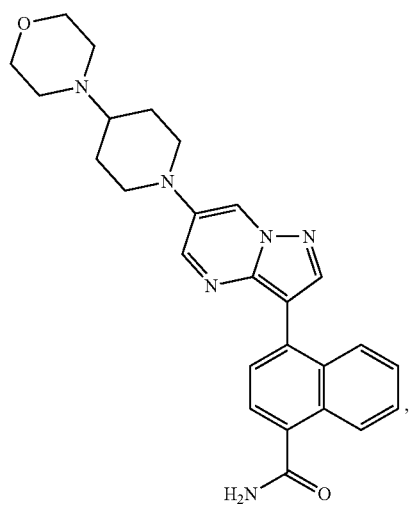
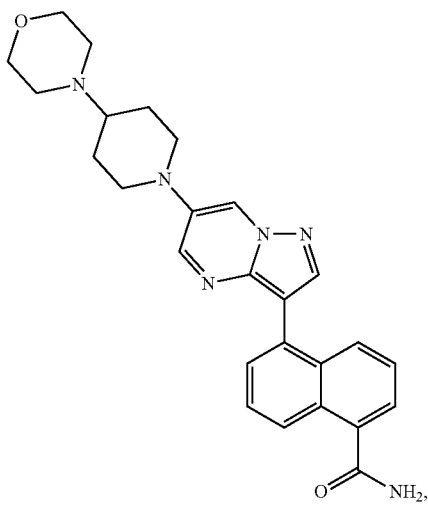
-continued
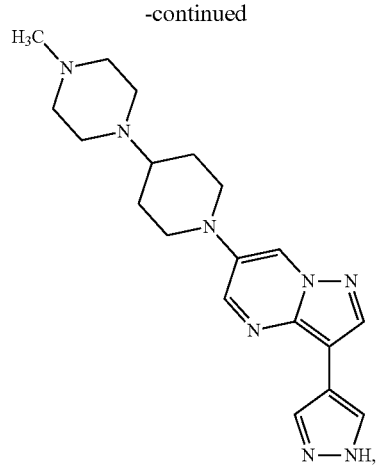
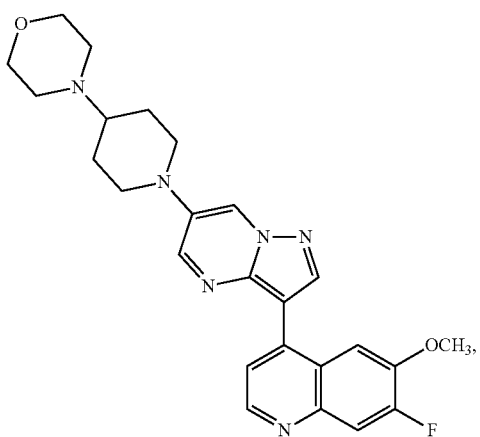

-continued
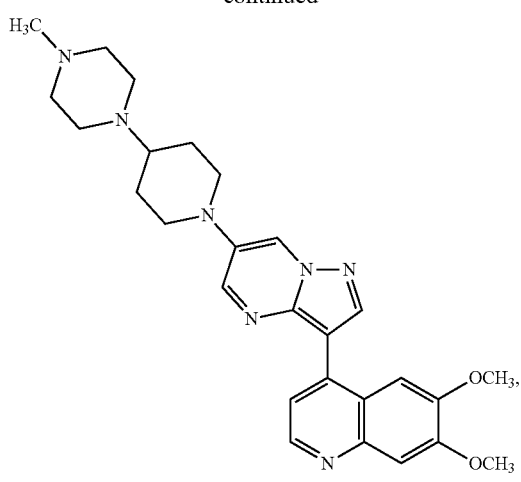
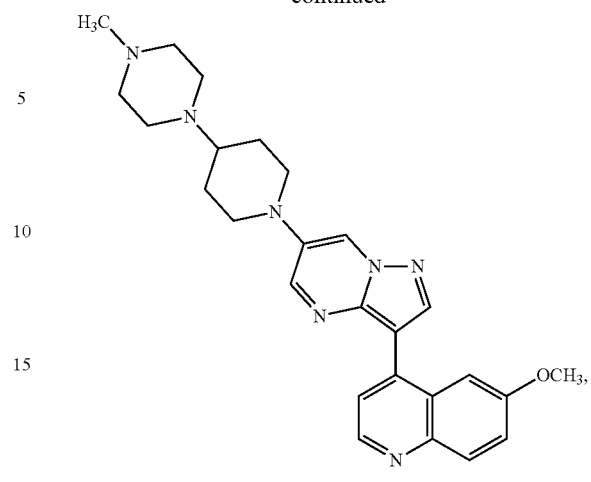
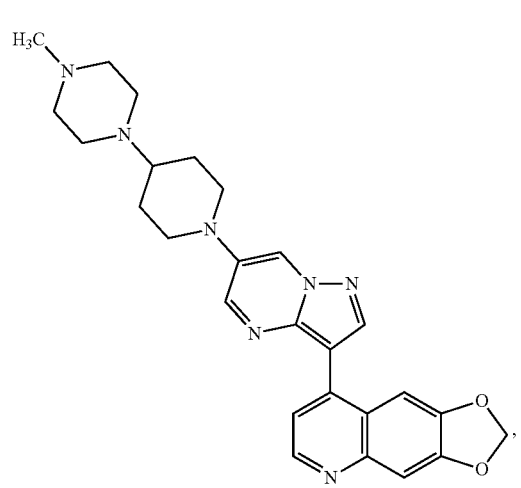
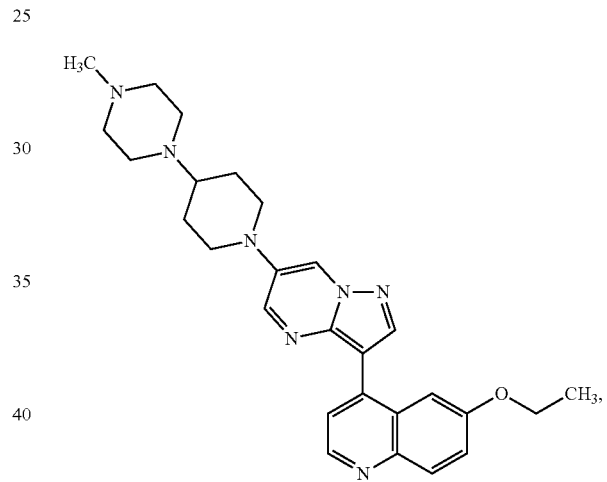
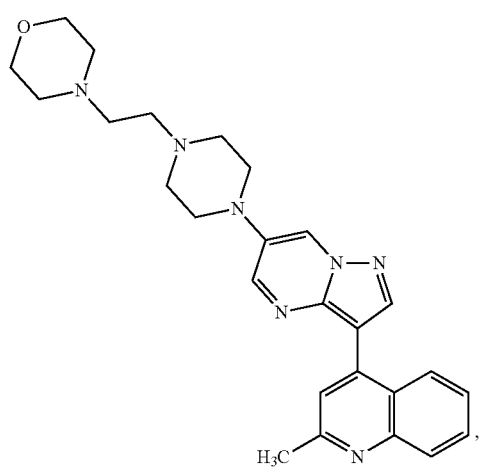
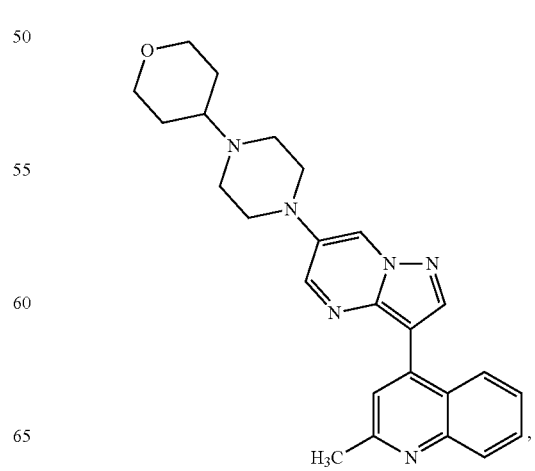

11
-continued
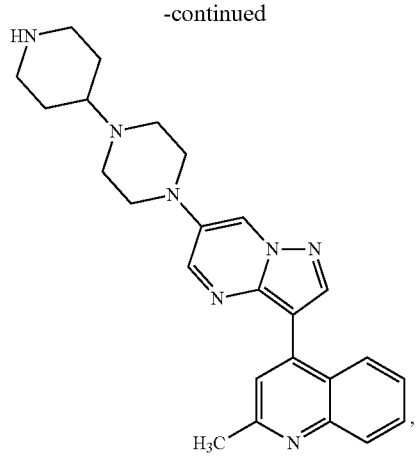
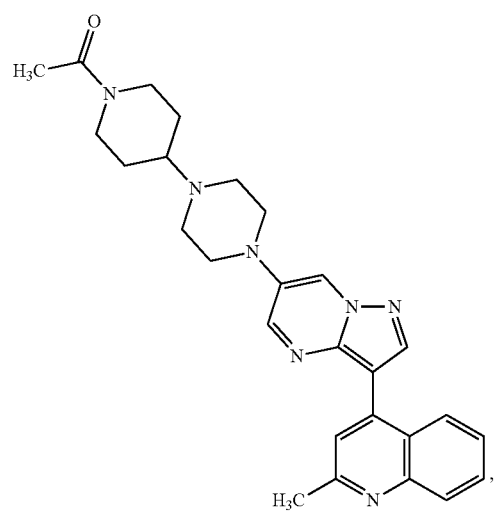
12
-continued
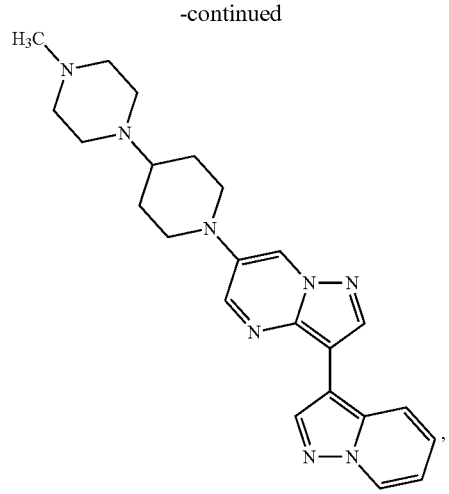
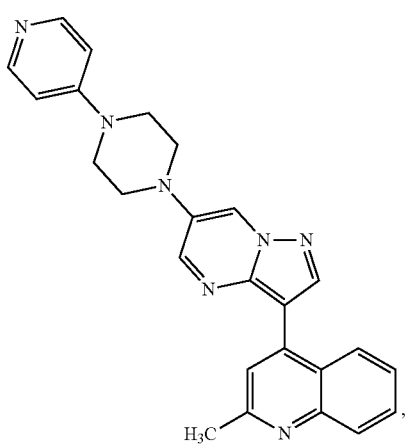
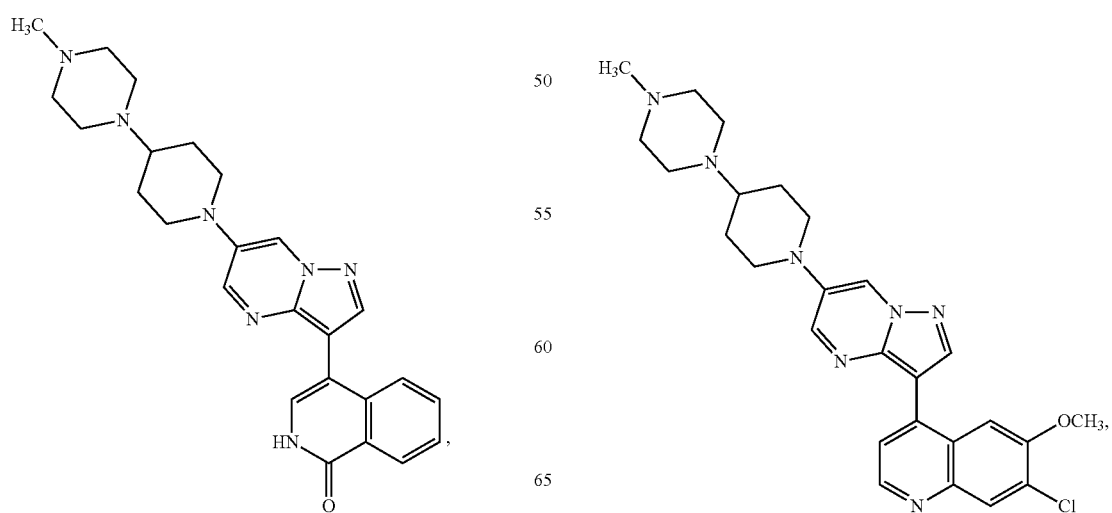

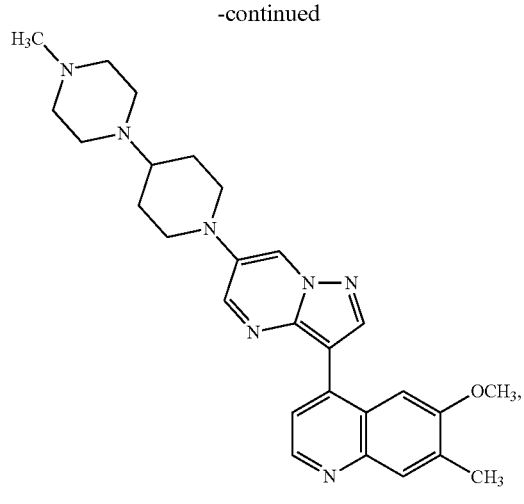
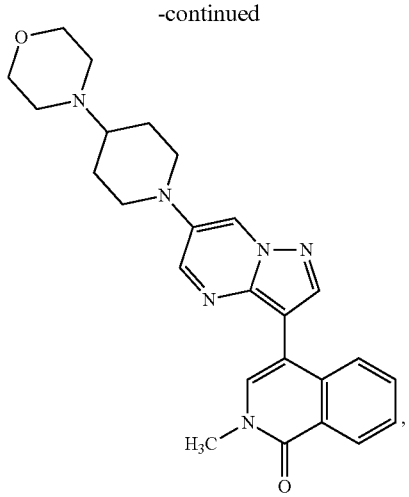
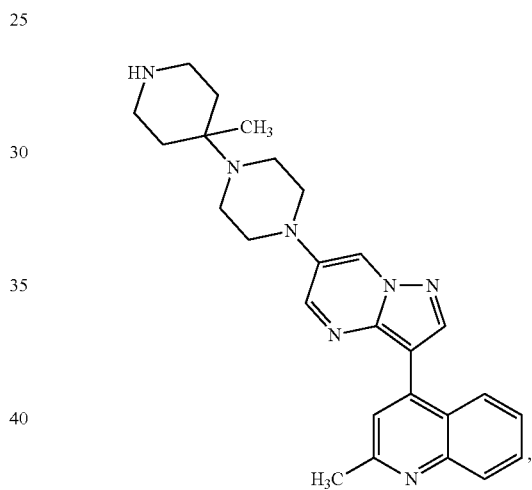
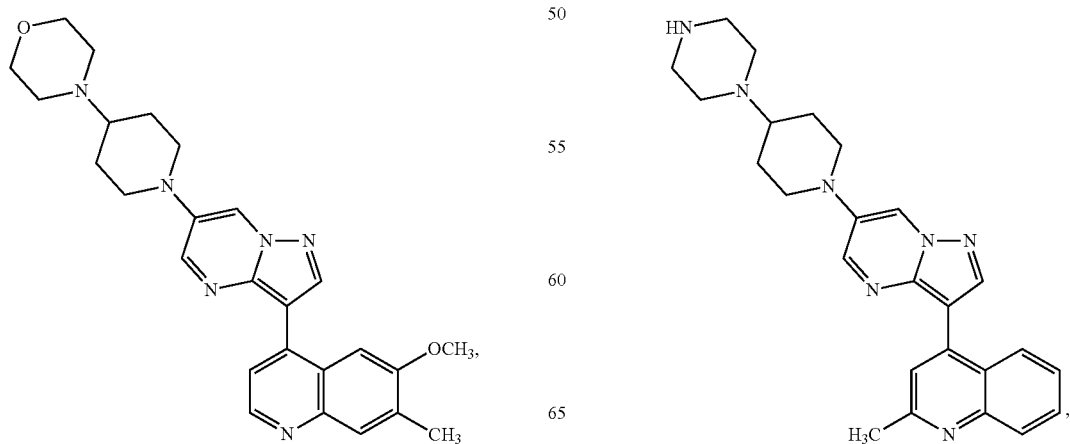

-continued
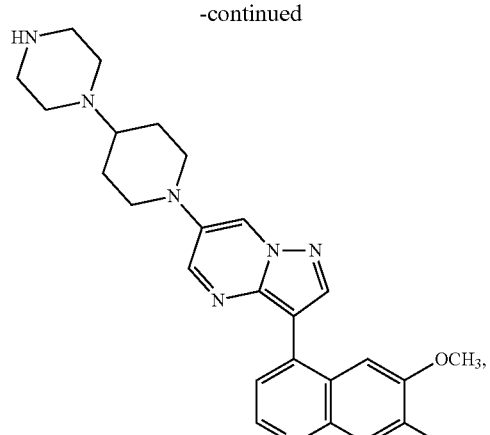
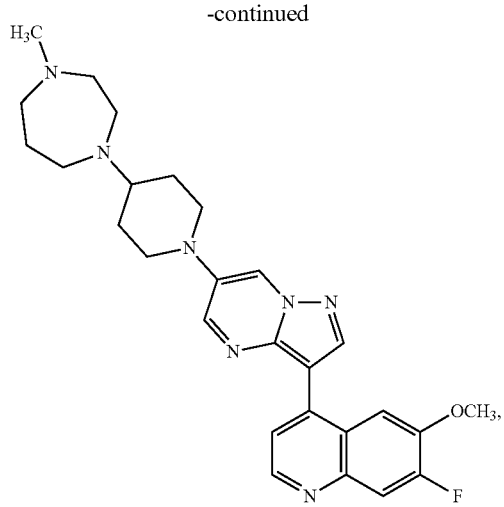
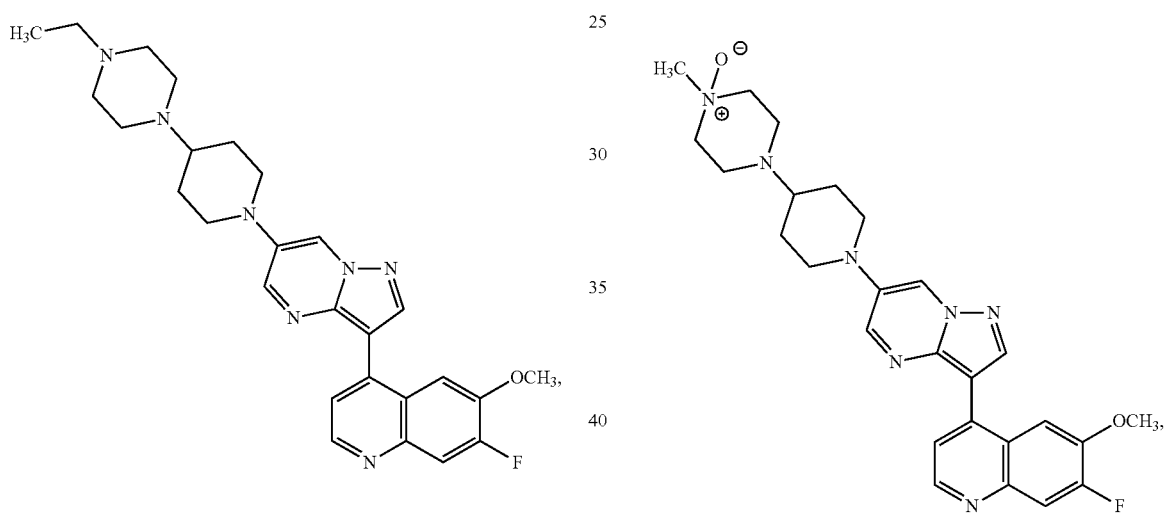
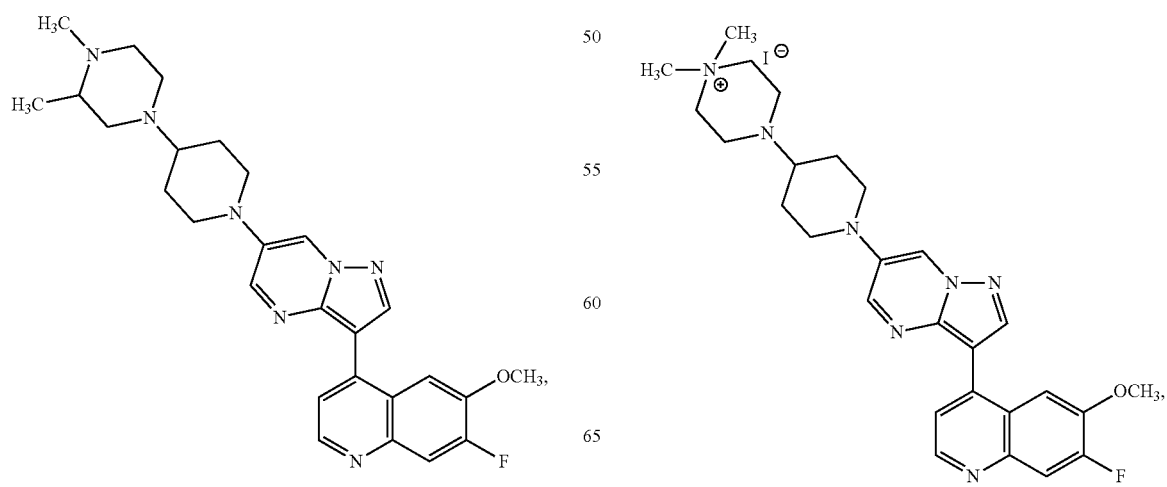

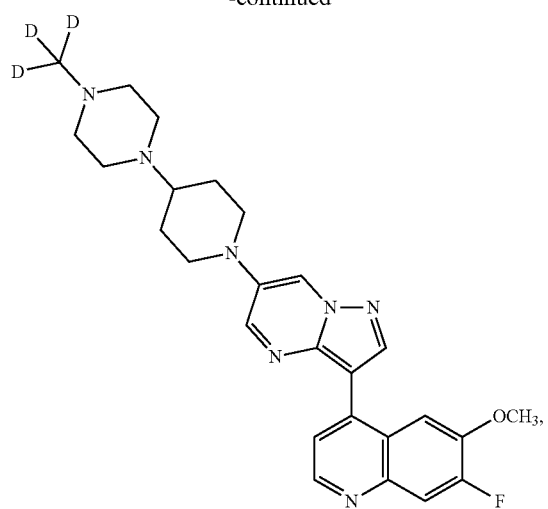
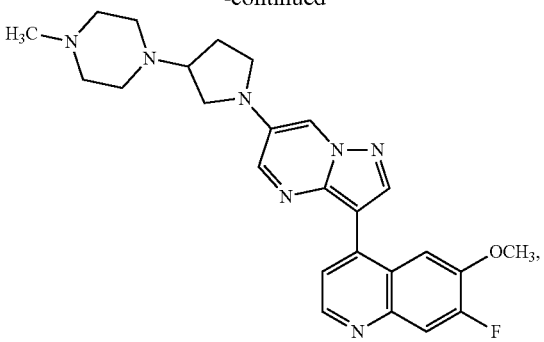
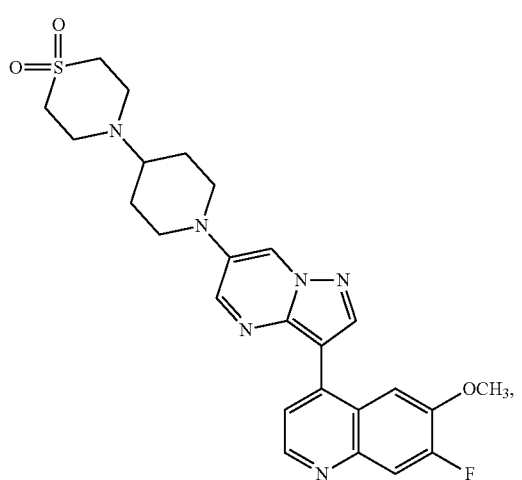
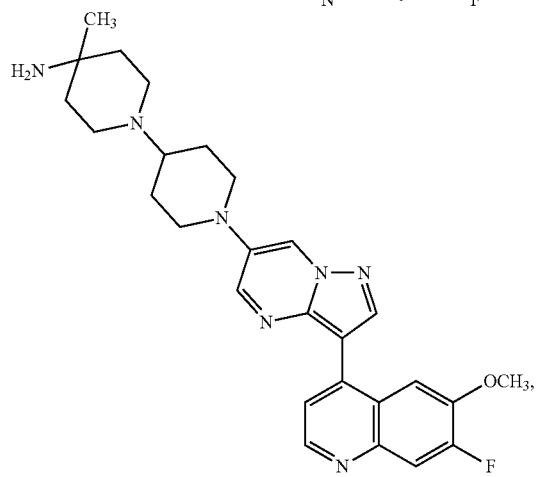
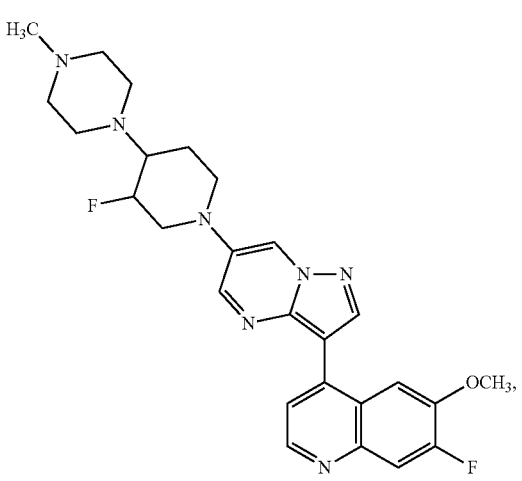
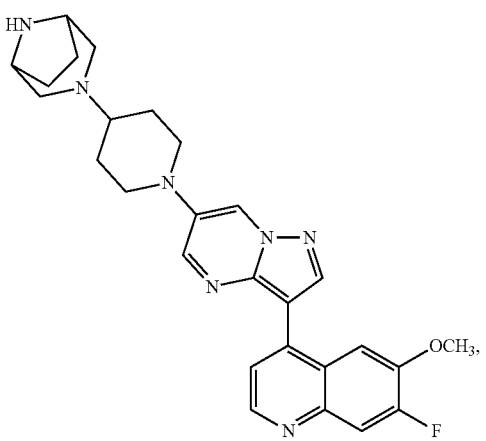

-continued
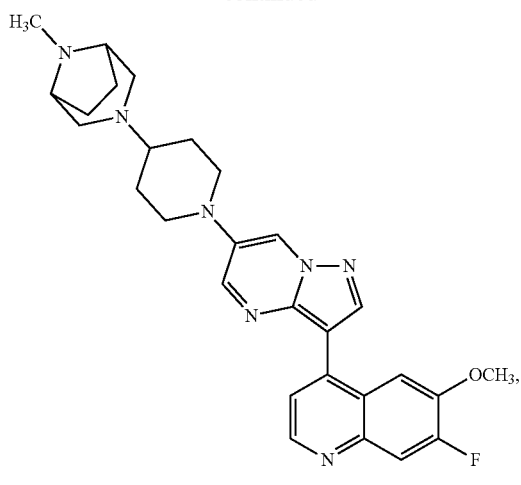
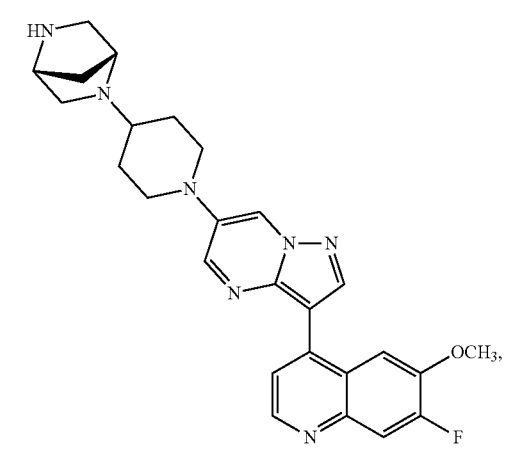
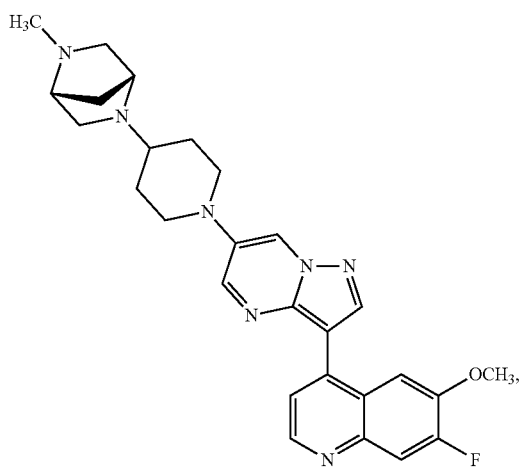
-continued
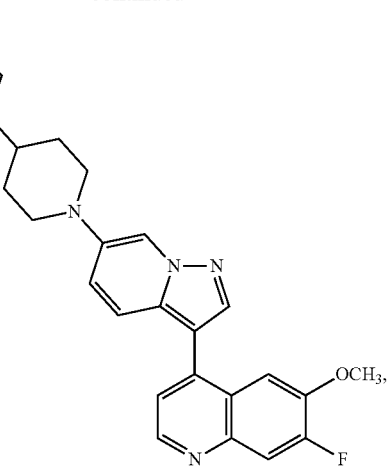
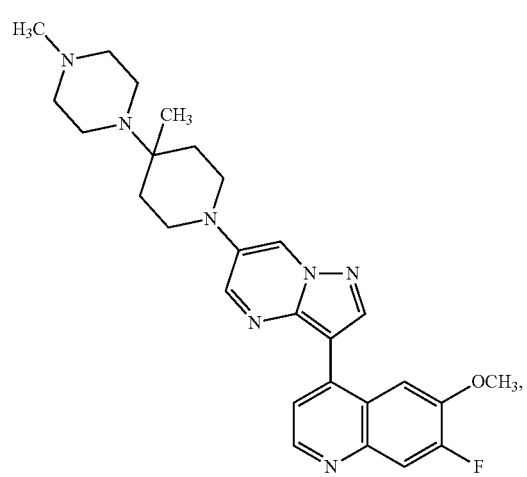
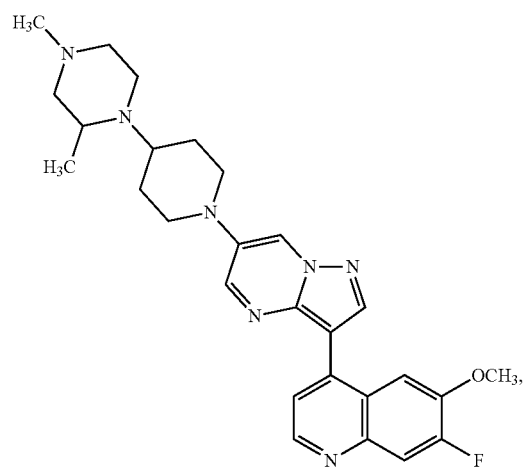

-continued
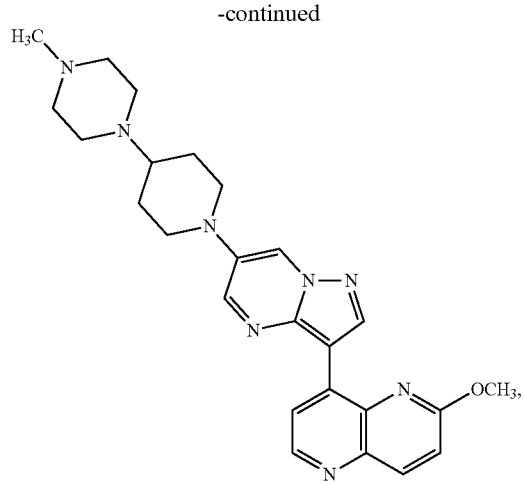
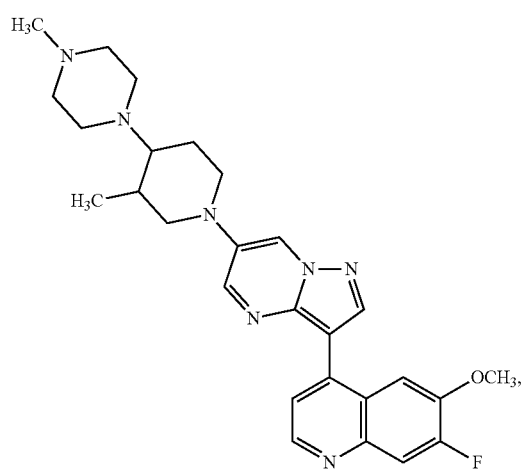
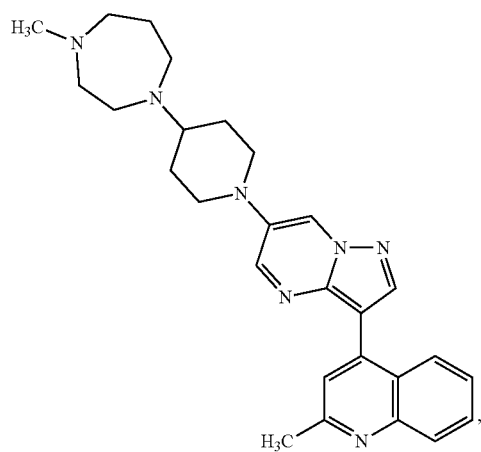
-continued
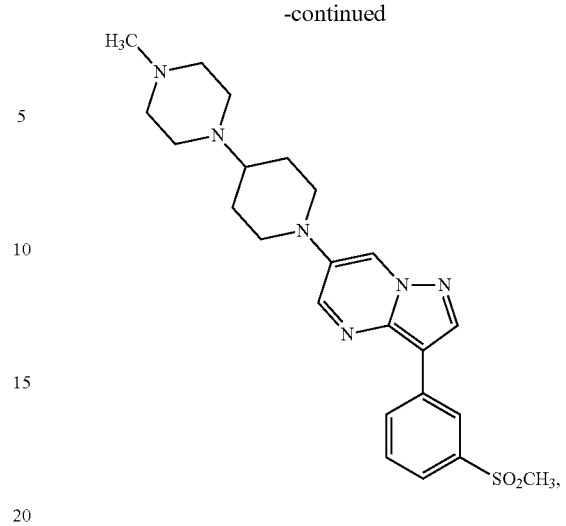
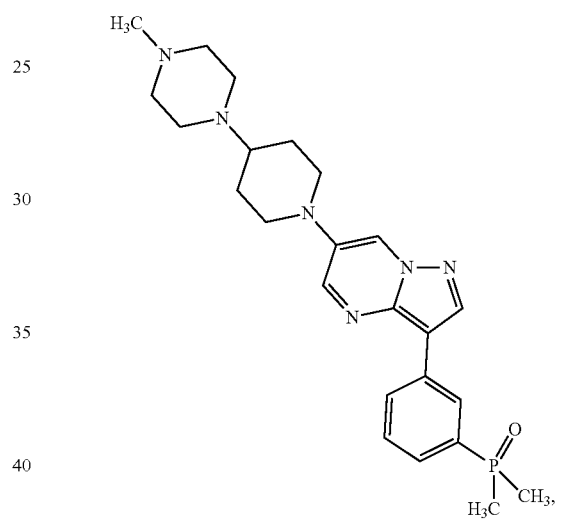
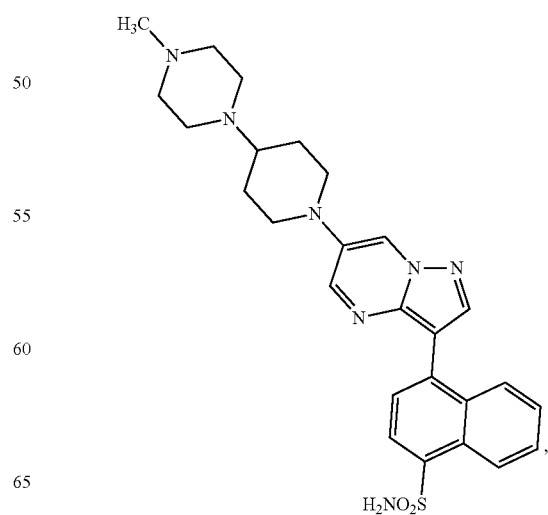

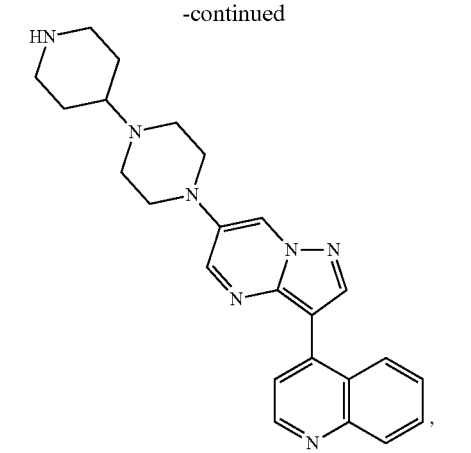
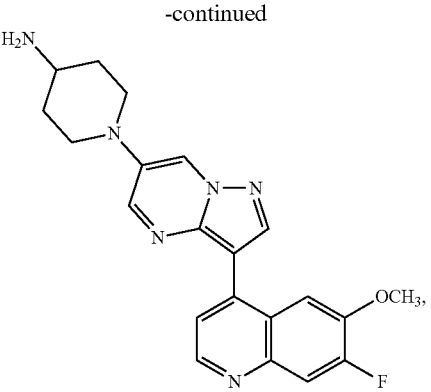
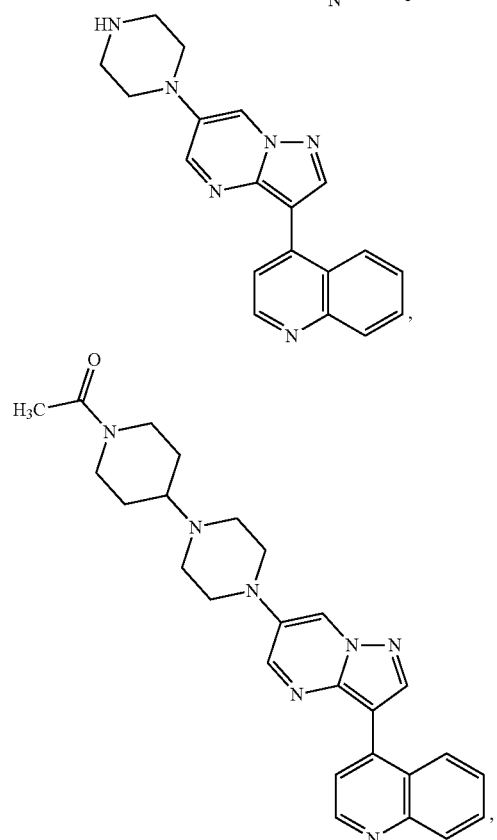
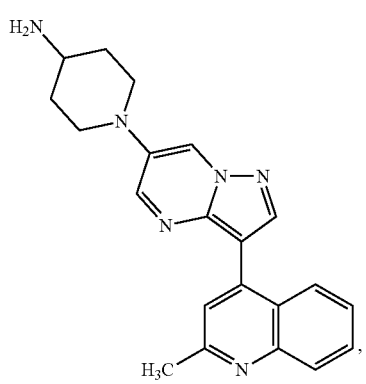
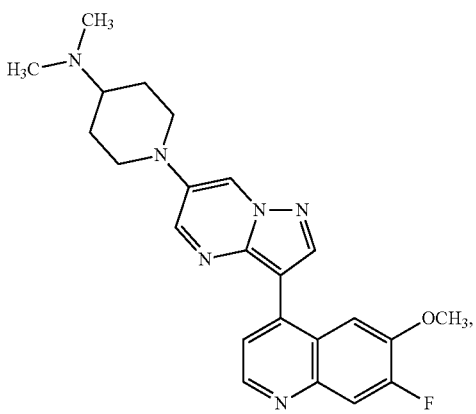
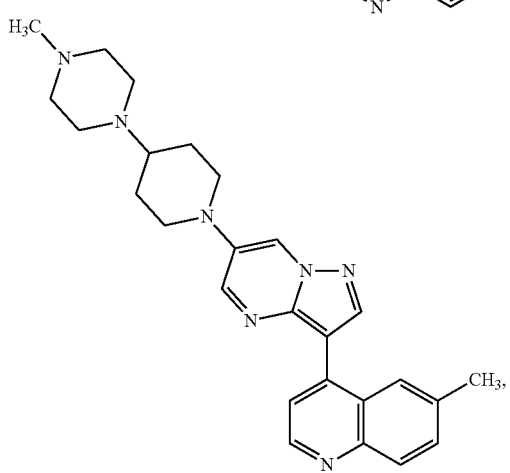
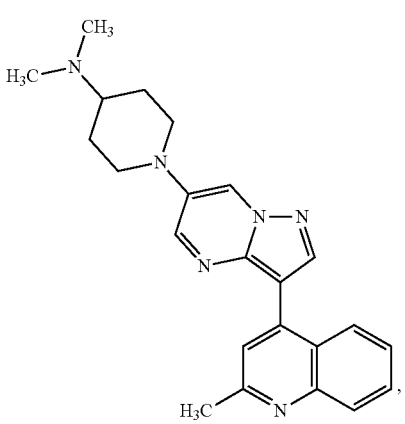

25
-continued
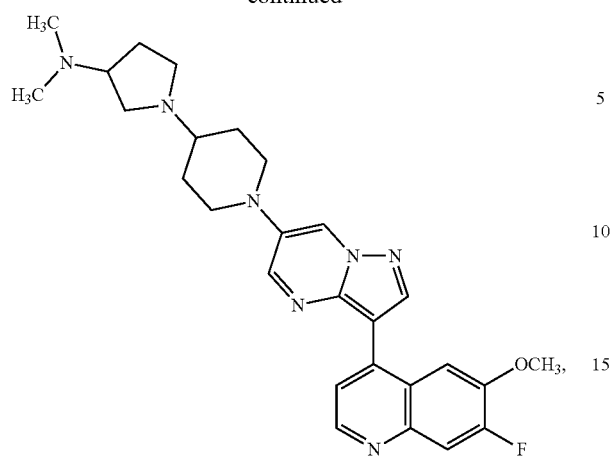
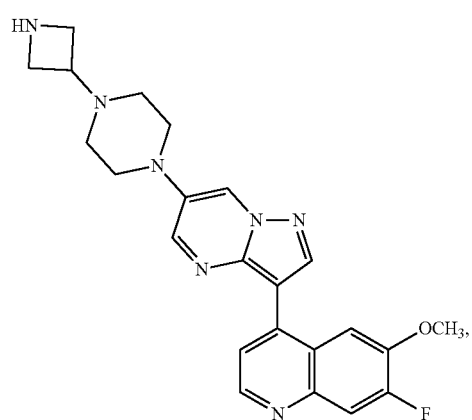
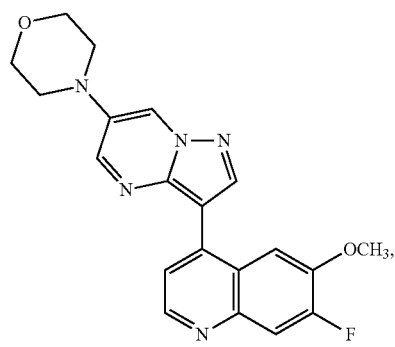
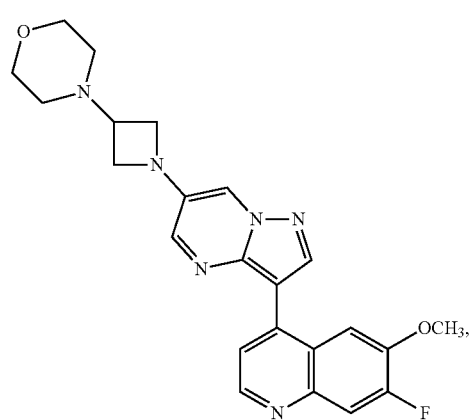
26
-continued
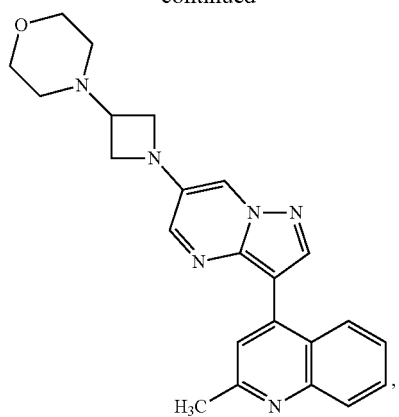
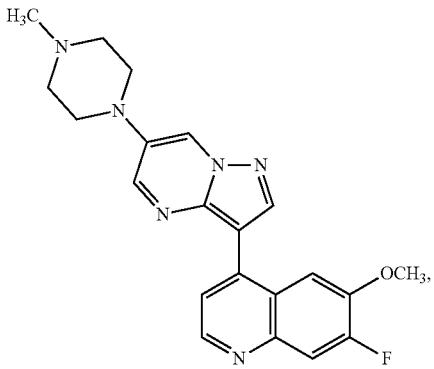
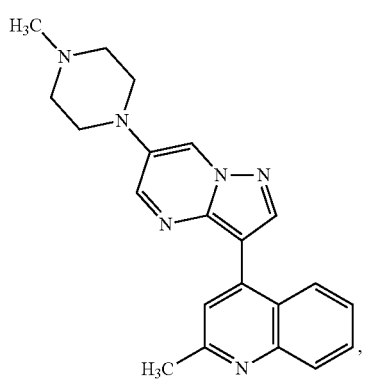
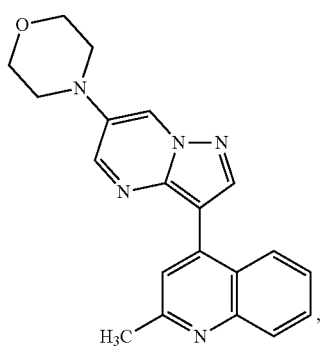

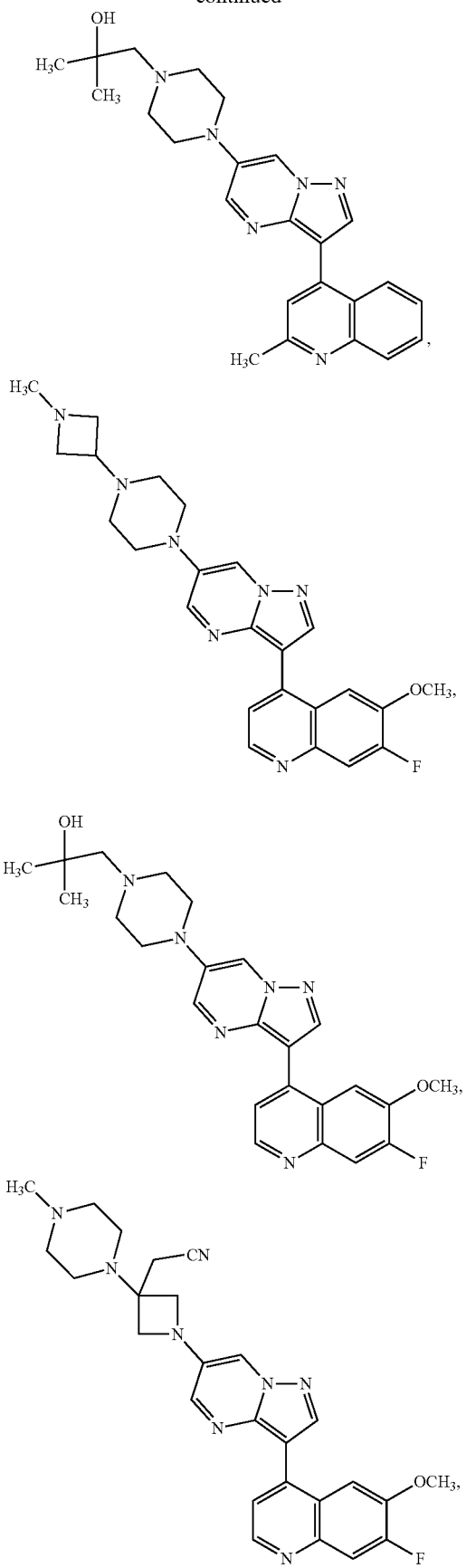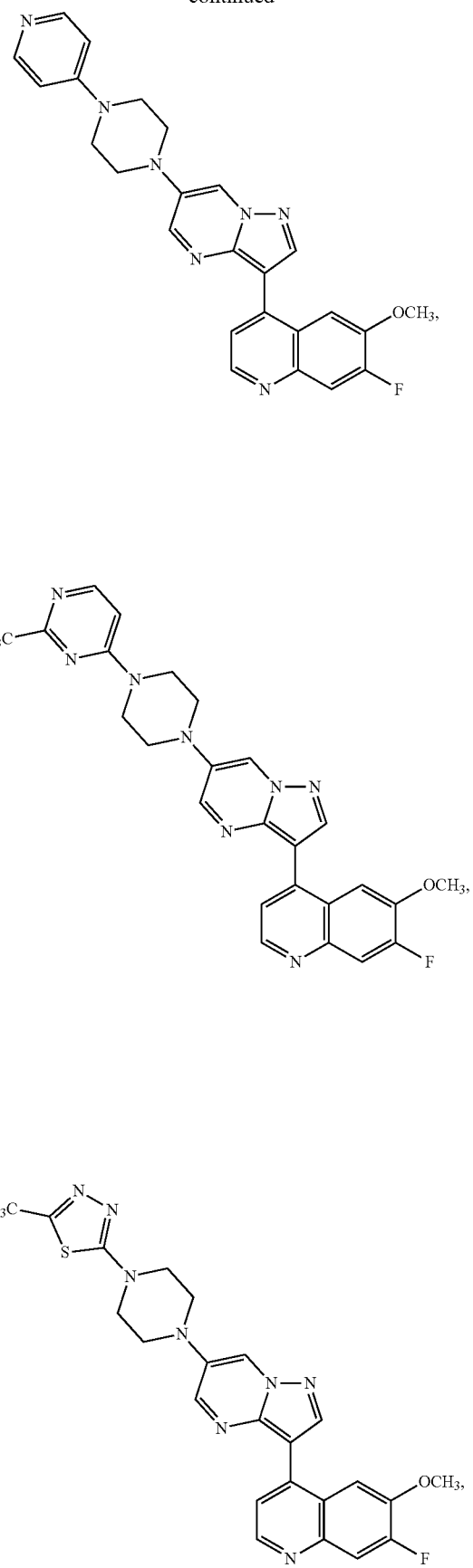

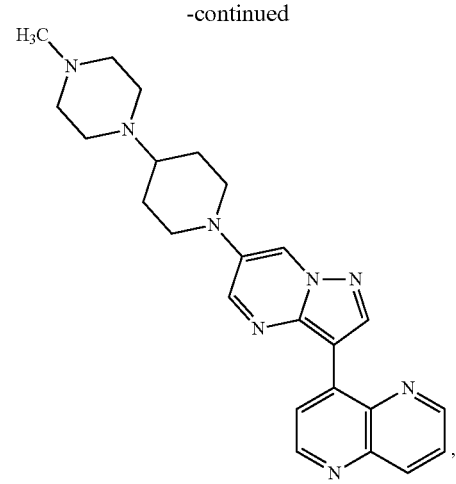
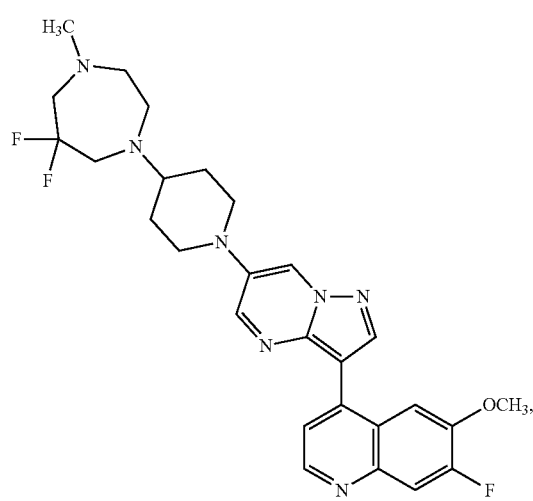
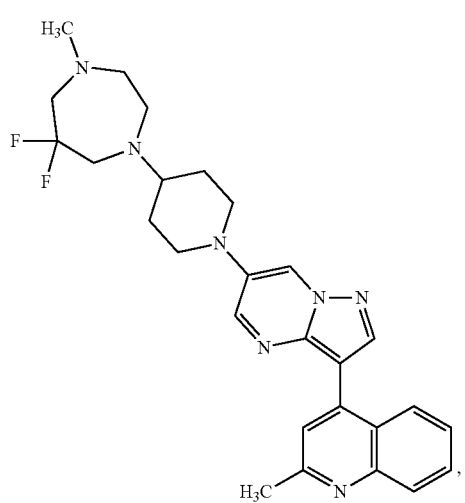
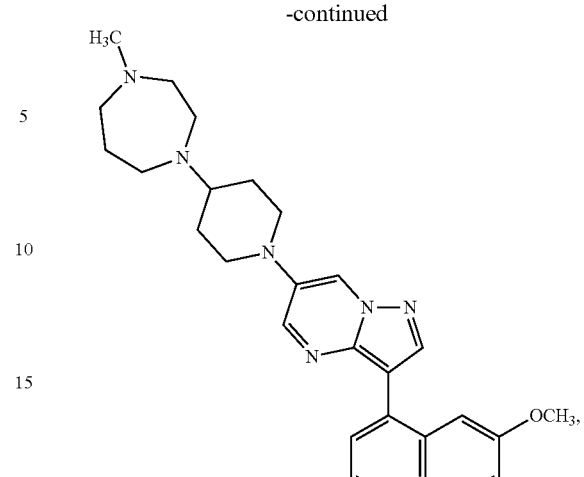
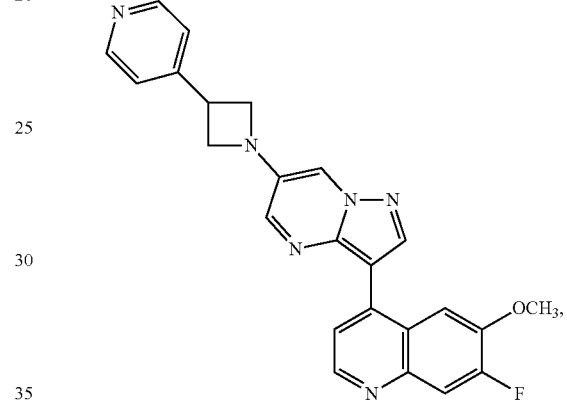
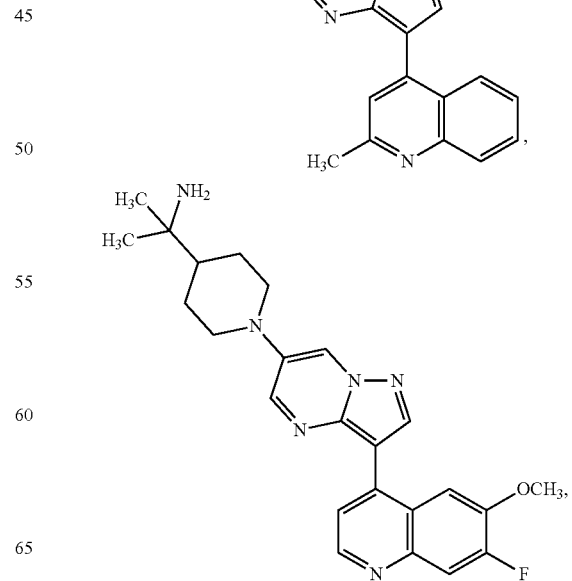

-continued
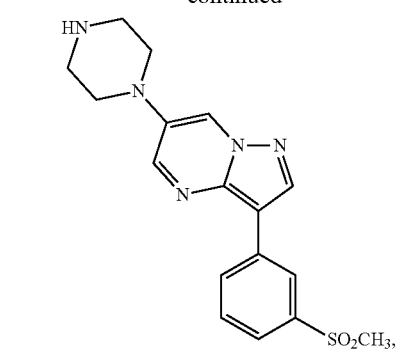
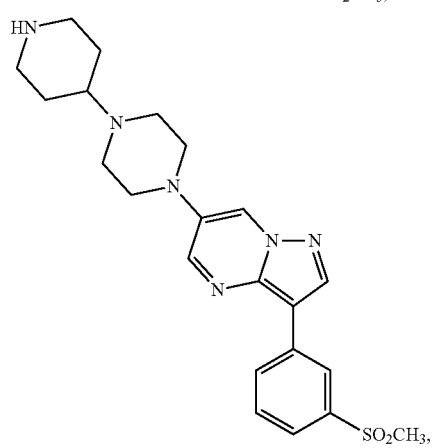
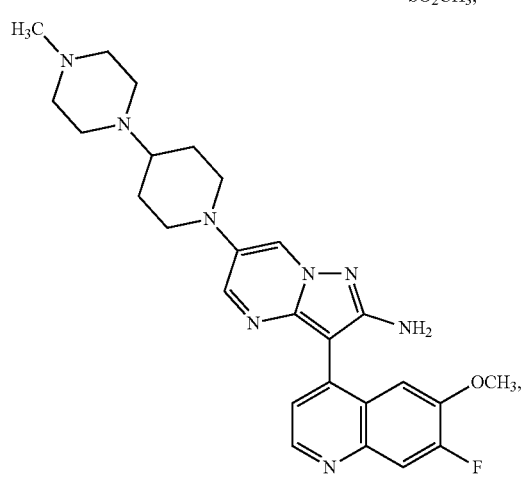
-continued
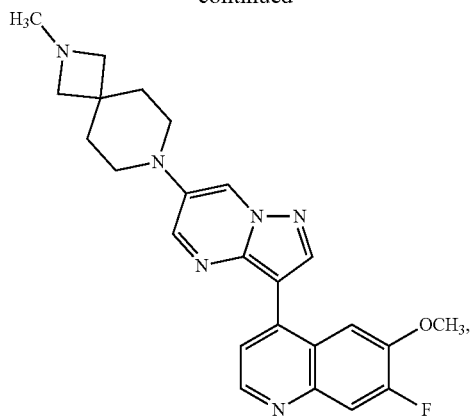
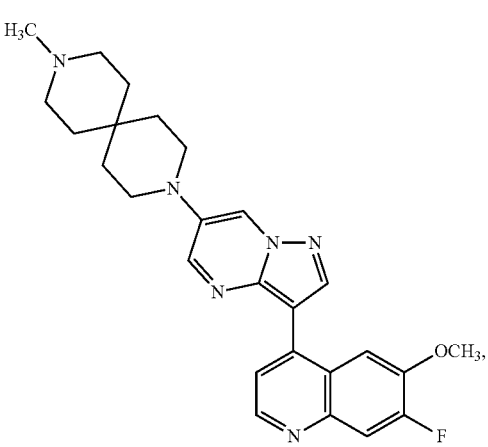
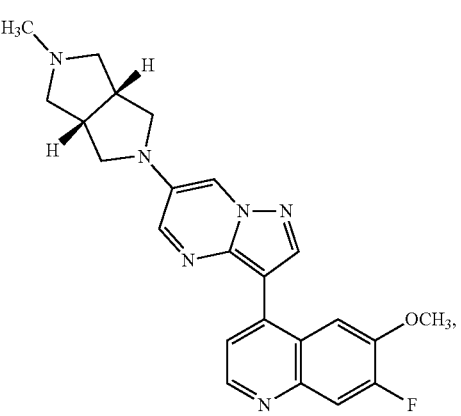

33
-continued
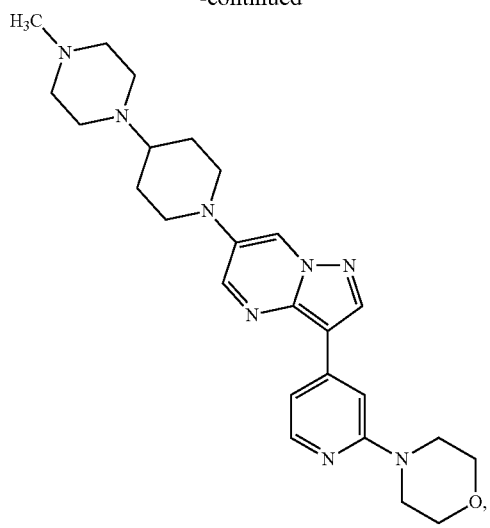
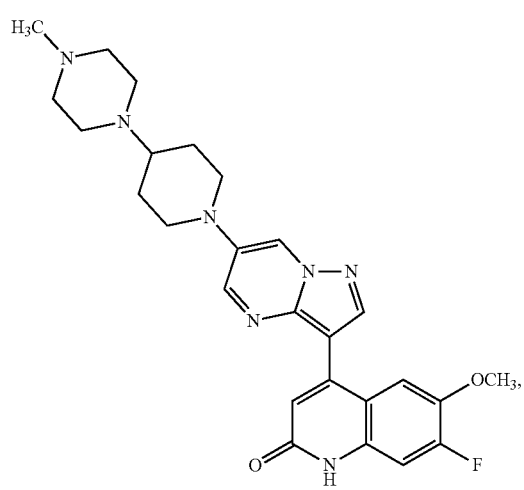
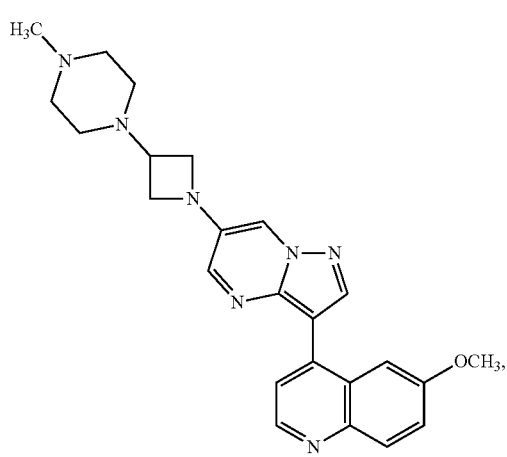
34
-continued
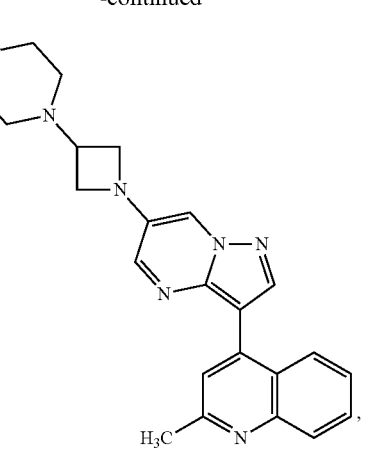
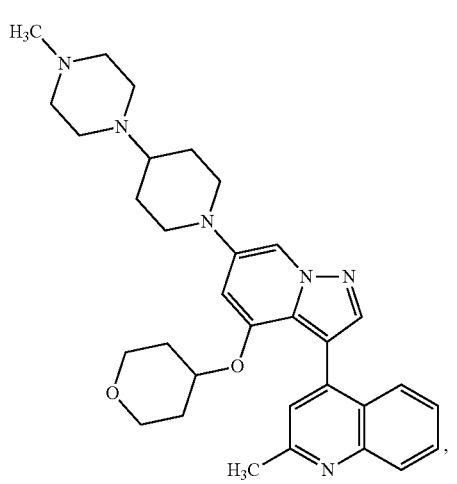

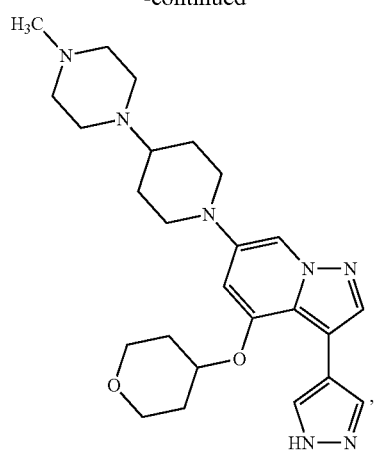
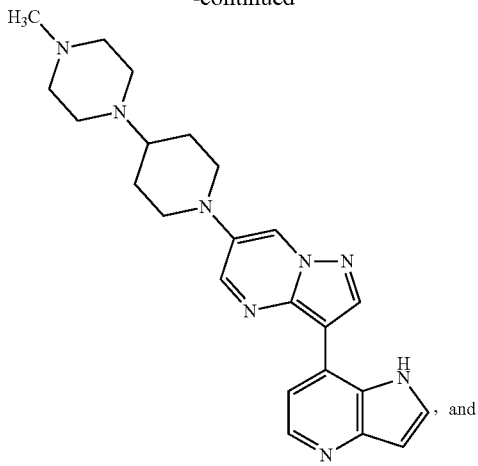
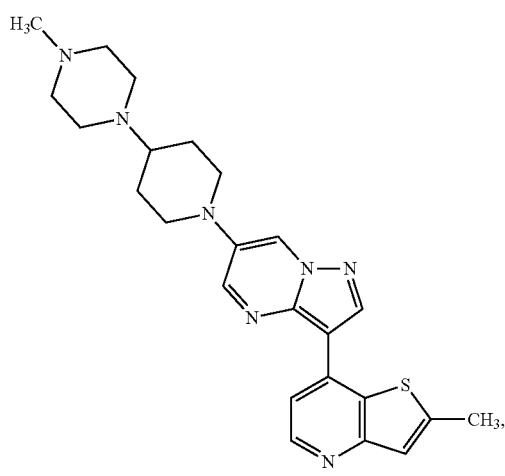
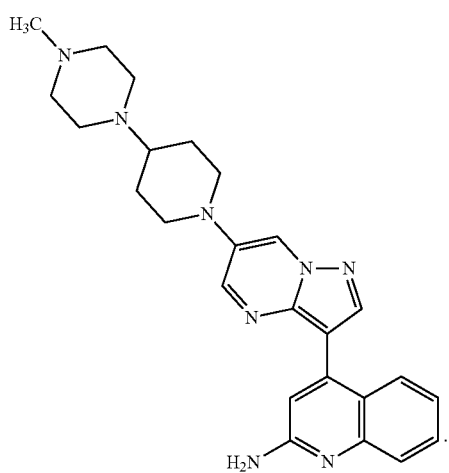
In some embodiments, the compound of Formula I is selected from:
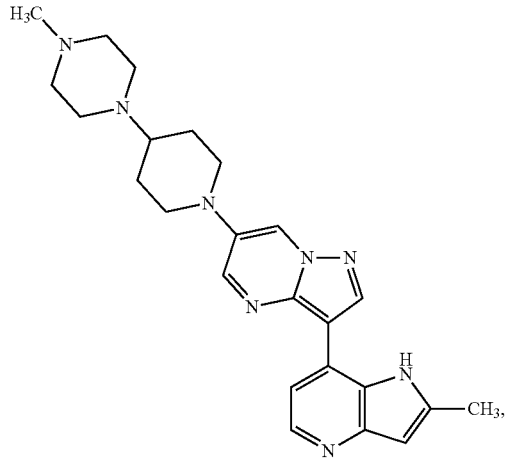
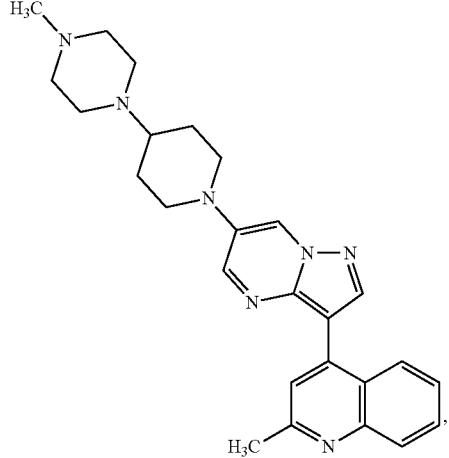

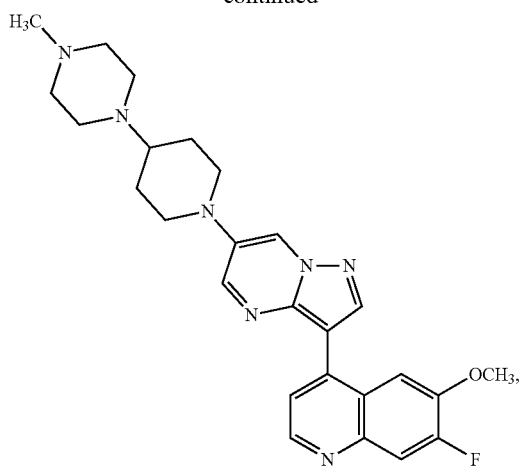

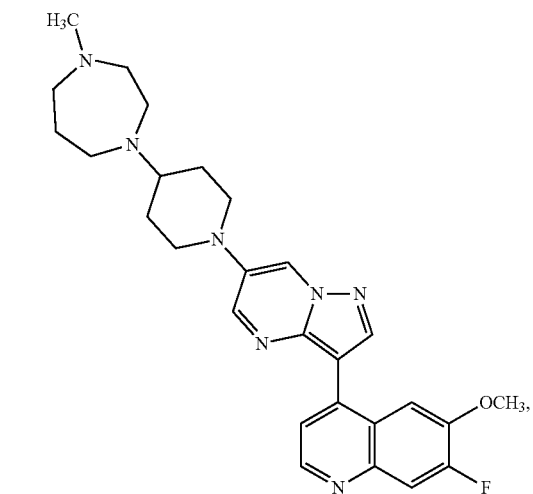

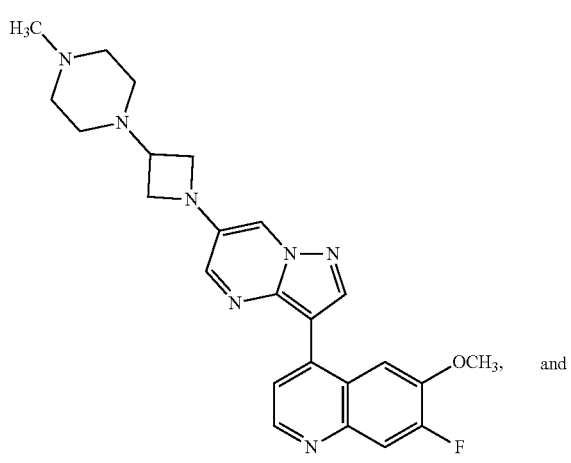

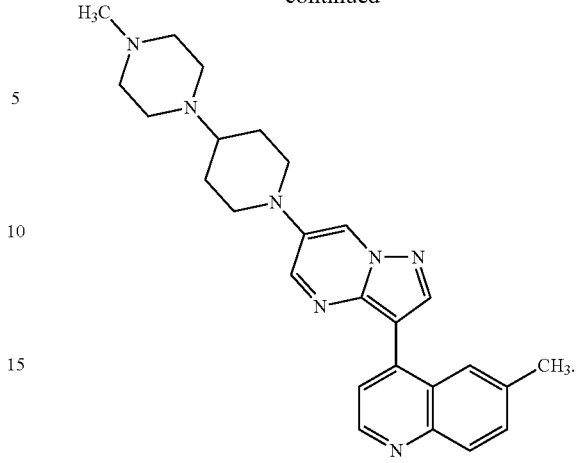 and

In various embodiments, the present invention provides a method for treating the formation of abnormal bone in a soft tissue of a subject, the method comprising: administering to the subject a therapeutically effective amount of one or more compounds of Formula I or Formula I-a, or a pharmaceutically acceptable salt, ester or prodrug thereof. In some embodiments, the subject is determined to have or be at risk of having abnormal bone formation prior to treatment. In some embodiments, the subject has been subjected to a musculoskeletal trauma, a spinal cord injury or a central nervous system injury. In some embodiments, the the formation of abnormal bone is associated with a heterotopic ossification disease. In some embodiments, the heterotopic ossification disease is selected from the group consisting of: acquired heterotopic ossification, fibrodysplasia ossificans progressive, ankylosing spondylosis, traumatic heterotopic ossification, burn- or blast-injury associated heterotopic ossification, and joint replacement surgery associated heterotopic ossification. In some embodiments, the the soft tissue comprises muscles, tendons, ligaments and/or fascia. In some embodiments, the method further comprises administering at least one additional agent to the subject. In some embodiments, the at least one additional agent comprises a corticosteroid, a non-steroidal anti-inflammatory drug (NSAID), a lipoxygenase inhibitor, a leukotriene inhibitor, a mast cell stabilizing agent, an anti-histamine, a TNF inhibitor, an IL-23 blocker, or an inhibitor of IL-1 signaling. In some embodiments, the at least one additional agent comprises an anti-inflammatory agent. In some embodiments, the anti-inflammatory agent is selected from one or more of an inhibitor of the activity of substance P; an inhibitor of the secretion of substance P; an inhibitor of the effects of substance P; an inhibitor of the activity of histamine; an inhibitor of the secretion of histamine; an inhibitor of the effects of histamine; an inhibitor of mast cell function; an inhibitor of Toll-like receptor signaling; an inhibitor of MyD88; an inhibitor of TRIF; apyrase; and an agent to catalyze hydrolysis of ATP. In some embodiments, the at least one additional agent comprises an anti-growth factor agent. In some embodiments, the anti-growth factor agent is selected from one or more of an inhibitor of PDGF ligands; an inhibitor of PDGF-AA; an inhibitor of PDGF-BB; an inhibitor of PDGFR-alpha receptor function; an inhibitor of PDGFR-beta receptor function; a neutralizing antibody against Activin A; a neutralizing antibody against Activin B; a neutralizing antibody against Activin A ligands; a neutralizing antibody against Activin B ligands; a neutralizing antibody against heterodimeric ligands containing Inhibin bA subunits encoded by the INHBA; a neutralizing antibody against heterodimeric ligands containing Inhibin bB subunits encoded by the INHBB gene; a ligand trap of BMP ligands; a ligand trap of Activin ligands; a ligand trap of soluble extracellular domains of a type II Activin receptor ActRIIA; a ligand trap of soluble extracellular domains of a type II Activin receptor ActRIIB; a ligand trap of soluble extracellular domains of a BMP type I receptor ALK2; a ligand trap of soluble extracellular domains of a BMP type I receptor ALK3; and a ligand trap of soluble extracellular domains of a BMP type I receptor ALK6. In some embodiments, the at least one additional agent comprises an anti-osteogenic signaling agent or an anti-chondrogenic signaling agent. In some embodiments, the anti-osteogenic signaling agent or the anti-chondrogenic signaling agent is selected from one or more of a RAR-gamma agonist; a nonselective RAR agonist; an agent that inhibits the activity of osteogenic transcription factor Runx2; an agent that inhibits the expression of osteogenic transcription factor Runx2; an agent that promotes the degradation of osteogenic transcription factor Runx2; an agent that inhibits the activity of chondrogenic transcription factor Sox9; an agent that inhibits the expression of chondrogenic transcription factor Sox9; an agent that promotes the degradation of chondrogenic transcription factor Sox9; an inhibitor of HIF-1 alpha activity; and an inhibitor of HIF-1 alpha expression.

In various embodiments, the present invention provides a pharmaceutical composition, comprising: one or more compounds of Formula I or Formula I-a, or a pharmaceutically acceptable salt, ester or prodrug thereof; and a pharmaceutically acceptable carrier.

In various embodiments, the present invention provides a method for treating the formation of abnormal bone in a soft tissue of a subject, the method comprising: administering a therapeutically effective amount of an inhibitor of a BMP type I serine-threonine kinase receptor to the subject, wherein the inhibitor of a BMP type I serine-threonine kinase receptor is one or more compounds of Formula I or Formula I-a, or a pharmaceutically acceptable salt, ester or prodrug thereof. In some embodiments, the BMP type I serine-thereonine receptor is ALK2, ALK3, or ALK6. In some embodiments, the BMP type I serine-thereonine receptor is ALK2 or ALK3.

In various embodiments, the present invention provides a method for treating the formation of abnormal bone in a soft tissue of a subject, the method comprising: administering a therapeutically effective amount of an inhibitor of a BMP type II serine-threonine kinase receptor to the subject, wherein the inhibitor of a BMP type II serine-threonine kinase receptor is one or more compounds of Formula I or Formula I-a, or a pharmaceutically acceptable salt, ester or prodrug thereof. In some embodiments, the BMP type II serine-thereonine receptor is ACVR2A, ACVR2B, BMPR2, or TGFβR2.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is one or more compounds of Formula I or Formula I-a, or a pharmaceutically acceptable salt, ester or prodrug thereof. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5.

In various embodiments, the present invention provides a method for identifying one or more compounds for inhibiting a serine-threonine kinase receptor, the method comprising: a) providing a sample comprising the serine-threonine kinase receptor; b) contacting the sample with one or more compounds of Formula I or Formula I-a, or a pharmaceutically acceptable salt, ester or prodrug thereof; and c) performing an assay to identify the one or more compounds that inhibit the serine-threonine kinase receptor, wherein the assay is an in vitro assay, an in vivo assay, or an ex vivo assay. In some embodiments, the serine-threonine kinase receptor is a BMP type I receptor, a BMP type II receptor, or a TGF-β type I receptor. In some embodiments, the assay is an in vitro assay.

In various embodiments, the present invention provides a method of treating a subject with Sjogren's syndrome, comprising: a) selecting a subject with increased expression of BMP6 in a salivary gland of the subject relative to a control; and b) administering to the subject a therapeutically effective amount of an agent that inhibits expression or activity of BMP6, thereby treating the subject with Sjogren's syndrome, wherein the agent that inhibits expression or activity of BMP6 is one or more compounds of Formula I or Formula I-a, or a pharmaceutically acceptable salt, ester or prodrug thereof. In some embodiments, the salivary gland is a minor labial salivary gland, parotid gland, or a submandibular gland.

In various embodiments, the present invention provides a method for treating a subject with diffuse intrinsic pontine glioma (DIPG), comprising selecting the subject with diffuse intrinsic pontine glioma (DIPG), and administering to the subject a therapeutically effective amount of one or more compounds of Formula I or Formula I-a, or a pharmaceutically acceptable salt, ester or prodrug thereof, thereby treating the subject with diffuse intrinsic pontine glioma (DIPG).

In various embodiments, the present invention provides a method for treating the formation of abnormal bone in a soft tissue of a subject, the method comprising: administering a therapeutically effective amount of an inhibitor of a TGF-β type I receptor serine-threonine kinase receptor to the subject, wherein the inhibitor of the TGF-β type I serine-threonine kinase receptor is one or more compounds of Formula I or Formula I-a, or a pharmaceutically acceptable salt, ester or prodrug thereof. In some embodiments, the TGF-β type I receptor is ALK5.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
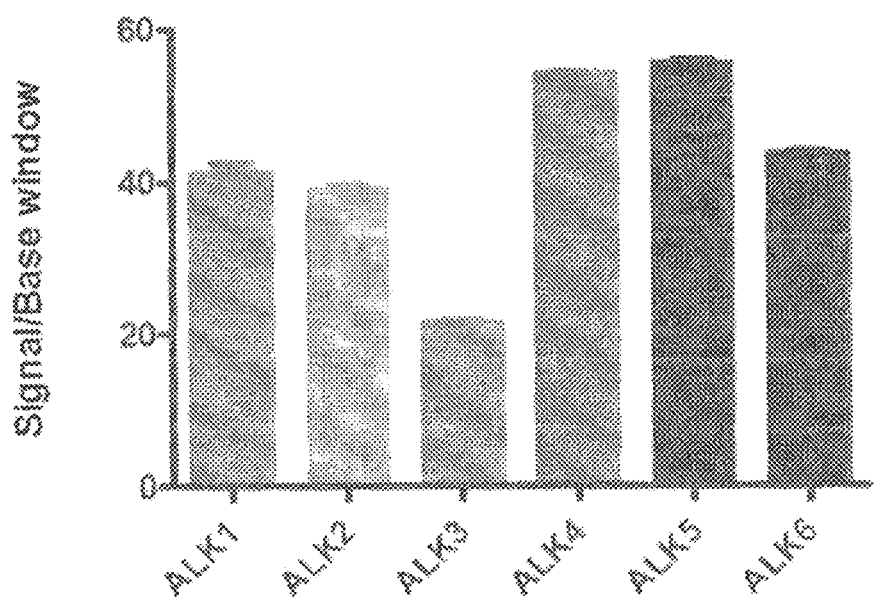
FIG. 1 depicts in accordance with various embodiments of the invention, an Assay window of signal to basal (S/B) ratios of optimized ALK kinase assays. The S/B ratios are greater than 20 fold, indicating robust compound screening assays.

In various embodiments, the present invention provides compounds that inhibit the BMP signaling pathway, as well as methods to treat or prevent a disease or condition in a subject that would benefit by inhibition of BMP signaling. In various embodiments, compounds of the present invention include compounds of Formula I as disclosed herein and their salts (including pharmaceutically acceptable salts). In some embodiments, the compound of Formula I has a structure of Formula I-a.

All references cited herein are incorporated by reference in their entirety as though fully set forth. Unless defined otherwise, technical and scientific terms used herein have the same meaning as commonly understood by one of ordinary skill in the art to which this invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

Unless stated otherwise, the terms "a" and "an" and "the" and similar references used in the context of describing one or more embodiments of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "soft tissue" is used to refer to tissues that connect, support or surround other structures and organs of the body. The term "soft tissue" can refer to muscles, ligaments, tendons, fascia, skin, fibrous tissues, fat, synovial membranes, nerves and/or blood vessels.

As used herein, the term "abnormal bone formation" refers to the generation or bone in an area, such as a soft tissue, where bone normally does not exist.

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In some embodiments, the subject is human. In another embodiment, the subject is an experimental animal or animal substitute as a disease model. In another embodiment, the subject is a domesticated animal including companion animals (e.g., dogs, cats, rats, guinea pigs, hamsters etc.).

As used herein, the term "at risk of having abnormal bone formation" refers to a subject that has been exposed to conditions that are known to cause abnormal bone formation in a population of subjects. While not every subject exposed to such conditions will go on to have abnormal bone formation, but all subjects exposed to these conditions can be considered to be "at risk." Such conditions typically include a trauma, for example, a musculoskeletal trauma, a central nervous system injury or a spinal cord injury.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. The term "pharmaceutically acceptable carriers" excludes tissue culture media.

The term "prodrug" is intended to encompass compounds which, under physiologic conditions, are converted into the therapeutically active agents of the present invention (e.g., one or more compounds of Formula I or Formula I-a). A common method for making a prodrug is to include one or more selected moieties which are hydrolyzed under physiologic conditions to reveal the desired molecule. In other embodiments, the prodrug is converted by an enzymatic activity of the host animal. For example, esters (e.g., esters of alcohols or carboxylic acids) are some examples of prodrugs of the present invention. In various embodiments disclosed herein (e.g., the various compounds, compositions, and methods), some or all of the compounds of Formula I or combination thereof or a portion of a compound of Formula I or combination thereof represented above can be replaced with a suitable prodrug, e.g., wherein a hydroxyl or carboxylic acid present in the parent compound is presented as an ester. In some embodiments, the compound of Formula I has a structure of Formula I-a.

In various embodiments, one or more compounds of Formula I is a BMP inhibitor. In some embodiments, the compound of Formula I has a structure of Formula I-a.

The term "small molecule" refers to an organic molecule having a molecular weight less than about 2500 amu, less than about 2000 amu, less than about 1500 amu, less than about 1000 amu, or less than about 750 amu. In some embodiments a small molecule contains one or more heteroatoms.

The phrase "activity of ALK2" means ALK-2 enzymatic activity (e.g., such as kinase activity; the ability of ALK-2 to phosphorylate BMP-responsive SMAD proteins) and/or ALK-2-mediated signaling (e.g., such as the ability of ALK-2 to mediate downstream signal transduction and transcriptional activity following activation of ALK-2 by binding of BMP ligands). In some embodiments, "activity of ALK2" means ALK2-mediated BMP signaling. In some embodiments, "activity of ALK2" means ALK2-mediated BMP-responsive gene transcription (e.g., transcriptional activity mediated by BMP/ALK2 signal transduction).

The phrase "activity of ALK5" means ALK-5 enzymatic activity (e.g., such as kinase activity; the ability of ALK-5 to phosphorylate TGF-β responsive SMAD proteins; the ability of ALK-5 to phosphorylate SMAD2 or SMAD3) and/or ALK-5-mediated signaling (e.g., such as the ability of ALK-5 to mediate downstream signal transduction and transcriptional activity following activation of ALK-5 by binding of TGF-β ligands). In some embodiments, "activity of ALK5" means ALK5-mediated TGF-β signaling. In some embodiments, "activity of ALK5" means ALK5-mediated TGF-β-responsive gene transcription (e.g., transcriptional activity mediated by TGF β/ALK5 signal transduction).

The phrase "activity of ALK1" means ALK-1 enzymatic activity (e.g., such as kinase activity; the ability of ALK-1 to phosphorylate BMP-responsive SMAD proteins) and/or ALK-1-mediated signaling (e.g., such as the ability of ALK-1 to mediate downstream signal transduction and transcriptional activity following activation of ALK-1 by binding of BMP ligands). In some embodiments, "activity of ALK1" means ALK1-mediated BMP signaling. In some embodiments, "activity of ALK1" means ALK1-mediated BMP-responsive gene transcription (e.g., transcriptional activity mediated by BMP/ALK1 signal transduction).

The phrase "activity of ALK4" means ALK-4 enzymatic activity (e.g., such as kinase activity; the ability of ALK-4 to phosphorylate activin-responsive SMAD proteins; the ability of ALK-4 to phosphorylate SMAD 2 or SMAD 3) and/or ALK-4-mediated signaling (e.g., such as the ability of ALK-4 to mediate downstream signal transduction and transcriptional activity following activation of ALK-4 by binding of activin ligands). In some embodiments, "activity of ALK4" means ALK4-mediated activin signaling. In some embodiments, "activity of ALK4" means ALK4-mediated activin-responsive gene transcription (e.g., transcriptional activity mediated by activin/ALK4 signal transduction).

The phrase "activity of ALK6" means ALK-6 enzymatic activity (e.g., such as kinase activity; the ability of ALK-6 to phosphorylate BMP-responsive SMAD proteins) and/or ALK-6-mediated signaling (e.g., such as the ability of ALK-6 to mediate downstream signal transduction and transcriptional activity following activation of ALK-6 by binding of BMP ligands). In some embodiments, "activity of ALK6" means ALK6-mediated BMP signaling. In some embodiments, "activity of ALK6" means ALK6-mediated GDF5 signaling. In some embodiments, "activity of ALK6" means ALK6-mediated BMP-responsive gene transcription (e.g., transcriptional activity mediated by BMP/ALK6 signal transduction).

Human ALK2 is a 509 amino acid protein. The protein sequence is published, for example, as GenBank accession number NP_001104537.1, (with corresponding nucleotide sequence at NM_001111067.2) UniProt entry Q04771.

Human ALK5 has, at least, two isoforms: a 503 amino acid protein (isoform 1) and a 426 amino acid protein. The protein sequence for human ALK5 isoform 1 is published, for example, as GenBank accession number NP_004603.1 (with corresponding nucleotide sequence at NM_004612.2). The protein sequence for the 426 amino acid isoform is published, for example, as GenBank accession number NP_001124388.1 9f with corresponding nucleotide sequence at NM_001130916.1). Information regarding both isoforms is also published as UniProt entry P36897.

Human ALK1 is a 503 amino acid protein. The protein sequence is published, for example, as GenBank accession number NP_001070869.1 (with corresponding nucleotide sequence at NM_001077401.1; transcript variant 2) and NP_000011.2 (with corresponding nucleotide sequence at NM_000020.2; transcript variant 1), UniProt entry P37023.

Human ALK3 is a 532 amino acid protein. The protein sequence is published, for example as GenBank accession number NP_004320 (with corresponding nucleotide sequence at NM_004329.2), UniProt entry P36894.

Human ALK4 has at least three isoforms. Isoform a is a 505 amino acid protein. The protein sequence is published, for example, as GenBank accession number NP_004293 (with corresponding nucleotide sequence at NM_004302), UniProt entry P36896.

Isoform a of human ALK6 is a 532 amino acid protein and isoform b is a 502 amino acid protein. The protein sequence for human ALK6 isoform a is published, for example, as GenBank accession number NP_001243722 (with corresponding nucleotide sequence at NM_001256793.1). The protein sequence for human ALK6 isoform b is published, for example, as GenBank accession number NP 001194 (with corresponding nucleotide sequence at NM_01203.2).

Note that each of the foregoing proteins are further processed in vivo, such as by the cleaving of a signal sequence, to yield a mature form.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the embodiment.

"Optional" or "optionally" means that the subsequently described circumstance may or may not occur, so that the description includes instances where the circumstance occurs and instances where it does not.

Agent: Any one or more compounds of Formula I; protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In some embodiments, the compound of Formula I has a structure of Formula I-a.

Agent that Promotes Salivary Production: Any compound that increases the amount of saliva produced in a subject (for example, a subject with Sjögren's syndrome). In some cases, an agent that promotes salivary production is a therapeutic agent prescribed by a physician, such as pilocarpine (Salagen™) or cevimeline (Evoxac™). In some examples, the agent that promotes salivary production is an inhibitor of BMP6 expression or activity. In some examples, the agent that promotes salivary production is one or more compounds of Formula I. In some embodiments, the compound of Formula I has a structure of Formula I-a.

Alteration in Expression: An alteration in expression refers to a change in the level of a gene transcript (for example, mRNA) or gene product (for example, protein) that is detectable in a biological sample (such as a sample from a patient with Sjögren's syndrome, for example, in a salivary gland biopsy) relative to a control (such as a healthy subject). An "alteration" in expression includes an increase in expression (up-regulation) or a decrease in expression (down-regulation).

Bone Morphogenetic Protein 6 (BMP6): A member of the TGF-0 superfamily of growth factors. Expression of BMP6 has been detected in several different mammalian tissues and cell types, including smooth muscle cells, growth plate chondrocytes, bronchiolar epithelium, cornea, epidermis, salivary gland and cells of the nervous system (Blessing et al., *J Cell Biol* 135(1):227-239, 1996). In vitro, BMP6 has been shown to inhibit cell division, promote terminal epithelial differentiation, and induce endochondral bone formation, osteoblastic differentiation and neuronal maturation (Heikinheimo et al., *Cancer Res* 59:5815-5821, 1999). BMP6 is also known as vegetal related growth factor (TGFB-related), VGR, VGR1 and VG-1-related protein. Genomic, mRNA and protein sequences for BMP6 from a number of different species are publically available, such as in the GenBank database from the National Center for Biotechnology Information.

Control: A "control" refers to a sample or standard used for comparison with an experimental sample, such as a salivary gland sample obtained from a patient with Sjögren's syndrome. In some embodiments, the control is a sample obtained from a healthy volunteer (also referred to herein as a "normal" control). In some embodiments, the control is a historical control or standard value (i.e. a previously tested control sample or group of samples that represent baseline or normal values).

Diagnosis: The process of identifying a disease by its signs, symptoms and/or results of various tests. The conclusion reached through that process is also called "a diagnosis." Forms of testing commonly performed include physical examination, blood tests, medical imaging, genetic analysis, urinalysis, and biopsy.

Diagnostically Significant Amount: In some embodiments, a "diagnostically significant amount" refers to an increase or decrease in the level of BMP6 (or any other gene or protein) in a biological sample that is sufficient to allow one to distinguish one patient population from another (such as a Sjögren's syndrome patient population from a group of healthy individuals). In some examples, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold. RT-PCR is provided herein as one example of how BMP6 expression can be detected. Immunoassays, such as an ELISA, are another example of a method for detecting expression of BMP6. However, one of skill in the art will recognize that other methods exist to measure gene expression and variation in detected expression levels can occur depending on the method that is used. Thus, the diagnostically significant amount may vary if another method of detection is used. In other embodiments, a "diagnostically significant amount" refers to an increase or decrease in electrical potential of a salivary gland that is sufficient to allow one to distinguish one patient population from another (such as a Sjögren's syndrome patient population from a group of healthy controls). In some examples, the diagnostically significant increase or decrease is about 10%, about 20%, about 30%, about 40% or about 50%.

Immunosuppressive Drug: Includes any agent or compound having the ability to decrease the body's immune system responses. In some embodiments, the immunosuppressive drug is a corticosteroid. In other embodiments, the immunosuppressive drug is a small molecule (such as cyclosporine) or a monoclonal antibody (such as a cytokine blocker).

Inhibitor: Any chemical compound, nucleic acid molecule, small molecule, peptide or polypeptide (such as an antibody) that can reduce activity of a gene product or interfere with expression of a gene. In some examples, an inhibitor can reduce or inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. In some examples, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization. In various embodiments of the present invention, an inhibitor is one or more compounds of Formula I. In some embodiments, the compound of Formula I has a structure of Formula I-a.

Inhibit Expression or Activity: As used herein, an agent that inhibits expression or activity of a gene (such as BMP6) is an agent that reduces the level of mRNA or protein expressed by the gene (such as BMP6) in a cell or tissue, or reduces (including eliminates) one or more activities of the gene or encoded protein (such as BMP6). Similarly, an agent that inhibits BMP signaling is any compound that inhibits, blocks or prevents signaling events in the BMP signaling pathway, such as phosphorylation of downstream targets, for example phosphorylation of SMAD1/5/8.

Measuring the Level of Expression: Quantifying the amount of a gene product present in a sample. Quantification can be either numerical or relative. Detecting expression of the gene product (such as BMP6 mRNA or protein) can be achieved using any method known in the art or described herein, such as by RT-PCR, antibody-binding (e.g., ELISA), or immunohistochemistry. In some embodiments, the change detected is an increase or decrease in expression as compared to a control. In some examples, the detected increase or decrease is an increase or decrease of at least two-fold, at least three fold or at least four-fold compared with the control. In other embodiments of the methods, the increase or decrease is of a diagnostically significant amount, which refers to a change of a sufficient magnitude to provide a statistical probability of the diagnosis.

Methyl CpG Binding Protein 2 (MECP2): DNA methylation is the major modification of eukaryotic genomes and plays an essential role in mammalian development. Human proteins MECP2, MBD1, MBD2, MBD3, and MBD4 comprise a family of nuclear proteins related by the presence in each of a methyl-CpG binding domain (MBD). Each of these proteins, with the exception of MBD3, is capable of binding specifically to methylated DNA. MECP2, MBD1 and MBD2 can also repress transcription from methylated gene promoters. In contrast to other MBD family members, MECP2 is X-linked and subject to X inactivation. MECP2 is dispensable in stem cells, but is essential for embryonic development. MECP2 gene mutations are the cause of most cases of Rett syndrome, a progressive neurologic developmental disorder and one of the most common causes of mental retardation in females. MECP2 is also known as RS; RTS; RTT; PPMX; MRX16; MRX79; MRXSL; AUTSX3; MRXS13; and DKFZp686A24160. Genomic, mRNA and protein sequences for MECP2 are publically available, such as in the GenBank database from the National Center for Biotechnology Information.

Noggin (NOG): A secreted protein that binds and inactivates members of the transforming growth factor-beta (TGF-beta) superfamily signaling proteins, such as BMP4 and BMP6. By diffusing through extracellular matrices more efficiently than members of the TGF-beta superfamily, this protein may have a principal role in creating morphogenic gradients. The protein appears to have pleiotropic effect, both early in development as well as in later stages. Nucleotide and amino acid sequences of noggin are publically available, such as in the GenBank database (see NCBI Gene ID 9241 for human noggin).

Non-Steroidal Anti-Inflammatory Drug (NSAID): A type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate.

Restoring Salivary Flow (or Increasing Salivary Flow): The process of increasing salivary production in a subject with diminished salivary flow, such as may result from Sjögren's syndrome and/or an increase in BMP6 expression. An increase in salivary flow can be indicated by, for example, an increase in salivary flow rate and/or an increase in salivary flow volume. In some embodiments, restoring salivary flow can be accomplished by administering a therapeutic agent. In some examples, the therapeutic agent is a pharmaceutical, such as pilocarpine (Salagen™) or cevimeline (Evoxac™). In other examples, the therapeutic agent is an inhibitor of BMP6 expression or activity.

Restoring Tear Production: The process of increasing tear production in a subject with diminished tearing, such as may result from Sjögren's syndrome. In some embodiments, restoring tear production can be accomplished by administering a therapeutic agent. In particular examples, the therapeutic agent is an inhibitor of BMP6 expression or activity.

Salivary Glands: Exocrine glands that produce saliva. As used herein, a "salivary gland" includes any salivary gland in a human subject, including, for example, the parotid glands, minor salivary glands, submandibular glands, sublingual glands and Von Ebner's glands. There are over 600 minor salivary glands located throughout the oral cavity.

Sjögren's Syndrome (SS): An autoimmune disorder characterized by immune cells that attack and destroy the glands that produce tears and saliva. Sjögren's syndrome is not life-threatening or life-shortening, but can significantly reduce quality of life. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis.

A number of different criteria can be used to identify a subject having Sjögren's syndrome and include one or more of: (i) ocular symptoms (for example, persistent dry eyes and/or recurrent sensation of sand or gravel in eyes); (ii) oral symptoms (for example, daily feeling of dry mouth, persistently swollen salivary glands, and/or drinking liquids to swallow dry food); (iii) objective evidence of ocular involvement defined as a positive result of a Schirmer's test performed without anesthesia (≤5 mm in 5 minutes) and/or Rose bengal score or other ocular surface staining score (≥4 according to van Bijsterveld's scoring system; (iv) histopathology in minor salivary glands (measuring focus score or Tarpley score); (v) salivary gland involvement demonstrated with objective evidence of salivary gland involvement by a positive result for unstimulated whole salivary flow (≤1.5 ml in 15 minutes), parotid sialography showing the presence of diffuse sialectasias (punctate, cavitary, or destructive pattern) without evidence of obstruction in the major ducts, and/or salivary scintigraphy showing delayed uptake, reduced concentration and/or delayed excretion of tracer; or (vi) autoantibodies (presence in the serum of antibodies to Ro (SSA) or La (SSB) antigens, or both. Thus, in some embodiments, a subject exhibiting one or more of the above signs or symptoms is selected for treatment according to the methods disclosed herein.

The presence of sicca (dryness) symptoms (sicca symptomology) in the absence of another connective tissue disease is designated "primary Sjögren's syndrome." Primary Sjögren's syndrome can also be characterized in subjects having a positive result for any four of the six criteria listed above, as long as either histopathology (item iv) or serology (item vi) is positive, or the presence of any three of the four objective criteria listed above (that is, items iii, iv, v, vi). Patients with an autoimmune process (such as rheumatoid arthritis, systemic lupus erythematosus, progressive systemic sclerosis, scleroderma, or polymyositis), in the presence of item i or item ii listed above, plus any two criteria from items iii, iv, and v, are characterized as having "secondary Sjögren's syndrome."

Specific Binding Agent: An agent that binds substantially or preferentially only to a defined target, such as a protein, enzyme, polysaccharide, oligonucleotide, DNA, RNA or a small molecule. For example, a "specific binding agent" includes an antisense oligonucleotide that specifically hybridizes with a target nucleic acid molecule, an antibody specific for a particular protein, an RNA aptamer that binds substantially to a specified protein, a small molecule that preferentially binds a specific protein target, or soluble binding molecules (such as soluble receptors). A protein-specific binding agent binds substantially only to the defined protein, or to a specific region within the protein. For example, a "specific binding agent" includes antibodies and other agents (such as an aptamer) that bind substantially to a specified polypeptide. The antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Therapeutic Agent: A chemical compound, small molecule, or other composition, such as an antisense compound, antibody, protease inhibitor, hormone, chemokine or cytokine, capable of inducing a desired therapeutic or prophylactic effect when properly administered to a subject. In some embodiments, a therapeutic agent is one or more compounds of Formula I. In some embodiments, the compound of Formula I has a structure of Formula I-a.

Therapeutically Effective Amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

X (Inactive)-Specific Transcript (Non-Protein Coding) (XIST): X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIST gene is expressed exclusively from the XIC of the inactive X chromosome.

The transcript is spliced but does not encode a protein. The transcript remains in the nucleus where it coats the inactive X chromosome. XIST is also known as XCE, XIC and SXI1. Genomic and RNA sequences for XIST are publically available, such as in the GenBank database from the National Center for Biotechnology Information.

Abbreviations
AAV adeno-associated virus
ATP adenosine triphosphate
BMP6 bone morphogenetic protein 6
BSA bovine serum albumin
BW body weight
CGH comparative genomic hybridization
ELISA enzyme-linked immunosorbent assay
EP electrical potential
FS focus score
HIF-1 alpha hypoxia-inducible factor 1-alpha
HO heterotopic ossification
HTS hypotonic solution
HV healthy volunteer
IFN interferon
IL interleukin
IM intramuscular
IPA Ingenuity Pathway Analysis
MECP2 methyl CpG binding protein 2
MyD88 myeloid differentiation primary response gene 88
NOD non-obese diabetic
OD optical density
O/N overnight
PDGF platelet-derived growth factor
pSS primary Sjögren's syndrome
qPCR quantitative polymerase chain reaction
RIN RNA integrity number
RT room temperature
RT-PCR reverse transcriptase polymerase chain reaction
Runx2 runt-related transcription factor 2
RVD regulated volume decrease
SFR salivary flow rate
SG salivary gland
SMG submandibular gland
SS Sjögren's syndrome
TEER trans epithelial electric resistance
TGF transforming growth factor
TRIF TIR-domain-containing adapter-inducing interferon-β
WT wild type
XIST X (inactive)-specific transcript (non-protein coding)

Further, unless otherwise required by context, singular terms shall include pluralities and plural terms shall include the singular.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

The methods and compositions provided herein are based, in part, on the discovery that one or more compounds of Formula I act as a BMP inhibitor by inhibiting signaling through ALK2, a BMP type I receptor. In addition, one or more compounds of Formula I is shown herein to be effective in the treatment and/or prevention of abnormal bone formation in soft tissue. Accordingly, provided herein are methods and compositions for the treatment of abnormal bone formation in soft tissue, comprising treatment with one or more compounds of Formula I. In some embodiments, the compound of Formula I has a structure of Formula I-a.

Compounds of the Invention
Disclosed herein are compounds of Formula I.

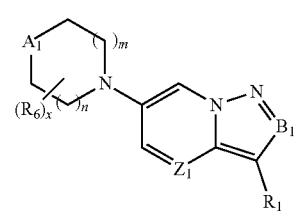

(I)

or a pharmaceutically acceptable salt and/or prodrug thereof, wherein
$A_1$ is $NR_{4a}$ or $CR_{4b}R_5$;
$B_1$ is N or $CR_2$;
$Z_1$ is N or $CR_3$;
$R_1$ is selected from cycloalkyl, aryl, heteroaryl, and heterocyclyl;
$R_2$ is H, CN, $NO_2$, alkyl, or amino;
$R_3$ is selected from H, CN, $NO_2$, alkyl, alkoxy, heterocyclyloxy, heteroaryloxy, aryloxy, cycloalkyloxy, carbonyl, amino, amido, sulfonyl, sulfonamido, cycloalkyl, aryl, heterocyclyl, and heteroaryl;
$R_{4a}$ is selected from alkyl, alkenyl, alkynyl, carbonyl, $O^-$, alkoxycarbonyl, cycloalkyl, aryl, heterocyclyl, and heteroaryl;
$R_{4b}$ is selected from halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl;
$R_5$ is selected from H, halo, hydroxy and alkyl, or
$R_{4b}$ and $R_5$ together with $A_1$ form a ring selected from cycloalkyl and heterocyclyl;
each $R_6$ is independently selected from H, halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl and oxo;
n is 0 or 1;
m is 0 or 1; and
x is 0, 1, 2, 3, or 4.

Also disclosed herein are compounds of Formula I:

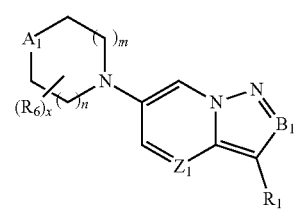

(I)

or a pharmaceutically acceptable salt and/or prodrug thereof, wherein
$A_1$ is $NR_{4a}$ or $CR_{4b}R_5$;
$B_1$ is N or $CR_2$;
$Z_1$ is N or $CR_3$;
$R_1$ is selected from aryl, heteroaryl, and heterocyclyl;
$R_2$ is H or amino;
$R_3$ is H or heterocyclyloxy;

R$_{4a}$ is selected from alkyl, O⁻, aryl, heterocyclyl, and heteroaryl;
R$_{4b}$ is selected from alkyl, alkoxy, amino, aryl, heterocyclyl, and heteroaryl;
R$_5$ is selected from H and alkyl, or
R$_{4b}$ and R$_5$ together with A$_1$ form a ring selected from cycloalkyl and heterocyclyl;
each R$_6$ is independently selected from H, halo, alkyl and oxo;
n is 0 or 1;
m is 0 or 1; and
x is 0, 1, 2, 3, or 4.

In some embodiments, A$_1$ is NR$_4$a. In other embodiments, A$_1$ is CR$_{4b}$R$_5$ and R$_5$ is H. In some embodiments, A$_1$ is CR$_{4b}$R$_5$ and R$_{4b}$ is heterocyclyl. In certain embodiments, B$_1$ is N. In some embodiments, B$_1$ is CR$_2$, and R$_2$ is H. In some embodiments, Z$_1$ is CR$_3$ and R$_3$ is H.

In some embodiments, R$_1$ is selected from H, aryl, 5-6 membered heteroaryl,

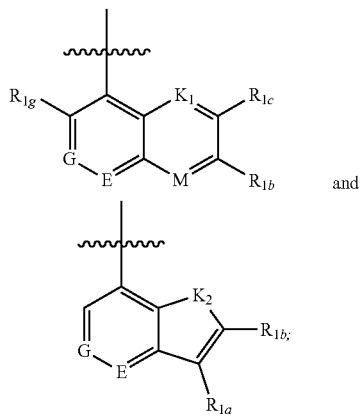

and

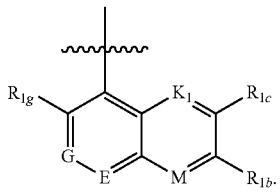

wherein:
each E is independently selected from N and CR$_{1d}$;
each G is independently selected from N and CR$_{1e}$;
K$_1$ is N or CH;
K$_2$ is NH or S;
M is N or CR$_{1a}$;
R$_{1a}$ is selected from H, halo, alkyl, haloalkyl, and amido;
R$_{1b}$ is selected from H, halo, CN, alkyl, haloalkyl, hydroxy, alkoxy, and haloalkoxy;
R$_{1c}$ is selected from H, halo, CN, alkyl, haloalkyl, hydroxy, alkoxy, haloalkoxy, amino and amido, or
R$_{1b}$ and R$_{1c}$ together with the carbon atoms to which they are attached form a heterocyclyl;
R$_{1d}$ is selected from H, CN, alkyl, haloalkyl, hydroxy, amido and sulfonamido;
R$_{1e}$ is selected from H, alkyl and amino; and
R$_{1g}$ is H or halo.

In some embodiments, R$_1$ is selected from H, pyrrolyl, phenyl, pyridinyl and isoquinolinyl. In other embodiments, R$_1$ is In certain embodiments, R$_1$ is

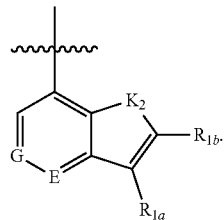

In some embodiments, E is N. In other embodiments, E is CR$_{1d}$ and R$_{1d}$ is selected from H, CONH$_2$, and SO$_2$NH$_2$. In some embodiments, G is CR$_{1e}$ and R$_{1e}$ is selected from H, Me, CN, CHF$_2$, CF$_3$, and NH$_2$. In certain embodiments, K$_1$ is N. In other embodiments, K$_1$ is CH. In some embodiments, K$_2$ is NH. In other embodiments, K$_2$ is S. In some embodiments, M is N. In other embodiments, M is CR$_{1a}$.

In certain embodiments, R$_{1a}$ is selected from H, F, Me, CF$_3$, and CONH$_2$. In some embodiments, R$_{1b}$ is selected from H, F, Cl, CN, Me, OH, OMe, OEt, CF$_3$, and OCF$_3$. In certain embodiments, R$_{1c}$ is selected from H, F, Cl, CN, Me, CHF$_2$, CF$_3$, OH, OMe, OCF$_3$, OEt, NH$_2$, NHMe, NMe$_2$, and NHCOMe. In some embodiments, R$_{1g}$ is H or F.

In some embodiments, R$_3$ is H or —O-dioxanyl. In some embodiments, R$_{4a}$ and/or R$_{4b}$ is alkyl. In some embodiments, A$_1$ is NR$_{4a}$ and R$_{4a}$ is O⁻ (e.g., N-oxide). In other embodiments. R$_{4b}$ is selected from Me, NH$_2$, NMe$_2$, —CH$_2$—C(Me$_2$)OH, CMe$_2$NH$_2$, OCH$_2$CH$_2$NH$_2$, OCH$_2$CH$_2$NMe$_2$, and N(Me)CH$_2$CH$_2$NMe$_2$.

In some embodiments, R$_{4b}$ is heterocyclyl. In some embodiments, the heterocyclyl is selected from pyrrolidinyl, diazolyl, thiomorpholinyl 1,1-dioxide, piperazin-2-onyl, piperidinyl, morpholino, tetrahydropyranyl, diazepanyl, azetidinyl, octahydropyrrolo[3,4-c]pyrrolyl, 3,8-diazabicyclo[3.2.1]octanyl, 8-Me-3,8-diazabicyclo[3.2.1]octanyl, 2,5-diazabicyclo[2.2.1]heptanyl, 2,5-diazabicyclo[2.2.1]heptanyl, and 4-Me-2,5-diazabicyclo[2.2.1]heptanyl. In some embodiments, R$_{4b}$ is heteroaryl. In certain embodiments, the heteroaryl is selected from pyridinyl, pyrimidinyl, thiadiazolo, and pyrazolopyridinyl.

In some embodiments, the heterocyclyl or heteroaryl is substituted with one or more substitutents selected from halo, alkyl, alkoxy, carbonyl, amido, amino, oxide and sulfoxide. In certain embodiments, the heterocyclyl is substituted with one or more substitutents selected from F, Me, Et, OMe, COMe, CONHMe, NH$_2$, —O⁻ (e.g., N-oxide), and SO$_2$.

In some embodiments, R$_5$ is alkyl. In certain embodiments, R$_5$ is selected from H, Me and CH$_2$CN. In other embodiments, R$_{4b}$ and R$_5$ together with A$_1$ form a ring selected from cyclobutyl, azetidinyl, pyrrolidinyl, and azabicyclohexanyl-6-amine. In certain embodiments, the ring is substituted by one or more substituents selected from Me, NH$_2$, and NMe$_2$.

In some embodiments, each R$_6$ is independently selected from H, F, Me, and oxo. In some embodiments, n and m are each 1. In other embodiments, n is 0 and m is 1. In other embodiments, n and m are each 0. In some embodiments, x is 0 or 1.

In some embodiments,
R$_{4a}$ is selected from alkyl, heterocyclyl, and heteroaryl;
R$_{4b}$ is selected from alkyl, alkoxy, amino, amido, heterocyclyl, and heteroaryl;
R$_5$ is selected from H and alkyl, or
R$_{4b}$ and R$_5$ together with A$_1$ form a heterocyclyl; and each $R_6$ is independently selected from H, halo, and alkyl; and x is 0 or 1.

In some embodiments, $R_1$ is selected from H, aryl, 5-6 membered heteroaryl,

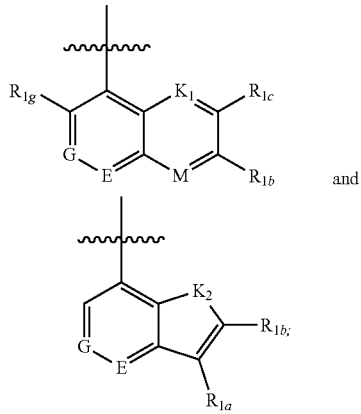

and wherein:
each E is independently selected from N and $CR_{1d}$;
each G is independently selected from N and $CR_{1e}$;
$K_1$ is N or CH;
$K_2$ is NH, S, or $CR_{1f}$;
M is $CR_{1a}$;
$R_{1a}$ is selected from H and amido;
$R_{1b}$ is selected from H, halo, alkyl, and alkoxy;
$R_{1c}$ is selected from H, alkyl, and alkoxy, or
$R_{1b}$ and $R_{1c}$ together with the carbon atoms to which they are attached form a heterocyclyl;
$R_{1d}$ is selected from H, alkyl, hydroxy, amido and sulfonamido;
$R_{1e}$ is selected from H, alkyl and amino;
$R_{1f}$ is H; and
$R_{1g}$ is H.

In some embodiments, $R_1$ is

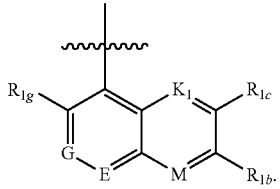

In other embodiments, $R_1$ is

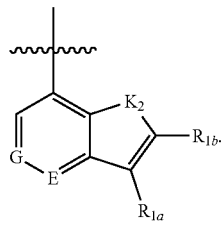

In some embodiments, E is N. In other embodiments, E is $CR_{1d}$ and $R_{1d}$ is selected from H, $CONH_2$, and $SO_2NH_2$. In certain embodiments, G is $CR_{1e}$ and $R_{1e}$ is selected from H, Me and $NH_2$. In some embodiments, $K_1$ is N. In other embodiments, $K_1$ is CH. In some embodiments, $K_2$ is NH or S. In some embodiments, M is $CR_{1a}$.

In some embodiments, $R_{1a}$ is selected from H and $CONH_2$. In other embodiments, $R_{1b}$ is selected from H, F, Cl, Me, and OMe. In some embodiments, $R_{1c}$ is selected from H, Me, OMe, and OEt. In certain embodiments, $R_{1g}$ is H.

In certain embodiments, $R_{4b}$ is selected from Me, $NH_2$, $NMe_2$, $—CH_2—C(Me_2)OH$, and $CMe_2NH_2$. In some embodiments, $R_{4b}$ is heterocyclyl. In certain embodiments, the heterocyclyl is selected from pyrrolidinyl, diazolyl, piperazin-2-onyl, piperidinyl, morpholino, tetrahydropyranyl, diazepanyl, azetidinyl, octahydropyrrolo[3,4-c]pyrrolyl, 3,8-diazabicyclo[3.2.1]octanyl, 8-Me-3,8-diazabicyclo[3.2.1]octanyl, 2,5-diazabicyclo[2.2.1]heptanyl, 2,5-diazabicyclo[2.2.1]heptanyl, and 4-Me-2,5-diazabicyclo[2.2.1]heptanyl. In some embodiments, $R_{4b}$ is heteroaryl. In certain embodiments, the heteroaryl is selected from pyridinyl, pyrimidinyl, and pyrazolopyridinyl.

In certain embodiments, the heterocyclyl or heteroaryl is substituted with one or more substitutents selected from halo, alkyl, carbonyl, amido, amino, oxide and sulfoxide. in some embodiments, the heterocyclyl is substituted with one or more substitutents selected from F, Me, Et, COMe, $CONHMe$, $NH_2$, $—O^-$ (e.g., N-oxide), and $SO_2$.

In some embodiments, $R_5$ is alkyl. In some embodiments, $R_5$ is selected from H, Me and $CH_2CN$. In other embodiments, $R_{4b}$ and $R_5$ together with $A_1$ form a ring selected from azetidinyl, piperidinyl and pyrrolidinyl. In some embodiments, $R_6$ is selected from H, F, and Me. In some embodiments, n and m are each 1. In some embodiments, n is 0 and m is 1. In some embodiments, n and m are each 0. In certain embodiments, x is 0.

In various embodiments, the present invention provides a compound of Formula I:

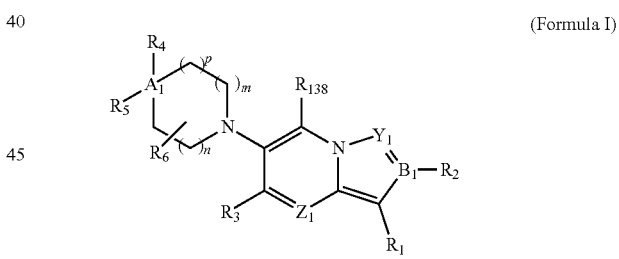

(Formula I)

or a pharmaceutically acceptable salt, ester or prodrug thereof,
wherein:
$R_1$ is hydrogen or an optionally substituted substituent;
$R_2$ is optionally absent, or hydrogen or an optionally substituted substituent;
$R_3$ is hydrogen or an optionally substituted substituent;
$R_4$ is optionally absent, hydrogen, or an optionally substituted substituent;
$R_5$ is optionally absent, hydrogen, or an optionally substituted substituent;
$R_{138}$ is hydrogen, or an optionally substituted substituent;
$R_6$ is independently one or more of hydrogen or an optionally substituted substituent;
$B_1$ is C or N;
$Y_1$ is N or $CR_{139}$, where $R_{139}$ is hydrogen or an optionally substituted substituent;

$Z_1$ is N or $CR_{140}$, where $R_{140}$ is hydrogen or an optionally substituted substituent;

$A_1$ is C, N, O, C(O), S, SO, or $SO_2$;

m is 0, 1, 2, or 3;

n is 0, 1, 2, or 3; and p is 0 or 1;

wherein optionally any two or more of $R_4$, $R_5$, or $R_6$ may be joined together to form one or more rings. In some embodiments, $R_6$ is independently one or more of hydrogen, oxo, or an optionally substituted substituent.

In various embodiments, the present invention provides a compound of Formula I:

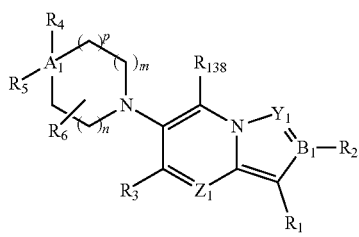

(Formula I)

or a pharmaceutically acceptable salt, ester or prodrug thereof, wherein:

$R_1$ is hydrogen or an optionally substituted substituent;

$R_2$ is optionally absent, or hydrogen or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_{138}$ is hydrogen, or an optionally substituted substituent;

$R_6$ is independently one or more of hydrogen or an optionally substituted substituent;

$B_1$ is C or N;

$Y_1$ is N or $CR_{139}$, where $R_{139}$ is hydrogen or an optionally substituted substituent;

$Z_1$ is N or $CR_{140}$, where $R_{140}$ is hydrogen or an optionally substituted substituent;

$A_1$ is C, N, O, C(O), S, SO, or $SO_2$;

m is 0, 1, 2, or 3;

n is 0, 1, 2, or 3; and p is 0 or 1;

wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; $R_2$ is optionally absent when $B_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent.

In various embodiments, the present invention provides a compound of Formula I:

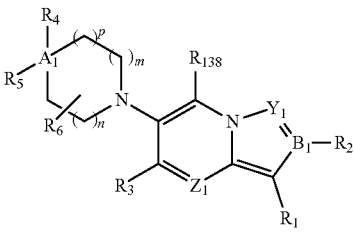

(Formula I)

wherein:

$R_1$ is hydrogen or an optionally substituted substituent;

$R_2$ is optionally absent, or hydrogen or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_{138}$ is hydrogen, or an optionally substituted substituent;

$R_6$ is independently one or more of hydrogen or an optionally substituted substituent;

$B_1$ is C or N;

$Y_1$ is N or $CR_{139}$, where $R_{139}$ is hydrogen or an optionally substituted substituent;

$Z_1$ is N or $CR_{140}$, where $R_{140}$ is hydrogen or an optionally substituted substituent;

$A_1$ is C, N, O, C(O), S, SO, or $SO_2$;

m is 0, 1, 2, or 3;

n is 0, 1, 2, or 3; and p is 0 or 1;

wherein optionally any two or more of $R_4$, $R_5$, or $R_6$ may be joined together to form one or more rings. In some embodiments, $R_6$ is independently one or more of hydrogen, oxo, or an optionally substituted substituent.

In various embodiments, the present invention provides a compound of Formula I:

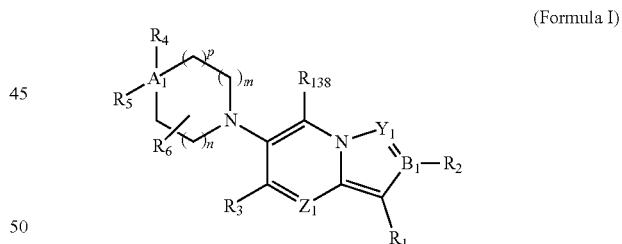

(Formula I)

wherein:

$R_1$ is hydrogen or an optionally substituted substituent;

$R_2$ is optionally absent, or hydrogen or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_{138}$ is hydrogen, or an optionally substituted substituent;

$R_6$ is independently one or more of hydrogen or an optionally substituted substituent;

$B_1$ is C or N;

$Y_1$ is N or $CR_{139}$, where $R_{139}$ is hydrogen or an optionally substituted substituent;

$Z_1$ is N or $CR_{140}$, where $R_{140}$ is hydrogen or an optionally substituted substituent;

$A_1$ is C, N, O, C(O), S, SO, or $SO_2$;

m is 0, 1, 2, or 3;

n is 0, 1, 2, or 3; and p is 0 or 1;

wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; $R_2$ is optionally absent when $B_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent In some embodiments, a provided compound of Formula I has a structure of Formula I-a:

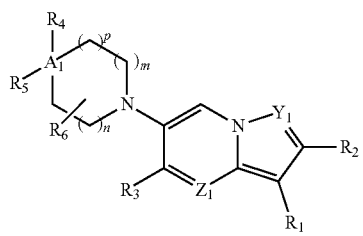

(Formula I-a)

or a pharmaceutically acceptable salt, ester or prodrug thereof, wherein:

$R_1$ is hydrogen or an optionally substituted substituent;

$R_2$ is hydrogen or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_6$ is independently one or more of hydrogen or an optionally substituted substituent;

$Y_1$ is CH or N;

$Z_1$ is CH or N;

$A_1$ is C, N, O, C(O), S, SO, or $SO_2$;

m is 0, 1, 2, or 3;

n is 0, 1, 2, or 3; and p is 0 or 1;

wherein optionally any two or more of $R_4$, $R_5$, or $R_6$ may be joined together to form one or more rings. In some embodiments, $R_6$ is independently one or more of hydrogen, oxo, or an optionally substituted substituent.

In some embodiments, a provided compound of Formula I has a structure of Formula I-a:

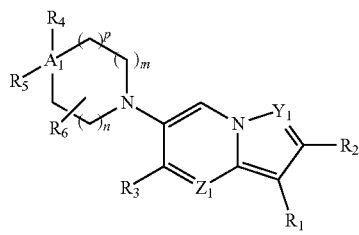

(Formula I-a)

or a pharmaceutically acceptable salt, ester or prodrug thereof, wherein:

$R_1$ is hydrogen or an optionally substituted substituent;

$R_2$ is hydrogen or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_6$ is independently one or more of hydrogen or an optionally substituted substituent;

$Y_1$ is CH or N;

$Z_1$ is CH or N;

$A_1$ is C, N, O, C(O), S, SO, or $SO_2$;

m is 0, 1, 2, or 3;

n is 0, 1, 2, or 3; and p is 0 or 1;

wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent In some embodiments, a provided compound of Formula I has a structure of Formula I-a:

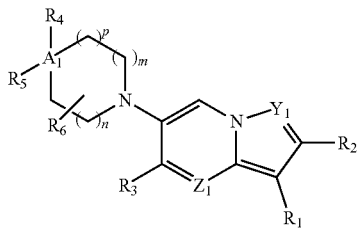

(Formula I-a)

or a pharmaceutically acceptable salt, ester or prodrug thereof, wherein:

$R_1$ is hydrogen or an optionally substituted substituent;

$R_2$ is hydrogen or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_6$ is independently one or more of hydrogen or an optionally substituted substituent;

$Y_1$ is N;

$Z_1$ is N;

$A_1$ is C, N, O, C(O), S, SO, or $SO_2$;

m is 0, 1, 2, or 3;

n is 0, 1, 2, or 3; and p is 0 or 1;

wherein optionally any two or more of $R_4$, $R_5$, or $R_6$ may be joined together to form one or more rings. In some embodiments, $R_6$ is independently one or more of hydrogen, oxo, or an optionally substituted substituent In some embodiments, a provided compound of Formula I has a structure of Formula I-a:

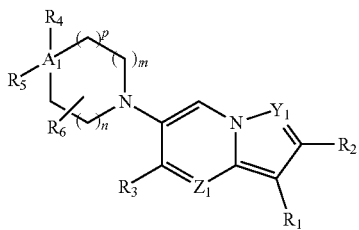

(Formula I-a)

or a pharmaceutically acceptable salt, ester or prodrug thereof,
wherein:
$R_1$ is hydrogen or an optionally substituted substituent;
$R_2$ is hydrogen or an optionally substituted substituent;
$R_3$ is hydrogen or an optionally substituted substituent;
$R_4$ is optionally absent, hydrogen, or an optionally substituted substituent;
$R_5$ is optionally absent, hydrogen, or an optionally substituted substituent;
$R_6$ is independently one or more of hydrogen or an optionally substituted substituent;
$Y_1$ is N;
$Z_1$ is N;
$A_1$ is C, N, O, C(O), S, SO, or $SO_2$;
m is 0, 1, 2, or 3;
n is 0, 1, 2, or 3; and
p is 0 or 1;
wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent.

In some embodiments, a provided compound of Formula I has a structure of Formula I-a:

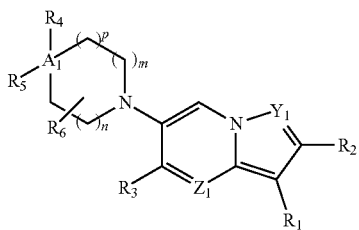

(Formula I-a)

or a pharmaceutically acceptable salt, ester or prodrug thereof,
wherein:
$R_1$ is hydrogen, halogen, aryl, or heteroaryl, wherein aryl or heteroaryl can be optionally substituted;
$R_2$ is hydrogen or a substituent selected from hydroxyl, alkoxy, amino, amido, carbamoyl, ureido, and sulfonamide, wherein each substituent can be optionally substituted;
$R_3$ is hydrogen, alkyl, substituted alkyl, or a substituent selected from hydroxyl, alkoxy, amino, thiol, alkylthio, arylthio, and carbonyl, wherein each substituent can be optionally substituted;
$R_4$ is optionally absent, hydrogen, cyclyl, heterocyclyl, aryl, or heteroaryl, wherein cyclyl, heterocyclyl, aryl, or heteroaryl can be optionally substituted;
$R_5$ is optionally absent, hydrogen, or an optionally substituted substituent;
$R_6$ is independently one or more of hydrogen or an optionally substituted substituent;
$Y_1$ is CH or N;
$Z_1$ is CH or N;
$A_1$ is C, N, O, C(O), S, SO, or $SO_2$;
m is 0, 1, 2, or 3;
n is 0, 1, 2, or 3; and
p is 0 or 1;
wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent In some embodiments, a provided compound of Formula I has a structure of Formula I-a:

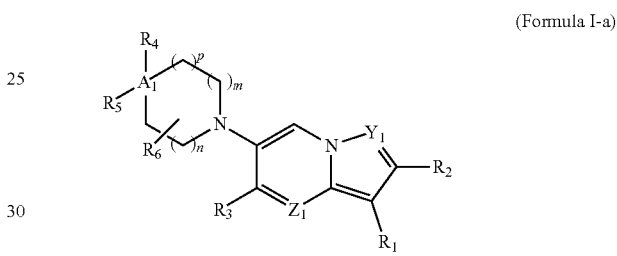

(Formula I-a)

or a pharmaceutically acceptable salt, ester or prodrug thereof,
wherein:
$R_1$ is hydrogen, halogen, aryl, or heteroaryl, wherein aryl or heteroaryl can be optionally substituted;
$R_2$ is hydrogen or a substituent selected from hydroxyl, alkoxy, amino, amido, carbamoyl, ureido, and sulfonamide, wherein each substituent can be optionally substituted;
$R_3$ is hydrogen, alkyl, substituted alkyl, or a substituent selected from hydroxyl, alkoxy, amino, thiol, alkylthio, arylthio, and carbonyl, wherein each substituent can be optionally substituted;
$R_4$ is optionally absent, hydrogen, cyclyl, heterocyclyl, aryl, or heteroaryl, wherein cyclyl, heterocyclyl, aryl, or heteroaryl can be optionally substituted;
$R_5$ is optionally absent, hydrogen, or an optionally substituted substituent;
$R_6$ is independently one or more of hydrogen or an optionally substituted substituent;
$Y_1$ is N;
$Z_1$ is N;
$A_1$ is C, N, O, C(O), S, SO, or $SO_2$;
m is 0, 1, 2, or 3;
n is 0, 1, 2, or 3; and
p is 0 or 1;
wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent In some embodiments, a provided compound of Formula I has a structure of Formula I-a:

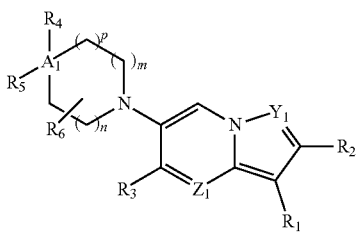

(Formula I-a)

wherein:
R$_1$ is hydrogen or an optionally substituted substituent;
R$_2$ is hydrogen or an optionally substituted substituent;
R$_3$ is hydrogen or an optionally substituted substituent;
R$_4$ is optionally absent, hydrogen, or an optionally substituted substituent;
R$_5$ is optionally absent, hydrogen, or an optionally substituted substituent;
R$_6$ is independently one or more of hydrogen or an optionally substituted substituent;
Y$_1$ is CH or N;
Z$_1$ is CH or N;
A$_1$ is C, N, O, C(O), S, SO, or SO$_2$;
m is 0, 1, 2, or 3;
n is 0, 1, 2, or 3; and
p is 0 or 1;
wherein R$_4$ and R$_5$ are absent when A$_1$ is O, C(O) or SO$_2$; one or both of R$_4$ or R$_5$ is optionally absent when A$_1$ is SO or S; one of R$_4$ or R$_5$ is optionally absent when A$_1$ is N; and/or optionally any two or more of R$_4$, R$_5$, or R$_6$ may be joined together to form one or more rings. In some embodiments, R$_6$ is independently one or more of hydrogen, oxo, or an optionally substituted substituent.

In some embodiments, a provided compound of Formula I has a structure of Formula I-a:

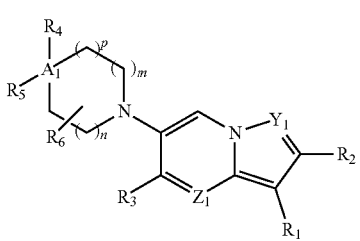

(Formula I-a)

wherein:
R$_1$ is hydrogen or an optionally substituted substituent;
R$_2$ is hydrogen or an optionally substituted substituent;
R$_3$ is hydrogen or an optionally substituted substituent;
R$_4$ is optionally absent, hydrogen, or an optionally substituted substituent;
R$_5$ is optionally absent, hydrogen, or an optionally substituted substituent;
R$_6$ is independently one or more of hydrogen or an optionally substituted substituent;
Y$_1$ is N;
Z$_1$ is N;
A$_1$ is C, N, O, C(O), S, SO, or SO$_2$;
m is 0, 1, 2, or 3;
n is 0, 1, 2, or 3; and
p is 0 or 1;
wherein R$_4$ and R$_5$ are absent when A$_1$ is O, C(O) or SO$_2$; one or both of R$_4$ or R$_5$ is optionally absent when A$_1$ is SO or S; one of R$_4$ or R$_5$ is optionally absent when A$_1$ is N; and/or optionally any two or more of R$_4$, R$_5$, or R$_6$ may be joined together to form one or more rings. In some embodiments, R$_6$ is independently one or more of hydrogen, oxo, or an optionally substituted substituent.

In some embodiments, a provided compound of Formula I has a structure of Formula I-a:

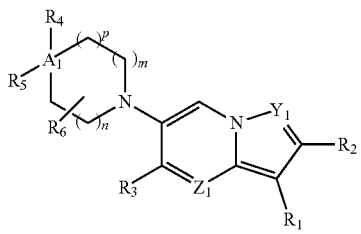

(Formula I-a)

wherein:
R$_1$ is hydrogen, halogen, aryl, or heteroaryl, wherein aryl or heteroaryl can be optionally substituted;
R$_2$ is hydrogen or a substitutent selected from hydroxyl, alkoxy, amino, amido, carbamoyl, ureido, and sulfonamide, wherein each substituent can be optionally substituted;
R$_3$ is hydrogen, alkyl, substituted alkyl, or a substituent selected from hydroxyl, alkoxy, amino, thiol, alkylthio, arylthio, and carbonyl, wherein each substituent can be optionally substituted;
R$_4$ is optionally absent, hydrogen, cyclyl, heterocyclyl, aryl, or heteroaryl, wherein cyclyl, heterocyclyl, aryl, or heteroaryl can be optionally substituted;
R$_5$ is optionally absent, hydrogen, or an optionally substituted substituent;
R$_6$ is independently one or more of hydrogen or an optionally substituted substituent;
Y$_1$ is CH or N;
Z$_1$ is CH or N;
A$_1$ is C, N, O, C(O), S, SO, or SO$_2$;
m is 0, 1, 2, or 3;
n is 0, 1, 2, or 3; and
p is 0 or 1;
wherein R$_4$ and R$_5$ are absent when A$_1$ is O, C(O) or SO$_2$; one or both of R$_4$ or R$_5$ is optionally absent when A$_1$ is SO or S; one of R$_4$ or R$_5$ is optionally absent when A$_1$ is N; and/or optionally any two or more of R$_4$, R$_5$, or R$_6$ may be joined together to form one or more rings. In some embodiments, R$_6$ is independently one or more of hydrogen, oxo, or an optionally substituted substituent In some embodiments, a provided compound of Formula I has a structure of Formula I-a:

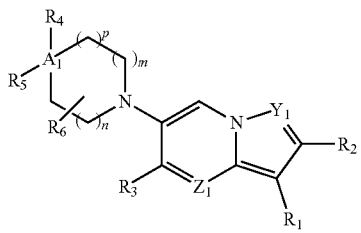

(Formula I-a)

wherein:

$R_1$ is hydrogen, halogen, aryl, or heteroaryl, wherein aryl or heteroaryl can be optionally substituted;

$R_2$ is hydrogen or a substitutent selected from hydroxyl, alkoxy, amino, amido, carbamoyl, ureido, and sulfonamide, wherein each substituent can be optionally substituted;

$R_3$ is hydrogen, alkyl, substituted alkyl, or a substituent selected from hydroxyl, alkoxy, amino, thiol, alkylthio, arylthio, and carbonyl, wherein each substituent can be optionally substituted;

$R_4$ is optionally absent, hydrogen, cyclyl, heterocyclyl, aryl, or heteroaryl, wherein cyclyl, heterocyclyl, aryl, or heteroaryl can be optionally substituted;

$R_5$ is optionally absent, hydrogen, or an optionally substituted substituent;

$R_6$ is independently one or more of hydrogen or an optionally substituted substituent;

$Y_1$ is N;

$Z_1$ is N;

$A_1$ is C, N, O, C(O), S, SO, or $SO_2$;

m is 0, 1, 2, or 3;

n is 0, 1, 2, or 3; and p is 0 or 1;

wherein $R_4$ and $R_5$ are absent when $A_1$ is O, C(O) or $SO_2$; one or both of $R_4$ or $R_5$ is optionally absent when $A_1$ is SO or S; one of $R_4$ or $R_5$ is optionally absent when $A_1$ is N; and/or optionally any two or more of $R_4$, $R_5$, or $R_6$ may be joined together to form one or more rings. In some embodiments, $R_6$ is independently one or more of hydrogen, oxo, or an optionally substituted substituent.

In some embodiments of compounds of Formula I or Formula I-a, $R_4$ is

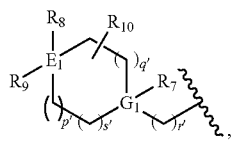

wherein:

$E_1$ is C, N, S, O, C(O), SO, or $SO_2$;

$G_1$ is C or N;

$R_7$ is optionally absent, hydrogen, or an optionally substituted substituent;

$R_8$ is optionally absent, hydrogen, or an optionally substituted substituent;

$R_9$ is optionally absent, hydrogen, or an optionally substituted substituent;

$R_{10}$ is independently one or more of hydrogen or an optionally substituted substituent;

p' is 0, 1, 2, or 3;

q' is 0, 1, 2, or 3;

r' is 0, 1, 2, or 3; and s' is 0 or 1;

wherein optionally any two or more of $R_7$, $R_8$, $R_9$, or $R_{10}$ may be joined together to form one or more rings.

In some embodiments of compounds of Formula I or Formula I-a, $R_4$ is

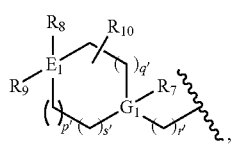

wherein:

$E_1$ is C, N, S, O, C(O), SO, or $SO_2$;

$G_1$ is C or N;

$R_7$ is optionally absent, hydrogen, or an optionally substituted substituent;

$R_8$ is optionally absent, hydrogen, or an optionally substituted substituent;

$R_9$ is optionally absent, hydrogen, or an optionally substituted substituent;

$R_{10}$ is independently one or more of hydrogen or an optionally substituted substituent;

p' is 0, 1, 2, or 3;

q' is 0, 1, 2, or 3;

r' is 0, 1, 2, or 3; and s' is 0 or 1;

wherein $R_8$ and $R_9$ are absent when $E_1$ is O, C(O), or $SO_2$; one or both of $R_8$ or $R_9$ is optionally absent when $E_1$ is SO or S; one of $R_8$ or $R_9$ is optionally absent when $E_1$ is N; $R_7$ is optionally absent when $G_1$ is N; and/or optionally any two or more of $R_7$, $R_8$, $R_9$, or $R_{10}$ may be joined together to form one or more rings.

In some embodiments of compounds of Formula I or Formula I-a, $R_4$ is

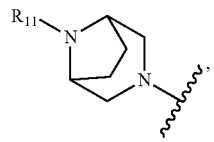

wherein:

$R_{11}$ is hydrogen or an optionally substituted substituent.

In some embodiments of compounds of Formula I or Formula I-a, $R_4$ is

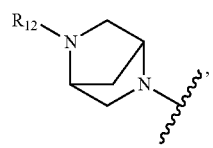

wherein:

$R_{12}$ is hydrogen or an optionally substituted substituent.

In some embodiments of compounds of Formula I or Formula I-a, $R_4$ is

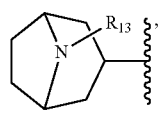

wherein:

$R_{13}$ is hydrogen or an optionally substituted substituent.

In some embodiments of compounds of Formula I or Formula I-a, R$_1$ is

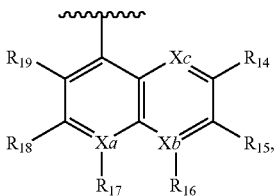

wherein:
Xa is C or N;
Xb is C or N;
Xc is CH or N;
R$_{14}$ is hydrogen or an optionally substituted substituent;
R$_{15}$ is hydrogen or an optionally substituted substituent;
R$_{16}$ is optionally absent, hydrogen, or an optionally substituted substituent;
R$_{17}$ is optionally absent, hydrogen, or an optionally substituted substituent;
R$_{18}$ is hydrogen or an optionally substituted substituent; and
R$_{19}$ is hydrogen or an optionally substituted substituent; wherein R$_{17}$ is optionally absent when Xa is N and/or R$_{16}$ is optionally absent when Xb is N.

In some embodiments of compounds of Formula I or Formula I-a, R$_1$ is

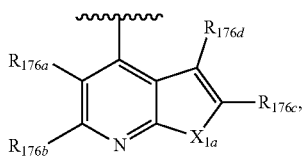

wherein,
X$_{1a}$ is O, S, or NR$_{198}$, where R$_{198}$ is hydrogen or C$_1$-C$_6$ alkyl;
R$_{176a}$ is hydrogen or an optionally substituted substituent;
R$_{176b}$ is hydrogen or an optionally substituted substituent;
R$_{176c}$ is hydrogen or an optionally substituted substituent; and
R$_{176d}$ is hydrogen or an optionally substituted substituent.

In some embodiments of compounds of Formula I or Formula I-a, R$_1$ is

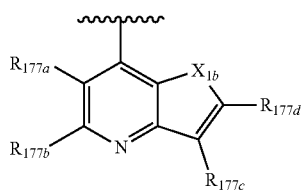

wherein,
X$_{1b}$ is O, S, or NR$_{199}$, where R$_{199}$ is hydrogen or C$_1$-C$_6$ alkyl;
R$_{177a}$ is hydrogen or an optionally substituted substituent;
R$_{177b}$ is hydrogen or an optionally substituted substituent;
R$_{177c}$ is hydrogen or an optionally substituted substituent; and
R$_{177d}$ is hydrogen or an optionally substituted substituent.

In some embodiments of compounds of Formula I or Formula I-a, R$_1$ is

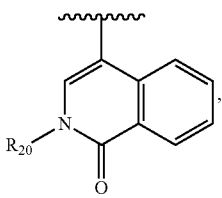

wherein:
R$_{20}$ is hydrogen, alkyl, or substituted alkyl.

In some embodiments of compounds of Formula I or Formula I-a, R$_1$ is:

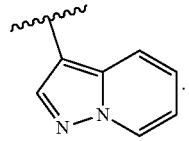 [SMILES: *c1cnn2ccccc12]

In some embodiments of compounds of Formula I or Formula I-a, R$_1$ is:

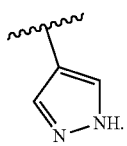 [SMILES: *c1cn[nH]c1]

In some embodiments of compounds of Formula I or Formula I-a, R$_1$ is Ar$_1$, wherein Ar$_1$ is optionally substituted aryl or optionally substituted heteroaryl.

In some embodiments, non-limiting examples of compounds of Formula I or Formula I-a are compounds 3-4, 7-34, 39-49, 51-58, 60-65, or 79-81, or 185-229:

| Compound ID | Compound Structure |
|---|---|
| 3 | 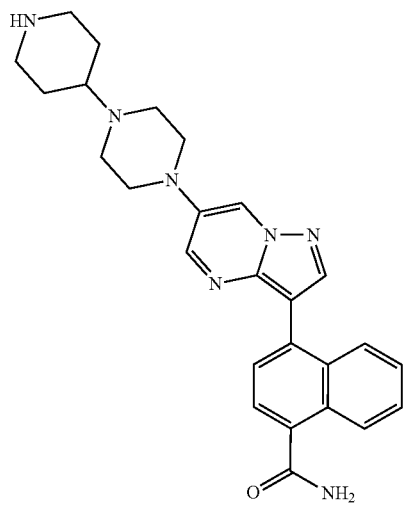 [SMILES: NC(=O)c1ccc(-c2cnn3cc(N4CCN(C5CCNCC5)CC4)cnc23)c2ccccc12] |
| 4 | 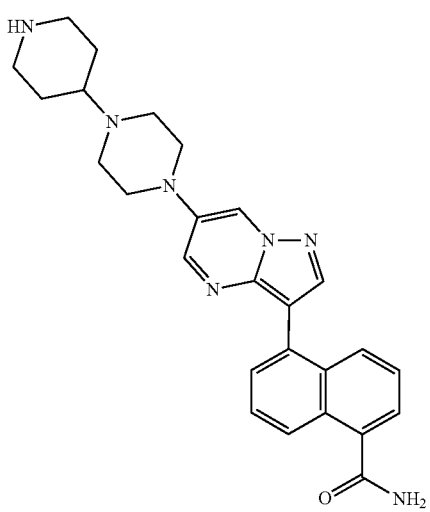 [SMILES: NC(=O)c1cccc2c(-c3cnn4cc(N5CCN(C6CCNCC6)CC5)cnc34)cccc12] |
| 7 | 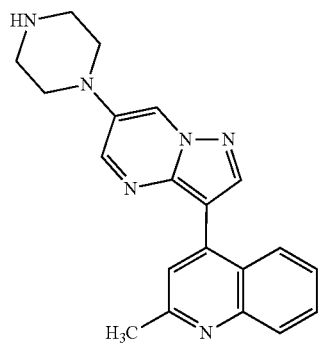 [SMILES: Cc1cc(-c2cnn3cc(N4CCNCC4)cnc23)c2ccccc2n1] |

-continued
| Compound ID | Compound Structure |
|---|---|
| 8 | 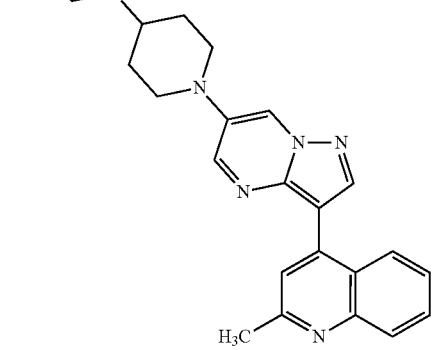 |
| 9 | 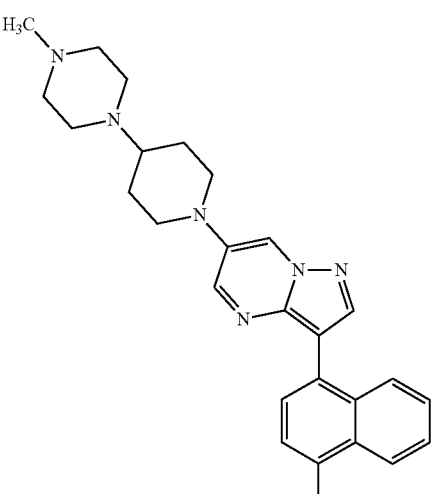 |
| 10 | 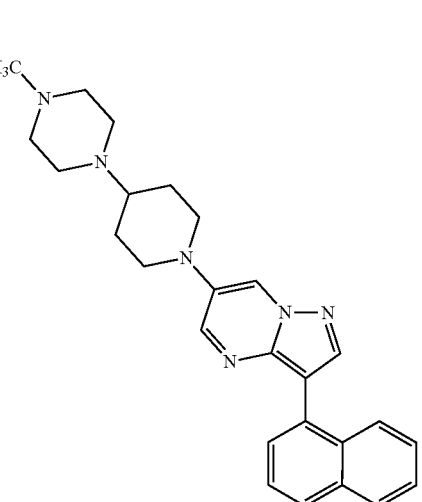 |

| Compound ID | Compound Structure |
|---|---|
| 11 | 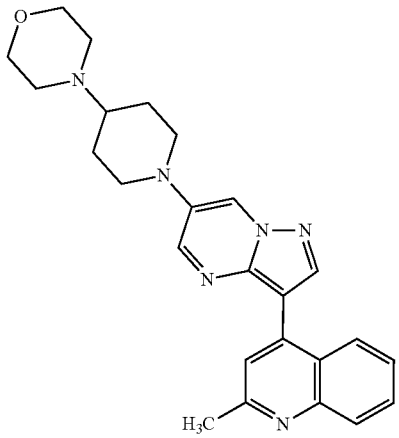 [SMILES: Cc1cc(-c2cnn3cc(N4CCC(N5CCOCC5)CC4)cnc23)c2ccccc2n1] |
| 12 | 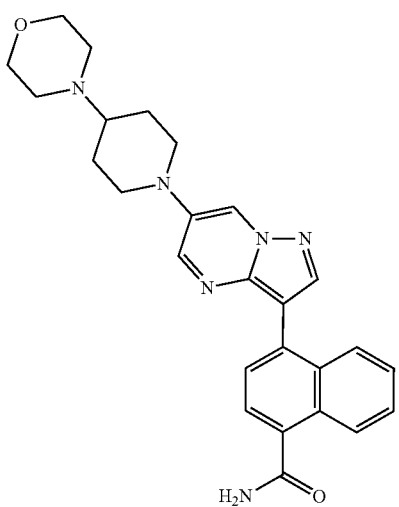 [SMILES: NC(=O)c1ccc(-c2cnn3cc(N4CCC(N5CCOCC5)CC4)cnc23)c2ccccc12] |
| 13 | 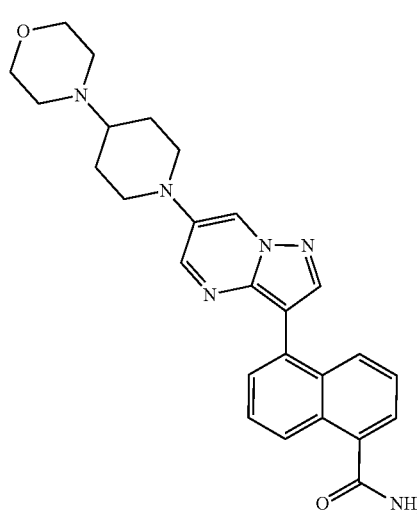 |

-continued
| Compound ID | Compound Structure |
|---|---|
| 14 | 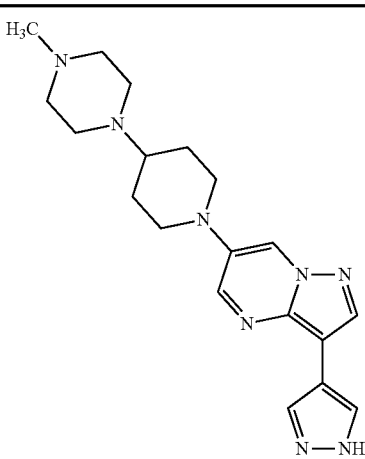 |
| 15 | 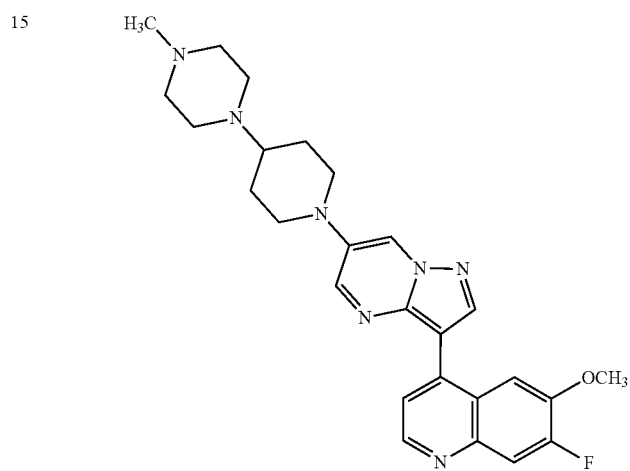 |
| 16 | 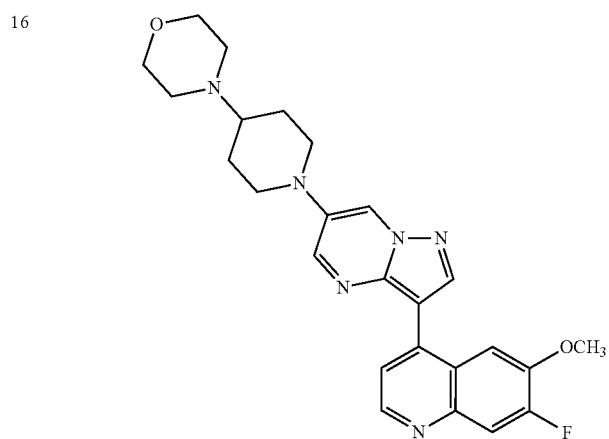 |

-continued
| Compound ID | Compound Structure |
|---|---|
| 17 | 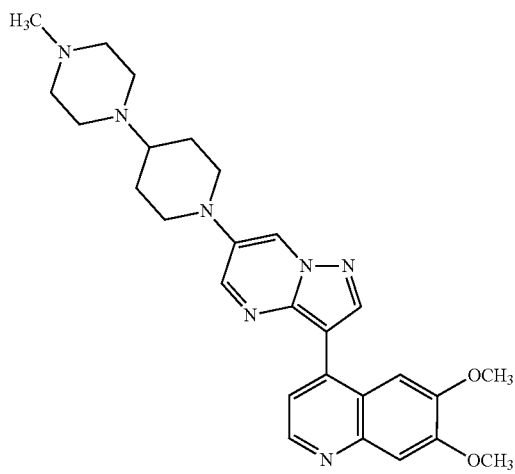 [SMILES: COc1cc2nccc(-c3cnn4cc(N5CCC(N6CCN(C)CC6)CC5)cnc34)c2cc1OC] |
| 18 | 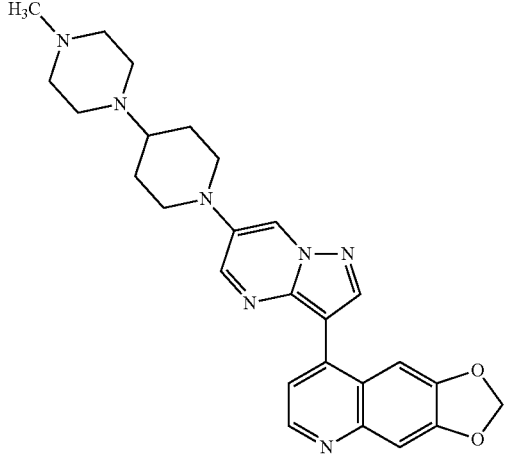 [SMILES: CN1CCN(C2CCN(c3cnc4c(-c5ccnc6cc7c(cc56)OCO7)cnn4c3)CC2)CC1] |
| 19 | 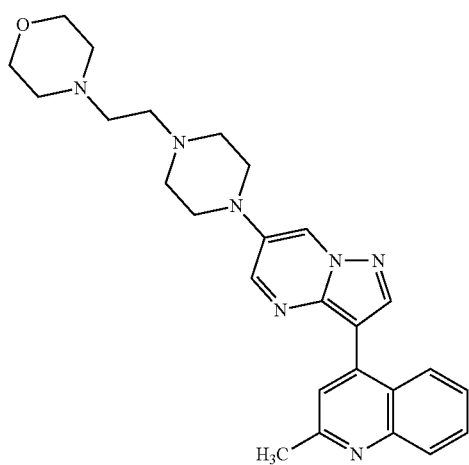 [SMILES: Cc1cc(-c2cnn3cc(N4CCN(CCN5CCOCC5)CC4)cnc23)c2ccccc2n1] |

-continued
| Compound ID | Compound Structure |
|---|---|
| 20 | 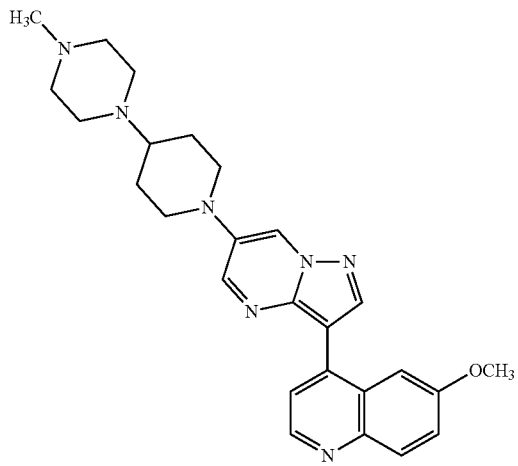 [SMILES: COc1ccc2nccc(-c3cnn4cc(N5CCC(N6CCN(C)CC6)CC5)cnc34)c2c1] |
| 21 | 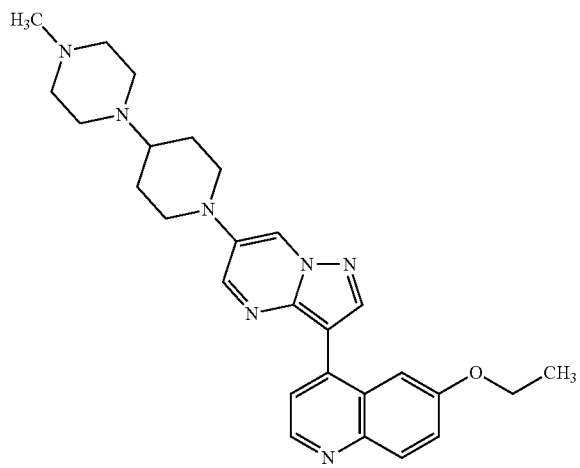 [SMILES: CCOc1ccc2nccc(-c3cnn4cc(N5CCC(N6CCN(C)CC6)CC5)cnc34)c2c1] |
| 22 | 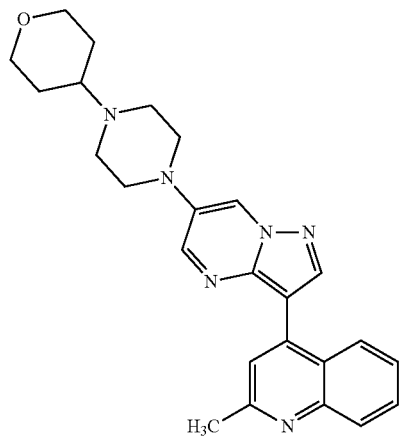 [SMILES: Cc1cc(-c2cnn3cc(N4CCN(C5CCOCC5)CC4)cnc23)c2ccccc2n1] |

-continued
| Compound ID | Compound Structure |
|---|---|
| 23 | 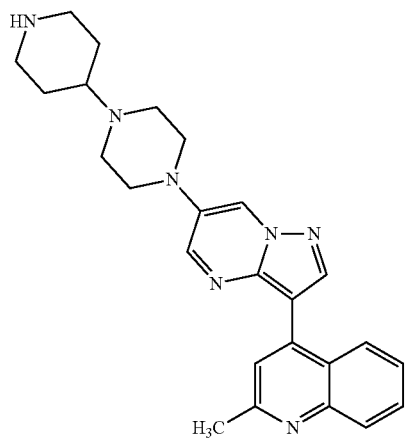 [SMILES: Cc1cc(-c2cnn3cc(N4CCN(C5CCNCC5)CC4)cnc23)c2ccccc2n1] |
| 24 | 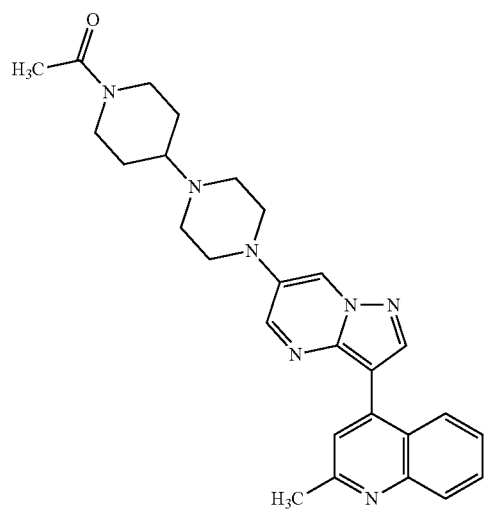 [SMILES: CC(=O)N1CCC(N2CCN(c3cnc4c(-c5cc(C)nc6ccccc56)cnn4c3)CC2)CC1] |
| 25 | 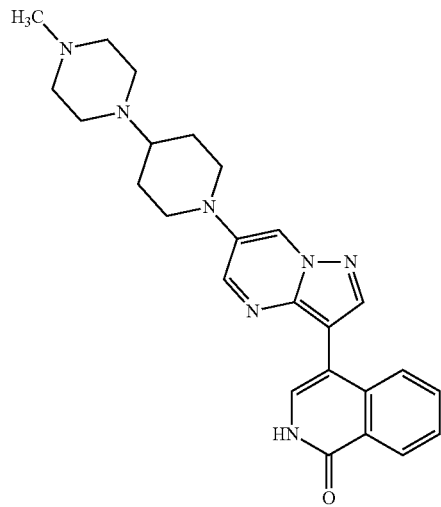 [SMILES: CN1CCN(C2CCN(c3cnc4c(-c5c[nH]c(=O)c6ccccc56)cnn4c3)CC2)CC1] |

-continued
| Compound ID | Compound Structure |
|---|---|
| 26 | 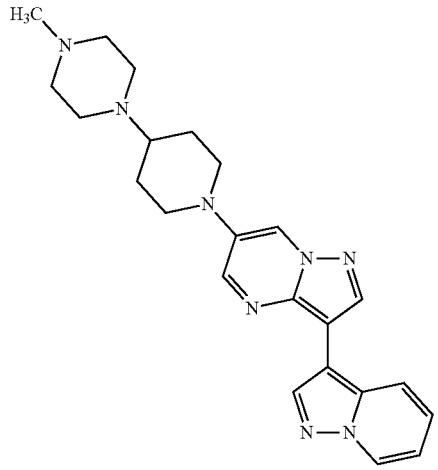 [SMILES: CN1CCN(C2CCN(c3cnc4c(-c5cnn6ccccc56)cnn4c3)CC2)CC1] |
| 27 | 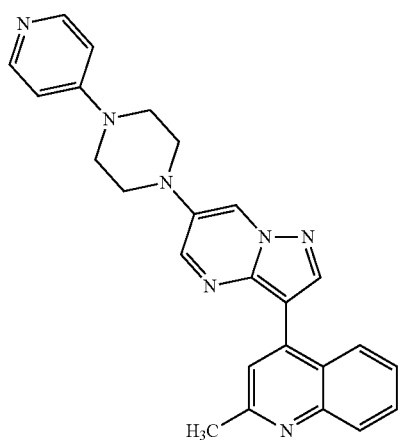 [SMILES: Cc1cc(-c2cnn3cc(N4CCN(c5ccncc5)CC4)cnc23)c2ccccc2n1] |
| 28 | 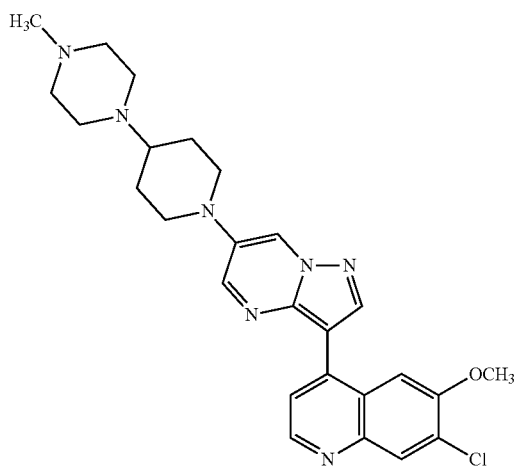 [SMILES: COc1cc2c(-c3cnn4cc(N5CCC(N6CCN(C)CC6)CC5)cnc34)ccnc2cc1Cl] |

| Compound ID | Compound Structure |
|---|---|
| 29 | (4-methylpiperazin-1-yl)-piperidinyl-pyrazolo[1,5-a]pyrimidine linked to 6-methoxy-7-methylquinolin-4-yl |
| 30 | morpholino-piperidinyl-pyrazolo[1,5-a]pyrimidine linked to 6-methoxyquinolin-4-yl |
| 31 | morpholino-piperidinyl-pyrazolo[1,5-a]pyrimidine linked to 6-methoxy-7-methylquinolin-4-yl |

-continued

| Compound ID | Compound Structure |
|---|---|
| 32 | 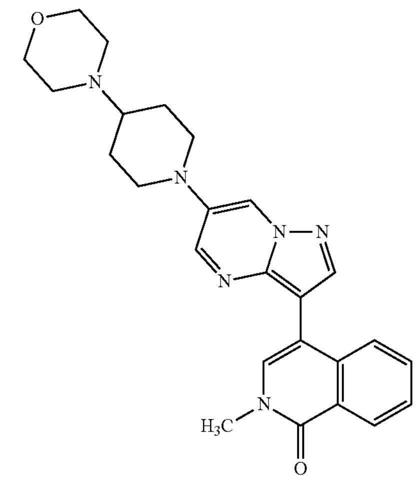 [SMILES: Cn1cc(-c2cnn3cc(N4CCC(N5CCOCC5)CC4)cnc23)c2ccccc2c1=O] |
| 33 | 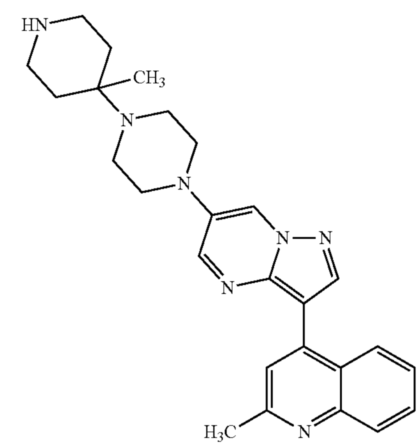 [SMILES: Cc1cc(-c2cnn3cc(N4CCN(C5(C)CCNCC5)CC4)cnc23)c2ccccc2n1] |
| 34 | 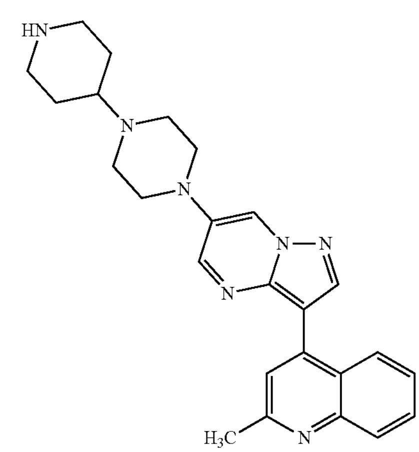 [SMILES: Cc1cc(-c2cnn3cc(N4CCN(C5CCNCC5)CC4)cnc23)c2ccccc2n1] |

-continued
| Compound ID | Compound Structure |
|---|---|
| 39 | 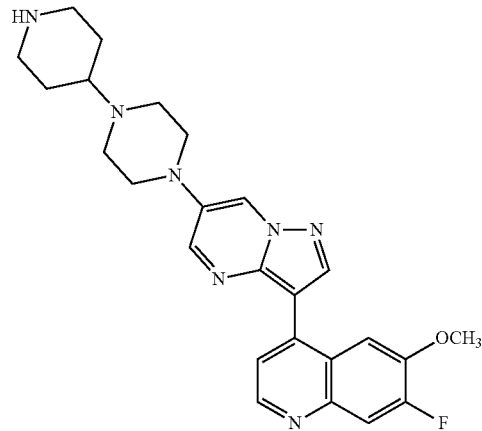 [SMILES: COc1cc2c(-c3cnn4cc(N5CCN(C6CCNCC6)CC5)cnc34)ccnc2cc1F] |
| 40 | 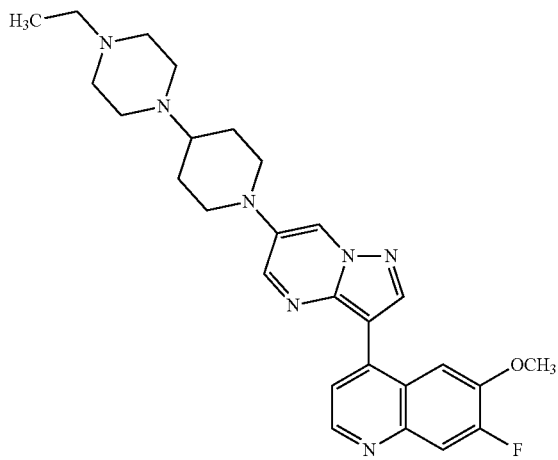 [SMILES: CCN1CCN(C2CCN(c3cnc4c(-c5ccnc6cc(F)c(OC)cc56)cnn4c3)CC2)CC1] |
| 41 | 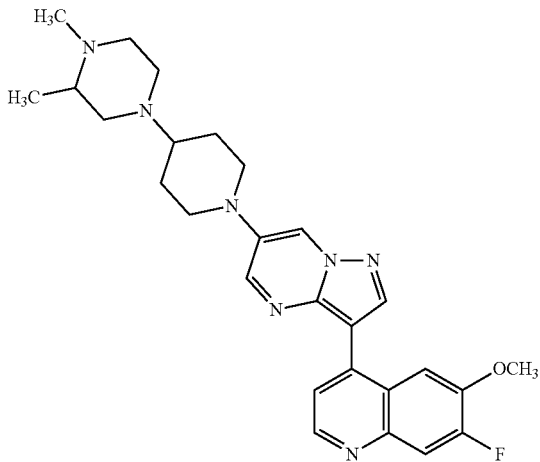 [SMILES: COc1cc2c(-c3cnn4cc(N5CCC(N6CCN(C)C(C)C6)CC5)cnc34)ccnc2cc1F] |

-continued
| Compound ID | Compound Structure |
|---|---|
| 42 | 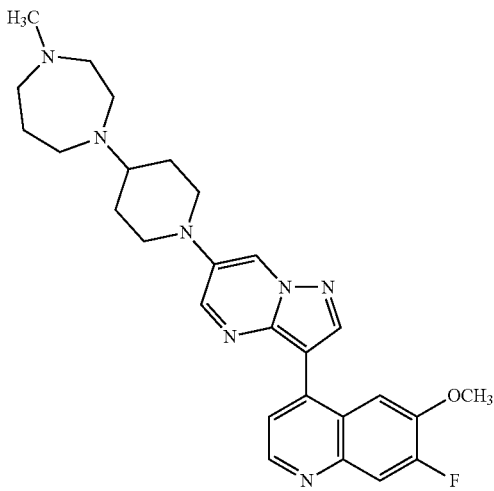 [SMILES: COc1cc2c(-c3cnn4cc(N5CCC(N6CCCN(C)CC6)CC5)cnc34)ccnc2cc1F] |
| 43 | 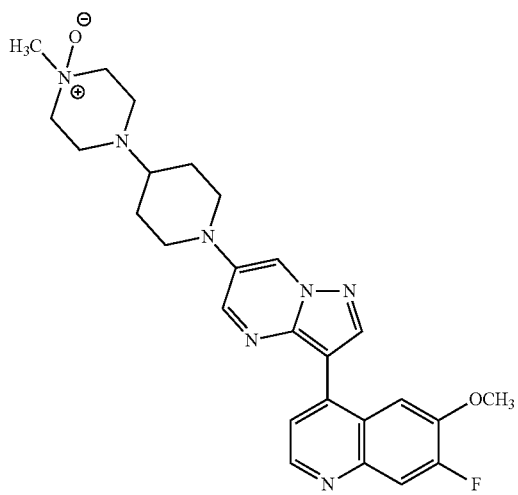 [SMILES: COc1cc2c(-c3cnn4cc(N5CCC(N6CC[N+](C)([O-])CC6)CC5)cnc34)ccnc2cc1F] |
| 44 | 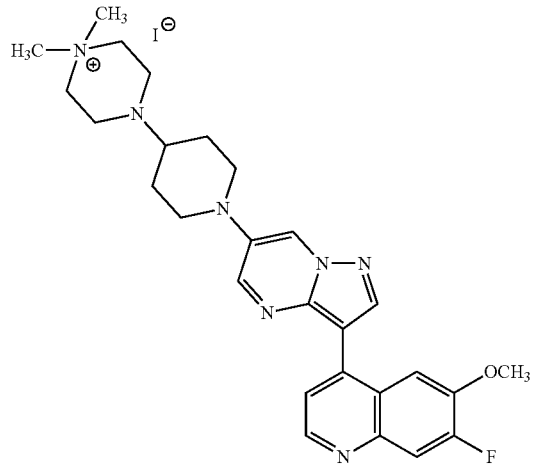 [SMILES: COc1cc2c(-c3cnn4cc(N5CCC(N6CC[N+](C)(C)CC6)CC5)cnc34)ccnc2cc1F ; [I-]] |

-continued
| Compound ID | Compound Structure |
|---|---|
| 45 | 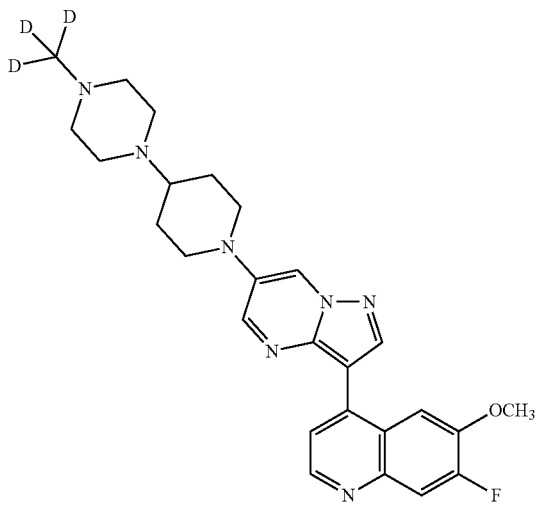 [SMILES: [2H]C([2H])([2H])N1CCN(C2CCN(c3cnc4c(-c5ccnc6cc(F)c(OC)cc56)cnn4c3)CC2)CC1] |
| 46 | 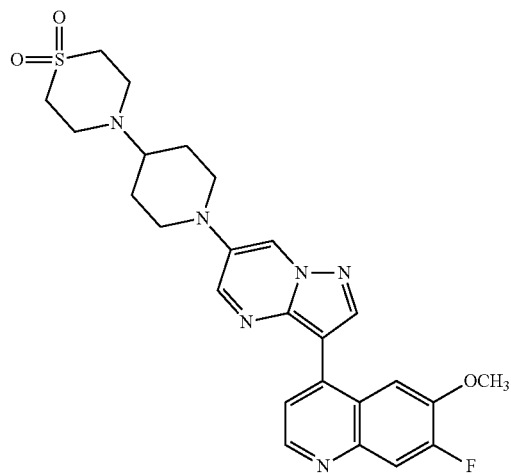 [SMILES: COc1cc2c(-c3cnn4cc(N5CCC(N6CCS(=O)(=O)CC6)CC5)cnc34)ccnc2cc1F] |
| 47 | 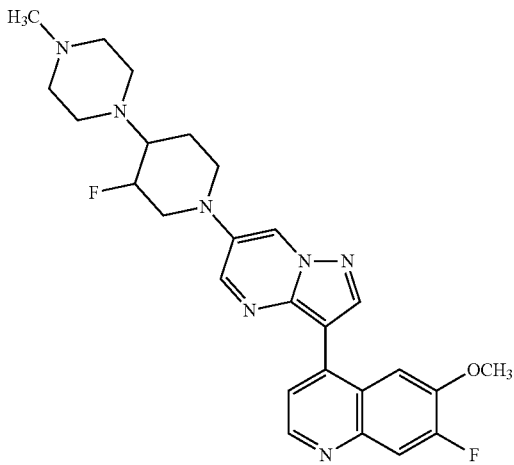 [SMILES: COc1cc2c(-c3cnn4cc(N5CCC(N6CCN(C)CC6)C(F)C5)cnc34)ccnc2cc1F] |

-continued
| Compound ID | Compound Structure |
|---|---|
| 48 | 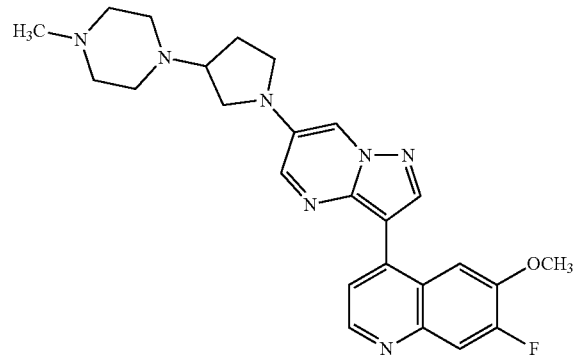 [SMILES: COc1cc2c(-c3cnn4cc(N5CCC(N6CCN(C)CC6)C5)cnc34)ccnc2cc1F] |
| 49 | 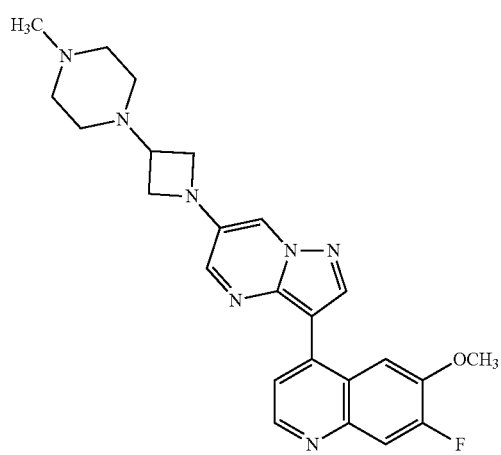 [SMILES: COc1cc2c(-c3cnn4cc(N5CC(N6CCN(C)CC6)C5)cnc34)ccnc2cc1F] |
| 51 | 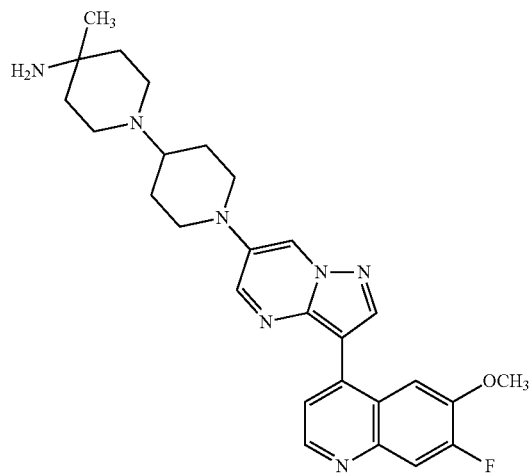 [SMILES: COc1cc2c(-c3cnn4cc(N5CCC(N6CCC(C)(N)CC6)CC5)cnc34)ccnc2cc1F] |

-continued
| Compound ID | Compound Structure |
|---|---|
| 52 | 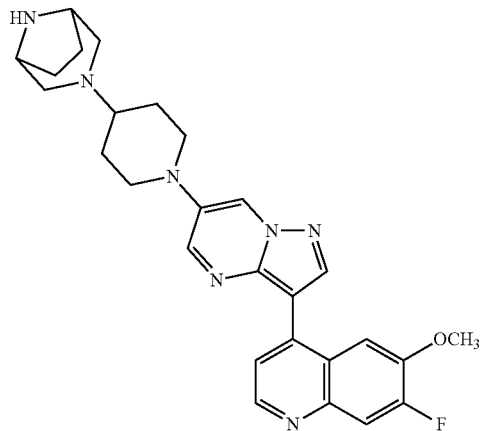 [SMILES: COc1cc2c(-c3cnn4cc(N5CCC(N6CC7CCC(C6)N7)CC5)cnc34)ccnc2cc1F] |
| 53 | 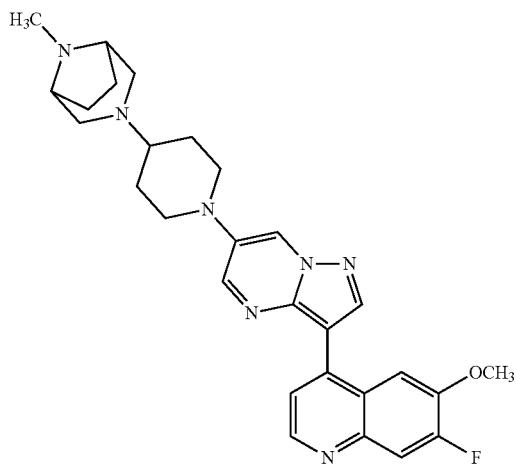 [SMILES: COc1cc2c(-c3cnn4cc(N5CCC(N6CC7CCC(C6)N7C)CC5)cnc34)ccnc2cc1F] |
| 54 | 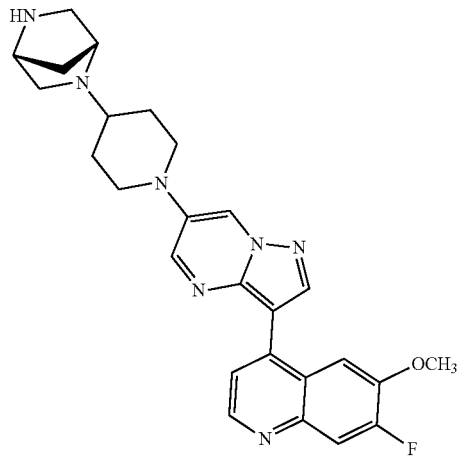 [SMILES: COc1cc2c(-c3cnn4cc(N5CCC(N6C[C@H]7C[C@@H]6CN7)CC5)cnc34)ccnc2cc1F] |

-continued

| Compound ID | Compound Structure |
| --- | --- |
| 55 | 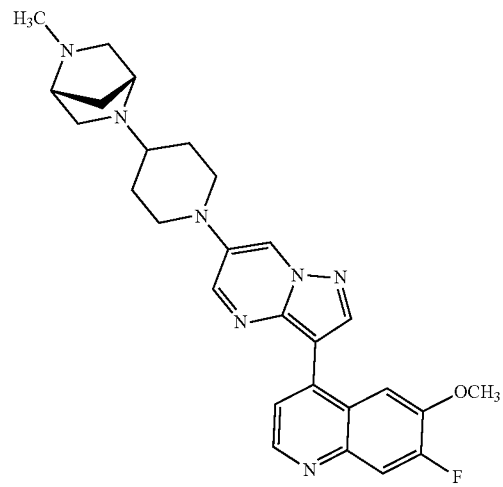 [SMILES: COc1cc2c(-c3cnn4cc(N5CCC(N6C[C@H]7C[C@@H]6CN7C)CC5)cnc34)ccnc2cc1F] |
| 56 | 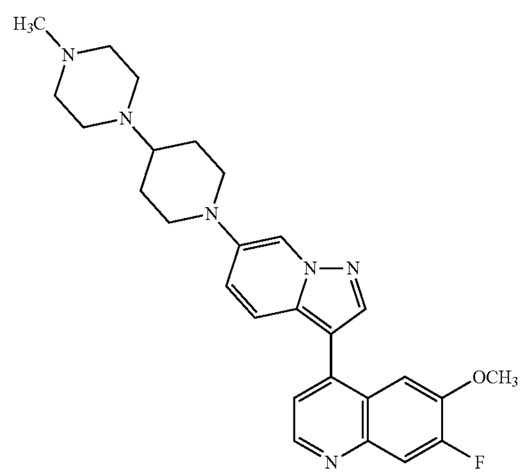 [SMILES: COc1cc2c(-c3cnn4cc(N5CCC(N6CCN(C)CC6)CC5)ccc34)ccnc2cc1F] |
| 57 | 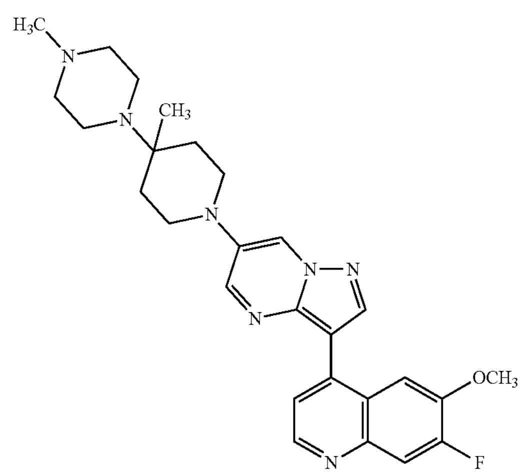 [SMILES: COc1cc2c(-c3cnn4cc(N5CCC(C)(N6CCN(C)CC6)CC5)cnc34)ccnc2cc1F] |

| Compound ID | Compound Structure |
|---|---|
| 58 | 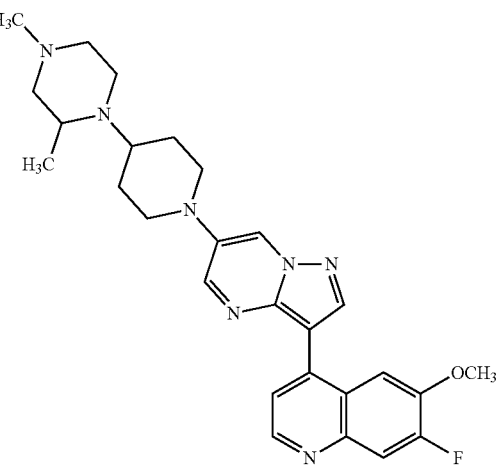 |
| 60 | 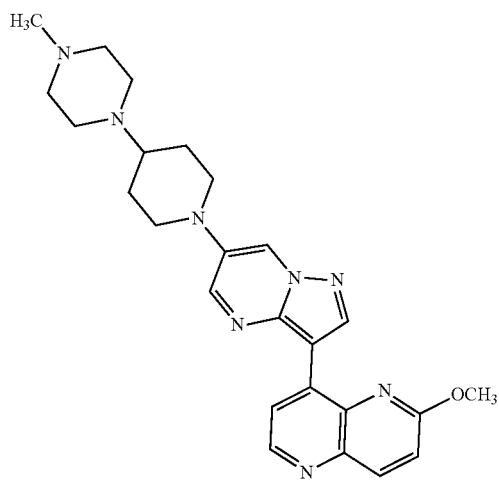 [SMILES: COc1ccc2nccc(-c3cnn4cc(N5CCC(N6CCN(C)CC6)CC5)cnc34)c2n1] |
| 61 | 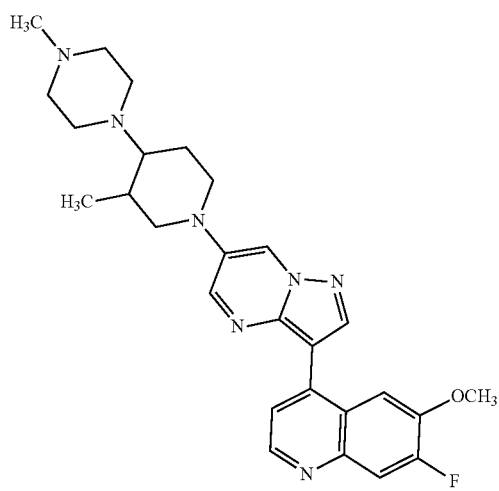 [SMILES: COc1cc2c(-c3cnn4cc(N5CCC(N6CCN(C)CC6)C(C)C5)cnc34)ccnc2cc1F] |

-continued
| Compound ID | Compound Structure |
|---|---|
| 62 | 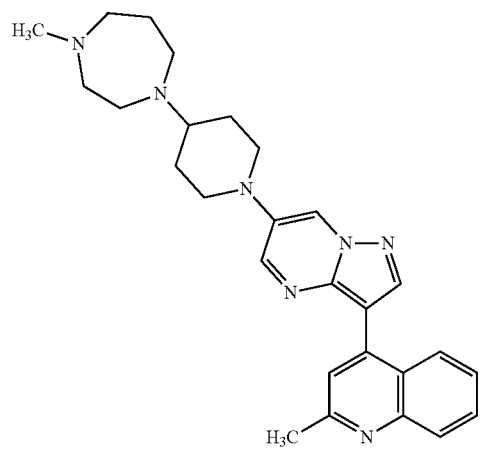 [SMILES: Cc1cc(-c2cnn3cc(N4CCC(N5CCCN(C)CC5)CC4)cnc23)c2ccccc2n1] |
| 63 | 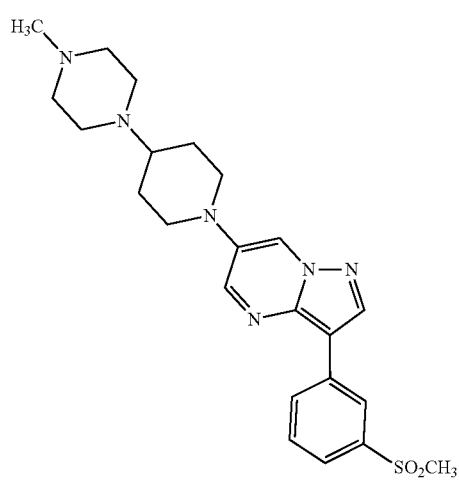 [SMILES: CN1CCN(C2CCN(c3cnc4c(-c5cccc(S(C)(=O)=O)c5)cnn4c3)CC2)CC1] |
| 64 | 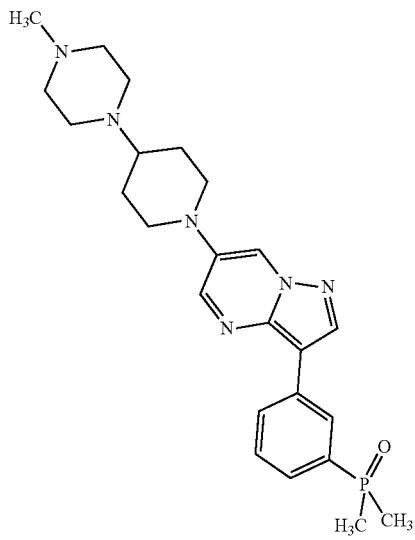 |

-continued
| Compound ID | Compound Structure |
| --- | --- |
| 65 | 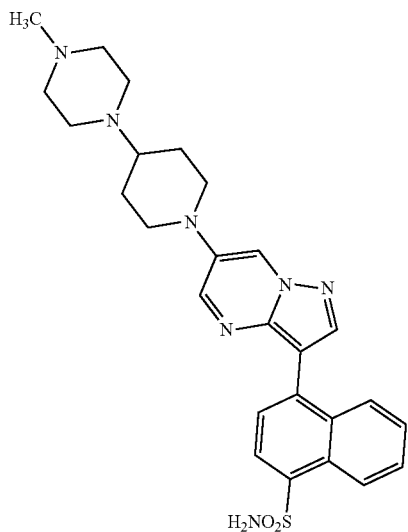 [SMILES: CN1CCN(C2CCN(c3cnc4c(-c5ccc(S(N)(=O)=O)c6ccccc56)cnn4c3)CC2)CC1] |
| 79 | 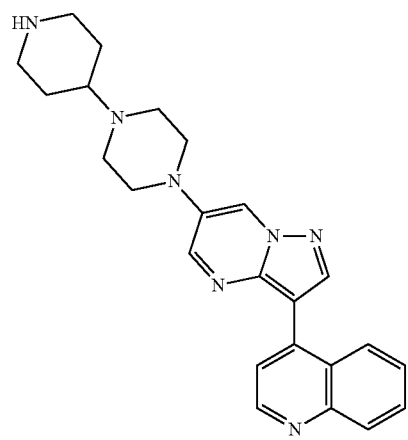 [SMILES: c1ccc2c(-c3cnn4cc(N5CCN(C6CCNCC6)CC5)cnc34)ccnc2c1] |
| 80 | 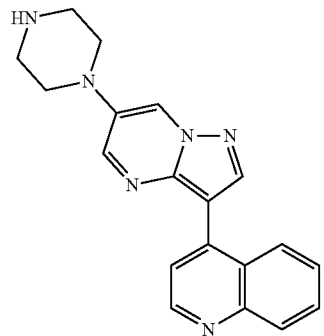 [SMILES: c1ccc2c(-c3cnn4cc(N5CCNCC5)cnc34)ccnc2c1] |

| Compound ID | Compound Structure |
|---|---|
| 81 | 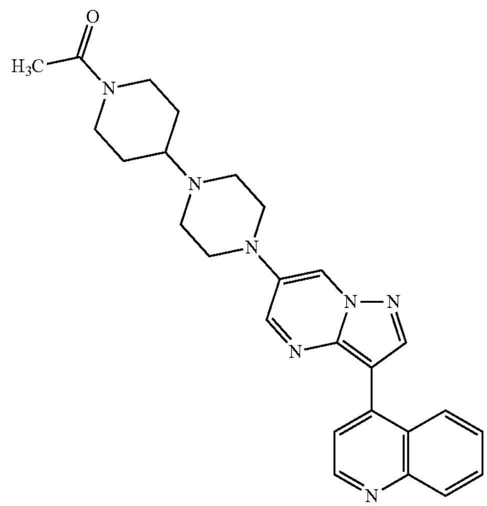 [SMILES: CC(=O)N1CCC(N2CCN(c3cnc4c(-c5ccnc6ccccc56)cnn4c3)CC2)CC1] |
| 185 | 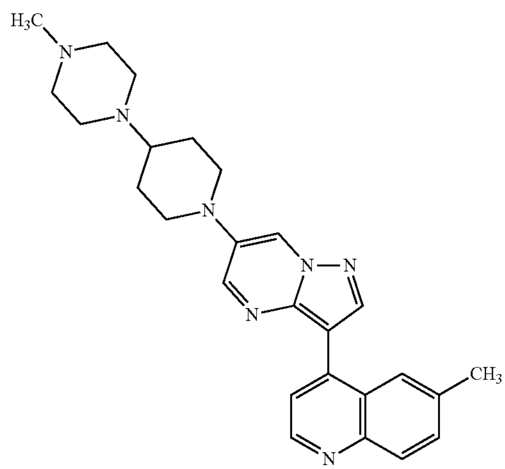 |
| 186 | 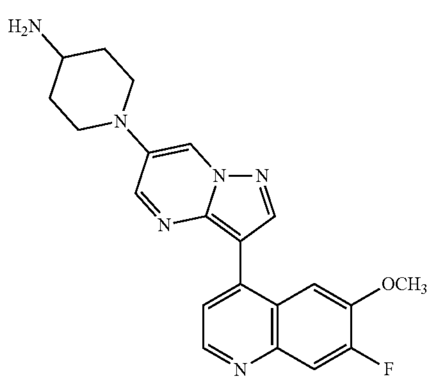 [SMILES: COc1cc2c(-c3cnn4cc(N5CCC(N)CC5)cnc34)ccnc2cc1F] |

-continued
| Compound ID | Compound Structure |
|---|---|
| 187 | 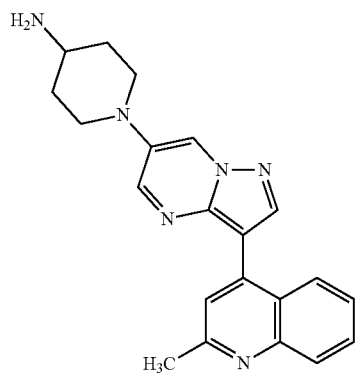 |
| 188 | 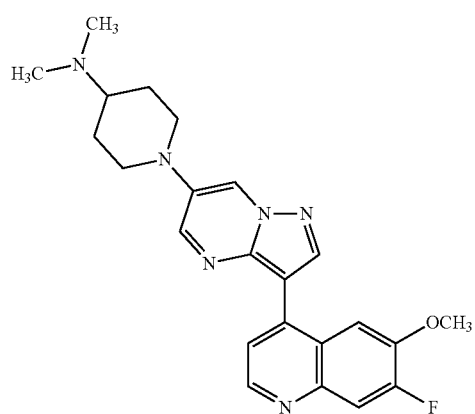 [SMILES: COc1cc2c(-c3cnn4cc(N5CCC(N(C)C)CC5)cnc34)ccnc2cc1F] |
| 189 | 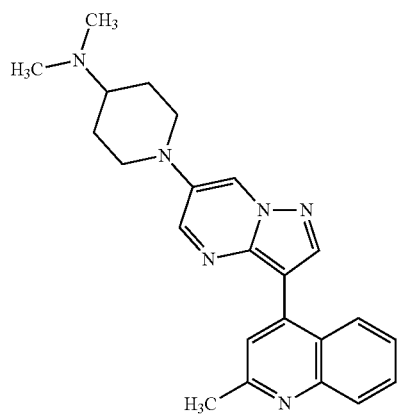 |

-continued

| Compound ID | Compound Structure |
|---|---|
| 190 | *(structure: N,N-dimethyl-pyrrolidin-3-amine linked to piperidine linked to pyrazolo[1,5-a]pyrimidine linked to 7-fluoro-6-methoxyquinoline)* |
| 191 | *(structure: azetidin-3-yl-piperazine linked to pyrazolo[1,5-a]pyrimidine linked to 7-fluoro-6-methoxyquinoline)* |
| 192 | *(structure: morpholine linked to pyrazolo[1,5-a]pyrimidine linked to 7-fluoro-6-methoxyquinoline)* |
| 193 | *(structure: morpholine linked to azetidine linked to pyrazolo[1,5-a]pyrimidine linked to 7-fluoro-6-methoxyquinoline)* |

-continued
| Compound ID | Compound Structure |
|---|---|
| 194 | 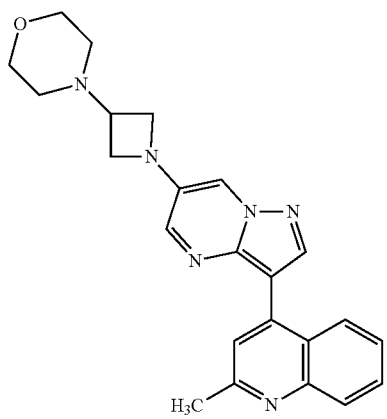 [SMILES: Cc1cc(-c2cnn3cc(N4CC(N5CCOCC5)C4)cnc23)c2ccccc2n1] |
| 195 | 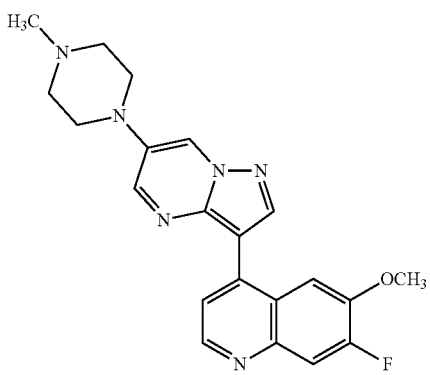 [SMILES: COc1cc2c(-c3cnn4cc(N5CCN(C)CC5)cnc34)ccnc2cc1F] |
| 196 | 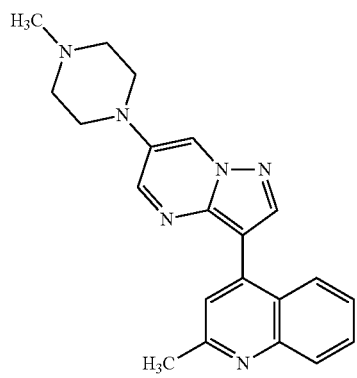 [SMILES: Cc1cc(-c2cnn3cc(N4CCN(C)CC4)cnc23)c2ccccc2n1] |
| 197 | 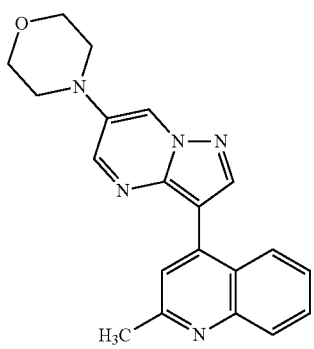 [SMILES: Cc1cc(-c2cnn3cc(N4CCOCC4)cnc23)c2ccccc2n1] |

| Compound ID | Compound Structure |
|---|---|
| 198 | 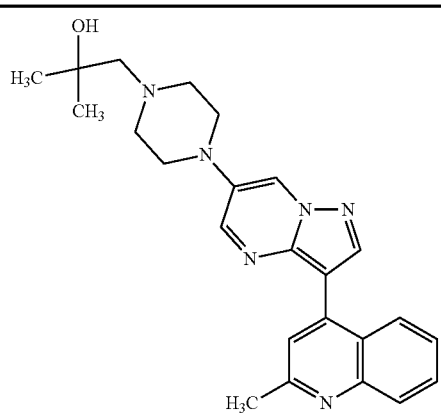 |
| 199 | 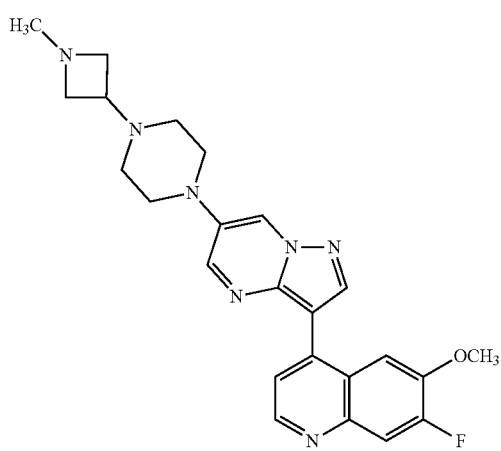 [SMILES: COc1cc2c(-c3cnn4cc(N5CCN(C6CN(C)C6)CC5)cnc34)ccnc2cc1F] |
| 200 | 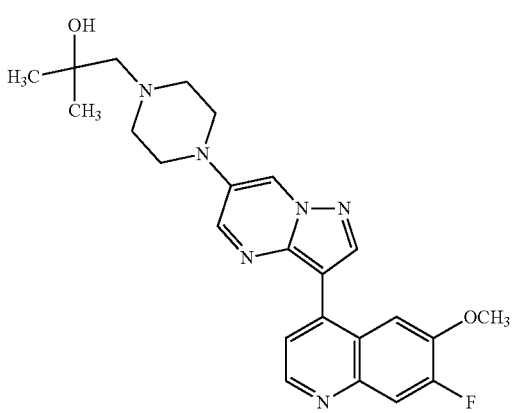 [SMILES: COc1cc2c(-c3cnn4cc(N5CCN(CC(C)(C)O)CC5)cnc34)ccnc2cc1F] |

| Compound ID | Compound Structure |
|---|---|
| 201 | 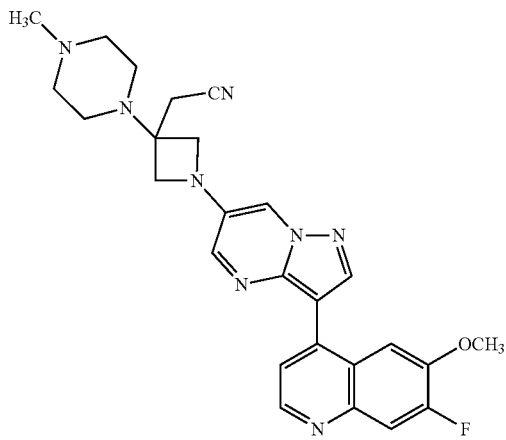 [SMILES: COc1cc2c(-c3cnn4cc(N5CC(CC#N)(N6CCN(C)CC6)C5)cnc34)ccnc2cc1F] |
| 202 | 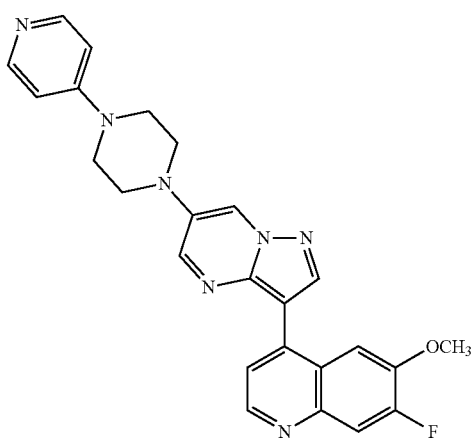 [SMILES: COc1cc2c(-c3cnn4cc(N5CCN(c6ccncc6)CC5)cnc34)ccnc2cc1F] |
| 203 | 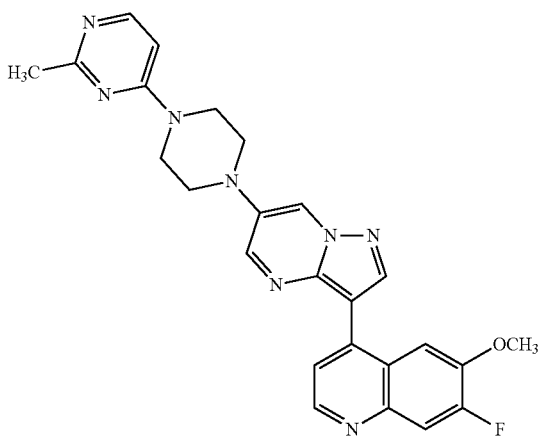 [SMILES: COc1cc2c(-c3cnn4cc(N5CCN(c6ccnc(C)n6)CC5)cnc34)ccnc2cc1F] |

| Compound ID | Compound Structure |
|---|---|
| 204 | 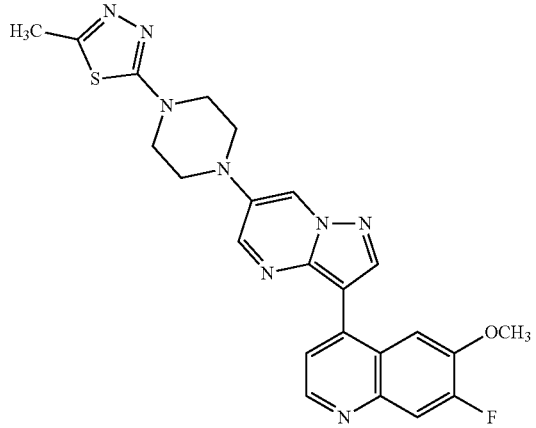 [SMILES: COc1cc2c(-c3cnn4cc(N5CCN(c6nnc(C)s6)CC5)cnc34)ccnc2cc1F] |
| 205 | 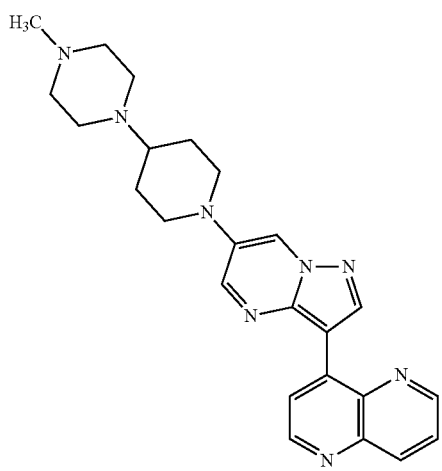 [SMILES: CN1CCN(C2CCN(c3cnc4c(-c5ccnc6cccnc56)cnn4c3)CC2)CC1] |
| 206 | 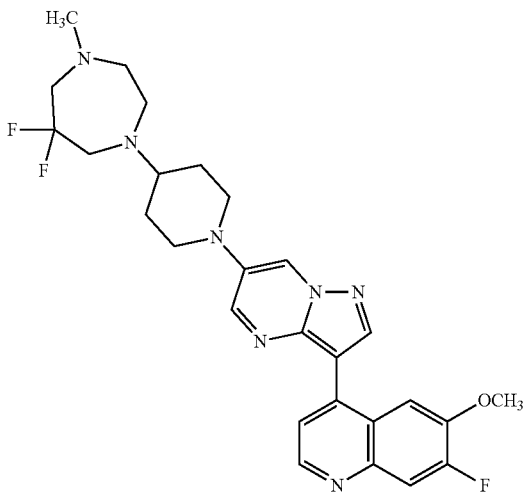 [SMILES: COc1cc2c(-c3cnn4cc(N5CCC(N6CCN(C)CC(F)(F)C6)CC5)cnc34)ccnc2cc1F] |

-continued

| Compound ID | Compound Structure |
|---|---|
| 207 | 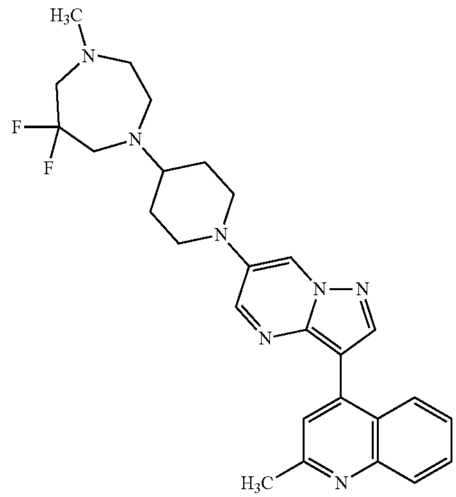 [SMILES: Cc1cc(-c2cnn3cc(N4CCC(N5CCN(C)CC(F)(F)C5)CC4)cnc23)c2ccccc2n1] |
| 208 | 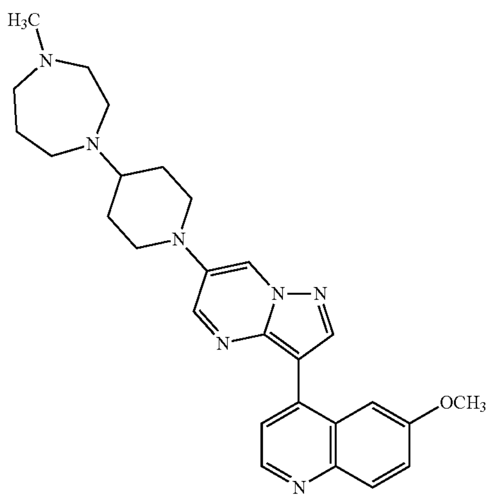 |
| 209 | 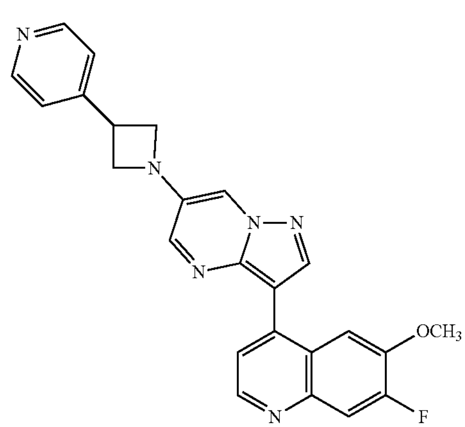 [SMILES: COc1cc2c(-c3cnn4cc(N5CC(c6ccncc6)C5)cnc34)ccnc2cc1F] |

| Compound ID | Compound Structure |
|---|---|
| 210 | 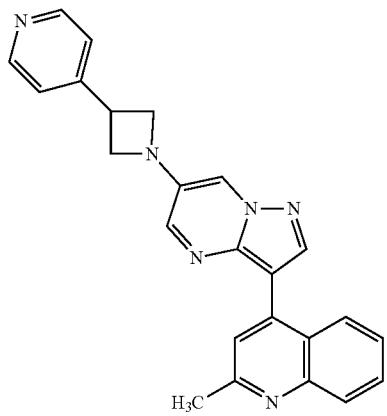 [SMILES: Cc1cc(-c2cnn3cc(N4CC(c5ccncc5)C4)cnc23)c2ccccc2n1] |
| 211 | 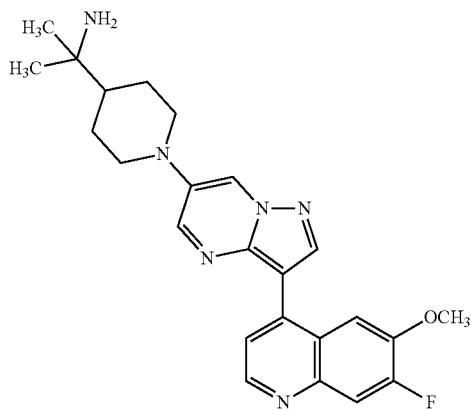 [SMILES: COc1cc2c(-c3cnn4cc(N5CCC(C(C)(C)N)CC5)cnc34)ccnc2cc1F] |
| 212 | 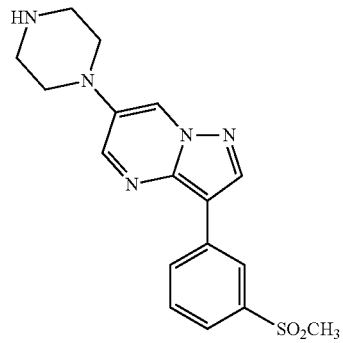 [SMILES: CS(=O)(=O)c1cccc(-c2cnn3cc(N4CCNCC4)cnc23)c1] |
| 213 | 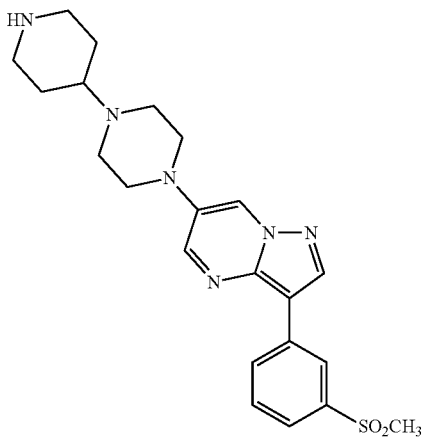 [SMILES: CS(=O)(=O)c1cccc(-c2cnn3cc(N4CCN(C5CCNCC5)CC4)cnc23)c1] |

| Compound ID | Compound Structure |
|---|---|
| 214 | 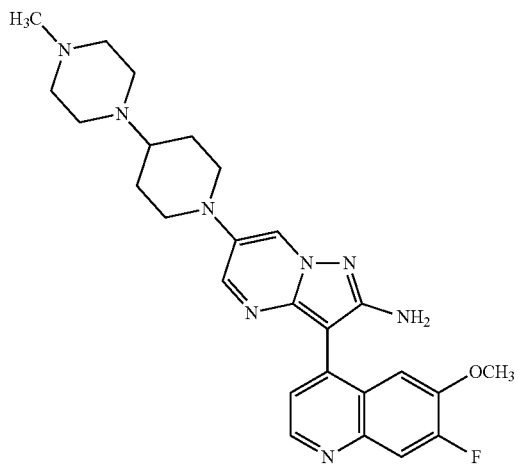 [SMILES: COc1cc2c(-c3c(N)nn4cc(N5CCC(N6CCN(C)CC6)CC5)cnc34)ccnc2cc1F] |
| 215 | 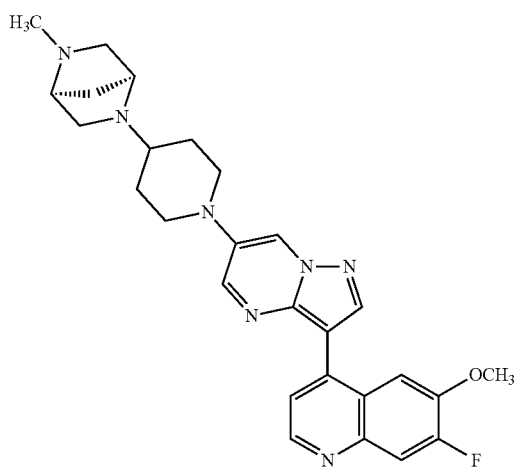 [SMILES: COc1cc2c(-c3cnn4cc(N5CCC(N6C[C@@H]7C[C@H]6CN7C)CC5)cnc34)ccnc2cc1F] |
| 216 | 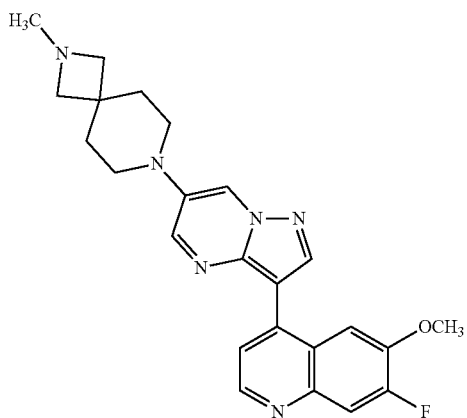 [SMILES: COc1cc2c(-c3cnn4cc(N5CCC6(CC5)CN(C)C6)cnc34)ccnc2cc1F] |

| Compound ID | Compound Structure |
|---|---|
| 217 | 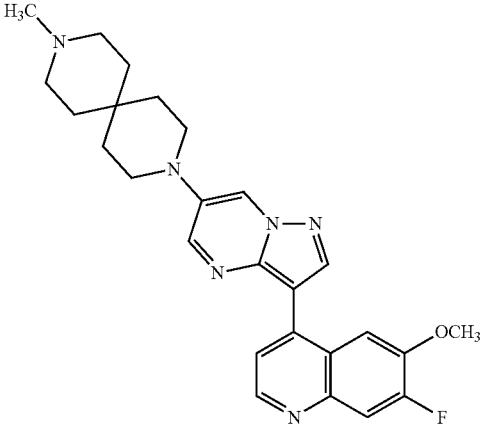 [SMILES: COc1cc2c(-c3cnn4cc(N5CCC6(CCN(C)CC6)CC5)cnc34)ccnc2cc1F] |
| 218 | 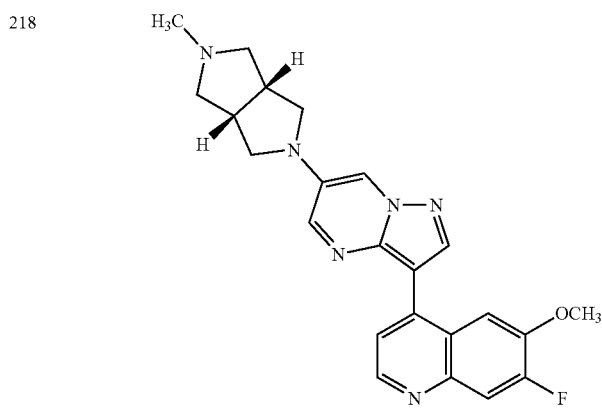 |
| 219 | 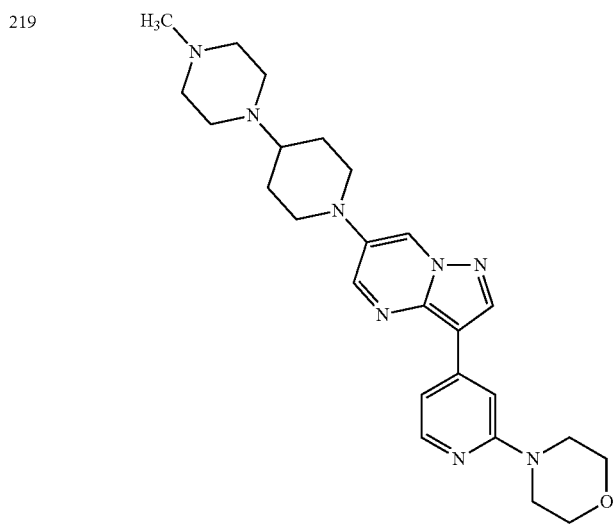 |

-continued
| Compound ID | Compound Structure |
|---|---|
| 220 | 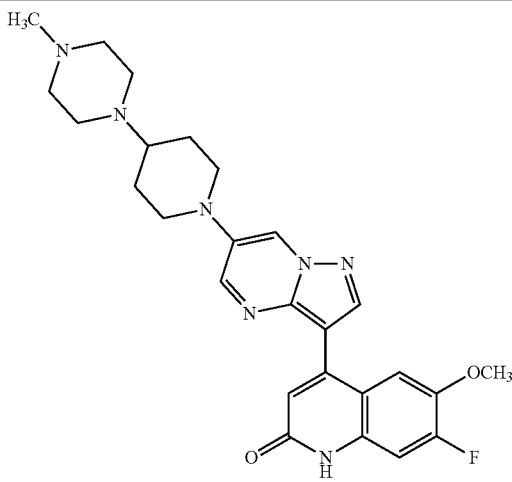 [SMILES: COc1cc2c(-c3cnn4cc(N5CCC(N6CCN(C)CC6)CC5)cnc34)cc(=O)[nH]c2cc1F] |
| 221 | 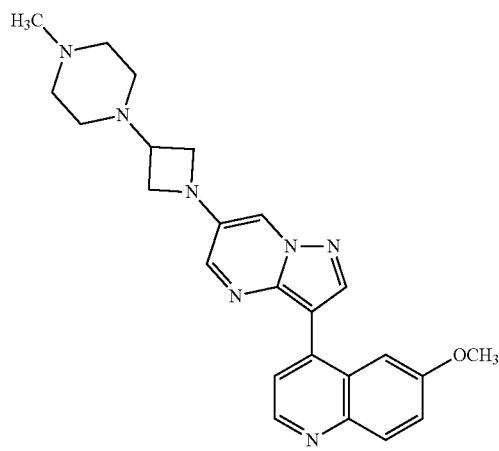 [SMILES: COc1ccc2nccc(-c3cnn4cc(N5CC(N6CCN(C)CC6)C5)cnc34)c2c1] |
| 222 | 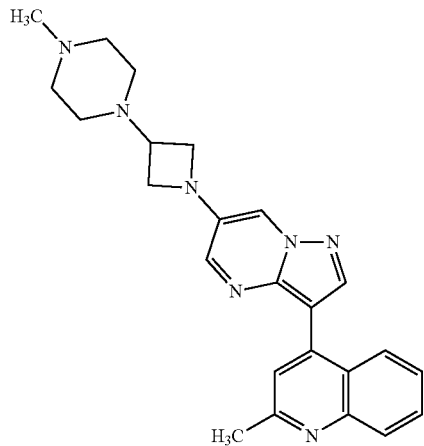 [SMILES: Cc1cc(-c2cnn3cc(N4CC(N5CCN(C)CC5)C4)cnc23)c2ccccc2n1] |

-continued
| Compound ID | Compound Structure |
|---|---|
| 223 | 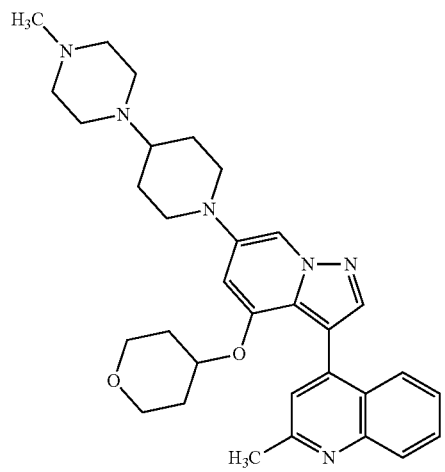 [SMILES: Cc1cc(-c2cnn3cc(N4CCC(N5CCN(C)CC5)CC4)cc(OC4CCOCC4)c23)c2ccccc2n1] |
| 224 | 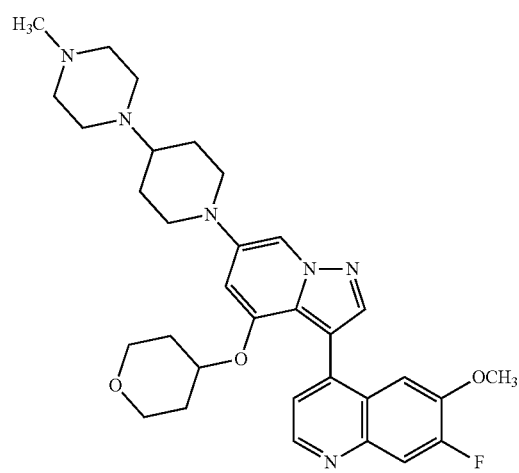 [SMILES: COc1cc2c(-c3cnn4cc(N5CCC(N6CCN(C)CC6)CC5)cc(OC5CCOCC5)c34)ccnc2cc1F] |
| 225 | 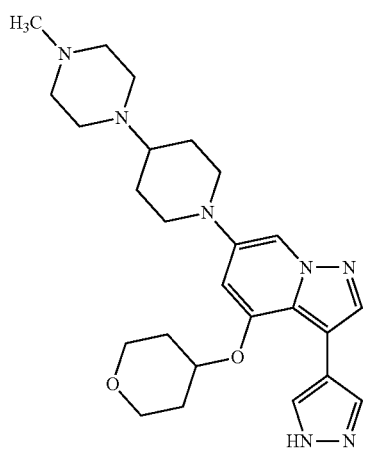 [SMILES: CN1CCN(C2CCN(c3cc(OC4CCOCC4)c4c(-c5cn[nH]c5)cnn4c3)CC2)CC1] |

-continued
| Compound ID | Compound Structure |
|---|---|
| 226 | 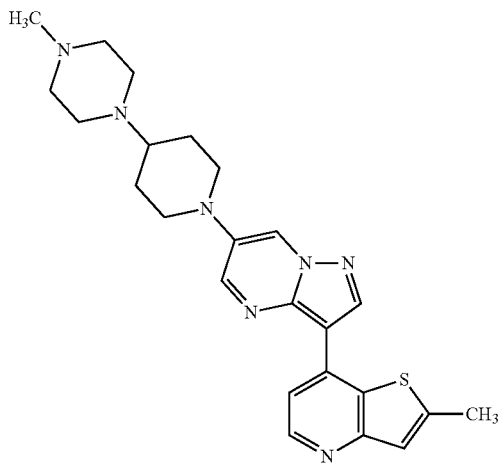 |
| 227 | 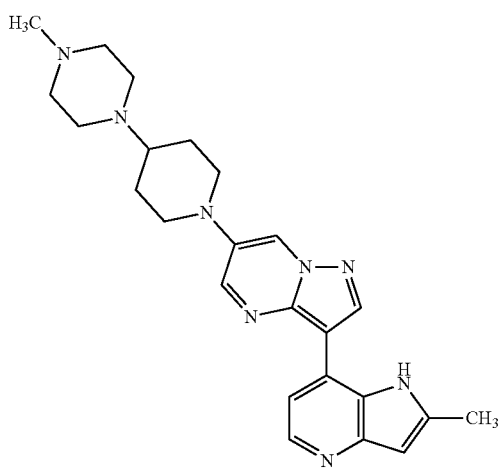 |
| 228 | 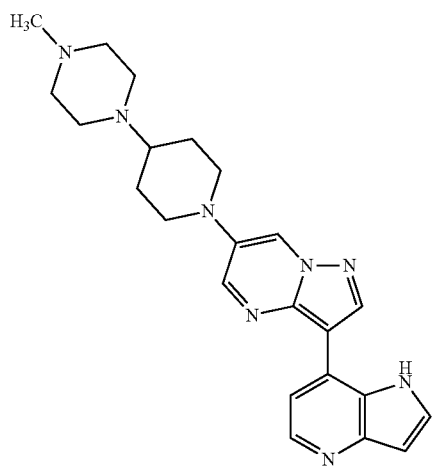 [SMILES: CN1CCN(C2CCN(c3cnc4c(-c5ccnc6cc[nH]c56)cnn4c3)CC2)CC1] |

| Compound ID | Compound Structure |
|---|---|
| 229 | *structure: N-methylpiperazine-piperidine-pyrazolo[1,5-a]pyrimidine-(2-aminoquinolin-4-yl)* |

In some embodiments, non-limiting examples of compounds of Formula I or Formula I-a are compounds 8, 15, 42, 49, or 185:

| Compound ID | Compound Structure |
|---|---|
| 8 | *structure: N-methylpiperazine-piperidine-pyrazolo[1,5-a]pyrimidine-(2-methylquinolin-4-yl)* |
| 15 | *structure: N-methylpiperazine-piperidine-pyrazolo[1,5-a]pyrimidine-(6-methoxy-7-fluoroquinolin-4-yl)* |
| 42 | *structure: N-methyl-1,4-diazepane-piperidine-pyrazolo[1,5-a]pyrimidine-(6-methoxy-7-fluoroquinolin-4-yl)* |
| 49 | *structure: N-methylpiperazine-azetidine-pyrazolo[1,5-a]pyrimidine-(6-methoxy-7-fluoroquinolin-4-yl)* |

| Compound ID | Compound Structure |
|---|---|
| 185 | 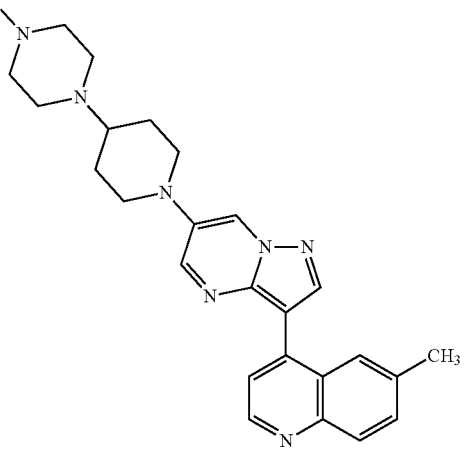 |

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Non-limiting examples of substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 2 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3- hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 2 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkenyl, and alkynyl" radicals. Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. Non-limiting examples of $R_a$ and $R_b$ are each independently hydrogen, alkyl, substituted alkyl, alkenyl, or substituted alkenyl. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=CH—CH=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. For example, $C_6$-$C_{12}$ aryl includes aryls that have 6 to 12 carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. For example, $C_4$-$C_9$ heteroaryl includes heteroaryls that have 4 to 9 carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1, 5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cycyl are typically used where X and Y indicate the number of carbon atoms in the ring system. For example, $C_3$-$C_8$ cyclyl includes cyclyls that have 3 to 8 carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heterocyclyl" refers to a nonaromatic 4-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. For example, $C_4$-$C_9$ heterocyclyl includes heterocyclyls that have 4-9 carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

The term "carbocyclyl" as used either alone or in combination with another radical, means a mono- bi- or tricyclic ring structure consisting of 3 to 14 carbon atoms. In some embodiments, one or more of the hydrogen atoms of a carbocyclyl may be optionally substituted by a substituent.

The term "carbocycle" refers to fully saturated ring systems and saturated ring systems and partially saturated ring systems and aromatic ring systems and non-aromatic ring systems and unsaturated ring systems and partially unsaturated ring systems. The term "carbocycle" encompasses monocyclic, bicyclic, polycyclic, spirocyclic, fused, bridged, or linked ring systems. In some embodiments, one or more of the hydrogen atoms of a carbocycle may be optionally substituted by a substituent. In some embodiments the carbocycle optionally comprises one or more heteroatoms. In some embodiments the heteroatoms are selected from N, O, S, or P.

The terms "cyclic" "cyclic group" and "ring" or "rings" means carbocycles, which can be fully saturated, saturated, partially saturated, unsaturated, partially unsaturated non-aromatic or aromatic that may or may not be substituted and which optionally can comprise one or more heteroatoms. In some embodiments the heteroatoms are selected from N, O, S, or P. In some embodiments, one or more of the hydrogen atoms of a ring may be optionally substituted by a substituent. In some embodiments, the ring or rings may be monocyclic, bicyclic, polycyclic, spirocyclic, fused, bridged, or linked.

The term "spiro-cycloalkyl" (spiro) means spirocyclic rings where the ring is linked to the molecule through a carbon atom, and wherein the resulting carbocycle is formed by alkylene groups. The term "spiro-$C_3$-$C_8$-cycloalkyl" (spiro) means 3-8 membered, spirocyclic rings where the ring is linked to the molecule through a carbon atom, and wherein the resulting 3-8 membered carbocycle is formed by alkylene groups with 2 to 7 carbon atoms. The term "spiro-$C_5$-cycloalkyl" (spiro) means 5 membered, spirocyclic rings where the ring is linked to the molecule through a carbon atom, wherein the resulting 5 membered carbocycle is formed by an alkylene group with 4 carbon atoms.

The term "spiro-cycloalkenyl" (spiro) means spirocyclic rings where the ring is linked to the molecule through a carbon atom, and wherein the resulting carbocycle is formed by alkenylene groups. The term "spiro-$C_3$-$C_8$-cycloalkenyl" (spiro) means 3-8 membered, spirocyclic rings where the ring is linked to the molecule through a carbon atom, wherein the resulting 3-8 membered carbocycle is formed by alkenylene groups with 2 to 7 carbon atoms. The term "spiro-$C_5$-cycloalkenyl" (spiro) means 5 membered, spirocyclic rings where the ring is linked to the molecule through a carbon atom, wherein the resulting 5 membered carbocycle is formed by alkenylene groups with 4 carbon atoms.

The term "spiro-heterocyclyl" (spiro) means saturated or unsaturated spirocyclic rings, which may contain one or more heteroatoms, where the ring may be linked to the molecule through a carbon atom or optionally through a nitrogen atom, if a nitrogen atom is present. In some embodiments, the heteroatom is selected from O, N, S, or P. In some embodiments, the heteroatom is O, S, or N. The term "spiro-$C_3$-$C_8$-heterocyclyl" (spiro) means 3-8 membered, saturated or unsaturated, spirocyclic rings which may contain one or more heteroatoms, where the ring may be linked to the molecule through a carbon atom or optionally through a nitrogen atom, if a nitrogen atom is present. In some embodiments, the heteroatom is selected from O, N, S, or P. In some embodiments, the heteroatom is O, S, or N. The term "spiro-$C_5$-heterocyclyl" (spiro) means 5 membered, saturated or unsaturated, spirocyclic rings which may contain one or more heteroatoms, where the ring may be linked to the molecule through a carbon atom or optionally through a nitrogen atom, if a nitrogen atom is present. In some embodiments, the heteroatom is selected from O, N, S, or P. In some embodiments, the heteroatom is O, S, or N.

In some embodiments, one or more of the hydrogen atoms of a spirocyclic ring may be optionally substituted by a substituent. In some embodiments, one or more hydrogen atoms of a spiro-cycloalkyl may be optionally substituted by a substituent. In some embodiments, one or more hydrogen atoms of a spiro-$C_3$-$C_8$-cycloalkyl may be optionally substituted by a substituent. In some embodiments, one or more hydrogen atoms of a spiro-$C_5$-cycloalkyl may be optionally substituted by a substituent. In some embodiments, one or more hydrogen atoms of a spiro-cycloalkenyl may be optionally substituted by a substituent. In some embodiments, one or more hydrogen atoms of a spiro-$C_3$-$C_8$-cycloalkenyl may be optionally substituted by a substituent. In some embodiments, one or more hydrogen atoms of a spiro-$C_5$-cycloalkenyl may be optionally substituted by a substituent. In some embodiments, one or more hydrogen atoms of a spiro-heterocycyl may be optionally substituted by a substituent. In some embodiments, one or more hydrogen atoms of a spiro-$C_3$-$C_8$- heterocycyl may be optionally substituted by a substituent. In some embodiments, one or more hydrogen atoms of a spiro-$C_5$- heterocycyl may be optionally substituted by a substituent.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, —NR$^N$—, —N$^+$(O$^-$)═, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term "oxo" means the substituent ═O.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amidine, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some cases, two or more substituents, together with the carbon(s) to which they are attached to, can form one or more rings.

Substituents may be protected as necessary and any of the protecting groups commonly used in the art may be employed. Non-limiting examples of protecting groups may be found, for example, in Greene and Wuts, Protective Groups in Organic Synthesis, 44$^{th}$. Ed., Wiley & Sons, 2006.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)CH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$-pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino"—NH-(alkyl)-(cycloalkyl), such as —NHCH$_2$-cyclohexyl, and the like.

Some commonly used abbreviations are: Me is methyl, Et is ethyl, Ph is phenyl, t-Bu is tert-butyl.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH$_3$) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls. Each substituent on a nitrogen, oxygen or sulfur atom is understood to be as valency and stability permit. For example, a neutral carbon atom can form four bonds to other atoms. A neutral oxygen atom has two bonds to other atoms. A neutral nitrogen atom has 3 bonds to other atoms, and a positively charged N$^+$ atom has 4 bonds to other atoms. In addition to satisfying valency, it is understood that structures disclosed herein include those commonly understood to be reasonably stable, e.g., they do not spontaneously decompose in aqueous solution.

In certain embodiments, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Isotopically labeled compounds of the present inventions can generally be prepared by following procedures well known in the art, such as by substituting an isotopically labeled reagent for a non-isotopically labeled reagent. In some cases, a compound can be enriched with an isotope such that the compound has a mixture of one or more isotopes (e.g., $^{15}$N or $^{14}$C) and the predominant natural atom (e.g. $^{14}$N or $^{12}$C) in a greater ratio than is usually found in nature.

Synthetic Preparation. In various embodiments, compounds of the present invention as disclosed herein may be synthesized using any synthetic method available to one of skill in the art. In various embodiment, the compounds of the present invention disclosed herein (e.g., compounds of Formula I or Formula I-a) can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, Protective Groups in Organic Synthesis, 44th. Ed., Wiley & Sons, 2006, which is incorporated herein by reference in its entirety. Non-limiting examples of synthetic methods used to prepare various embodiments of compounds of the present invention are disclosed in the Examples section herein. The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Use with Polymers. In various embodiments, the compounds of the present invention as disclosed herein (e.g., compounds of Formula I or Formula I-a) may be conjugated to a polymer matrix, e.g., for controlled delivery of the compound. The compound may be conjugated via a covalent bond or non-covalent association. In certain embodiments wherein the compound is covalently linked to the polymer matrix, the linkage may comprise a moiety that is cleavable under biological conditions (e.g., ester, amide, carbonate, carbamate, imide, etc.). In certain embodiments, the conjugated compound may be a pharmaceutically acceptable salt, ester, or prodrug of a compound disclosed herein. A compound as disclosed herein may be associated with any type of polymer matrix known in the art for the delivery of therapeutic agents.

Methods of the Invention

In various embodiments, the present invention provides a method for treating the formation of abnormal bone in a soft tissue of a subject, the method comprising: administering a therapeutically effective amount of one or more compounds of Formula I. In some embodiments, the subject is determined to have or be at risk of having abnormal bone formation prior to treatment. In some embodiments, the subject has been subjected to a musculoskeletal trauma, a spinal cord injury or a central nervous system injury. In some embodiments, the formation of abnormal bone is associated with a heterotopic ossification disease. In some embodiments, the heterotopic ossification disease is selected from the group consisting of: acquired heterotopic ossification, fibrodysplasia ossificans progressive, anklyosing spondylosis, traumatic heterotopic ossification, burn- or blast-injury associated heterotopic ossification, and joint replacement surgery associated heterotopic ossification. In some embodiments, the soft tissue comprises muscles, tendons, ligaments and/or fascia. In some embodiments, at least one additional agent is administered to the subject. In some embodiments, the at least one additional agent comprises a corticosteroid, a non-steroidal anti-inflammatory drug (NSAID), a lipoxygenase inhibitor, a leukotriene inhibitor, a mast cell stabilizing agent, an anti-histamine, a TNF inhibitor, an IL-23 blocker, or an inhibitor of IL-I signaling. In some embodiments, the therapeutically effective amount of one or more compounds of Formula I comprises a dose within the range of 5 mg/kg to 250 mg/kg. In some embodiments, the therapeutically effective amount of one or more compounds of Formula I does not cause weight loss greater than 20% of total body mass. In some embodiments, the compound of Formula I has a structure of Formula I-a.

In various embodiments, the present invention provides a method for treating the formation of abnormal bone in a soft tissue of a subject, the method comprising: administering a therapeutically effective amount of an inhibitor of a BMP type I serine-threonine kinase receptor to the subject, wherein the inhibitor of a BMP type I serine-threonine kinase receptor is one or more compounds of Formula I. In some embodiments, the BMP type I serine-thereonine receptor is ALK2, ALK3, or ALK6. In some embodiments, the BMP type I serine-thereonine receptor is ALK2 or ALK3. In some embodiments, the compound of Formula I has a structure of Formula I-a.

In various embodiments, the present invention provides a method for treating the formation of abnormal bone in a soft tissue of a subject, the method comprising: administering a therapeutically effective amount of an inhibitor of a BMP type II serine-threonine kinase receptor to the subject, wherein the inhibitor of a BMP type II serine-threonine kinase receptor is a one or more compounds of Formula I. In some embodiments, the BMP type II serine-thereonine receptor is ACVR2A, ACVR2B, BMPR2, or TGFβR2. In some embodiments, the compound of Formula I has a structure of Formula I-a.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is one or more compounds of Formula I. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5. In some embodiments, the compound of Formula I has a structure of Formula I-a.

In various embodiments, the present invention provides a method for identifying one or more compounds for inhibiting a serine-threonine kinase receptor, the method comprising: a) providing a sample comprising the serine-threonine kinase receptor; b) contacting the sample with one or more compounds of Formula I; and c) performing an assay to identify the one or more compounds that inhibit the serine-threonine kinase receptor, wherein the assay is an in vitro assay, an in vivo assay, or an ex vivo assay. In some embodiments, the serine-threonine kinase receptor is a BMP type I receptor, a BMP type II receptor, or a TGF-β type I receptor. In some embodiments, the assay is an in vitro assay. In some embodiments, the compound of Formula I has a structure of Formula I-a.

In various embodiments, the present invention provides a method of treating a subject with Sjogren's syndrome, comprising: a) selecting a subject with increased expression of BMP6 in a salivary gland of the subject relative to a control; and b) administering to the subject a therapeutically effective amount of an agent that inhibits expression or activity of BMP6, thereby treating the subject with Sjogren's syndrome, wherein the agent that inhibits expression or activity of BMP6 is one or more compounds of Formula I. In some embodiments, the salivary gland is a minor labial salivary gland, parotid gland, or a submandibular gland. In some embodiments, the compound of Formula I has a structure of Formula I-a.

In various embodiments, the present invention provides a method for treating a subject with diffuse intrinsic pontine glioma (DIPG), comprising selecting the subject with diffuse intrinsic pontine glioma (DIPG), and administering to the subject a therapeutically effective amount of one or more compounds of Formula I, thereby treating the subject with diffuse intrinsic pontine glioma (DIPG). In some embodiments, the compound of Formula I has a structure of Formula I-a.

In various embodiments, the present invention provides a method for treating the formation of abnormal bone in a soft tissue of a subject, the method comprising: administering a therapeutically effective amount of an inhibitor of a TGF-β type I receptor serine-threonine kinase receptor to the subject, wherein the inhibitor of the TGF-β type I serine-threonine kinase receptor is a one or more compounds of Formula I. In some embodiments, the TGF-β type I receptor is ALK5. In some embodiments, the compound of Formula I has a structure of Formula I-a.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is one or more compounds of Formula I. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5. In some embodiments, the compound of Formula I has a structure of Formula I-a.

In various embodiments, the present invention provides a method of increasing salivary flow in a subject, comprising: a) selecting a subject with increased expression of BMP6 in a salivary gland of the subject relative to a control; and b) administering to the subject a therapeutically effective amount of an agent that inhibits expression or activity of BMP6, thereby increasing salivary flow in the subject, wherein the agent that inhibits expression or activity of BMP6 is one or more compounds of Formula I, or a submandibular gland. In some embodiments, the compound of Formula I has a structure of Formula I-a.

In various embodiments, the present invention provides method of increasing salivary flow in a subject, comprising: a) selecting a subject with increased expression of BMP6 in a salivary gland of the subject relative to a control; and b) administering to the subject a therapeutically effective amount of an agent that inhibits BMP signaling, thereby increasing salivary flow in the subject, wherein the agent that inhibits BMP signaling is one or more compounds of Formula I. In some embodiments, the salivary gland is a minor labial salivary gland, parotid gland, or a submandibular gland. In some embodiments, the compound of Formula I has a structure of Formula I-a.

Heterotopic Ossification Diseases

The term "heterotopic ossification" refers to the abnormal formation of bone in soft tissue where bone typically does not exist. Acquired heterotopic ossification can occur with essentially any musculoskeletal trauma, spinal cord injury, central nervous system injury, head injury, cerebrovascular accident, sickle cell anemia, hemophilia, tetanus, poliomyelitis, multiple sclerosis, toxic epidermal necrolysis and burns. Examples of musculoskeletal trauma include, but are not limited to, hip, knee, shoulder, or elbow arthroplasty; fractures; joint dislocations; or soft-tissue trauma, with the musculus quadriceps femoris and musculus brachialis. Acquired heterotopic ossification can also be associated with fever, swelling, and erythema (e.g., local, patchy reddening of the skin). In one embodiment, neurogenic heterotopic ossification is not associated with local trauma.

Genetic diseases fibrodysplasia ossificans progressiva (FOP) and progressive osseous heterplasia (POH) are the most severe manifestations of heterotopic bone formation. FOP occurs rarely and is a result of a mutation in ACVR1, which encodes a bone morphogenetic protein type I receptor. Patients with POH have inactivating mutations of the GNAS gene, which also can give rise to Albright's hereditary osteodystrophy (AHO) when the mutations are inherited from the mother.

Myositis ossificans circumscripta is characterized by the intramuscular proliferation of fibroblasts, new bone, and/or cartilage.

HO typically occurs between 3 weeks and 12 weeks following an injury. Heterotopic ossification can be reliably diagnosed by computed tomography, bone scintigraphy and ultrasonography. Two to six weeks later, the abnormal bone formation has progressed to the point that it is detectable by radiography. Bony maturation typically occurs within six months.

Conventional treatment of Heterotopic ossification: Conventional treatment usually involves non-steroidal anti-inflammatory drugs (indomethecin, rofecoxib), or bisphosphonate (etidronate, pamidronate), Coumadin/warfarin, salicylates, and/or local radiation can also be administered. Often, surgery is the only option for treatment.

Outcome of treatment can be measured by a standard radiological grading system for HO, which includes measurements related to changes in range of motion in the affected joint measured by goniometry, mean length of time to objective improvement of HO-related clinical symptoms or signs, changes in standardized functional or joint-specific measures.

Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension, Juvenile Familial Polyposis, as well as sporadic renal cell and prostate carcinomas. It has been suggested that in certain disease states associated with defective signaling components, attenuated BMP signaling might be a cause, while other findings have suggested that in some contexts excess BMP signaling might be pathogenic (Waite et al. *Nat. Rev. Genet.* 4:763-773, 2005; Yu et. *J. Biol. Chem.* 280:24443-24450, 2003). The ability to modulate BMP signaling experimentally would provide a means for investigating therapy, and for determining the root causes of these conditions. One or more compounds of Formula are inhibitors of ALK2, a BMP type 1 receptor and can be used to disrupt signaling through the BMP pathway.

A. Treatment of Anemia, Including Iron Deficiency and Anemia of Chronic Disease

For a review, see Weiss et al. *N. Engl. J Med.* 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP antagonists increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N. Engl. J. Med.* 352:1011-1023, 2005). It has been shown that stimulating hepatoma cell lines with IL-6 induces hepcidin expression, while treatment with a BMP antagonist abrogates IL-6-induced hepcidin expression (Yu et al. *Nat. Chem. Biol.* 4:33-41, 2008). Moreover, the inventors have previously found that BMP antagonists can inhibit hepcidin expression induced by injection of pathogenic bacteria in vivo. It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by the inventors' previous finding that BMP antagonists can inhibit hepcidin expression and raise serum iron levels in vivo (data not shown). Taken together these data indicate that iron- and inflammation-mediated regulation of hepcidin and circulating iron levels require BMP signaling. Thus, one or more compounds of Formula I which disrupt BMP signaling through ALK2 can be used to alter iron availability in diverse circumstances for therapeutic benefit. In some embodiments, the compound of Formula I has a structure of Formula I-a.

Compounds and/or pharmaceutical compositions as described herein can be used in anemic states to (i) augment the efficacy of dietary iron or oral iron supplementation (which is safer than intravenous administration of iron) to increase serum iron concentrations; (ii) augment build-up of hemoglobin in the blood in anticipation of surgery or to enable blood donation for self in anticipation of surgery; and (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth).

B. Treatment of Fibrodysplasia Ossificans Progressiva (FOP)

In various embodiments, the present disclosure relates to the treatment and/or prevention of a disease or disorder comprising abnormal bone growth in a soft tissue of a subject. Heterotopic ossification (HO) involves unwanted bone growth that may be characterized by inappropriate differentiation of cells into bone-forming cells. This condition leads to bone formation, usually near joints, where the bone formation often limits the mobility of the joint. HO may follow neurological injury and direct injury to soft tissue such as muscles or connective tissue around the joint in which HO later develops.

There are three recognized etiologies of HO: traumatic, neurogenic, and genetic. Traumatic HO typically follows fractures, dislocations, operative procedures, and severe burns. Most commonly, HO is seen around the hip after fracture and open reduction-internal fixation (ORIF) procedures or total hip arthroplasties (THA). As well, HO is often associated with pathologies such as traumatic brain injury (TBI), spinal cord injury (SCI), infections of the central nervous system (CNS), tumors, strokes, tetanus, polio, tabes dorsalis, multiple sclerosis, and selective posterior rhizotomy. The presence of idiopathic muscle spasticity is also associated with the development of HO.

Bone morphogenetic proteins (BMP) exhibit broad spectrum of biological activities in various tissues, including bone, cartilage, blood vessels, heart, kidney, neurons, liver and lung. BMPs are members of the transforming growth factor-β (TGF-β) family that bind to type II and type I serine-threonine kinase receptors, and transduce signals through Smad and non-Smad signaling pathways. Fibrodysplasia ossificans progressiva (FOP), one type of heterotopic ossification disease, is an autosomal-dominant rare disease that affects one person in every 1-2 million. It is characterized by malformation of the great (big) toes during embryonic development and by progressive heterotopic endochondral ossification (HEO) postnatally, which leads to the formation of a second skeleton of heterotopic bone. Individuals with the classical features of FOP have the identical heterozygous activating mutation (R206H) in the gene encoding ACRV1 (also known as ALK2), a BMP type 1 receptor. No effective treatment currently exists for this rare and devastating disease. As such, there remains a need for compositions and methods for treating heterotopic ossification and heterotopic ossification diseases and disorders.

FOP is caused by the presence of a constitutively-active mutant form of ALK2 in affected individuals (Shore et al. *Nat. Genet.* 38:525-527, 2006). A specific inhibitor of BMP signaling such as one or more compounds of Formula I can be used to prevent excessive bone formation in response to trauma, musculoskeletal stress or inflammation. Such compounds can also be used to aid in regression of pathologic bone. One or more compounds of Formula I can be administered systemically or locally to concentrate or limit effects to areas of trauma or inflammation. In some embodiments, the compound of Formula I has a structure of Formula I-a.

One or more compounds of Formula I, ALK2 inhibitors, can be used as chronic therapy to suppress spontaneous bone formation in individuals who are highly susceptible. One or more compounds of Formula I can be used as a chronic therapy to suppress spontaneous bone formation in individuals who are highly susceptible. Transient therapy can be used to prevent abnormal bone formation in FOP individuals who develop osteomas or pathologic bone most frequently in association with trauma by administration before, during, or even after the traumatic incident. Transient therapy with BMP inhibitors (e.g., one or more compounds of Formula I) as described herein can be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSAIDs, steroids, cyclosporine, cyclophosphamide, azathioprine, methotrexate, rituxumab, etanercept, or similar drugs) may increase the effectiveness of BMP antagonists in inhibiting heterotopic bone formation in this disorder. In some embodiments, the compound of Formula I has a structure of Formula I-a.

Provided herein are methods and compositions for the treatment and/or prevention of abnormal bone formation in a soft tissue. In certain embodiments, the methods and compositions treat and/or prevent a disease or disorder comprising abnormal bone formation in soft tissue. Exemplary diseases or disorders that can be treated with the methods and compositions described herein include, but are not limited to, heterotopic ossification diseases such as fibrodysplasia ossificans progressiva, anklyosing spondylosis, traumatic heterotopic ossification, burn- or blast-injury associated heterotopic ossification, and joint replacement surgery associated heterotopic ossification.

Accordingly, provided herein in one aspect is a method for treating and/or preventing the formation of abnormal bone in a soft tissue of a subject, the method comprising: administering a therapeutically effective amount of a pharmaceutical composition comprising one or more compounds of Formula I. In some embodiments, the compound of Formula I has a structure of Formula I-a.

C. Treatment of Cancers

Excessive BMP signaling, which could arise due to over-expression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. *J Biol. Chem.* 280:24443-24450, 2008; Waite et al. *Nat. Rev. Genet.* 4:763-773, 2003; Alarmo et al. *Genes, Chromosomes Cancer* 45:411-419, 2006; Kim et al. *Cancer Res.* 60:2840-2844, 2000; Kim et al. *Clin. Cancer Res.* 9:6046-6051, 2003; Kim et al. *Oncogene* 23:7651-7659, 2004). If increased BMP activity associated with BMP over-expression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

One or more compounds of Formula I are contemplated herein for use in treating cancer, for example, they can be used to slow or arrest the growth or metastasis of such tumor cells (as well as other tumor constituent cell types) for clinical benefit, either as adjunctive or primary chemotherapy. Also, BMP inhibitors as described herein can be used to interfere with the bone metastatic properties of certain types of cancers (e.g., adenocarcinoma, such as prostate and breast carcinomas). In addition, one or more compounds of Formula I as described herein can be used to inhibit osteoblastic activity in tumors that either form bone or are bone-derived, such as osteosarcomas (as adjunctive or primary chemotherapy). Further, one or more compounds of Formula I as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement. In some embodiments, the cancer is diffuse intrinsic pontine glioma (DIPG). In some embodiments, the compound of Formula I has a structure of Formula I-a.

D. Treatment of Pathologic Bone Formation

Compositions comprising one or more compounds of Formula I as described herein can be used to treat or ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compositions comprising one or more compounds of Formula I as described herein can also be used to prevent calcinosis (dystrophic soft-tissue calcification) in diseases such as systemic lupus erythematosus, scleroderma, or dermatomyositis. In some embodiments, the compound of Formula I has a structure of Formula I-a.

Blunt traumatic injury to muscles can cause abnormal bone formation within muscle in certain individuals, resulting in a disorder called myositis ossificans traumatica (Cushner et al. *Orthop. Rev.* 21:1319-1326, 1992.). Head trauma and burn injury can also induce heterotopic bone formation markedly impairing patient rehabilitation and recovery. Treatment with one or more compounds of Formula I as described herein, optionally in addition to anti-inflammatory medications usually prescribed for such a condition (e.g., non-steroidal anti-inflammatory drugs such as indomethacin or ibuprofen) can help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances. In some embodiments, the compound of Formula I has a structure of Formula I-a.

E. Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. *J. Clin. Invest.* 91:1800-1809, 1993; Tyson et al. *Arterioscler. Thromb. Vasc. Biol.* 23:489-494, 2003). BMPs and BMP-induced osteodifferentation are also implicated in cardiac valvular calcification. Native cardiac valves can calcify particularly when they are already abnormal. A classic example is bicuspid aortic valve—these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

One or more compounds of Formula I as described herein can be used to inhibit vascular or valvular calcific disease alone or in combination with atheromatous disease, renal disease, renal osteodystrophy or parathyroid disease. In some embodiments, the compound of Formula I has a structure of Formula I-a.

Pharmaceutical compositions comprising one or more compounds of Formula I as described herein can be used to inhibit vascular or valvular calcific disease alone or in combination with atheromatous disease, renal disease, renal osteodystrophy or parathyroid disease. In some embodiments, the compound of Formula I has a structure of Formula I-a.

One or more compounds of Formula I as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis). In some embodiments, the compound of Formula I has a structure of Formula I-a.

Pharmaceutical compositions comprising one or more compounds of Formula I as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis). In some embodiments, the compound of Formula I has a structure of Formula I-a.

In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing can be temporarily "suspended" by use of one or more compounds of Formula I as described herein, until definitive surgery or manipulation can be performed. This could prevent the need for subsequent intentional re-fracture in order to ensure correct apposition of bone fragments, for example. It is expected that upon stopping administration of one or more compounds of Formula I normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP antagonist as described herein via diffusion from a local implant or matrix) can be used to inhibit fracture healing or prevent fracture calluses at the critical areas. In some embodiments, the compound of Formula I has a structure of Formula I-a.

F. Immune Modulation Via BMP Antagonists

BMPs have been reported to attenuate the inflammatory or immune response (Choi et al. Nat. Immunol. 7:1057-

1065, 2006; Kersten et al. BMC Immunol. 6:9, 2005), which can impair an individual's ability to fight infections (i.e., viral, bacterial, fungal, parasitic, or tuberculosis). One or more compounds of Formula I, inhibitors of BMP signaling through ALK2, can be used to augment the inflammatory or immune response enabling individuals to clear infections more rapidly. One or more compounds of Formula I can be used to augment the inflammatory or immune response enabling individuals to clear infections more rapidly. In some embodiments, the compound of Formula I has a structure of Formula I-a.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP antagonists as described herein may also be effective in some contexts for the intentional induction of immune tolerance (i.e., in allotransplantation or autoimmunity).

G. Treatment of Skin Diseases

Expansion of cultured keratinocytes—In vitro, BMPs inhibit keratinocyte proliferation and promote differentiation (reviewed in Botchkarev et al. Differentiation 72:512-526, 2004). In patients in need of skin grafting (e.g., after burns), skin grafts are made from cultured keratinocytes. The keratinocytes can be derived from other animals (xenografts), but these are only temporary as they are typically rejected by the immune system. Keratinocytes can be derived from the patient themselves and can be grown into sheets of cells in the laboratory (cultured epithelial autografts). It is unlikely that the patient will reject keratinocytes derived from his/her own body. Addition of BMP antagonists as described herein to keratinocyte cultures can be used to facilitate keratinocyte proliferation enabling patients to receive grafts sooner.

Improved epithelialization—BMP6 is highly expressed in skin injury, and high levels of BMP6 are detected in chronic human wounds of different etiologies (Kaiser et al. J. Invest. Dermatol. 111:1145-1152, 1998). In mice overexpressing BMP6 in their skin, reepithelialization and healing skin wounds were significantly delayed (Kaiser et al. J. Invest. Dermatol. 111:1145-1152, 1998). Improved epithelialization can reduce scar formation. Topical or systemic administration of one or more compounds of Formula I is contemplated herein to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation. In some embodiments, the compound of Formula I has a structure of Formula I-a.

Promotion of hair growth—Growth of hair follicles on the scalp is cyclic with three phases: anagen (the growth phase), catagen (the involutional phase), and telogen (resting phase). Recent evidence indicates that BMP signals delay the transition from telogen to anagen (Plikus et al. Nature 451:340-344, 2008). Inhibition of BMP signaling using one or more compounds of Formula I is described herein can shorten the telogen phase and increase the number of follicles in the anagen phase. One or more compounds of Formula I can be used to treat circumstances wherein hair follicles are insufficient or when hairs are being lost more frequently than they are grown. These circumstances include androgenic alopecia (male pattern balding), alopecia greata, and telogen effluvium. In some embodiments, the compound of Formula I has a structure of Formula I-a.

Treatment of psoriasis—Psoriasis is an inflammatory skin disorder which can occur following skin trauma and the ensuing repair and inflammation (Koebner phenomenon). BMPs can participate in repair and inflammatory mechanisms that cause psoriasis, since over-expression of BMP6 in the skin of mice leads to skin lesions similar to those seen in patients with psoriasis (Blessing et al. J. Cell. Biol. 135:227-239, 1996). One or more compounds of Formula I can be administered topically or systemically to treat established psoriasis or prevent its development after skin injury. In some embodiments, the compound of Formula I has a structure of Formula I-a.

Treatment of corneal scarring—BMP6 expression is associated with conjunctival scarring (Andreev et al. Exp. Eye Res. 83:1162-1170, 2006). One or more compounds of Formula I can be used to prevent or treat corneal scarring and the resulting blindness. In some embodiments, the compound of Formula I has a structure of Formula I-a.

H. Treatment of Systemic Hypertension

Infusion of BMP4 induces systemic hypertension in mice (Miriyala et al. Circulation 113:2818-2825, 2006). Vascular smooth muscle cells express a variety of BMP ligands. BMPs increase the expression of voltage gated potassium channels and thereby increase constriction of vascular smooth muscle (Fantozzi et al. Am. J. Physiol. Lung Cell. Mol. Physiol. 291:L993-1004, 2006). Thus, one or more compounds of Formula I are contemplated herein to inhibit BMP signaling, which can be used to reduce blood pressure. Sustained reduction of blood pressure in patients with hypertension is expected to prevent myocardial infarction, congestive heart failure, cerebrovascular accidents, and renal failure. Treatment as described herein can be used to target the hypertension in specific vascular beds, such as in pulmonary hypertension via local delivery (e.g., via aerosol). In some embodiments, the compound of Formula I has a structure of Formula I-a.

I. Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. Circ. Res. 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. J. Biol. Chem. 280:24443-24450, 2008) reported that BMPRII deficiency paradoxically increases BMP signaling by subsets of BMP ligands, and thus increased BMP signaling may actually contribute to the development of pulmonary hypertension.

One or more compounds of Formula I can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated as described herein are expected to have a decrease in shortness of breath, right ventricular hypertrophy, and right ventricular failure. In some embodiments, the compound of Formula I has a structure of Formula I-a.

Pharmaceutical compositions comprising one or more compounds of Formula I can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated as described herein are expected to have a decrease in shortness of breath, right ventricular hypertrophy, and right ventricular failure. In some embodiments, the compound of Formula I has a structure of Formula I-a.

J. Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. Am. J. Physiol. Heart. Circ. Physiol. 293:H3396-3403, 2007). Inhibition of BMP-10 signaling can be used to prevent/treat ventricular hypertrophy. Ventricular hypertrophy can lead to congestive heart failure due to diastolic dysfunction. Pharmaceutical compositions comprising one or more compounds of Formula I may prevent/treat congestive heart failure. In some embodiments, the compound of Formula I has a structure of Formula I-a.

K. Treatment of Neurologic Disorders

Treatment of spinal cord injury and neuropathy—BMPs are potent inhibitors of axonal regeneration in the adult spinal cord after spinal cord injury (Matsuura et al. J. Neurochem. 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re-formation, effects which are blocked by an antibody directed against RGMa (Hata et al. J. Cell. Biol. 173:47-58, 2006; Kyoto et al. Brain Res. 1186:74-86, 2007). RGMa enhances BMP signaling (Babitt et al. J. Biol. Chem. 280:29820-29827, 2005) suggesting that BMP signaling may be responsible for preventing axonal growth and recovery.

Based on these considerations, treatment with one or more compounds of Formula I as described herein would be expected to increase axonal growth and recovery after spinal cord injury. Treatment as described herein would be expected to prevent/treat neuropathies associated with a wide spectrum of disorders including diabetes mellitus. In addition, treatment with one or more compounds of Formula I as described herein can be used treat both the pain and motor dysfunction associated with neuropathies. In some embodiments, the compound of Formula I has a structure of Formula I-a.

Treatment of neurologic disorders associated with central nervous system inflammation—BMP4 and 5 have been detected in multiple sclerosis and Creutzfeldt-Jakob disease lesions (Deininger et al. Acta Neuropathol. 90:76-79, 1995). BMPs have also been detected in mice with experimental autoimmune encephalomyelitis, an animal model of multiple sclerosis (Ara et al. J. Neurosci. Res. 86:125-135, 2008). Treatment as described herein can be used to prevent or treat multiple sclerosis as well as other neurologic disorders associated with central nervous system inflammation, or maladaptive injury repair processes mediated by BMP signals.

Treatment of dementias—Inhibitors of BMP signaling can promote neurogenesis in mouse neural precursor cells (Koike et al. J. Biol. Chem. 282: 15843-15850, 2007). Treatment with one or more compounds of Formula I as described herein can be used to augment neurogenesis in a variety of neurologic disorders associated with accelerated loss of neurons including cerebrovascular accidents and Alzheimer's Disease, as well as other dementias. In some embodiments, the compound of Formula I has a structure of Formula I-a.

Altering memory and learning—BMP signaling has an important role in the development and maintenance of neurons involved in memory and cognitive behavior. For example, mice deficient in the BMP antagonist, chordin, have enhanced spatial learning but less exploratory activity in a novel environment (Sun et al. J. Neurosci. 27:7740-7750, 2007). Treatment with one or more compounds of Formula I as described herein can be used to alter or prevent memory or learning, for example, inducing amnesia for anesthesia or in other situations likely to cause distress, or to prevent Post-Traumatic Stress Disorder. In some embodiments, the compound of Formula I has a structure of Formula I-a.

L. Treatment of Atherosclerosis

Abundant evidence indicates that BMP ligands are pro-inflammatory and pro-atherogenic in the blood vessel wall (Chang et al. Circulation 116:1258-1266, 2007). Knocking-down expression of BMP4 decreased inflammatory signals, whereas knocking-down BMP antagonists (eg follistatin or noggin) increased inflammatory signals. Treatment with one or more compounds of Formula I as described herein can be used to reduce vascular inflammation associated with atherosclerosis, autoimmune disease, and other vasculitides. By decreasing atherosclerosis, treatment as described herein would decrease acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal structure and the requirement for vascular surgery. In some embodiments, the compound of Formula I has a structure of Formula I-a.

As BMPs and many of the BMP-induced gene products that affect matrix remodeling are overexpressed in early atherosclerotic lesions, BMP signals can promote plaque formation and progression (Bostrom et al. J Clin Invest. 91: 1800-1809. 1993; Dhore et al. Arterioscler Thromb Vasc Biol. 21: 1998-2003. 2001). BMP signaling activity in the atheromatous plaque can thus represent a form of maladaptive injury-repair, or can contribute to inflammation. Over time, BMP signals can also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, treatment with one or more compounds of Formula I as described herein can be used to limit the progression of atheromatous plaques and vascular calcification in vivo. In some embodiments, the compound of Formula I has a structure of Formula I-a.

M. Treatment of Sjogren's Syndrome

Sjögren's syndrome is an autoimmune disorder in which immune cells attack and destroy the glands that produce tears and saliva. Sjögren's syndrome is considered a rheumatic disorder, meaning it causes inflammation in the joints, muscles, skin and/or other organs. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, and is currently the second most common autoimmune rheumatic disease in the United States. The majority of Sjögren's sufferers are at least 40 years old at the time of diagnosis, and women are nine times more likely to develop the disease. Sjögren's syndrome can occur as a primary rheumatic condition or as a secondary disorder in association with other rheumatic diseases, such as systemic lupus erythematosus ("lupus"), scleroderma biliary cirrhosis or rheumatoid arthritis.

Sjögren's syndrome can damage vital organs of the body with symptoms that may remain stable, worsen, or go into remission. Some patients experience only the mild symptoms of dry eyes and mouth, while others go through cycles of good health followed by severe disease. While many patients are able to treat problems symptomatically, others suffer from blurred vision, constant eye discomfort, recurrent mouth infections, swollen parotid glands, hoarseness, and difficulty in swallowing and eating. Debilitating fatigue and joint pain can seriously impair quality of life.

There is currently no known cure for Sjögren's syndrome, nor is there a specific treatment to restore gland secretion. Treatment is generally symptomatic and supportive, including moisture replacement therapies to relieve the symptoms of eye and mouth dryness. Non-steroidal anti-inflammatory drugs can be used to treat musculoskeletal symptoms. For individuals with severe complications, corticosteroids or immunosuppressive drugs are often prescribed. These drugs can have serious side effects. Moreover, diagnosis of the disease is currently based on a combination of indications, such as objective and subjective dryness, autoantibodies, and mononuclear infiltrates and is primarily a process of elimination of other known diseases to arrive at the diagnosis of Sjögren's syndrome. Therefore, a need exists to not only accurately diagnose patients with Sjögren's syndrome, but to identify viable therapeutic targets for treatment of the disease.

Bone morphogenetic protein 6 (BMP6) is a member of the TGF-β superfamily of growth factors. Expression of BMP6 has been detected in several different mammalian tissues and cell types, including smooth muscle cells, growth plate chondrocytes, bronchiolar epithelium, cornea, epidermis, salivary gland and cells of the nervous system (Blessing et al., *J Cell Biol* 135(1):227-239, 1996). In vitro, BMP6 has been shown to inhibit cell division, promote terminal epithelial differentiation, and induce endochondral bone formation, osteoblastic differentiation and neuronal maturation (Heikinheimo et al., *Cancer Res* 59:5815-5821, 1999).

DNA methylation is the major modification of eukaryotic genomes and plays an essential role in mammalian development. The human proteins MECP2, MBD1, MBD2, MBD3, and MBD4 comprise a family of nuclear proteins related by the presence in each of a methyl-CpG binding domain (MBD). Each of these proteins, with the exception of MBD3, is capable of binding specifically to methylated DNA. MECP2, MBD1 and MBD2 can also repress transcription from methylated gene promoters. In contrast to other MBD family members, MECP2 is X-linked and subject to X inactivation.

X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIST gene (X (inactive)-specific transcript (non-protein coding)) is expressed exclusively from the XIC of the inactive X chromosome. The transcript is spliced but does not encode a protein. The transcript remains in the nucleus where it coats the inactive X chromosome.

Also provided herein is a method of treating a subject with Sjögren's syndrome by selecting a subject with increased BMP6 expression and administering to the subject a therapeutically effective amount of an agent that inhibits expression or activity of BMP6, wherein the agent is one or more compounds of Formula I. Also provided herein is a method of treating a subject with Sjögren's syndrome comprising administering to the subject a therapeutically effective amount of one or more compounds of Formula I, thereby treating the subject. In some embodiments, the compound of Formula I has a structure of Formula I-a.

Male Sjögren's syndrome patients express XIST, anoncoding RNA that is typically not expressed in males. Also described is the finding that male Sjögren's syndrome patients down-regulate MECP2, as well as other proteins involved in DNA methylation. In some embodiments, the biological sample is a salivary gland, such as a minor salivary gland.

A subset of male Sjögren's syndrome patients, Y-chromosome gene expression is down-regulated, as is expression of ribosomal proteins that regulate RNA processing and viral replication, and proteins that regulate DNA methylation. These findings provide additional markers that can be utilized for the diagnosis and treatment of Sjögren's syndrome.

Further provided is a method of treating a male subject with Sjögren's syndrome by selecting a male subject with increased expression of XIST, and administering to the subject a therapeutically effective amount of an agent that inhibits expression of XIST. Also provided is a method of treating a male subject with Sjögren's syndrome by selecting a male subject with increased expression of XIST, and administering to the subject a therapeutically effective amount of one or more compounds of Formula I. Also provided is a method of treating a male subject with Sjögren's syndrome by selecting a male subject with decreased expression of MECP2 and administering to the subject a therapeutically effective amount of one or more compounds of Formula I. Also provided is a method of treating a male subject with Sjögren's syndrome comprising administering to the male subject a therapeutically effective amount of one or more compounds of Formula I, thereby treating the male subject. In some embodiments, the compound of Formula I has a structure of Formula I-a.

Sjögren's syndrome patients exhibit a statistically significant increase in expression of BMP6 in salivary glands compared to healthy control subjects. Overexpression of BMP6 in the salivary gland increases electrical potential across the salivary gland. Disclosed herein is the finding that administration of an inhibitor of BMP6 signaling increases salivary flow in the salivary gland, wherein the inhibitor is one or more compounds of Formula I. In some embodiments, the compound of Formula I has a structure of Formula I-a.

Provided herein are methods of increasing salivary flow in a subject. In some embodiments, the method includes administering to the subject an inhibitor of BMP6 signaling, wherein the inhibitor is one or more compounds of Formula I. In other embodiments, the method includes selecting a subject with increased expression of BMP6 in a salivary gland of the subject relative to a control, and administering to the subject an inhibitor of BMP6 signaling, wherein the inhibitor is one or more compounds of Formula I. In some cases, the subject has Sjögren's syndrome. In some embodiments, the compound of Formula I has a structure of Formula I-a.

In some embodiments, the salivary gland exhibiting increased expression of BMP6 is a minor labial salivary gland, a parotid gland or a submandibular gland.

In some embodiments, the inhibitor of BMP6 is administered locally to the salivary gland, wherein the inhibitor is one or more compounds of Formula I. In some embodiments, the compound of Formula I has a structure of Formula I-a.

In some embodiments, the inhibitor of BMP6 signaling inhibits BMP type I receptor ALK2 and/or BMP type I receptor ALK3, wherein the inhibitor is one or more compounds of Formula I. In some embodiments, the compound of Formula I has a structure of Formula I-a.

In some embodiments, the biological sample is a tissue sample, such as salivary gland tissue (for example, tissue obtained by biopsy of a salivary gland). In some examples, the salivary gland is a minor labial salivary gland, parotid gland or a submandibular gland. In other embodiments, the biological sample is a bodily fluid sample, such as a saliva, tear, blood or serum sample.

In some embodiments, the disclosed methods further include providing an appropriate therapy to the subject diagnosed with Sjögren's syndrome. In some examples, the appropriate therapy comprises administering an agent that promotes salivary production (e.g., one or more compounds of Formula I) administering a corticosteroid, administering an immunosuppressive drug, administering a non-steroidal anti-inflammatory drug, administering an agent that inhibits expression or activity of BMP6, administering an agent that inhibits BMP signaling (e.g., one or more compounds of Formula I), or any combination thereof. In some embodiments, the compound of Formula I has a structure of Formula I-a.

Also provided is a method of increasing salivary flow in a subject by selecting a subject with increased expression of BMP6 in a salivary gland and administering to the subject a therapeutically effective amount of an agent that inhibits expression or activity of BMP6. In some examples, the agent is one or more compounds of Formula I. In some embodiments, the salivary gland is a minor labial salivary gland, parotid gland or a submandibular gland. In some embodiments, the compound of Formula I has a structure of Formula I-a.

In some embodiments, the agent that inhibits BMP signaling is one or more compounds of Formula I. In some embodiments, the compound of Formula I has a structure of Formula I-a.

In some embodiments, the agent that inhibits expression or activity of BMP6, or inhibits BMP signaling, is administered locally to the salivary gland, wherein the agent is one or more compounds of Formula I. In other embodiments, the agent that inhibits expression or activity of BMP6, or inhibits BMP signaling, is administered systemically, wherein the agent is one or more compounds of Formula I. In some embodiments, the compound of Formula I has a structure of Formula I-a.

In some embodiments, the method further includes providing an appropriate therapy to the subject diagnosed with Sjögren's syndrome. In some examples, the appropriate therapy comprises administering an agent that promotes salivary production (e.g., one or more compounds of Formula I), administering a corticosteroid, administering an immunosuppressive drug, administering a non-steroidal anti-inflammatory drug, administering an agent that inhibits expression or activity of BMP6, administering an agent that inhibits BMP signaling (e.g., one or more compounds of Formula I), or any combination thereof. In some embodiments, the compound of Formula I has a structure of Formula I-a.

In some embodiments, the disclosed methods further include providing an appropriate therapy to the male subject diagnosed with Sjögren's syndrome. In some examples, the appropriate therapy comprises administering an agent that promotes salivary production (e.g., one or more compounds of Formula I), administering a corticosteroid, administering an immunosuppressive drug, administering a non-steroidal anti-inflammatory drug, administering an agent that inhibits expression or activity of BMP6, administering an agent that inhibits BMP signaling (e.g, one or more compounds of Formula I), administering an agent that inhibits expression of XIST, administering a nucleic acid molecule encoding MECP2, or any combination thereof. In some embodiments, the compound of Formula I has a structure of Formula I-a.

Further provided are methods of treating a male subject with Sjögren's syndrome by selecting a male subject with increased expression of XIST and/or decreased expression of MECP2, and (i) administering to the subject a therapeutically effective amount of an agent that inhibits expression of XIST, or (ii) administering to the subject a therapeutically effective amount of nucleic acid molecule encoding MECP2, or both (i) and (ii).

Also provided are methods of increasing salivary flow in a male subject by selecting a subject with increased expression of XIST and/or decreased expression of MECP2, and administering to the subject (i) a therapeutically effective amount of an agent that inhibits expression of XIST, or (ii) a therapeutically effective amount of a nucleic acid molecule encoding MECP2 (such as a vector encoding MECP2), or both (i) and (ii).

Exemplary XIST inhibitors include, for example, antisense oligonucleotides or siRNA molecules that specifically hybridize with a XIST nucleic acid molecule. XIST nucleic acid sequences are publically available, such as the human XIST RNA sequence deposited under GenBank™ Accession No. NR-001564. Appropriate antisense oligonucleotides or siRNAs targeting XIST can be designed by one of skill in the art using publically available XIST sequences. The XIST antisense transcript Tsix is a known inhibitor of XIST (Senner and Brockdorff, Curr Opin Genet Dev 19(2):

122-126, 2009; Stavropoulos et al., *Proc Natl Acad Sci USA* 98(18):10232-10237, 2001) that can be used with the disclosed methods.

As described herein, significant alterations in sex-chromosome gene expression were identified in male SS patients, including XIST expression, decreased MECP2 expression and apparent silencing of Y-chromosome gene expression. This gene expression pattern, called Autoimmune Xist Y-chromosome Inactivation Syndrome (AXYIS), was also identified in affected tissues from males diagnosed with autoimmune diseases associated with pSS, including rheumatoid arthritis, type II diabetes mellitus, systemic sclerosis and lymphoma.

In particular, described herein is the finding that in a subset of male Sjögren's syndrome patients, Y-chromosome gene expression is down-regulated (for example, expression of the genes RPS4Y1, RPS4Y2, JARIDID, CYORF15B and CYORF14 is down-regulated), as is expression of ribosomal proteins that regulate RNA processing and viral replication (e.g., RPS4Y1, RPS4Y2 and RPS4X), and proteins that regulate DNA methylation (such as MDB6 and NASP). In addition, a significant number of duplications and/or deletions were identified in the opsin (OPN1LW, OPN1MW and OPN1MW2) and tex28 region of the X-chromosomes of male patients with Sjögren's syndrome. These findings provide additional markers that can be utilized for the diagnosis and treatment of Sjögren's syndrome in men.

Provided herein are methods of treating Sjögren's syndrome in a subject in need of treatment (such as a subject with increased expression of BMP6 in a salivary gland), by administering to the subject an agent that inhibits BMP6, such as a compound that inhibits expression (mRNA or protein expression) or at least one biological activity of BMP6, wherein the agent or compound is one or more compounds of Formula I. The agent or compound can also be an agent or compound that inhibits BMP signaling, such as one or more compounds of Formula I. In some embodiments, the compound of Formula I has a structure of Formula I-a.

In various embodiments, the present invention provides a method of treating a subject with Sjogren's syndrome, or a method of increasing salivary flow in a subject comprising selecting a subject with increased expression of BMP6 in a salivary gland of the subject relative to a control, and administering to the subject a therapeutically effective amount of an agent that inhibits expression or activity of BMP6, or an agent that inhibits BMP signaling, thereby treating the subject with Sjogren's syndrome, or increasing salivary flow in the subject, wherein the agent is one or more compounds of Formula I. In some embodiments, the salivary gland is a minor labial salivary gland, parotid gland or a submandibular gland. In some embodiments, the agent that inhibits expression or activity of BMP6 is one or more compounds of Formula I. In some embodiments, the compound of Formula I has a structure of Formula I-a.

N. Treatment of Diffuse Intrinsic Pontine Glioma (DIPG)

Diffuse Intrinsic Pontine Glioma (DIPG) (also known as diffuse intrinsic pontine glioma) is a tumor located in the pons (middle) of the brain stem. The brain stem is the bottommost portion of the brain, connecting the cerebrum with the spinal cord. Diffuse Intrinsic Pontine Glioma has been associated with the same gain of function mutations in ACVR1 as fibrodysplasia ossificans progressiva.

In various embodiments, the present invention provides a method for treating a subject with diffuse intrinsic pontine glioma (DIPG), comprising selecting the subject with diffuse intrinsic pontine glioma (DIPG), and administering to the subject a therapeutically effective amount of one or more compounds of Formula I, thereby treating the subject with diffuse intrinsic pontine glioma (DIPG). In some embodiments, the compound of Formula I has a structure of Formula I-a.

O. Propagation, Engraftment and Differentiation of Progenitor Cells Including Embryonic and Adult Stem Cells In Vitro and In Vivo BMP signals are important for regulating the differentiation and regeneration of precursor and stem cell populations, in some contexts and tissues preventing (while in other contexts directing) differentiation towards a lineage. Treatment with one or more compounds of Formula I as described herein can be used to (i) maintain a pluripotential state in stem cell or multipotent cell populations in vivo or in vitro; (ii) expand stem cell or multipotent cell populations in vivo or in vitro; (iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the de-differentiation of differentiated cell populations into multipotent or progenitor populations. In some embodiments, the compound of Formula I has a structure of Formula I-a.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, PIGF, and others), Sonic Hedgehog (SHH), notch, and Wnt signaling pathways to effect these changes (Okita et al. Curr. Stem Cell Res. Ther. 1:103-111, 2006). Treatment with one or more compounds of Formula I as described herein can be used to direct the differentiation of stem cells (e.g., embryonic stem cells) or tissue progenitor cells towards specific lineages for therapeutic application (Park et al. Development 131:2749-2762, 2004; Pashmforoush et al. Cell 117:373-386, 2004). Alternatively for certain cell populations, BMP inhibitors as described herein may be effective in preventing differentiation and promoting expansion, in order to produce sufficient numbers of cells to be effective for a clinical application. The exact dose and/or combination of one or more compounds of Formula I and other BMP antagonists or growth factor(s) or signaling molecule(s) may be highly specific to each cell and tissue type. In some embodiments, the compound of Formula I has a structure of Formula I-a.

For example, certain embryonic stem cell lines require co-culture with leukemia inhibitory factor (LIF) to inhibit differentiation and maintain the pluripotency of certain cultured embryonic stem cell lines (Okita et al. Curr. Stein Cell Res. Ther. 1:103-111, 2006). Use of one or more compounds of Formula I as described herein may be used to maintain pluripotency in the absence of LIF. Other ES cell lines require coculture with a specific feeder cell layer in order to maintain pluripotency. Use of one or more compounds of Formula I as described herein, alone or in combination with other agents, may be effective in maintaining pluripotency when concerns of contamination with a feeder cell layer, or its DNA or protein components would complicate or prevent use of cells for human therapy. In some embodiments, the compound of Formula I has a structure of Formula I-a.

In another example, in some circumstances antagonizing BMP signals with a protein such as noggin shortly before cessation of LIF in culture is able to induce differentiation into a cardiomyocyte lineage (Yuasa et al. Nat. Biotechnol. 23:607-611, 2005). Use of a pharmacologic BMP antagonist, such as one or more compounds of Formula I as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein antagonist of BMP such as noggin would be prohibitively expensive and entail complicated dosing. Delivery of a BMP antagonist as described herein, systemically or locally, could bias the differentiation of such precursor cells into functioning cardiomyocytes in situ. In some embodiments, the compound of Formula I has a structure of Formula I-a.

P. Applications of Compounds in Mammals

Pharmaceutical compositions comprising one or more compounds of Formula I as described herein can be used to treat subjects (e.g., humans, domestic pets, livestock, or other animals) by use of dosages and administration regimens that are determined to be appropriate by those of skill in the art, and these parameters can vary depending on, for example, the type and extent of the disorder treated, the overall health status of the subject, the therapeutic index of the compound, and the route of administration. Standard clinical trials can be used to optimize the dose and dosing frequency for any particular pharmaceutical composition comprising one or more compounds of Formula I as described herein. Exemplary routes of administration that can be used include oral, parenteral, intravenous, intraarterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used with the methods and compositions described herein are well known in the art and can be found, for example, in Remington: The Science and Practice of Pharmacy (20th edition, Ed., A. R. Gennaro), Lippincott Williams & Wilkins, 2000. In some embodiments, the compound of Formula I has a structure of Formula I-a.

Q. Inhibition of BMP Signaling in Insects

One or more compounds of Formula I may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and drosophila when this pathway is inhibited. BMP antagonists having very strong selectivity for arthropod BMP receptors versus those of humans can be used as insecticides or pest control agents that are demonstrably less toxic or more environmentally sound than current strategies. In some embodiments, the compound of Formula I has a structure of Formula I-a.

R. Ex Vivo Applications

In addition to being administered to patients in therapeutic methods, one or more compounds of Formula I as described herein can also be used to treat cells and tissues, as well as structural materials to be implanted into patients (see above), ex vivo. For example, the one or more compounds of Formula I can be used to treat explanted tissues that may be used, for example, in transplantation. In some embodiments, the compound of Formula I has a structure of Formula I-a.

S. Treatment of Hypercholesterolemia or Hyperlipoproteinemia

Treatment with small molecule or recombinant BMP inhibitors reduces vascular inflammation (via macrophage accumulation and cathepsin activity), atheroma formation, and vascular calcification in mice deficient in low-density lipoprotein receptor (LDLR$^{-/-}$). Without wishing to be bound by theory, as potential explanations for impact on vascular inflammation, oxidized LDL (oxLDL) has been found to increase BMP2 expression and induce the production of reactive oxygen species (ROS) in human aortic endothelial cells. ROS production induced by oxLDL appears to require BMP signaling, based on inhibition by small molecule or recombinant BMP inhibitors. Treatment with small molecule BMP inhibitors reduces plasma low-density lipoprotein levels without inhibiting HMG-CoA reductase activity, suggesting a role of BMP signaling in the regulation of LDL cholesterol biosynthesis. Small molecule BMP inhibitors have also been found to inhibit hepatosteatosis seen in LDLR-deficient mice fed a high-fat diet. Small molecule or recombinant BMP inhibitors inhibit the synthesis of ApoB-100 in hepatoma cells in vitro. These findings implicate BMP signaling in vascular calcification and atherogenesis and provide at least two novel mechanisms by which BMP signaling may contribute to the pathogenesis of atherosclerosis. These studies highlight the BMP signaling pathway as a therapeutic target in the treatment of atherosclerosis while identifying several novel functions of BMP signaling in the regulation of vascular oxidative stress, inflammation and lipid metabolism.

In various embodiments, one or more compounds of Formula I as described herein may be used for the reduction of circulating levels of ApoB-100 in patients. In various embodiments, one or more compounds of Formula I as described herein may be used for the reduction of circulating levels of LDL in patients. In various embodiments, one or more compounds of Formula I as described herein may be used for the treatment of hypercholesterolemia, hyperlipidemia, or hyperlipoproteinemia, including congenital or acquired hypercholesterolemia, hyperlipidemia, or hyperlipoproteinemia. In some embodiments, the congenital hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyperapobetalipoproteinemia, or small dense LDL syndrome (LDL phenotype B). In some embodiments, the compound of Formula I has a structure of Formula I-a.

In some embodiments, the acquired hypercholesterolemia, hyperlipidemia, or hyperlipoproteinemia is associated with diabetes mellitus, hyperlipidemic diet and/or sedentary lifestyle, obesity, metabolic syndrome, intrinsic or secondary liver disease, primary biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids. In various embodiments, one or more compounds of Formula I as described herein may be used for the treatment of diseases, disorders, or syndromes associated with defects in lipid absorption or metabolism, such as sitosterolemia, cerebrotendinous xanthomatosis, or familial hypobetalipoproteinemia. In some embodiments, the compound of Formula I has a structure of Formula I-a.

In various embodiments, one or more compounds of Formula I as described herein may be used for the treatment of diseases, disorders, or syndromes caused by hyperlipidemia, such as coronary artery disease and its manifestations (e.g., myocardial infarction; angina pectoris; acute coronary artery syndromes, such as unstable angina pectoris; cardiac dysfunction, such as congestive heart failure, caused by myocardial infarction; or cardiac arrhythmia associated with myocardial ischemia/infarction), stroke due to occlusion of arteries supplying portions of the brain, cerebral hemorrhage, peripheral arterial disease (e.g., mesenteric ischemia; renal artery stenosis; limb ischemia and claudication; subclavian steal syndrome; abdominal aortic aneurysm; thoracic aortic aneurysm, pseudoaneurysm, intramural hematoma; or penetrating aortic ulcer, aortic dissection, aortic stenosis, vascular calcification, xanthoma, such as xanthoma affecting tendons or scleral and cutaneous xanthomas, xanthelasma, or hepatosteatosis. In some embodiments, the compound of Formula I has a structure of Formula I-a.

In various embodiments, one or more compounds of Formula I or combination thereof as described herein may be used for the treatment of the foregoing diseases, disorders, or syndromes regardless of circulating lipid levels, such as in individuals exhibiting normal circulating lipid levels or metabolism. In some embodiments, the compound of Formula I has a structure of Formula I-a.

In various embodiments, one or more compounds of Formula I as described herein may be used for the reduction of secondary cardiovascular events arising from coronary, cerebral, or peripheral vascular disease. In various embodiments, one or more compounds of Formula I as described herein may be used to treat individuals regardless of lipid levels, such as used in the treatment of individuals exhibiting normal circulating cholesterol and lipid levels. In various embodiments, one or more compounds of Formula I as described herein may be administered conjointly with a HMG-CoA reductase inhibitor. In some embodiments, the compound of Formula I has a structure of Formula I-a.

In various embodiments, one or more compounds of Formula I as described herein may be used for the prevention of cardiovascular disease, such as in individuals with elevated markers of cardiovascular risk (e.g., C-reactive protein) or, for example, an elevated Framingham Risk Score. In various embodiments, one or more compounds of Formula I as described herein as described herein may be used to prevent cardiovascular disease in individuals exhibiting normal circulating cholesterol and lipid levels. In some embodiments, the compound of Formula I has a structure of Formula I-a.

In various embodiments, one or more compounds of Formula I as described herein are used in the treatment or prevention of the foregoing diseases, disorders, or syndromes, the patient being treated is not diagnosed with and/or is not suffering from one or more of the following conditions: vascular inflammation associated with atherosclerosis, automimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events. In some embodiments, the compound of Formula I has a structure of Formula I-a.

In various embodiments, one or more compounds of Formula I as described herein are used in the treatment or prevention of the foregoing diseases, disorders, or syndromes (e.g., for the reduction of circulating levels of ApoB-100 and/or LDL in patients; for the treatment of hypercholesterolemia, hyperlipidemia, or hyperlipoproteinemia, including congenital or acquired hypercholesterolemia, hyperlipidemia, or hyperlipoproteinemia; for the treatment of diseases, disorders, or syndromes associated with defects in lipid absorption or metabolism; for the treatment of diseases, disorders, or syndromes caused by hyperlipidemia; for the reduction of secondary cardiovascular events arising from coronary, cerebral, or peripheral vascular disease; or for the reduction of secondary cardiovascular events arising from coronary, cerebral, or peripheral vascular disease), the patient being treated is also diagnosed with and/or is also suffering from one or more of the following conditions: vascular inflammation associated with atherosclerosis, automimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events. In some embodiments, the compound of Formula I has a structure of Formula I-a.

T. Treatment of Cartilage Defects

The selective inhibition of specific BMP receptors enables cartilage formation by preventing calcification and mineralization of scaffolds produced by mesenchymal stem cells (Hellingman et al. Tissue Eng Part A. 2011 April; 17(7-8): 1157-67. Epub 2011 Jan. 17.) Accordingly, in some embodiments compounds of the invention as described herein may be useful to promote cartilage repair/regeneration in patients with cartilage injuries or defects, as well as in the ex vivo or in vitro production of cartilage tissue, e.g., for implantation, from appropriate cells, such as mesenchymal stem cells.

U. Application of Compounds with Varying Degrees of Selectivity: Compounds which Inhibit BMP Signaling Via Particular BMP Type I Receptors, or Compounds which Also Affect Signaling Via TGF-U, Activin, AMP Kinase, or VEGF Receptors.

In various embodiments several of the compounds of the present invention described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. Nat. Chem. Biol. 4:33-41, 2008). In such instances, in various embodiments compounds of the present invention as described herein which specifically antagonize the function of a subset of the BMP type I receptors may have the advantage of reduced toxicity or side effects, or greater effectiveness, or both.

In some embodiments compounds of the invention as described herein may have a high degree of selectivity for BMP vs. TGF-0, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g., decrease tumor size), when molecular phenotyping of specific patients' tumors reveals dysregulation of multiple pathways.

In some embodiments compounds of the invention as described herein (e.g., one or more compounds of Formula I) have a high degree of selectivity for ALK2 versus ALK1 or ALK3 or ALK4 or ALK5 or ALK6. Selective inhibition of ALK2 versus ALK1 or ALK3 or ALK4 or ALK5 or ALK6 may minimize unwanted effects or toxicity. Chronic ALK3 inhibition might impair normal mucosal epithelial turnover due to known importance in intestinal crypt stem cell recycling, and implication of ALK3 function in juvenile familial polyposis. ALK1 inhibition might impair normal vascular remodeling and lead to complications similar to human hereditary telangiectasia syndrome type 2 (HHT2), such as leaky capillaries, AV malformations, and bleeding. Accordingly, compounds that selectively inhibit ALK2 relative to ALK3 and ALK1 may help avoid toxicities of this type that might be encountered through the use of an unselective inhibitor. In some embodiments, the compound of Formula I has a structure of Formula I-a.

In certain embodiments, the invention provides a method of inhibiting the activity of ALK2 in a human, comprising administering to the human one or more compounds of Formula I that selectively inhibits the activity of human ALK2 relative to the activity of human ALK1. In some such embodiments, the one or more compounds of Formula I inhibits the activity of human ALK2 with an $IC_{50}$ that is lower by a factor of about 2 than its $IC_{50}$ for inhibiting the activity of human ALK1. In some such embodiments, the one or more compounds of Formula I inhibits the activity of human ALK2 with an $IC_{50}$ that is lower by a factor of 5 than its $IC_{50}$ for inhibiting the activity of human ALK1. In some such embodiments, the one or more compounds of Formula I inhibits the activity of human ALK2 with an $IC_{50}$ that is lower by a factor of 10 than its $IC_{50}$ for inhibiting the activity of human ALK1. In some such embodiments, the one or more compounds of Formula I inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK1. In some embodiments, the compound of Formula I has a structure of Formula I-a.

In certain embodiments, the invention provides a method of inhibiting the activity of ALK2 in a human, comprising administering to the human one or more compounds of Formula I that selectively inhibits the activity of human ALK2 relative to the activity of human ALK3. In some such embodiments, the one or more compounds of Formula I inhibits the activity of human ALK2 with an $IC_{50}$ that is lower by a factor of 15 than its $IC_{50}$ for inhibiting the activity of human ALK3. In some such embodiments, the one or more compounds of Formula I inhibits the activity of human ALK2 with an $IC_{50}$ that is lower by a factor of 20 than its $IC_{50}$ for inhibiting the activity of human ALK3. In some such embodiments, the one or more compounds of Formula I inhibits the activity of human ALK2 with an $IC_{50}$ that is lower by a factor of 30 than its $IC_{50}$ for inhibiting the activity of human ALK3. In some such embodiments, the one or more compounds of Formula I inhibits the activity of human ALK2 with an $IC_{50}$ that is lower by a factor of 50 or 100 or 200 or 300 or 400 or 500 or 600 or 800 or 1000 or 1500 or 2000 or 5000 or 10000 or 15,000 or 20,000 or 40,000 or 60,000 or 70,000 or 80,000 or 90,000 or 100,000 than its $IC_{50}$ for inhibiting the activity of human ALK3. In some embodiments, the compound of Formula I has a structure of Formula I-a.

In certain embodiments, the invention provides a method of inhibiting the activity of ALK2 in a human, comprising administering to the human one or more compounds of Formula I that selectively inhibits the activity of human ALK2 relative to the activity of human ALK4. In some such embodiments, the one or more compounds of Formula I inhibits the activity of human ALK2 with an $IC_{50}$ that is lower by a factor of 1000 than its $IC_{50}$ for inhibiting the activity of human ALK4. In some such embodiments, the one or more compounds of Formula I inhibits the activity of human ALK2 with an $IC_{50}$ that is lower by a factor of 2000 than its $IC_{50}$ for inhibiting the activity of human ALK4. In some such embodiments, the one or more compounds of Formula I inhibits the activity of human ALK2 with an $IC_{50}$ that is lower by a factor of 3000 than its $IC_{50}$ for inhibiting the activity of human ALK4. In some such embodiments, the one or more compounds of Formula I inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK4. In some embodiments, the compound of Formula I has a structure of Formula I-a.

In certain embodiments, the invention provides a method of inhibiting the activity of ALK2 in a human, comprising administering to the human one or more compounds of Formula I that selectively inhibits the activity of human ALK2 relative to the activity of human ALK6. In some such embodiments, the one or more compounds of Formula I inhibits the activity of human ALK2 with an $IC_{50}$ that is lower by a factor of 2 than its $IC_{50}$ for inhibiting the activity of human ALK6. In some such embodiments, the one or more compounds of Formula I inhibits the activity of human ALK2 with an $IC_{50}$ that is lower by a factor of 5 than its $IC_{50}$ for inhibiting the activity of human ALK6. In some such embodiments, the one or more compounds of Formula I inhibits the activity of human ALK2 with an $IC_{50}$ that is lower by a factor of 10 than its $IC_{50}$ for inhibiting the activity of human ALK6. In some such embodiments, the one or more compounds of Formula I inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK6. In some embodiments, the compound of Formula I has a structure of Formula I-a.

In one aspect, the invention provides a method of inhibiting the activity of ALK2 in a human, comprising administering to the human one or more compounds of Formula I that selectively inhibits the activity of human ALK2 relative to the activity of human ALK5. In some such embodiments, the one or more compounds of Formula I inhibits the activity of human ALK2 with an $IC_{50}$ that is lower by a factor of 1000 than its $IC_{50}$ for inhibiting the activity of human ALK5. In some such embodiments, the one or more compounds of Formula I inhibits the activity of human ALK2 with an $IC_{50}$ that is lower by a factor of 2000 than its $IC_{50}$ for inhibiting the activity of human ALK5. In some such embodiments, the one or more compounds of Formula I inhibits the activity of human ALK2 with an $IC_{50}$ that is lower by a factor of 3000 than its $IC_{50}$ for inhibiting the activity of human ALK5. In some such embodiments, the one or more compounds of Formula I inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK5. In some embodiments, the compound of Formula I has a structure of Formula I-a.

Pharmaceutical Compositions of the Invention

In various embodiments, the present invention provides a pharmaceutical composition, comprising: one or more compounds of Formula I; and a pharmaceutically acceptable carrier. In some embodiments, the compound of Formula I has a structure of Formula I-a.

One or more compounds of Formula I can be used in a pharmaceutical composition, e.g., combined with a pharmaceutically acceptable carrier, for administration to a patient. Such a composition can also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents can be included in the pharmaceutical composition to produce a synergistic effect with compounds of the invention, or to minimize side effects caused by the one or more compounds of Formula I. In some embodiments, the compound of Formula I has a structure of Formula I-a.

The pharmaceutical compositions as described herein can be in the form of a liposome or micelles in which one or more compounds of Formula I are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art and is therefore not described in detail herein. In some embodiments, the compound of Formula I has a structure of Formula I-a.

The terms "pharmaceutically effective amount" or "therapeutically effective amount", as used herein, means the total amount of each active component of the pharmaceutical composition or method that is sufficient to show a meaningful patient benefit, e.g., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods of treatment or use as described herein, comprises administering to a mammal in need of such treatment or use a pharmaceutically or therapeutically effective amount of one or more compounds of Formula I or a derivative, a pharmaceutically acceptable salt or ester form thereof. One or more compounds of Formula I as described herein can be administered in accordance with the methods described herein either alone or in combination with other therapies. In some embodiments, the compound of Formula I has a structure of Formula I-a.

Administration of the pharmaceutical compositions or to practice the methods described herein can be carried out in a variety of conventional ways, such as oral ingestion, inhalation, or cutaneous, subcutaneous, or intravenous, intramuscular, and intraperitoneal injection.

When a therapeutically effective amount of a one or more compounds of Formula I or pharmaceutical composition is administered orally, such compounds or compositions can be in the form of a tablet, capsule, powder, solution or elixir. When administered in tablet form, the pharmaceutical composition can additionally contain a solid carrier such as a gelatin or an adjuvant. The tablet, capsule, and powder can contain from about 5 to 95% of one or more compounds of Formula I and preferably from about 10% to 90% of one or more of a compound of Formula I or combination thereof. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils can be added. The liquid form of the pharmaceutical composition can further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of the active compound (i.e., one or more compounds of Formula I), and preferably from about 1 to 50% of the active compound. In some embodiments, the compound of Formula I has a structure of Formula I-a.

When a therapeutically effective amount of one or more compounds of Formula I or a composition thereof is administered by intravenous, cutaneous or subcutaneous injection, the composition can be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active compound (i.e., one or more compounds of Formula I, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition(s) can also contain stabilizers, preservatives, buffers, antioxidants, or other additives known to those of skill in the art. In some embodiments, the compound of Formula I has a structure of Formula I-a.

The amount of active compound(s) in the pharmaceutical composition will depend upon the nature and severity of the condition being treated, and on the nature of prior treatments the patient has undergone. Ultimately, the practitioner will decide the amount of compound with which to treat each individual patient. Initially, the practitioner may administer low doses of compound to observe the patient's response. Larger doses of compounds can be administered until the optimal therapeutic effect is obtained for the patient, and at that point the dosage is not increased further. It is contemplated that the various pharmaceutical compositions used to practice the methods described herein will contain about 0.1 µg to about 100 mg (preferably about 0.1 mg to about 50 mg, more preferably about 1 mg to about 2 mg) of one or more compounds of Formula I or additional bioactive compound per kg body weight. In some embodiments, the compound of Formula I has a structure of Formula I-a.

The duration of intravenous therapy using the pharmaceutical composition(s) will vary, depending on the severity of the disease being treated and the condition and potential idiosyncratic response of each individual patient. It is contemplated that the duration of each administration will be in the range of 12 to 24 hours of continuous intravenous administration. Ultimately the practitioner will decide on the appropriate duration of intravenous therapy using the pharmaceutical compositions as described herein.

Combination Therapies

In certain instances one or more compounds of Formula I as described herein can be used in combination with other current or future drug therapies, because the effects of inhibiting BMP alone may be less optimal by itself, and/or can be synergistic or more highly effective in combination with therapies acting on distinct pathways which interact functionally with BMP signaling, or on the BMP pathway itself. In certain instances, conjoint administration of a BMP inhibitor as described herein (e.g., one or more compounds of Formula I) with an additional drug therapy reduces the dose of the additional drug therapy such that it is less than the amount that achieves a therapeutic effect when used in a monotherapy (e.g., in the absence of a BMP inhibitor as described herein). In some embodiments, the compound of Formula I has a structure of Formula I-a.

Some non-limiting examples of combination therapies could include the following.

Coadministration of erythropoietin (Epogen) and BMP antagonists as described herein may be especially effective for certain types of anemia of inflammation, as described above, particularly in diseases such as end-stage renal disease in which chronic inflammation and erythropoietin insufficiency both act to promote anemia.

In certain embodiments, BMP inhibitors as described herein (e.g., one or more compounds of Formula I) may be administered conjointly with other antihyperlipidemic agents or antilipidemic agents including, but not limited to, HMG-CoA reductase inhibitors (e.g., atorvastatin, cerivastatin, fluvastatin, lovastatin, mevastatin, pitavastain, pravastatin, rosuvastatin, or simvastatin), fibrates (e.g., bezafibrate, ciprofibrate, clofibrate, gemfibrozil, or fenofibrate), ezetimibe, niacin, cholesteryl ester transfer protein (CETP) inhibitors (e.g., torcetrapib, anacetrapib, or dalcetrapib), cholestyramine, colestipol, probucol, dextrothyroxine, bile acid sequestrants, or combinations of the above. In some embodiments, the compound of Formula I has a structure of Formula I-a.

In certain embodiments, BMP inhibitors as described herein (e.g., one or more compounds of Formula I) may be administered conjointly with a treatment for diabetes including, but not limited to, sulfonyl ureas (e.g., chlorpropamide, tolbutamide, glyburide, glipizide, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, thiazolidinones (e.g., troglitazone, ciglitazone, pioglitazone, or rosiglitazone), oxadiazolidinediones, alpha-glucosidase inhibitors (e.g., miglitol or acarbose), agents acting on the ATP-dependent postassium channel of the beta cells (e.g., tolbutamide, glibenclamide, glipizide, glicazide, or repaglinide), nateglinide, glucagon inhibitors, inhibitors of hepatic enzymes involved in stimulation of gluconeogenesis and/or glycogenolysis, or combinations of the above. In some embodiments, the compound of Formula I has a structure of Formula I-a.

In certain embodiments, BMP inhibitors as described herein (e.g., one or more compounds of Formula I) may be administered conjointly with a treatment for obesity including, but not limited to, orlistat, sibutramine, phendimetrazine, phentermine, diethylpropion, benzphetamine, mazindol, dextroamphetamine, rimonabant, cetilistat, GT 389-255, APD356, pramlintide/AC137, PYY3-36, AC 162352/PYY3-36, oxyntomodulin, TM 30338, AOD 9604, oleoyl-estrone, bromocriptine, ephedrine, leptin, pseudoephedrine, or pharmaceutically acceptable salts thereof, or combinations of the above. In some embodiments, the compound of Formula I has a structure of Formula I-a.

In certain embodiments, BMP inhibitors as described herein (e.g., one or more compounds of Formula I) may be administered conjointly with an antihypertensive agent including, but not limited to, beta-blockers (e.g., alprenolol, atenolol, timolol, pindolol propranolol and metoprolol), ACE (angiotensin converting enzyme) inhibitors (e.g., benazepril, captopril, enalapril, fosinopril, lisinopril, quinapril and ramipril), calcium channel blockers (e.g., nifedipine, felodipine, nicardipine, isradipine, nimodipine, diltiazem and verapamil), and alpha-blockers (e.g., doxazosin, urapidil, prazosin and terazosin), or combinations of the above. In certain embodiments, BMP inhibitors as described herein may be administered conjointly with a treatment for anemia (e.g., anemia of inflammation associated with renal failure and hemodialysis), including but not limited to erythopoiesis-stimulating agents (e.g. erythropoietin). In some embodiments, the compound of Formula I has a structure of Formula I-a.

Tyrosine kinase receptor inhibitors, such as SU-5416, and BMP inhibitors as described herein (e.g., one or more of a compound of) may have synergistic effects at inhibiting angiogenesis, particularly for anti-angiogenic therapy against tumors. BMP signals (BMP-4) are thought to be critical for the commitment of stem or precursor cells to a hematopoietic/endothelial common progenitor, and may promote the proliferation, survival, and migration of mature endothelial cells necessary for angiogenesis (Park et al. Development 131:2749-2762, 2004). Thus antagonism of BMP signals using compounds as described herein may provide additional inhibition of angiogenesis at the level of endothelial precursors and cells. Similarly, co-treatment with BMP inhibitors as described herein (e.g., one or more compounds of Formula I) and other tyrosine kinase receptor inhibitors such as imatinib (Gleevec) could be used to inhibit vascular remodeling and angiogenesis of certain tumors. In some embodiments, the compound of Formula I has a structure of Formula I-a.

The combination of a sonic hedgehog agonist and a BMP inhibitor as described herein (e.g., one or more compounds of Formula I) may be particularly useful for promoting hair growth, as SHH activity is known to stimulate the transition of follicles out of telogen (resting) phase (Paladini et al. J. Invest. Dermatol. 125:638-646, 2005), while inhibiting the BMP pathway shortens the telogen phase (Plikus et al. Nature 451:340-344, 2008). The use of both would be expected to cause relatively increased time in the anagen or growth phase. In some embodiments, the compound of Formula I has a structure of Formula I-a.

Combined use of Notch modulators (e.g., gamma-secretase inhibitors) and BMP antagonists as described herein (e.g., one or more compounds of Formula I) may be more effective than either agent alone in applications designed to inhibit bone differentiation, because increasing evidence suggests both pathways function cooperatively to effect cell differentiation (Kluppel et al. *Bioessays* 27:115-118, 2005). These therapies may be synergistic in the treatment of tumors in which one or both pathways is deranged (Katoh, *Stem Cell Rev.* 3:30-38, 2007). In some embodiments, the compound of Formula I has a structure of Formula I-a.

Combined use of an Indian Hedgehog (IHH) antagonist and a BMP antagonist (e.g., one or more compounds of Formula I as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. *J. Biol. Chem.* 279:18544-18549, 2004; Minina et al. *Development* 128: 4523-4534, 2001). Coadministration of an IHH antagonist with one or more compounds of Formula I as described herein, therefore, may be more effective in inhibiting pathological bone growth due to hyperactive BMP signaling (such as in FOP), or in any of the inflammatory or traumatic disorders of pathologic bone formation described above. In some embodiments, the compound of Formula I has a structure of Formula I-a.

Strong experimental evidence exists for an effect of both Smo antagonism and BMP antagonism for treating glioblastoma. Compounds as described herein (e.g., one or more compounds of Formula I) may be used in combination with Smo antagonists to treat glioblastoma. In some embodiments, the compound of Formula I has a structure of Formula I-a.

In some embodiments, one or more compounds of Formula I is administered in combination with an agent selected from the group consisting of: a corticosteroid, a non-steroidal anti-inflammatory drug (NSAID), a lipoxygenase inhibitor, a leukotriene inhibitor, a mast cell stabilizing agent, an anti-histamine, a tumor necrosis factor (TNF) inhibitor, an IL-23 blocker, an IL1-RA therapy, a cytotoxic therapy, a bisphosphonate, an anti-rheumatic drug, CTA4-Ig therapy, anti-growth factor therapies, and an inhibitor of interleukin-1 signaling. In some embodiments, the compound of Formula I has a structure of Formula I-a.

Exemplary corticosteroids for use in combination with one or more compounds of Formula I include, but are not limited to, prednisone, cortisol, and hydrocortisone. In one embodiment, the corticosteroid is prednisone. In some embodiments, the compound of Formula I has a structure of Formula I-a.

Exemplary NSAIDs for use in combination with one or more compounds of Formula I include, but are not limited to, naproxen, ibuprofen, meloxicam, diclofenac, aspirin, piroxicam, sulindac, meclofenamic acid, and indomethacin. In some embodiments, the compound of Formula I has a structure of Formula I-a.

In some embodiments, one or more compounds of Formula I is administered in combination with a lipoxygenase inhibitor such as meclofenamate sodium or zileuton. In some embodiments, the compound of Formula I has a structure of Formula I-a.

Exemplary leukotriene inhibitors for use in combination with one or more compounds of Formula I include e.g., montelukast, zafirlukast, and pranlukast. In some embodiments, the compound of Formula I has a structure of Formula I-a.

Non-limiting examples of mast cell stabilizing agents for use in combination with one or more compounds of Formula I include, but are not limited to, cromolyn sodium, cromoglicic acid, ketotifen, olopatadine, omalizumab, pemirolast, quercetin, theophylline, caffeine, paraxanthine, aminophylline, and theobromine. In some embodiments, the compound of Formula I has a structure of Formula I-a.

In some embodiments, one or more compounds of Formula I is administered in combination with an anti-histamine, for example, diphenhydramine, cetirizine, ranitidine, famotidine, chlorphenamine, chlorodiphenhydramine, and fexofenidine, among others. In some embodiments, the compound of Formula I has a structure of Formula I-a.

Exemplary anti-tumor necrosis factor (anti-TNF) drugs contemplated for use with one or more compounds of Formula I include, but are not limited to, infliximab, etanercept, adalimumab, certolizumab, bupropion, and golimumab. In some embodiments, the compound of Formula I has a structure of Formula I-a.

Exemplary inhibitors of interleukin-23 (IL-23) signaling contemplated for use with one or more compounds of Formula I include, but are not limited to, ustekinumab and BI-855066. In some embodiments, the compound of Formula I has a structure of Formula I-a.

Exemplary inhibitors of interleukin-1 (IL-1) signaling or IL-iRA therapies contemplated for use with one or more compounds of Formula I include, but are not limited to, anakinra, canakinumab, and rilonacept. In some embodiments, the compound of Formula I has a structure of Formula I-a.

Exemplary cytotoxic therapies for use in combination with one or more compounds of Formula I include, but are not limited to, methotrexate, cyclophosphamide, 5-fluorouracil, doxorubicin, vincristine, bleomycin, procarbazine, prednisilone, dacarbazine, etoposide, cisplatin, oxaliplatin, among others. In some embodiments, the compound of Formula I has a structure of Formula I-a.

Exemplary bisphosphonates for use in combination with one or more compounds of Formula I include, but are not limited to, alendronate (FOSAMAX™), ibandronate (BONIVA™), risedronate (ACTONEL™, ATELVIA™), and zoledronic acid (RECLAST™) In some embodiments, the compound of Formula I has a structure of Formula I-a.

Exemplary anti-growth factor therapies for use in combination with one or more compounds of Formula I include, but are not limited to, anti-PDGF, anti-FGF, and anti-VEGF therapies. In some embodiments, the compound of Formula I has a structure of Formula I-a.

Exemplary disease modifying anti-rheumatic drugs for use in combination with one or more compounds of Formula I include, but are not limited to, azathioprine (IMURAN™) cyclophosphamide (CYTOXAN™), cyclosporine (NEORAL™), hydroxychloroquine (PLAQUENIL™), leflunomide (ARAVA™), methotrexate (RHEUMATREX™, TREXALL™), sulfasalazine (AZULFIDINE™), and tofacitinib (XELJANZ™), among others. In some embodiments, the compound of Formula I has a structure of Formula I-a.

In further embodiments, one or more compounds of Formula I can be administered in combination with cyclosporine, mycophenylate mofetil, among others. In some embodiments, the compound of Formula I has a structure of Formula I-a.

In some embodiments, one or more compounds of Formula I is administered in combination with at least one additional agent, wherein the at least one additional agent comprises an anti-inflammatory agent. Exemplary anti-inflammatory agents include, but are not limited to, an inhibitor of the activity of substance P; an inhibitor of the secretion of substance P; an inhibitor of the effects of substance P; an inhibitor of the activity of histamine; an inhibitor of the secretion of histamine; an inhibitor of the effects of histamine; an inhibitor of mast cell function; an inhibitor of Toll-like receptor signaling; an inhibitor of MyD88; an inhibitor of TRIF; apyrase; and an agent to catalyze hydrolysis of ATP. In some embodiments, the compound of Formula I has a structure of Formula I-a.

In some embodiments, one or more compounds of Formula I is administered in combination with at least one additional agent, wherein the at least one additional agent comprises an anti-growth factor agent. Exemplary anti-growth factor agents include, but are not limited to, an inhibitor of PDGF ligands; an inhibitor of PDGF-AA; an inhibitor of PDGF-BB; an inhibitor of PDGFR-alpha receptor function; an inhibitor of PDGFR-beta receptor function; a neutralizing antibody against Activin A; a neutralizing antibody against Activin B; a neutralizing antibody against Activin A ligands; a neutralizing antibody against Activin B ligands; a neutralizing antibody against heterodimeric ligands containing Inhibin bA subunits encoded by the INHBA; a neutralizing antibody against heterodimeric ligands containing Inhibin bB subunits encoded by the INHBB gene; a ligand trap of BMP ligands; a ligand trap of Activin ligands; a ligand trap of soluble extracellular domains of a type II Activin receptor ActRIIA; a ligand trap of soluble extracellular domains of a type II Activin receptor ActRIIB; a ligand trap of soluble extracellular domains of a BMP type I receptor ALK2; a ligand trap of soluble extracellular domains of a BMP type I receptor ALK3; and a ligand trap of soluble extracellular domains of a BMP type I receptor ALK6. In some embodiments, the compound of Formula I has a structure of Formula I-a.

In some embodiments, one or more compounds of Formula I is administered in combination with at least one additional agent, wherein the at least one additional agent comprises an anti-osteogenic signaling agent or an anti-chondrogenic signaling agent. Exemplary anti-osteogenic signaling agents or an anti-chondrogenic signaling agents include, but are not limited to a RAR-gamma agonist; a nonselective RAR agonist; an agent that inhibits the activity of osteogenic transcription factor Runx2; an agent that inhibits the expression of osteogenic transcription factor Runx2; an agent that promotes the degradation of osteogenic transcription factor Runx2; an agent that inhibits the activity of chondrogenic transcription factor Sox9; an agent that inhibits the expression of chondrogenic transcription factor Sox9; an agent that promotes the degradation of chondrogenic transcription factor Sox9; an inhibitor of HIF-1 alpha activity; and an inhibitor of HIF-1 alpha expression. In some embodiments, the compound of Formula I has a structure of Formula I-a.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of the compound of formula I, the compound of formula II, or the compound of formula III. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

When used in combination, one or more compounds of Formula I can be administered separately or in different formulations from at least one additional agent as described herein or can be administered in a single formulation comprising one or more compounds of Formula I and the additional agent. One or more compounds of Formula I can be administered simultaneously or concurrently with the at least one additional agent. Administration of one or more compounds of Formula I can be administered using the same or different modes of administration (e.g., oral, intravenous, injection, etc). Administration of one or more compounds of Formula I and the at least one additional agent can occur simultaneously, within 15 min, within 30 min, or can be separated by at least one hour (e.g., at least 2, at least 3, at least 4, at least 5, at least 6, at least 7, at least 8, at least 9, at least 10, at least 11, at least 12 or more hours). One of skill in the art can easily determine an appropriate dosing regimen for a combination treatment comprising one or more compounds of Formula I and at least one additional agent, for example, to reduce side effects, to prevent metabolic interference from one of the agents, to enhance activity of one or more compounds of Formula I, or to otherwise improve pharmacodynamic or pharmacokinetic factors. In some embodiments, the compound of Formula I has a structure of Formula I-a.

It is contemplated herein that a combination of at least one additional agent as described above with one or more compounds of Formula I can produce a synergistic effect that is greater than the sum of the effects of each agent administered alone. In such embodiments, it is contemplated that a lower dose of one or more compounds of Formula I is administered in combination with a second agent than is required for a therapeutic effect when one or more compounds of Formula I is administered alone. In some embodiments, the compound of Formula I has a structure of Formula I-a.

Dosage and Administration

The term "treatment" includes prophylaxis and therapy. Prophylaxis or treatment can be accomplished by a single administration at a single time point or multiple time points.

In one aspect, the methods described herein provide a method for treating a disease or disorder comprising abnormal bone formation in a subject (e.g., a heterotopic ossification diseases). In one embodiment, the subject can be a mammal. In another embodiment, the mammal can be a human, although the approach is effective with respect to all mammals. The method comprises administering to the subject an effective amount of a pharmaceutical composition comprising one or more compounds of Formula I. In some embodiments, the compound of Formula I has a structure of Formula I-a.

The dosage range for the agent depends upon the potency, and includes amounts large enough to produce the desired effect, e.g., reduction in at least one symptom of abnormal bone formation. The dosage should not be so large as to cause unacceptable adverse side effects. Generally, the dosage will vary with the type of inhibitor (e.g., an antibody or fragment, small molecule, siRNA, etc.) and with the age, condition, and sex of the patient. The dosage can be determined by one of skill in the art and can also be adjusted by the individual physician in the event of any complication. Typically, the dosage ranges from 0.1 mg/kg body weight to 1 g/kg body weight. In some embodiments, the dosage range is from 0.1 mg/kg body weight to 1 g/kg body weight, from 0.1 mg/kg body weight to 500 mg/kg body weight, from 0.1 mg/kg body weight to 250 mg/kg body weight, from 0.1 mg/kg body weight to 100 mg/kg body weight, from 0.1 mg/kg body weight to 50 mg/kg body weight, from 0.1 mg/kg body weight to 10 mg/kg body weight, from 10 mg/kg to 100 mg/kg, from 15 mg/kg to 100 mg/kg, from 20 mg/kg to 100 mg/kg, from 25 mg/kg to 100 mg/kg, from 30 mg/kg to 100 mg/kg, from 40 mg/kg to 100 mg/kg, from 50 mg/kg to 100 mg/kg, from 60 mg/kg to 100 mg/kg, from 70 mg/kg to 100 mg/kg, from 75 mg/kg to 100 mg/kg, from 25 mg/kg to 50 mg/kg, from 50 mg/kg to 200 mg/kg, from 75 mg/kg to 250 mg/kg, from 100 mg/kg to 300 mg/kg, from 100 mg/kg to 200 mg/kg, from 100 mg/kg to 400 mg/kg, from 100 mg/kg to 500 mg/kg, from 100 mg/kg to 750 mg/kg from 200 mg/kg to 1000 mg/kg, from 300 mg/kg to 1000 mg/kg, from 400 mg/kg to 1000 mg/kg, from 500 mg/kg to 1000 mg/kg, from 600 mg/kg to 1000 mg/kg, from 700 mg/kg to 1000 mg/kg, from 800 mg/kg to 1000 mg/kg, from 900 mg/kg to 1000 mg/kg, from 250 mg/kg to 750 mg/kg, from 300 mg/kg to 600 mg/kg, or any range there between.

In certain embodiments, the dose of the agent is at least 10 mg/kg/day; in other embodiments the dose of the agent is at least 20 mg/kg/day, at least 25 mg/kg/day, at least 30 mg/kg/day, at least 40 mg/kg/day, at least 50 mg/kg/day, at least 60 mg/kg/day, at least 70 mg/kg/day, at least 80 mg/kg/day, at least 90 mg/kg/day, at least 100 mg/kg/day, at least 125 mg/kg/day, at least 150 mg/kg/day, at least 175 mg/kg/day, at least 200 mg/kg/day, at least 250 mg/kg/day, at least 300 mg/kg/day, at least 400 mg/kg/day, at least 500 mg/kg/day or more.

In some embodiments, the dosage range of the agent for use in a human subject is from 10 mg/day to 250 mg/day, from at 15 mg/day to 200 mg/day, from 20 mg/day to 200 mg/day, from 25 mg/day to 200 mg/day, from 25 mg/day to 175 mg/day, from 25 mg/day to 150 mg/day, from 25 mg/day to 125 mg/day, from 25 mg/day to 100 mg/day, from 25 mg/day to 75 mg/day, from 25 mg/day to 50 mg/day, from 50 mg/day to 200 mg/day, from 75 mg/day to 200 mg/day, from 100 mg/day to 200 mg/day, from 125 mg/day to 200 mg/day, from 150 mg/day to 200 mg/day, from 175 mg/day to 200 mg/day, from 50 mg/day to 200 mg/day, from 50 mg/day to 175 mg/day, from 50 mg/day to 150 mg/day, from 50 mg/day to 100 mg/day, from 50 mg/day to 75 mg/day, from 75 mg/day to 200 mg/day, from 75 mg/day to 175 mg·day, from 75 mg/day to 150 mg/day, from 75 mg/day to 125 mg/day, from 75 mg/day to 100 mg/day, from 100 mg/day to 200 mg/day, from 100 mg/day to 175 mg/day, from 100 mg/day to 125 mg/day, from 125 mg/day to 200 mg/day, from 125 mg/day to 175 mg/day, from 125 mg/day to 150 mg/day, from 150 mg/day to 200 mg/day, from 150 mg/day to 175 mg/day, from 175 mg/day to 200 mg/day, or any range there between.

In one embodiment, the dose of one or more compounds of Formula I used in humans for the treatment of abnormal bone formation in soft tissue is less than the dose of one or more compounds of Formula I typically used in treatment of oncologic diseases and cancers. In some embodiments, the compound of Formula I has a structure of Formula I-a.

Administration of the doses recited above can be repeated for a limited period of time. In some embodiments, the doses are given once a day, or multiple times a day, for example but not limited to three times a day. In another embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in at least one symptom of a cancer (see "Efficacy Measurement" below). Such effective amounts can be gauged in clinical trials as well as animal studies for a given agent.

Agents useful in the methods and compositions described herein can be administered systemically or can be administered orally. It is also contemplated herein that the agents can also be delivered intravenously (by bolus or continuous infusion), by inhalation, intranasally, intraperitoneally, intramuscularly, subcutaneously, intracavity, and can be delivered by peristaltic means, if desired, or by other means known by those skilled in the art.

In some embodiments, the pharmaceutically acceptable formulation used to administer the active compound provides sustained delivery, such as "slow release" of the active compound to a subject. For example, the formulation can deliver the agent or composition for at least one, two, three, or four weeks after the pharmaceutically acceptable formulation is administered to the subject. Preferably, a subject to be treated in accordance with the methods described herein is treated with the active composition for at least 30 days (either by repeated administration or by use of a sustained delivery system, or both).

As used herein, the term "sustained delivery" is intended to include continual delivery of the composition in vivo over a period of time following administration, preferably at least several days, a week, several weeks, one month or longer. Sustained delivery of the active compound can be demonstrated by, for example, the continued therapeutic effect of the composition over time (such as sustained delivery of the agents can be demonstrated by continued improvement or maintained improvement in cancer symptoms in a subject).

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., tumor site). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood or skeletal muscle tissue in the ranges specified for in vivo therapies are contemplated.

Efficacy Measurement

The efficacy of a given treatment for a disorder comprising abnormal bone growth as described herein can be determined by the skilled clinician. However, a treatment is considered "effective treatment," as the term is used herein, if any one or all of the signs or symptoms of the disease or disorder is/are altered in a beneficial manner (e.g., reduced ossification, regression of abnormal bone growths, reduced pain, increased range of motion etc.), other clinically accepted symptoms or markers of disease are improved, or even ameliorated, e.g., by at least 10% following treatment with an agent comprising one or more compounds of Formula I. Efficacy can also be measured by failure of an individual to worsen as assessed by stabilization of the disease or disorder, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of abnormal bone growth; or (2) relieving the disease, e.g., causing regression of symptoms; and (3) preventing or reducing the likelihood of the development of a disease (e.g., ossification following trauma). In some embodiments, the compound of Formula I has a structure of Formula I-a.

An effective amount for the treatment of a disease means that amount which, when administered to a mammal in need thereof, is sufficient to result in effective treatment as that term is defined herein, for that disease. Efficacy of an agent can be determined by assessing physical indicators of abnormal bone growth, such as e.g., reduced size of abnormal bone growth, slowed deposition of abnormal bone, regression of bone growth, improvement in mobility etc.

Non-Limiting Embodiments of the Invention

In various embodiments, the present invention provides selective and potent small molecule inhibitors of the BMP type I receptor ALK2, encoded by gene ACVR1, wherein the inhibitor are one or more compounds of Formula I. Activating mutations in ACVR1 lead to a pediatric autosomal dominant syndrome called fibrodysplasia ossificans progressiva (FOP). Affected individuals develop debilitating ossification of soft tissues early in life leading to severe loss of function and reduced life expectancy. The ALK2 inhibitors described herein have therapeutic potential for attenuating the heterotopic ossification of FOP. In some embodiments, the compound of Formula I has a structure of Formula I-a.

In various embodiments, the one or more compounds of Formula I show potent enzymatic and cellular activity, are selective ALK2 inhibitors and inhibitors of other BMP and TGFβ type I receptors, and showed cellular activity with improved absorption, distribution, metabolism, and excretion (ADME) properties (e.g., decreased susceptibility to aldehyde oxidase metabolism). In some embodiments, the compound of Formula I has a structure of Formula I-a.

In some embodiments of the invention, a highly selective ALK2 and RIPK2 kinase inhibitor is a compound selected from Compound 79:

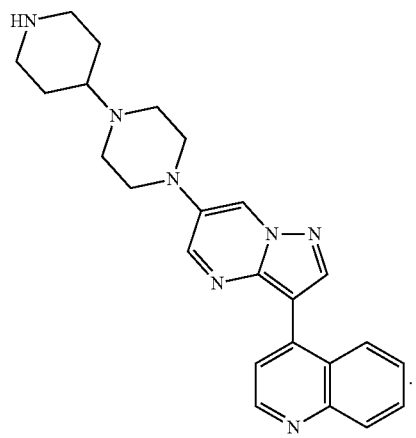 [SMILES: c1ccc2c(-c3cnn4cc(N5CCN(C6CCNCC6)CC5)cnc34)ccnc2c1]

In various embodiments, the present invention provides a therapy for treating a subject with fibrodysplasia ossificans progressiva (FOP) or non-genetic forms of heterotopic ossification (HO), wherein the therapy comprises administering one or more compounds of Formula I to the subject. In some embodiments the therapy is a prophylactic therapy. In some embodiments, the compound of Formula I has a structure of Formula I-a.

In various embodiments, the present invention provides a post-surgical or post-procedural prophylaxis given to patients with fibrodysplasia ossificans progressiva (FOP) or heterotopic ossification (HO) following intentional surgical removal of heterotopic bone, or other necessary surgical or medical procedures, to prevent the recurrence or formation of bone that normally follows any kind of soft tissue injury, wherein the prophylaxis comprises one or more compounds of Formula I. In some embodiments, the compound of Formula I has a structure of Formula I-a.

In various embodiments, the present invention provides a therapy for treating a subject with FOP or HO at the time of a spontaneous flare, or around the time of an unplanned or an unanticipated soft tissue injury, wherein the therapy comprises administering one or more compounds of Formula I to the subject. In some embodiments, the therapy is an acute therapy. In some embodiments, the compound of Formula I has a structure of Formula I-a.

In various embodiments, one or more compounds of Formula I may be used as a prophylactic therapy, acute therapy, or chronic therapy for patients with heterotopic ossification (HO) or heterotopic ossification (HO) diseases (e.g., fibrodysplasia ossificans progressiva (FOP)), including but not limited to diseases and disorders associated with altered BMP signaling. In some embodiments, the compound of Formula I has a structure of Formula I-a.

In certain embodiments, the compounds of the present invention inhibit BMP-induced phosphorylation of SMAD1/5/8.

In some embodiments, the present invention provides a pharmaceutical composition comprising a compound of the invention as disclosed herein and a pharmaceutically acceptable excipient or solvent. In certain embodiments, a pharmaceutical composition may comprise a prodrug of a compound as disclosed herein.

In some embodiments, the present invention provides a method of inhibiting BMP-induced phosphorylation of SMAD1/5/8, comprising contacting a cell with a compound of the invention as disclosed herein.

In certain embodiments, the method treats or prevents a disease or condition in a subject that would benefit by inhibition of Bone Morphogenetic Protein (BMP) signaling. In certain embodiments, the disease or condition is selected from pulmonary hypertension, hereditary hemorrhagic telangiectasia syndrome, cardiac valvular malformations, cardiac structural malformations, fibrodysplasia ossificans progressiva, juvenile familial polyposis syndrome, parathyroid disease, cancer (e.g., breast carcinoma, diffuse intrinsic pontine glioma (DIPG), prostate carcinoma, renal cell carcinoma, bone metastasis, lung metastasis, osteosarcoma, and multiple myeloma), anemia, vascular calcification, atherosclerosis, valve calcification, renal osteodystrophy, inflammatory disorders (e.g., ankylosing spondylitis), infections with viruses, bacteria, fungi, tuberculosis, and parasites. In some embodiments, the cancer is selected from adenocarcinoma, prostate carcinoma, breast carcinoma, renal cell carcinoma, bone metastasis, lung metastasis, osteosarcoma, and multiple myeloma.

In certain embodiments, the method reduces the circulating levels of ApoB-100 and/or LDL and/or total cholesterol in a subject that has levels of ApoB-100 and/or LDL and/or total cholesterol that are abnormally high or that increase a patient's risk of developing a disease or unwanted medical condition. In certain embodiments, the method of reducing circulating levels of ApoB-100 and/or LDL and/or total cholesterol in a subject reduces the risk of primary or secondary cardiovascular events. In certain embodiments, the method treats or prevents a disease or condition in a subject that would benefit by inhibition of Bone Morphogenetic Protein (BMP) signaling. In certain embodiments, the disease or condition is selected from pulmonary hypertension; hereditary hemorrhagic telangiectasia syndrome; cardiac valvular malformations; cardiac structural malformations; fibrodysplasia ossificans progressive; juvenile familial polyposis syndrome; parathyroid disease; cancer (e.g., breast carcinoma, prostate carcinoma, renal cell carcinoma, bone metastasis, lung metastasis, osteosarcoma, and multiple myeloma); anemia; vascular calcification; vascular inflammation; atherosclerosis; acquired or congenital hypercholesterolemia or hyperlipoproteinemia; diseases, disorders, or syndromes associated with defects in lipid absorption or metabolism; diseases, disorders, or syndromes caused by hyperlipidemia; valve calcification; renal osteodystrophy; inflammatory disorders (e.g., ankylosing spondylitis); infections with viruses; bacteria; fungi; tuberculosis; and parasites.

In some embodiments, the invention provides a method of treating hypercholesterolemia, hyperlipidemia, hyperlipoproteinemia or hepatic steatosis in a subject comprising administering an effective amount of a compound of the invention as disclosed herein. In certain such embodiments, the hypercholesterolemia, hyperlipidemia, hyperlipoproteinemia or hepatic steatosis is acquired hypercholesterolemia, hyperlipidemia, hyperlipoproteinemia or hepatic steatosis. In certain such embodiments, the hypercholesterolemia, hyperlipidemia, hyperlipoproteinemia, or hepatic steatosis is associated with diabetes mellitus, hyperlipidemic diet and/or sedentary lifestyle, obesity, metabolic syndrome, intrinsic or secondary liver disease, biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids. In some embodiments, the invention provides a method of reducing primary and secondary cardiovascular events arising from coronary, cerebral, or peripheral vascular disease in a subject, comprising administering an effective amount of a compound of the invention as disclosed herein.

In some embodiments, the present invention provides a method of preventing and treating hepatic dysfunction in a subject associated with nonalcoholic fatty liver disease (NAFLD), steatosis-induced liver injury, fibrosis, cirrhosis, or non-alcoholic steatohepatitis (NASH) in a subject comprising administering an effective amount of a compound of the invention as disclosed herein.

In some embodiments, the present invention provides a method of inducing expansion or differentiation of a cell, comprising contacting the cell with a compound of the invention as disclosed herein. In certain embodiments, the cell is selected from an embryonic stem cell and an adult stem cell. In certain embodiments, the cell is in vitro.

In certain embodiments, a method of the present invention may comprise contacting a cell with a prodrug of a compound of the invention as disclosed herein.

In various embodiments, the present invention provides a method of inhibiting BMP-induced phosphorylation of SMAD1/5/8, comprising SMAD1/5/8, comprising contacting the cell with a compound of the invention as disclosed herein. In some embodiments, the method treats or prevents a disease or condition in a subject that would benefit by inhibition of Bone Morphogenetic Protein (BMP) signaling. In some embodiments, the disease or condition is selected from pulmonary hypertension, hereditary hemorrhagic telangiectasia syndrome, cardiac valvular malformations, cardiac structural malformations, fibrodysplasia ossificans progressiva, juvenile familial polyposis syndrome, parathyroid disease, cancer, anemia, vascular calcification, atherosclerosis, valve calcification, renal osteodystrophy, inflammatory disorders, and infections with viruses, bacteria, fungi, tuberculosis, and parasites. IN some embodiments, the disease or condition is a cancer selected from breast carcinoma, prostate carcinoma, renal cell carcinoma, bone metastasis, lung metastasis, osteosarcoma, and multiple myeloma. In some embodiments, the disease or condition is an inflammatory disorder such as ankylosing spondylitis.

In various embodiments, the present invention provides method of inducing expansion or differentiation of a cell, comprising contacting the cell with a compound of the invention as disclosed herein. In some embodiments, the cell is selected from an embryonic stem cell and an adult stem cell. In some embodiments, the cell is in vitro.

In various embodiments, the present invention provides method of reducing circulating levels of ApoB-100 or LDL in a subject, comprising administering an effective amount of a compound of the invention as disclosed herein.

In various embodiments, the present invention provides a method of treating hypercholesterolemia, hyperlipidemia, or hyperlipoproteinemia in a subject, comprising administering an effective amount of a compound of the invention as disclosed herein. In some embodiments, the hypercholesterolemia, hyperlipidemia, or hyperlipoproteinemia is congenital hypercholesterolemia, hyperlipidemia, or hyperlipoproteinemia. In some embodiments, the hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyperapobetalipoproteinemia, or small dense LDL syndrome (LDL phenotype B). In some embodiments, the hypercholesterolemia, hyperlipidemia, or hyperlipoproteinemia is acquired hypercholesterolemia, hyperlipidemia, or hyperlipoproteinemia. In some embodiments, the hypercholesterolemia, hyperlipidemia, or hyperlipoproteinemia is associated with diabetes mellitus, hyperlipidemic diet and/or sedentary lifestyle, obesity, metabolic syndrome, intrinsic or secondary liver disease, primary biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids.

In various embodiments, the present invention provides a method of treating diseases, disorders, or syndromes associated with defects in lipid absorption or metabolism or caused by hyperlipidemia in a subject, comprising administering an effective amount of a compound of the invention as disclosed herein.

In various embodiments, the present invention provides a method of reducing secondary cardiovascular events arising from coronary, cerebral, or peripheral vascular disease in a subject, comprising administering an effective amount of a compound of the invention as disclosed herein.

In various embodiments, the present invention provides a method of preventing cardiovascular disease in a subject with elevated markers of cardiovascular risk, comprising administering an effective amount of a compound of the invention as disclosed herein.

In various embodiments, the present invention provides a method of treating diseases, disorders, or syndromes associated with defects in a fibrilin-2 gene in a subject, comprising administering an effective amount of a compound of the invention as disclosed herein. In some embodiments, the disease, disorder or syndrome is congenital muscular dystrophy.

EXAMPLES

The invention is further illustrated by the following examples which are intended to be purely exemplary of the invention, and which should not be construed as limiting the invention in any way. The following examples are illustrative only, and are not intended to limit, in any manner, any of the aspects described herein. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

General Methods

All air or moisture sensitive reactions were performed under positive pressure of nitrogen with oven-dried glassware. Chemical reagents and anhydrous solvents were obtained from commercial sources and used as is. Preparative purification was performed on a Waters semipreparative HPLC instrument. The column used was a Phenomenex Luna C18 (5 μm, 30 mm×75 mm) at a flow rate of 45 mL/min. The mobile phase consisted of acetonitrile and water (each containing 0.1% trifluoroacetic acid). A gradient from 10% to 50% acetonitrile over 8 min was used during the purification. Fraction collection was triggered by UV detection (220 nm). Alternately, flash chromatography on silica gel was performed using forced flow (liquid) of the indicated solvent system on Biotage KP-Sil pre-packed cartridges and using the Biotage SP-1 automated chromatography system.

Analytical analysis for purity was determined by four different methods denoted as final QC methods 1, 2, 3, and 4.

Final QC Method 1. Analysis was performed on an Agilent 1290 Infinity series HPLC instrument. UHPLC long gradient equivalent from 4% to 100% acetonitrile (0.05% trifluoroacetic acid) in water over 3 min run time of 4.5 min with a flow rate of 0.8 mL/min. A Phenomenex Luna C18 column (3 μm, 3 mm×75 mm) was used at a temperature of 50° C.

Final QC Method 2. Analysis was performed on an Agilent 1260 with a 7 min gradient from 4% to 100% acetonitrile (containing 0.025% trifluoroacetic acid) in water (containing 0.05% trifluoroacetic acid) over 8 min run time at a flow rate of 1 mL/min. A Phenomenex Luna C18 column (3 μm, 3 mm×75 mm) was used at a temperature of 50° C.

Final QC Method 3. Analysis was performed on a Shimadzu LCMS-2010 series HPLC instrument with a gradient of 0% to 60% acetonitrile (0.05% trifluoroacetic acid) in water over 6.5 min run time of 7 min with a flow rate of 0.8 mL/min. An Xtimate C18 column (3 m, 2.1 mm×30 mm) was used at a temperature of 50° C.

Final QC Method 4. Analysis was performed on a Shimadzu LCMS-2010 series HPLC instrument with a gradient of 0 to 60% acetonitrile (0.05% ammonium hydroxide) in water over 6 min then kept at 60% acetonitrile for 0.5 min with a flow rate of 0.8 m/min. An Xbridge Shield RP C18 column (5 μM, 2.1 mm×50 mm) was used at a temperature of 30° C.

Purity determination was performed using an Agilent diode array detector for both final QC method 1, 2, 3 and 4. Mass determination was performed using an Agilent 6130 mass spectrometer or Shimadzu LCMS-2010 series mass spectrometer with electrospray ionization in the positive mode. All of the analogs for assay have purity greater than 95% based on both analytical methods through the quantitation of area-under-curve (AUC) at 220 and 254 nm wavelength. $^1$H NMR spectra were recorded on Varian 400 MHz or Bruker 400 MHz spectrometers. Chemical Shifts were reported in ppm. Following are the references of different deuterated solvents: DMSO-$d_6$ reference (2.50 ppm), CD$_3$OD (3.31 ppm), CDCl$_3$ (7.26 ppm) and D$_2$O (4.80 ppm). Data are reported as follows: chemical shift, multiplicity (s=singlet, d=doublet, t=triplet, q=quartet, br=broad, m=multiplet), coupling constants, and number of protons. High resolution mass spectrometry results were recorded on Agilent 6210 time-of-flight (TOF) LC-MS system.

General Procedure for the Synthesis of Compounds of Formula I or Formula I-a (Examples 1-4).

Example 1

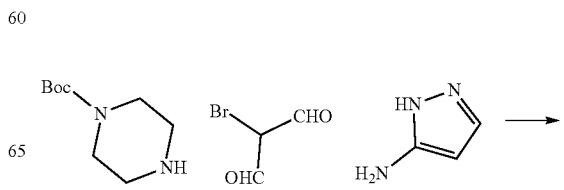

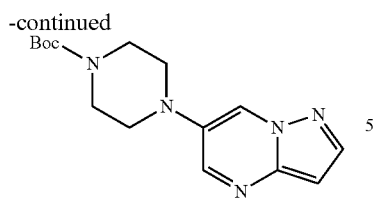

To a solution of tert-butyl piperazine-1-carboxylate (0.50 g, 2.68 mmol) in dioxane (2.5 ml), 2-bromomalonaldehyde (0.27 g, 1.79 mmol) and Hunig's base (0.47 ml, 2.68 mmol) were added and the reaction was stirred at room temperature for 24 h. After this time, 1H-pyrazol-5-amine (0.06 ml, 0.89 mmol) was added and the reaction mixture was heated in a microwave for 1 h at 100° C. After cooling to room temperature, the reaction mixture was partitioned between ethyl acetate (60 ml) and 10% citric acid aqueous solution (60 ml). The organic layer was washed with water, brine and dried with MgSO$_4$. After the removal of the organic solvent in vacuo the residue was purified using Biotage silica gel column chromatography (gradient: 10% NH$_3$ in MeOH/CH$_2$Cl$_2$=0/100 to 10/100) to give tert-butyl 4-(pyrazolo[1,5-a]pyrimidin-6-yl)piperazine-1-carboxylate (0.102 g, 0.336 mmol, 37.6% yield). LC/MS (method 1): $t_R$=3.08 min, m/z (M+H)$^+$=304.4.

Example 2

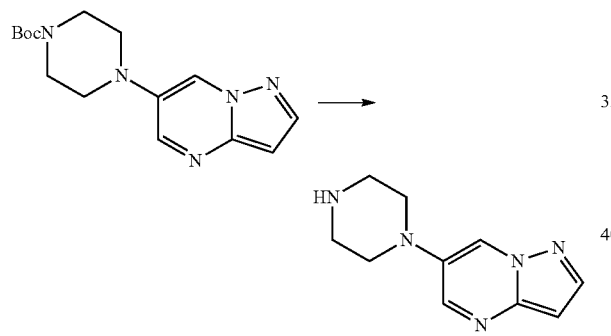

To a solution of tert-butyl 4-(pyrazolo[1,5-a]pyrimidin-6-yl)piperazine-1-carboxylate (0.10 g, 0.33 mmol) in DCM (2 ml), TFA (0.5 ml) was added. The mixture was stirred at room temperature for 30 min and LC/MS showed the completion of the reaction. The reaction mixture was then concentrated in vacuo and azeotroped with MeOH three times. The crude product was used without purification for the next reaction. LC/MS (method 1): $t_R$=1.80 min, m/z (M+H)$^+$=204.2.

Example 3

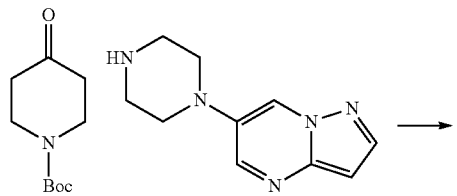

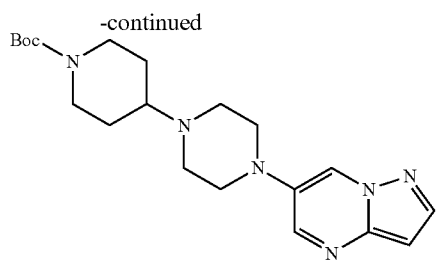

To a suspension of tert-butyl 4-oxopiperidine-1-carboxylate (0.10 g, 0.49 mmol) and 6-(piperazin-1-yl)pyrazolo[1,5-a]pyrimidine (0.07 g, 0.33 mmol) in DCE (1.8 ml), DMF (0.2 ml) was added. Sodium triacetoxy borohydride (0.21 g, 0.99 mmol) was then added to the reaction mixture and it was stirred at room temperature for 3 h. The reaction mixture was then neutralized with saturated aqueous NaHCO$_3$ solution (5 ml), and partitioned between water (20 ml) and CH$_2$Cl$_2$ (20 ml). The organic layer was separated and washed with brine and dried over MgSO$_4$. After the removal of the organic solvent in vacuo the residue was purified using Biotage silica gel column chromatography (gradient: 10% NH$_3$ in MeOH/CH$_2$Cl$_2$=0/100 to 10/100) to give tert-butyl 4-(4-(pyrazolo[1,5-a]pyrimidin-6-yl)piperazin-1-yl)piperidine-1-carboxylate (0.066 g, 0.171 mmol, 52% yield). LC/MS (method 1): $t_R$=2.51 min, m/z (M+H)$^+$=387.2.

Example 4

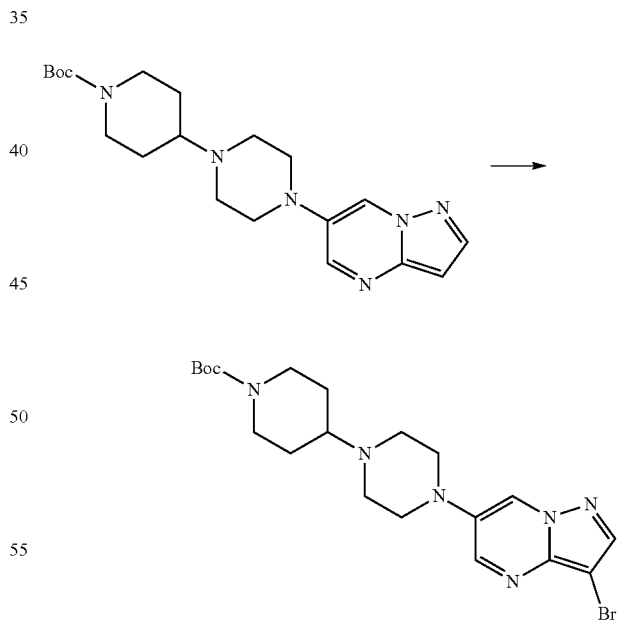

A solution of tert-butyl 4-(4-(pyrazolo[1,5-a]pyrimidin-6-yl)piperazin-1-yl)piperidine-1-carboxylate (0.06 g, 0.17 mmol) in THF (2.8 ml) was cooled to 0° C. At this temperature, NBS (0.03 g, 0.17 mmol) dissolved in THF (1 ml) was added dropwise. The addition was completed in 5 min and the reaction mixture was stirred for another 30 min at that temperature. After the completion of the reaction, as ascertained by LC/MS, THF was removed in vacuo and the residue was partitioned between DCM (20 ml) and saturated aqueous Na$_2$CO$_3$ solution (20 ml). The organic layer was separated and washed with brine (10 ml), dried (MgSO$_4$), filtered and concentrated. The product obtained was used without purification. LC/MS (method 1): t$_R$=2.63 min, m/z (M+H)$^+$=467.3

General Procedure 1: 3-Component Condensation Reaction to Form Pyrazolo[1,5-a]pyrimidine Core (Example 5).

Example 5

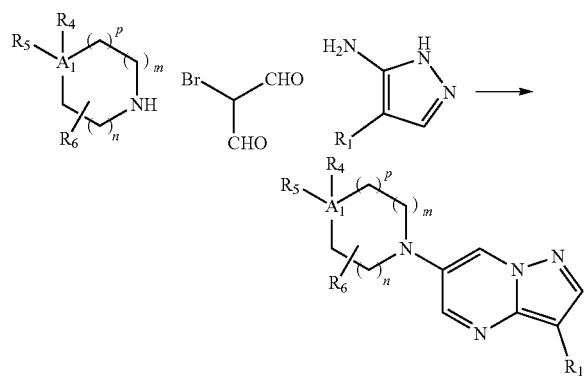

m = 0, 1, 2, or 3
n = 0, 1, 2, or 3
p = 0 or 1;
A$_1$ = N or C
R$_1$ = hydrogen or an optionally substituted substituent (e.g., halogen, heteroaryl, or sustituted aryl)
R$_4$ = optionally absent, hydrogen or an optionally substituted substituent (e.g., heterocyclyl, heteroaryl, or substituted aryl), wherein on of R$_4$ or R$_5$ is optionally absent when A$_1$ is N
R$_5$ = optionally absent, hydrogen or an optionally substituted substituent, wherein one of R$_4$ or R$_5$ is optionally absent when A$_1$ is N
R$_6$ = independently one or more of hydrogen or an optionally substituted substituent To a suspension of 2-bromomalonaldehyde (0.30 g, 1.96 mmol) and suitably substituted cyclic amines (2.94 mmol) in 1,4-dioxane (2 ml), Hunig's base (0.5 ml, 2.94 mmol) was added and the reaction mixture was stirred at room temperature for 12 h. After this time, 1H-Pyrazol-5-amine (0.06 ml, 0.98 mmol) was added and the reaction mixture was heated in a microwave for 1 h at 100° C. It was then cooled to room temperature, concentrated and directly subjected to flash silica gel column chromatography via Biotage silica gel column (gradient: 10% NH$_3$ in MeOH/CH$_2$Cl$_2$=0/100 to 15/100) to give the desired product.

General procedure 2: Bromination of Pyrazolo[1,5-a] pyrimidine Core (Example 6).

Example 6

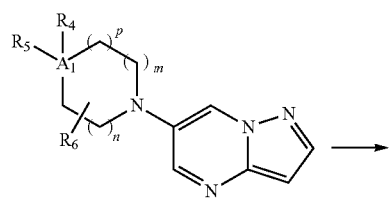

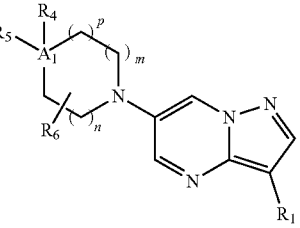

m = 0, 1, 2, or 3
n = 0, 1, 2, or 3
p = 0 or 1
A$_1$ = N or C
R$_1$ = Br or I
R$_4$ = optionally absent, hydrogen or an optionally substituted substituent (e.g., heterocyclyl, heteroaryl or substituted aryl), wherein one of R$_4$ or R$_5$ is optionally absent when A$_1$ is N
R$_5$ = optionally absent, hydrogen or an optionally substituted substituent, wherein one of R$_4$ or R$_5$ is optionally absent when A$_1$ is N
R$_6$ = independently one or more of hydrogen or an optionally substituted substituent To a solution of piperidin-1-yl-pyrazolo[1,5-a]pyrimidine (0.07 mmol) in THF (2 ml), maintained at 0° C., NBS (0.07 mmol) dissolved in THF (1 ml) was added dropwise. The reaction was stirred at 0° C. for 10 min and then quenched with saturated aqueous NaHCO$_3$ solution (5 ml). The organic layer was separated, washed with brine (2×10 ml), dried (MgSO$_4$), filtered and concentrated. The crude bromide was directly used for the next step without further purification.

General Procedure 3A: Suzuki Coupling Using Pd(PPh$_3$)$_4$ as Catalyst (Example 7).

Example 7

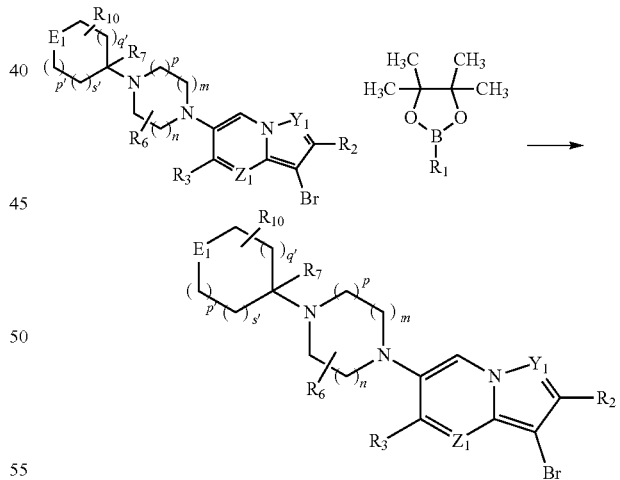

E$_1$ = O, NH, S, —SO—, —SO$_2$—, or NR (where R = an optionally substituted substituent, e.g., alkyl, carbamoyl, ureido, guanidino, or sulfonamido)
m/n = independently 0, 1, 2, or 3
p = 0 or 1
p'/q' = independently 0, 1, 2, or 3
s' = 0 or 1
R$_1$ = substituted aryl or heteroaryl
Y$_1$/Z$_1$ = independently N or CH
R$_6$/R$_{10}$ = independently one or more of hydrogen or an optionally substituted substituent
R$_2$/R$_3$ = independently hydrogen or an optionally substituted substituent (e.g., alkyl, hydroxy, alkoxy, amino, amido, carbamoyl, ureido, or sulfonamido)
R$_7$ = hydrogen or an optionally substituted substituent (e.g., alkyl, amido, ester, cyano or other substituent)

A mixture of bromopyrazolo[1,5-a]pyrimidinylpiperazine (0.11 mmol) and boronate ester (0.13 mmol) in 1,4-dioxane (3 ml) was flushed with $N_2$ for 5 min. 2M $Na_2CO_3$ (0.16 ml, 0.33 mmol) and $Pd(Ph_3P)_4$ (0.02 g, 0.02 mmol) were added followed by a further flushing of the reaction mixture with $N_2$ for 5 min. The reaction vial was then sealed and heated at 110° C. for 2 h. The reaction mixture was then cooled to room temperature. DCM (3 ml) and SiliaMetS® Dimercaptotriazine (DMT) were added and the reaction mixture was stirred for 30 min at room temperature. It was then filtered and the filtrate was concentrated in vacuo. The residue was subjected to flash silica gel column chromatography on Biotage silica gel column (gradient: 10% $NH_3$ in MeOH/$CH_2Cl_2$=0/100 to 15/100) or reverse phase HPLC to yield the desired compound.

General Procedure 3B: Suzuki Coupling Using SphosPd (Crotyl)Cl as Catalyst (Examples 8-10).

Example 8

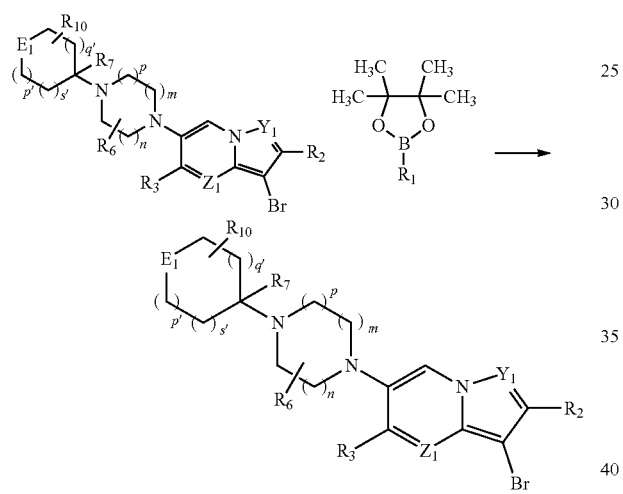

$E_1$ = O, NH, S, —SO—, —$SO_2$—, or NR (where R = an optionally substituted substituent, e.g., alkyl, carbamoyl, ureido, guanidino, or sulfonamido)
m/n = independently 0, 1, 2, or 3
p = 0 or 1
p'/q' = independently 0, 1, 2, or 3
s' = 0 or 1
$R_1$ = substituted aryl or heteroaryl
$Y_1/Z_1$ = independently N or CH
$R_6/R_{10}$ = independently one or more of hydrogen or an optionally substituted substituent
$R_2/R_3$ = independently hydrogen or an optionally substituted substituent (e.g., alkyl, hydroxy, alkoxy, amino, amido, carbamoyl, ureido, or sulfonamido)
$R_7$ = hydrogen or an optionally substituted substituent (e.g., alkyl, amido, ester, cyano or other substituent)

A suspension of bromo-piperazinyl-pyrazolo[1,5-a]pyrimidine (0.079 mmol) and boronate ester (0.12 mmol) in 1,4-Dioxane (1 ml) and water (0.2 ml) was flushed with $N_2$ for 5 min after which potassium phosphate (0.05 g, 0.24 mmol) was added followed by SPhosPd(crotyl)Cl (2.4 mg, 3.95 µmol). The reaction mixture was again flushed with $N_2$ for 5 min and the reaction vessel was sealed and heated at 100° C. for 1 h. The reaction mixture was then cooled to room temperature, DCM (3 ml) and SiliaMetS® Dimercaptotriazine (DMT) were added and stirred at room temperature for 30 min. It was then filtered and the filtrate was concentrated in vacuo. The residue was subjected to flash silica gel column chromatography on Biotage silica gel column (gradient: 10% $NH_3$ in MeOH/$CH_2Cl_2$=0/100 to 15/100) or reverse phase HPLC to yield the desired compound.

Example 9

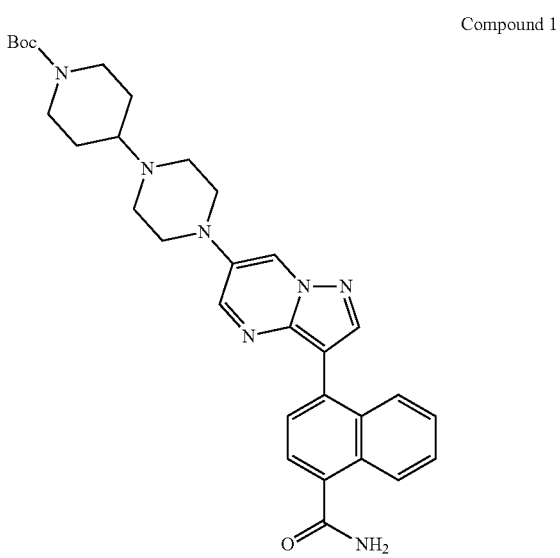 [SMILES: CC(C)(C)OC(=O)N1CCC(N2CCN(c3cnc4c(-c5ccc(C(N)=O)c6ccccc56)cnn4c3)CC2)CC1]

Compound 1

Compound 1 was prepared according to the representative procedure and general procedure 3A. LC/MS (method 1): $t_R$=2.59 min, m/z $(M+H)^+$=556.

Example 10

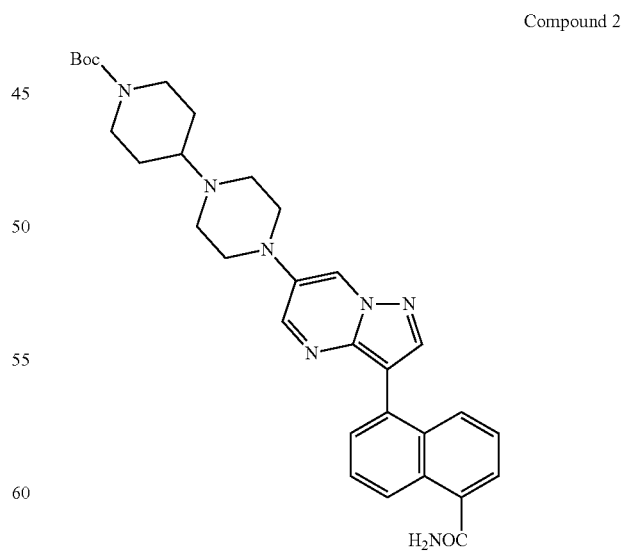

Compound 2

Compound 2 was prepared according to the representative procedure and general procedure 3A. LC/MS (method 1): $t_R$=2.56 min, m/z $(M+H)^+$=556.

General Procedure 4: Boc Deprotection. (Examples 11-15).

Example 11

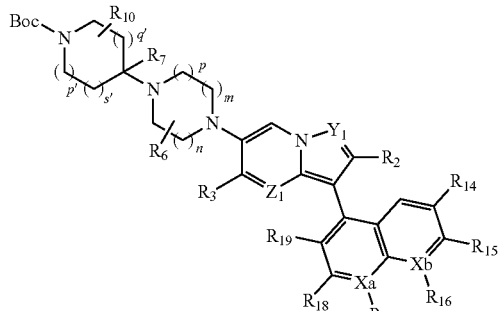

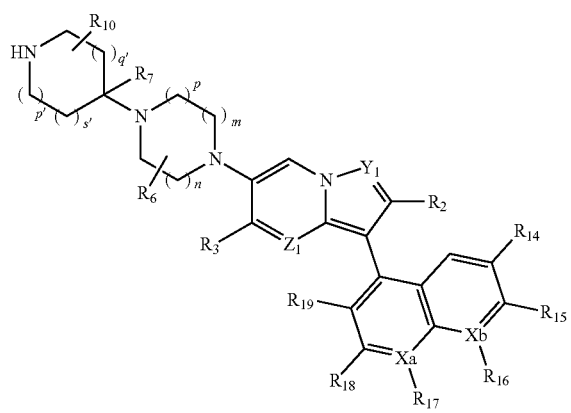

m/n = independently 0, 1, 2, or 3
p = 0 or 1
p'/q' = independently 0, 1, 2, or 3
s' = 0 or 1
$Y_1/Z_1$ = independently N or CH
Xa/Xb = independently C or N
$R_3/R_{13}/R_{14}$ = independently hydrogen or an optionally substituted substituent (alkyl, halogen, amino, hydroxy, alkoxy, thiol, thioether, or carbonyl)
$R_{17}$ = optionally absent, hydrogen, or an optionally substituted substituent (e.g., alkyl, halogen, amino, hydroxy, alkoxy, thiol, thioether, or carbonyl), wherein $R_{17}$ is optionally when Xa is N
$R_{15}$ = hydrogen or carbamoyl
$R_{16}$ = optionally absent, hydrogen, or carbamoyl, wherein $R_{16}$ is optionally absent when Xb is N
$R_6/R_{10}$ = independently one or more of hydrogen or an optionally substituted substituent
$R_2$ = hydrogen or an optionally substituted substituent (e.g., alkyl, hydroxy, alkoxy, amino, amido, carbamoyl, ureido, or sulfonamido)
$R_7$ = hydrogen or an optionally substituted substituent (e.g., alkyl, amido, cyano, or other substituent)

To a solution of substituted pyrazolo[1,5-a]pyrimidin-yl (piperazin-1-yl)piperidine (0.1 mmol) in DCM (2 ml), TFA (0.5 ml) was added dropwise at room temperature. The reaction was completed in 30 min, concentrated in vacuo and azeotroped with MeOH. It was then purified via reverse phase HPLC.

Example 12

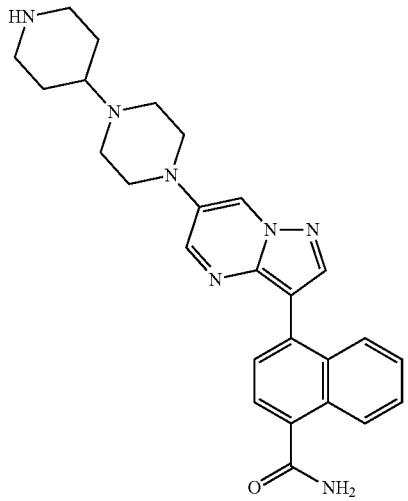

Compound 3

Compound 3 was prepared according to the representative procedures and general procedures 3A and 4. LC/MS (method 2): $t_R$=2.85 min, m/z $(M+H)^+$=456.

Example 13

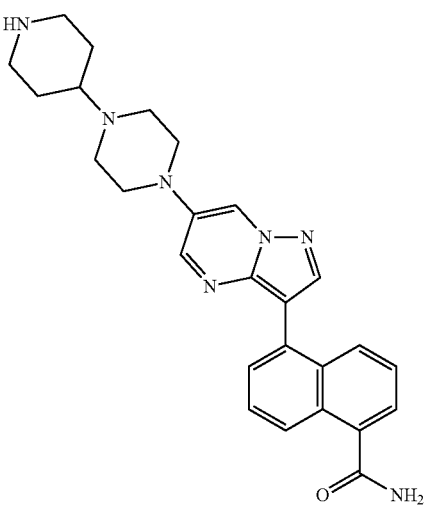

Compound 4

Compound 4 was prepared according to the representative procedures and general procedure 3A and 4. LC/MS (method 2): $t_R$=2.80 min, m/z $(M+H)^+$=456.

Example 14
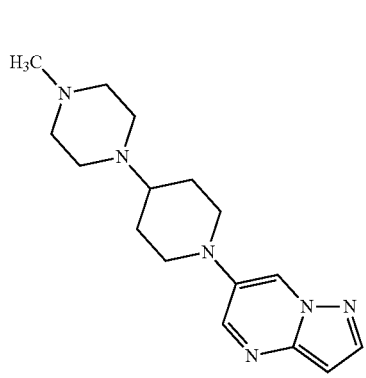
Compound 5
Compound 5 was prepared according to the general procedure 1. LC/MS (method 1): $t_R$=1.93 min, m/z (M+H)$^+$=301.
Example 15
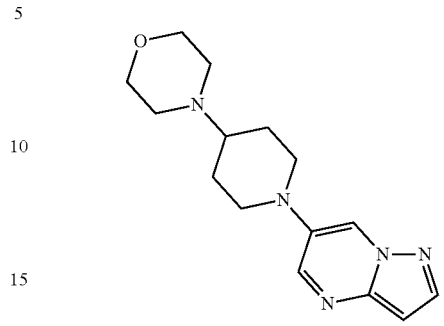
Compound 6
Compound 6 was prepared according to the general procedure 1. LC/MS (method 1): $t_R$=2.10 min, m/z (M+H)$^+$=288.
General Procedure 5: One Pot-Two Step Reaction (In Situ Formation of the Boronate Ester Followed by Suzuki). (Examples 16-31).
Example 16
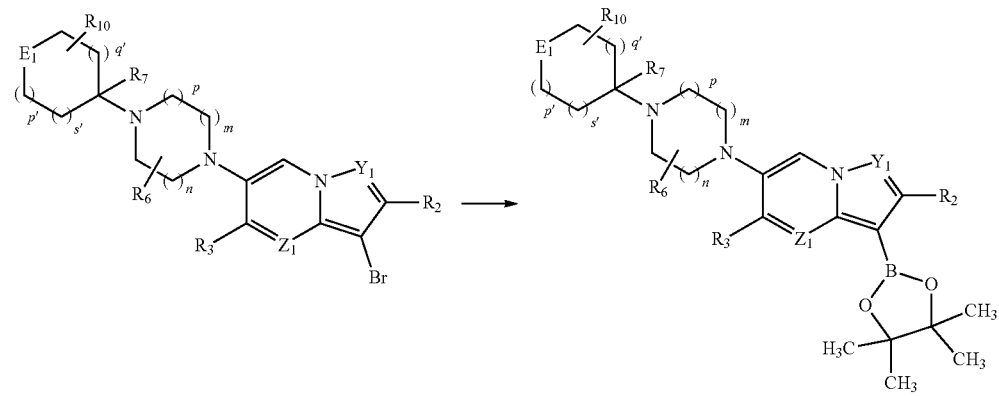
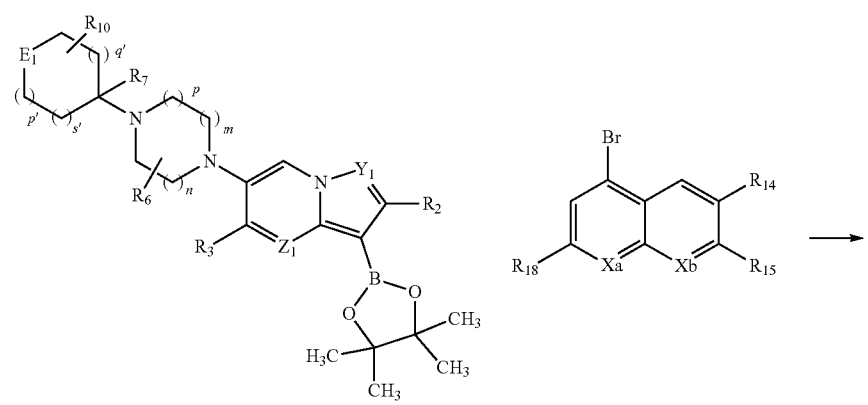

-continued

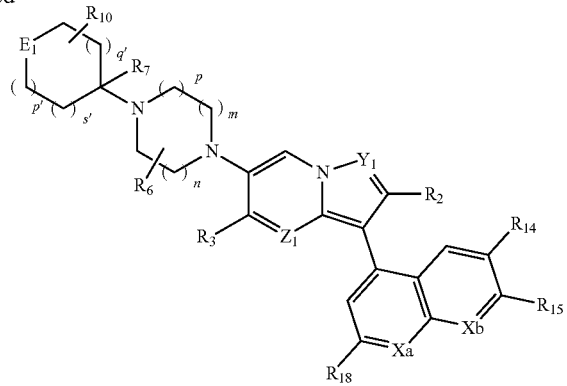

$E_1$ = O, NH, S, —SO—, —SO$_2$—, or NR (where R = an optionally substituted substituent, e.g., alkyl, carbamoyl, ureido, guanidino, or sulfonamido)
m/n = independently 0, 1, 2, or 3
p = 0 or 1
p'/q' = independently 0, 1, 2, or 3
s' = 0 or 1
$Y_1/Z_1$ = independently N or CH
Xa/Xb = independently N or CH
$R_3/R_{14}/R_{15}/R_{18}$ = independently hydrogen or an optionally susbstituted substituent (e.g., alkyl, halogen, amino, hydroxy, alkoxy, thiol, thioether, or carbonyl)
$R_6/R_{10}$ = independently one or more of hydrogen or an optionally substituted substituent
$R_2$ = hydrogen or an optionally substituted substituent (e.g., alkyl, hydroxy, alkoxy, amino, amido, carbamoyl, ureido, or sulfonamido)
$R_7$ = hydrogen or an optionally substituted substituent (e.g., alkyl, amido, ester, cyano or other substituent)

To an oven dried microwave vial, under a $N_2$ atmosphere, 3-bromo-6-(4-(4-methylpiperazin-1-yl)piperidin-1-yl)pyrazolo[1,5-a]pyrimidine (0.03 g, 0.092 mmol), Pd$_2$(dba)$_3$ (4.22 mg, 4.61 μmol) and 2-Dicyclohexylphosphino-2',4',6'-tri-iso-propyl-1,1'-biphenyl (4.40 mg, 9.23 μmol) were added followed by 1,4-dioxane (0.9 ml). The reaction mixture was flushed with $N_2$ for 5 min and then Et$_3$N (0.04 ml, 0.28 mmol) and 4,4,5,5-Tetramethyl-1,3,2-dioxaborolane (0.04 ml, 0.28 mmol) were added. The reaction mixture was flushed again with $N_2$ for 5 min, the reaction vessel was then sealed and heated at 110° C. for 30 min. After this the reaction mixture was cooled and analyzed by LC/MS to show the formation of the corresponding boronic ester/boronic acid and disappearance of the starting bromide.

To the same reaction mixture a degassed solution of potassium phosphate (0.8M) (0.34 ml, 0.27 mmol) was added followed by the corresponding bromide (0.14 mmol) and Sphos Pd(crotyl)Cl (4.57 μmol). It was then flushed again with $N_2$ for 5 min, sealed and heated at 100° C. for 15 min. Analysis by LC/MS showed the disappearance of the starting boronate ester and the formation of the product. The reaction was then cooled to room temperature and stirred with SiliaMetS® Dimercaptotriazine (DMT) for 30 min. It was then filtered, concentrated in vacuo and subjected to column chromatography to yield the desired compound.

Example 17

Compound 7

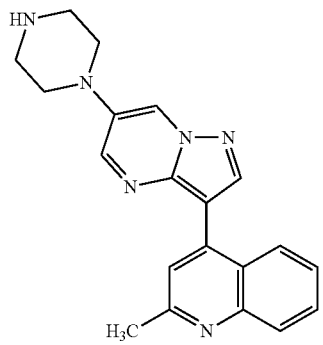

Compound 7 was prepared according to the general procedures 1, 2, 3B and 4. LC/MS (method 1): $t_R$=2.09 min, m/z (M+H)$^+$=345.

Example 18

Compound 8

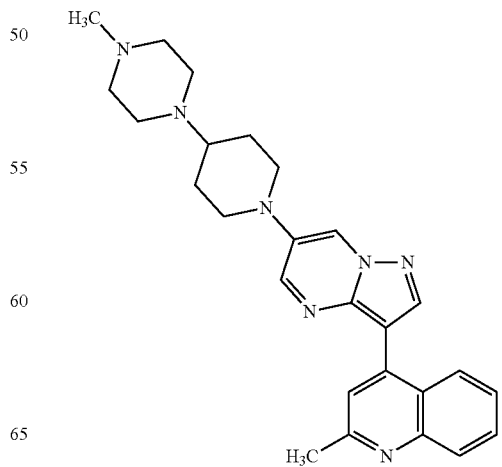

Compound 8 was prepared according to the general procedures 1, 2 and 3B. LC/MS (method 2): $t_R$=2.62 min, m/z (M+H)$^+$=442. $^1$H NMR (400 MHz, DMSO-d$_6$) δ 8.77 (d, J=2.7 Hz, 1H), 8.62 (d, J=2.6 Hz, 1H), 8.44 (s, 1H), 8.08 (ddd, J=8.4, 1.4, 0.6 Hz, 1H), 7.95 (ddd, J=8.5, 1.4, 0.6 Hz, 1H), 7.70 (ddd, J=8.4, 6.8, 1.4 Hz, 1H), 7.61 (s, 1H), 7.48 (ddd, J=8.3, 6.8, 1.3 Hz, 1H), 3.71 (d, J=12.2 Hz, 2H), 2.72 (td, J=12.1, 2.4 Hz, 2H), 2.66 (s, 3H), 2.51 (s, 5H), 2.30 (d, J=8.7 Hz, 4H), 2.13 (s, 3H), 1.91-1.82 (m, 2H), 1.56 (qd, J=12.0, 3.9 Hz, 2H).

Example 19

Compound 9

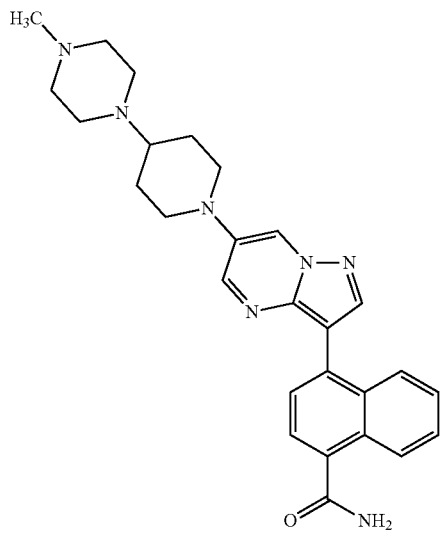

Compound 9 was prepared according to the general procedures 1, 2 and 3B. LC/MS (method 2): $t_R$=2.83 min, m/z (M+H)$^+$=470. $^1$H NMR (400 MHz, DMSO-d$_6$) δ 8.69 (d, J=2.6 Hz, 1H), 8.63 (d, J=2.6 Hz, 1H), 8.40-8.29 (m, 2H), 8.04-7.96 (m, 2H), 7.65 (d, J=9.4 Hz, 2H), 7.53 (dddd, J=32.2, 8.3, 6.7, 1.4 Hz, 3H), 3.75 (d, J=11.9 Hz, 3H), 3.10 (d, J=136.6 Hz, 8H), 2.72 (q, J=13.6, 12.8 Hz, 5H), 1.94 (s, 2H), 1.62 (d, J=12.4 Hz, 2H).

Example 20

Compound 10

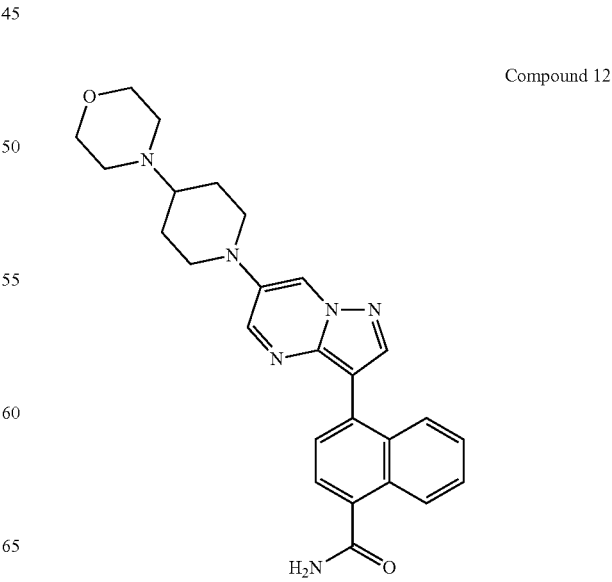

Compound 10 was prepared according to the general procedures 1, 2 and 3B. LC/MS (method 2): $t_R$=2.77 min, m/z (M+H)$^+$=470.

Example 21

Compound 11

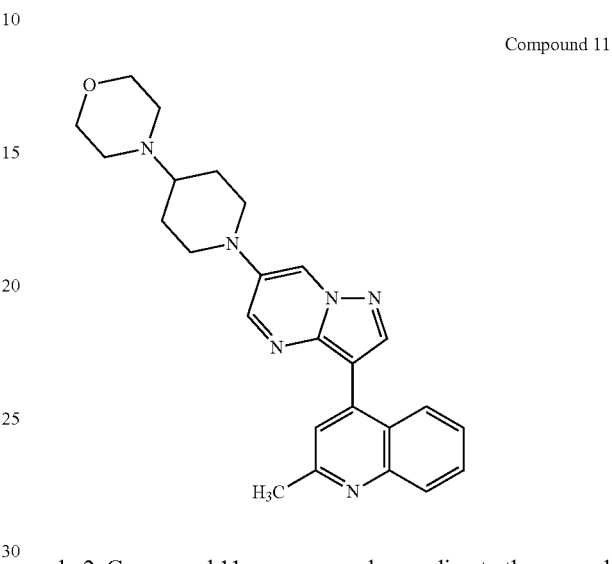

1e;2qCompound 11 was prepared according to the general procedures 1, 2 and 3B. LC/MS (method 2): $t_R$=2.71 min, m/z (M+H)$^+$=429. $^1$H NMR (400 MHz, DMSO-d$_6$) δ 8.78 (d, J=2.6 Hz, 1H), 8.63 (d, J=2.7 Hz, 1H), 8.44 (s, 1H), 8.08 (ddd, J=8.3, 1.4, 0.6 Hz, 1H), 7.95 (ddd, J=8.4, 1.4, 0.6 Hz, 1H), 7.70 (ddd, J=8.3, 6.8, 1.4 Hz, 1H), 7.61 (s, 1H), 7.49 (ddd, J=8.3, 6.8, 1.3 Hz, 1H), 3.71 (d, J=12.4 Hz, 2H), 3.62-3.47 (m, 4H), 3.32-3.25 (s, 4H), 2.73 (td, J=12.1, 2.4 Hz, 2H), 2.66 (s, 3H), 2.29 (tt, J=11.0, 3.6 Hz, 1H), 1.89 (d, J=11.1 Hz, 2H), 1.56 (qd, J=12.1, 3.9 Hz, 2H).

Example 22

Compound 12

Compound 12 was prepared according to the general procedures 1, 2 and 3B. LC/MS (method 2): $t_R$=3.38 min, m/z (M+H)$^+$=457.

Example 23

Compound 13

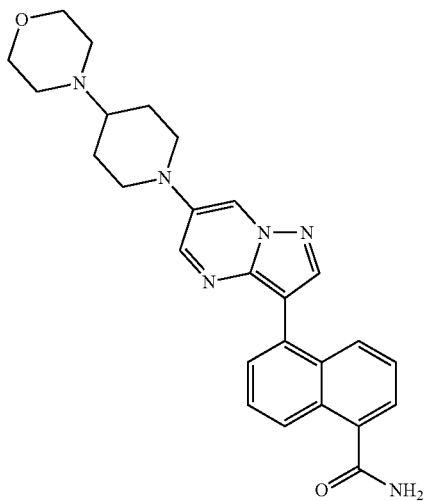

Compound 13 was prepared according to the general procedures 1, 2 and 3B. LC/MS (method 2): $t_R$=2.99 min, m/z (M+H)$^+$=457.

Example 24

Compound 14

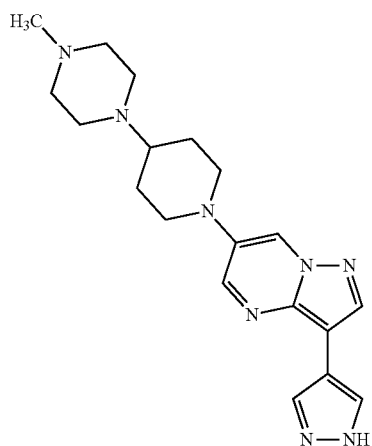

Compound 14 was prepared according to the general procedures 1, 2 and 3B. LC/MS (method 2): $t_R$=2.63 min, m/z (M+H)$^+$=367.

Example 25

Compound 15

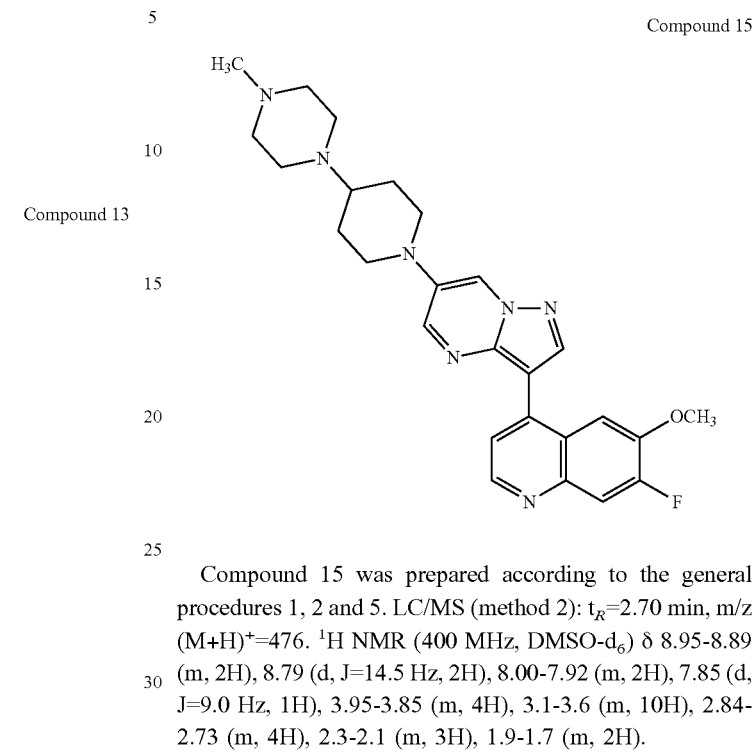

Compound 15 was prepared according to the general procedures 1, 2 and 5. LC/MS (method 2): $t_R$=2.70 min, m/z (M+H)$^+$=476. $^1$H NMR (400 MHz, DMSO-d$_6$) δ 8.95-8.89 (m, 2H), 8.79 (d, J=14.5 Hz, 2H), 8.00-7.92 (m, 2H), 7.85 (d, J=9.0 Hz, 1H), 3.95-3.85 (m, 4H), 3.1-3.6 (m, 10H), 2.84-2.73 (m, 4H), 2.3-2.1 (m, 3H), 1.9-1.7 (m, 2H).

Example 26

Compound 16

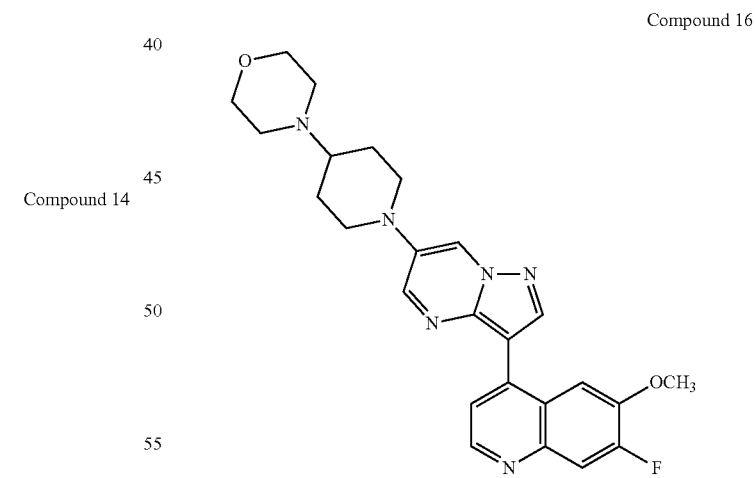

Compound 16 was prepared according to the general procedures 1, 2 and 5. LC/MS (method 2): $t_R$=2.84 min, m/z (M+H)$^+$=463. $^1$H NMR (400 MHz, DMSO-d$_6$) δ 9.65 (s, 1H), 8.88-8.74 (m, 3H), 8.66 (s, 1H), 7.84 (d, J=12.2 Hz, 1H), 7.76-7.65 (m, 2H), 4.01 (d, J=11.9 Hz, 2H), 3.88 (s, 4H), 3.65 (t, J=12.2 Hz, 3H), 3.48 (d, J=11.5 Hz, 2H), 3.12 (q, J=10.9 Hz, 3H), 2.81-2.70 (m, 2H), 2.17 (d, J=11.9 Hz, 2H), 1.76 (td, J=12.5, 8.6 Hz, 2H).

Example 27

Compound 17

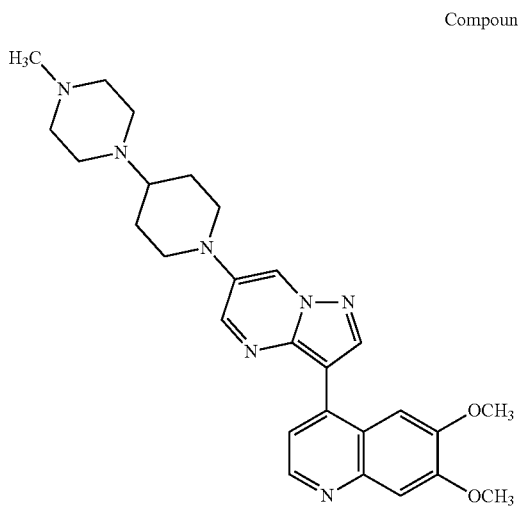

Compound 17 was prepared according to the general procedures 1, 2 and 5. LC/MS (method 2): $t_R$=2.38 min, m/z (M+H)$^+$=488.

Example 28

Compound 18

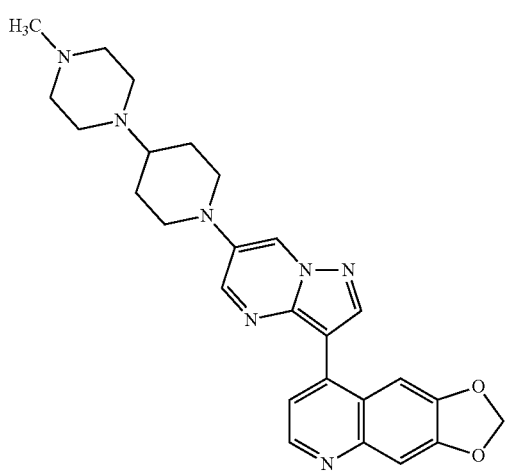

Compound 18 was prepared according to the general procedures 1, 2 and 5. LC/MS (method 2): $t_R$=2.55 min, m/z (M+H)$^+$=472. $^1$H NMR (400 MHz, DMSO-d$_6$) δ 8.84 (d, J=2.7 Hz, 1H), 8.76 (d, J=5.2 Hz, 1H), 8.71 (s, 1H), 8.55 (s, 1H), 7.74 (s, 1H), 7.55 (s, 1H), 7.45 (s, 1H), 6.27 (s, 2H), 3.78 (d, J=12.1 Hz, 4H), 3.60-3.20 (m, 4H), 2.72 (q, J=14.7, 13.5 Hz, 6H), 1.92 (s, 3H), 1.60 (s, 3H).

Example 29

Compound 19

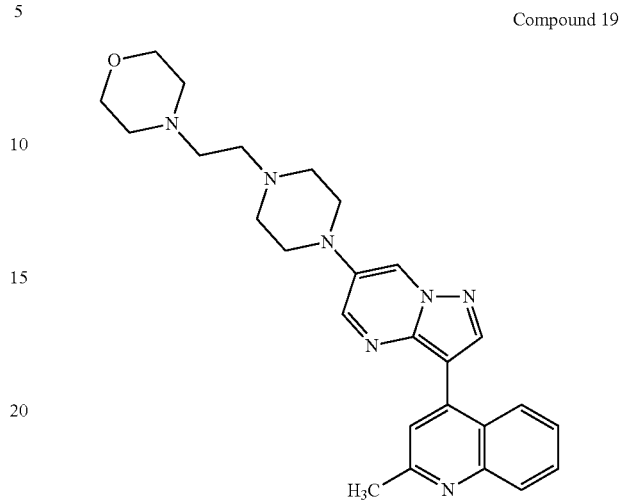

Compound 19 was prepared according to the general procedures 1, 2 and 3B. LC/MS (method 2): $t_R$=2.58 min, m/z (M+H)$^+$=458. $^1$H NMR (400 MHz, DMSO-d$_6$) δ 8.79 (d, J=2.7 Hz, 1H), 8.62 (d, J=2.7 Hz, 1H), 8.45 (s, 1H), 8.06 (dd, J=8.5, 1.4 Hz, 1H), 7.94 (dd, J=8.5, 1.3 Hz, 1H), 7.69 (ddd, J=8.4, 6.8, 1.4 Hz, 1H), 7.60 (s, 1H), 7.48 (ddd, J=8.2, 6.8, 1.3 Hz, 1H), 3.53 (t, J=4.6 Hz, 3H), 3.35-3.27 (m, 2H), 3.16 (t, J=4.9 Hz, 3H), 2.65 (s, 3H), 2.58 (t, J=5.0 Hz, 3H), 2.45-2.40 (m, 6H), 2.38 (d, J=4.6 Hz, 3H).

Example 30

Compound 20

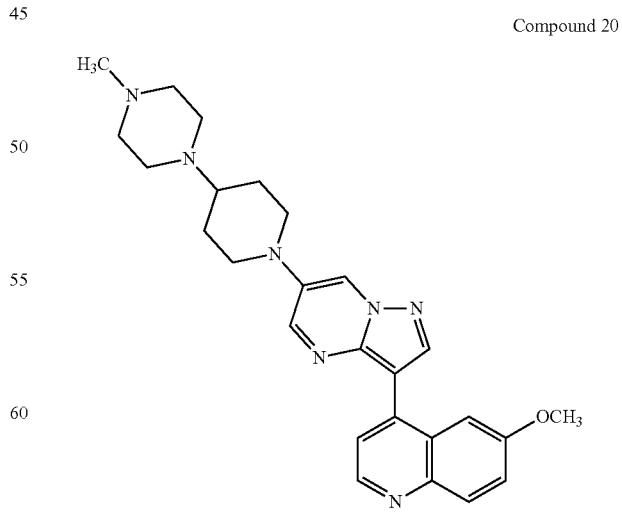

Compound 20 was prepared according to the general procedures 1, 2 and 5. LC/MS (method 2): $t_R$=2.65 min, m/z (M+H)⁺=458. ¹H NMR (400 MHz, DMSO-d₆) δ 8.78 (d, J=2.7 Hz, 1H), 8.73 (d, J=4.5 Hz, 1H), 8.62 (d, J=2.7 Hz, 1H), 8.55 (s, 1H), 7.95 (d, J=9.2 Hz, 1H), 7.65 (d, J=4.5 Hz, 1H), 7.48 (d, J=2.8 Hz, 1H), 7.40 (dd, J=9.1, 2.8 Hz, 1H), 3.78 (s, 3H), 3.70 (d, J=12.1 Hz, 1H), 2.75-2.65 (m, 2H), 2.54-2.47 (m, 8H), 2.29 (d, J=11.2 Hz, 2H), 2.12 (d, J=1.9 Hz, 3H), 1.90-1.82 (m, 2H), 1.56 (qd, J=12.0, 3.8 Hz, 2H).

Example 31

Compound 21

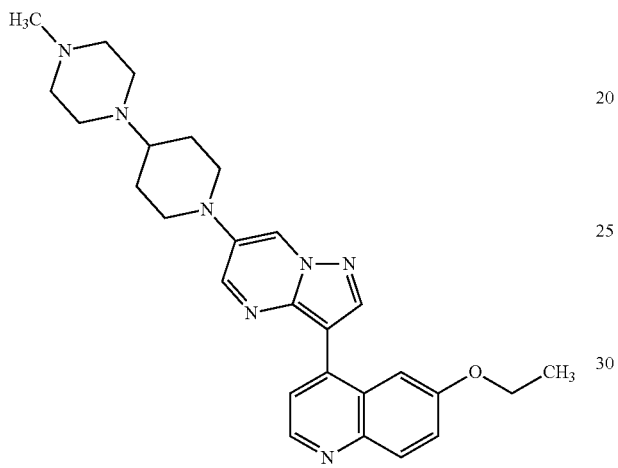

Compound 21 was prepared according to the general procedures 1, 2 and 5. LC/MS (method 2): $t_R$=2.84 min, m/z (M+H)⁺=472. ¹H NMR (400 MHz, DMSO-d₆) δ 8.77 (d, J=2.7 Hz, 1H), 8.72 (d, J=4.5 Hz, 1H), 8.62 (d, J=2.6 Hz, 1H), 8.52 (s, 1H), 7.94 (d, J=9.1 Hz, 1H), 7.63 (d, J=4.5 Hz, 1H), 7.44 (d, J=2.7 Hz, 1H), 7.39 (dd, J=9.1, 2.8 Hz, 1H), 4.03 (q, J=6.9 Hz, 2H), 3.70 (d, J=12.1 Hz, 2H), 3.31 (m, 6H), 2.76-2.65 (m, 2H), 2.60-2.50 (m, 2H), 2.34 (s, 2H), 2.19 (s, 2H), 1.90-1.82 (m, 2H), 1.64-1.46 (m, 2H), 1.32 (t, J=6.9 Hz, 3H).

General Procedure 6A: Reductive Amination Using Na(OAc)₃BH. (Examples 32-33).

Example 32

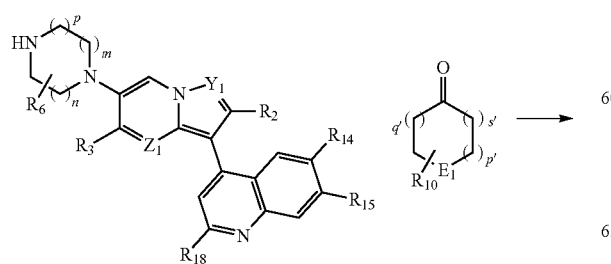

-continued

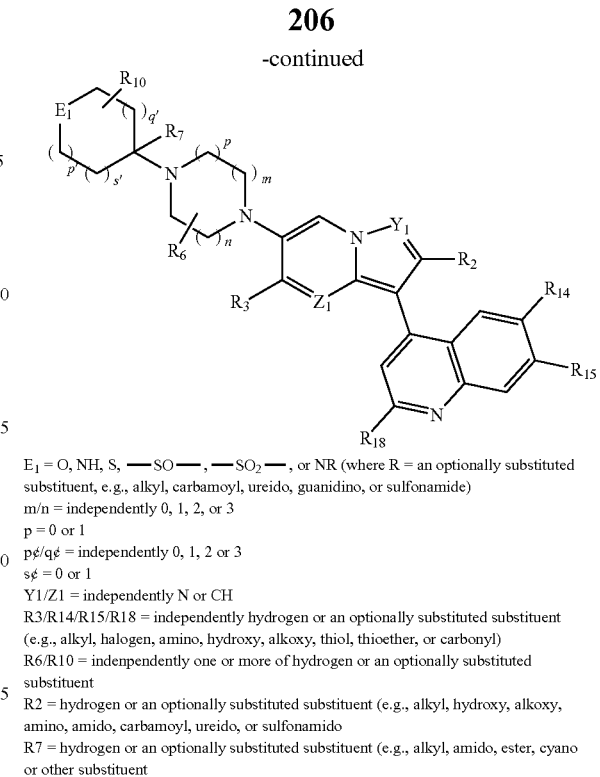

$E_1$ = O, NH, S, —SO—, —SO₂—, or NR (where R = an optionally substituted substituent, e.g., alkyl, carbamoyl, ureido, guanidino, or sulfonamide)
m/n = independently 0, 1, 2, or 3
p = 0 or 1
p′/q′ = independently 0, 1, 2 or 3
s′ = 0 or 1
Y1/Z1 = independently N or CH
R3/R14/R15/R18 = independently hydrogen or an optionally substituted substituent (e.g., alkyl, halogen, amino, hydroxy, alkoxy, thiol, thioether, or carbonyl)
R6/R10 = independently one or more of hydrogen or an optionally substituted substituent
R2 = hydrogen or an optionally substituted substituent (e.g., alkyl, hydroxy, alkoxy, amino, amido, carbamoyl, ureido, or sulfonamido
R7 = hydrogen or an optionally substituted substituent (e.g., alkyl, amido, ester, cyano or other substituent To a solution of piperazinyl-pyrazolo[1,5-a]pyrimidine (0.07 mmol) and cyclic ketone (0.22 mmol) in DCE (0.5 ml), sodium triacetoxyborohydride (0.08 g, 0.36 mmol) and AcOH (0.01 ml, 0.218 mmol) were added and the reaction mixture was left to stir at room temperature. After 2 h, complete consumption of starting materials was observed by LC/MS and saturated aqueous NaHCO₃ solution (10 ml) was added to the reaction mixture. It was then extracted with DCM (2×20 ml). The organic layers were combined, dried over Na₂SO₄, filtered, concentrated in vacuo and purified by reverse phase HPLC.

Example 33

Compound 22

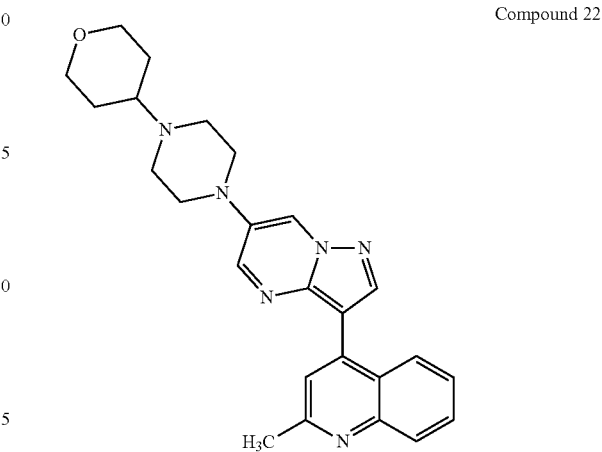

Compound 22 was prepared according to the general procedures 1, 2, 3B, 4 and 6A. LC/MS (method 2): $t_R$=2.62 min, m/z (M+H)$^+$=429. 1H NMR (400 MHz, DMSO-d$_6$) δ 9.64 (s, 1H), 8.93 (d, J=10.6 Hz, 2H), 8.68 (s, 1H), 8.30 (s, 1H), 8.07 (d, J=8.4 Hz, 1H), 7.91 (s, 2H), 7.68 (s, 1H), 4.03-3.91 (m, 3H), 3.66 (d, J=11.9 Hz, 2H), 3.35-3.16 (m, 6H), 3.11 (t, J=12.4 Hz, 2H), 2.79 (s, 3H), 2.03 (d, J=12.0 Hz, 2H), 1.65 (tt, J=13.2, 6.5 Hz, 2H).

General procedure 6B: Reductive Amination Using ZnCl$_2$ and NaBH$_3$CN. (Examples 34-46).

Example 34

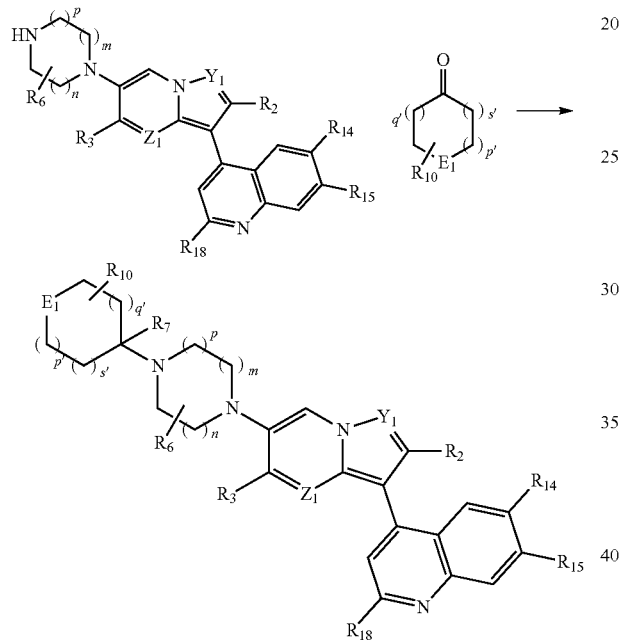

$E_1$ = O, NH, S, —SO—, —SO$_2$—, or NR (where R = an optionally substituted substituent, e.g., alkyl, carbamoyl, ureido, guanidino, or sulfonamide)
m/n = independently 0, 1, 2, or 3
p = 0 or 1
p'/q' = independently 0, 1, 2, or 3
s' = 0 or 1
$Y_1/Z_1$ = independently N or CH
$R_3/R_{14}/R_{15}/R_{18}$ = independently hydrogen or an optionally susbstituted substituent (e.g., alkyl, halogen, amino, hydroxy, alkoxy, thiol, thioether, or carbonyl)
$R_6/R_{10}$ = independently one or more of hydrogen or an optionally substituted substituent
$R_2$ = hydrogen or an optionally substituted substituent (e.g., alkyl, hydroxy, alkoxy, amino, amido, carbamoyl, ureido, or sulfonamido)
$R_7$ = hydrogen or an optionally substituted substituent (e.g., alkyl, amido, ester, cyano or other substituent)

To a solution of piperazinyl-pyrazolo[1,5-a]pyrimidine (0.07 mmol) and cyclic ketone (0.15 mmol) in MeOH (0.5 ml), zinc chloride (0.03 g, 0.22 mmol) was added and it was let to stir overnight. After 10 h, sodium cyanoborohydride (0.02 g, 0.36 mmol) was added and was again left to stir overnight at room temperature. After this time, saturated aqueous NaHCO$_3$ solution (10 ml) was added and the reaction mixture was extracted with CH$_2$Cl$_2$ (2×20 ml). The organic layers were separated, combined, dried over Na$_2$SO$_4$, filtered and concentrated in vacuo. The product was then purified by reverse phase HPLC.

Example 35

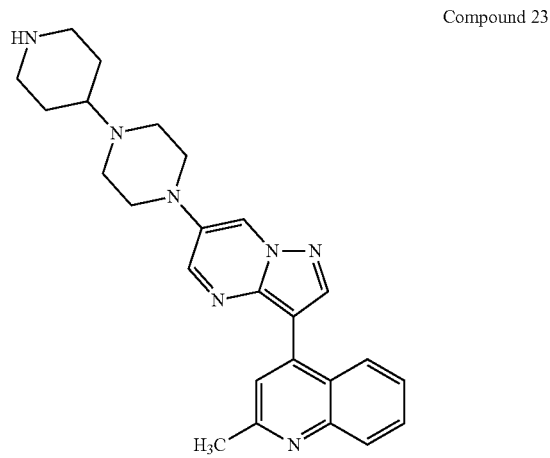 [SMILES: Cc1cc(-c2cnn3cc(N4CCN(C5CCNCC5)CC4)cnc23)c2ccccc2n1]

Compound 23

Compound 23 was prepared according to the general procedures 1, 2, 3B, 4 and 6B. LC/MS (method 2): $t_R$=2.38 min, m/z (M+H)$^+$=428.

Example 36

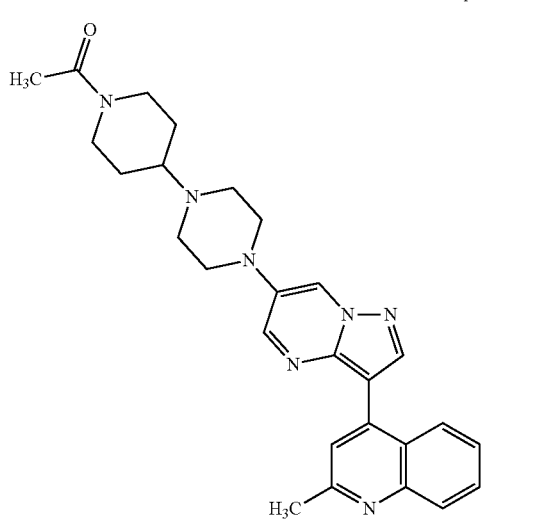

Compound 24

Compound 24 was prepared according to the general procedures 1, 2, 3B, 4 and 6A. LC/MS (method 2): $t_R$=2.59 min, m/z (M+H)$^+$=470. $^1$H NMR (400 MHz, DMSO-d$_6$) δ 9.67 (s, 1H), 8.92 (d, J=9.5 Hz, 2H), 8.67 (s, 1H), 8.29 (m, 2H), 8.06 (d, J=8.4 Hz, 1H), 7.90 (s, 1H), 7.67 (s, 1H), 4.51 (d, J=13.3 Hz, 1H), 3.95 (d, J=13.2 Hz, 3H), 3.62 (d, J=11.8 Hz, 2H), 3.07 (dt, J=37.7, 12.4 Hz, 5H), 2.78 (s, 3H), 2.09 (m, 2H), 2.00 (s, 3H), 1.62 (t, J=11.5 Hz, 2H), 1.46 (dt, J=12.4, 6.4 Hz, 2H).

Example 37

Compound 25

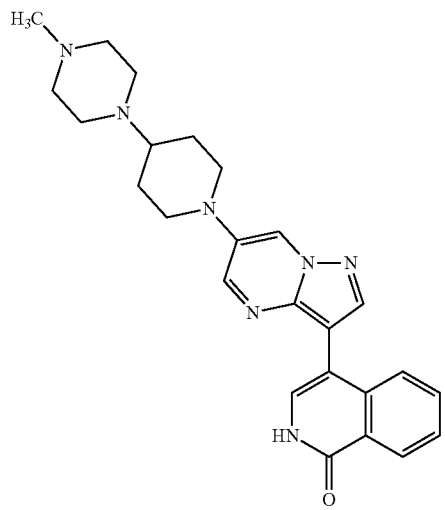

Compound 25 was prepared according to the general procedures 1, 2 and 3B. LC/MS (method 2): $t_R$=2.79 min, m/z (M+H)$^+$=444.

Example 38

Compound 26

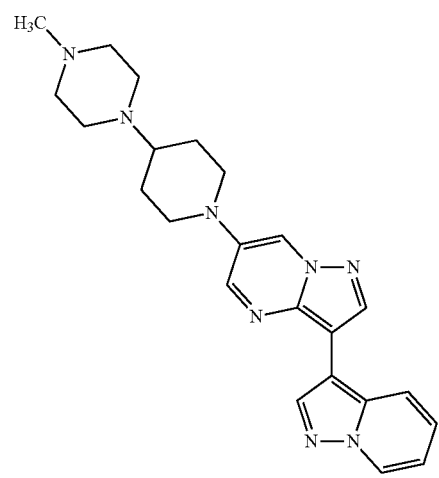

Compound 26 was prepared according to the general procedures 1, 2 and 3B. LC/MS (method 2): $t_R$=3.00 min, m/z (M+H)$^+$=417. $^1$H NMR (400 MHz, DMSO-d$_6$) δ 8.72 (d, J=2.6 Hz, 1H), 8.67 (dt, J=7.0, 1.1 Hz, 1H), 8.53 (s, 1H), 8.49 (d, J=0.6 Hz, 2H), 8.19 (dt, J=9.1, 1.3 Hz, 1H), 7.23 (ddd, J=9.0, 6.7, 1.1 Hz, 1H), 6.89 (td, J=6.8, 1.3 Hz, 1H), 3.74 (d, J=11.9 Hz, 3H), 3.60-3.32 (m, 8H), 2.77-2.65 (m, 4H), 2.0-1.85 (m, 2H), 1.70-1.55 (m, 3H).

Example 39

Compound 27

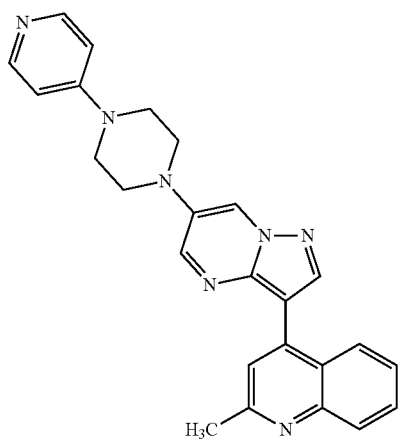

Compound 27 was prepared according to the general procedures 1, 2 and 3B. LC/MS (method 2): $t_R$=2.92 min, m/z (M+H)$^+$=422.

Example 40

Compound 28

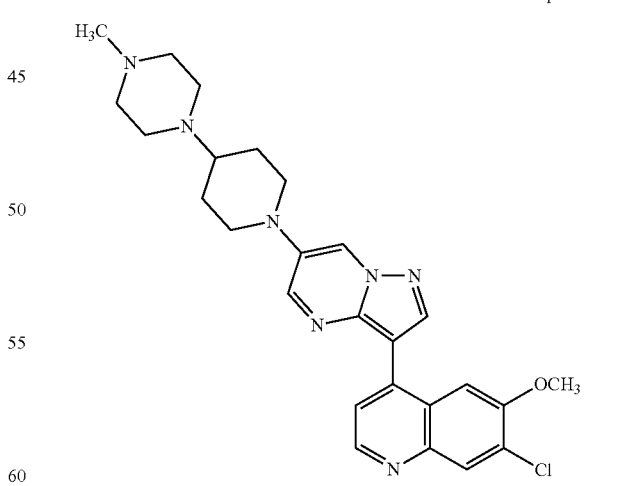

Compound 28 was prepared according to the general procedures 1, 2 and 5. LC/MS (method 2): $t_R$=2.92 min, m/z (M+H)$^+$=492. $^1$H NMR (400 MHz, DMSO-d$_6$) δ 8.83-8.74 (m, 2H), 8.63 (d, J=15.2 Hz, 2H), 8.12 (s, 1H), 7.70 (d, J=4.6 Hz, 1H), 7.64 (s, 1H), 3.96 (s, 1H), 3.88 (s, 3H), 3.71 (d, J=12.2 Hz, 2H), 3.31 (s, 8H), 2.77-2.65 (m, 3H), 2.36 (m, 1H), 2.25 (s, 1H), 1.87 (m, 2H), 1.56 (m, 2H).

Example 41

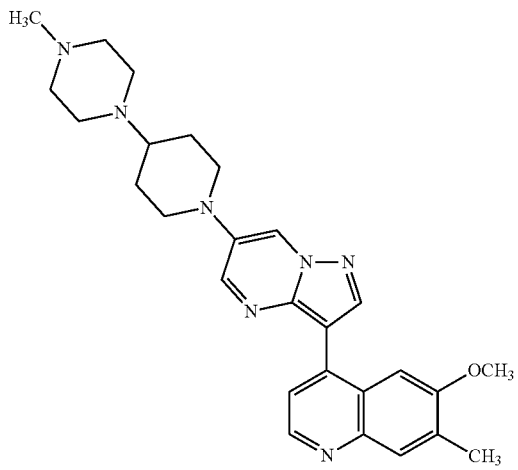

Compound 29

Compound 29 was prepared according to the general procedures 1, 2 and 5. LC/MS (method 2): $t_R$=2.88 min, m/z (M+H)$^+$=472. $^1$H NMR (400 MHz, DMSO-d$_6$) δ 8.78 (d, J=2.7 Hz, 1H), 8.68 (d, J=4.6 Hz, 1H), 8.62 (d, J=2.6 Hz, 1H), 8.56 (s, 1H), 7.81 (t, J=1.0 Hz, 1H), 7.59 (d, J=4.6 Hz, 1H), 7.44 (s, 1H), 3.80 (s, 3H), 3.70 (d, J=12.1 Hz, 2H), 3.3 (m, 8H), 2.70 (m, 2H), 2.60-2.50 (m, 2H), 2.34 (d, J=1.0 Hz, 3H), 2.23 (s, 2H), 1.85 (m, 2H), 1.56 (q, J=10.5, 9.7 Hz, 2H).

Example 42

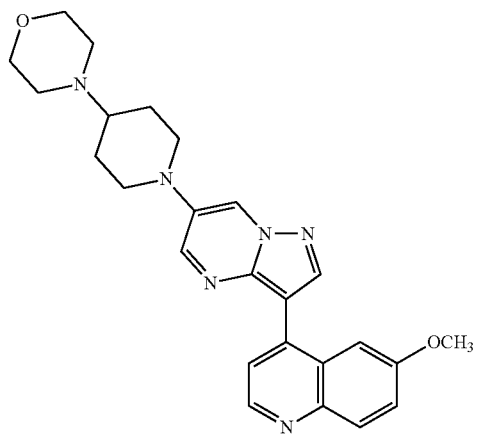

Compound 30

Compound 30 was prepared according to the general procedures 1, 2 and 5. LC/MS (method 2): $t_R$=2.76 min, m/z (M+H)$^+$=445. $^1$H NMR (400 MHz, DMSO-d$_6$) δ 8.79 (d, J=2.6 Hz, 1H), 8.73 (d, J=4.5 Hz, 1H), 8.63 (s, 1H), 8.56 (s, 1H), 7.95 (d, J=9.1 Hz, 1H), 7.65 (d, J=4.5 Hz, 1H), 7.48 (d, J=2.8 Hz, 1H), 7.40 (dd, J=9.1, 2.8 Hz, 1H), 3.78 (s, 3H), 3.72 (s, 2H), 3.56 (s, 4H), 3.30 (m, 5H), 2.71 (t, J=11.9 Hz, 2H), 1.87 (m, 2H), 1.57 (m, 2H).

Example 43

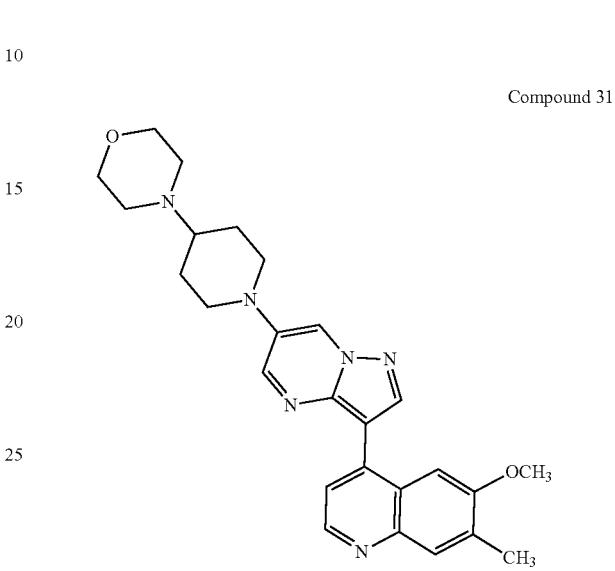

Compound 31

Compound 31 was prepared according to the general procedures 1, 2 and 5. LC/MS (method 2): $t_R$=3.10 min, m/z (M+H)$^+$=459.

Example 44

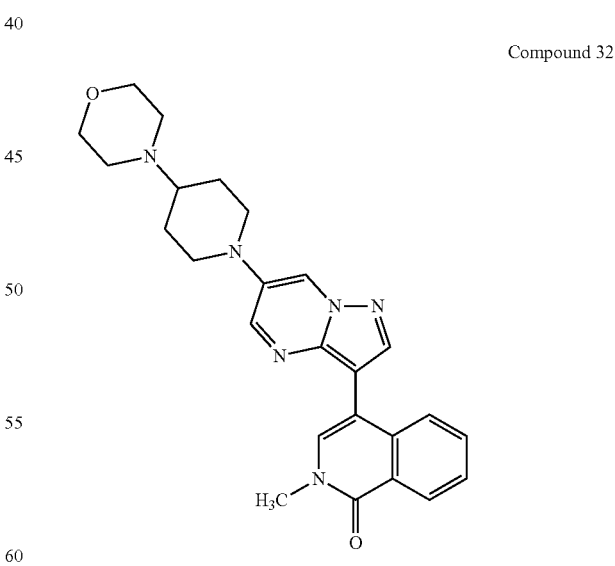

Compound 32

Compound 32 was prepared according to the general procedures 1, 2 and 3B. LC/MS (method 2): $t_R$=3.17 min, m/z (M+H)$^+$=445. $^1$H NMR (400 MHz, DMSO-d$_6$) δ 8.65 (d, J=2.2 Hz, 1H), 8.55 (s, 1H), 8.29 (ddd, J=7.9, 1.5, 0.8 Hz, 1H), 8.18 (s, 1H), 7.68-7.47 (m, 4H), 3.66 (d, J=11.8 Hz, 2H), 3.54 (s, 4H), 3.31 (s, 5H), 2.73-2.62 (m, 2H), 2.34-2.17 (m, 2H), 1.96-1.78 (m, 2H), 1.53 (d, J=12.1 Hz, 3H).
Compound 15 Analogs (Examples 47-57, 59-64).
Example 45
Compound 33
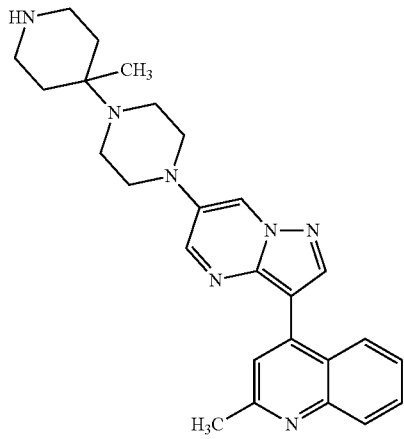
Compound 33 was prepared according to the general procedures 1, 2 and 3B. LC/MS (method 2): $t_R$=2.47 min, m/z (M+H)$^+$=442.
Example 46
Compound 34
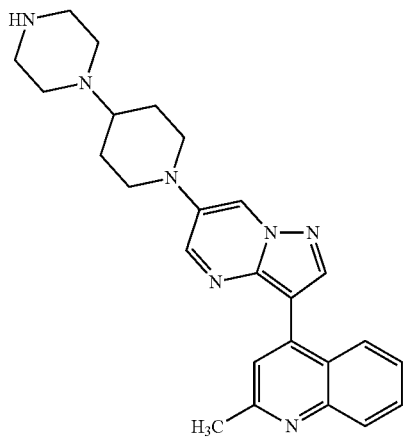
Compound 34 was prepared according to the general procedures 1, 2, 3B and 4. LC/MS (method 2): $t_R$=2.5 min, m/z (M+H)$^+$=428.
Example 47
Compound 39
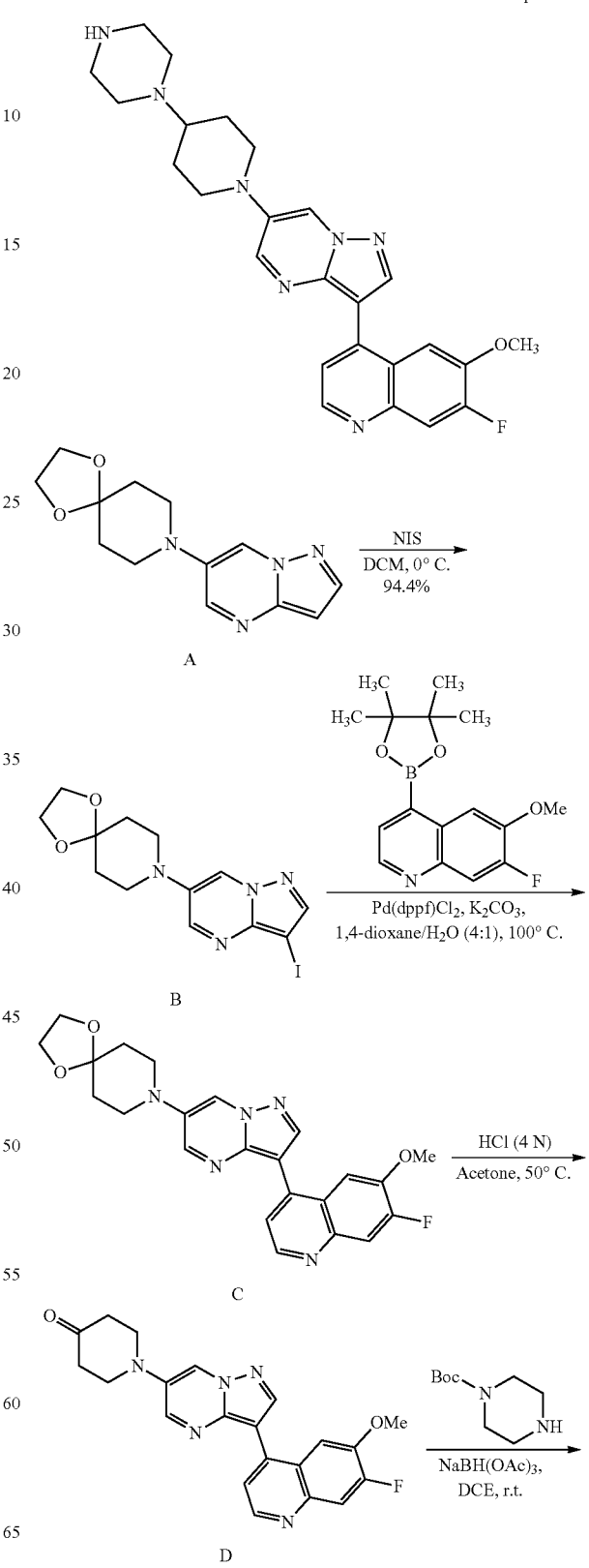

-continued

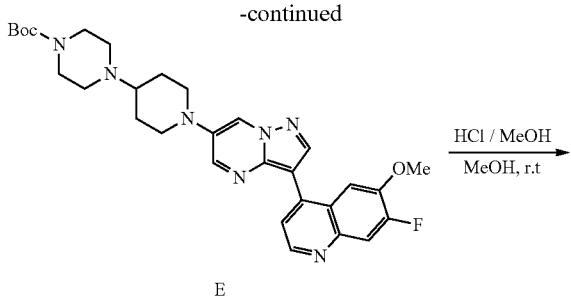

E

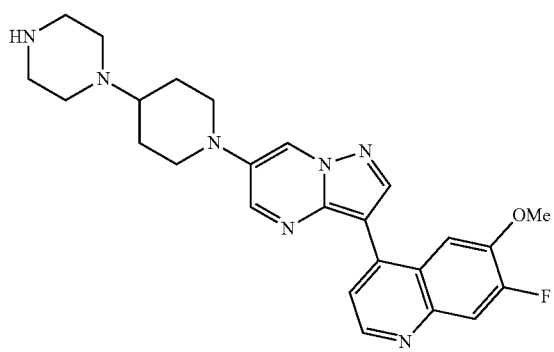

39

Experimental Procedure:

Step 1: To a solution of 8-pyrazolo[1,5-a]pyrimidin-6-yl-1,4-dioxa-8-azaspiro[4.5]decane (prepared according to general procedure 1 by using 1,4-dioxa-8-azaspiro[4.5]decane as the starting material) (2.00 g, 7.68 mmol, 1.00 eq) in DCM (100.00 mL) cooled at 0° C. was added NIS (1.73 g, 7.68 mmol, 1.00 eq) portionwise. The reaction mixture was stirred at 0° C. for 5 min until TLC (Hexane: Ethyl acetate=3/1) showed the reaction was complete. The mixture was quenched with water (50 mL), and then separated. The organic layer was washed with sat. aq. NaHCO₃ (50 mL×3), and brine (50 mL), dried over Na₂SO₄, filtered and concentrated in vacuo to give the residue, which was purified by Biotage flash column eluted with EtOAc in PE (0% to 50%) to give the desired product of 8-(3-iodopyrazolo[1,5-a]pyrimidin-6-yl)-1,4-dioxa-8-azaspiro[4.5]decane B (2.80 g, 94.40% yield) as a pale yellow solid.

Step 2: To a suspension of 8-(3-iodopyrazolo[1,5-a]pyrimidin-6-yl)-1,4-dioxa-8-azaspiro[4.5]decane B (1.58 g, 4.08 mmol, 1.20 eq), 7-fluoro-6-methoxy-4-(4,4,5,5-tetramethyl-1,3,2-dioxaborolan-2-yl)quinoline (1.03 g, 3.40 mmol, 1.00 eq) in 1,4-dioxane (21.5 ml) were added K₂CO₃ (1.17 g, 8.50 mmol, 2.50 eq) and Pd(dppf)Cl₂ (497.24 mg, 680.00 µmol, 0.20 eq) and water (5.4 mL). The mixture was degassed and then heated at 100° C. for 2 hours under N₂ until LCMS showed the reaction was completed. The mixture was concentrated in vacuo and the residue was purified by column chromatography on silica gel eluted with DCM/MeOH (100/1) to DCM/MeOH (50/1, with 0.1% NH₃.H₂O) to give the desired product of 8-[3-(7-fluoro-6-methoxy-4-quinolyl)pyrazolo[1,5-a]pyrimidin-6-yl]-1,4-dioxa-8-azaspiro[4.5]decane C as a pale yellow solid.

Step 3: To a suspension of 8-[3-(7-fluoro-6-methoxy-4-quinolyl)pyrazolo[1,5-a]pyrimidin-6-yl]-1,4-dioxa-8-azaspiro[4.5]decane (2.40 g, 5.51 mmol, 1.00 eq) in acetone (20.00 mL) was added 4 N HCl aqueous solution (12 mL). The reaction mixture was stirred at 50° C. for 0.5 h until LCMS showed the reaction was complete. The mixture was basified to pH=8 with saturated NaHCO₃ aqueous solution, extracted with DCM (30 ml×3). The organic layer was dried over Na₂SO₄, filtered and concentrated in vacuo to give a brown solid, which was triturated with EtOAc (20 mL) for 0.5 h. The pale yellow solid was collected by filtration and dried under high vacuum to give the desired product of 1-[3-(7-fluoro-6-methoxy-4-quinolyl)pyrazolo[1,5-a]pyrimidin-6-yl]piperidin-4-one D (910 mg, 38% yield).

Step 4: To a suspension of 1-[3-(7-fluoro-6-methoxy-4-quinolyl)pyrazolo[1,5-a]pyrimidin-6-yl]piperidin-4-one D (50.0 mg, 127.8 µmol, 1.00 eq) in 1,2-dichloroethane (1.00 ml) was added tert-butyl piperazine-1-carboxylate (47.59 mg, 255.50 umol, 2.00 eq). The resulting mixture was adjusted pH to about 5 with AcOH. The reaction mixture was stirred at room temperature (30° C.) for 15 h, followed by the addition of NaBH(OAc)₃ (54.15 mg, 255.50 umol, 2.00 eq). The reaction mixture was stirred at room temperature (30° C.) for another 3 h until LCMS showed the reaction was completed. The mixture was quenched with sat. aq. NaHCO₃ (0.1 mL), then concentrated in vacuo and the residue was purified by silica gel column chromatography (DCM: MeOH=100/1 to 30:1) to give the product of tert-butyl 4-[1-[3-(7-fluoro-6-methoxy-4-quinolyl)pyrazolo[1,5-a]pyrimidin-6-yl]-4-piperidyl]piperazine-1-carboxylate E (40 mg, 74% purity) as a yellow solid, which was used in next step directly.

Step 5: To a suspension of tert-butyl 4-[1-[3-(7-fluoro-6-methoxy-4-quinolyl)pyrazolo[1,5-a]pyrimidin-6-yl]-4-piperidyl]piperazine-1-carboxylate E (40.0 mg, 71.2 umol, 1.00 eq) in MeOH (0.5 ml) was added 4 N HCl/MeOH (1 ml). The reaction mixture was stirred at room temperature (30° C.) for 0.5 h. Solid was precipitated. LCMS showed the reaction was complete. The mixture was diluted with MeOH (5 ml) and stirred at room temperature (30° C.) for 10 min. The suspension was filtered, and the yellow solid was dried under high vacuum to give the desired product of 7-fluoro-6-methoxy-4-[6-(4-piperazin-1-yl-1-piperidyl)pyrazolo[1,5-a]pyrimidin-3-yl]quinoline 39 (10.7 mg, 26% yield) as an orange solid.

Example 48

Compound 40

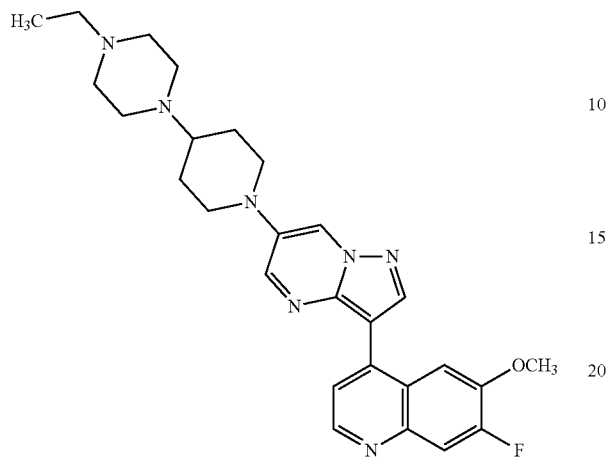

Compound 40 was prepared through reductive amination by using intermediate D in an analogous manner as compound 39. LC/MS (method 3): $t_R$=1.86 min, m/z (M+H)$^+$=490.2; $^1$H NMR (400 MHz, CDCl$_3$): δ 8.81 (d, J=4.4 Hz, 1H), 8.57 (d, J=2.4 Hz, 1H), 8.31 (s, 1H), 8.21 (d, J=2.8 Hz, 1H), 7.78 (d, J=12.0 Hz, 1H), 7.58 (d, J=4.4 Hz, 1H), 7.53 (d, J=9.6 Hz, 1H), 3.89 (s, 3H), 3.60-3.66 (m, 2H), 2.80-2.82 (m, 2H), 2.41-2.77 (m, 11H), 2.04-2.07 (m, 2H), 1.77-1.80 (m, 2H), 1.09 (t, J=6.8 Hz, 3H).

Example 49

Compound 41

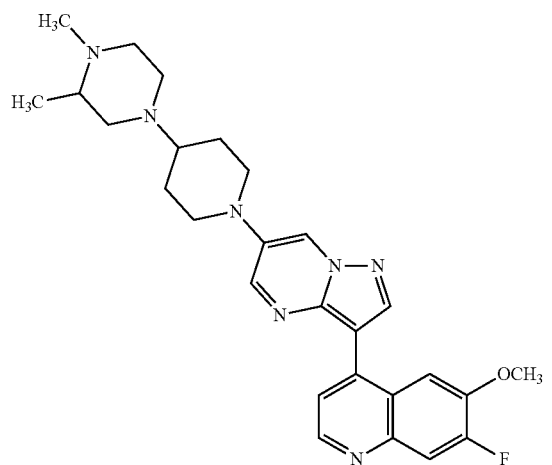

Compound 41 was prepared through reductive amination by using intermediate D in an analogous manner as compound 39. LC/MS (method 4): $t_R$=5.55 min, m/z (M+H)$^+$=490.2. $^1$H NMR (400 MHz, CDCl$_3$): δ 8.82 (d, J=4.4 Hz, 1H), 8.58 (d, J=2.4 Hz, 1H), 8.32 (s, 1H), 8.22 (d, J=2.4 Hz, 1H), 7.79 (d, J=12.0 Hz, 1H), 7.58 (d, J=4.4 Hz, 1H), 7.53 (d, J=9.2 Hz, 1H), 3.90 (s, 3H), 3.63-3.66 (m, 2H), 2.78-2.88 (m, 5H), 3.31 (s, 3H), 2.33-2.46 (m, 3H), 2.06-2.12 (m, 4H), 1.77-1.80 (m, 2H), 1.08 (t, J=6.0 Hz, 3H).

Example 50

Compound 42

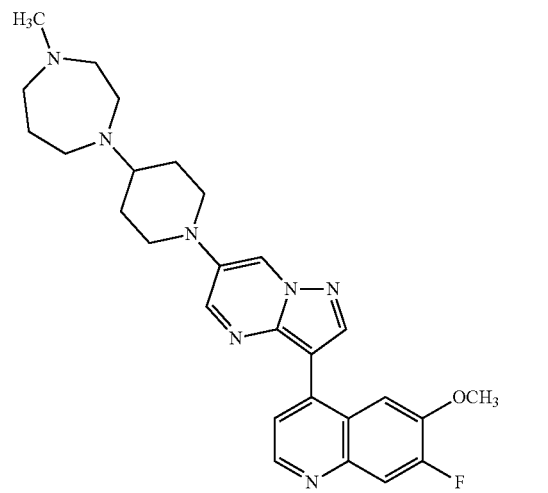

Compound 42 was prepared through reductive amination by using intermediate D in an analogous manner as compound 39. LC/MS (method 3): $t_R$=1.86 min, m/z (M+H)$^+$=490.2; $^1$H NMR (400 MHz, CDCl$_3$): δ 8.81 (d, J=4.4 Hz, 1H), 8.57 (d, J=2.4 Hz, 1H), 8.31 (s, 1H), 8.21 (d, J=2.8 Hz, 1H), 7.78 (d, J=12.0 Hz, 1H), 7.58 (d, J=4.4 Hz, 1H), 7.53 (d, J=9.6 Hz, 1H), 3.89 (s, 3H), 3.60-3.66 (m, 2H), 2.80-2.82 (m, 2H), 2.41-2.77 (m, 11H), 2.04-2.07 (m, 2H), 1.77-1.80 (m, 2H), 1.09 (t, J=6.8 Hz, 3H).

Example 51

Compound 43

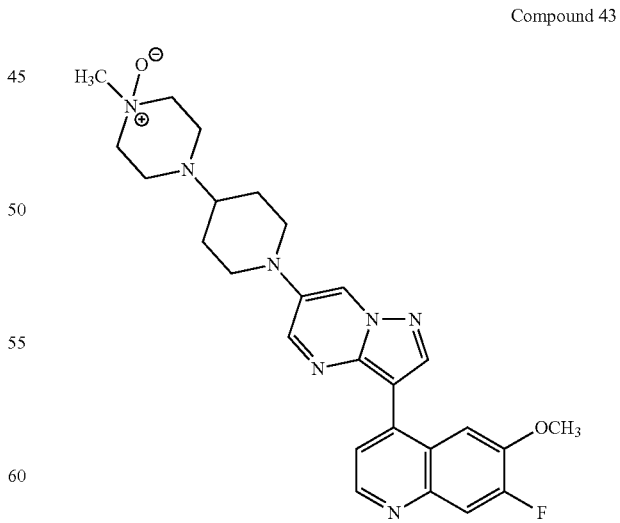

Compound 43 was prepared through reductive amination by using intermediate D in an analogous manner as compound 39. LC/MS (method 4): $t_R$=5.66 min, m/z (M+H)$^+$=492.2; $^1$H NMR (400 MHz, CD$_3$OD) δ 8.67-8.65 (m, 2H), 8.38 (s, 2H), 7.73-7.56 (m, 3H), 3.89 (s, 3H), 3.69 (d, J=11.3 Hz, 2H), 3.54-3.40 (m, 2H), 3.27-3.15 (m, 5H), 3.06 (t, J=11.4 Hz, 2H), 2.87 (d, J=12.0 Hz, 2H), 2.77 (t, J=11.8 Hz, 2H), 2.53 (t, J=11.2 Hz, 1H), 2.04 (d, J=11.8 Hz, 2H), 1.73 (q, J=10.8 Hz, 2H).

Example 52

Compound 44

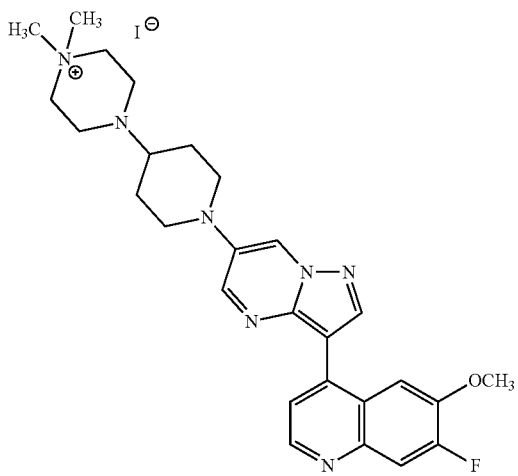

Compound 44 was prepared through reductive amination by using intermediate D in an analogous manner as compound 39. LC/MS (method 3): $t_R$=1.90 min, m/z (M+H)+=490.2; $^1$H NMR (400 MHz, D$_2$O) δ=8.76 (d, J=6.0 Hz, 1H), 8.72 (d, J=2.5 Hz, 1H), 8.57 (d, J=2.5 Hz, 1H), 8.55 (s, 1H), 8.03 (d, J=6.3 Hz, 1H), 7.90 (d, J=10.5 Hz, 1H), 7.72 (d, J=8.5 Hz, 1H), 3.92 (s, 3H), 3.87 (s, 10H), 3.68-3.61 (m, 1H), 3.36 (s, 6H), 3.01-2.95 (m, 2H), 2.41 (d, J=11.8 Hz, 2H), 2.01-1.92 (m, 2H).

Example 53

Compound 45

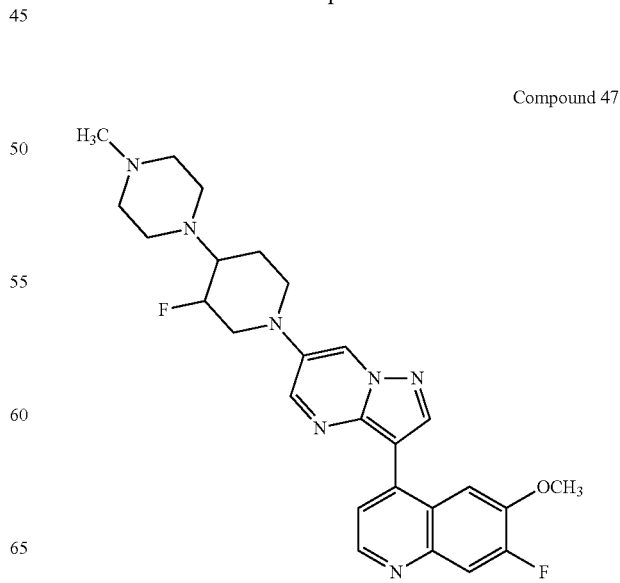

Compound 45 was prepared through reductive amination by using intermediate D in an analogous manner as compound 39. LC/MS (method 4): $t_R$=5.46 min, m/z (M+H)+=479.2; $^1$H NMR (400 MHz, CDCl$_3$): δ 8.82 (d, J=4.4 Hz, 1H), 8.58 (d, J=2.8 Hz, 1H), 8.32 (s, 1H), 8.22 (d, J=2.8 Hz, 1H), 7.79 (d, J=12.0 Hz, 1H), 7.58 (d, J=4.4 Hz, 1H), 7.53 (d, J=8.8 Hz, 1H), 3.90 (s, 3H), 3.63-3.66 (m, 2H), 2.78-2.83 (m, 2H), 2.44-2.68 (m, 9H), 2.04-2.07 (m, 2H), 1.77-1.81 (m, 2H).

Example 54

Compound 46

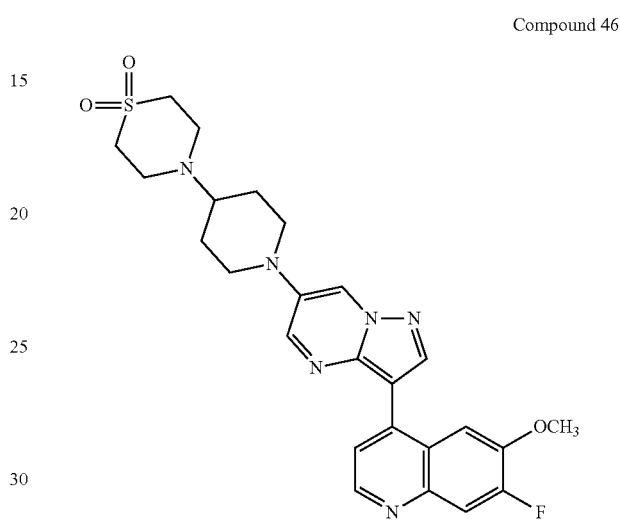

Compound 46 was prepared through reductive amination by using intermediate D in an analogous manner as compound 39. LC/MS (method 4): $t_R$=6.00 min, m/z (M+H)+=511.1; $^1$H NMR (400 MHz, CDCl$_3$): δ 8.83 (d, J=4.4 Hz, 1H), 8.57 (d, J=2.4 Hz, 1H), 8.34 (s, 1H), 8.24 (d, J=2.4 Hz, 1H), 7.80 (d, J=12.0 Hz, 1H), 7.59 (d, J=4.4 Hz, 1H), 7.53 (d, J=8.8 Hz, 1H), 3.90 (s, 3H), 3.66-3.69 (m, 2H), 3.05-3.14 (m, 8H), 2.71-2.83 (m, 3H), 1.96-1.99 (m, 2H), 1.80-1.84 (m, 2H).

Example 55

Compound 47

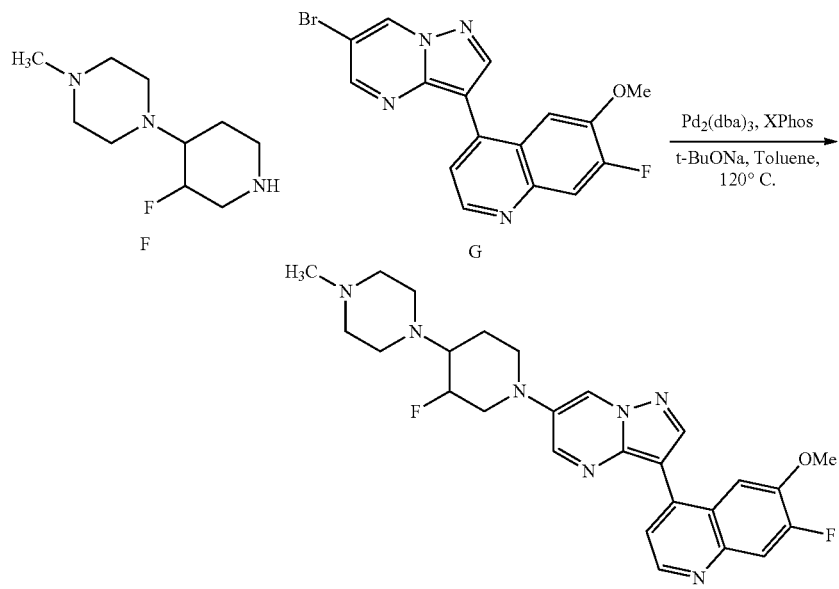

39

A stirred mixture of 1-(3-fluoro-4-piperidyl)-4-methyl-piperazine (161.65 mg, 589.53 umol, 2.20 eq, 2HCl), 4-(6-bromopyrazolo[1,5-a]pyrimidin-3-yl)-7-fluoro-6-methoxy-quinoline (100.00 mg, 267.97 umol, 1.00 eq), t-BuONa (64.38 mg, 669.92 umol, 2.50 eq), Pd$_2$(dba)$_3$ (24.54 mg, 26.80 umol, 0.10 eq) and XPhos (51.10 mg, 107.19 umol, 0.40 eq) in toluene (4.00 mL) was degassed and purged with N$_2$ for 3 times, then stirred at 110° C. for 16 hour under N$_2$ atmosphere until TLC (DCM/MeOH=20/1) and LCMS analysis showed the starting material was consumed completely. The mixture was diluted with water (10 mL) and extracted with DCM (20 mL×3). The combined organic layers was washed with brine (20 mL×3), dried over anhydrous Na$_2$SO$_4$, filtered and concentrated in vacuo to give the residue, which was purified by prep-TLC (SiO$_2$, DCM/MeOH=10/1 with 1% ammonia) to afford the impure product (20 mg) as a yellow solid. LC/MS (method 3): t$_R$=2.03 min, m/z (M+H)$^+$=494.2; $^1$H NMR (400 MHz, CD$_3$OD) δ 8.93-8.90 (m, 2H), 8.80 (s, 1H), 8.69 (d, J=2.4 Hz, 1H), 8.39 (d, J=6.0 Hz, 1H), 8.16 (d, J=8.8 Hz, 1H), 7.93 (d, J=10.4 Hz, 1H), 5.21 (d, J=47.6 Hz, 1H), 4.08 (s, 3H), 3.98-3.95 (m, 1H), 3.48-3.31 (m, 4H), 3.21-3.05 (m, 6H), 2.91 (s, 3H), 2.26-2.22 (m, 2H), 1.95-1.92 (m, 2H).

Example 56

Compound 48

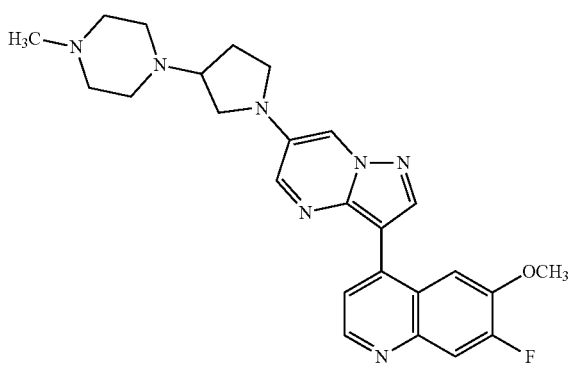

Compound 48 was prepared by using corresponding amine in an analogous manner as compound 47. LC/MS (method 3): t$_R$=2.07 min, m/z (M+H)$^+$=462.1; $^1$H NMR (400 MHz, CD$_3$OD) δ 8.71 (d, J=4.8 Hz, 1H), 8.51 (d, J=2.8 Hz, 1H), 8.38 (s, 1H), 8.19 (d, J=2.4 Hz, 1H), 7.72-7.65 (m, 3H), 3.91 (s, 3H), 3.67-3.56 (m, 2H), 3.46-3.40 (m, 1H), 3.18-3.10 (m, 1H), 2.82-2.70 (m, 8H), 2.48 (s, 3H), 2.40-2.36 (m, 1H), 2.03-1.96 (m, 2H).

Example 57

Compound 49

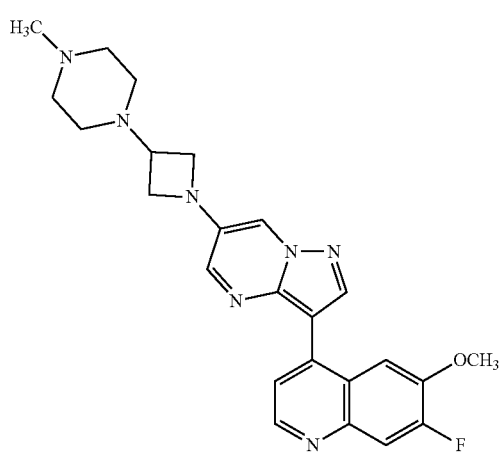

Compound 49 was prepared by using corresponding amine in an analogous manner as compound 47. LC/MS (method 3): t$_R$=1.91 min, m/z (M+H)$^+$=448.1; $^1$H NMR (400 MHz, CD$_3$OD) δ 8.65 (d, J=4.8 Hz, 1H), 8.33 (s, 1H), 8.23 (d, J=2.8 Hz, 1H), 8.12 (d, J=2.4 Hz, 1H), 7.66-7.59 (m, 3H), 4.11 (t, J=7.2 Hz, 2H), 3.88 (s, 3H), 3.83-3.80 (m, 2H), 3.48-3.42 (m, 1H), 2.61 (m, 8H), 2.38 (s, 3H).

Example 59

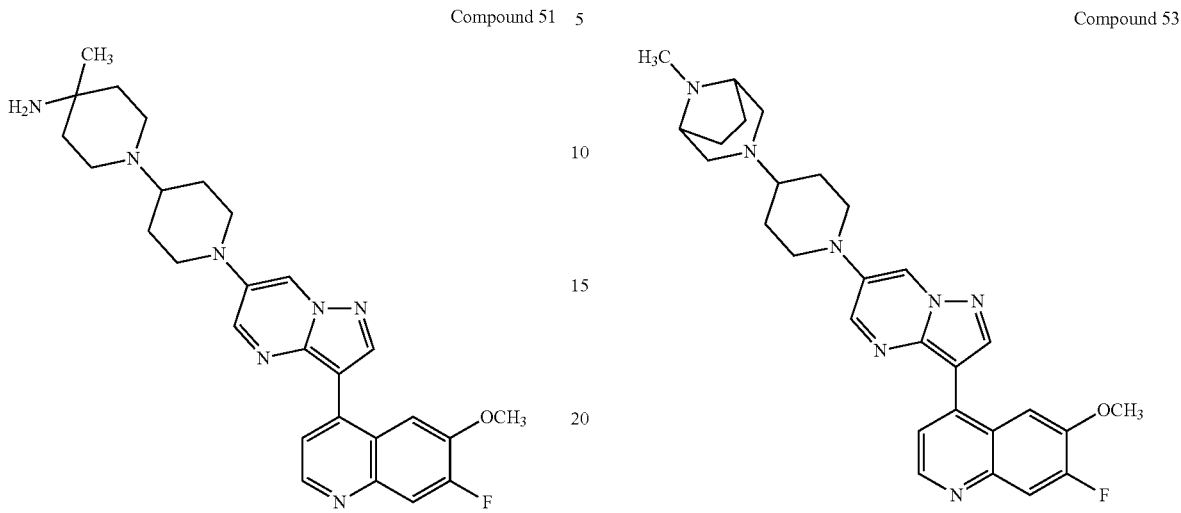

Compound 51

Compound 51 was prepared through reductive amination by using intermediate D in an analogous manner as compound 39 followed by deprotection of Boc with HCl/MeOH. LC/MS (method 4): $t_R$=5.32 min, m/z (M+H)$^+$=490.2; $^1$H NMR (400 MHz, CD$_3$OD): δ 8.96-8.93 (m, 2H), 8.83 (s, 1H), 8.74 (s, 1H), 8.40 (d, J=10.0 Hz, 1H), 8.17 (d, J=8.4 Hz, 1H), 7.96 (d, J=10.8 Hz, 1H), 4.10 (s, 3H), 3.99 (d, J=9.2 Hz, 2H), 3.80-3.55 (m, 4H), 3.02-2.96 (m, 2H), 2.44-2.27 (m, 5H), 2.18-2.06 (m, 5H), 1.59 (s, 3H).

Example 60

Compound 52

Compound 52 was prepared through reductive amination by using intermediate D followed by de-Boc procedure in an analogous manner as compound 39. LC/MS (method 3): $t_R$=2.23 min, m/z (M+H)$^+$=488.2; $^1$H NMR (400 MHz, CD$_3$OD) δ 8.93-8.91 (m, 2H), 8.81 (s, 1H), 8.69 (d, J=2.8 Hz, 1H), 8.39 (d, J=6.0 Hz, 1H), 8.16 (d, J=8.5 Hz, 1H), 7.94 (d, J=10.4 Hz, 1H), 4.29 (br s, 2H), 4.08 (s, 3H), 3.91 (d, J=12.0 Hz, 2H), 3.64-3.48 (m, 4H), 3.13 (m, 1H), 2.96 (t, J=11.8 Hz, 2H), 2.40-2.38 (m, 2H), 2.24 (m, 4H), 2.08-2.06 (m, 2H).

Example 61

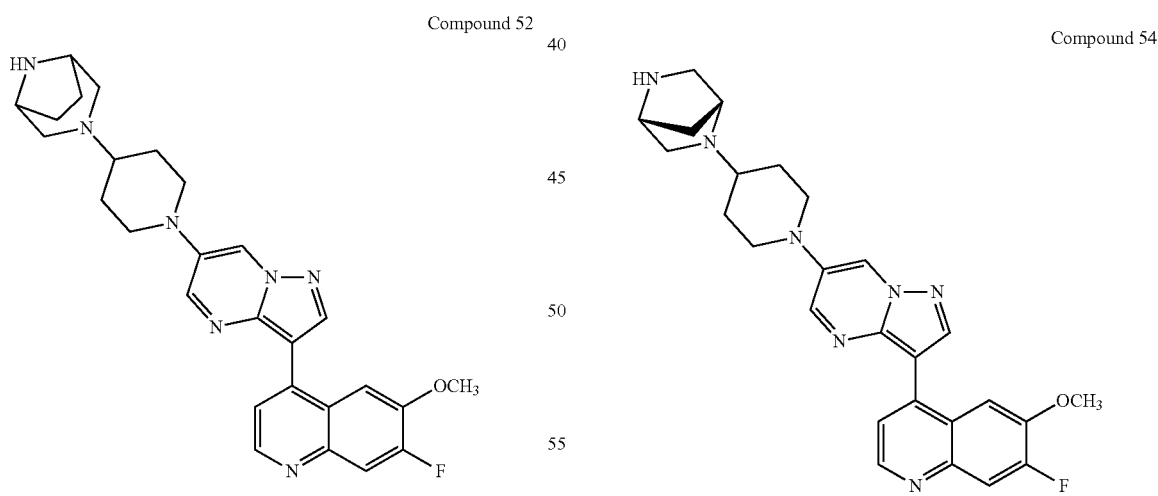

Compound 53

Compound 53 was prepared through reductive amination from compound 52. LC/MS (method 3): $t_R$=2.41 min, m/z (M+H)$^+$=501.3; $^1$H NMR (400 MHz, CD$_3$OD) δ 8.83 (d, J=4.4 Hz, 1H), 8.58 (d, J=2.4 Hz, 1H), 8.32 (s, 1H), 8.22 (d, J=2.4 Hz, 1H), 7.80 (d, J=12.0 Hz, 1H), 7.59 (d, J=4.4 Hz, 1H), 7.55 (d, J=8.8 Hz, 1H), 3.90 (s, 3H), 3.57-3.54 (m, 2H), 3.15 (m, 2H), 2.86-2.81 (m, 2H), 2.68-2.65 (m, 2H), 2.55-2.53 (m, 2H), 2.41-2.36 (m, 1H), 2.30 (s, 3H), 1.97-1.94 (m, 4H), 1.78-1.69 (m, 4H).

Example 62

Compound 54

Compound 54 was prepared through reductive amination by using intermediate D followed by de-Boc procedure in an analogous manner as compound 39. LC/MS (method 3): $t_R$=1.96 min, m/z (M+H)$^+$=473.2; $^1$H NMR (400 MHz, D$_2$O): δ 8.76 (d, J=6.0 Hz, 1H), 8.72 (d, J=2.8 Hz, 1H), 8.56 (s, 1H), 8.56 (d, J=2.4 Hz, 1H), 8.02 (d, J=6.0 Hz, 1H), 7.89 (d, J=10.4 Hz, 1H), 7.70 (d, J=8.8 Hz, 1H), 4.93 (s, 1H), 3.93 (s, 3H), 3.81-3.88 (m, 5H), 3.60-3.75 (m, 3H), 2.95, 2.99 (m, 2H), 2.32-2.48 (m, 4H), 1.94-1.98 (m, 2H).

Example 63

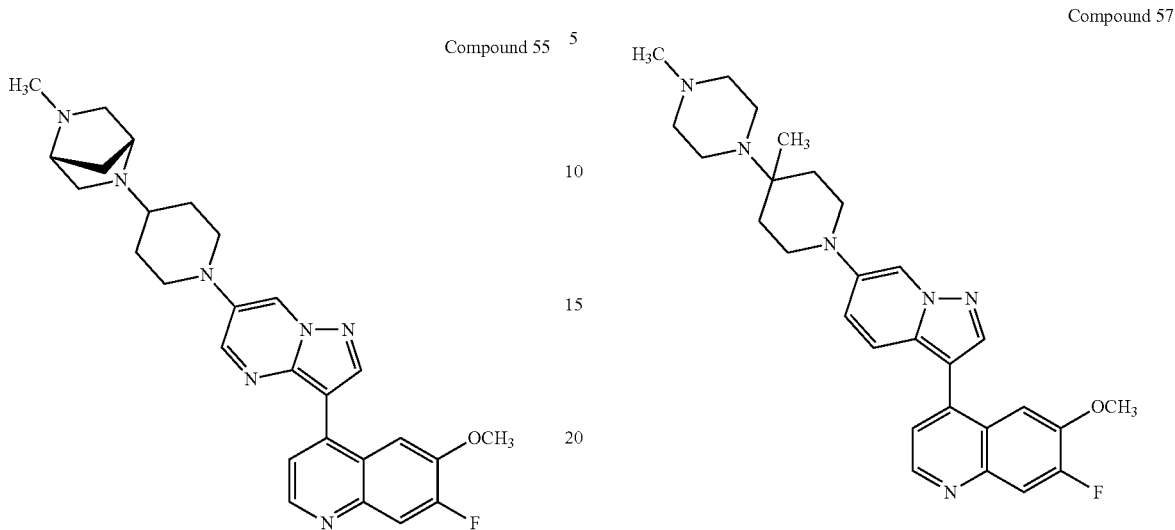

Compound 55

Compound 54 was prepared through reductive amination from compound 53. LC/MS (method 3): $t_R$=1.99 min, m/z (M+H)$^+$=488.2; $^1$H NMR (400 MHz, CDCl$_3$): δ 8.82 (d, J=4.4 Hz, 1H), 8.58 (d, J=2.4 Hz, 1H), 8.31 (s, 1H), 8.22 (d, J=2.4 Hz, 1H), 7.78 (d, J=12.0 Hz, 1H), 7.58 (d, J=4.4 Hz, 1H), 7.53 (d, J=8.8 Hz, 1H), 4.14 (s, 3H), 3.53-3.90 (m, 3H), 3.25 (s, 1H), 2.99-3.03 (m, 2H), 2.88-2.89 (m, 2H), 2.55-2.62 (m, 3H), 2.43 (s, 3H), 1.73-1.93 (m, 13H).

Example 64

Compound 56

Compound 56 was prepared in an analogous manner as compound 47. LC/MS (method 3): $t_R$=1.94 min, m/z (M+H)$^+$=475.1; $^1$H NMR (400 MHz, D$_2$O): δ 8.67 (d, J=6.0 Hz, 1H), 8.21 (s, 1H), 7.95 (s, 1H), 7.93-7.88 (m, 1H), 7.66 (d, J=6.0 Hz, 1H), 7.46 (d, J=9.8 Hz, 1H), 7.29-7.26 (m, 2H), 3.96-3.50 (m, 14H), 3.07 (s, 3H), 3.01 (s, 1H), 2.91-2.85 (s, 1H), 2.41 (d, J=12.0 Hz, 2H), 2.01-1.92 (m, 2H).

Example 65

Compound 57

Compound 57 was prepared in an analogous manner as 47 through Buchwald-Hartwig amination. LC/MS (method 3): $t_R$=3.19 min, m/z (M+H)$^+$=490.2; $^1$H NMR (400 MHz, CD$_3$OD) δ 8.94 (m, 2H), 8.80 (s, 1H), 8.71 (d, J=2.4 Hz, 1H), 8.39 (d, J=6.0 Hz, 1H), 8.16 (d, J=8.4 Hz, 1H), 7.96 (d, J=10.8 Hz, 1H), 4.08 (s, 3H), 3.50-3.85 (m, 6H), 3.10-3.18 (m, 4H), 3.02 (s, 3H), 2.30-2.40 (m, 2H), 2.06-2.22 (m, 4H), 1.57 (s, 3H).

Example 66

Compound 58

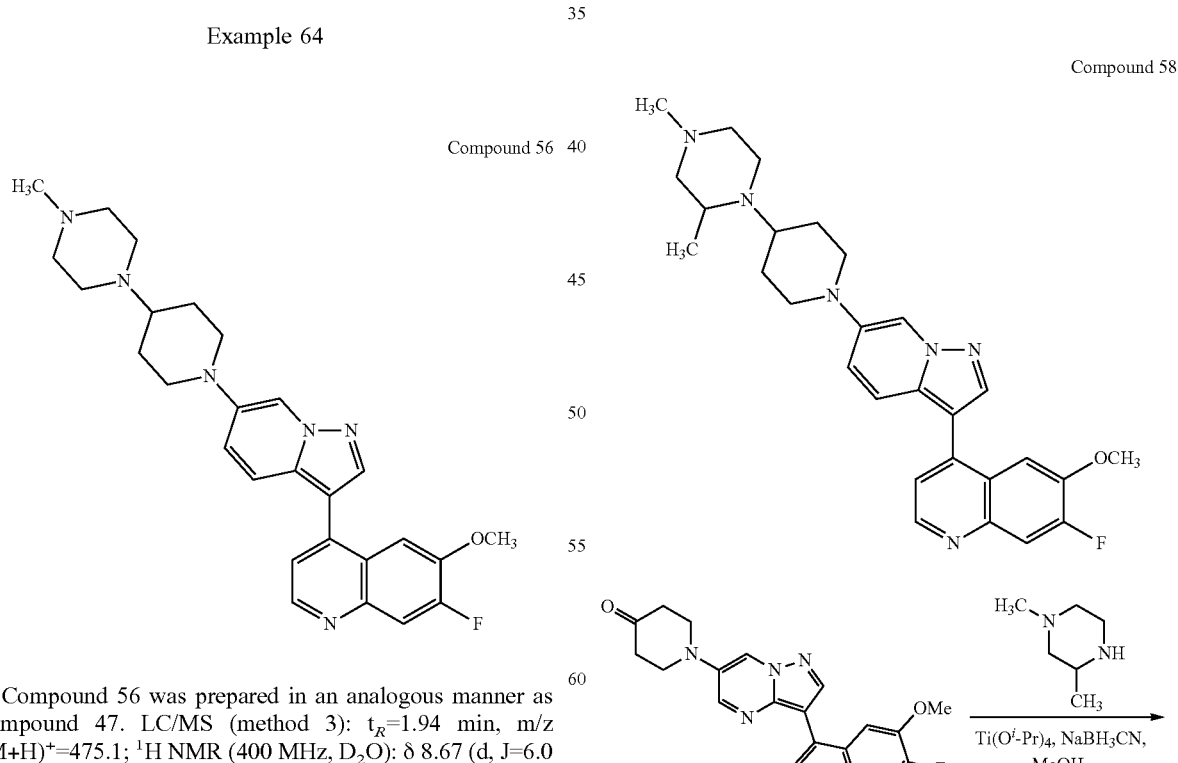

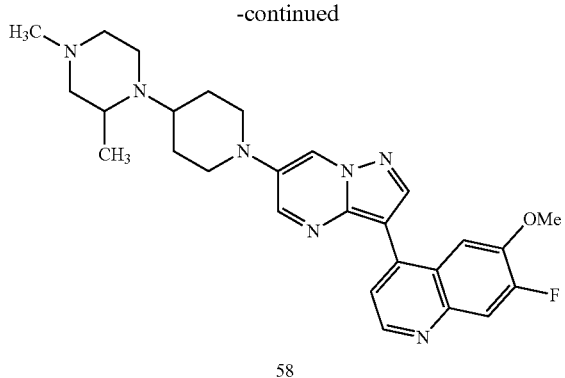

58

A suspension intermediate D and 1,3-dimethylpiperazine (11.67 mg, 102.20 umol, 2.00 eq) in DCE (500.00 uL) was adjust pH to 5 with AcOH. The reaction mixture was stirred at 80° C. for 1 h, followed by the addition of NaBH(OAc)$_3$ (32.49 mg, 153.30 umol, 3.00 eq). The reaction mixture was stirred at 30° C. for another 15 h. TLC (DCM/MeOH=20/1) showed about 90% of the starting material remained. The suspension was stirred at 50° C. for 15 h. TLC (DCM/MeOH=20/1) showed about 60% of the starting material remained. To the suspension was added NaBH(OAc)$_3$ (32.49 mg, 153.3 umol), the reaction mixture was stirred at 30° C. for another 15 h. TLC (DCM/MeOH=20/1) showed no more conversion. The suspension was stirred at 50° C. for 1 h. From LCMS, 25% of the desired product and 74% of the alcohol were detected. The mixture was quenched with sat. aq. NaHCO$_3$ (10 mL), extracted with DCM (10 mL×3). The combined organic layer was concentrated in vacuo to give the residue, which was purified by prep-TLC (DCM/MeOH=10/1) to give the desired product as a brown solid. The desired product was further purified by prep-HPLC in HCl system and dried by lyophilization to give the desired product of 4-[6-[4-(2,4-dimethylpiperazin-1-yl)-1-piperidyl]pyrazolo[1,5-a]pyrimidin-3-yl]-7-fluoro-6-methoxy-quinoline (totally 2.60 mg with 4.9% average yield, 94% purity) as a yellow solid. LC/MS (method 3): $t_R$=2.58 min, m/z (M+H)$^+$=490.2; $^1$H NMR (400 MHz, D$_2$O): δ 8.78 (d, J=6.4 Hz, 1H), 8.73 (d, J=2.4 Hz, 1H), 8.60 (d, J=2.4 Hz, 1H), 8.59 (s, 1H), 8.05 (d, J=6.0 Hz, 1H), 7.91 (d, J=10.8 Hz, 1H), 7.75 (d, J=8.4 Hz, 1H), 3.80-3.98 (m, 1 OH), 3.49-3.51 (m, 3H), 2.93-3.02 (m, 5H), 2.13-2.21 (m, 3H), 1.92-1.98 (m, 1H), 1.49 (t, J=6.4 Hz, 3H).

Example 68

Compound 60

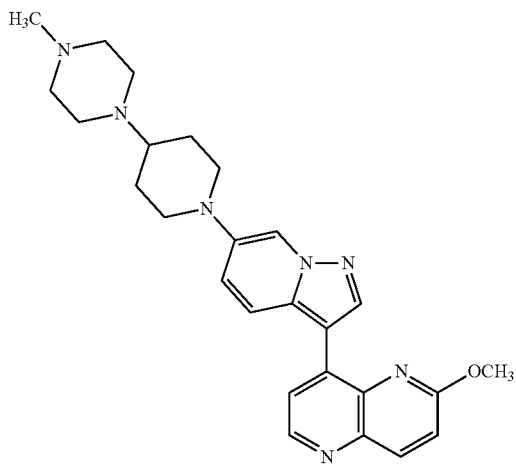

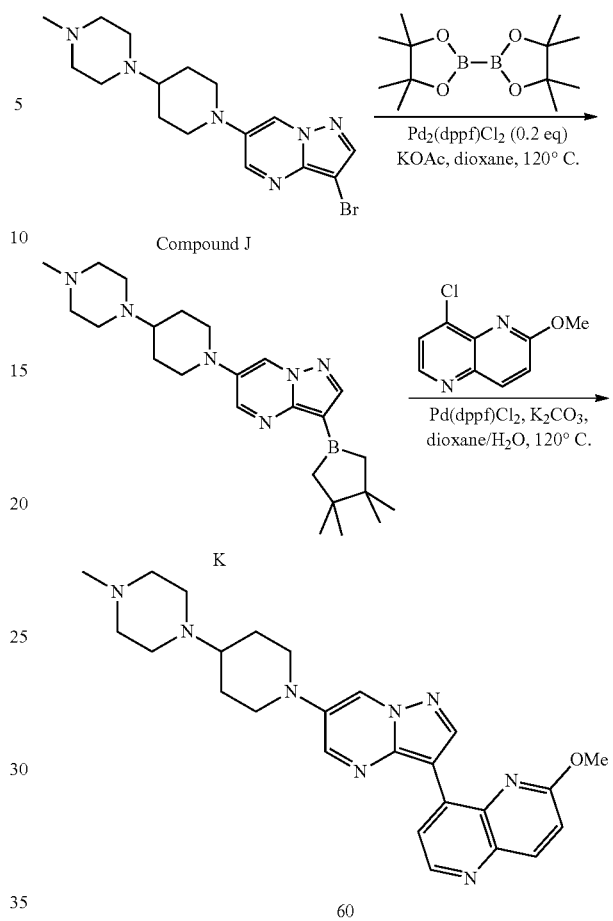

Step 1. A mixture of 3-bromo-6-[4-(4-methylpiperazin-1-yl)-1-piperidyl]pyrazolo[1,5-a]pyrimidine (66.00 mg, 174.00 umol, 1.00 eq), 4,4,5,5-tetramethyl-2-(4,4,5,5-tetramethyl-1,3,2-dioxaborolan-2-yl)-1,3,2-dioxaborolane (176.75 mg, 696.00 umol, 4.00 eq), Pd(dppf)Cl$_2$ (25.46 mg, 34.80 umol, 0.20 eq), KOAc (37.57 mg, 382.80 umol, 2.20 eq) in dioxane (6.00 mL) was degassed and purged with N$_2$ for 3 times, and then the mixture was stirred at 120° C. for 0.5 hour under N$_2$ atmosphere until LCMS showed the starting material was consumed completely. The reaction mixture was cooled to room temperature and its crude product in dioxane as dark-brown solution was used in the next step directly.

Step 2: A mixture of 8-chloro-2-methoxy-1,5-naphthyridine (31.83 mg, 163.56 umol, 2.00 eq), 6-[4-(4-methylpiperazin-1-yl)-1-piperidyl]-3-(4,4,5,5-tetramethyl-1,3,2-dioxaborolan-2-yl)pyrazolo[1,5-a]pyrimidine (74.19 mg, 81.78 umol, 1.00 eq), Pd(dppf)Cl$_2$ (11.97 mg, 16.36 umol, 0.20 eq), K$_2$CO$_3$ (33.91 mg, 245.34 umol, 3.00 eq) in dioxane/H$_2$O (6.00 mL/0.9 mL) was degassed and purged with N$_2$ for 3 times, and then the mixture was stirred at 120° C. for 1 hour under N$_2$ atmosphere until LCMS showed the starting material was consumed completely. The reaction mixture was concentrated in vacuo to give a residue, which was purified by Biotage flash reversed-phase C-18 column chromatography eluting with MeOH/H$_2$O (MeOH in water from 10% to 100%) to give the product of 2-methoxy-8-[6-[4-(4-methylpiperazin-1-yl)-1-piperidyl]pyrazolo[1,5-a]pyrimidin-3-yl]-1,5-naphthyridine (60) as a yellow solid. LC/MS (method 3): $t_R$=2.22 min, m/z (M+H)$^+$=459.2; $^1$H NMR (400 MHz, MeOD) δ 9.50 (s, 1H), 8.88 (d, J=5.2 Hz, 1H), 8.77 (d, J=2.4 Hz, 1H), 8.67 (d, J=4.8 Hz, 1H), 8.41 (d, J=2.8 Hz, 1H), 8.19 (d, J=9.2 Hz, 1H), 7.24 (d, J=9.2 Hz, 1H), 4.15 (s, 3H), 3.77-3.74 (m, 2H), 2.82-2.40 (m, 11H), 2.30 (s, 3H), 2.10-2.07 (m, 2H), 1.80-1.69 (m, 2H).

Example 69

Compound 61

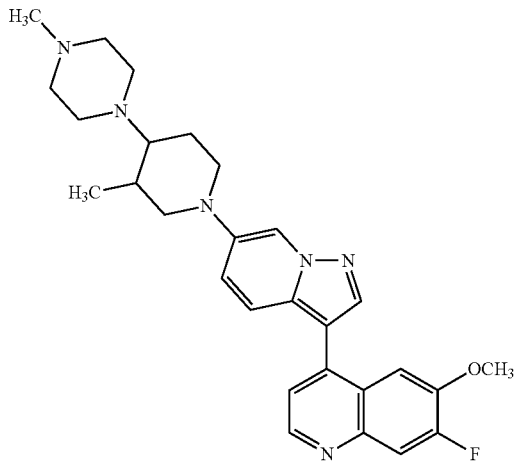

Compound 61 was prepared in an analogous manner as 47 through Buchwald-Hartwig amination. LC/MS (method 3): $t_R$=2.28 min, m/z (M+H)$^+$=490.2; $^1$H NMR (400 MHz, D$_2$O): δ 8.66 (d, J=6.4 Hz, 1H), 8.44 (d, J=8.0 Hz, 1H), 8.43 (s, 1H), 8.13 (d, J=6.0 Hz, 1H), 7.78 (d, J=8.8 Hz, 1H), 7.42 (d, J=3.6 Hz, 1H), 6.83 (d, J=8.0 Hz, 1H), 4.40-4.43 (m, 1H), 3.96 (s, 3H), 3.44-3.66 (m, 9H), 3.23-3.24 (m, 1H), 2.90-3.01 (m, 5H), 2.58 (m, 1H), 2.13-2.15 (m, 1H), 1.79-1.84 (m, 1H), 0.96 (d, J=7.2 Hz, 3H).

Example 70

Compound 62

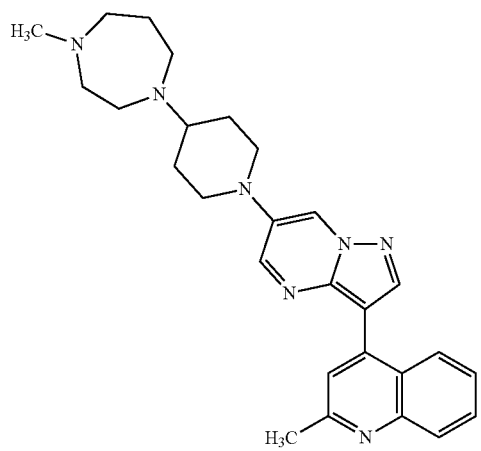

Compound 62 was prepared in an analogous manner as 42. LC/MS (method 4): $t_R$=5.62 min, m/z (M+H)$^+$=456.2; $^1$H NMR (400 MHz, D$_2$O): δ 8.59 (d, J=2.3 Hz, 1H), 8.42-8.40 (m, 2H), 8.19 (d, J=8.5 Hz, 1H), 7.98-7.97 (m, 2H), 7.88 (s, 1H), 7.72-7.70 (m, 1H), 3.84-3.81 (m, 6H), 3.72-3.558 (m, 5H), 2.98 (s, 3H), 2.97-2.91 (m, 2H), 2.84 (s, 3H), 2.34-2.28 (m, 4H), 2.05-1.96 (m, 2H).

Example 71

Compound 63

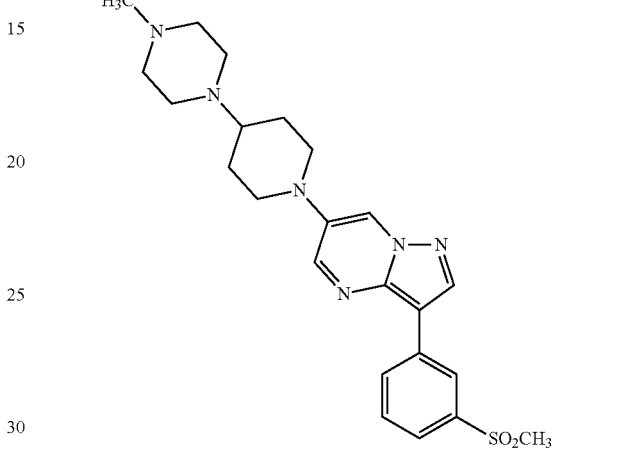

Compound 63 was prepared in an analogous manner as compound 10. LC/MS (method 2): $t_R$=2.84 min, m/z (M+H)$^+$=455.1;

Example 72

Compound 64

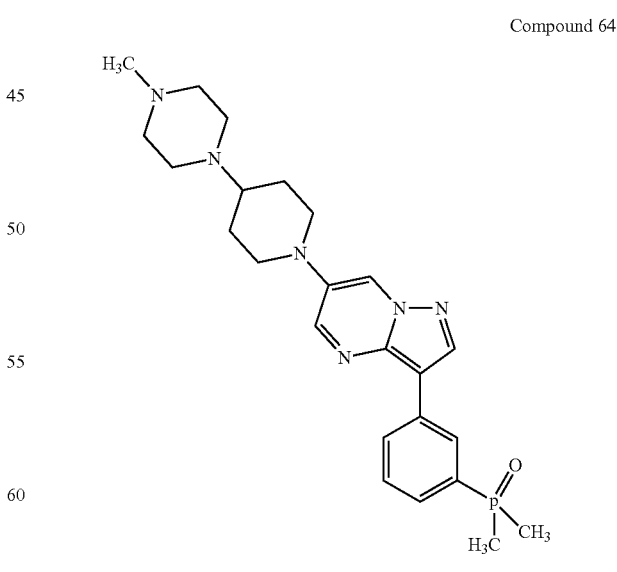

Compound 64 was prepared in an analogous manner as compound 10. LC/MS (method 2): $t_R$=2.56 min, m/z (M+H)$^+$=453.1.

Example 73
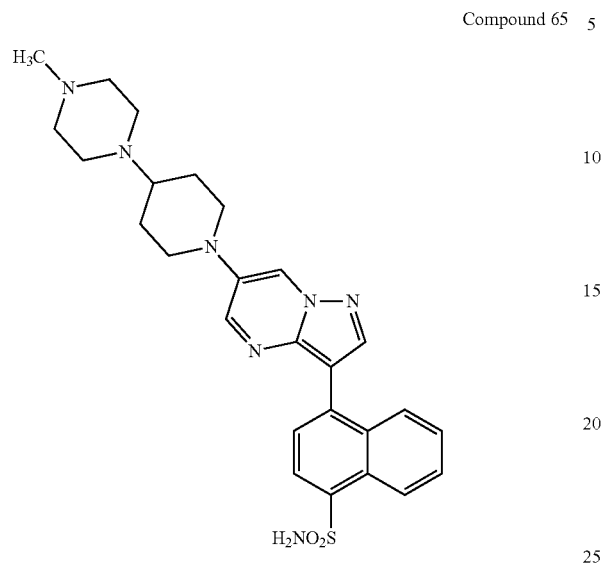
Compound 65
Compound 65 was prepared in an analogous manner as compound 10. LC/MS (method 2): $t_R$=3.14 min, m/z (M+H)$^+$=506.1;
Synthesis of Compound 15. (Examples 78-82).
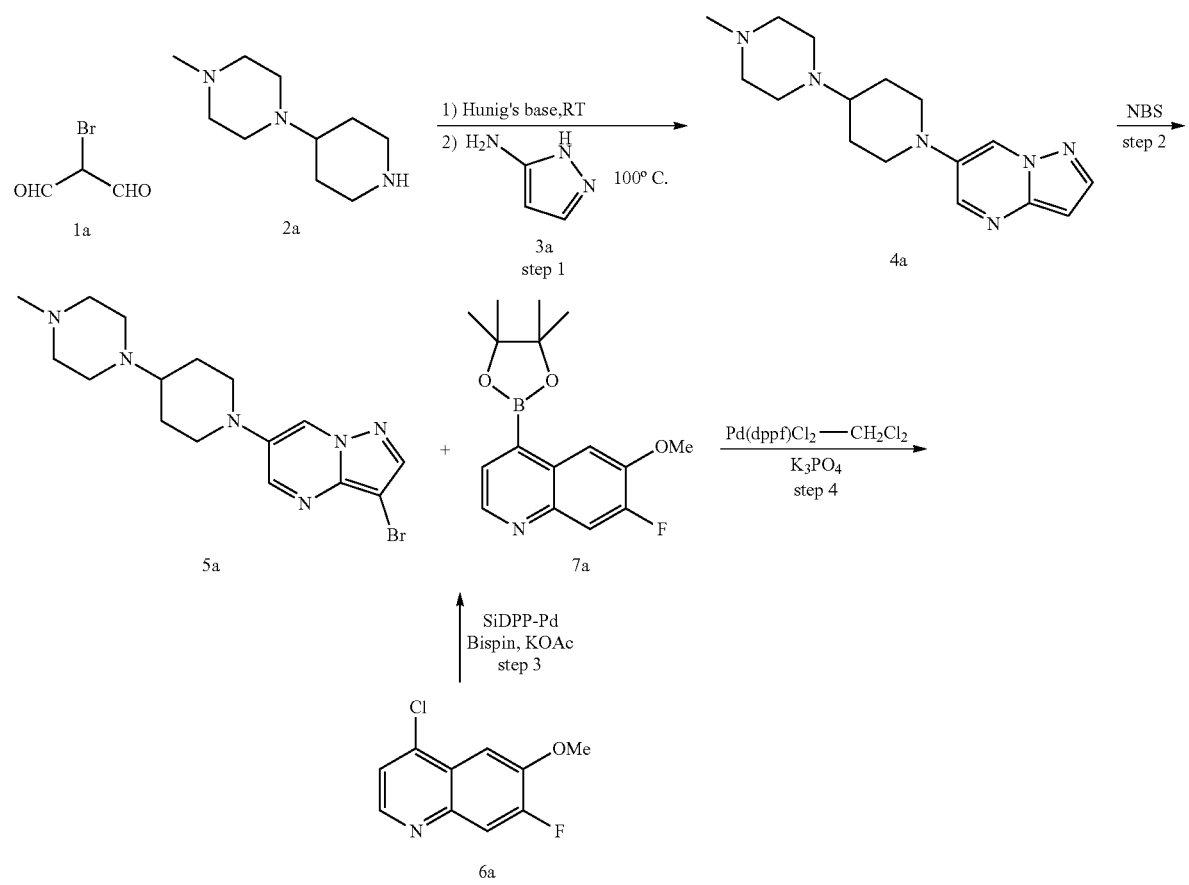

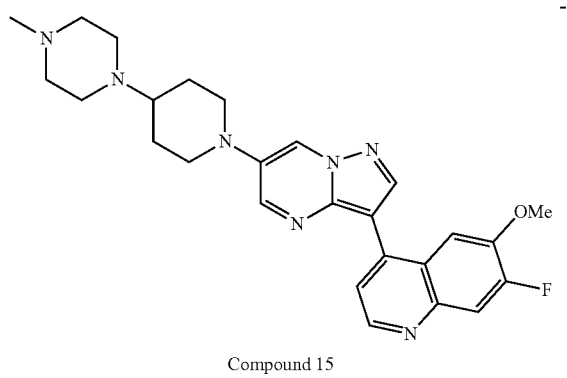

Compound 15

HCl
step 5

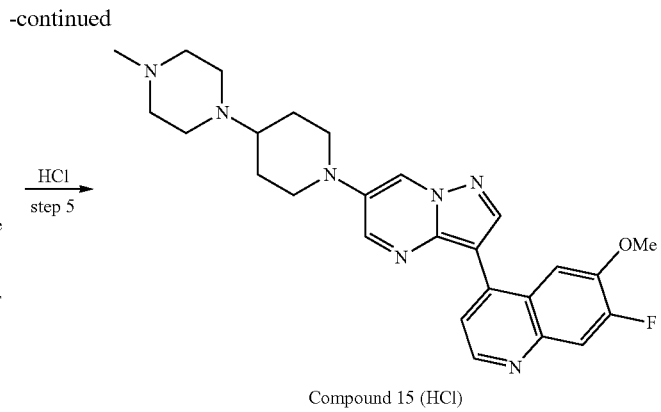

Compound 15 (HCl)

Example 78. Step 1: 6-(4-(4-methylpiperazin-1-yl)piperidin-1-yl)pyrazolo[1,5-a]pyrimidine (4a)

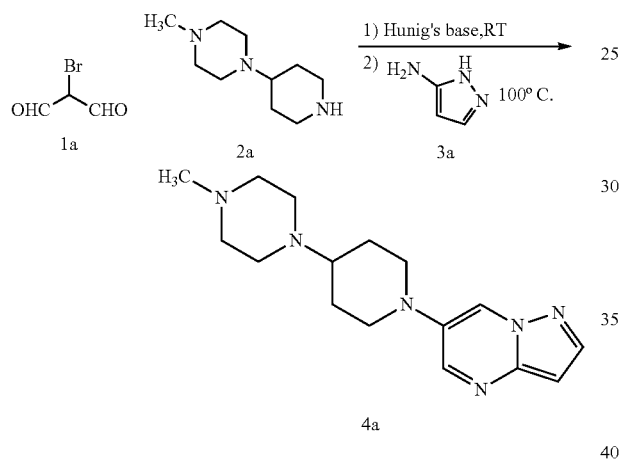

2-Bromomalonaldehyde (1a) (36.3 g, 241 mmol, 1.0 equiv) was suspended in dioxane (500 ml) followed by the addition of Hunig's base (46.2 ml, 265 mmol, 1.1 equiv). The reaction was stirred for 5 minutes, and then 1-methyl-4-(piperidin-4-yl)piperazine (2a) (88 g, 481 mmol, 2.0 equiv) was added. The reaction was stirred at room temperature for 16 hours. 1H-pyrazol-5-amine (3a) (20 g, 241 mmol, 1.0 equiv) was added followed by the addition of acetic acid (68.8 ml, 1203 mmol, 5 equiv). The reaction was heated to 95° C. for 4 hours. The reaction was cooled to room temperature, filtered, and the solid was washed with dioxane (50 mL). The filtrate was concentrated to remove most of solvent. The residue was basified with saturated NaHCO₃ solution (~500 mL) to pH=8. The resulting solid was filtered, and washed with water (100 ml). The filtrate was extracted with 10% methanol in DCM (200 mL×5). The organic was dried over Na₂SO₄, filtered and concentrated. The residue was treated with MTBE (300 mL) and stirred for 30 minutes and filtered. The resulting solid was triturated with MeTHF (50 mL) to give 6-(4-(4-methylpiperazin-1-yl)piperidin-1-yl)pyrazolo[1,5-a]pyrimidine (4a) (28 g, 93 mmol, 38.7% yield) as a light yellow solid.

¹H NMR (400 MHz, Chloroform-d) δ 8.44 (d, J=2.6 Hz, 1H), 8.10 (d, J=2.7 Hz, 1H), 7.95 (d, J=2.4 Hz, 1H), 6.58 (d, J=2.4 Hz, 1H), 3.55 (d, J=12.3 Hz, 2H), 2.79-2.33 (m, 9H), 2.30 (s, 3H), 1.99 (d, J=13.4 Hz, 2H), 1.84-1.60 (m, 4H). ¹³C NMR (101 MHz, CDCl₃) δ 146.89, 144.58, 143.31, 136.39, 120.28, 96.52, 77.31, 77.19, 76.99, 76.67, 60.94, 55.38, 50.40, 49.06, 45.98, 28.03. MS: m/z 301.2 (M+H⁺).

Example 79. Step 2: 3-bromo-6-(4-(4-methylpiperazin-1-yl)piperidin-1-yl) pyrazolo[1,5-a]pyrimidine (5a)

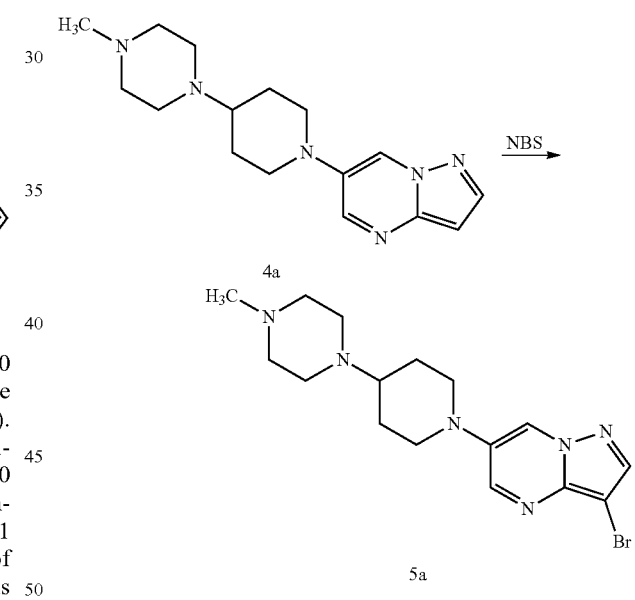

6-(4-(4-Methylpiperazin-1-yl)piperidin-1-yl)pyrazolo[1,5-a]pyrimidine (4a) (24.6 g, 82 mmol, 1.0 equiv) was dissolved in CHCl₃ (360 ml) and THF (90 ml) and cooled to 0-5° C. then N-bromosuccinimide (14.57 g, 82 mmol, 1.0 equiv) was added in portions in 35 minutes, and stirred for 30 minutes, and LC-MS showed a 95% conversion. Then more N-bromosuccinimide (0.3 g, 1.69 mmol, 0.02 equiv) was added. The reaction was stirred for 1 hour, LC-MS showed the reaction was completed. The reaction was filtered, washed with DCM (100 mL). the filtrate was washed with sat. NaHCO₃ (200 ml×2), water (100 mL), brine (100 mL×2), dried and concentrated. The resulting solid was triturated with MTBE (200 mL), and EtOAc (120 mL) to give 3-bromo-6-(4-(4-methylpiperazin-1-yl)piperidin-1-yl) pyrazolo[1,5-a]pyrimidine (5a) 27 g, 71.2 mmol, 87% yield) as a yellow solid.

¹H NMR (400 MHz, Chloroform-d) δ 8.49 (d, J=2.6 Hz, 1H), 8.04 (d, J=2.6 Hz, 1H), 7.93 (s, 1H), 3.56 (d, J=13.0 Hz, 2H), 2.79-2.46 (m, 9H), 2.40 (tt, J=11.3, 3.6 Hz, 2H), 2.33 (s, 3H), 2.00 (m, 2H), 1.75 (m, 2H). ¹³C NMR (101 MHz, CDCl₃) δ 147.63, 143.04, 141.35, 137.00, 120.37, 83.85, 77.30, 76.99, 76.67, 60.82, 55.22, 50.12, 48.75, 45.75, 27.91. MS: m/z 379.1, 381.1 (M+H⁺).

Example 80. Step 3: 7-fluoro-6-methoxy-4-(4,4,5,5-tetramethyl-1,3,2-dioxaborolan-2-yl)quinoline (7a)

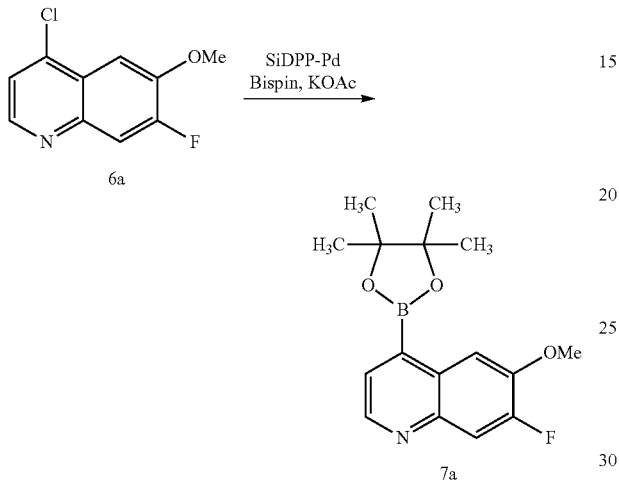

4-Chloro-7-fluoro-6-methoxyquinoline (6a) (13.4 g, 63.3 mmol, 1.0 equiv) was suspended in dioxane (250 ml) followed by the addition of 4,4,4',4',5,5,5',5'-octamethyl-2,2'-bi(1,3,2-dioxaborolane) (19.30 g, 76 mmol, 1.2 equiv), potassium acetate (18.64 g, 190 mmol, 3.0 equiv). The reaction was passed through by a stream of nitrogen gas for 15 minutes, and then SiDDP-Pd (10 g, 2.5 mmol, 0.04 equiv) was added. The reaction was heated at 95° C. overnight, cooled to room temperature, filtered, and washed with dioxane (100 mL). The filtrate was concentrated and triturated with hexane (100 mL). The solid was dissolved in MTBE (800 mL) and washed with water (200 mL×2), brine (100 mL), dried over Na₂SO₄, filtered and concentrated to give crude 7-fluoro-6-methoxy-4-(4,4,5,5-tetramethyl-1,3,2-dioxaborolan-2-yl)quinoline (7a) (16.44 g, 54.2 mmol, 86% yield) as a light yellow solid.

Example 81. Step 4: 7-fluoro-6-methoxy-4-(6-(4-(4-methylpiperazin-1-yl)piperidin-1-yl)pyrazolo[1,5-a]pyrimidin-3-yl)quinoline (15)

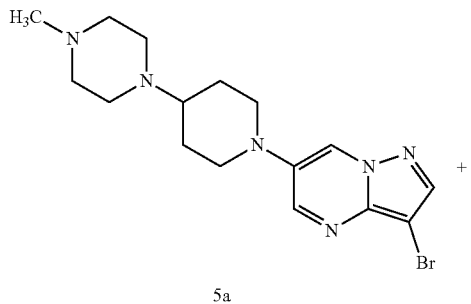

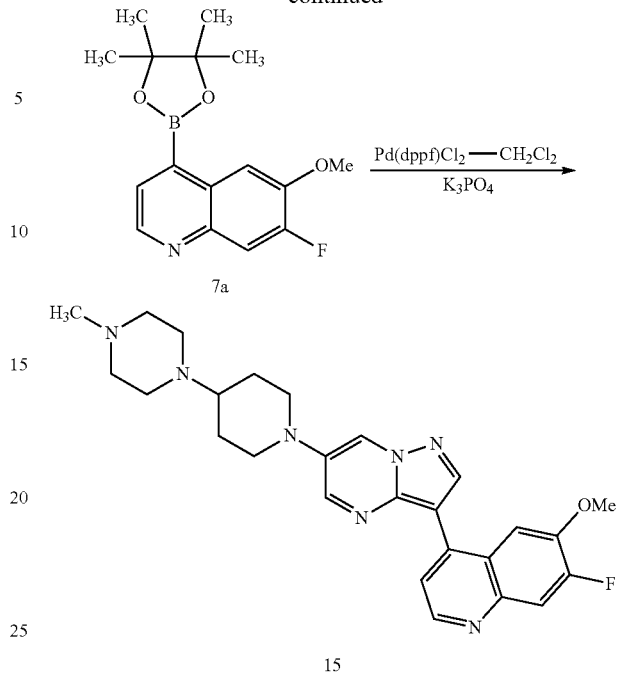

3-Bromo-6-(4-(4-methylpiperazin-1-yl)piperidin-1-yl)pyrazolo[1,5-a]pyrimidine (5a) (19.5 g, 51.4 mmol, 1.0 equiv) was suspended in MeTHF (350 ml) followed by the addition of 7-fluoro-6-methoxy-4-(4,4,5,5-tetramethyl-1,3,2-dioxaborolan-2-yl)quinoline (7a) (23.38 g, 77 mmol, 1.5 equiv) and a 3.0 M potassium phosphate solution (51.4 ml, 154 mmol, 3.0 equiv). The reaction was passed through by a stream of nitrogen gas for 15 minutes, and PdCl₂(dppf)-CH₂Cl₂ adduct (2.94 g, 3.60 mmol, 0.07 equiv) was added. The reaction was heated at 82-83° C. overnight. The reaction was cooled to 40-50° C., and the aqueous layer was separated. The organic layer was washed with water (70 mL), the organic layer was concentrated to volume 150 mL, and filtered. The resulting solid was dissolved in 5% methanol in THF-DCM (1:1) (500 mL), and treated with SilicaMetS DMT (0.6 mmol/g) (36 g) at 40° C. for 4 hours, filtered, washed with 5% methanol in DCM (50 mL), and then treated with SilicaMetS Thiol (1.28 mmol/g) (17 g) at room temperature overnight for 2 times. The solvent was removed by concentration, and the resulting solid was triturated with EtOAc (45 mL) to give 7-fluoro-6-methoxy-4-(6-(4-(4-methylpiperazin-1-yl)piperidin-1-yl)pyrazolo[1,5-a]pyrimidin-3-yl)quinoline (15) (14.5 g, 30.5 mmol, 59.3% yield) as a light yellow solid.

¹H NMR (400 MHz, Chloroform-d) δ 8.80 (d, J=4.6 Hz, 1H), 8.55 (d, J=2.7 Hz, 1H), 8.29 (s, 1H), 8.19 (d, J=2.7 Hz, 1H), 7.77 (d, J=12.1 Hz, 1H), 7.56 (d, J=4.6 Hz, 1H), 7.52 (d, J=9.1 Hz, 1H), 3.87 (s, 3H), 3.62 (d, J=12.3 Hz, 2H), 2.78 (t, J=11.9 Hz, 2H), 2.70-2.36 (m, 7H), 2.29 (s, 3H), 2.02 (m, 2H), 1.78 (m, 4H). ¹³C NMR (101 MHz, CDCl₃) δ 155.71, 153.19, 148.65, 148.13, 148.00, 147.43, 145.10, 144.98, 143.24, 141.67, 137.31, 136.88, 124.25, 121.41, 120.21, 114.49, 114.32, 107.78, 105.79, 60.82, 56.07, 55.39, 50.05, 49.09, 46.00, 27.93. MS: m/z 476.2 (M+H⁺).

Example 82. Step 5: 7-fluoro-6-methoxy-4-(6-(4-(4-methylpiperazin-1-yl)piperidin-1-yl)pyrazolo[1,5-a]pyrimidin-3-yl)quinoline trichloride (15 HCl)

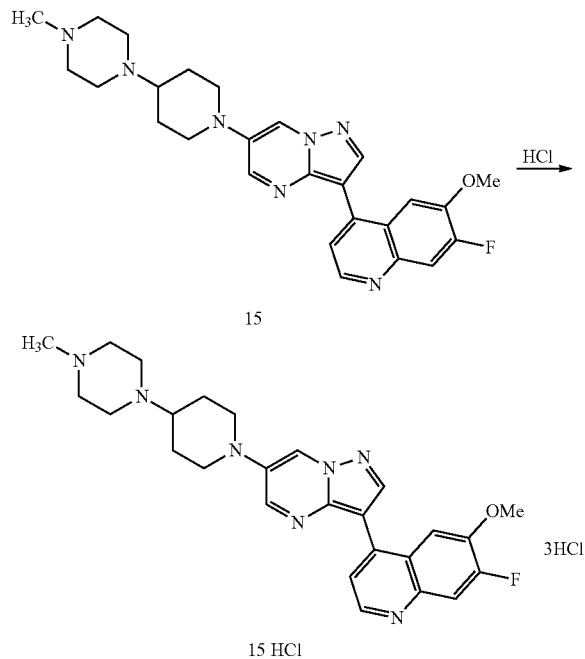

7-Fluoro-6-methoxy-4-(6-(4-(4-methylpiperazin-1-yl)piperidin-1-yl)pyrazolo[1,5-a]pyrimidin-3-yl)quinoline (15) (14.0 g, 29.4 mmol) was suspended in diethyl ether (250 ml) followed by the addition of 1M hydrogen chloride (147 ml, 147 mmol, 5.0 equiv) in EtOAc. the reaction was stirred for 2 hours at room temperature, and then filtered, washed with diethyl ether (100 mL), and then suspended in diethyl ether (300 mL) and stirred for 1 hour, filtered, washed with diethyl ether (100 mL), dried under vacuum at 50° C. for 2 days to give 7-fluoro-6-methoxy-4-(6-(4-(4-methylpiperazin-1-yl)piperidin-1-yl)pyrazolo[1,5-a]pyrimidin-3-yl)quinoline trichloride (15 HCl) (16.5 g, 28.2 mmol, 96% yield) as an orange solid.

$^1$H NMR (400 MHz, Deuterium Oxide) δ 8.72 (d, J=6.0 Hz, 1H), 8.68 (d, J=2.6 Hz, 1H), 8.50-8.43 (m, 2H), 7.96 (dd, J=6.0, 0.9 Hz, 1H), 7.86 (d, J=10.6 Hz, 1H), 7.62 (d, J=8.4 Hz, 1H), 3.94 (s, 3H), 3.93-3.54 (m, 11H), 3.05 (s, 3H), 3.04-2.93 (m, 2H), 2.41 (d, J=11.9 Hz, 2H), 2.07-1.92 (m, 2H). $^{13}$C NMR (101 MHz, D₂O) δ 155.24, 149.24, 149.11, 148.62, 147.00, 144.40, 141.04, 140.04, 136.98, 134.18, 134.06, 123.84, 121.86, 120.16, 108.01, 106.45, 106.23, 105.25, 63.02, 56.44, 50.35, 48.13, 46.01, 42.69, 25.69. MS: m/z 476.3 (M+H⁺). Anal. Calcd for C₂₆H₃₀FN₇O.3HCl: C, 53.39, H, 5.69, N, 16.76, Cl, 18.18. Found: C, 53.31, H, 5.57, N, 16.62, Cl, 18.55.

Example 185

Compound 79

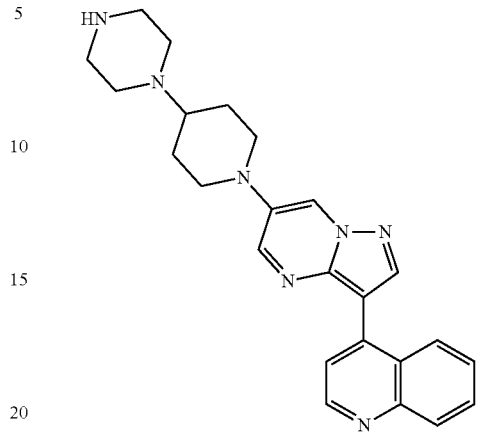

To a suspension of compound 80 (50 mg, 0.15 mmol) in DCM/DMF (1 ml/0.2 ml) was added tert-butyl 4-oxopiperidine-1-carboxylate (45 mg, 0.23 mmol), then NaBH(OAc)₃ (85 mg, 0.45 mmol) was added and the mixture was stirred at room temperature overnight. The mixture was diluted with EtOAc (20 ml) and washed with sat. aq. NaHCO₃ solution (10 ml) and brine, dried over Na₂SO₄. After the removal of organic solvent, the residue was purified through Biotage SiO₂ column chromatography (gradient: MeOH/DCM=1/100 to 10/100) to give the Boc-protected compound 79, which was subjected to de-Boc according the general procedure 4 and the final product was purified through preparative HPLC to give compound 79. LCMS (method 2): t$_R$=2.50 min, m/z (M+H)⁺=413.9; $^1$H NMR (400 MHz, DMSO-d₆) δ 11.80 (s, 1H), 9.24 (s, 1H), 9.16 (d, J=5.7 Hz, 1H), 9.03 (dd, J=23.8, 13.4 Hz, 1H), 8.99 (s, 2H), 8.83 (s, 1H), 8.55 (d, J=8.6 Hz, 1H), 8.32 (dd, J=18.2, 7.1 Hz, 2H), 8.09 (t, J=7.7 Hz, 1H), 7.87 (t, J=7.8 Hz, 1H), 3.98 (d, J=13.1 Hz, 2H), 3.75-3.30 (m, 6H), 3.25 (d, J=10.5 Hz, 3H), 2.89 (q, J=12.0, 11.4 Hz, 2H), 2.35 (d, J=12.9 Hz, 2H), 2.03 (qd, J=12.9, 4.0 Hz, 2H).

Example 186

Compound 80

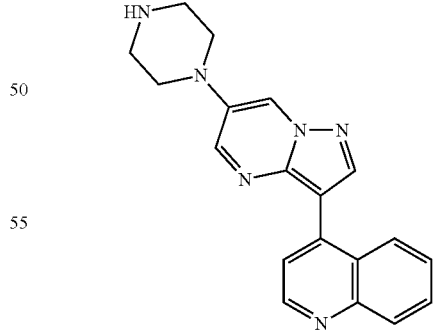

Compound 80 was prepared according to the general procedure 1, 2 and 3A, followed by de-Boc with 1N HCl. LC/MS (method 2): t$_R$=1.52 min, m/z (M+H)⁺=331.2; $^1$H NMR (400 MHz, DMSO-d₆) δ 9.13 (br. s. 2H), 9.09 (d, J=4.4 Hz, 1H), 8.91 (dt, J=14.3, 2.8 Hz, 2H), 8.74 (d, J=5.2 Hz, 1H), 8.43 (s, 1H), 8.22 (dd, J=8.7, 3.2 Hz, 1H), 8.13 (s, 1H), 7.99 (d, J=7.4 Hz, 1H), 7.78 (q, J=7.0 Hz, 1H), 3.54-3.45 (m, 4H), 3.28-3.19 (m, 4H).

Example 187

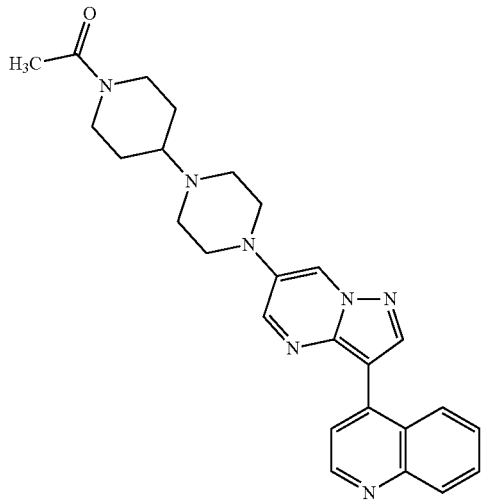

Compound 81

Compound 81 was synthesized through treating compound 79 with Ac$_2$O/Et$_3$N in DCM followed by preparative HPLC purification. LC/MS (method 2): t$_R$=2.85 min, m/z (M+H)+=455.2; $^1$H NMR (400 MHz, DMSO-d$_6$) δ 9.32 (s, 1H), 9.17 (d, J=2.3 Hz, 1H), 9.00 (d, J=4.8 Hz, 1H), 8.76-8.68 (m, 1H), 8.22 (d, J=8.5 Hz, 1H), 8.11 (dd, J=9.9, 8.5 Hz, 1H), 7.91-7.82 (m, 2H), 7.77 (d, J=13.7 Hz, 1H), 7.66 (t, J=7.2 Hz, 1H), 4.53 (d, J=13.4 Hz, 1H), 3.95 (s, 1H), 3.89 (dd, J=12.3, 9.2 Hz, 1H), 3.59 (d, J=11.9 Hz, 2H), 3.46 (d, J=13.0 Hz, 2H), 3.38 (d, J=12.0 Hz, 1H), 3.22-3.06 (m, 5H), 2.26 (d, J=13.6 Hz, 2H), 2.02 (s, 3H), 1.72-1.39 (m, 2H).

Example 188

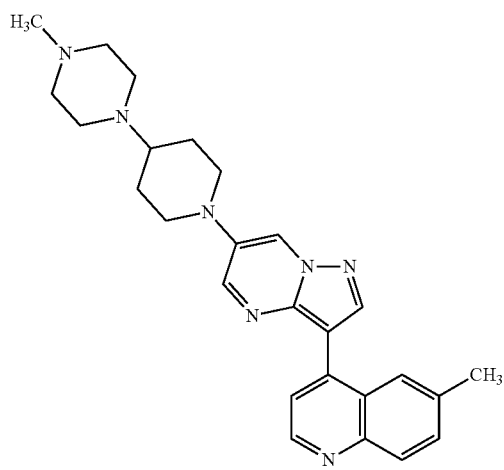

Compound 185

Compound 185 was prepared according to the general procedures 1, 2, and 5. LC/MS (method 2): t$_R$=2.87 min, m/z (M+H)+=442.

Example 189

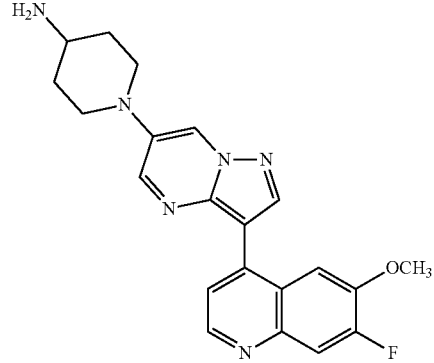

Compound 186

Compound 186 was prepared according to the general procedures 1, 2, 3B and 4. LC/MS (method 2): t$_R$=2.97 min, m/z (M+H)+=393.

Example 190

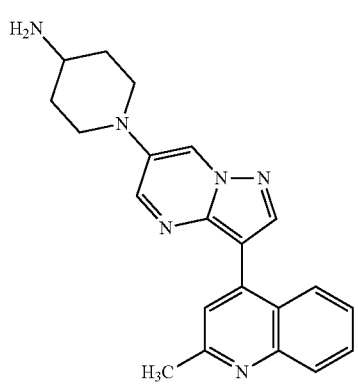

Compound 187

Compound 187 was prepared according to the general procedures 1, 2, 3B and 4. LC/MS (method 2): t$_R$=2.78 min, m/z (M+H)+=359.

Example 191

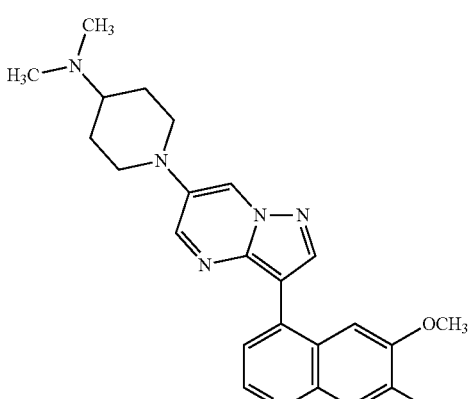

Compound 188

Compound 188 was prepared from Compound 186 after a reductive amination with paraformaldehyde. LC/MS (method 2): $t_R$=2.96 min, m/z (M+H)$^+$=421. $^1$H NMR (400 MHz, DMSO-d$_6$) δ 9.53 (s, 1H), 8.87-8.79 (m, 2H), 8.76 (d, J=2.7 Hz, 1H), 8.67 (s, 1H), 7.85 (d, J=12.1 Hz, 1H), 7.79-7.67 (m, 2H), 3.91-3.80 (ms, 5H), 3.33 (ddt, J=11.9, 8.0, 3.8 Hz, 2H), 2.83-2.72 (m, 7H), 2.08 (d, J=11.8 Hz, 2H), 1.76 (qd, J=12.2, 4.0 Hz, 2H).

Example 192

Compound 189

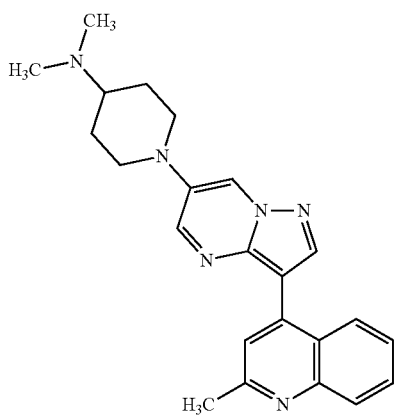

Compound 189 was prepared from Compound 87 after a reductive amination with paraformaldehyde. LC/MS (method 2): $t_R$=2.84 min, m/z (M+H)$^+$=387. $^1$H NMR (400 MHz, DMSO-d$_6$) δ 9.59 (s, 1H), 8.91 (d, J=2.6 Hz, 1H), 8.83 (d, J=2.6 Hz, 1H), 8.67 (m, 1H), 8.35 (m, 1H), 8.08 (d, J=8.4 Hz, 1H), 7.94 (m, 1H), 7.70 (m, 1H), 3.90 (d, J=12.7 Hz, 2H), 3.33 (ddt, J=12.0, 8.1, 3.9 Hz, 2H), 2.79 (m, 10H), 2.09 (d, J=12.3 Hz, 2H), 1.76 (qd, J=12.1, 4.0 Hz, 2H).

Example 193

Compound 190

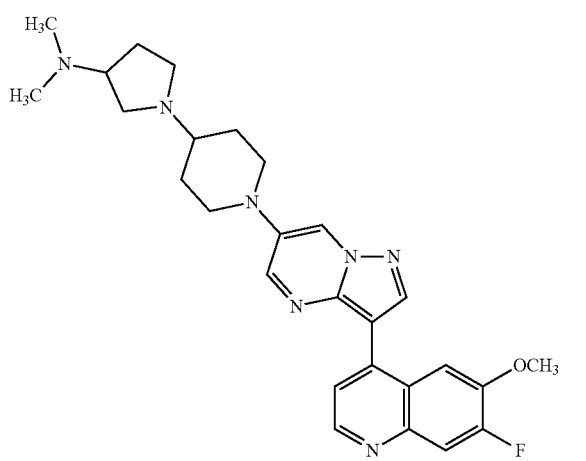

Compound 190 was prepared in an analogous manner to Compound 39. LC/MS (method 2): $t_R$=2.83 min, m/z (M+H)$^+$=490.

Example 194

Compound 191

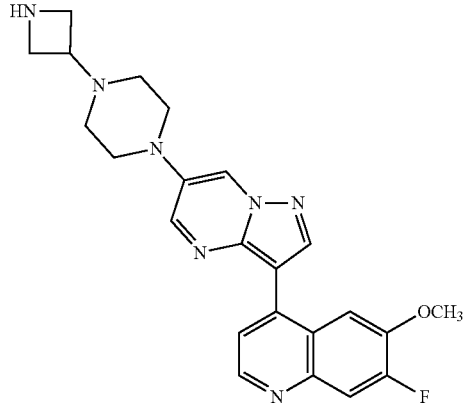

Compound 191 was prepared in an analogous manner to Compound 47. LC/MS (method 2): $t_R$=2.80 min, m/z (M+H)$^+$=434.

Example 195

Compound 192

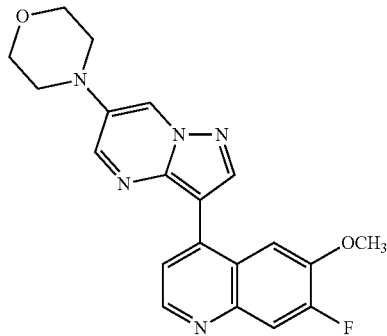

Compound 192 was prepared in an analogous manner to Compound 47. LC/MS (method 2): $t_R$=3.59 min, m/z (M+H)$^+$=380.

Example 196

Compound 193

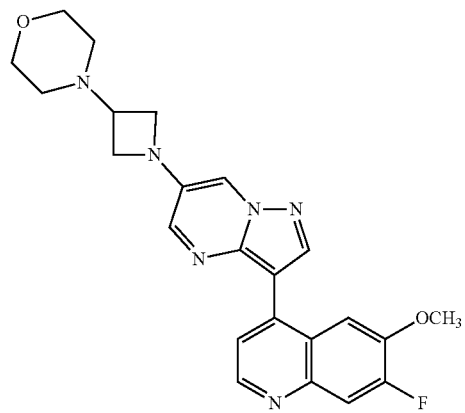

Compound 193 was prepared in an analogous manner to Compound 47. LC/MS (method 2): $t_R$=2.95 min, m/z (M+H)$^+$=435.

Example 197

Compound 194

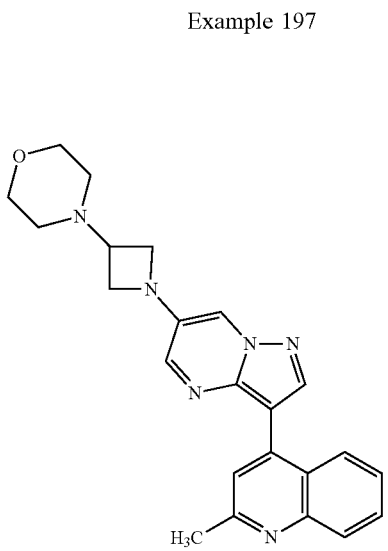

Compound 194 was prepared in an analogous manner to Compound 47. LC/MS (method 2): $t_R$=2.85 min, m/z (M+H)$^+$=401. $^1$H NMR (400 MHz, DMSO-d$_6$) δ 8.43-8.37 (m, 2H), 8.33 (d, J=2.6 Hz, 1H), 8.11-8.03 (m, 1H), 7.94 (ddd, J=8.4, 1.3, 0.6 Hz, 1H), 7.69 (ddd, J=8.3, 6.8, 1.4 Hz, 1H), 7.60 (s, 1H), 7.47 (ddd, J=8.3, 6.8, 1.3 Hz, 1H), 4.07-3.98 (m, 2H), 3.75 (dd, J=7.8, 5.5 Hz, 2H), 3.58 (t, J=4.6 Hz, 4H), 3.38-3.31 (m, 1H), 2.65 (s, 3H), 2.37-2.31 (m, 4H).

Example 198

Compound 195

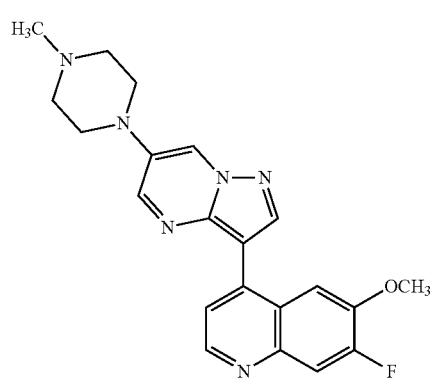

Compound 195 was prepared in an analogous manner to Compound 47. LC/MS (method 2): $t_R$=2.71 min, m/z (M+H)$^+$=393. $^1$H NMR (400 MHz, DMSO-d$_6$) δ 9.72 (s, 1H), 8.88 (d, J=2.7 Hz, 1H), 8.83 (d, J=2.7 Hz, 1H), 8.81 (d, J=4.7 Hz, 1H), 8.68 (s, 1H), 7.84 (d, J=12.2 Hz, 1H), 7.72 (d, J=4.7 Hz, 1H), 7.67 (d, J=9.3 Hz, 1H), 3.92-3.82 (m, 5H), 3.55 (d, J=12.2 Hz, 2H), 3.27-3.17 (m, 2H), 3.09 (q, J=12.5, 11.0 Hz, 2H), 2.86 (d, J=3.0 Hz, 3H).

Example 199

Compound 196

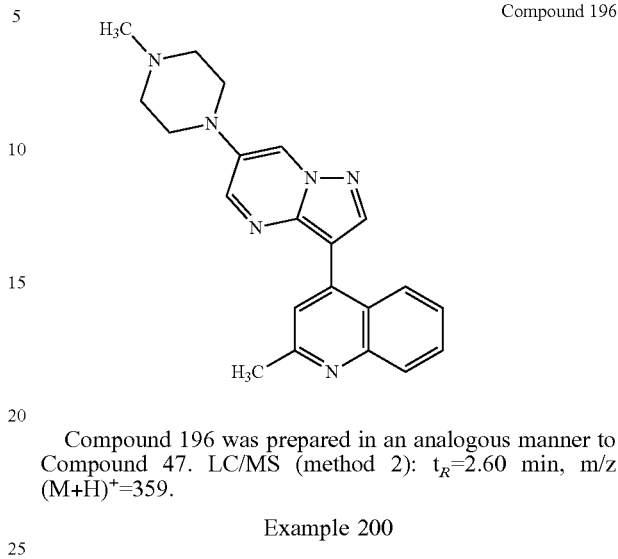

Compound 196 was prepared in an analogous manner to Compound 47. LC/MS (method 2): $t_R$=2.60 min, m/z (M+H)$^+$=359.

Example 200

Compound 197

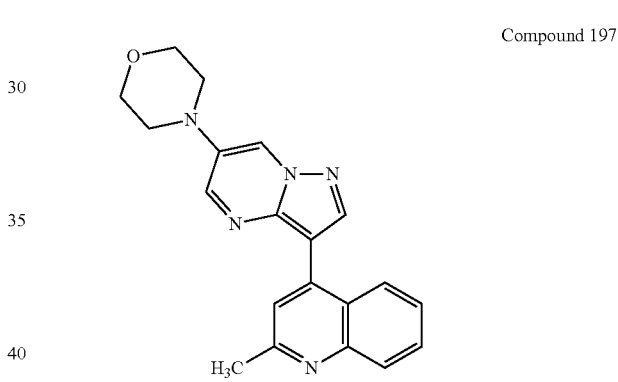

Compound 197 was prepared in an analogous manner to Compound 47. LC/MS (method 2): $t_R$=3.38 min, m/z (M+H)$^+$=346.

Example 201

Compound 198

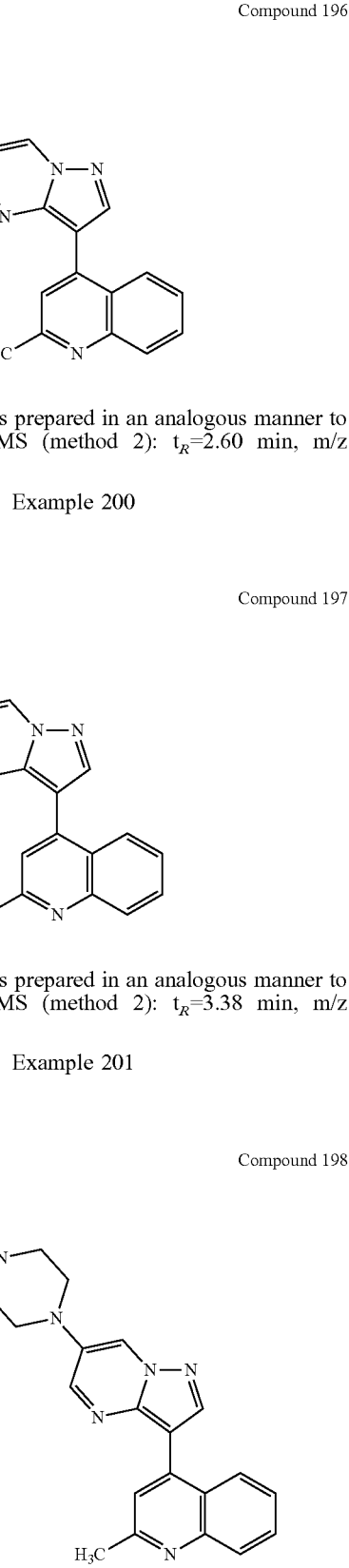

Compound 198 was prepared in an analogous manner to Compound 47. LC/MS (method 2): $t_R$=2.73 min, m/z $(M+H)^+$=417.

Example 202

Compound 199

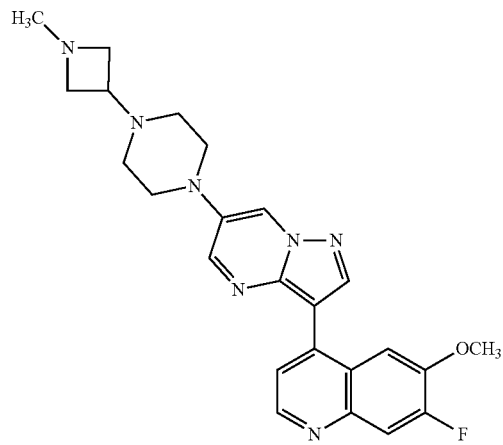

Compound 199 was prepared in an analogous manner to Compound 47. LC/MS (method 2): $t_R$=2.95 min, m/z $(M+H)^+$=448.

Example 203

Compound 200

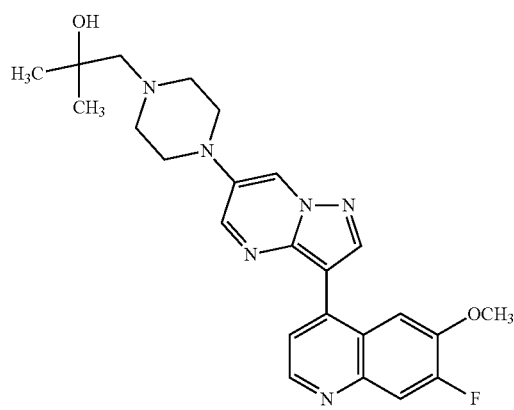

Compound 200 was prepared in an analogous manner to Compound 47. LC/MS (method 2): $t_R$=2.92 min, m/z $(M+H)^+$=451.

Example 204

Compound 201

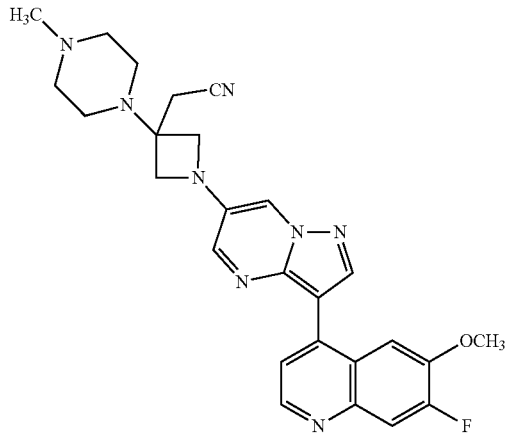

Compound 201 was prepared in an analogous manner to Compound 47. LC/MS (method 2): $t_R$=3.09 min, m/z $(M+H)^+$=487.

Example 205

Compound 202

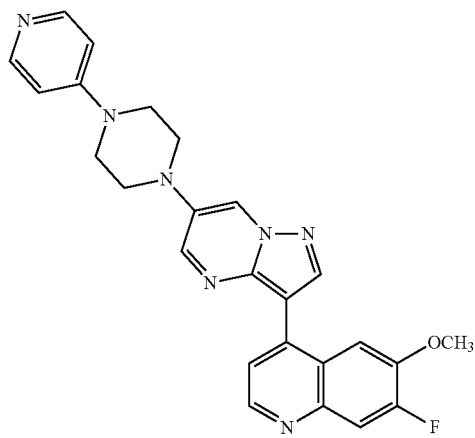

Compound 202 was prepared in an analogous manner to Compound 47. LC/MS (method 2): $t_R$=3.17 min, m/z $(M+H)^+$=456.

Example 206

Compound 203

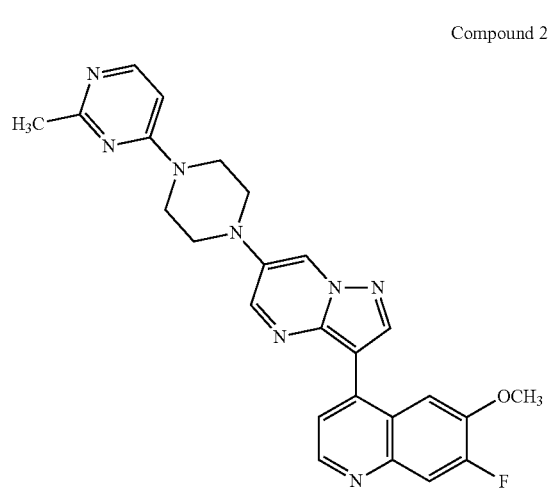

Compound 203 was prepared in an analogous manner to Compound 47. LC/MS (method 2): $t_R$=3.22 min, m/z (M+H)$^+$=471.

Example 207

Compound 204

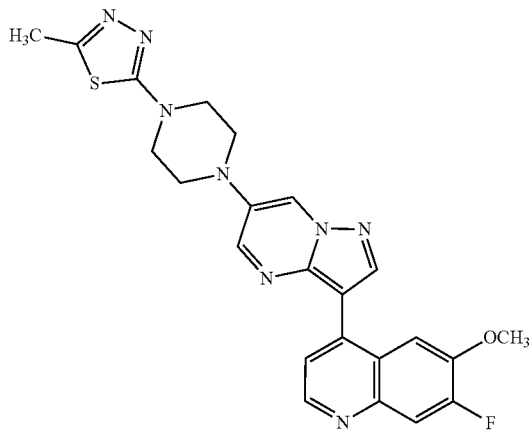

Compound 204 was prepared in an analogous manner to Compound 47. LC/MS (method 2): $t_R$=3.70 min, m/z (M+H)$^+$=477.

Example 208

Compound 205

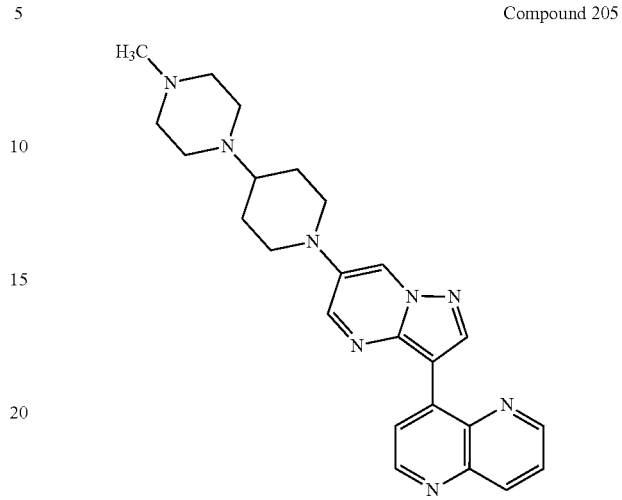

Compound 205 was prepared in an analogous manner as compound 60. LC/MS (method 3): $t_R$=1.75 min, m/z (M+H)$^+$=429.0; $^1$H NMR (400 MHz, CD$_3$OD) δ 9.54 (s, 1H), 9.08 (dd, J=4.4, 1.6 Hz, 1H), 8.97 (d, J=4.8 Hz, 1H), 8.90 (d, J=4.8 Hz, 1H), 8.83 (d, J=2.8 Hz, 1H), 8.46 (d, J=2.8 Hz, 1H), 8.40 (dd, J=8.4, 1.6 Hz, 1H), 7.79 (dd, J=8.8, 4.4 Hz, 1H), 3.80-3.77 (m, 2H), 2.85-2.41 (m, 11H), 2.30 (s, 3H), 2.11-2.08 (m, 2H), 1.78-1.70 (m, 2H).

Example 209

Compound 206

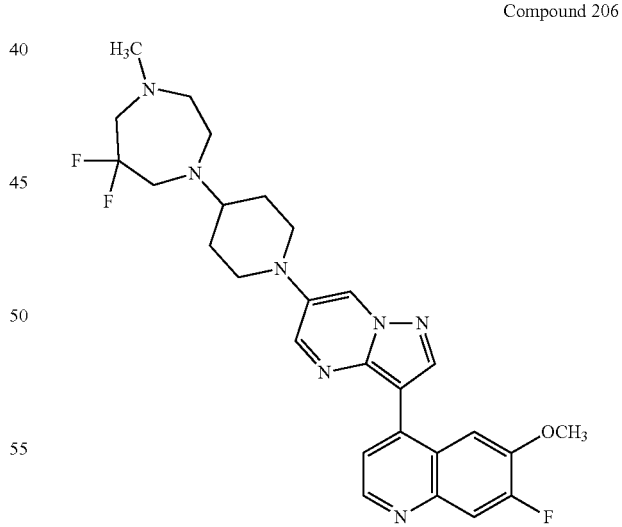

Compound 206 was prepared in an analogous manner as compound 39 through reductive amination with tert-butyl 6,6-difluoro-1,4-diazepane-1-carboxylate followed by de-Boc with 1N HCl. The methylation was accomplished through reductive amination with formaldehyde. LC/MS (method 3): $t_R$=2.46 min, m/z (M+H)$^+$=526.1; $^1$H NMR (400 MHz, CD$_3$Cl): δ 8.83 (d, J=4.8 Hz, 1H), 8.57 (d, J=2.8 Hz, 1H), 8.33 (s, 1H), 8.22 (d, J=2.8 Hz, 1H), 7.81 (d, J=12.0 Hz, 1H), 7.60 (d, J=4.4 Hz, 1H), 7.54 (d, J=9.2 Hz, 1H), 3.90 (s, 3H), 3.64 (d, J=12.0 Hz, 2H), 3.11 (t, J=14.4 Hz, 2H), 2.97 (t, J=14.4 Hz, 2H), 2.90-2.87 (m, 2H), 2.78 (t, J=11.2 Hz, 2H), 2.70-2.67 (m, 3H), 2.45 (s, 3H), 1.96 (d, J=12.0 Hz, 2H), 1.80-1.73 (m, 2H).

Example 210

Compound 207

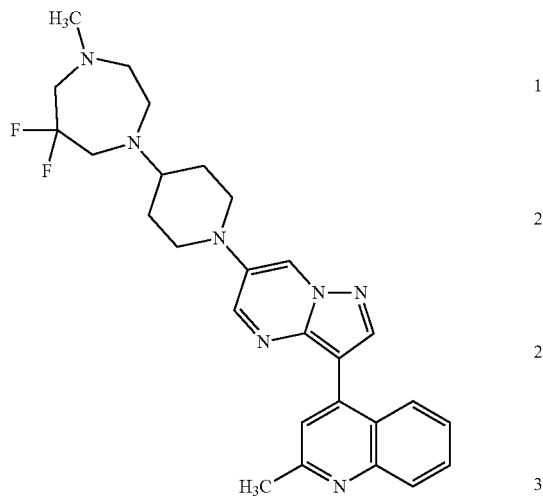

Compound 207 was prepared in an analogous manner as compound 70. LC/MS (method 4): $t_R$=3.10 min, m/z (M+H)$^+$=492.0; $^1$H NMR (400 MHz, CDCl$_3$): δ 8.55 (d, J=2.6 Hz, 1H), 8.31 (s, 1H), 8.21 (d, J=2.6 Hz, 1H), 8.11-8.08 (m, 2H), 7.73-7.71 (m, 1H), 7.58 (s, 1H), 7.53-7.44 (m, 1H), 3.63 (d, J=12.1 Hz, 2H), 3.11 (t, J=14.6 Hz, 2H), 2.97 (t, J=14.6 Hz, 2H), 2.90-2.87 (m, 2H), 2.81 (s, 3H), 2.79-2.72 (m, 2H), 2.70-2.67 (m, 3H), 2.45 (s, 3H), 1.95 (d, J=12.3 Hz, 2H), 1.80-1.70 (m, 2H).

Example 211

Compound 208

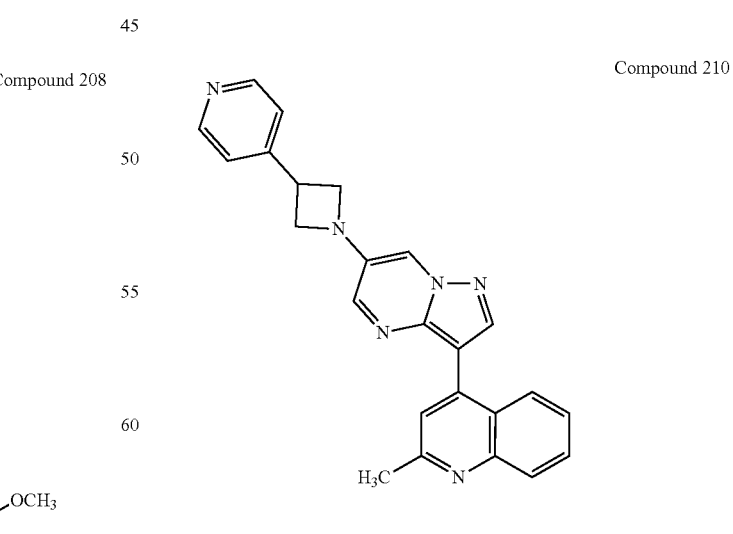

Compound 208 was prepared in an analogous manner as Compound 70. LC/MS (method 3): $t_R$=1.89 min, m/z (M+H)$^+$=472.1; $^1$H NMR (400 MHz, D$_2$O) δ 8.72-8.67 (m, 1H), 8.67 (m, 1H), 8.52 (m, 2H), 8.02-8.01 (m, 2H), 7.70-7.68 (m, 1H), 7.55 (d, J=8.0 Hz, 1H), 3.90-3.80 (m, 9H), 3.62-3.30 (m, 5H), 2.94-2.87 (m, 5H), 2.27-2.24 (m, 4H), 1.99-1.96 (m, 2H)

Example 212

Compound 209

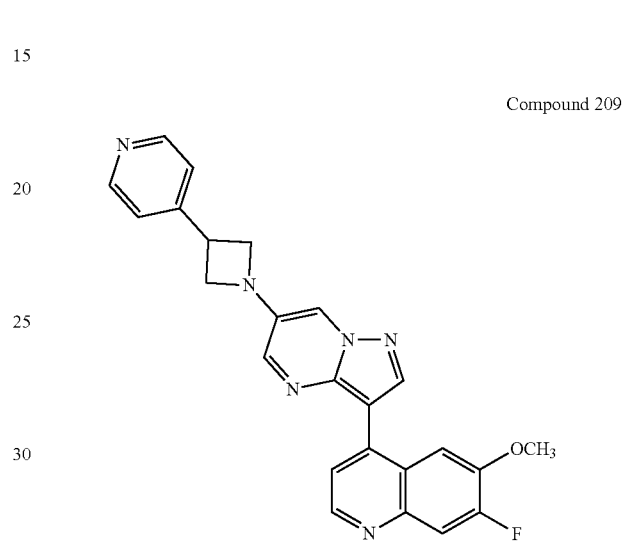

Compound 209 was prepared in an analogous manner to Compound 47. LC/MS (method 2): $t_R$=2.98 min, m/z (M+H)$^+$=427.

Example 213

Compound 210

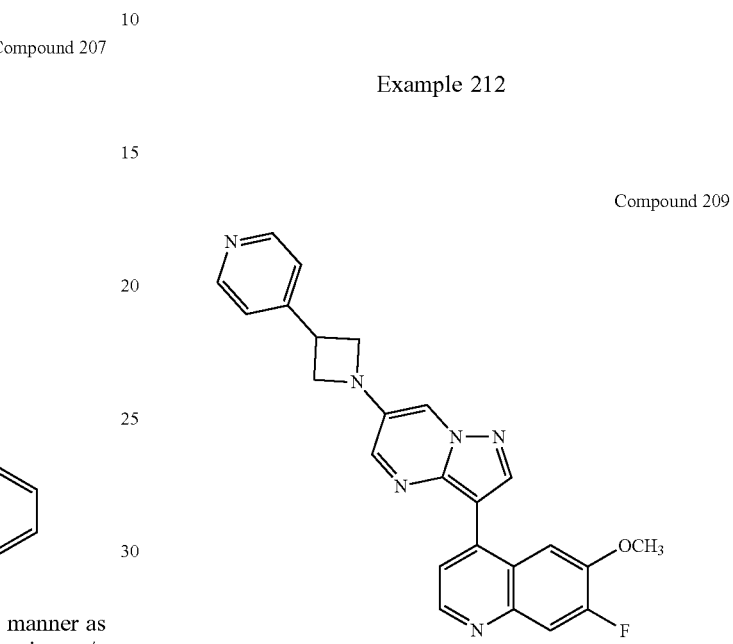

Compound 210 was prepared in an analogous manner to Compound 47. LC/MS (method 2): $t_R$=2.92 min, m/z (M+H)$^+$=393.

Example 214
Compound 211
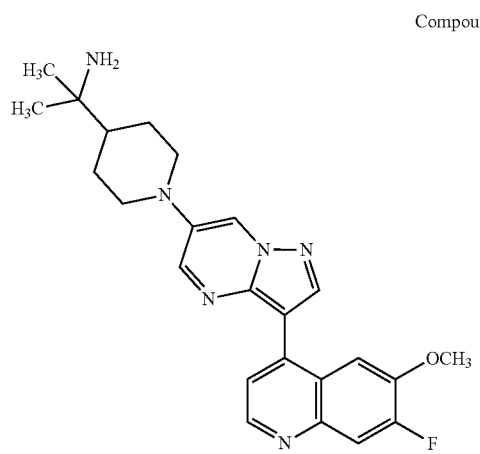
Compound 211 was prepared in an analogous manner to Compound 47. LC/MS (method 2): $t_R$=3.19 min, m/z $(M+H)^+$=435.
Example 215
Compound 212
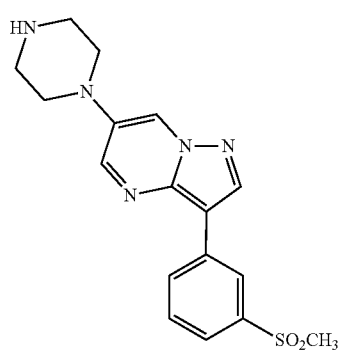
Compound 212 was prepared in an analogous manner as Compound 39. LC/MS (method 2): $t_R$=3.09 min; m z $(M+H)^+$=358.2. ($^1$H NMR (400 MHz, DMSO-$d_6$) δ 9.04 (br. s. 2H), 8.85 (d, J=2.8 Hz, 1H), 8.75 (d, J=8.8 Hz, 2H), 8.67 (d, J=1.6 Hz, 1H), 8.38 (dd, J=6.2, 1.6 Hz, 1H), 7.73 (d, J=3.2 Hz, 1H), 7.67 (t, J=8 Hz, 1H), 3.66 (t, J=5.1 Hz, 4H), 3.22-2.98 (m, 4H), 3.11 (s, 3H).
Example 216
Compound 213
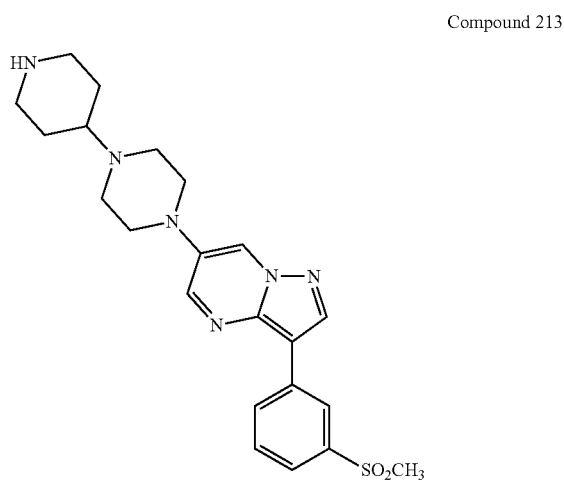 [SMILES: CS(=O)(=O)c1cccc(-c2cnn3cc(N4CCN(C5CCNCC5)CC4)cnc23)c1]
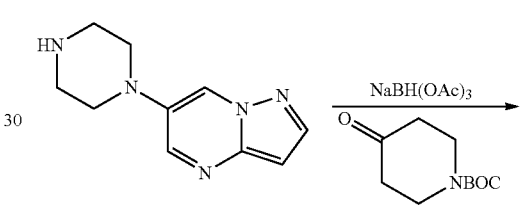
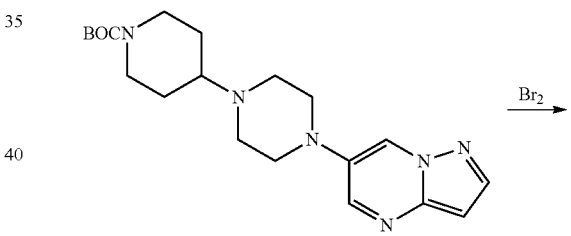
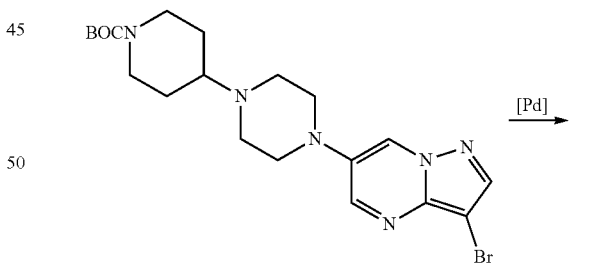
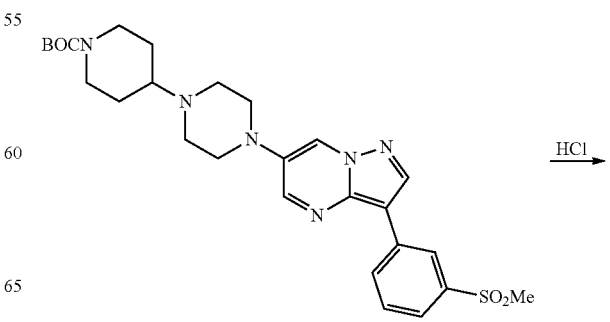

-continued

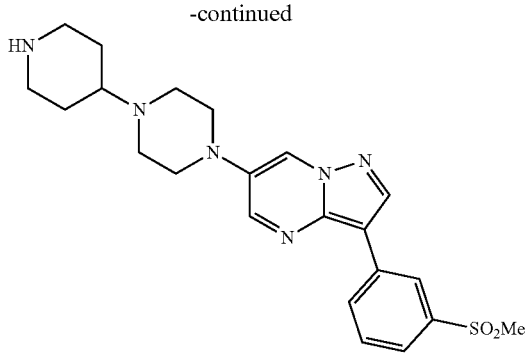

213

Example 217. Synthesis of tert-butyl 4-(4-(pyrazolo[1,5-a]pyrimidin-6-yl)piperazin-1-yl)piperidine-1-carboxylate

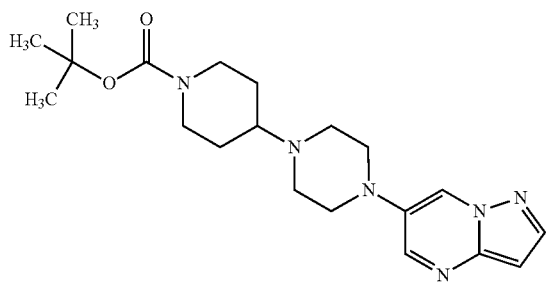 [SMILES: CC(C)(C)OC(=O)N1CCC(N2CCN(c3cnc4ccnn4c3)CC2)CC1]

To a suspension of 6-(piperazin-1-yl)pyrazolo[1,5-a]pyrimidine (0.11 g, 0.54 mmol) in 3 mL of DCM was added 0.45 mL of DMF. A clear solution was obtained. To it, N-BOC piperidone (0.16 g, 1.5 eq.) was added, and was followed by the addition of sodium triacetoxyborohydride (0.34 g, 3 eq.). The resulted suspension was stirred at RT overnight. After an additional amount of sodium triacetoxyborohydride (0.16 g, 1.5 eq.) was added and stirred for 2.5 h, the starting material was almost consumed. The reaction was quenched with NaHCO₃(sat.) and DCM was used for extraction (2×). The organic layer was washed with brine and dried over sodium sulfate. Biotage purification with 1-10% MeOH in DCM gave the desired product, tert-butyl 4-(4-(pyrazolo[1,5-a]pyrimidin-6-yl)piperazin-1-yl)piperidine-1-carboxylate in 34% yield (70 mg).

Example 218. Synthesis of tert-butyl 4-(4-(3-bromopyrazolo[1,5-a]pyrimidin-6-yl)piperazin-1-yl)piperidine-1-carboxylate

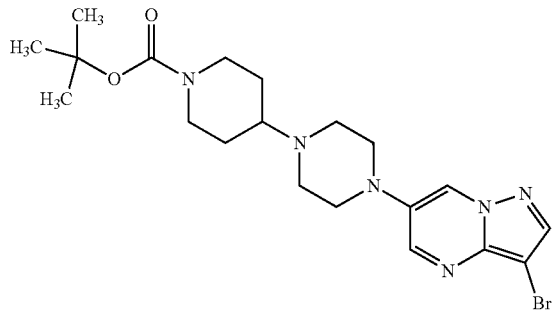 [SMILES: CC(C)(C)OC(=O)N1CCC(N2CCN(c3cnc4c(Br)cnn4c3)CC2)CC1]

To a solution of tert-butyl 4-(4-(pyrazolo[1,5-a]pyrimidin-6-yl)piperazin-1-yl)piperidine-1-carboxylate (70 mg, 0.18 mmol) in 1.5 mL of AcOH in an ice bath, was added bromine (0.01 ml, 1.05 eq.) in 0.5 mL of AcOH. The mixture was stirred at RT for 15 min and was quenched with water. The mixture was partitioned between DCM and water. The organic layer was washed with NaHCO₃(sat.), brine and dried (Na₂SO₄). Concentration afforded 80 mg of the desired product (95% yield).

Example 219. Synthesis of 3-(3-(methylsulfonyl)phenyl)-6-(4-(piperidin-4-yl)piperazin-1-yl)pyrazolo[1,5-a]pyrimidine trihydrochloride

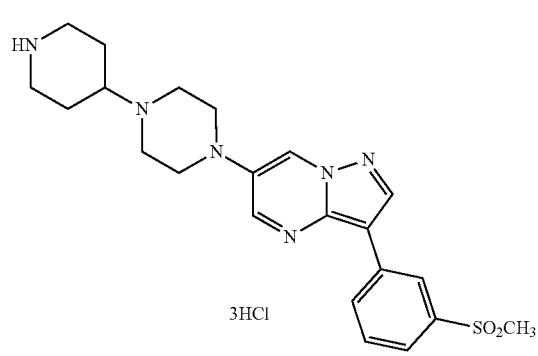 [SMILES: CS(=O)(=O)c1cccc(-c2cnn3cc(N4CCN(C5CCNCC5)CC4)cnc23)c1]

In an analogous manner to 4-(6-(piperazin-1-yl)pyrazolo[1,5-a]pyrimidin-3-yl)quinoline dihydrochloride, 3-(3-(methylsulfonyl)phenyl)-6-(4-(piperidin-4-yl)piperazin-1-yl)pyrazolo[1,5-a]pyrimidine trihydrochloride (30 mg) was synthesized from tert-butyl 4-(4-(3-bromopyrazolo[1,5-a]pyrimidin-6-yl)piperazin-1-yl)piperidine-1-carboxylate (74 mg, 0.16 mmol) and 3-SO₂Me phenylboronic acid (48 mg, 1.5 eq.) and was followed by HCl hydrolysis in 43% yield over two steps. LC/MS (method 2): $t_R$=0.78 min; m z (M+H)⁺=441.2. ¹H NMR (400 MHz, DMSO-$d_6$) δ 11.21 (s, 1H), 8.89 (d, J=2.7 Hz, 1H), 8.8 (br. s. 2H), 8.78 (d, J=2.7 Hz, 1H), 8.76-8.63 (m, 2H), 8.38 (dt, J=7.7, 1.4 Hz, 1H), 7.74 (dt, J=7.8, 1.4 Hz, 1H), 7.68 (t, J=7.8 Hz, 1H), 3.90 (d, J=11.7 Hz, 2H), 3.61 (d, J=10.6 Hz, 2H), 3.43 (d, J=12.9 Hz, 3H), 3.23 (s, 3H), 3.30-3.12 (m, 4H), 2.88 (q, J=12.0 Hz, 2H), 2.31 (d, J=12.8 Hz, 2H), 1.94 (d, J=7.7 2 Hz, 2H).

Example 220

Compound 214

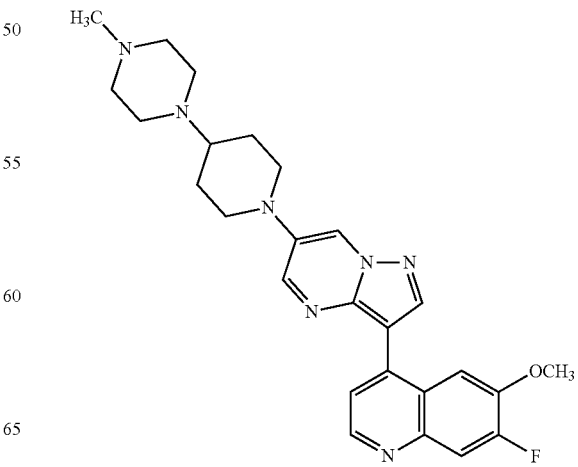

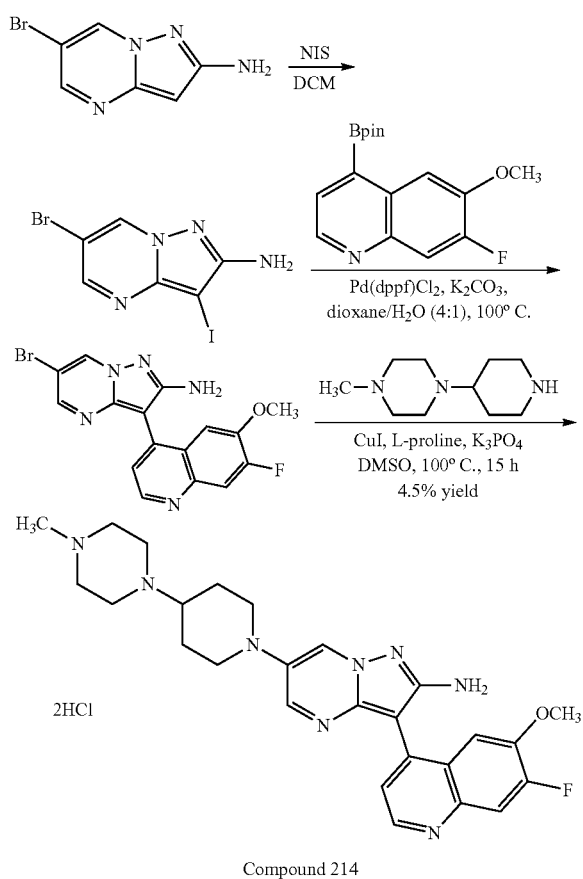

Compound 214

Step 1: To a solution of 6-bromopyrazolo[1,5-a]pyrimidin-2-amine (900.00 mg, 4.22 mmol, 1.00 eq) in DCM (100.00 mL) at 0° C. was added NIS (950.49 mg, 4.22 mmol, 1.00 eq) portionwise. The reaction mixture was stirred at 0° C. for 5 min. Yellow solid was precipitated. TLC (DCM/MeOH=20/1) showed the reaction was complete. The suspension was filtered (10 mL of DCM rinsed) to give the desired product of 6-bromo-3-iodo-pyrazolo[1,5-a]pyrimidin-2-amine (810.00 mg, 2.39 mmol, 56.63% yield) as a yellow solid. The filtrate was concentrated in vacuo to give the crude product (1.1 g), which was triturated with DCM (20 mL) for 0.5 h. The suspension was filtered (10 mL of DCM rinsed) to give a second batch of product as yellow solid. $^1$H NMR (400 MHz, DMSO-$d_6$): δ 9.16 (s, 1H), 8.34 (s, 1H), 5.94 (s, 2H).

Step 2: A mixture of 7-fluoro-6-methoxy-4-(4,4,5,5-tetramethyl-1,3,2-dioxaborolan-2-yl)quinoline (400.00 mg, 1.32 mmol, 1.00 eq), 6-bromo-3-iodo-pyrazolo[1,5-a]pyrimidin-2-amine (639.76 mg, 1.89 mmol, 1.43 eq) and $K_2CO_3$ (547.11 mg, 3.96 mmol, 3.00 eq) in dioxane (16.00 mL) and Water (4.00 mL) was de-gassed and purged with $N_2$. Pd(dppf)Cl$_2$ (193.10 mg, 264.00 umol, 0.20 eq) was added. The reaction mixture was de-gassed and purged with $N_2$ for three times, and then heated to 100° C. for 2 hours under $N_2$ atmosphere. From TLC (DCM/MeOH=50/1), the desired product and a little starting material were detected. The mixture was concentrated in vacuo to give the residue, which was purified through SiO2 flash column chromatography (gradient: MeOH/DCM=1/100 to 1/50) to give the desired product of 6-bromo-3-(7-fluoro-6-methoxy-4-quinolyl)pyrazolo[1,5-a]pyrimidin-2-amine (305.00 mg, 59.5% yield) as yellow solid. $^1$H NMR (400 MHz, DMSO-$d_6$) δ 9.31 (d, J=2.0 Hz, 1H), 8.79 (d, J=2.8 Hz, 1H), 8.38 (s, 1H), 7.83 (d, J=12.8 Hz, 1H), 7.53 (d, J=4.8 Hz, 1H), 7.33 (d, J=9.6 Hz, 1H), 6.02 (br s, 2H), 3.81 (s, 3H).

Step 3: A mixture of 6-bromo-3-(7-fluoro-6-methoxy-4-quinolyl)pyrazolo[1,5-a]pyrimidin-2-amine (70.00 mg, 180.32 umol, 1.00 eq), free amine of 1-methyl-4-(4-piperidyl)piperazine (66.10 mg, 360.64 umol, 2.00 eq), L-proline (20.76 mg, 180.32 umol, 1.00 eq), $K_3PO_4$ (95.69 mg, 450.80 umol, 2.50 eq) in DMSO (2.00 mL) was de-gassed and purged with $N_2$. CuI (17.17 mg, 90.16 umol, 0.50 eq) was added in one portion quickly. The resulting mixture was de-gassed and purged with $N_2$ for three times, then stirred at 100° C. for 15 h. The reaction mixture was diluted with 10% MeOH in DCM (20 mL). The mixture was filtered through a pad of celite (10 mL of 10% MeOH in DCM rinsed), and the filtrate was washed with water (15 mL×3). The combined aqueous layer was washed with 10% MeOH in DCM (10 mL). The combined organic layer was dried over $Na_2SO_4$, filtered and concentrated in vacuo to give the residue (90 mg), which was purified by prep-HPLC (HCl system) and dried by lyophilization to give the desired product of 3-(7-fluoro-6-methoxy-4-quinolyl)-6-[4-(4-methylpiperazin-1-yl)-1-piperidyl]pyrazolo[1,5-a]pyrimidin-2-amine (5.00 mg, 8.25 umol, 4.58% yield, 93% purity, 2HCl) as an orange solid. LC/MS (method 4): $t_R$=2.10 min, m z (M+H)$^+$=491.0. $^1$H NMR (400 MHz, $D_2O$) δ 8.72 (d, J=6.0 Hz, 1H), 8.47-8.35 (m, 2H), 7.98 (m, 1H), 7.88 (d, J=11.2 Hz, 1H), 7.51 (d, J=7.2 Hz, 1H), 3.86 (m, 3H), 3.71-3.57 (m, 4H), 3.03-2.83 (m, 6H), 2.32 (m, 2H), 1.92 (m, 2H).

Example 221

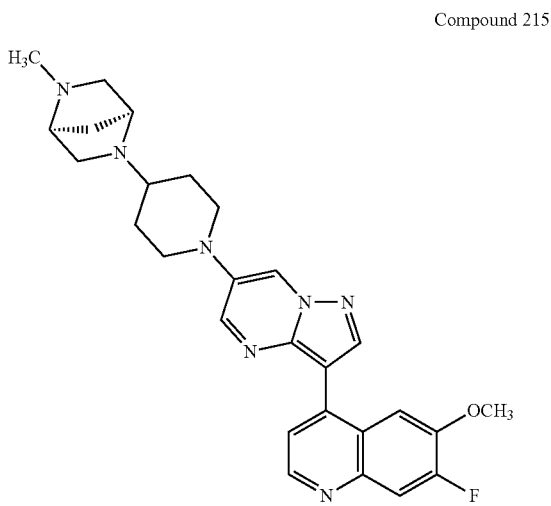 [SMILES: COc1cc2c(-c3cnn4cc(N5CCC(N6CCN(C)CC6)CC5)cnc34)ccnc2cc1F]

Compound 215

Compound 215 was the enantiomer of compound 55. The synthesis and spectral data (NMR and LCMS) are identical to compound 55 which is include in the writeup.

Example 222
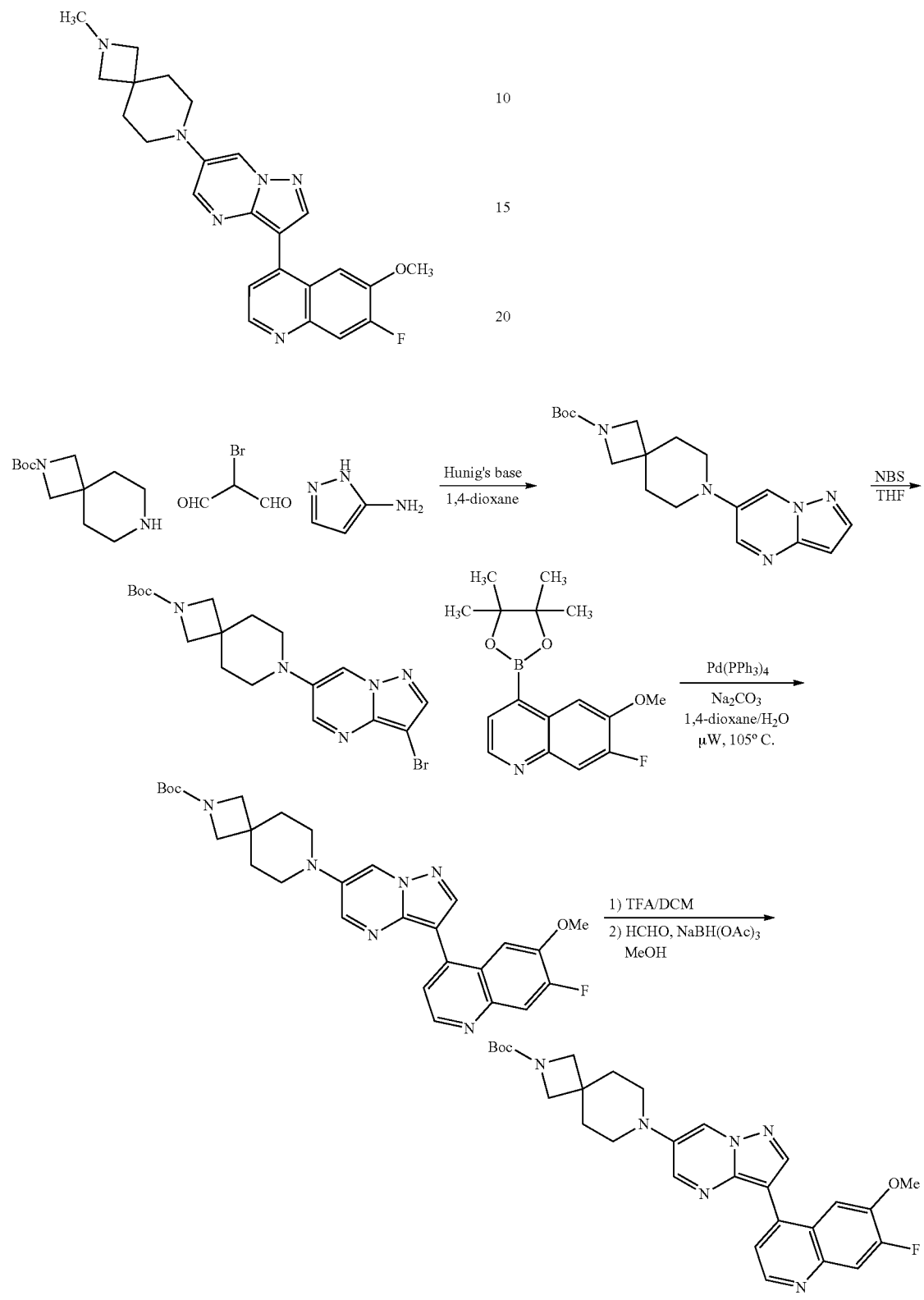
Compound 216

Compound 216 was prepared in analogous manner as Compound 15 followed by de-Boc and the N-methylation through reductive amination. LC/MS (method 2): $t_R$=3.10 min, m/z (M+H)$^+$=433.1.
Compound 217 was prepared in analogous manner as Compound 216. LC/MS (method 2): $t_R$=3.28 min, m/z (M+H)$^+$=461.1.
Example 223
Example 224
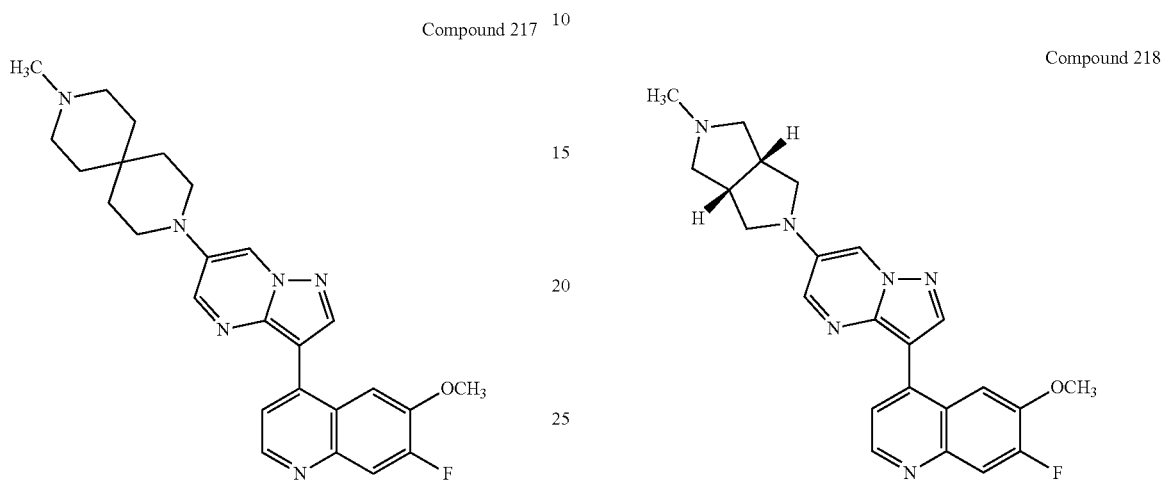
Compound 217
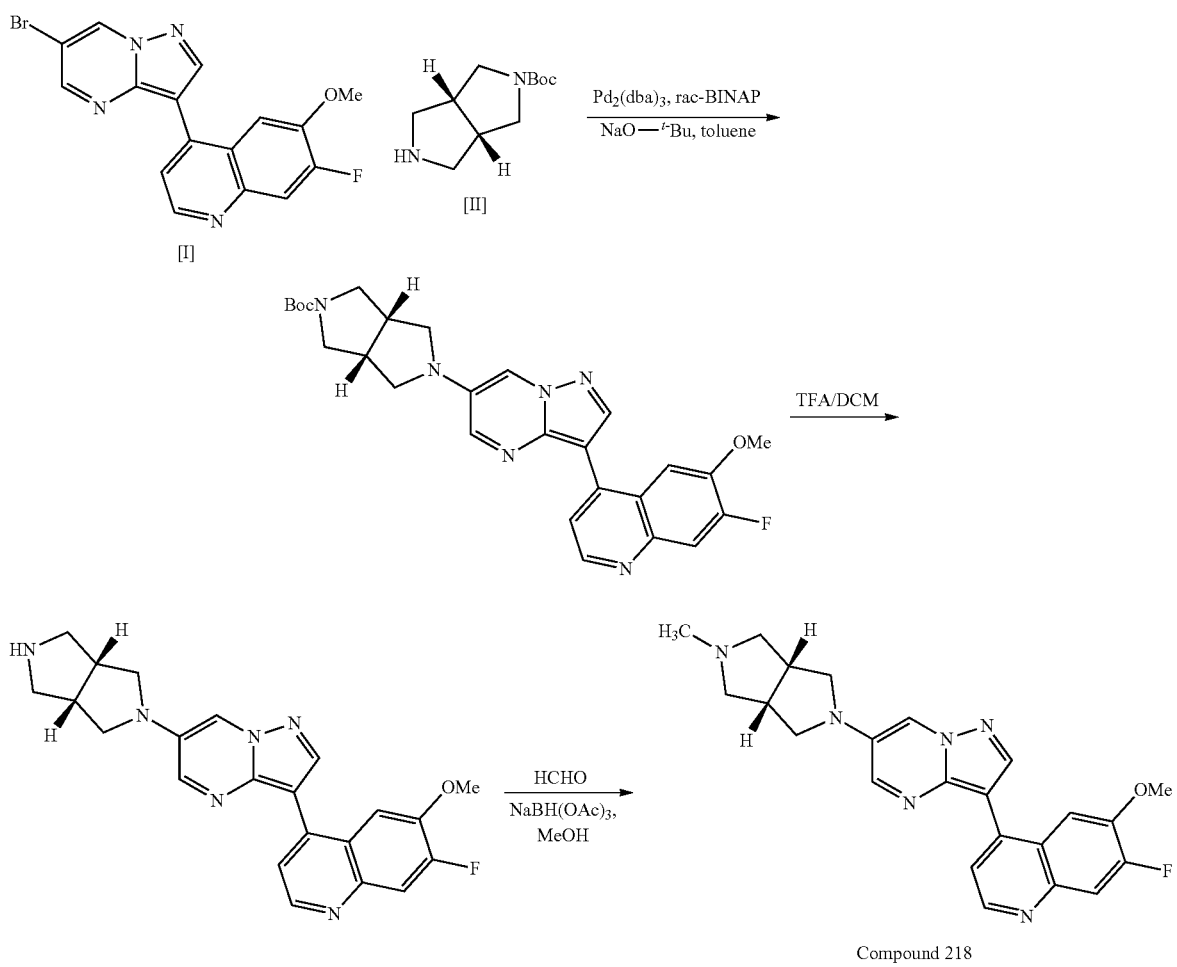
Compound 218

Step 1: To a 4-(6-bromopyrazolo[1,5-a]pyrimidin-3-yl)-7-fluoro-6-methoxyquinoline (70 mg, 0.188 mmol) in toluene (3 ml) was added tert-butyl cis-hexahydropyrrolo[3,4-c]pyrrole-2(1H)-carboxylate (48 mg, 0.225 mmol), $Pd_2(dba)_3$ (8.6 mg, 9.38 umol), rac-BINAP (14.0 mg, 23.0 ummol) and NaO$^t$—Bu (27 mg, 0.281 mmol) and the mixture was purged with $N_2$ for 1 minutes and subjected to microwave irradiation at 110° C. for 3 hrs. The mixture was partitioned between EtOAc (20 ml) and water (20 ml). The organic layer was separated and washed with brine, dried over $Na_2SO_4$. After the removal of solvent in vacuo, the residue was purified through Biotage flash column chromatography (gradient: MeOH/DCM=0/100 to 10/100) to give tert-butyl cis-5-(3-(7-fluoro-6-methoxyquinolin-4-yl)pyrazolo[1,5-a]pyrimidin-6-yl)hexahydropyrrolo[3,4-c]pyrrole-2(1H)-carboxylate (20 mg, 21.1% yield).

The synthesis of compound 218 was accomplished by following the same procedure as compound 216 for de-Boc and N-methylation. LC/MS (method 2): $t_R$=2.90 min, m/z (M+H)+=419.2.

Example 225

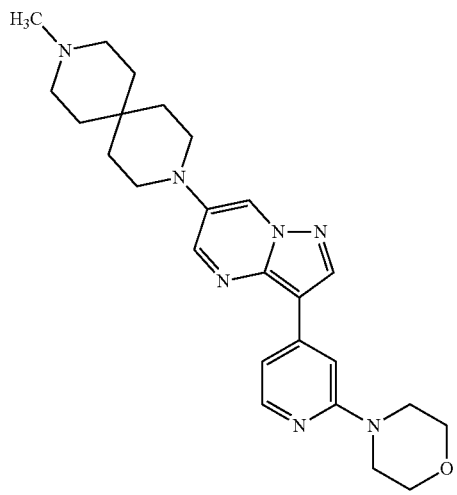

Compound 219

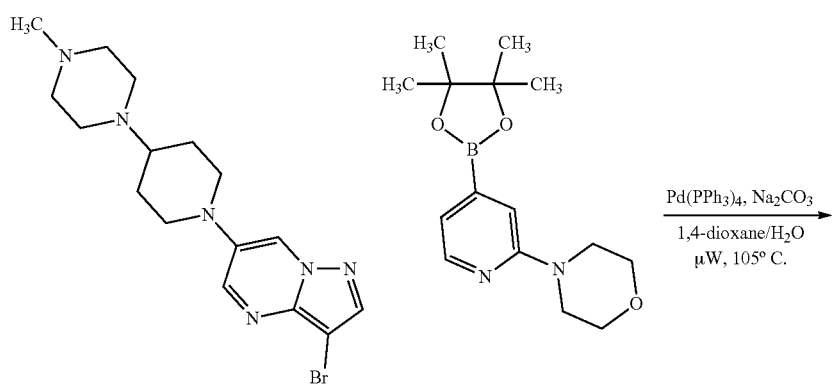

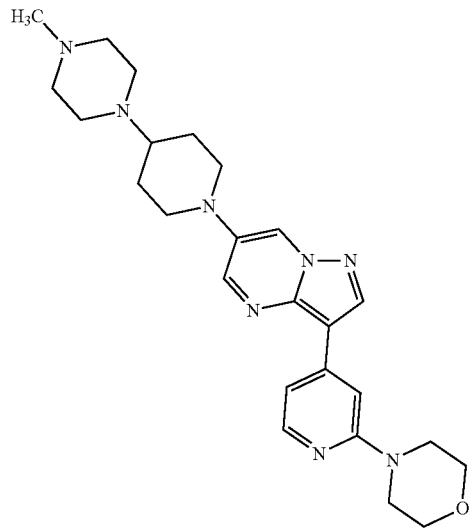

Compound 219

Compound 219 was prepared in an analogous manner as compound 15. LC/MS (method 2): $t_R$=2.70 min, m/z $(M+H)^+$=463.3.

Example 226

Compound 220

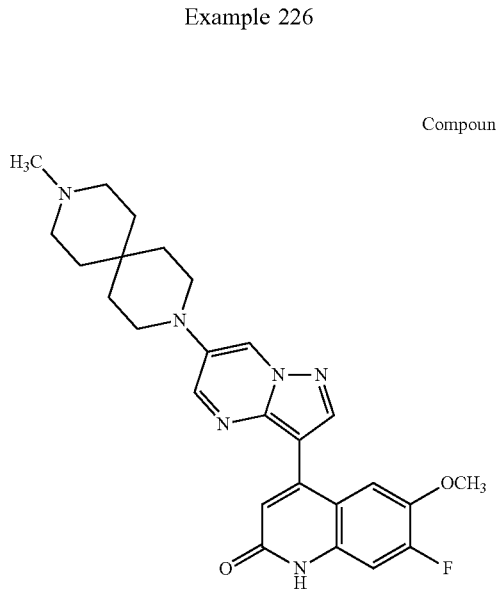

This analog was prepared in an analogous manner as compound 15. LC/MS (method 3): $t_R$=2.66 min, m z $(M+H)^+$=492.0. $^1$H NMR (400 MHz, CD$_3$OD) δ 8.73 (d, J=2.8 Hz, 1H), 8.48 (d, J=2.8 Hz, 1H), 7.50 (d, J=8.8 Hz, 1H), 7.22 (d, J=11.6 Hz, 1H), 6.84 (s, 1H), 3.81 (s, 3H), 3.80-3.75 (m, 2H), 2.87-2.72 (m, 2H), 2.75-2.45 (m, 9H), 2.36 (s, 3H), 2.11-2.06 (m, 2H), 1.77-1.69 (m, 2H).

Example 227

Compound 221

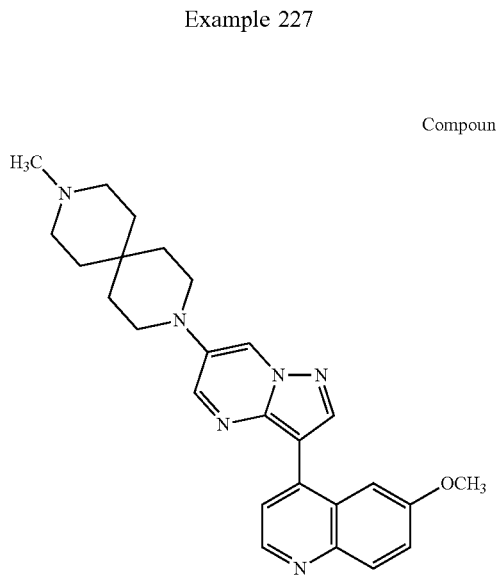

Compound 221 was prepared in an analogous manner as compound 49. LC/MS (method 3): $t_R$=2.34 min, m z $(M+H)^+$=430.0. $^1$H NMR (400 MHz, CD$_3$OD) δ 8.69 (d, J=4.8 Hz, 1H), 8.40 (s, 1H), 8.31 (d, J=2.8 Hz, 1H), 8.22 (d, J=2.8 Hz, 1H), 7.97 (s, J=9.6 Hz, 1H), 7.73 (d, J=4.4 Hz, 1H), 7.53 (d, J=2.8 Hz, 1H), 7.47-7.43 (m, 1H), 4.20-4.13 (m, 2H), 3.87-3.82 (m, 5H), 3.50-3.44 (m, 1H), 2.80-2.40 (m, 8H), 2.33 (s, 3H).

Example 228

Compound 222

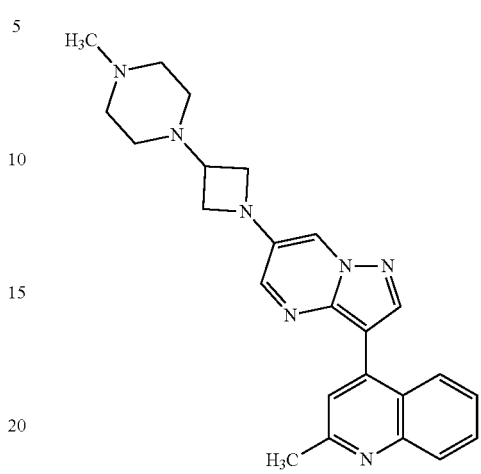

Compound 222 was prepared in an analogous manner as compound 49. LC/MS (method 3): $t_R$=2.32 min, m z $(M+H)^+$=414.1. $^1$H NMR (400 MHz, CD$_3$OD) δ 8.35 (s, 1H), 8.29 (s, 1H), 8.20 (d, J=2.4 Hz, 1H), 8.17 (d, J=8.4 Hz, 1H), 8.00 (d, J=8.4 Hz, 1H), 7.75-7.73 (m, 1H), 7.69 (s, 1H), 7.55-7.52 (m, 1H), 4.15 (t, J=7.2 Hz, 2H), 3.84 (t, J=7.2 Hz, 2H), 3.50-3.47 (m, 1H), 2.75 (s, 3H), 2.72-2.32 (m, 8H), 2.31 (s, 3H).

Example 229

Compound 223

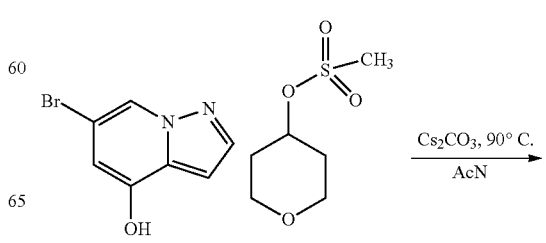

-continued

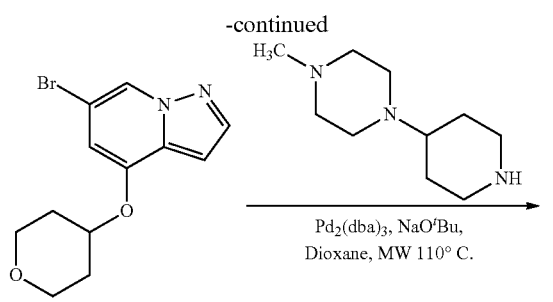

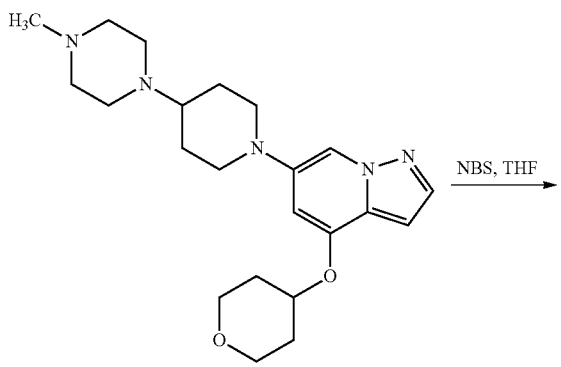

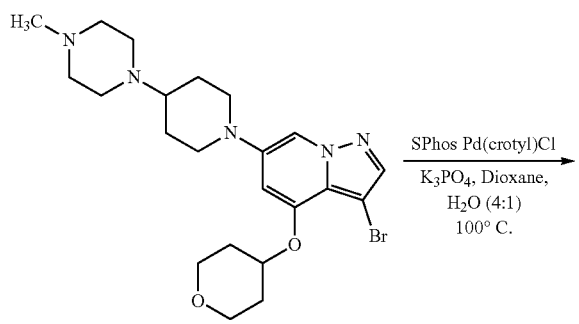

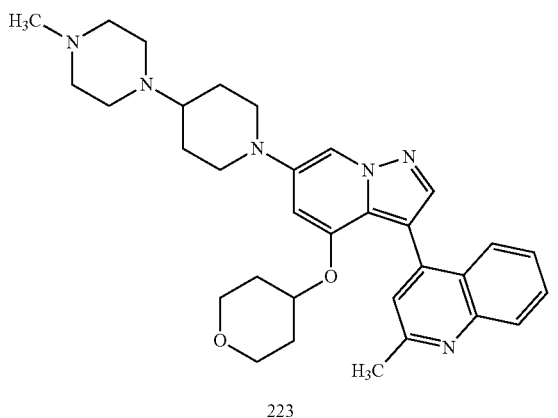

223

Step 1—To a solution of 6-bromopyrazolo[1,5-a]pyridin-4-ol (0.100 g, 0.469 mmol) in Acetonitrile (2.347 ml), tetrahydro-2H-pyran-4-yl methanesulfonate (0.127 g, 0.704 mmol) was added followed by $Cs_2CO_3$ (0.459 g, 1.408 mmol) and the reaction mixture was heated at 90° C. for 2 h. After this time, saturated aqueous $NH_4Cl$ (10 ml) and DCM (10 ml) were added and the layers were separated. The organic layer was washed with water (10 ml) and brine (10 ml), dried over $Na_2SO_4$, filtered and concentrated in vacuo. The crude reaction mixture was then used as such for the next reaction.

Step 2—To a degassed solution of 6-bromo-4-((tetrahydro-2H-pyran-4-yl)oxy)pyrazolo[1,5-a]pyridine (0.139 g, 0.468 mmol) and 1-methyl-4-(piperidin-4-yl)piperazine (0.171 g, 0.936 mmol) in Dioxane (2.339 ml), $Pd_2(dba)_3$ (0.043 g, 0.047 mmol), XPhos (0.029 g, 0.094 mmol) and sodium tert-butoxide (0.135 g, 1.403 mmol) were added and the solution was degassed again for 5 min. After this time, the reaction mixture was capped and heated in a microwave at 110° C. for 2 h. The reaction mixture was then cooled to room temperature, DCM (3 ml) and SiliaMetS® Dimercaptotriazine (DMT) were added and stirred at room temperature for 30 min. It was then filtered and the filtrate was concentrated in vacuo. The residue was subjected to flash silica gel chromatography on Biotage silica gel column (gradient: 10% $NH_3$ in MeOH/$CH_2Cl_2$=0/100 to 15/100) to give 6-(4-(4-methylpiperazin-1-yl)piperidin-1-yl)-4-((tetrahydro-2H-pyran-4-yl)oxy)pyrazolo[1,5-a]pyridine (0.0955 g, 0.239 mmol, 51.1% yield).

Step 3—6-(4-(4-methylpiperazin-1-yl)piperidin-1-yl)-4-((tetrahydro-2H-pyran-4-yl)oxy) pyrazolo [1,5-a]pyridine (0.095 g, 0.238 mmol) was dissolved in THF (1.189 ml) and cooled to 0° C. NBS (0.042 g, 0.238 mmol) was then slowly added at that temperature and the reaction stirred at 0° C. for 15 min. After the completion of the reaction, saturated aqueous $NaHCO_3$ (10 ml) was added followed by EtOAC (10 ml) and the layers were separated. The organic layer was washed with water (5 ml) and brine (5 ml) and dried over $Na_2SO_4$, filtered and concentrated in vacuo. The crude reaction mixture was then used as such for the next reaction.

Step 4—Followed general procedure 3B to form Compound 223. LC/MS (method 2): $t_R$=3.33 min, m/z (M+H)$^+$=541.

Example 230

Compound 224

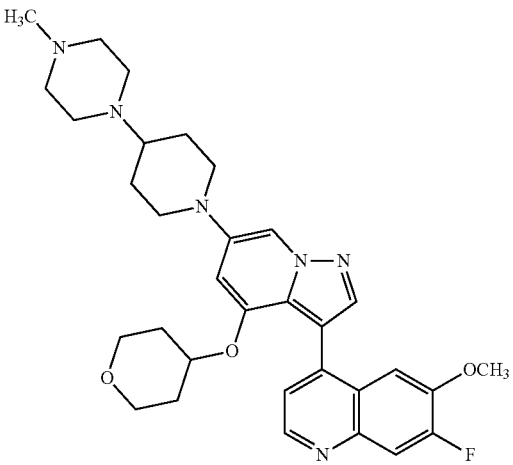

Compound 224 was synthesized in an analogous manner to Compound 223. LC/MS (method 2): $t_R$=3.48 min, m/z (M+H)$^+$=575.

Example 231

Compound 225

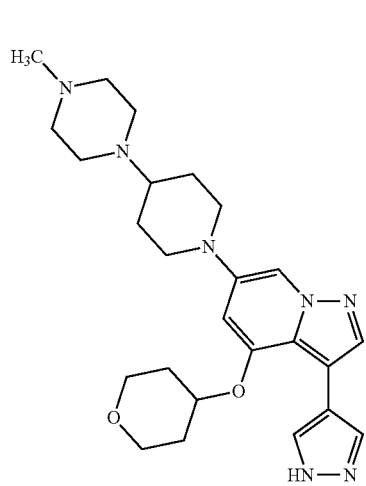

Compound 225 was synthesized in an analogous manner to Compound 223. LC/MS (method 2): $t_R$=3.29 min, m/z $(M+H)^+$=466.

Example 232

Compound 226

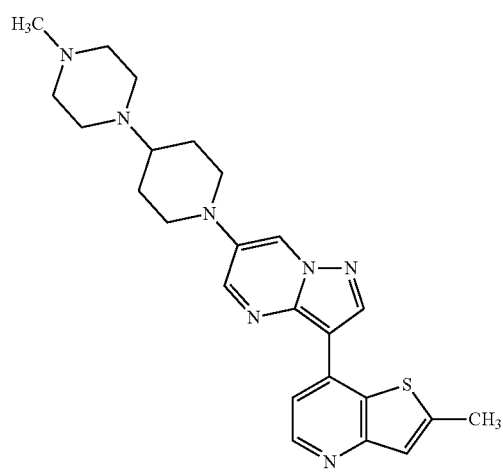

Compound 226 was synthesized using the general procedures 1, 2 and 5. LC/MS (method 2): $t_R$=2.88 min, m/z $(M+H)^+$=448.

Example 233

Compound 227

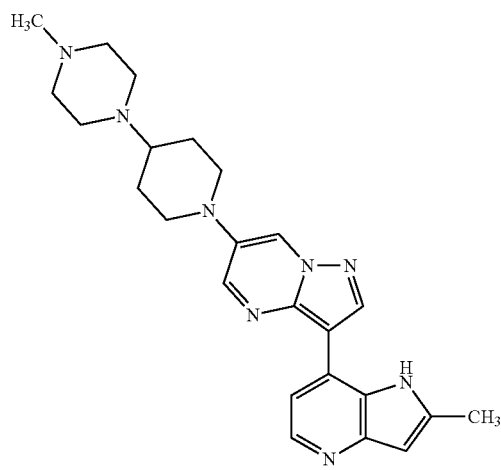

Compound 227 was synthesized using the general procedures 1, 2 and 5. LC/MS (method 2): $t_R$=2.79 min, m/z $(M+H)^+$=431.

Example 234

Compound 228

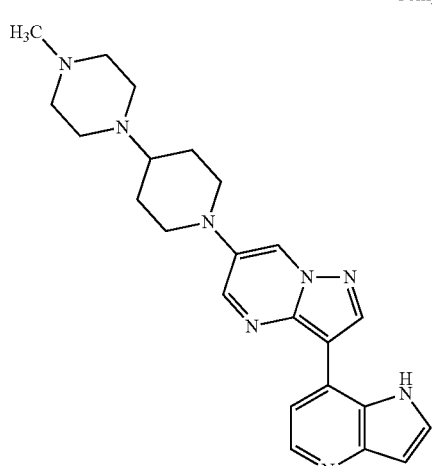

Compound 228 was synthesized using the general procedures 1, 2 and 5. LC/MS (method 2): $t_R$=2.65 min, m/z $(M+H)^+$=417.

Example 235

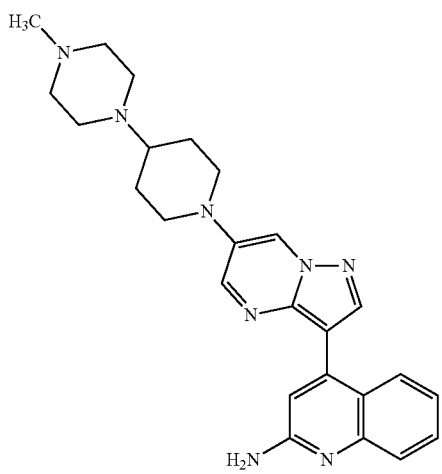

Compound 229

Compound 229 was synthesized using the general procedures 1, 2 and 5. LC/MS (method 1): $t_R$=2.22 min, m/z $(M+H)^+$=443.

Example 236

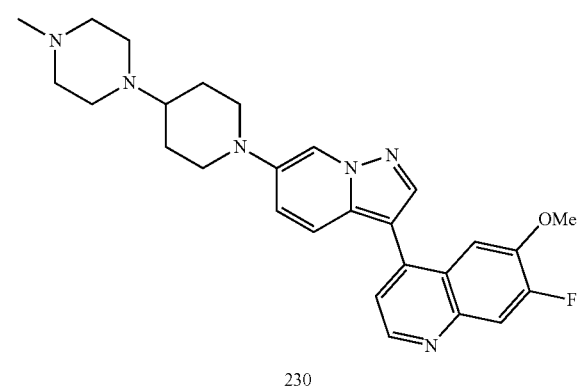

230

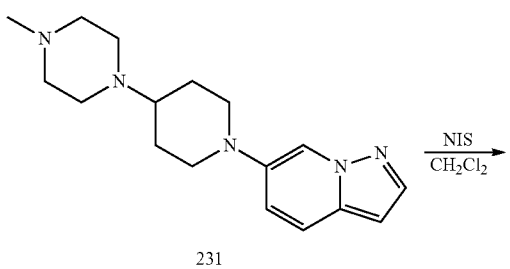

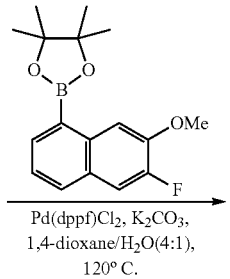

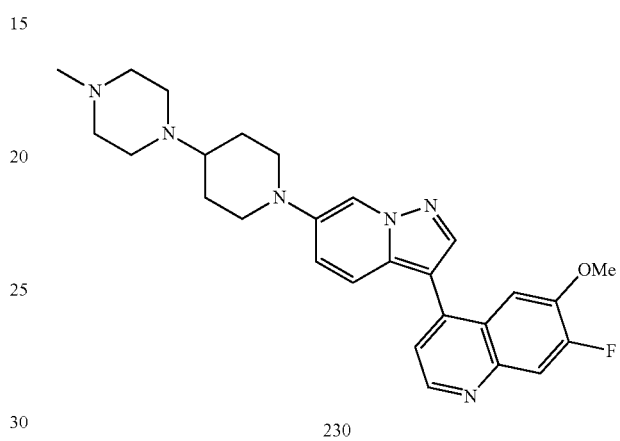

230

Compound 230 was prepared according to the following procedures: To a solution of 6-bromopyrazolo[1,5-a]pyridine (500.0 mg, 2.54 mmol, 1.0 eq) and 1-methyl-4-(4-piperidyl)piperazine (697.7 mg, 2.38 mmol, 0.94 eq, trisHCl salt) in toluene (10.00 mL), $Pd_2(dba)_3$ (348.9 mg, 381.0 umol, 0.15 eq), XPhos (544.9 mg, 1.14 mmol, 0.45 eq), and NaO$^t$Bu (610.2 mg, 6.35 mmol, 2.50 eq) was added. The resulting mixture was de-gassed and purged with nitrogen, then heated to 110° C. under nitrogen atmosphere for 7 hours until there was no more starting material as indicated by LCMS analysis. The reaction mixture was cooled to room temperature, and filtered over celite, and washed with $CH_2Cl_2$ (10 mL) and EtOAc (10 mL). The organic phase was then concentrated under vacuum after which the resulting residue was purified by silica gel column chromatography (5:1 petroleum ether:EtOAc), and further purified by prep-TLC (7:1 $CH_2Cl_2$/MeOH) to afford the compound 231 (90.0 mg, 270.5 umol, 11% yield, 90% purity) as a brown yellow solid.

To a solution of compound 231 (88.0 mg, 293.9 umol, 1.0 eq) in $CH_2Cl_2$ (3.0 mL), NIS (66.1 mg, 293.9 umol, 1.0 eq) was added at 0° C. The resulting mixture was then stirred at 25° C. for 10 min after which there was no more starting material by LCMS analysis. Sat. aq. $NaHCO_3$ (5 mL) was added, and the organic phase was collected, washed with brine (8 mL), dried over anhydrous $Na_2SO_4$, filtered and concentrated under vacuum to provide a residue, which was purified by prep-TLC (10:1 $CH_2Cl_2$/MeOH) to afford the compound pyridine 232 (39.0 mg, 90.8 umol, 30.9% yield, 99% purity) as a yellow solid.

To a solution of compound 232 (39.0 mg, 91.7 umol, 1.0 eq) in H$_2$O:1,4-dioxane (4:1 v/v) (1.0 mL), 7-fluoro-6-methoxy-4-(4,4,5,5-tetramethyl-1,3,2-dioxaborolan-2-yl)quinoline (27.8 mg, 91.7 umol, 1.0 eq), Pd(dppf)Cl$_2$ (13.42 mg, 18.3 umol, 0.20 eq) and K$_2$CO$_3$ (31.7 mg, 229.3 umol, 2.50 eq) were added. The resulting mixture was de-gassed and purged with nitrogen, then heated at 120° C. under nitrogen atmosphere for 3 hours until there was no more starting material observed by LCMS analysis. The reaction was cooled to room temperature and concentrated under vacuum to remove the solvent. The resulting residue was purified by prep-TLC (10:1 CH$_2$Cl$_2$/MeOH) to provide 230 (20.0 mg, 40.5 umol, 44% yield, 96% purity) as a brown solid. LC/MS (method 2): t$_R$=3.07 min, m/z (M+H)$^+$=475.3. $^1$H NMR (400 MHz, D$_2$O) 8.58 (d, J=6.0 Hz, 1H), 8.12 (s, 1H), 7.86 (d, J=2.1 Hz, 1H), 7.80 (d, J=10.6 Hz, 1H), 7.57 (d, J=5.9 Hz, 1H), 7.37 (d, J=9.7 Hz, 1H), 7.23-7.14 (m, 2H), 3.89-3.78 (m, 1H), 3.77 (s, 3H), 3.75-3.65 (m, 4H), 3.65-3.55 (m, 4H), 3.10-2.90 (m, 3H), 2.98 (s, 3H), 2.85-2.75 (m, 2H), 2.35-2.25 (m, 3H).

Example 237

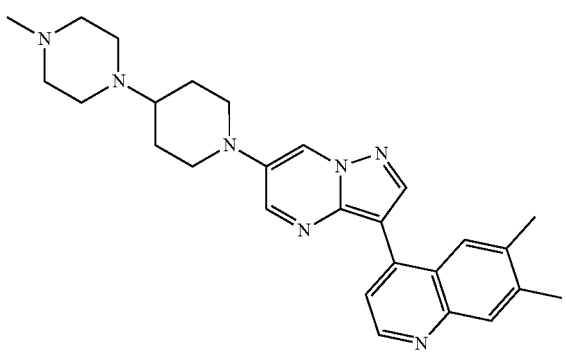

233

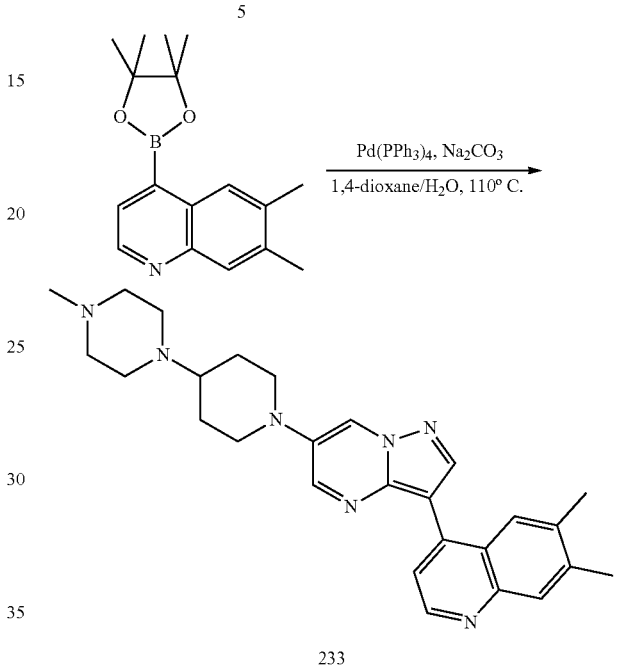

Compound 233 was prepared from compound 5 and 6,7-dimethylquinoline-4-boronic acid pinacol ester using general procedure 2 and 3A. LC/MS (method 2): t$_R$=2.98 min, m/z (M+H)$^+$=456.3.

The following compounds were prepared in analogous fashion to 233 in Example 237:

| Example | Compound | $^1$H NMR | LC/MS QC Method | m/z (M + H)$^+$ |
|---|---|---|---|---|
| 238 | 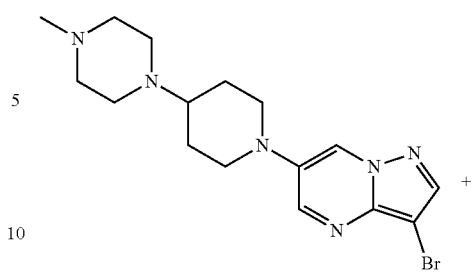 | | Method 2: t$_R$ = 2.88 min | 453.3 |

234

-continued
| Example | Compound | ¹H NMR | LC/MS QC Method | m/z (M + H)⁺ |
|---|---|---|---|---|
| 239 | 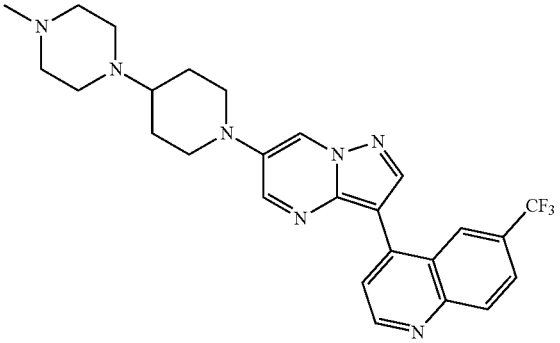 [SMILES: CN1CCN(C2CCN(c3cnc4c(-c5ccnc6ccc(C(F)(F)F)cc56)cnn4c3)CC2)CC1] 235 | | Method 2: $t_R$ = 3.20 min | 496.3 |
| 240 | 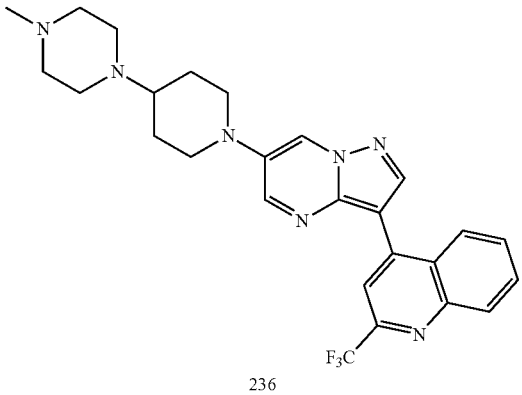 236 | | Method 2: $t_R$ = 4.01 min | 496.3 |
| 241 | 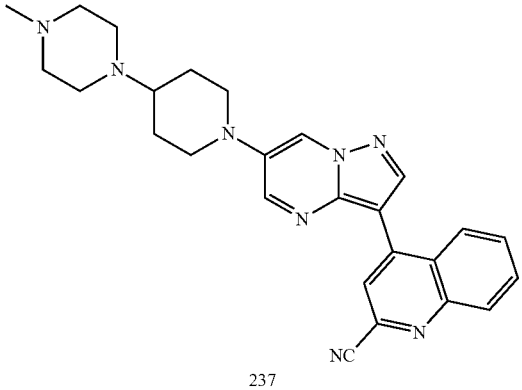 237 | | Method 2: $t_R$ = 3.57 min | 453.4 |
| 242 | 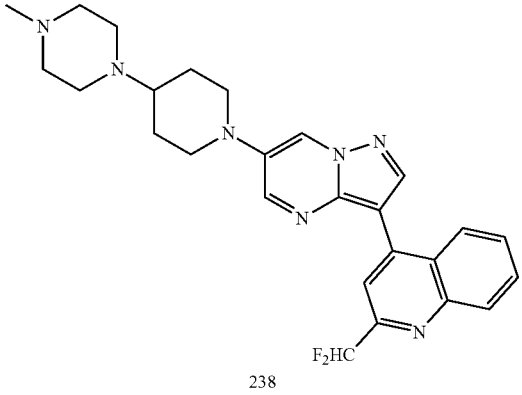 238 | | Method 2: $t_R$ = 3.60 min | 478.3 |

-continued

| Example | Compound | ¹H NMR | LC/MS QC Method | m/z (M + H)⁺ |
|---|---|---|---|---|
| 243 | 239 | | Method 2: t$_R$ = 2.68 min | 474.3 |
| 244 | 240 | ¹H NMR (400 MHz, D₂O) δ 8.85 (d, J = 5.9 Hz, 1H), 8.65 (d, J = 2.6 Hz, 1H), 8.54-8.43 (m, 3H), 8.04 (d, J = 6.0 Hz, 1H), 7.93 (d, J = 9.0 Hz, 1H), 3.78 (d, J = 12.6 Hz, 2H), 3.70-3.50 (m, 8H), 3.45-3.35 (m, 2H), 2.92 (s, 3H), 2.89-2.80 (m, 2H), 2.27 (d, J = 12.2 Hz, 2H), 1.90-1.79 (m, 1H). | Method 2: t$_R$ = 2.68 min | 480.1 |
| 245 | 241 | | Method 2: t$_R$ = 2.98 min | 462.3 |
| 246 | 242 | ¹H NMR (400 MHz, CD₃OD) δ 8.85 (d, J = 2.4 Hz, 1H), 8.81 (d, J = 5.6 Hz, 1H), 8.59 (m, 2H), 8.19-8.17 (m, 1H), 7.95 (d, J = 8.8 Hz, 1H), 7.86 (d, J = 10.8 Hz, 1H), 3.85-3.82 (m, 2H), 3.58-3.48 (m, 2H), 3.17-2.85 (m, 12H), 2.16-2.04 (m, 2H), 1.88-1.80 (m, 2H) | Method 2: t$_R$ = 2.81 m | 462.1 |

| Example | Compound | ¹H NMR | LC/MS QC Method | m/z (M + H)⁺ |
|---|---|---|---|---|
| 247 | 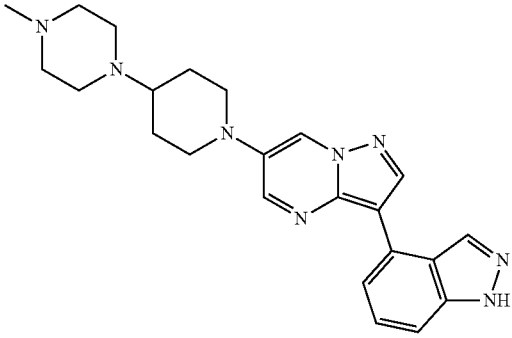 [SMILES: CN1CCN(C2CCN(c3cnc4c(-c5cccc6[nH]ncc56)cnn4c3)CC2)CC1]<br>243 | | Method 2: t_R = 2.88 m | 417.2 |
| 248 | 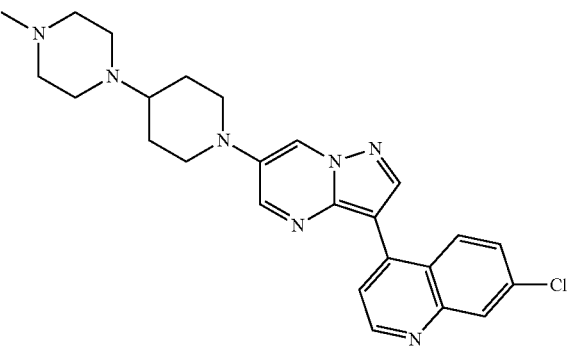 [SMILES: CN1CCN(C2CCN(c3cnc4c(-c5ccnc6cc(Cl)ccc56)cnn4c3)CC2)CC1]<br>244 | | Method 2: t_R = 3.00 m | 462.3 |
| 249 | 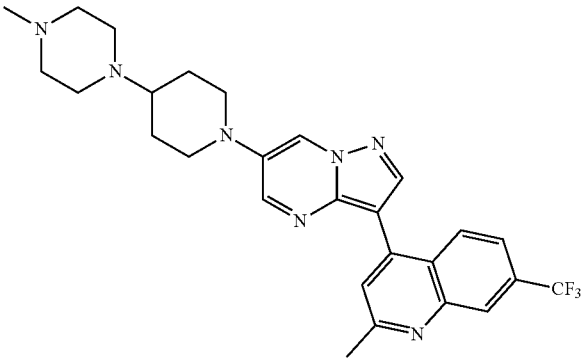 [SMILES: Cc1cc(-c2cnn3cc(N4CCC(N5CCN(C)CC5)CC4)cnc23)c2ccc(C(F)(F)F)cc2n1]<br>245 | | Method 2: t_R = 3.26 m | 510.3 |
| 250 | 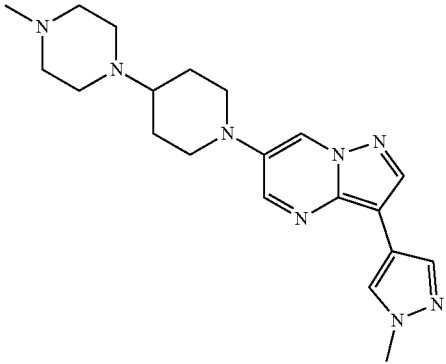 [SMILES: CN1CCN(C2CCN(c3cnc4c(-c5cnn(C)c5)cnn4c3)CC2)CC1]<br>246 | | Method 2: t_R = 2.68 m | 381.3 |

| Example | Compound | ¹H NMR | LC/MS QC Method | m/z (M + H)⁺ |
|---|---|---|---|---|
| 251 | 247 | | Method 2: $t_R$ = 2.63 m | 417.3 |
| 252 | 248 | | Method 2: $t_R$ = 2.71 m | 434.3 |
| 253 | 249 | | Method 2: $t_R$ = 2.43 m | 393.3 |
| 254 | 250 | | Method 2: $t_R$ = 3.06 m | 434.3 |

-continued
| Example | Compound | ¹H NMR | LC/MS QC Method | m/z (M + H)⁺ |
|---|---|---|---|---|
| 255 | 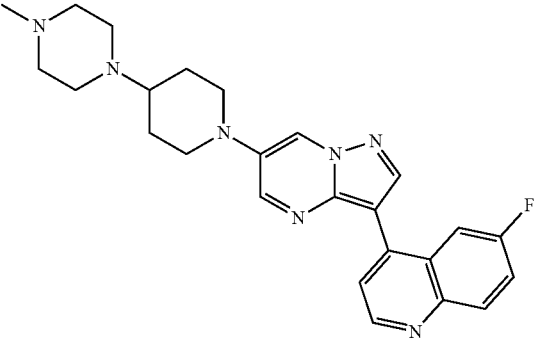 [SMILES: CN1CCN(C2CCN(c3cnc4c(-c5ccnc6ccc(F)cc56)cnn4c3)CC2)CC1]<br>251 | | Method 2: $t_R$ = 2.73 m | 446.3 |
| 256 | 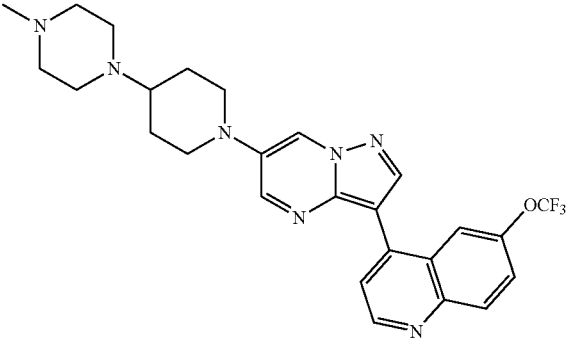 [SMILES: CN1CCN(C2CCN(c3cnc4c(-c5ccnc6ccc(OC(F)(F)F)cc56)cnn4c3)CC2)CC1]<br>252 | | Method 2: $t_R$ = 3.22 m | 512.3 |
| 257 | 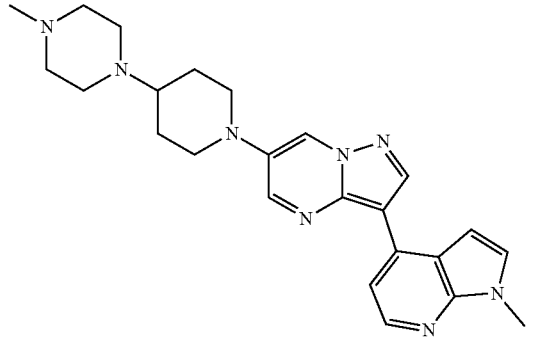<br>253 | | Method 2: $t_R$ = 2.73 m | 431.3 |
| 258 | 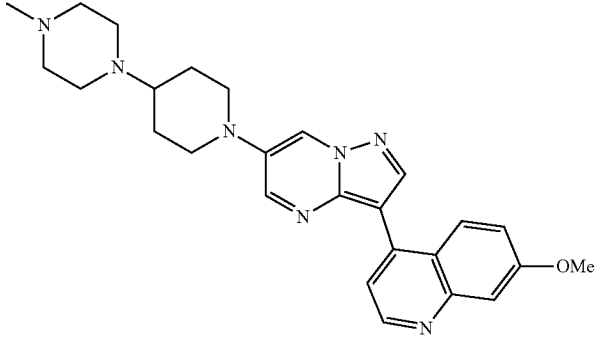 [SMILES: COc1ccc2c(-c3cnn4cc(N5CCC(N6CCN(C)CC6)CC5)cnc34)ccnc2c1]<br>254 | | Method 2: $t_R$ = 2.82 m | 458.3 |

-continued

| Example | Compound | ¹H NMR | LC/MS QC Method | m/z (M + H)⁺ |
|---|---|---|---|---|
| 259 | 255 | | Method 2: $t_R$ = 2.88 m | 460.2 |
| 260 | 256 | | Method 2: $t_R$ = 2.78 m | 446.2 |
| 261 | 257 | | Method 2: $t_R$ = 3.42 m | 496.2 |
| 262 | 258 | | Method 2: $t_R$ = 2.78 m | 435.3 |

| Example | Compound | ¹H NMR | LC/MS QC Method | m/z (M + H)⁺ |
|---|---|---|---|---|
| 263 | 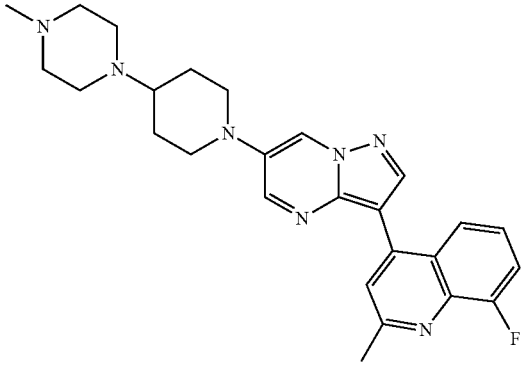 [SMILES: Cc1cc(-c2cnn3cc(N4CCC(N5CCN(C)CC5)CC4)cnc23)c2cccc(F)c2n1] 259 | | Method 2: $t_R$ = 2.77 m | 442.3 |
| 264 | 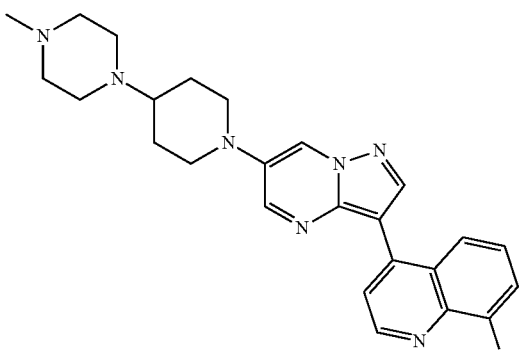 260 | | Method 2: $t_R$ = 2.84 m | 446.2 |
| 265 | 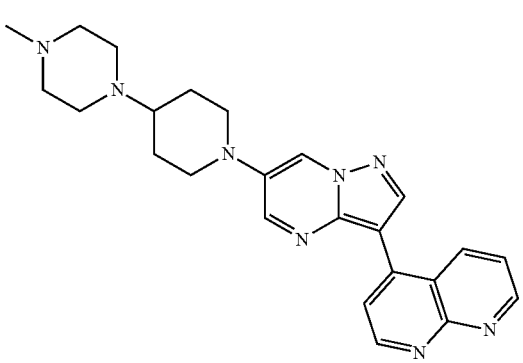 [SMILES: CN1CCN(C2CCN(c3cnc4c(-c5ccnc6ncccc56)cnn4c3)CC2)CC1] 261 | | Method 2: $t_R$ = 2.45 m | 429.2 |
| 266 | 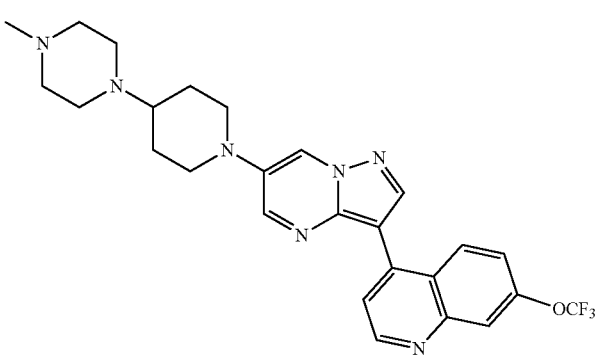 [SMILES: CN1CCN(C2CCN(c3cnc4c(-c5ccnc6cc(OC(F)(F)F)ccc56)cnn4c3)CC2)CC1] 262 | | Method 2: $t_R$ = 3.35 m | 512.2 |

| Example | Compound | ¹H NMR | LC/MS QC Method | m/z (M + H)⁺ |
|---|---|---|---|---|
| 267 | 263 | | Method 2: $t_R$ = 2.94 m | 453.3 |
| 268 | 264 | ¹H NMR (400 MHz, D₂O) δ 8.66 (s, 1H), 8.58 (d, J = 5.6 Hz, 1H), 8.49 (s, 1H), 8.44 (s, 1H), 7.91 (d, J = 6.0 Hz, 1H), 7.75 (d, J = 11.2 Hz, 1H), 7.48 (d, J = 9.2 Hz, 1H), 3.91-3.24 (m, 11H), 3.01-2.83 (m, 5H), 2.29 (s, 2H), 1.88 (d, J = 10.8 Hz, 2H) | Method 2: $t_R$ = 2.81 m | 461.1 |
| 269 | 265 | ¹H NMR (400 MHz, CDCl₃) δ 8.82 (d, J = 4.5 Hz, 1H), 8.49 (d, J = 2.6 Hz, 1H), 8.20-8.14 (m, 2H), 7.99 (dd, J = 9.3, 1.8 Hz, 1H), 7.61-7.51 (m, 2H), 4.00 (s, 3H), 3.61 (d, J = 11.8 Hz, 2H), 2.82-2.52 (m, 10H), 2.50-2.43 (m, 1H), 2.41 (s, 3H), 2.04 (d, J = 12.5 Hz, 2H), 1.78 (dd, J = 12.3, 11.6 Hz, 2H) | Method 2: $t_R$ = 2.14 m | 476.3 |
| 270 | 266 | ¹H NMR (400 MHz, D₂O) δ 8.87 (br. s, 1H), 8.72 (br. s, 1H), 8.61 (br. s, 2H), 8.30 (br. s, 1H), 8.11 (br. s, 1H), 7.84 (br. s, 1H), 3.84 (br. d, J = 11.6 Hz, 2H), 3.61 (br s, 9H), 3.02-2.86 (m, 5H), 2.45 (s, 3H), 2.31 (br. s, 1H), 2.39-2.21 (m, 1H), 1.91 (br. d, J = 9.2 Hz, 2H) | Method 2: $t_R$ = 3.09 m | 460.2 |

-continued
| Example | Compound | ¹H NMR | LC/MS QC Method | m/z (M + H)⁺ |
|---|---|---|---|---|
| 271 | 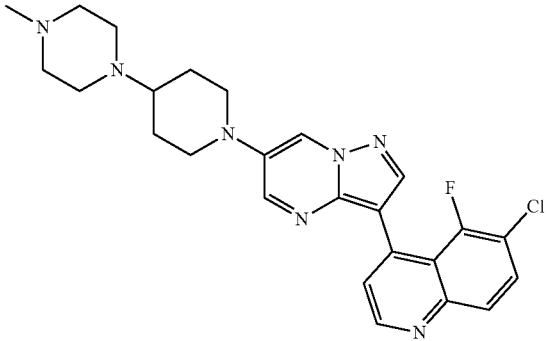 [SMILES: CN1CCN(C2CCN(c3cnc4c(-c5ccnc6ccc(Cl)c(F)c56)cnn4c3)CC2)CC1]<br>267 | ¹H NMR (400 MHz, CD₃OD) δ 8.89 (d, J = 4.8 Hz, 1H), 8.63 (d, J = 2.4 Hz, 1H), 8.43 (d, J = 2.4 Hz, 1H), 8.24 (d, J = 3.8 Hz, 1H), 7.94 (dd, J = 1.2, 9.0 Hz, 1H), 7.87-7.81 (m, 1H), 7.72 (d, J = 4.4 Hz, 1H), 3.73 (d, J = 12.4 Hz, 2H), 2.88-2.42 (m, 11H), 2.37 (s, 3H), 2.08 (d, J = 12.2 Hz, 2H), 1.78-1.68 (m, 2H) | Method 2: t_R = 3.49 m | 480.1 |
| 272 | 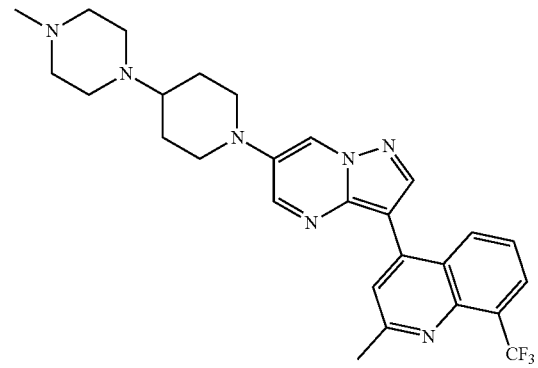 [SMILES: Cc1cc(-c2cnn3cc(N4CCC(N5CCN(C)CC5)CC4)cnc23)c2cccc(C(F)(F)F)c2n1]<br>268 | | Method 2: t_R = 4.10 m | 510.3 |
| 273 | 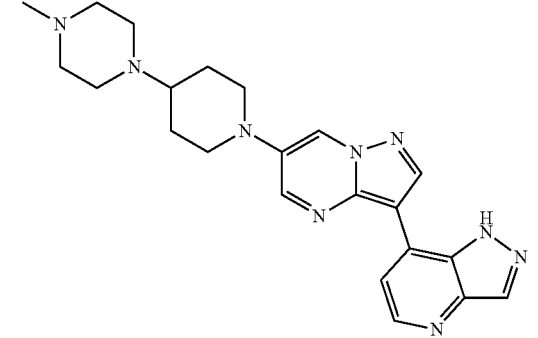 [SMILES: CN1CCN(C2CCN(c3cnc4c(-c5ccnc6cn[nH]c56)cnn4c3)CC2)CC1]<br>269 | | Method 2: t_R = 2.57 m | 418.2 |
| 274 | 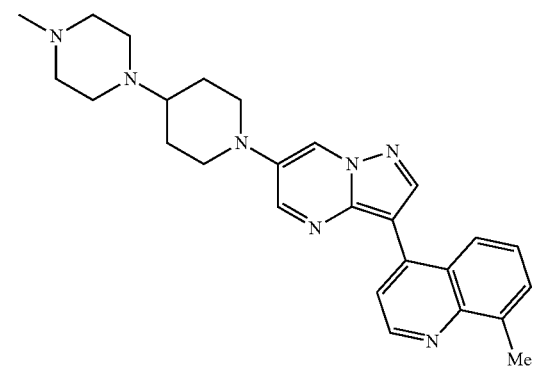 [SMILES: Cc1cccc2c(-c3cnn4cc(N5CCC(N6CCN(C)CC6)CC5)cnc34)ccnc12]<br>270 | | Method 2: t_R = 2.86 m | 442.3 |

-continued
| Example | Compound | ¹H NMR | LC/MS QC Method | m/z (M + H)⁺ |
|---|---|---|---|---|
| 275 | 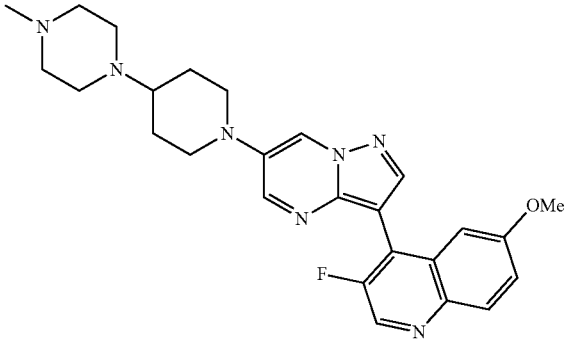 [SMILES: COc1ccc2ncc(F)c(-c3cnn4cc(N5CCC(N6CCN(C)CC6)CC5)cnc34)c2c1]<br>271 | | Method 2: $t_R$ = 3.25 m | 476.3 |
| 276 | 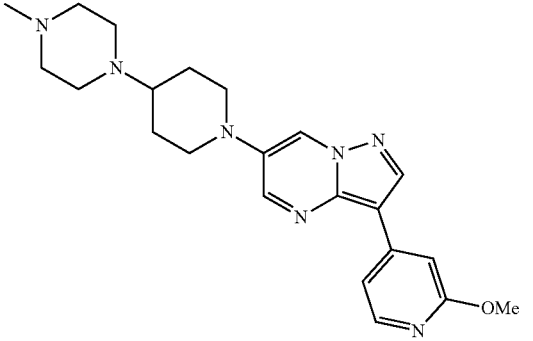 [SMILES: COc1cc(-c2cnn3cc(N4CCC(N5CCN(C)CC5)CC4)cnc23)ccn1]<br>272 | | Method 2: $t_R$ = 2.72 m | 408.2 |
| 277 | 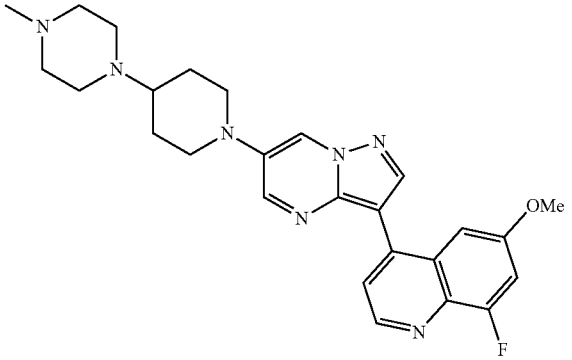 [SMILES: COc1cc(F)c2nccc(-c3cnn4cc(N5CCC(N6CCN(C)CC6)CC5)cnc34)c2c1]<br>273 | | Method 2: $t_R$ = 2.97 m | 476.2 |
| 278 | 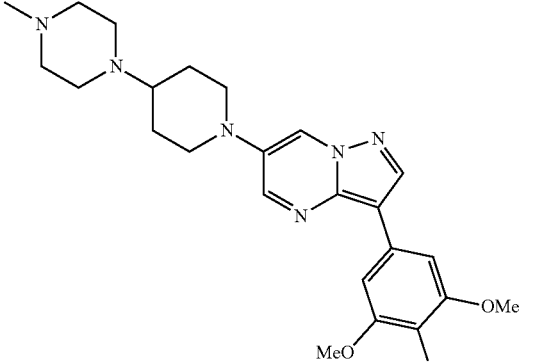<br>274 | | Method 2: $t_R$ = 3.63 m | 467.2 |

-continued
| Example | Compound | ¹H NMR | LC/MS QC Method | m/z (M + H)⁺ |
|---|---|---|---|---|
| 279 | 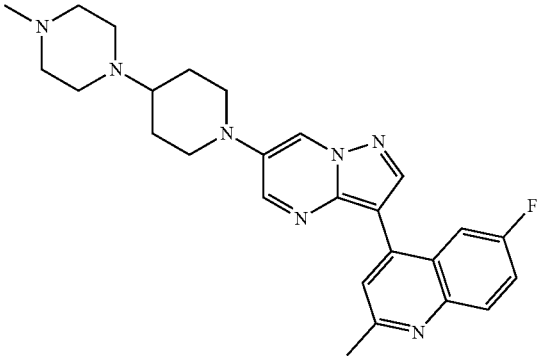 [SMILES: Cc1cc(-c2cnn3cc(N4CCC(N5CCN(C)CC5)CC4)cnc23)c2cc(F)ccc2n1] 275 | | Method 2: $t_R$ = 2.78 m | 460.3 |
| 280 | 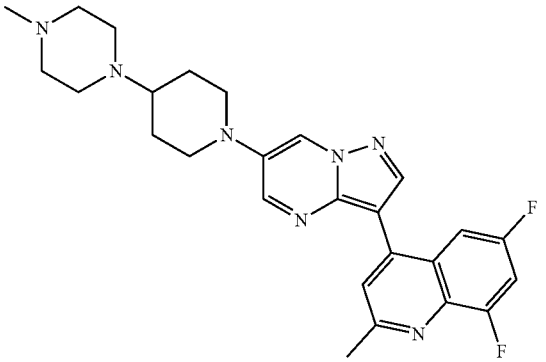 [SMILES: Cc1cc(-c2cnn3cc(N4CCC(N5CCN(C)CC5)CC4)cnc23)c2cc(F)cc(F)c2n1] 276 | | Method 2: $t_R$ = 3.05 m | 478.2 |
| 281 | 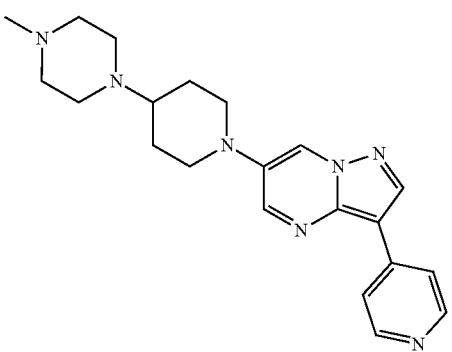 [SMILES: CN1CCN(C2CCN(c3cnc4c(-c5ccncc5)cnn4c3)CC2)CC1] 277 | ¹H NMR (400 MHz, CDCl₃) δ 8.55-8.50 (m, 3H), 8.30 (s, 1H), 8.06 (d, J = 2.7 Hz, 1H), 7.92-7.84 (m, 2H), 3.55 (d, J = 12.5 Hz, 2H), 2.70 (td, J = 11.9, 2.5 Hz, 2H), 2.65-2.51 (m, 4H), 2.51-2.37 (m, 4H), 2.34 (tt, J = 11.1, 3.5 Hz, 1H), 2.23 (s, 3H), 1.96 (d, J = 11.9 Hz, 2H), 1.71 (dt, J = 12.1, 5.9 Hz, 2H) | Method 2: $t_R$ = 2.68 m | 378.1 |
| 282 | 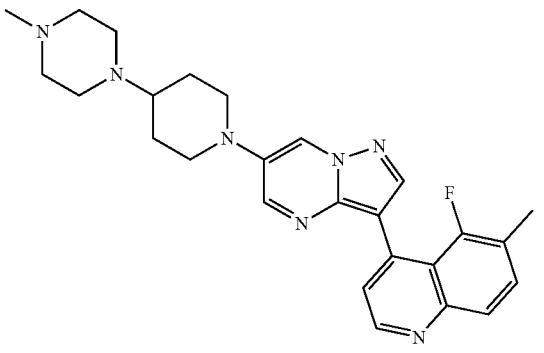 289 | ¹H NMR (400 MHz, D₂O) δ = 8.88 (d, J = 6.0 Hz, 1H), 8.67 (d, J = 2.4 Hz, 1H), 8.58 (d, J = 2.4 Hz, 1H), 8.45 (d, J = 5.6 Hz, 1H), 8.10 (d, J = 6.0 Hz, 1H), 8.02-7.96 (m, 1H), 7.94-7.89 (m, 1H), 3.87-3.31 (m, 1H), 3.91-3.24 (m, 10H), 2.99-2.86 (m, 5H), 2.41 (d, J = 2.8 Hz, 3H), 2.32 (d, J = 12.0 Hz, 2H), 1.97-1.82 (m, 2H) | Method 3: $t_R$ = 2.43 m | 460.1 |

Example 283

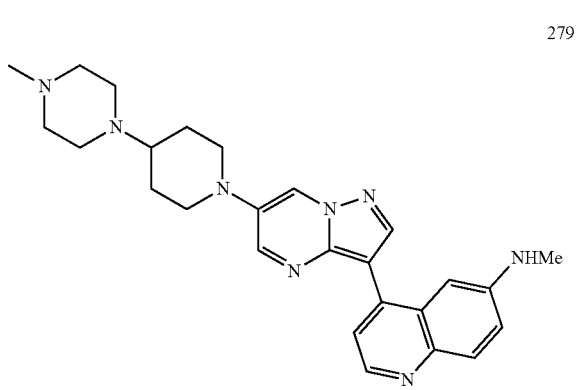 [SMILES: CNc1ccc2nccc(-c3cnn4cc(N5CCC(N6CCN(C)CC6)CC5)cnc34)c2c1]

Compound 279 was prepared through reduction of free amine by using NaBH₃CN/paraformaldehyde followed by preparative HPLC separation. LC/MS (method 2): $t_R$=2.78 min, m/z (M+H)⁺=457.3.

Example 284

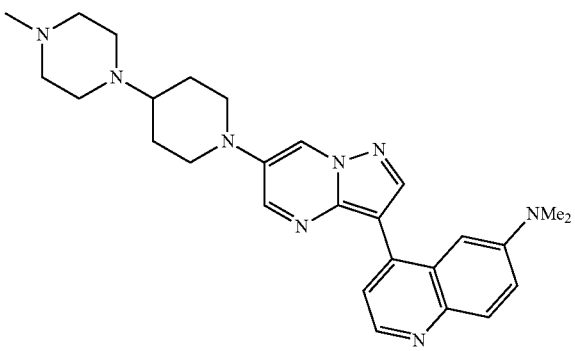

Compound 280 was prepared through reduction of free amine by using NaBH₃CN/paraformaldehyde followed by preparative HPLC separation. LC/MS (method 2): $t_R$=2.98 min, m/z (M+H)⁺=471.3.

Example 285

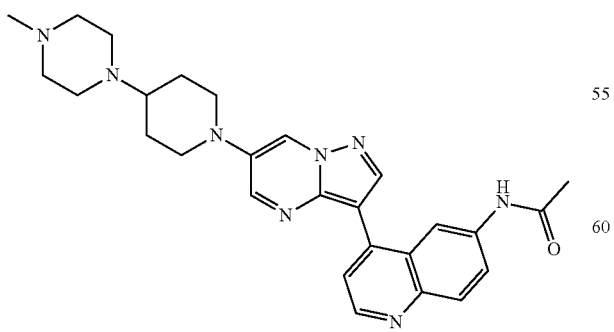

Compound 281 was prepared through acetylation of the corresponding free amine. LC/MS (method 2): $t_R$=2.64 min, m/z (M+H)⁺=485.3.

Example 286

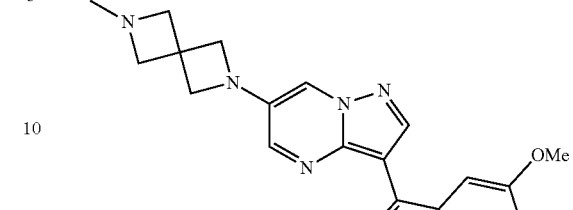
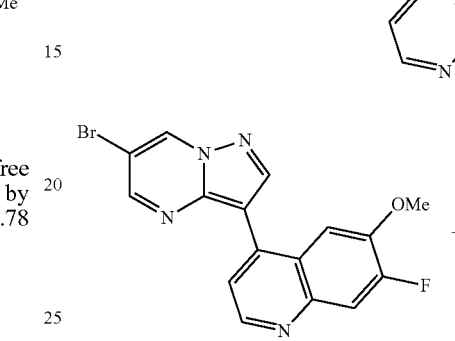
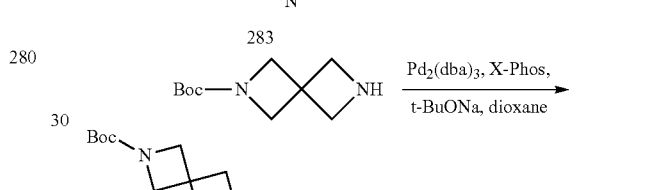
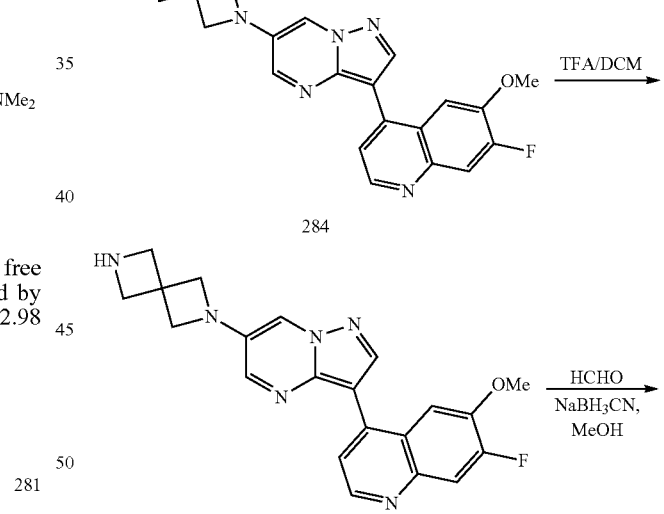

Compound 282 was synthesized according to the following procedures: 4-(6-Bromopyrazolo[1,5-a]pyrimidin-3-yl)-7-fluoro-6-methoxy-quinoline 283 was synthesized using the analogous procedures for the synthesis of 4-(6-bromopyrazolo[1,5-a]pyrimidin-3-yl)-quinoline in WO2009114180.

A mixture of tert-butyl 2,6-diazaspiro[3.3]heptane-2-carboxylate (370.8 mg, 1.29 mmol, 1.2 eq, oxalic acid salt) and tert-BuONa (515.1 mg, 5.36 mmol, 5 eq) in dioxane (15 mL) was degassed and purged with $N_2$ for 3 times, then stirred at 20° C. for 1 h under $N_2$ atmosphere. Compound 283 (400 mg, 1.07 mmol, 1 eq), $Pd_2(dba)_3$ (196.3 mg, 214.37 umol, 0.2 eq), and XPhos (204.4 mg, 428.8 umol, 0.4 eq) were added and the mixture was stirred at 110° C. for 1 h under $N_2$ atmosphere until there was no more starting material as indicated by LC/MS analysis. The reaction mixture was then concentrated under vacuum to give a residue, which was purified by prep-TLC ($SiO_2$, 20:1 DCM/MeOH) to provide compound 284 (285 mg, 511 umol, 48% yield, 88% purity) as a yellow solid.

To a solution of compound 284 (285 mg, 581 umol, 1 eq) in DCM (6 mL) was added TFA (3.1 g, 27 mmol, 2 mL, 47 eq). The mixture was stirred at 20° C. for 1 hr until LC/MS showed the starting material was consumed completely. The reaction mixture was basified with $NEt_3$ (0.8 mL) until the pH=8 and concentrated under vacuum to give the crude product of 285, which was used directly in next step.

A mixture of compound 285 (226.8 mg, 581.0 umol, 1.0 eq) in MeOH (10 mL) was added formaldehyde (86.51 uL, 1.16 mmol, 2.0 eq). The resulting mixture was acidified with acetic acid to pH ~5 and stirred at room temperature (20° C.) for 1 h, after which $NaBH_3CN$ (109.5 mg, 1.74 mmol, 3.0 eq) was added. The mixture was stirred at room temperature (20° C.) for 15 h until LC/MS analysis showed the starting material was consumed completely. The reaction mixture was quenched with sat. aq. $NaHCO_3$ (50 mL) and extracted with DCM (100 mL×3). The combined organic layer was washed with brine (50 mL×3), dried over anhydrous $Na_2SO_4$, filtered and concentrated in vacuo to give a residue, which was purified by column chromatography ($SiO_2$, 10:1 DCM/MeOH) to give 282 (85 mg, 206 umol, 36% yield, 98% purity) as a yellow solid. LC/MS (method 2): $t_R$=2.29 min, m z $(M+H)^+$=405.2; $^1H$ NMR (400 MHz, $CD_3OD$) δ 8.70 (d, J=4.4 Hz, 1H), 8.40 (s, 1H), 8.28 (d, J=2.8 Hz, 1H), 8.18 (d, J=2.4 Hz, 1H), 7.71-7.64 (m, 3H), 4.10 (s, 4H), 3.90 (s, 3H), 3.58 (s, 4H), 2.41 (s, 3H).

Example 287

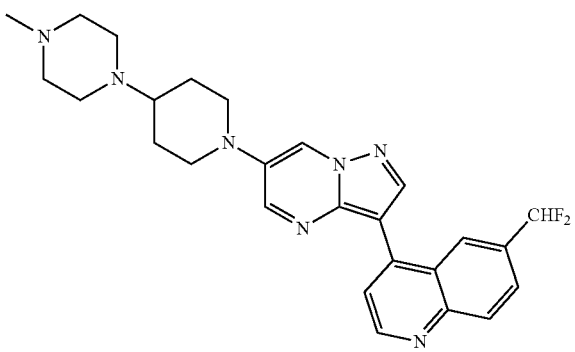

286

Compound 286 was prepared according to the following procedures:

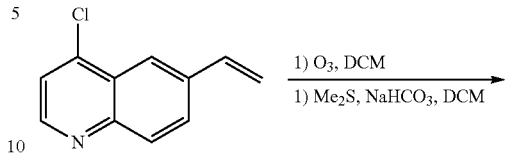

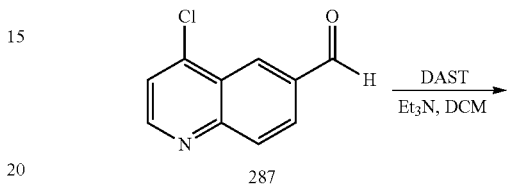

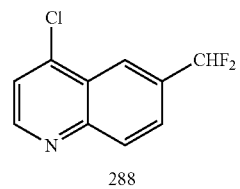

288

A suspension of 4-chloro-6-vinyl-quinoline (200 mg, 1.05 mmol, 1 eq) in DCM (20 mL) and MeOH (5 mL) was cooled to −78° C. The reaction was subjected to ozonolysis until a blue color persisted (~15 min), after which nitrogen was bubbled through the reaction mixture for 15 min to purge the ozone. The mixture was treated with $NaHCO_3$ (88.6 mg, 1.05 mmol, 1.0 eq) and $Me_2S$ (232 uL, 3.16 mmol, 3.0 eq). Then it was allowed to warm to 15° C. and stirred at this temperature for 3 h until LC/MS analysis indicted that the reaction was complete. The reaction mixture was concentrated under vacuum after which water (20 mL) was added to the residue and the aqueous layer was extracted with dichloromethane (3×20 mL). The combined organics were dried over magnesium sulfate, filtered and concentrated in vacuo to give a residue, which was purified by column chromatography on silica-gel (gradient of 50:1 to 30:1 petroleum ether/ethyl acetate) to give the desired product of 4-chloroquinoline-6-carbaldehyde 287 (100 mg, 522 umol, 50% yield) as a white solid.

To a stirred solution of 287 (50 mg, 261 umol, 1.0 eq) in DCM (5 mL) at 0° C. was added DAST (50.5 mg, 313 umol, 44 uL, 1.2 eq) under $N_2$ atmosphere. The reaction mixture was allowed to warm to 20° C. and stirred for 12 h until LC/MS analysis indicated that the reaction was complete. The reaction mixture was then quenched with water (20 mL) and extracted with DCM (25 mL×3). The combined organic phases were dried over anhydrous sodium sulfate, and concentrated under vacuum to give a residue which was purified by prep-TLC (3.5:1 petroleum ether/EtOAc) to give the desired product of 4-chloro-6-(difluoromethyl)quinoline 288 (20 mg, 94 umol, 36% yield) as a white solid.

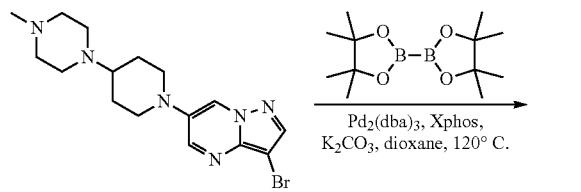

Compound J
from
Example 68

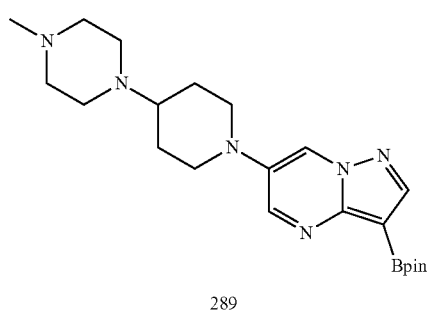

289

To a mixture of compound J from Example 68 (80 mg, 211 umol, 1.0 eq), 4,4,5,5-tetramethyl-2-(4,4,5,5-tetramethyl-1,3,2-dioxaborolan-2-yl)-1,3,2-dioxaborolane (214 mg, 844 umol, 4.0 eq) in dioxane (5 mL) was added XPhos (40.2 mg, 84.3 umol, 0.4 eq) and K$_2$CO$_3$ (72.9 mg, 527 umol, 2.5 eq). The mixture was degassed and purged with N$_2$ for 3 times, and then Pd(dba)$_2$ (24.3 mg, 42.2 umol, 0.2 eq) was added quickly. The mixture was stirred at 120° C. for 0.5 hour under N$_2$ atmosphere until there was no more starting material by LC/MS analysis. The desired product 289 (crude) in dioxane was obtained as a red solution. The mixture was used in the next step directly.

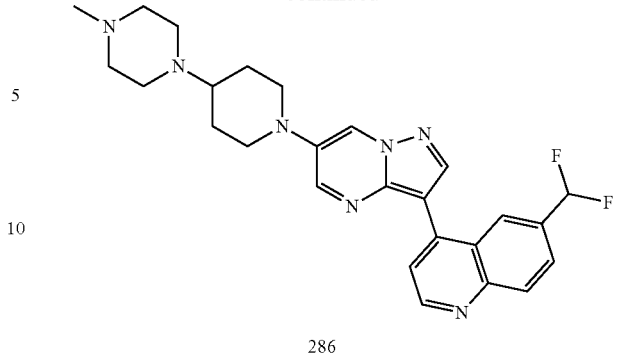

286

To a stirred mixture of 4-chloro-6-(difluoromethyl)quinoline 288 (40 mg, 187 umol, 1.0 eq) and compound 289 (119.8 mg, 280.9 umol, 1.5 eq) in 6 mL dioxane/H$_2$O (5:1 v/v) was added K$_2$CO$_3$ (64.7 mg, 468.1 umol, 2.5 eq). The mixture was degassed and purged with N$_2$ for 3 times and Pd(dppf)Cl$_2$ (27.4 mg, 37.5 umol, 0.2 eq) was added quickly. The resulting mixture was stirred at 120° C. for 4 hours under N$_2$ atmosphere until LC/MS analysis indicated the reaction was complete. The reaction mixture was then cooled to ambient temperature, quenched with water (20 mL) and extracted with DCM (25 mL×3). The combined organic phases were dried over anhydrous sodium sulfate and concentrated in vacuo to give a residue, which was purified by column chromatography on silica-gel (100% DCM) and further purified by prep-TLC (10:1 DCM/MeOH). The crude product obtained was dissolved in MeOH (2 mL) and a yellow solid precipitated. The solid was collected and dried in vacuo to give the product of compound 286 (12.1 mg, 24.1 umol, 13% yield, 95% purity) as a yellow solid. LC/MS (method 4): t$_R$=2.11 min, m z (M+H)$^+$=478.2. $^1$H NMR (400 MHz, CDCl$_3$) δ 9.03 (d, J=4.4 Hz, 1H), 8.58 (d, J=2.8 Hz, 1H), 8.32 (s, 2H), 8.28-8.21 (m, 2H), 7.86 (dd, J=1.6, 8.8 Hz, 1H), 7.74 (d, J=4.4 Hz, 1H), 6.94-6.60 (s, 1H), 3.65 (d, J=12.0 Hz, 2H), 2.86-2.75 (m, 2H), 2.75-2.60 (m, 4H), 2.58-2.38 (m, 5H), 2.31 (s, 3H), 2.05 (d, J=12.4 Hz, 2H), 1.79 (dd, J=2.8, 11.6 Hz, 2H).

Example 288

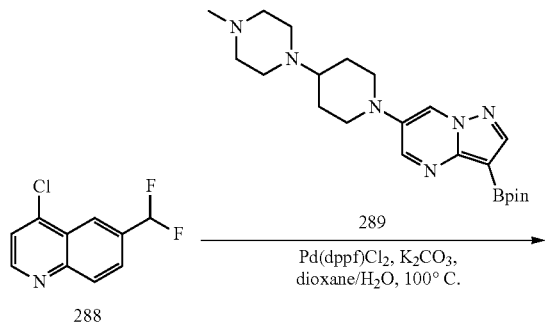

288

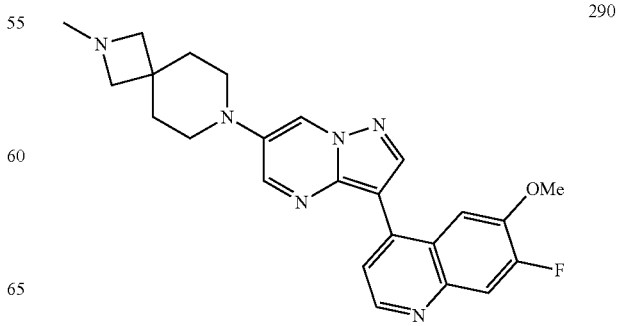

290

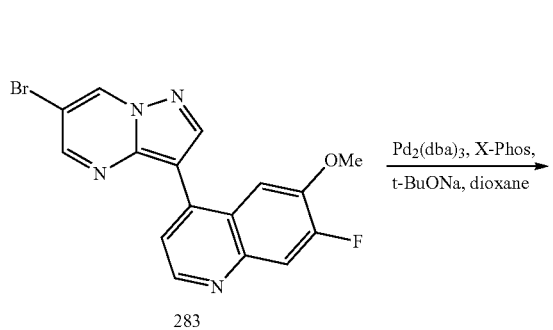

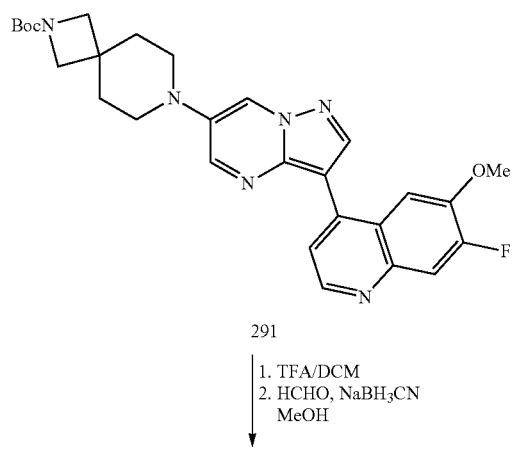

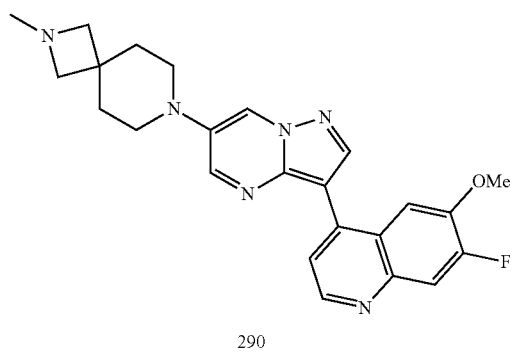

Compound 290/9558 was synthesized using the analogous procedures for compound 282 in Example 286. LC/MS (method 2): $t_R$=2.43 min, m z (M+H)$^+$=433.3. $^1$H NMR (400 MHz, CDCl$_3$) δ 8.83 (d, J=4.6 Hz, 1H), 8.55 (d, J=2.6 Hz, 1H), 8.32 (s, 1H), 8.21 (d, J=2.7 Hz, 1H), 7.80 (d, J=12.0 Hz, 1H), 7.61-7.50 (m, 2H), 3.90 (s, 3H), 3.35 (s, 4H), 3.10 (t, J=5.6 Hz, 4H), 2.53 (s, 3H), 2.06 (s, 4H).

The following compounds were synthesized using analogous Buchwald coupling conditions for compounds 282 and 290:

| Example | Compound | $^1$H NMR | LC/MS QC Method | m/z (M + H)$^+$ |
|---|---|---|---|---|
| 289 | 292 | | Method 2: $t_R$ = 2.92 min | 447.2 |

-continued

| Example | Compound | ¹H NMR | LC/MS QC Method | m/z (M + H)⁺ |
|---|---|---|---|---|
| 290 | 293 | | Method 2: $t_R$ = 3.27 min | 405.2 |
| 291 | 294 | ¹H NMR (400 MHz, CDCl₃) δ 8.83 (d, J = 4.4 Hz, 1H), 8.31 (s, 1H), 8.20 (d, J = 2.4 Hz, 1H), 7.96 (d, J = 2.4 Hz, 1H), 7.81 (d, J = 12.0 Hz, 1H), 7.59 (d, J = 4.8 Hz, 1H), 7.54 (d, J = 9.0 Hz, 1H), 4.19 (t, J = 6.8 Hz, 2H), 3.90 (s, 3H), 3.81 (t, J = 6.4 Hz, 2H), 3.70 (q, J = 6.0 Hz, 1H), 3.17-3.09 (m, 4H), 3.02-2.94 (m, 4H) | Method 2: $t_R$ = 3.67 min | 483.0 |
| 292 | 295 | | Method 2: $t_R$ = 3.06 min | 393.1 |
| 293 | 296 | ¹H NMR (400 MHz, CDCl₃) δ 8.54 (d, J = 2.4 Hz, 1H), 8.30 (s, 1H), 8.20 (d, J = 2.4 Hz, 1H), 8.09 (d, J = 8.8 Hz, 2H), 7.70 (m, 1H), 7.57 (s, 1H), 7.47 (m, 1H), 3.35-3.20 (m, 2H), 3.11-3.08 (m, 4H), 2.80 (s, 3H), 2.70-2.40 (m, 2H), 2.49 (s, 3H), 2.04-2.02 (m, 4H) | Method 3: $t_R$ = 2.35 min | 399.0 |

| Example | Compound | ¹H NMR | LC/MS QC Method | m/z (M + H)⁺ |
|---|---|---|---|---|
| 294 | 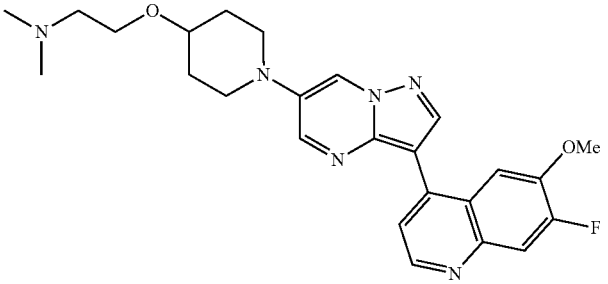 [SMILES: COc1cc2c(-c3cnn4cc(N5CCC(OCCN(C)C)CC5)cnc34)ccnc2cc1F]<br>297 | | Method 2: $t_R$ = 3.16 min | 465.2 |
| 295 | 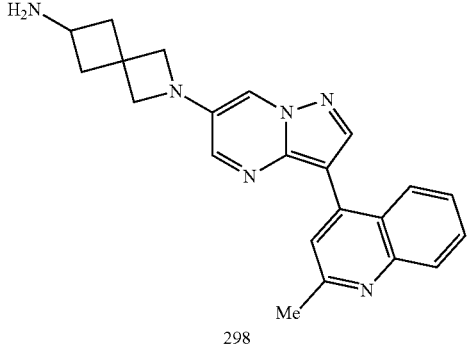<br>298 | | Method 2: $t_R$ = 2.95 min | 371.2 |
| 296 | 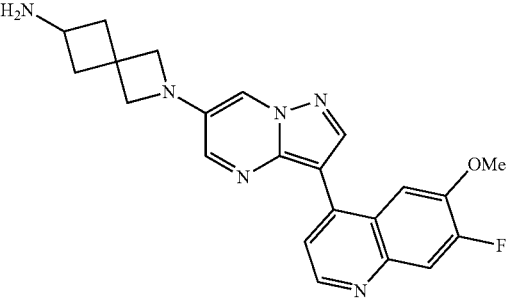 [SMILES: COc1cc2c(-c3cnn4cc(N5CC6(CC(N)C6)C5)cnc34)ccnc2cc1F]<br>299 | | Method 2: $t_R$ = 3.07 min | 405.2 |
| 297 | 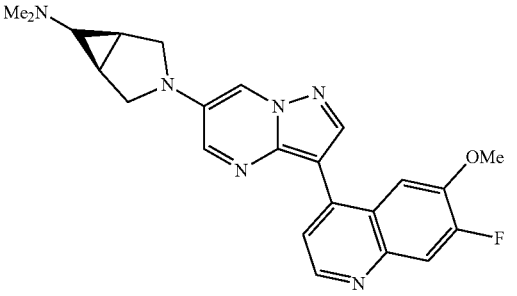<br>300 | | Method 2: $t_R$ = 3.08 min | 419.2 |

| Example | Compound | ¹H NMR | LC/MS QC Method | m/z (M + H)⁺ |
|---|---|---|---|---|
| 298 | 301 | ¹H NMR (400 MHz, CD₃OD) δ 8.35 (s, 1H), 8.27 (d, J = 2.4 Hz, 1H), 8.19 (d, J = 2.4 Hz, 1H), 8.15 (d, J = 8.8 Hz, 1H), 8.01 (d, J = 8.4 Hz, 1H), 7.74 (t, J = 7.6 Hz, 1H), 7.69 (s, 1H), 7.53 (t, J = 7.2 Hz, 1H), 4.10 (s, 4H), 3.57 (s, 4H), 2.75 (s, 3H), 2.40 (s, 3H) | Method 2: t_R = 3.04 min | 371.1 |
| 299 | 302 | ¹H NMR (400 MHz, CDCl₃) δ 8.75 (d, J = 4.6 Hz, 1H), 8.22 (s, 1H), 8.11 (d, J = 2.6 Hz, 1H), 7.86 (d, J = 2.6 Hz, 1H), 7.72 (d, J = 12.0 Hz, 1H), 7.55-7.44 (m, 2H), 7.19 (s, 1H), 4.48 (q, J = 5.6 Hz, 1H), 4.19 (t, J = 6.9 Hz, 2H), 3.89-3.75 (m, 5H), 3.51 (t, J = 5.5 Hz, 2H), 2.50 (t, J = 5.5 Hz, 2H), 2.24 (s, 6H) | Method 2: t_R = 3.28 min | 437.1 |
| 300 | 303 | | Method 3: t_R = 2.33 min | 419.1 |
| 301 | 304 | ¹H NMR (400 MHz, CDCl₃) δ 8.81 (d, J = 4.6 Hz, 1H), 8.20 (s, 1H), 8.11 (d, J = 2.7 Hz, 1H), 7.93-7.82 (m, 2H), 7.66 (d, J = 10.8 Hz, 1H), 7.53 (d, J = 4.6 Hz, 1H), 4.05 (t, J = 6.8 Hz, 2H), 3.77 (t, J = 5.5 Hz, 2H), 3.73-3.63 (m, 2H), 3.37 (quint., J = 6.2 Hz, 1H), 2.43-2.34 (m, 9H) | Method 3: t_R = 2.51 min | 419.2 |

Example 302

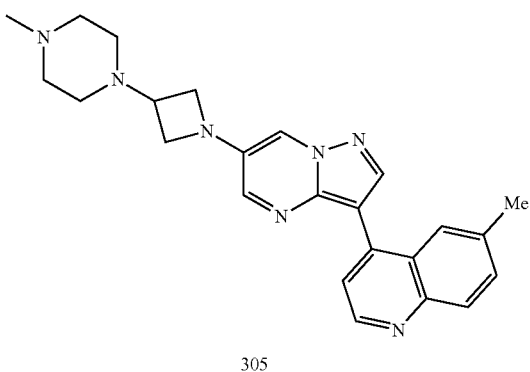

305

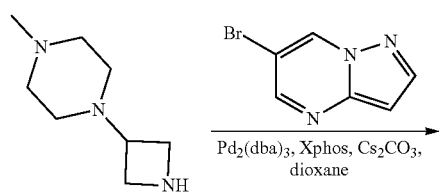

306

Compound 305/7905 was prepared in 3 steps according the following procedures: To a solution of 1-(3-azetidinyl)-4-methyl-piperizine (3.00 g, 19.3 mmol) and 6-bromopyrazolo[1,5-a]pyrimidine (4.59 g, 23.2 mmol) in dioxane (30.0 mL) was added XPhos (1.84 g, 3.86 mmol) and $Cs_2CO_3$ (12.6 g, 38.7 mmol) at 25° C. The mixture was degassed and purged with $N_2$ (3×) after which $Pd_2(dba)_3$ (1.77 g, 1.93 mmol) was added and the mixture was degassed and repurged with $N_2$. The mixture was stirred at 100° C. for 36 hrs until there was no more starting material detected by LC/MS. The reaction mixture was then diluted with MeOH (30.0 mL) and filtered after which the filter cake was washed with MeOH (50.0 mL). The combined the organic layers were concentrated under reduced pressure to give a residue which was redissolved with water (30.0 mL) and EtOAc (30.0 mL). The aqueous phase was extracted with EtOAc (30.0 mL) and the combined organic layers were washed with water (30.0 mL×2). All aqueous layers were combined and extracted with $CH_2Cl_2$/MeOH (5/1, 50.0 mL×3). The combined organic phases was washed with brine (30.0 mL), dried over $Na_2SO_4$, filtered and concentrated under reduced pressure to give a residue. The residue was purified by column chromatography ($SiO_2$, Dichloromethane/Methanol, gradient of 100/1 to 1/1) to afford compound 306 (1.50 g, 5.51 mmol, 28.5% yield) as a yellow solid.

Compound 306 was then converted to compound 305/7905 using general procedures 2 and 3A. LC/MS (method 2): $t_R$=2.98 min, m/z $(M+H)^+$=456.3.

The following compounds were prepared in analogous fashion to compound 305/7095 in Example 302:

| Example | Compound | $^1$H NMR (400 MHz) | LC/MS QC Method | m/z (M + H)$^+$ |
|---|---|---|---|---|
| 333 | 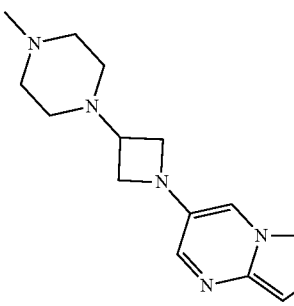<br>307 | | Method 2: $t_R$ = 3.11 min | 442.3 |

| Example | Compound | ¹H NMR (400 MHz) | LC/MS QC Method | m/z (M + H)⁺ |
|---|---|---|---|---|
| 334 | 308 | ¹H NMR (400 MHz, CDCl₃): δ 8.86 (d, J = 4.4 Hz, 1H), 8.26 (s, 1H), 8.17 (d, J = 2.8 Hz, 1H), 7.96 (d, J = 8.4 Hz, 1H), 7.92 (d, J = 2.4 Hz, 1H), 7.73 (d, J = 10.8 Hz, 1H), 7.59 (d, J = 4.4 Hz, 1H), 4.19-4.08 (m, 2H), 3.86-3.78 (m, 2H), 3.51-3.39 (m, 1H), 2.61-2.29 (m, 14H) | Method 2: t$_R$ = 3.31 m | 432.1 |
| 335 | 309 | ¹H NMR (400 MHz, CD₃OD) δ 8.23 (s, 1H), 8.17 (d, J = 2.6 Hz, 1H), 7.93 (d, J = 2.6 Hz, 1H), 7.30 (s, 1H), 7.12 (s, 2H), 4.01 (t, J = 7.1 Hz, 2H), 3.75-3.75 (m, 5H), 3.40-3.27 (m, 1H), 2.67-2.27 (m, 8H). | Method 2: t$_R$ = 3.88 min | 4.39 |
| 336 | 310 | | Method 2: t$_R$ = 2.96 min | 432.2 |
| 337 | 311 | | Method 2: t$_R$ = 3.17 min | 450.2 |

-continued

| Example | Compound | ¹H NMR (400 MHz) | LC/MS QC Method | m/z (M + H)⁺ |
|---|---|---|---|---|
| 338 | (structure 312) | | Method 2: $t_R$ = 2.98 min | 456.3 |
| 339 | (structure 313) | ¹H NMR (400 MHz, CDCl₃) δ 8.52 (d, J = 5.2 Hz, 2H), 8.28 (s, 1H), 8.14 (d, J = 2.7 Hz, 1H), 7.87 (d, J = 5.3 Hz, 2H), 7.77 (d, J = 2.7 Hz, 1H), 4.03 (t, J = 6.8 Hz, 2H), 3.74 (t, J = 6.3 Hz, 2H), 3.37 (quint., J = 6.1 Hz, 1H), 2.58-2.31 (m, 8H), 2.25 (s, 3H). | Method 2: $t_R$ = 2.79 min | 350.1 |
| 340 | (structure 314) | ¹H NMR (400 MHz, CD₃OD) δ 8.70 (d, J = 4.6 Hz, 1H), 8.39 (s, 1H), 8.29 (d, J = 2.6 Hz, 1H), 8.18 (d, J = 2.6 Hz, 1H), 7.78 (d, J = 4.6 Hz, 1H), 7.36 (d, J = 2.6 Hz, 1H), 7.23 (dd, J = 11.9, 2.6 Hz, 1H), 4.16 (t, J = 7.2 Hz, 1H), 3.89-3.82 (m, 5H), 3.49 (quint., J = 6.2 Hz, 1H), 2.90-2.51 (m, 8H), 2.48 (s, 3H) | Method 2: $t_R$ = 3.39 min | 448.1 |
| 341 | (structure 315) | | Method 2: $t_R$ = 3.14 min | 450.2 |

-continued

| Example | Compound | ¹H NMR (400 MHz) | LC/MS QC Method | m/z (M + H)⁺ |
|---|---|---|---|---|
| 342 | 316 | | Method 2: $t_R$ = 2.98 min | 432.2 |
| 343 | 317 | ¹H NMR (400 MHz, CDCl₃) δ 8.16 (s, 1H), 8.11 (d, J = 2.6 Hz, 1H), 7.84 (d, J = 2.6 Hz, 1H), 7.32 (d, J = 8.7 Hz, 1H), 7.13 (d, J = 8.7 Hz, 1H), 6.85 (s, 1H), 4.06 (t, J = 6.8 Hz, 2H), 3.78-3.68 (m, 5H), 3.45-3.36 (m, 1H), 2.69-2.36 (m, 8H), 2.32 (s, 3H) | Method 2: $t_R$ = 2.89 min | 464.1 |
| 344 | 318 | | Method 2: $t_R$ = 2.78 min | 444.2 |
| 345 | 319 | | Method 2: $t_R$ = 2.20 min | 444.2 |

Example 346

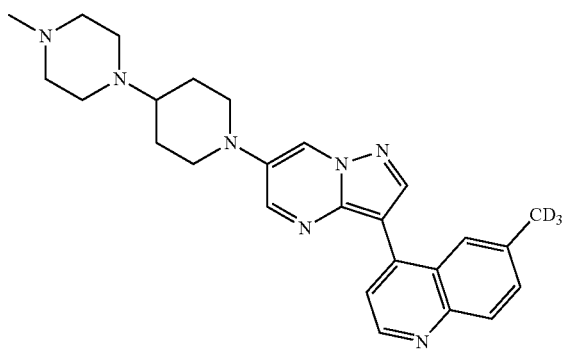

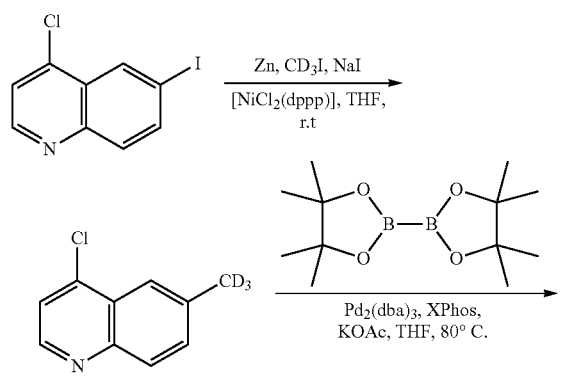

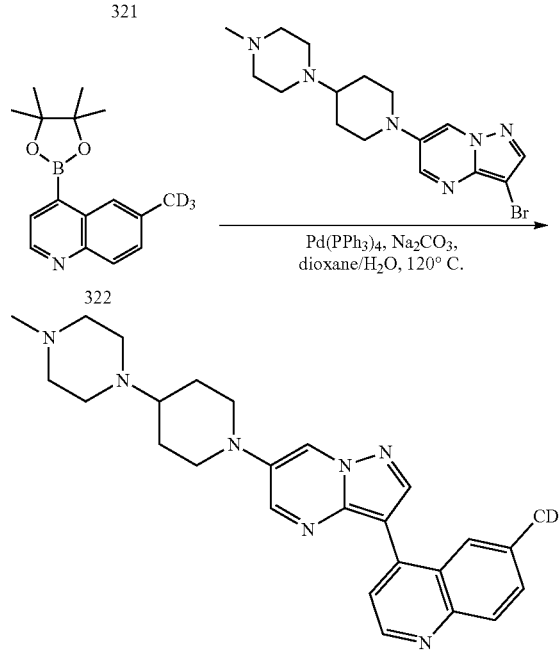

Compound 320 was prepared in 3 steps according the following procedures: To a stirred mixture of Zn (677.6 mg, 10.4 mmol, 6.0 eq) (treated with aq. 1 M HCl, dried under high vacuum with toluene), NiCl$_2$(dppp)(187.2 mg, 345.4 umol, 0.2 eq) and NaI (776.7 mg, 5.18 mmol, 3.0 eq) was degassed and purged with nitrogen for three times, was added a solution of 4-chloro-6-iodo-quinoline (500 mg, 1.73 mmol, 1.0 eq) in anhydrous THF (10 mL). The resulting mixture was degassed and purged with nitrogen three times, after which CD$_3$I (1.07 mL, 17.3 mmol, 10 eq) was added via syringe under nitrogen atmosphere. The resulting mixture was then stirred at 20° C. for 4 h under N$_2$ atmosphere. The brown suspension turned green. LC/MS analysis of the crude reaction mixture showed 13% of the desired product and 32% of de-I by-product. The reaction mixture was concentrated under vacuum to provide the residue, which was triturated with DCM/MeOH (10:1, 30 mL), and filtered through a pad of celite. The filtrate was concentrated to provide a residue which was then purified by flash silica gel chromatography eluted with (gradient of 20:1 to 4:1 petroleum ether/ethyl acetate) twice to give the desired product 321 (38 mg, 7.6% yield, 82% purity) as a yellow oil (solidified after standing at room temperature).

Compound 321 was then converted to its corresponding boronate using the analogous procedure in Example 286 to provide compound 322. Compound 320 was then prepared in an analogous manner as compound 233. LC/MS (method 3): t$_R$=2.27 min, m z (M+H)$^+$=445.1. $^1$H NMR (400 MHz, D$_2$O) δ 8.80 (d, J=6.0 Hz, 1H), 8.66 (d, J=2.8 Hz, 1H), 8.50 (s, 1H), 8.47 (d, J=2.4 Hz, 1H), 8.08 (d, J=6.0 Hz, 1H), 8.06-8.04 (m, 1H), 7.99 (s, 1H), 7.95-7.89 (m, 1H), 3.87 (m, 11H), 3.07-3.02 (s, 3H), 3.01-2.93 (m, 2H), 2.44-2.35 (m, 2H), 2.05-1.92 (m, 2H).

Example 347

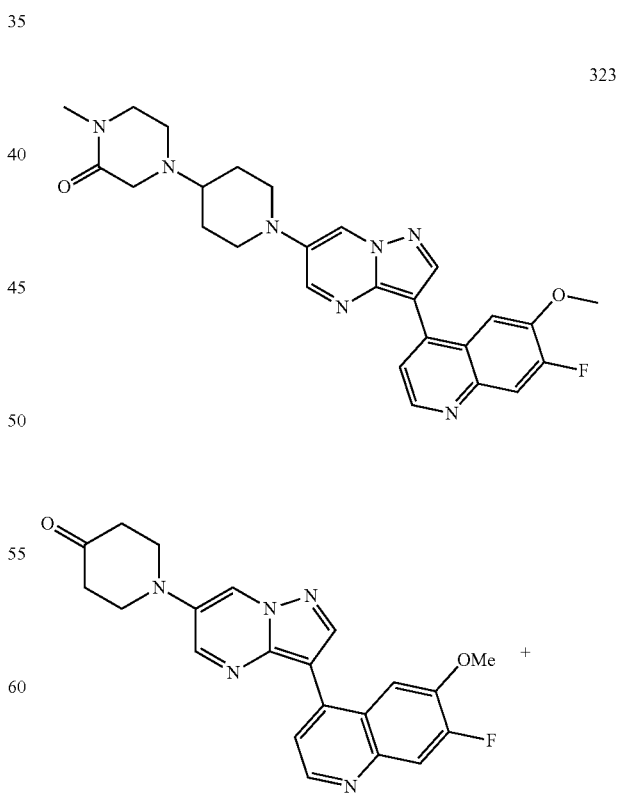

Compound D
from Example 47

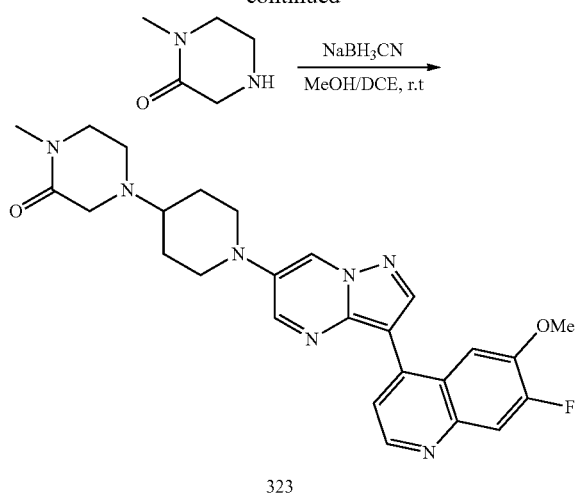

A solution of 1-methylpiperazin-2-one (40.8 mg, 357 umol, 1.4 eq) and Compound D from Example 47 (0.10 g, 255.5 umol, 1.0 eq) in MeOH (10 mL) and DCE (10 mL) was adjusted to pH ~5 with AcOH and stirred for 1 hour. NaBH$_3$CN (64.2 mg, 1.0 mmol, 4.0 eq) was added after which the mixture was stirred at 25° C. for 15 hours until there was no more starting material by LC/MS analysis. The mixture was quenched with sat.NaHCO$_3$ to pH=8 and then extracted with DCM (100 mL×3). The organic phases were combined and washed with brine (50 mL), dried over anhydrous Na$_2$SO$_4$, filtered and concentrated under vacuum to give the crude product which was purified by prep-TLC (15:1 DCM/MeOH) 3 times to give the desired product 323 (20 mg, 15% yield, 95% purity) as a yellow solid. LC/MS (method 2): t$_R$=3.16 min, m z (M+H)$^+$=490.1. $^1$H NMR (400 MHz, CD$_3$OD) δ 8.74-8.70 (m, 2H), 8.49-8.43 (m, 2H), 7.75-7.65 (m, 3H), 3.91 (s, 3H), 3.79-3.71 (m, 2H), 3.42 (t, J=5.2 Hz, 2H), 3.35 (s, 2H), 3.00-2.92 (m, 5H), 2.83 (t, J=11.2 Hz, 2H), 2.64-2.53 (m, 1H), 2.13-2.05 (m, 2H), 1.82-1.68 (m, 2H).

Example 348

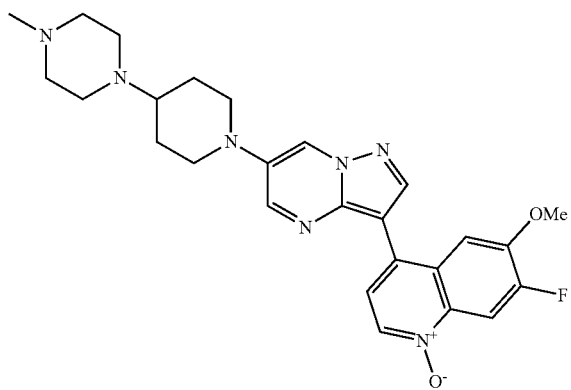

324

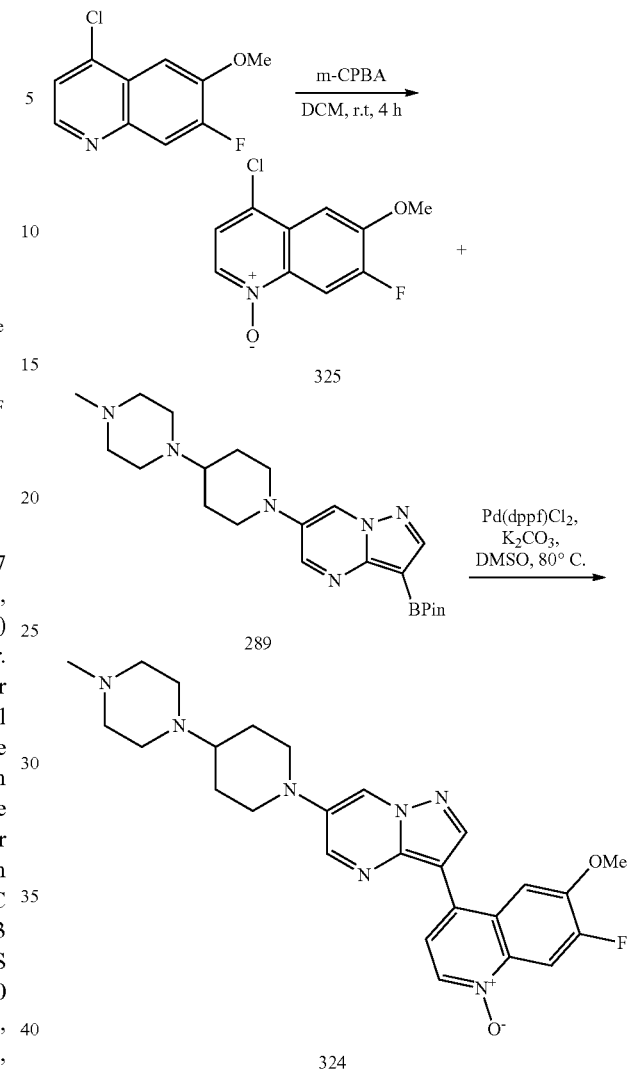

Compound 324 was synthesized in 2 steps according to the following procedures: To a solution of 4-chloro-7-fluoro-6-methoxy-quinoline (1.0 g, 4.7 mmol, 1.0 eq) in DCM (10 mL) was added m-CPBA (1.44 g, 7.09 mmol, 85% purity, 1.5 eq). The mixture was stirred at 30° C. for 4 hr during which a while solid precipitated. TLC analysis (PE/EtOAc=3/1) showed the starting material was consumed completely. The suspension was filtered and washed with DCM (20 mL). The filtrate was then stirred with aq. 10% of Na$_2$SO$_3$ (20 mL) for 30 min. The organic layer was separated, and then washed with sat. aq. NaHCO$_3$ (20 mL×2) and brine (10 mL×2), dried over Na$_2$SO$_4$, filtered and concentrated in vacuo to give the desired compound 325 (1.1 g, 4.5 mmol, 96% yield, 94% purity) as an orange solid.

To a mixture of crude compound 289 (337.2 mg, 790.8 umol, 0.90 eq) in DMSO (6 mL) was added compound 325 (200 mg, 878 umol, 1.0 eq) and K$_2$CO$_3$ (182.2 mg, 1.32 mmol, 1.5 eq). The reaction mixture was de-gassed and purged with N$_2$. Pd(dppf)Cl$_2$ (128.6 mg, 176 umol, 0.20 eq) was added quickly, and the resulting mixture was de-gassed and purged with N$_2$ three times, then heated at 80° C. for 20 min under N$_2$ atmosphere. A brown suspension was observed. LC/MS analysis showed 23% of the desired product, 19% de-O product and 20% of the chloride. The mixture was diluted with water (15 mL), and extracted with DCM (10 mL×3). The combined organic layer was dried over Na$_2$SO$_4$, filtered and concentrated under vacuum to provide crude residue, which was purified by prep-TLC (10:1 DCM/MeOH with 0.5% NH$_4$OH) to give the desired product 324 (79.5 mg, 153 umol, 17% yield, 95% purity) as a yellow solid. LC/MS (method 2): t$_R$=3.26 min, m z (M+H)$^+$=492.2. 1H NMR (400 MHz, CDCl3): δ 8.62-8.45 (m, 3H), 8.29 (s, 1H), 8.24-8.17 (m, 1H), 7.58 (d, J=8.4 Hz, 1H), 7.53 (d, J=6.4 Hz, 1H), 3.91 (s, 3H), 3.65 (m, 2H), 2.87-2.76 (m, 2H), 2.74-2.61 (m, 4H), 2.59-2.39 (m, 5H), 2.32 (s, 3H), 2.10-1.99 (m, 2H), 1.81-1.73 (m, 2H).

Example 349 in 1,4-dioxane (2 ml) was added tert-butyl 3-oxopiperazine-1-carboxylate (64 mg, 0.32 mmol), CuI (10 mg, 0.054 mmol), and N,N'-dimethylcyclohexyldiamine (17 ul, 0.11 mmol). The mixture was purged with N$_2$ and subjected to microwave irradiation at 105° C. for 2 hr. The mixture was partitioned between EtOAc and saturated aqueous NH$_4$Cl solution. The organic layer was separated and washed with brine, dried over Na$_2$SO$_4$. After the removal of organic solvent under vacuum, the crude residue was purified through Biotage chromatography (gradient of 1:100 to 1:10 MeOH/DCM) to give the desired intermediate which was further treated with TFA/DCM to deprotect the Boc group under standard conditions to provide compound 326. LC/MS (method 2): t$_R$=2.58 min, m z (M+H)$^+$=393.1.

Example 350

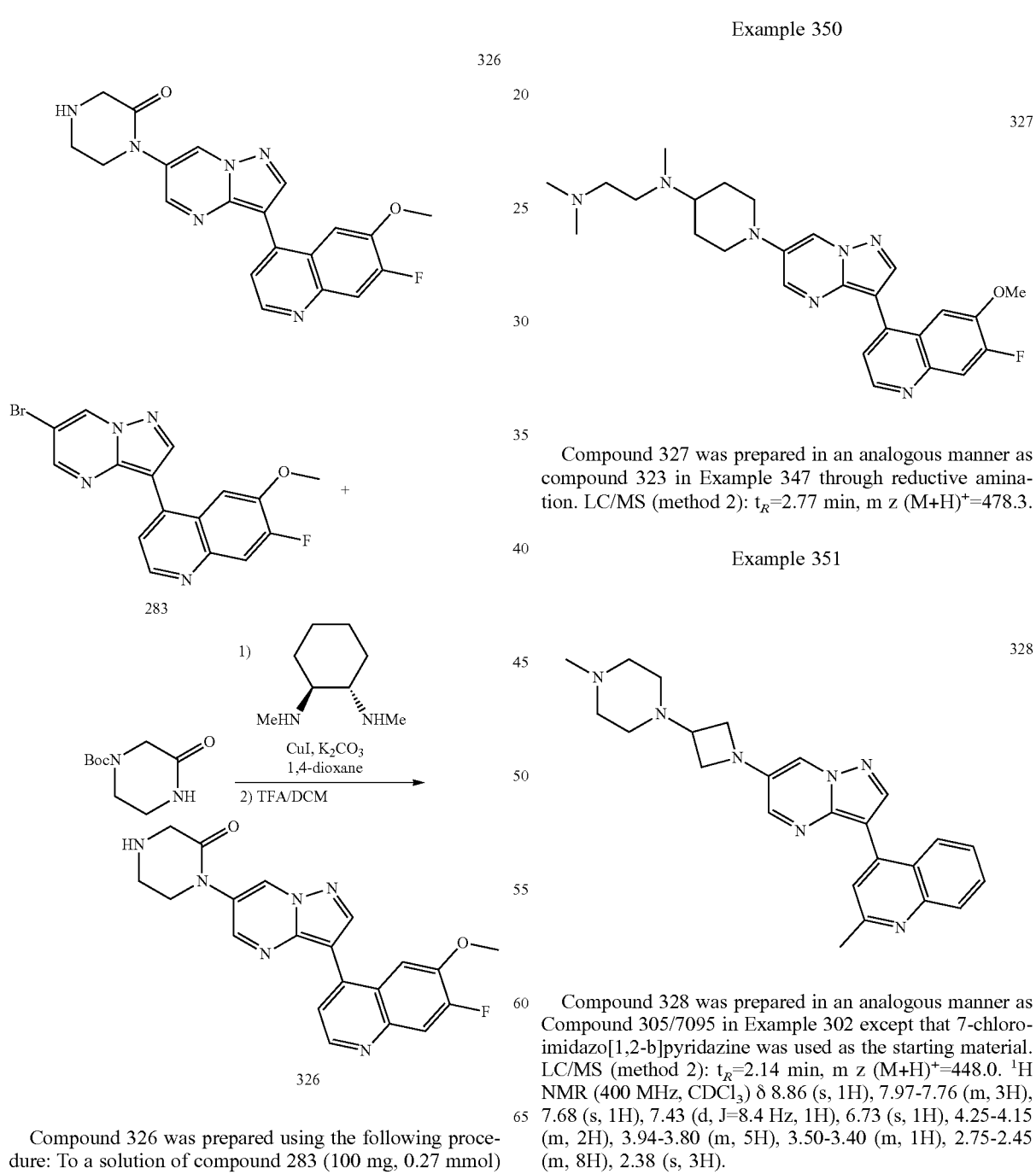

Compound 327 was prepared in an analogous manner as compound 323 in Example 347 through reductive amination. LC/MS (method 2): t$_R$=2.77 min, m z (M+H)$^+$=478.3.

Example 351

Compound 326 was prepared using the following procedure: To a solution of compound 283 (100 mg, 0.27 mmol)

Compound 328 was prepared in an analogous manner as Compound 305/7095 in Example 302 except that 7-chloro-imidazo[1,2-b]pyridazine was used as the starting material. LC/MS (method 2): t$_R$=2.14 min, m z (M+H)$^+$=448.0. $^1$H NMR (400 MHz, CDCl$_3$) δ 8.86 (s, 1H), 7.97-7.76 (m, 3H), 7.68 (s, 1H), 7.43 (d, J=8.4 Hz, 1H), 6.73 (s, 1H), 4.25-4.15 (m, 2H), 3.94-3.80 (m, 5H), 3.50-3.40 (m, 1H), 2.75-2.45 (m, 8H), 2.38 (s, 3H).

Example 352

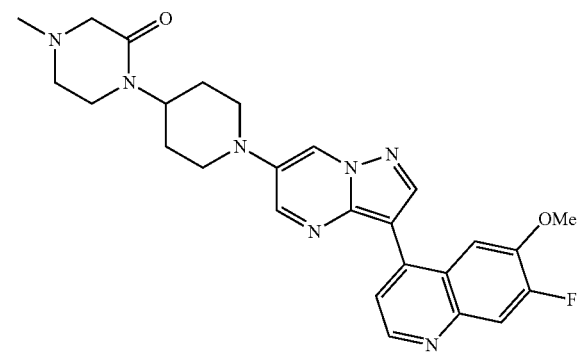

329

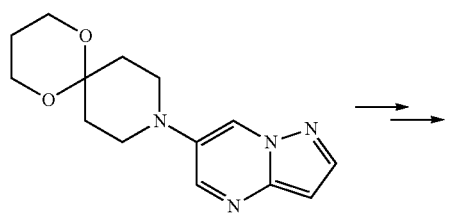

Compound A
from Example 47

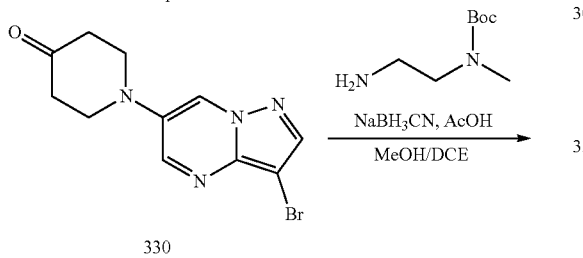

330

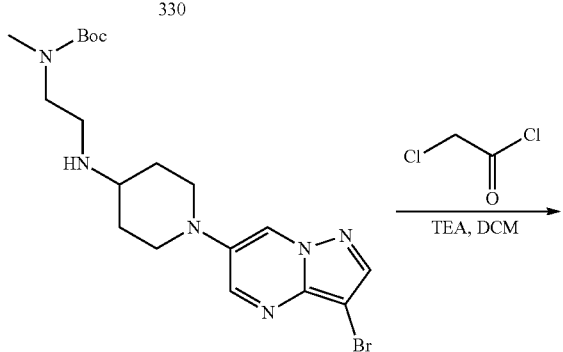

331

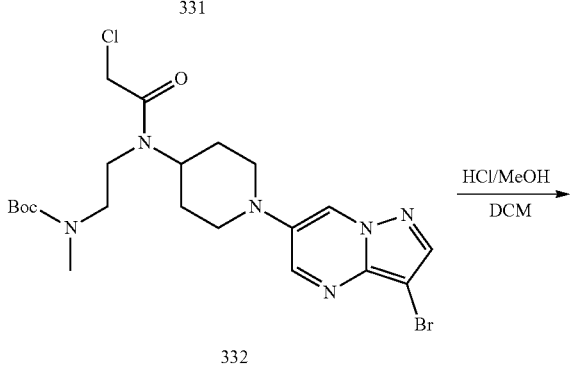

332

-continued

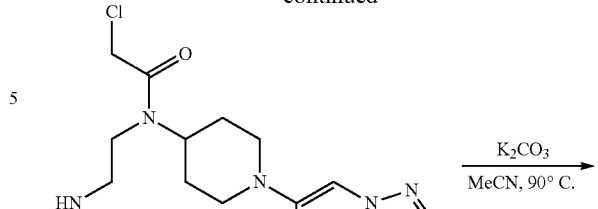

333

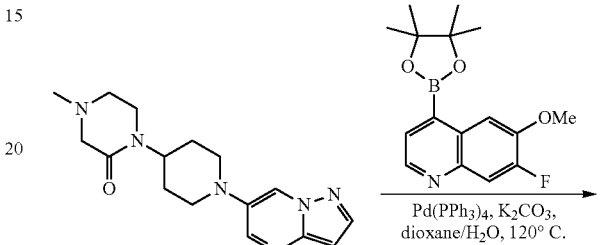

334

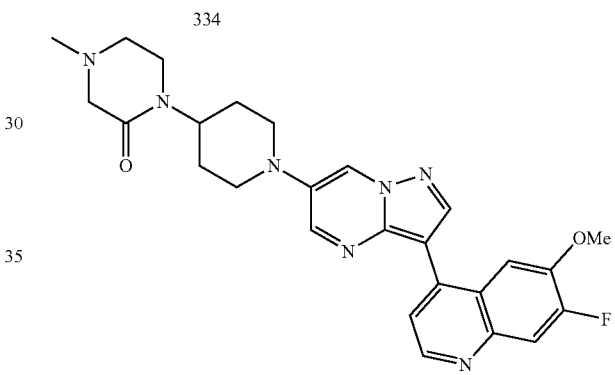

329

Compound 329 was synthesized according the following procedures: Compound A (from Example 47) was halogenated and deprotected according to the related procedures in Example 47 except that NIS is used in place of NBS to provide ketone 330. A suspension of compound 330 (300 mg, 1.02 mmol, 1 eq) and tert-butyl N-(2-aminoethyl)-N-methyl-carbamate (218 uL, 1.22 mmol, 1.2 eq) in MeOH (10 mL) and DCE (2 mL) was adjusted to pH ~5 with AcOH after which the suspension turned clear. The reaction mixture was stirred at room temperature (25° C.) for 1 h, followed by the addition of NaBH₃CN (191.6 mg, 3.05 mmol, 3.00 eq). The reaction mixture was stirred at room temperature (25° C.) for 1.5 h. A yellow solution was observed. TLC analysis (20:1 DCM/MeOH) showed the starting material was consumed completely. The mixture was quenched with sat. aq. NaHCO₃ (20 mL), then extracted with DCM (20 mL×3). The combined organic layer was dried over Na₂SO₄, filtered and concentrated under vacuum to give the crude product 331 (530 mg) as a pale yellow solid, which was used in next step directly.

A mixture of compound 331 (410 mg, 904 umol, 1.0 eq) and TEA (377 uL, 2.71 mmol, 3.0 eq) in anhydrous DCM (8 mL) was cooled to 0° C. after which 2-chloroacetyl chloride (144 uL, 1.81 mmol, 144 uL, 2.0 eq) was added. The reaction mixture was stirred at 25° C. for 1 hr. A yellow solution was observed. TLC analysis (20:1 DCM/MeOH) showed the starting material was consumed completely. The reaction was then quenched with sat. aq. NaHCO₃ (5 mL).

The phases were separated, and the organic layer was washed with water (5 mL×2), dried over Na$_2$SO$_4$, filtered and concentrated under vacuum to provide the crude product 332 (totally 700 mg) as a brown gum.

To a solution of compound 332 (650 mg, 852 umol, 1.0 eq) in DCM (5 mL) was added HCl in MeOH (4 M, 5 mL, 23 eq). The reaction mixture was stirred at 25° C. for 2 h. Yellow solid precipitated. The suspension was diluted with EtOAc (30 mL), and more solid precipitated. The suspension was filtered and washed with EtOAc (10 mL) to give the desired product 333 (67% yield, 100% purity, isolated as the bis HCl salt) as a yellow solid.

A suspension of compound 333 (258 mg, 513.3 umol, 1.0 eq, bis HCl salt) and K$_2$CO$_3$ (354.7 mg, 2.57 mmol, 5.0 eq) in MeCN (26 mL) was stirred at 90° C. for 1 hr. A yellow suspension was observed. LC/MS showed the reaction was complete after which it was concentrated under vacuum. The residue was triturated DCM (20 mL) for 0.5 h, and then filtered. The isolated solid was washed with DCM (10 mL). The filtrate was concentrated under vacuum to give the crude product 334 as an off-white solid, which was used in next step directly.

To a de-gassed mixture of compound 334 (80 mg, 203 umol, 1.0 eq), 7-fluoro-6-methoxy-4-(4,4,5,5-tetramethyl-1,3,2-dioxaborolan-2-yl)quinoline (74.0 mg, 244.1 umol, 1.2 eq) and K$_2$CO$_3$ (84.4 mg, 610.3 umol, 3.00 eq) in dioxane (4 mL) and H$_2$O (1 mL) was added Pd(PPh$_3$)$_4$ (47.0 mg, 40.7 umol, 0.2 eq) quickly. The reaction mixture was de-gassed and purged with N$_2$ three times, and then stirred at 120° C. for 2 hr under N$_2$ atmosphere. LC/MS analysis shows complete consumption of the bromide. The mixture was then concentrated in vacuo to give the residue, which was purified by prep-TLC (15:1 DCM/MeOH) to give the desired product 329 (68 mg, 125 umol, 61% yield, 90% purity) as a yellow solid. LC/MS (method 2): $t_R$=3.29 min, m z (M+H)$^+$=490.1. $^1$H NMR (400 MHz, CDCl$_3$) δ=8.83 (d, J=4.8 Hz, 1H), 8.56 (d, J=2.4 Hz, 1H), 8.33 (s, 1H), 8.25 (d, J=2.4 Hz, 1H), 7.80 (d, J=12.0 Hz, 1H), 7.59 (d, J=4.4 Hz, 1H), 7.53 (d, J=8.8 Hz, 1H), 4.75-4.61 (m, 1H), 3.90 (s, 3H), 3.70-3.60 (m, 2H), 3.40-3.30 (m, 2H), 3.19-3.13 (m, 2H), 2.98-2.85 (m, 2H), 2.73-2.65 (m, 2H), 2.36 (s, 3H), 2.11-1.90 (m, 2H), 1.91-1.83 (m, 2H).

Example 353

335

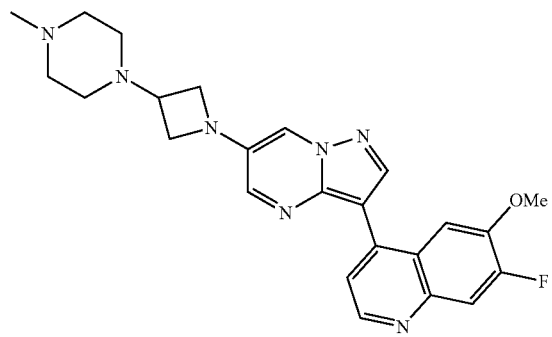 [SMILES: Cc1cc2c(-c3cnn4cc(N5CC(N6CCN(C)CC6)C5)cnc34)ccnc2cc1F]

Compound 335 was prepared in an analogous manner as Compound 305/7095 in Example 302 by using 7-chloroimidazo[1,2-b]pyridazine as the starting material. LC/MS (method 3): $t_R$=2.14 min, m z (M+H)$^+$=448.0. $^1$H NMR (400 MHz, CDCl$_3$) δ 8.86 (s, 1H), 7.97-7.76 (m, 3H), 7.68 (s, 1H), 7.43 (d, J=8.4 Hz, 1H), 6.73 (s, 1H), 4.20-4.02 (m, 2H), 3.95-3.73 (m, 5H), 3.48-3.28 (m, 1H), 2.75-2.40 (m, 8H), 2.38 (s, 3H).

Example 354

336

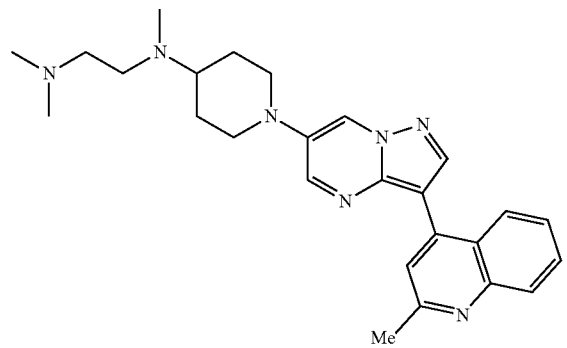

Compound 336 was prepared in an analogous manner as 323 in Example 286 through reductive amination. LC/MS (method 2): $t_R$=2.95 min, m z (M+H)$^+$=371.2.

Example 355

337

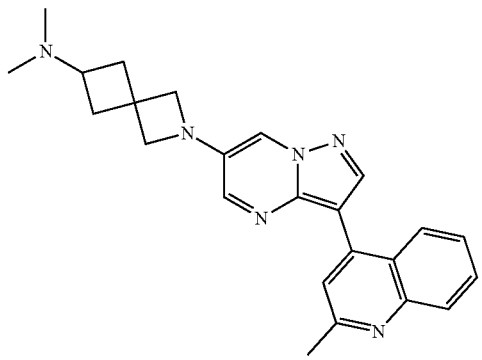

Compound 337 was prepared through reductive amination from compound 298. LC/MS (method 2): $t_R$=3.05 min, m z (M+H)$^+$=399.2.

Example 356

338

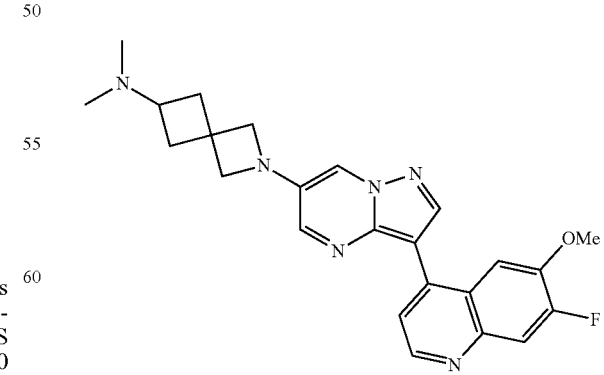

Compound 338 was prepared through reductive amination from compound 299. LC/MS (method 2): $t_R$=3.20 min, m z (M+H)$^+$=433.2.

Example 357

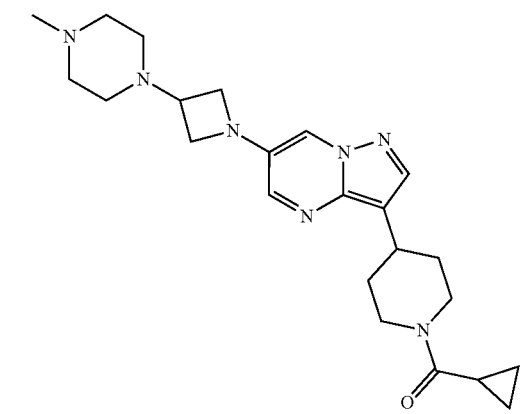

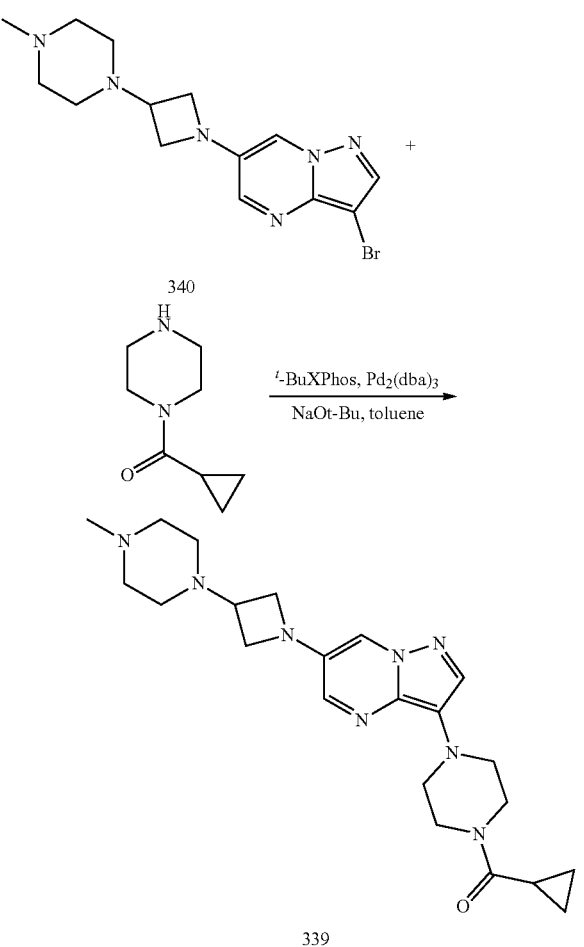

Compound 339 was prepared according to the following procedures: Compound 340 was synthesized from compound 306 using General Method 2. To a microwave vessel were added 3-bromo-6-(3-(4-methylpiperazin-1-yl)azetidin-1-yl)pyrazolo[1,5-a]pyrimidine (80 mg, 0.23 mmol), cyclopropyl(piperazin-1-yl)methanone (49 mg, 0.32 mmol), Pd$_2$(dba)$_3$ (21 mg, 0.023 mmol), t-BuXPhos (39 mg, 0.091 mmol), sodium tert-butoxide (66 mg, 0.68 mmol) and toluene (3 ml). The vessel was purged with nitrogen for 1 min, sealed and subjected to microwave irradiation for 3 hr. The mixture was partitioned between EtOAc and water. The organic layer was separated, washed with brine and dried over Na$_2$SO$_4$. After the removal of solvent under vacuum, the residue was directly purified through preparative HPLC to give desired product 339. LC/MS (method 2): t$_R$=2.92 min, m z (M+H)$^+$=425.4.

Example 358

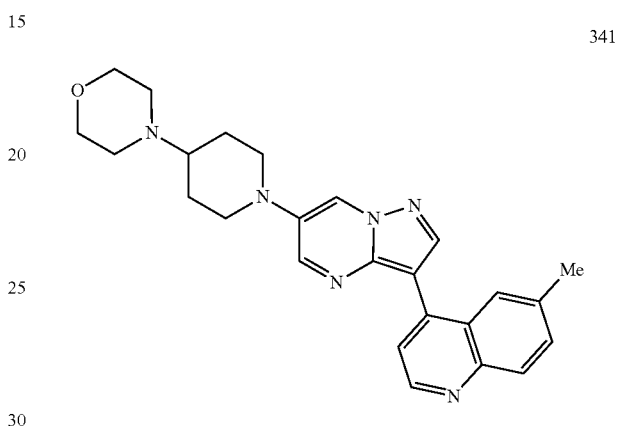

Compound 341 was prepared in an analogous manner as compound 233 in Example 236 except that compound 6 is used in place of compound 5 as starting material. LC/MS (method 2): t$_R$=3.13 min, m/z (M+H)$^+$=429.1.

Example 359

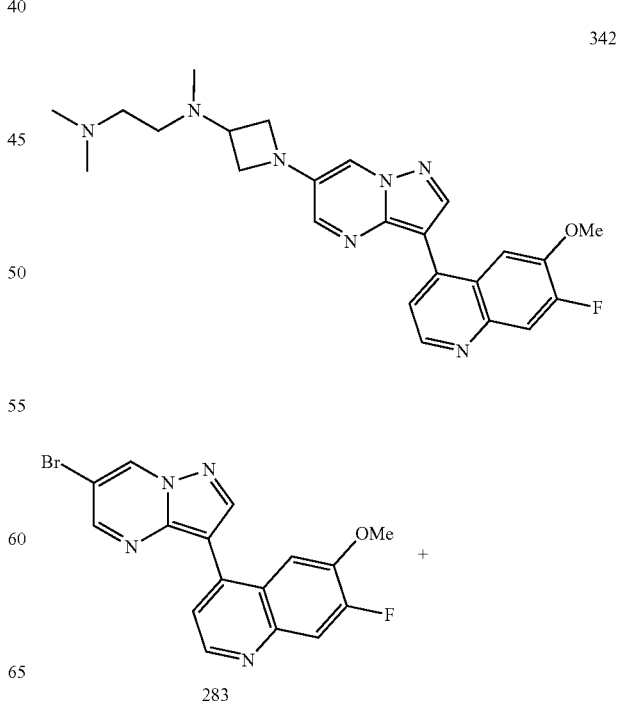

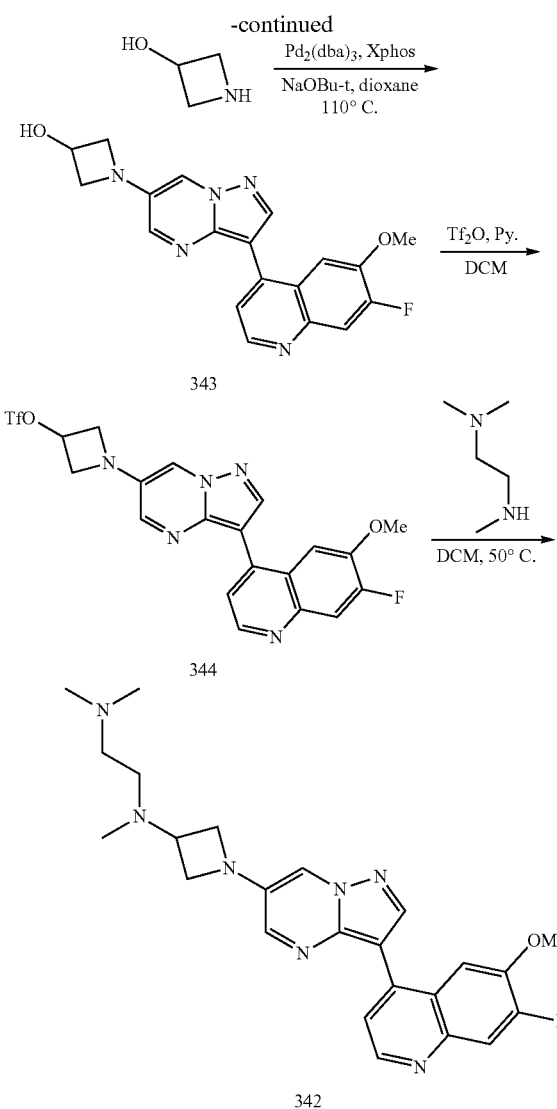

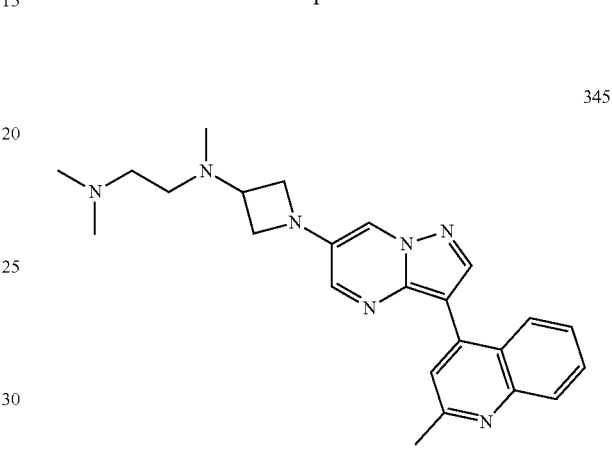

Compound 342 was prepared according to the following procedures: A mixture of azetidin-3-ol (141.0 mg, 1.93 mmol, 2.4 eq), t-BuONa (231.8 mg, 2.41 mmol, 3 eq) and compound 283 (300 mg, 803.9 umol, 1.0 eq) in dioxane (15 mL) was de-gassed and purged with $N_2$ 3 times. XPhos (153.29 mg, 321.6 umol, 0.4 eq) and $Pd_2(dba)_3$ (147.2 mg, 160.8 umol, 0.2 eq) were then added. The mixture was de-gassed and purged with $N_2$ 3 times, and then stirred at 110° C. for 4 hr until there was no more starting material by LCMS analysis. The reaction mixture was concentrated under vacuum to give a residue, which was purified by flash silica gel chromatography (gradient of 100:1 to 20:1 DCM/MeOH) to give the desired product 1-[3-(7-fluoro-6-methoxy-4-quinolyl)pyrazolo[1,5-a]pyrimidin-6-yl]azetidin-3-ol 343 (18% yield) as a yellow solid.

To a solution of compound 343 (80 mg, 219 umol, 1.0 eq) and pyridine (8.8 uL, 110 umol, 4.0 eq) in DCM (10 mL) was added trifluoromethylsulfonyl trifluoromethanesulfonate (72 uL, 438 umol, 2.0 eq) at 0° C. The mixture was stirred at 15° C. for 1 hr, after which an additional equivalent of trifluoromethylsulfonyl trifluoromethanesulfonate was added. The mixture was stirred at 15° C. for another 1.5 hr until there was no more starting material by LC/MS analysis. The crude product 344 in DCM was used directly in the next step.

To a solution of compound 344 (108 mg, 217.12 umol, 1 eq) in DCM (10 mL) was added N,N',N'-trimethylethane-1,2-diamine (565 uL, 4.34 mmol, 20 eq). The mixture was stirred at 15° C. for 1 hour and then heated at 50° C. for 1 hour. The mixture was concentrated under vacuum to give a residue, which was purified by prep-TLC (10:1 DCM/MeOH with 1% $NH_4OH$) twice to give the desired product 342 (5.7 mg, 5% yield) as a yellow solid. LC/MS (method 3): $t_R$=2.55 min, m z $(M+H)^+$=450.2. $^1H$ NMR (400 MHz, $CDCl_3$) δ 8.83 (d, J=4.4 Hz, 1H), 8.87-8.80 (m, 1H), 8.29 (s, 1H), 8.19 (d, J=2.4 Hz, 1H), 7.94 (d, J=2.4 Hz, 1H), 7.80 (d, J=12.0 Hz, 1H), 7.63-7.52 (m, 2H), 4.13 (t, J=6.8 Hz, 2H), 3.90 (s, 3H), 3.83 (t, J=6.4 Hz, 2H), 3.56 (q, J=6.4 Hz, 1H), 2.50 (s, 4H), 2.33 (s, 6H), 2.26 (s, 3H).

Example 360

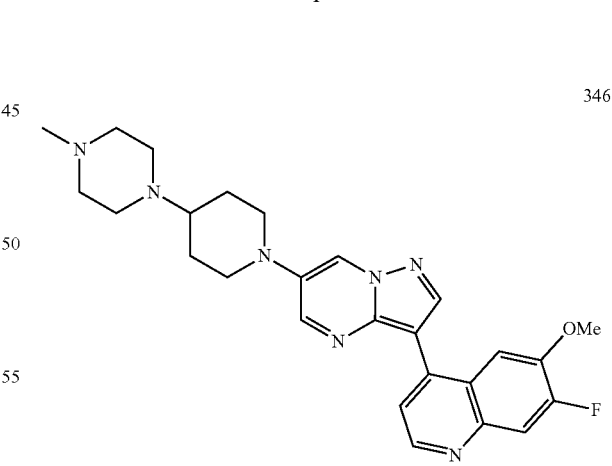

Compound 345 was prepared in an analogous manner as compound 342. LC/MS (method 3): $t_R$=2.31 min, m z $(M+H)^+$=416.2. $^1H$ NMR (400 MHz, $CDCl_3$) δ 8.27 (s, 1H), 8.19 (s, 1H), 8.14-8.10 (m, 2H), 7.92 (s, 1H), 7.70 (s, 1H), 7.59 (s, 1H), 7.48 (s, 1H), 4.11 (t, J=4.8 Hz, 2H), 3.80 (t, J=4.8 Hz, 2H), 3.60-3.45 (m, 1H), 2.84 (s, 3H), 2.55-2.35 (m, 4H), 2.35 (s, 3H). 2.27 (s, 6H).

Example 361

346

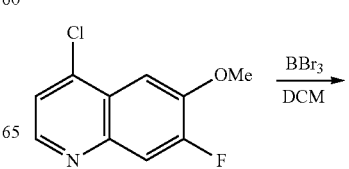

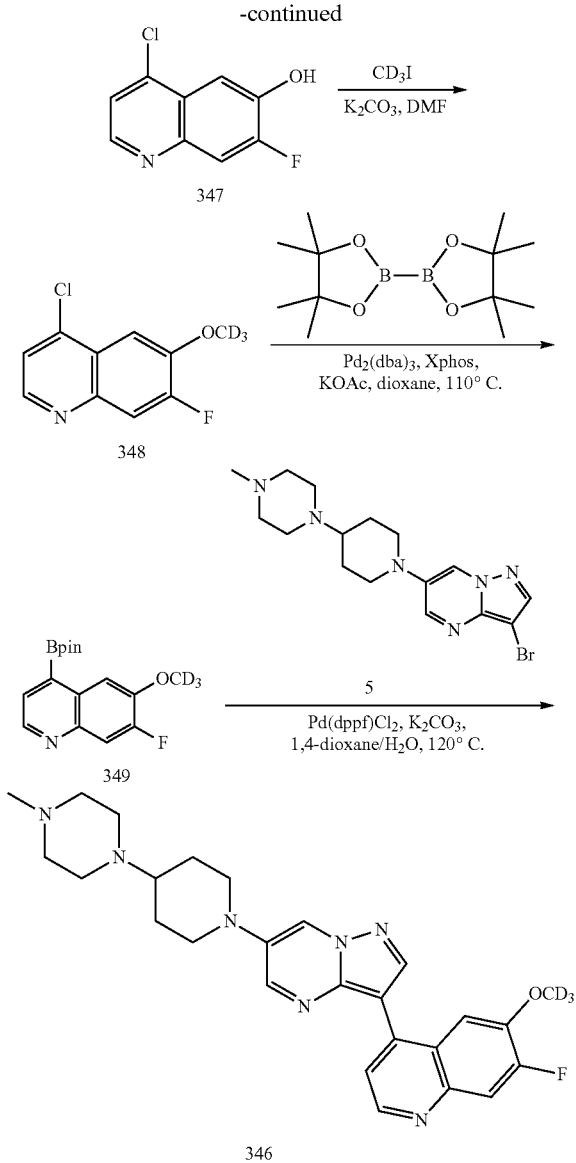

346

Compound 346 was prepared according to the following procedures: To a solution of 4-chloro-7-fluoro-6-methoxy-quinoline (300 mg, 1.42 mmol, 1 eq) in DCM (15 mL) was added BBr₃ (1.37 mL, 14.3 mmol, 1.37 mL, 10 eq) dropwise at 0° C. Then the mixture was warmed to room temperature (20° C.) and stirred at this temperature for 16 hr until there was no more starting material observed by LC/MS analysis. The reaction mixture was quenched with iced water (10 mL) drop-wise at 0° C., then sat. NaHCO₃ (20 mL) was added and extracted with DCM (50 mL×3). The combined organic layer was washed with brine (10 mL×3), dried over anhydrous Na₂SO₄, filtered and concentrated in vacuum to give a residue which was purified by flash silica gel chromatography (gradient of 100:1 to 10:1 DCM/MeOH) to give the product of 4-chloro-7-fluoro-quinolin-6-ol 347 (200 mg, 8901 umol, 63% yield, 88% purity) as a white solid.

To a solution of 347 (100 mg, 446 umol, 1.0 eq) and K₂CO₃ (184.7 mg, 1.34 mmol, 3.0 eq) in DMF (3 mL) was added trideuterio(iodo)methane (64.6 mg, 445.7 umol, 27.7 uL, 1.0 eq). The mixture was stirred at 20° C. for 2 hrs after which it had turned to a dark red suspension and there was no more starting material remaining by LC/MS analysis. Water (5 mL) was added to the crude reaction mixture and the resulting precipitate was filtered. The filter cake was washed with water (3 mL), dried in vacuo to give the desired product 348 (150 mg, 664 umol, 75% yield, 95% purity) as brown solid.

Compound 348 was then converted to its corresponding boronate 349 using the analogous conditions for compound 333 in Example 352 except that dioxane was used in place of THF and the reaction temperature was 110° C.

Compound 349 was then coupled to compound 5 using analogous Suzuki coupling conditions for compound 233 in Example 237. LC/MS (method 3): $t_R$=2.18 min, m z (M+H)⁺=479.1. ¹H NMR (400 MHz, D₂O) δ 8.76 (d, J=6.0 Hz, 1H), 8.70 (d, J=2.8 Hz, 1H), 8.61-8.56 (m, 2H), 8.03 (d, J=6.0 Hz, 1H), 7.90 (d, J=10.4 Hz, 1H), 7.74 (d, J=8.4 Hz, 1H), 3.78 (d, J=12.4 Hz, 2H), 3.65-3.25 (m, 9H), 2.93-2.85 (m, 5H), 2.26 (d, J=11.6 Hz, 2H), 1.84 (d, J=9.6 Hz, 2H).

Example 362

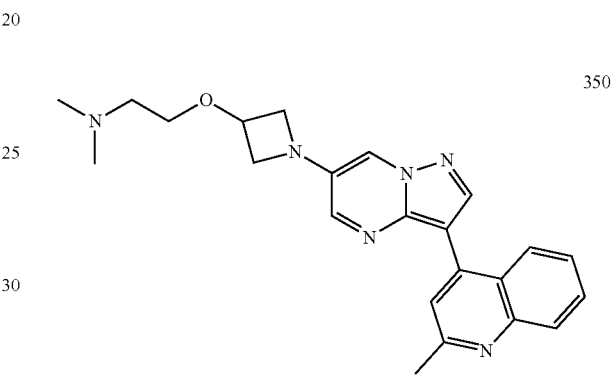

Compound 350/2297 was synthesized using analogous Buchwald coupling conditions for compounds 282/7671 and 290/9558. LC/MS (method 3): $t_R$=2.18 min.

Example 363

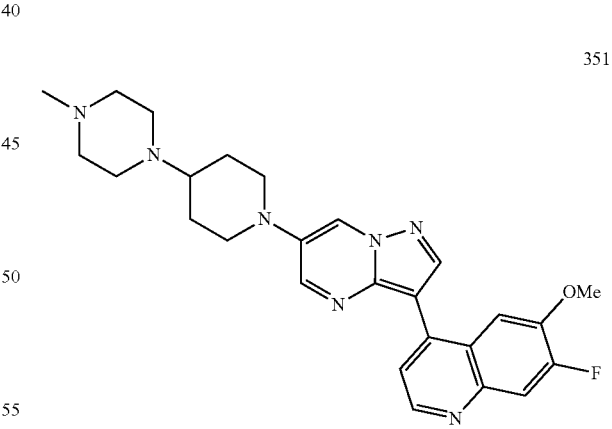

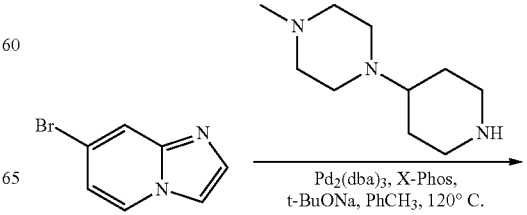

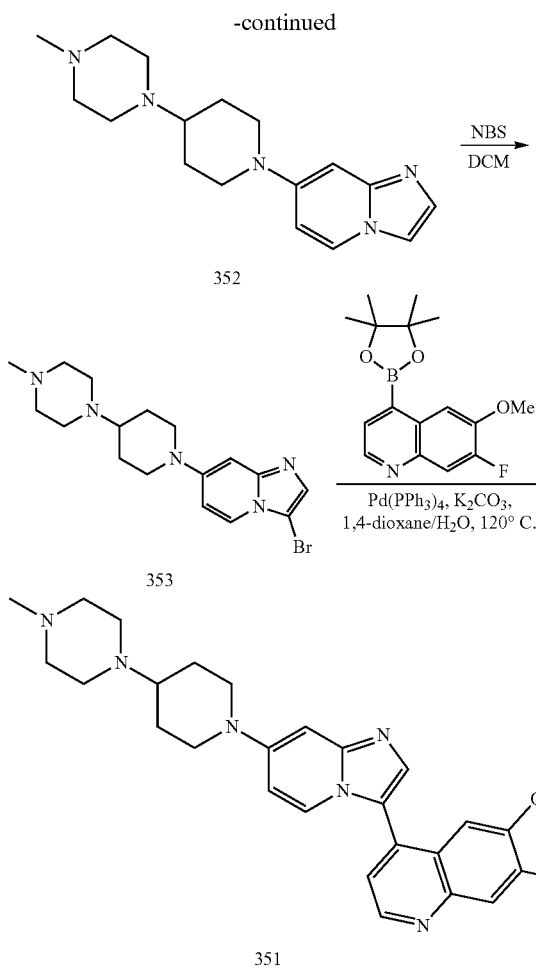

352

353

351

Compound 351/492340 was prepared according to the following procedures: To a solution of 7-bromoimidazo[1,2-a]pyridine (200.0 mg, 1.02 mmol, 1.00 eq) and 1-methyl-4-(4-piperidyl)piperazine (447.8 mg, 2.44 mmol, 2.40 eq) in dioxane (5.00 mL) was added Pd$_2$(dba)$_3$ (186.8 mg, 204 umol, 0.20 eq), XPhos (389.0 mg, 816 umol, 0.80 eq), and t-BuONa (392.1 mg, 4.08 mmol, 4.00 eq). The resulting mixture was de-gassed and purged with nitrogen, then heated to 110° C. under nitrogen atmosphere for 3 hours until there was no more starting material remaining by LC/MS analysis. The reaction mixture was cooled to room temperature and concentrated under vacuum to provide a residue, which was purified by prep-TLC (1:1 DCM/MeOH) to give compound 352 (150.0 mg, 441 umol, 43% yield, 88% purity) as a yellow oil.

To a solution of compound 352 in DCM (10.0 mL) was added NBS (98.1 mg, 552 umol, 1.10 eq) at 0° C. and the resulting mixture was stirred at 0° C. for 10 min until there was no more starting material remaining by LC/MS analysis. Sat. aq. NaHCO$_3$ (8 mL) was then added to the reaction mixture, and extracted with DCM (10 mL×3). The organic phases were combined, dried over Na$_2$SO$_4$, and concentrated under vacuum to give the crude product, which was purified by prep-TLC (2:3 DCM/MeOH) to give compound 353 (26% yield, 99% purity) as a yellow oil.

To a solution of compound 353 (75.0 mg, 198 umol, 1.00 eq) in 10 mL dioxane/H$_2$O (4:1 v/v) was added 7-fluoro-6-methoxy-4-(4,4,5,5-tetramethyl-1,3,2-dioxaborolan-2-yl)quinoline (60.1 mg, 198 umo, 1.00 eq), and Pd(dppf)Cl$_2$ (29.0 mg, 39.7 umol, 0.20 eq) and K$_2$CO$_3$ (68.5 mg, 495 umol, 2.5 eq). The resulting mixture was de-gassed and purged with nitrogen, then heated at 120° C. under nitrogen atmosphere for 2 h until there was no more starting material by LC/MS analysis. The reaction was cooled to room temperature and concentrated under vacuum to give the residue, which was purified by prep-TLC (8:1 DCM/MeOH) to provide desired product 351 (32.0 mg, 66.8 umol, 34% yield, 99% purity) as yellow solid. LC/MS (method 4): $t_R$=5.31 min, m/z (M+H)$^+$=475.1; $^1$H NMR (400 MHz, CDCl$_3$): δ 8.86 (d, J=4.4 Hz, 1H), 7.85-7.80 (m, 2H), 7.74 (s, 1H), 7.43 (d, J=4.8 Hz, 1H), 7.25-7.22 (m, 1H), 6.93 (d, J=2.3 Hz, 1H), 6.66-6.64 (m, 1H), 3.86-3.84 (s, 5H), 2.90-2.87 (t, J=11.5 Hz, 2H), 2.84-2.69 (m, 8H), 2.43 (s, 3H), 2.00 (d, J=12.5 Hz, 2H), 1.74-1.65 (m, 3H).

Example 364

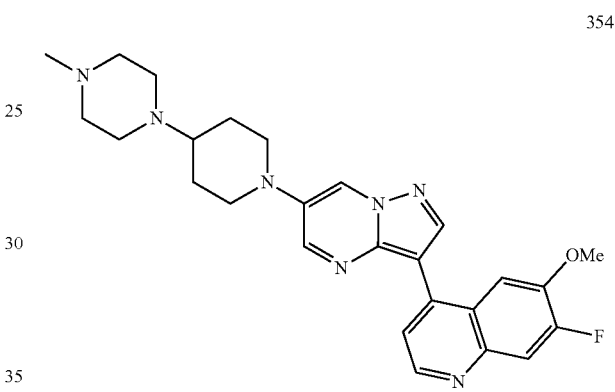

354

Compound 354/496941 was prepared in an analogous manner as compound 351 by using 7-bromo-[1,2,4]triazolo[4,3-a]pyridine as the starting material. LC/MS (method 4): $t_R$=4.01 min, m/z (M+H)$^+$=476.1; $^1$H NMR (400 MHz, CDCl$_3$) δ 8.91 (d, J=4.5 Hz, 1H), 8.75 (s, 1H), 8.12 (d, J=7.5 Hz, 1H), 7.81 (d, J=11.8 Hz, 1H), 7.60 (d, J=4.5 Hz, 1H), 6.94 (d, J=9.0 Hz, 1H), 6.84 (d, J=7.5 Hz, 1H), 3.78 (s, 3H), 3.33-3.17 (m, 2H), 2.67-2.61 (m, 3H), 2.53-2.50 (m, 9H), 2.33 (s, 3H), 2.26-2.13 (m, 1H), 1.64 (d, J=12.5 Hz, 1H), 1.51 (d, J=12.8 Hz, 1H).

Example 365

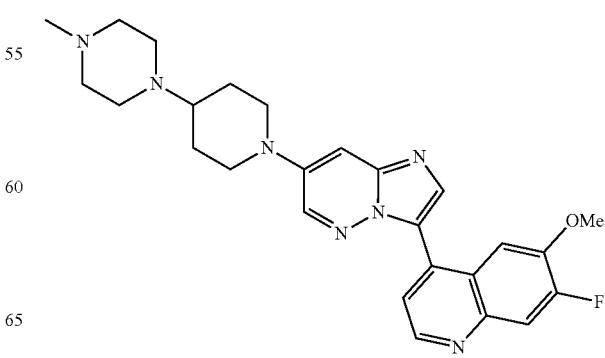

355

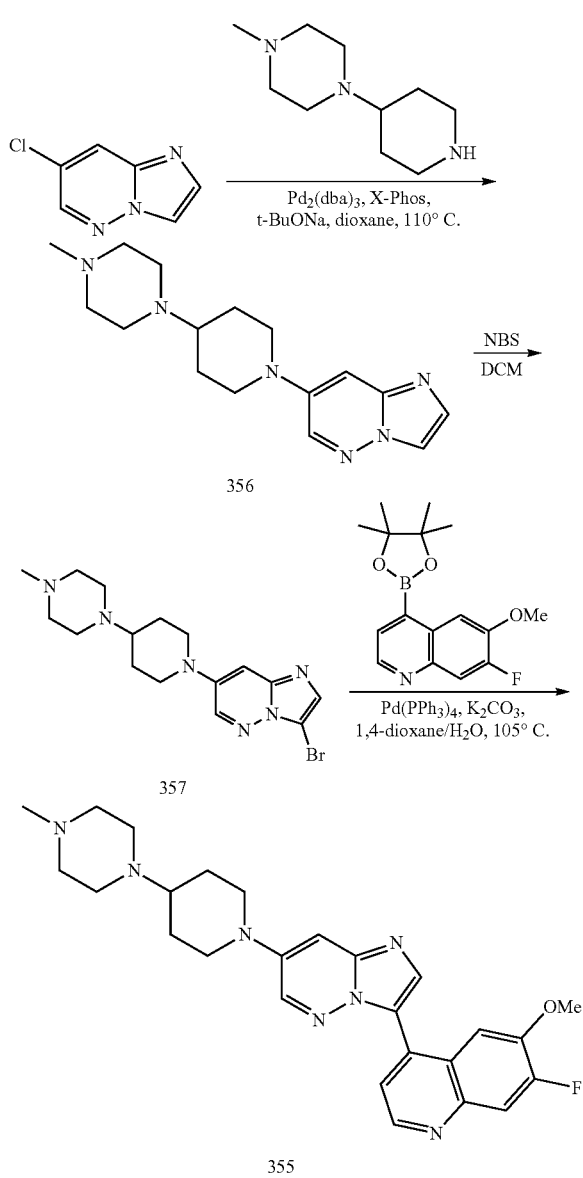

Compound 355/499396 was prepared according to the following procedures: A mixture of 7-chloroimidazo[1,2-b]pyridazine (200 mg, 1.30 mmol, 1.0 eq), 1-methyl-4-(piperidin-4-yl)piperazine (287 mg, 1.56 mmol, 1.2 eq), Pd$_2$(dba)$_3$ (238.52 mg, 261 umol, 0.20 eq), XPhos (248.4 mg, 520.9 umol, 0.40 eq) and t-BuONa (626 mg, 6.51 mmol, 5.0 eq) in dioxane (16 mL) was degassed and purged with N$_2$ for 3 times, then stirred at 110° C. for 16 hr under N$_2$ atmosphere until there was no more starting material remaining by LC/MS analysis. The reaction mixture was concentrated under vacuum to give a residue, which was purified by prep-TLC (5:1 DCM/MeOH with 1% ammonia) to provide compound 356 (222 mg, 53% yield) as a yellow solid. LC/MS (method 3): t$_R$=1.62 min, m/z (M+H)$^+$=301.2; $^1$H NMR (400 MHz, CD$_3$OD) δ 8.48 (d, J=2.8 Hz, 1H), 7.80 (s, 1H), 7.46 (s, 1H), 7.02 (d, J=2.4 Hz, 1H), 3.92-3.89 (m, 2H), 2.89-2.45 (m, 11H), 2.33 (s, 3H), 2.07-2.04 (m, 2H), 1.70-1.62 (m, 2H).

To a solution compound 356 (222 mg, 739 umol, 1.0 eq) in DCM (5 mL) was added NBS (131 mg, 739 umol, 1.0 eq). The mixture was stirred at 0° C. for 5 hr until the was no more starting material by LC/MS analysis. The reaction mixture was quenched with sat. aq. NaHCO$_3$ solution (30 mL) and extracted with DCM (80 mL×3). The combined organic layer was washed with brine (30 mL×3), dried over anhydrous Na$_2$SO$_4$, filtered and concentrated under vacuum to give the crude residue, which was purified through flash silica gel chromatography (10:1 DCM/MeOH with 1% ammonia hydroxide) to give compound 357 (122 mg, 44% yield). LC/MS (method 3): t$_R$=1.92 min, m/z (M+H)$^+$=379.1, 381.1; $^1$H NMR (400 MHz, CD$_3$OD) δ 8.60 (d, J=2.4 Hz, 1H), 7.48 (s, 1H), 7.03 (d, J=2.8 Hz, 1H), 3.96-3.93 (m, 2H), 2.93-2.46 (m, 11H), 2.31 (s, 3H), 2.08-2.05 (m, 2H), 1.70-1.61 (m, 2H).

A mixture of compound 357 (60 mg, 159 umol, 1.06 eq), 7-fluoro-6-methoxy-4-(4,4,5,5-tetramethyl-1,3,2-dioxaborolan-2-yl)quinoline (45.4 mg, 150 umol, 1.0 eq), Pd(dppf)Cl$_2$ (21.9 mg, 29.9 umol, 0.20 eq), K$_2$CO$_3$ (82.7 mg, 599 umol, 4.0 eq) in dioxane/H$_2$O (3 mL/0.75 mL) was degassed and purged with N$_2$ for 3 times, then stirred at 105° C. for 3 hr under N$_2$ atmosphere until there was no more starting material by LC/MS analysis. The reaction mixture was concentrated under vacuum give the crude residue, which was purified through SiO$_2$ flash silica gel chromatography (8:1 DCM/MeOH with 1% ammonia) to give the desired product 355 (56.4 mg, 119 umol, 79% yield) as a yellow solid. LC/MS (method 3): t$_R$=2.15 min, m/z (M+H)$^+$=476.0; $^1$H NMR (400 MHz, CD$_3$OD) δ 8.78 (d, J=4.8 Hz, 1H), 8.58 (d, J=2.8 Hz, 1H), 7.96 (s, 1H), 7.80 (d, J=4.8 Hz, 1H), 7.74 (d, J=11.6 Hz, 1H), 7.48 (d, J=9.2 Hz, 1H), 7.17 (d, J=2.8 Hz, 1H), 4.02-3.99 (m, 2H), 3.90 (s, 3H), 2.98-2.93 (m, 2H), 2.70-2.52 (m, 9H), 2.32 (s, 3H), 2.09-2.06 (m, 2H), 1.68-1.66 (m, 2H).

Examples 83(a), 83(b), 83(e) and 83(f); 84(a), 84(b), 84(e) and 84(f); 85(a)-85(f), 85(l), 85(n)-85(s), 85(u)-85(x), 85(aa)-85(ab), 85(ad)-85(ai), and 85(ak)-85(ar)

Enzymatic Assays for 6 ALK Kinases in 1536-Well Plate Format.

We have developed six ALK kinase enzyme assays for determination of compound activities on ALK1, ALK2, ALK3, ALK4, ALK5 and ALK6. For the assay development, we had tested a number of substrates and assay conditions that led to the final optimized assay protocols with good assay windows with signal to basal (S/B) ratios above 20 fold for all six ALK assays (FIG. 1). In our knowledge, these ALK kinase assays have not been reported elsewhere.

Reagents and Buffer

ALK1 and ALK2-ALK6 were obtained from Life technology (Fredrick, Md.) and CARNA BIOSCIENCES Inc. (Kobe, Japan). Ulight-DNA Topoisomerase 2 alpha (Thr-1342) peptide and Europium anti-phospho-DNA Topoisomerase 2 alpha (Thr-1342) antibody was from Perkin Elmer Inc. The kinase buffer was composed of 50 mM HEPES pH7.0, 10 mM MgCl2, 3 mM MnCl2, 0.005% Tween-20 and 2 mM DTT. The compound plates and the white solid MB assay plates were purchased from Greiner Bio-one (Monroe, N.C.).

TR-FRET Enzymatic Assays for Six ALKs

Figure 2:
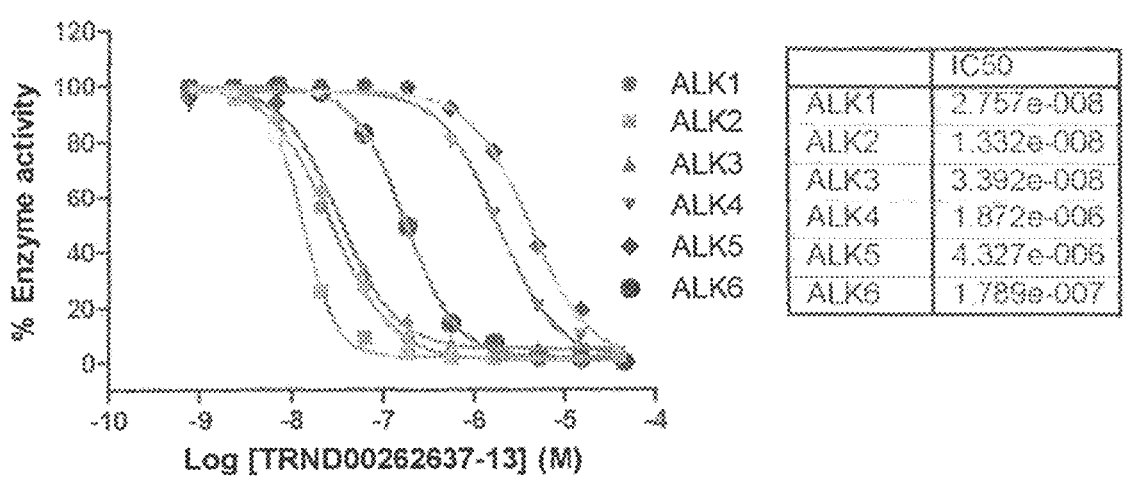
FIG. 2 depicts in accordance with various embodiments of the invention, concentration-response curves of TRND00262637-13 determined in six ALK enzymes. The compound exhibited different activities against six ALKs.
Figure 3:
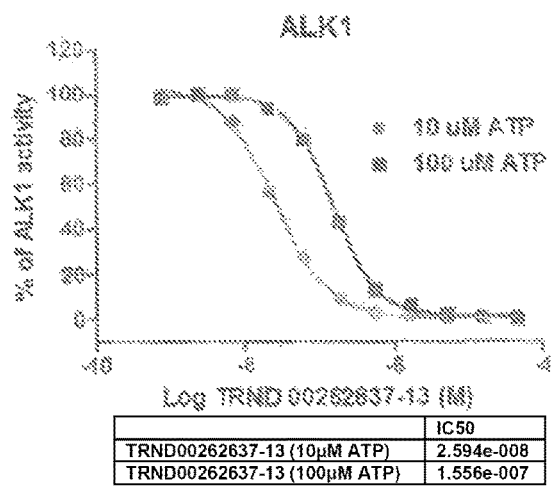
FIG. 3 depicts in accordance with various embodiments of the invention, concentration-response curves of TRND00262637-13 determined in the presence of 10, 100, or 1,000 uM ATP in ALK1 and ALK2. The compound's activity reduced in the higher ATP concentrations (100 uM or 1 mM), indicating an ATP binding competitive kinase inhibitor. Higher ATP concentrations mimic that in cell-based kinase assay condition.
Figure 3:
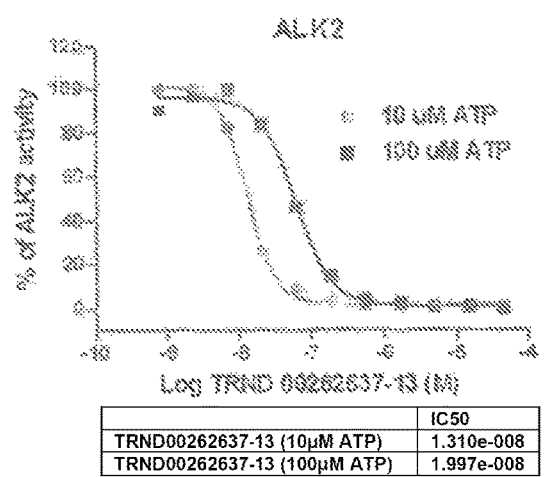
Figure 3:
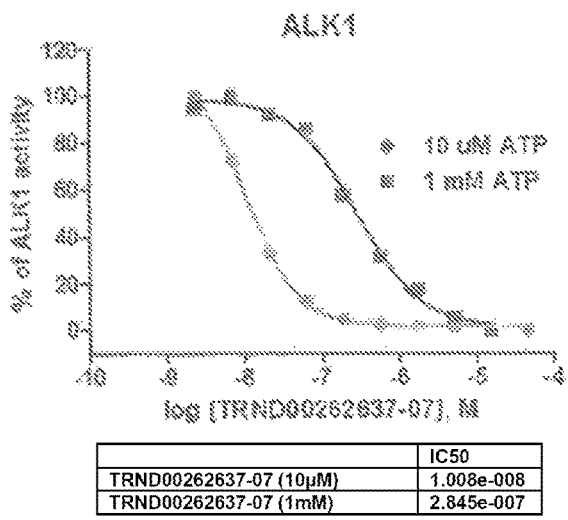
Figure 3:
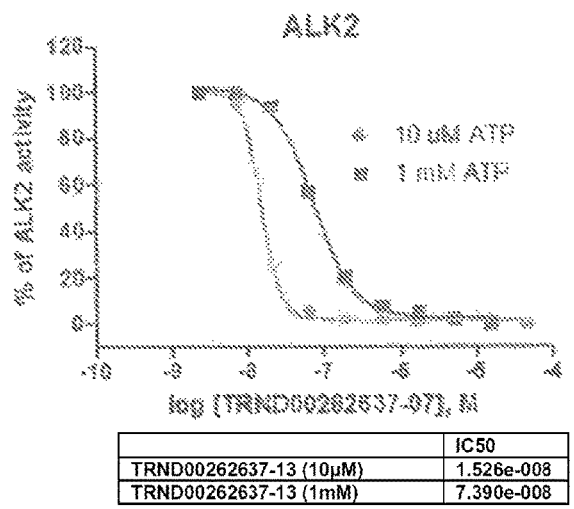

The substrate used for ALKs enzyme was initially screened and identified from the substrate list and Ulight-Topo IIa (Thr 1342) peptide was found to be phosphorylated by all six ALKs. The binding of Eu-anti-phospho-peptide antibody to the phosphorylated Ulight peptide substrate bring both Eu donor and Ulight acceptor dye into close proximity. Upon excitation at 320-340 nm, the emission energy from Eu donor is transferred to Ulight acceptor dye that will generate light at 665 nm. The intensity light emission is proportional to the level of the peptide phosphorylation by ALKs. The assay was optimized and performed in 1536 plate (Table 1). Briefly, the ALKs enzymatic assay was initiated by dispense 2.5 ul enzyme with a final concentration at 10 nM prepared in 1× kinase reaction buffer. The assay plate was then added with compounds with the Pintool station (23 nl/well compound dilutions in DMSO solution) that was followed by incubation at room temperature for 10 minutes. Then 2.5 ul/well substrate was added in which 50 nM peptide substrate mixed with 10 uM, 100 uM or 1 mM ATP (final concentration). The assay plate was incubated at room temperature for 60 minutes and the kinase reaction was stopped by addition of 5 ul/well of 4 nM Eu-anti-phospho-peptide antibody with 12 mM EDTA prepared in 1× detection buffer. The assay plate was measured in an EnVision plate reader (Perkin Elmer) in the TR-FRET detection mode (excitation at 340 nm and emission at 665 nm). The previously reported compound (TRND00262637) showed differentiated activities in six ALK kinases (FIG. 2) and in the different ATP concentrations (FIG. 3).

The previously reported compound (TRND00262637; also known as LDN189) has the structure:

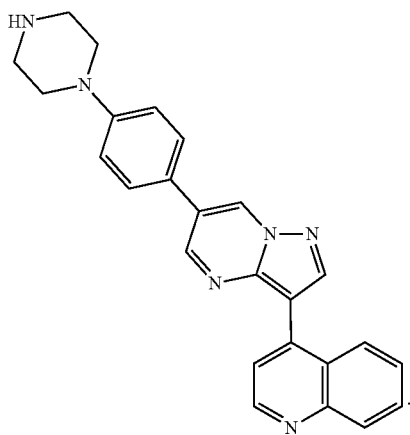 [SMILES: c1ccc2c(-c3cnn4cc(-c5ccc(N6CCNCC6)cc5)cnc34)ccnc2c1]

TABLE 1

Assay protocol for the six FOP ALK enzyme assays in 1,536-well plate format.

| Step | Parameter | Value | Description |
|------|-----------|-------|-------------|
| 1 | Dispense ALK* | 2.5 µl/well | 10 nM ALK (final) in enzymatic buffer In white/solid-bottom plates |
| 2 | Pin compound | 23 nl | Compound in DMSO |
| 3 | Incubation | 10 min | Room temperature |
| 4 | Dispense substrate/ATP buffer | 2.5 ul/well | Ulight topo II substrate (50 nM) with ATP (10 uM), both are final in enzyme |
| 5 | Incubation | 1 hr | Room temperature |
| 6 | Dispense detection buffer | 5 ul/well | 4 nM Eu-anti phospho-peptide antibody With 12 mM EDTA in 1× dtection buffer |
| 7 | Plate reading | TR-FRET model | Envision plate reader (Ex = 340, Em = 665 nm) |

*ALK1, AIK2, ALK3, ALK4, ALK5, ALK6 (final concentration is 10 nM)

TABLE 3

Examples 83(a), 83(b), 83(e) and 83(f)

| Example No. | Compound ID | ALK1 (nM) | | ALK2 (nM) | | ALK3 (nM) | |
|---|---|---|---|---|---|---|---|
| | | IC50 | Span | IC50 | Span | IC50 | Span |
| 83(a) | 11 | 269.4 | 91.4 | 111.1 | ~117.5 | 1280.0 | ~115.7 |
| 83(b) | 8 | 324.6 | 89.1 | 54.3 | 109.4 | 1239.0 | 97.0 |
| 83(e) | 15 | 1522 | 92.3 | 102.5 | ~117.8 | 2818 | 96.93 |
| 83(f) | 34 | 670.8 | 93.42 | 178.1 | ~117.8 | 1869 | 104.4 |

TABLE 4

Examples 84(a), 84(b), 84(e) and 84(f).

| Example No. | Compound ID | ALK4 (nM) | | ALK5 (nM) | | ALK6 (nM) | |
|---|---|---|---|---|---|---|---|
| | | IC50 | Span | IC50 | Span | IC50 | Span |
| 84(a) | 11 | 1032.0 | 100.0 | 2077.0 | 102.1 | 2983.0 | 89.9 |
| 84(b) | 8 | 993.7 | 96.6 | 2469.0 | 100.3 | 2402.0 | 86.5 |
| 84(e) | 15 | 4206 | 101 | 8925 | 96 | 10350 | 80.81 |
| 84(f) | 34 | 2030 | 101.1 | 4680 | 105.678 | 4064 | 91.28 |

Example 88

Cells and Reagents

All cell lines were cultured in DMEM, supplemented with 10% Fetal Bovine Serum and 1% Pen/Strep. All media reagents were obtained from Gibco. BMP6, BMP9, and TGFβ were obtained from R&D Systems. C2Cl2-BRE and HEK293T-SBE were kept in selection with 400 ug/mL G418 from Invivogen.

Luciferase Reporter Gene Assay for ALK2 and TGFβ Activity

In this reporter gene cell based ALK2 and TGFβ assay, the C2Cl2 cell line was employed for the measurement of ALK2 activity, using a BRE-Luc SMAD1/5/8 reporter and BMP6 as the agonist. The HEK293T cell line was employed to measure TGFβ activity, using a SBE-Luc SMAD2/3 reporter and TGFβ as the agonist. Luciferase reporter assays were read using Promega Steady-Glo Luciferase Assay System.

Cells were plated in 96 well white clear bottom assay plates at 10 k cells/well for C2Cl2-BRE, 15 k cells/well for HEK293-SBE in DMEM containing 2% FBS 1% P/S. Cells were given a minimum of 4 hours in incubator at 37° C./5% $CO_2$ to adhere prior to further treatment. Compounds were diluted in DMSO to a 10-point dilution curve and added to the plate to reach the following final concentrations: 10000, 3000, 1000, 300, 100, and 30 nM in the HEK293-SBE assay and 1000, 300, 100, 30, 10, 3, 1, 0.3 nM in the C2Cl2-BRE assay. Negative and positive control wells received 2 µL DMSO as vehicle treatment. Plates were returned to incubator for 45 minutes and then BMP6 and TGFB were added to a final concentration of 50 ng/mL and 5 ng/mL, respectively. Plates were returned to the incubator and left overnight. After a minimum of 18 hours post BMP6/TGFβ addition, the plates were read using Promega Steady-Glo Luciferase Assay System. A 1:1 mixture of prepared steady-glo and phenol free DMEM was prepared, and 50 µL/well was added to the assay plates whose media had been flicked off. Plates were given 10 minutes post steady-glo addition before luminescence was read on a Spectramax M5e microplate reader. Negative control wells were averaged and subtracted from all other wells on the plate. Inhibition was calculated as the percent of signal loss compared to the averaged positive control wells.

HTRF Cell-Based ALK1 Assay

The BAOEC cell line was employed for the measurement of ALK1 activity, using BMP9 as the agonist. The kinase activity was determined by the level of SMAD1 phosphorylation caused by the agonist. The HTRF Phospho-SMAD1 (S463/465) cellular assay kit from Cisbio were used for the measurement of ALK1 activity.

BAOEC cells were plated in a 96 well white clear bottom assay plate at 40 k cells/well in DMEM containing 2% FBS 1% P/S. Cells were given a minimum of 4 hours in incubator at 37° C./5% $CO_2$ to adhere prior to further treatment. Compounds were diluted in DMSO to a 10-point dilution curve and added to the plate to reach the following final concentrations: 10000, 3000, 1000, 300, 100, and 30 nM. Negative and positive control wells received 2 µL DMSO as vehicle treatment. Plates were returned to incubator for 45 minutes and then BMP9 was added to the plate to a final concentration of 1 ng/mL. After 45 minutes of treatment with BMP9, the Cisbio protocol was followed exactly. In short, cells were lysed in supplied buffer containing protease and phosphatase inhibitors. Sample volumes from each well were moved to a Cisbio HTRF low volume 96 well plate. Supplied positive and negative control solutions were added to wells. HTRF detection antibodies were added, and plates were incubated at room temperature overnight. The following day, the plates were read at 665 nm and 620 nm using the HTRF function on the Spectramax M5e microplate reader. The readout is calculated as (Signal 665 nm/Signal 620 nm)×10'. Cells that were treated with DMSO only served as background, and the average was subtracted from all other wells. Inhibition was calculated as the percent of signal loss compared to the averaged positive control wells.

TABLE 5

In vitro $IC_{50}$ data for selected compounds.

| Compound | ALK2 $IC_{50}$ (nM) | TGFβ $IC_{50}$ (nM) |
|---|---|---|
| 3 | 13 | <1 |
| 4 | >3000 | >3000 |
| 8 | 5 | 22 |
| 9 | 36 | 23 |
| 10 | 41 | 76 |
| 11 | 54 | 55 |
| 12 | 87 | 458 |
| 13 | 56 | 261 |
| 14 | 186 | >3000 |
| 15 | 19 | 284 |
| 16 | 8 | 20 |
| 17 | 681 | 271 |
| 18 | 29 | 176 |
| 19 | 113 | 64 |
| 20 | 8 | 218 |
| 21 | 27 | 1285 |
| 22 | 261 | 86 |
| 23 | 145 | 88 |
| 24 | 223 | 56 |
| 25 | 31 | 88 |
| 26 | 334 | 118 |
| 27 | 7 | 10 |
| 28 | 72 | 248 |
| 29 | 83 | 384 |
| 30 | 37 | 120 |
| 31 | ND | ND |
| 32 | 25 | 37 |
| 33 | 94 | 37 |
| 34 | 37 | 27 |
| 39 | 11 | 69 |
| 40 | 114 | 327 |
| 41 | 236 | 1233 |

TABLE 5-continued

In vitro $IC_{50}$ data for selected compounds.

| Compound | ALK2 $IC_{50}$ (nM) | TGFβ $IC_{50}$ (nM) |
|---|---|---|
| 42 | 9 | 59 |
| 43 | 631 | 1918 |
| 44 | >3000 | 210 |
| 45 | 24 | 376 |
| 46 | 108 | 454 |
| 47 | 76 | 483 |
| 48 | 50 | 914 |
| 49 | 11 | 631 |
| 51 | 60 | 410 |
| 52 | 29 | 358 |
| 53 | 9 | 198 |
| 54 | 71 | 539 |
| 55 | 9 | 268 |
| 56 | 46 | 505 |
| 57 | 207 | >1000 |
| 58 | 377 | 970 |
| 60 | 42 | >3000 |
| 61 | >1000 | >3000 |
| 62 | 90 | 37 |
| 63 | 977 | 6833 |
| 64 | 28 | >3000 |
| 65 | ND | ND |
| 79 | ND | ND |
| 80 | 25 | 33 |
| 81 | >3000 | >3000 |
| 185 | 22 | 514 |
| 186 | 57 | 370 |
| 187 | 37 | 32 |
| 188 | 50 | 126 |
| 189 | 137 | 92 |
| 190 | 31 | 128 |
| 191 | 964 | 635 |
| 192 | 89 | 184 |
| 193 | 118 | 449 |
| 194 | 221 | 138 |
| 195 | 298 | 286 |
| 196 | 935 | 126 |
| 197 | 395 | 623 |
| 198 | 300 | 283 |
| 199 | 23 | 498 |
| 200 | 94 | 324 |
| 201 | 13 | 327 |
| 202 | 507 | 359 |
| 203 | 26 | >3000 |
| 204 | 11 | >3000 |
| 205 | 593 | >3000 |
| 206 | 356 | 817 |
| 207 | 331 | 215 |
| 208 | 104 | 685 |
| 209 | 15 | 62 |
| 210 | 17 | 91 |
| 211 | 51 | 416 |
| 212 | 38 | 760 |
| 213 | <1 | <1 |
| 214 | >1000 | >1000 |
| 215 | 34 | 142 |
| 216 | 24 | 44 |
| 217 | 33 | 116 |
| 218 | 26 | 141 |
| 219 | 381 | >3000 |
| 220 | >1000 | >1000 |
| 221 | 6 | 277 |
| 222 | 14 | 70 |
| 223 | 272 | >3000 |
| 224 | >1000 | >3000 |
| 225 | >1000 | >3000 |
| 226 | 18 | >1000 |
| 227 | 903 | 826 |
| 228 | 476 | 605 |
| 229 | 52 | 9 |
| 230 | 46 | 505 |
| 233 | 70 | 589 |
| 234 | >1000 | >1000 |
| 235 | 25 | >1000 |
| 236 | 975 | 267 |
| 237 | 6 | 240 |

TABLE 5-continued

In vitro IC$_{50}$ data for selected compounds.

| Compound | ALK2 IC$_{50}$ (nM) | TGFβ IC$_{50}$ (nM) |
|---|---|---|
| 238 | 175 | 306 |
| 239 | 32 | >1000 |
| 240 | 16 | 291 |
| 241 | 92 | >1000 |
| 242 | 37 | <10 |
| 243 | >1000 | >2000 |
| 244 | 30 | 328 |
| 245 | >1000 | 468 |
| 246 | >1000 | >1000 |
| 247 | 13 | >3000 |
| 248 | 57 | 2875 |
| 249 | >1000 | >1000 |
| 250 | 17 | 202 |
| 251 | 26 | 209 |
| 252 | 85 | 12 |
| 253 | 193 | >1000 |
| 254 | 244 | >1000 |
| 255 | 68 | 28 |
| 256 | 10 | 104 |
| 257 | >1000 | >1000 |
| 258 | 197 | 964 |
| 259 | 29 | 55 |
| 260 | 12 | 229 |
| 261 | 19 | 916 |
| 262 | >1000 | >3000 |
| 263 | 295 | 424 |
| 264 | 18 | 383 |
| 265 | ND | ND |
| 266 | 17 | 138 |
| 267 | 162 | >2000 |
| 268 | 98 | >1000 |
| 269 | 311 | >3000 |
| 270 | 558 | >3000 |
| 271 | >3000 | >3000 |
| 272 | 153 | >1000 |
| 273 | 14 | 267 |
| 274 | 32 | 321 |
| 275 | 133 | 72 |
| 276 | 164 | 64 |
| 277 | >1000 | >3000 |
| 278 | 31 | 897 |
| 279 | 55 | >1000 |
| 280 | 26 | >2000 |
| 281 | >3000 | >3000 |
| 282 | 10 | 96 |
| 286 | ND | ND |
| 290 | 12 | 63 |
| 292 | 159 | 595 |
| 293 | 6 | 110 |
| 294 | 15 | 99 |
| 295 | 13 | 389 |
| 296 | 48 | 18 |
| 297 | 21 | >1000 |
| 298 | 3 | <1 |
| 299 | 11 | 67 |
| 300 | 8 | 24 |
| 301 | 18 | <20 |
| 302 | 4 | 44 |
| 303 | 276 | 145 |
| 304 | ND | ND |
| 305 | 10 | 304 |
| 307 | >1000 | >3000 |
| 308 | 159 | 595 |
| 309 | 28 | 335 |
| 310 | 21 | 38 |
| 311 | 33 | 60 |
| 312 | 26 | 21 |
| 313 | 2 | >3000 |
| 314 | 8 | 27 |
| 315 | 23 | 30 |
| 316 | 22 | <20 |
| 317 | ND | ND |
| 318 | ND | ND |
| 319 | ND | ND |
| 320 | 27 | 605 |
| 323 | 194 | >1000 |
| 324 | 178 | 723 |
| 326 | >1000 | >3000 |
| 327 | 35 | 453 |
| 328 | 48 | 439 |
| 329 | >1000 | >3000 |
| 335 | 47 | >2000 |
| 336 | 42 | 29 |
| 337 | 9 | <1 |
| 338 | 3 | 33 |
| 339 | >1000 | >3000 |
| 341 | 15 | 771 |
| 342 | ND | ND |
| 345 | ND | ND |
| 346 | 18 | 686 |
| 350 | 477 | 975 |
| 351 | 372 | >3000 |
| 354 | >1000 | >3000 |
| 355 | 146 | 791 |

(ND = not determined)

Example 89(a)

Experimental Procedure for Aldehyde Oxidase (AO) Oxidation Study (Frontage Laboratories (700 Pennsylvania Dr. Exton, Pa. 19341).

Determination of the of metabolic stability in human liver cytosol (HLC) and the identification of corresponding metabolites was done by incubating substrates (1 µM final concentration for metabolic stability or 10 µM final concentration for metabolite ID) with HLC (2 mg/ml, final concentration) in 100 mM potassium phosphate at pH 7.4. The reaction was initiated by adding HLC without preincubation. The mixture was then incubated at 37° C. for 1 h and samples were taken at 0, 30 and 60 min for analysis. The reaction was terminated by adding acetonitrile (ACN) (3×) followed by vortexing for 1 min then centrifuged. For the metabolic stability study, aliquots of the supernatants were transferred to clean tubes and directly used for LC/MS/MS analysis. For the identification of metabolites, aliquots of supernatants were transferred to clean tubes and dried under a stream of $N_2$. The residue was reconstituted in 30/70 (v/v) acetonitrile/water solution and injected onto LC/UV/MS system.

The instrument and method for the metabolic stability are as following: LC/MS/MS system: Agilent 1100 HPLC interfaced to Sciex API4000 mass spectrometer (ESI); HPLC column: ACE 3 C18-PFP, 50×2.1 mm, 5 µm. HPLC column: ACE 3 C18-PFP, 50×2.1 mm, 5 µm; HPLC mobile phase gradient for LC/MS analysis of all compounds using 0.1% formic acid in water (A) and 0.1% formic acid in ACN (B) at a flow rate of 0.5 mL/min: 0-1 min, 95% A; 2-3.6 min, 5% A; 3.61-5 min, 95% A.

The instrument and method for the metabolite ID and profiling study are as following: MRM transitions: LC/UV/MS system: Agilent 1100 HPLC (pumps, autosampler and PDA) interfaced to LTQ-Orbitrap mass spectrometer (ThermoFinnigan). HPLC column: Luna C18 column, 150×2.0 mm, 5 µm; HPLC mobile phase gradient for LC/MS analysis and metabolite profiling for all compounds.

TABLE 12

Example 89(a)

| Example No. | Compound ID | 30 minutes (%) | 60 minutes (%) | BMP6 (uM) |
|---|---|---|---|---|
| 89(a) (Comparative) | TRND00262637-13 (LDN189) | 0.06 | 0.02 | N/A |

Examples 366(a), 366(c), 366(d), and 366(h)

Kinase Profiling BMP type II Receptor Experimental Procedure (Life Technologies, 5225 Vernona Road, Madison, Wis. 53744).

The measurement of each compound's half maximal inhibitory concentration ($IC_{50}$) for BMP type II receptors (ACVR2A, ACVR2B, BMPR2 and TGFbR2) was carried out at Life Technologies by using its 10-point titration (starting concentration: 10 µM with 3-fold serial dilution) LanthaScreen™ biochemical kinase assay protocol. For the detailed description of LanthaScreen™ Eu kinase binding assay condition, please see: https://www.thermofisher.com/us/en/home/industrial/pharma-biopharma/drug-discovery-development/target-and-lead-identification-and-validation/kinasebiology/kinase-activity-assays/lanthascreentm-eu-kinase-binding-assay/lanthascreen-eu-kinase-binding-assay-validation-table.html.

TABLE 15

Examples 366(a), 366(c), 366(d), and 366(h).

| | | Type II BMP receptors | | | | Cell assays | | |
| | | | | | | HTRF | HRTF | |
| Example No. | Compound ID | ACVR2A (IC50, nM) | ACVR2B (IC50, nM) | BMPR2 (IC50, nM) | TGFPR2 (IC50, nM) | BMP6 (IC50, nM) | TGFb (IC50, nM) | ALK2 (nM) |
|---|---|---|---|---|---|---|---|---|
| 366(a) (Comparative) | TRND00262637-13 (LDN189) | 14.5 | 20 | >10,000 | 8.06 | 69 | 9290 | 8 |
| 366(c) | 79 | 851 | 1280 | >10,000 | 71.3 | 97.4 | 4614 | 110 |
| 366(d) | 80 | 3710 | 3610 | 10,000 | 194 | 250 | 5790 | 93 |
| 366(h) | 8 | 1280 | 745 | >10,000 | 191 | 270 | 2040 | N/A |

Example 367

Inhibition of BMP6 Mediated Heterotopic Ossification

C57Bl/6 WT mice are injected intramuscularly in the Tibialis Anterior with Bone-morphogenetic Protein (BMP6 R&D Systems cat #507-BP-020) at 2.5 ug in 40 uL of 0.1% BSA in PBS (62.5 ug/ml) to induce development of heterotopic bone. Cardiotoxin (10 uM in 40 uL of 0.1% BSA in PBS) is administered to the same site 72 hrs prior to BMP6 injection to induce muscular injury/repair and accelerate heterotopic ossification (HO) development. Radiologically detectable HO is generally observed by 9-days post BMP6 administration with maximal HO volume and density observed 11-14 days post BMP6.

Figure 4:
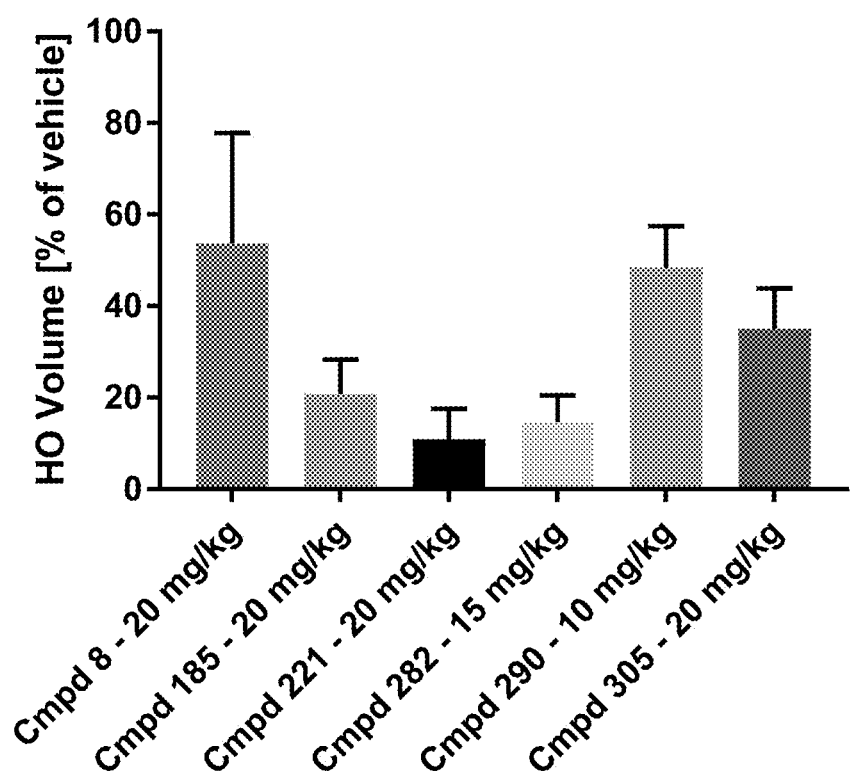
FIG. 4 depicts the percent of HO volume measured at the end of dosing as compared to vehicle.

Mice are dosed daily with candidate therapeutic compounds varying between 1 and 50 mg/kg starting on day of cardiotoxin administration (72 hr prior to BMP-6 administration). Mice are imaged on a Quantum FX Micro-CT instrument (PerkinElmer, Hopkinton Mass.) 11-days post BMP-6 administration. Radiologically detectable HO is volumetrically quantitated using AnalyzePro (AnalyzeDirect, Overland Park Kans.) and/or AccuCT (PerkinElmer, Hopkinton Mass.) software packages. Data is represented in FIG. 4 as the percent of HO volume measured at the end of dosing as compared to vehicle.

The various methods and techniques described above provide a number of ways to carry out the application. Of course, it is to be understood that not necessarily all objectives or advantages described can be achieved in accordance with any one or more embodiments described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A compound of formula (I):

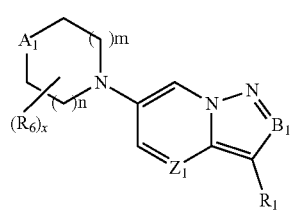

(I)

or a pharmaceutically acceptable salt thereof, wherein
$A_1$ is $NR_{4a}$ or $CR_{4b}R_5$;
$B_1$ is N or $CR_2$;
$Z_1$ is N or $CR_3$;
$R_1$ is selected from cycloalkyl, aryl, heteroaryl, and heterocyclyl;
$R_2$ is H, CN, $NO_2$, alkyl, or amino;
$R_3$ is selected from H, CN, $NO_2$, alkyl, alkoxy, heterocyclyloxy, heteroaryloxy, aryloxy, cycloalkyloxy, carbonyl, amino, amido, sulfonyl, sulfonamido, cycloalkyl, aryl, heterocyclyl, and heteroaryl;
$R_{4a}$ is selected from alkyl, alkenyl, alkynyl, carbonyl, $O^-$, alkoxycarbonyl, cycloalkyl, aryl, heterocyclyl, and heteroaryl;
$R_{4b}$ is selected from halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl;
$R_5$ is selected from H, halo, hydroxy and alkyl, or $R_{4b}$ and $R_5$ together with $A_1$ form a ring selected from cycloalkyl and heterocyclyl;
each $R_6$ is independently selected from H, halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl and oxo;
n is 0 or 1;
m is 0 or 1; and
x is 0, 1, 2, 3, or 4.

2. The compound of claim 1, or a pharmaceutically acceptable salt thereof, wherein
$A_1$ is $NR_{4a}$ or $CR_{4b}R_5$;
$B_1$ is N or $CR_2$;
$Z_1$ is N or $CR_3$;
$R_1$ is selected from aryl, heteroaryl, and heterocyclyl;
$R_2$ is H or amino;
$R_3$ is H or heterocyclyloxy;
$R_{4a}$ is selected from alkyl, $O^-$, aryl, heterocyclyl, and heteroaryl;
$R_{4b}$ is selected from alkyl, alkoxy, amino, aryl, heterocyclyl, and heteroaryl;
$R_5$ is selected from H and alkyl, or
$R_{4b}$ and $R_5$ together with $A_1$ form a ring selected from cycloalkyl and heterocyclyl;
each $R_6$ is independently selected from H, halo, alkyl and oxo;
n is 0 or 1;
m is 0 or 1; and
x is 0, 1, 2, 3, or 4.

3. The compound of claim 1, or a pharmaceutically acceptable salt thereof, wherein $R_1$ is selected from H, aryl, 5-6 membered heteroaryl,

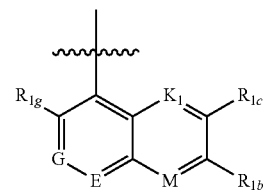

and

-continued

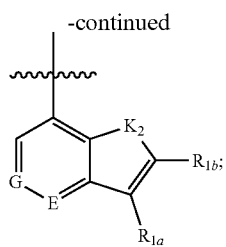

wherein:
each E is independently selected from N and $CR_{1d}$;
each G is independently selected from N and $CR_{1e}$;
$K_1$ is N or CH;
$K_2$ is NH or S;
M is N or $CR_{1a}$;
$R_{1a}$ is selected from H, halo, alkyl, haloalkyl, and amido;
$R_{1b}$ is selected from H, halo, CN, alkyl, haloalkyl, hydroxy, alkoxy, and haloalkoxy;
$R_{1c}$ is selected from H, halo, CN, alkyl, haloalkyl, hydroxy, alkoxy, haloalkoxy, amino and amido, or
$R_{1b}$ and $R_{1c}$ together with the carbon atoms to which they are attached form a heterocyclyl;
$R_{1d}$ is selected from H, CN, alkyl, haloalkyl, hydroxy, amido and sulfonamido;
$R_{1e}$ is selected from H, alkyl and amino; and
$R_{1g}$ is H or halo.

4. The compound of claim 1, or a pharmaceutically acceptable salt thereof, wherein
$R_{4a}$ is selected from alkyl, O, heterocyclyl, and heteroaryl;
$R_{4b}$ is selected from alkyl, alkoxy, amino, amido, heterocyclyl, and heteroaryl;
$R_5$ is selected from H and alkyl, or
$R_{4b}$ and $R_5$ together with $A_1$ form a heterocyclyl; and
each $R_6$ is independently selected from H, halo, and alkyl; and
x is 0 or 1.

5. The compound of claim 4, or a pharmaceutically acceptable salt thereof, wherein $R_1$ is selected from H, aryl, 5-6 membered heteroaryl,

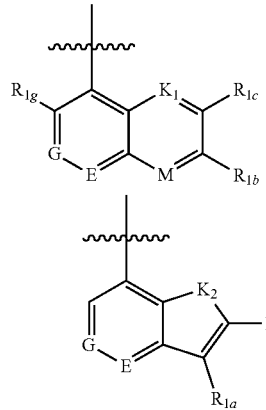

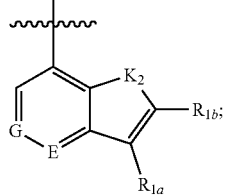

and wherein:
each E is independently selected from N and $CR_{1d}$;
each G is independently selected from N and $CR_{1e}$;
$K_1$ is N or CH;
$K_2$ is NH or S;
M is $CR_{1a}$;

$R_{1a}$ is selected from H and amido;
$R_{1b}$ is selected from H, halo, alkyl, and alkoxy;
$R_{1c}$ is selected from H, alkyl, and alkoxy, or
$R_{1b}$ and $R_{1c}$ together with the carbon atoms to which they are attached form a heterocyclyl;
$R_{1d}$ is selected from H, alkyl, hydroxy, amido and sulfonamido;
$R_{1e}$ is selected from H, alkyl and amino;
$R_{1f}$ is H; and
$R_{1g}$ is H.

6. A compound having a formula selected from:

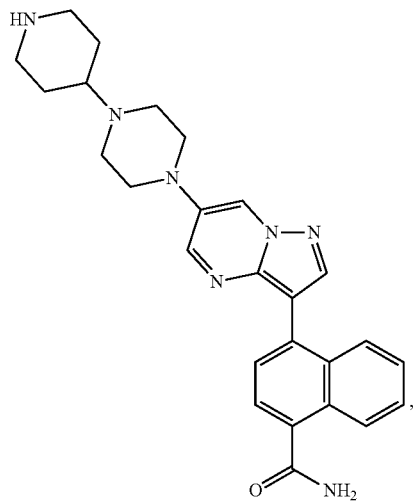

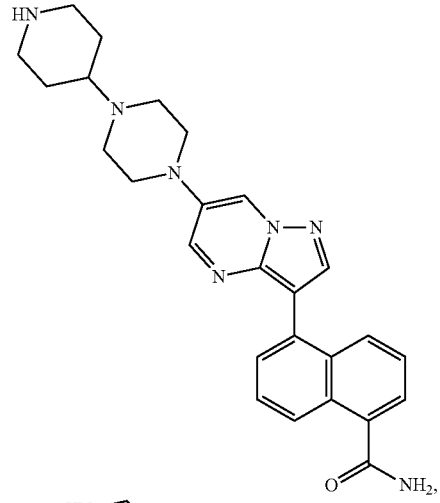

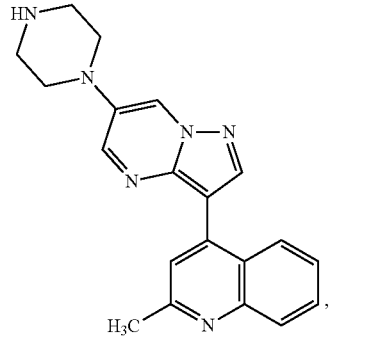

349
-continued
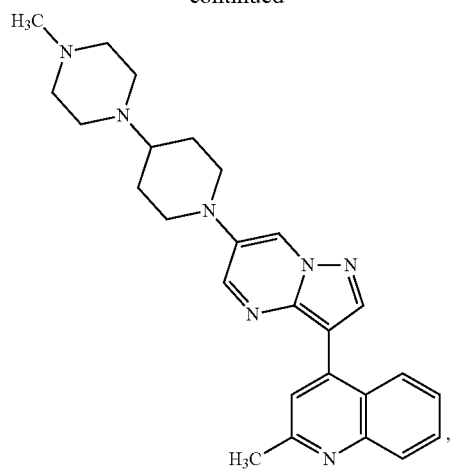
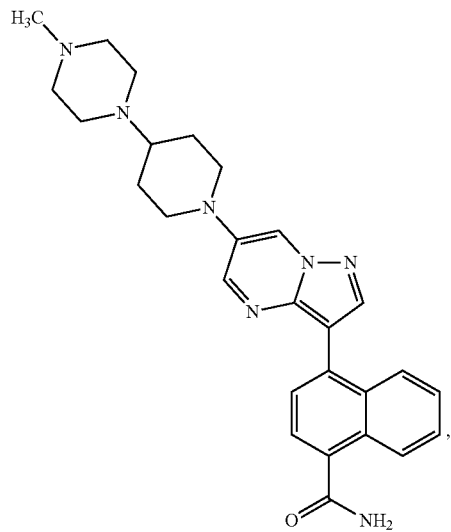
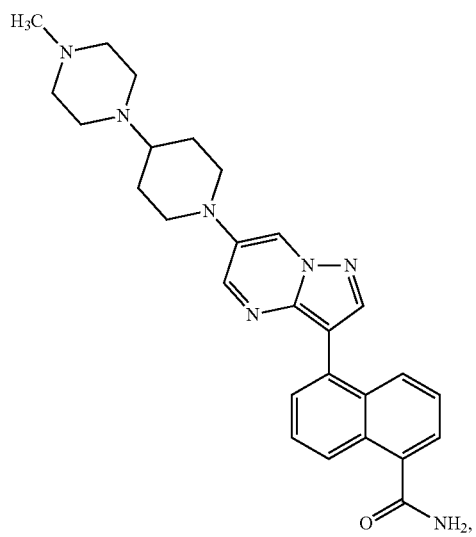
350
-continued
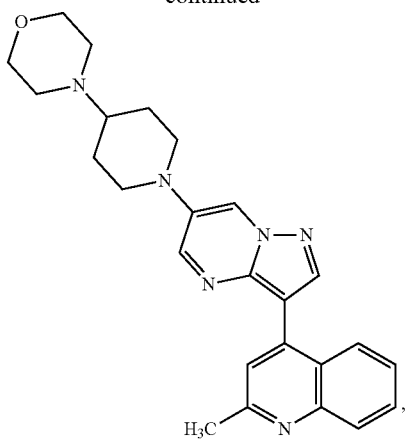
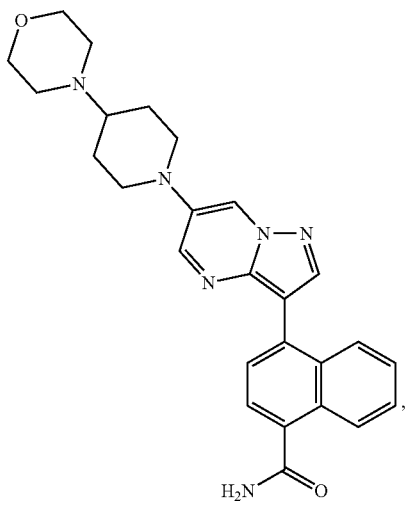
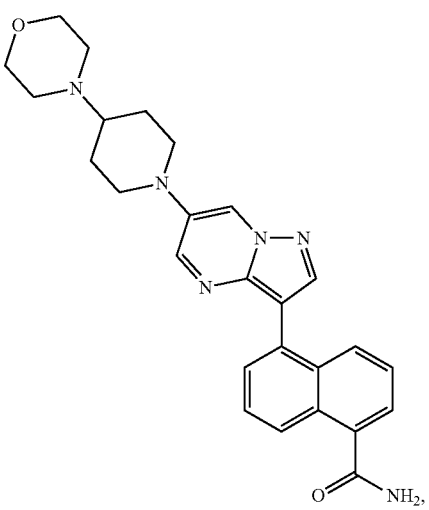

351
-continued
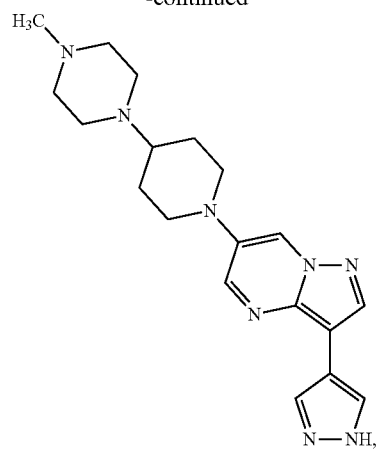
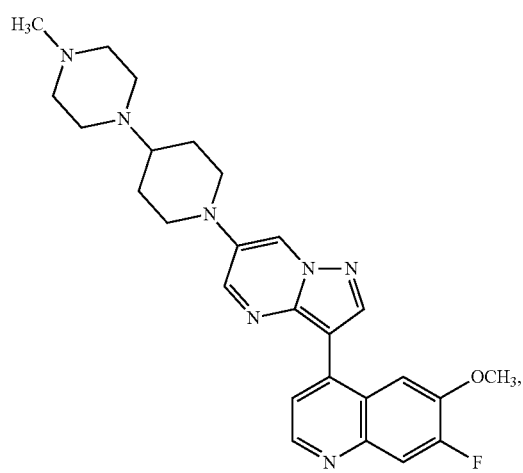
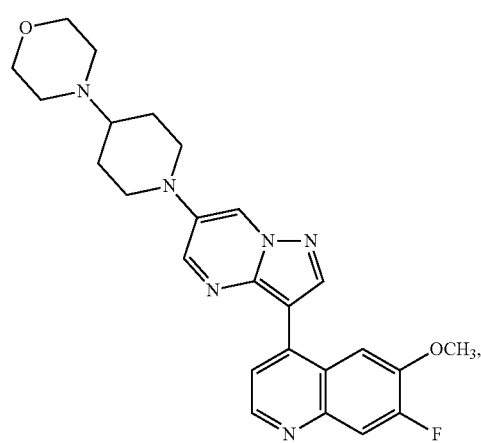
352
-continued
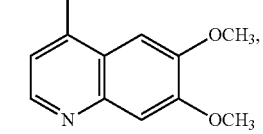
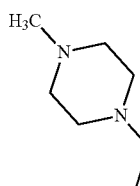
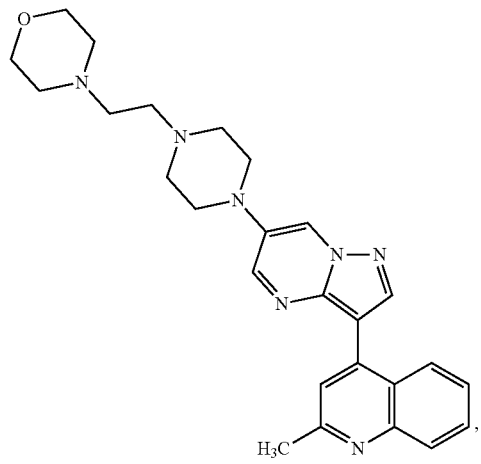

353
-continued
354
-continued
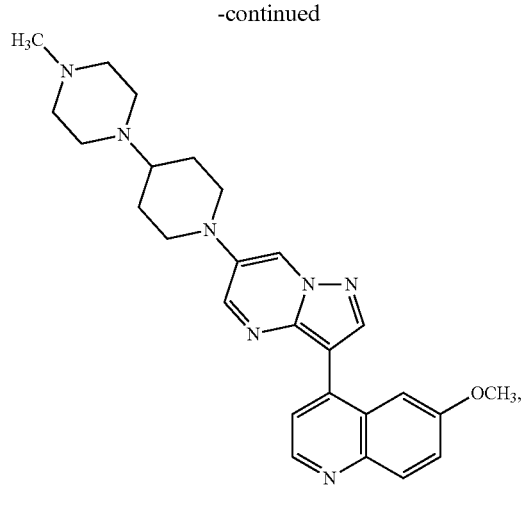
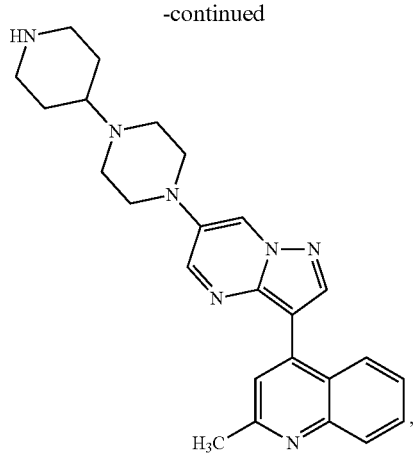
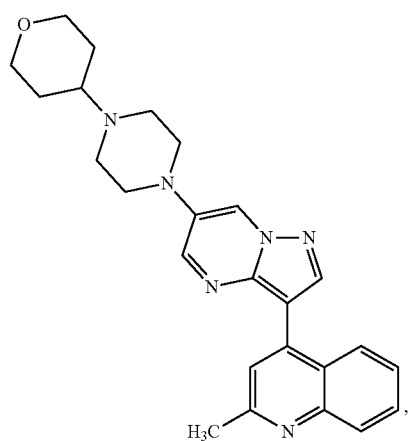
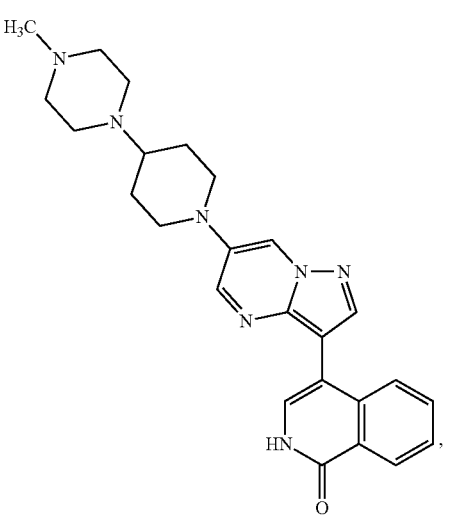

355
-continued
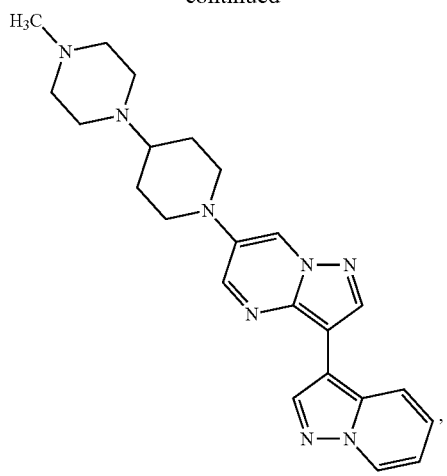
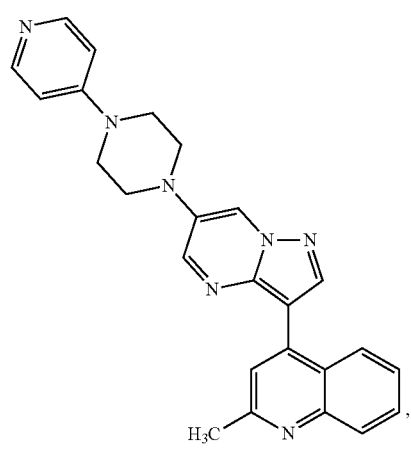
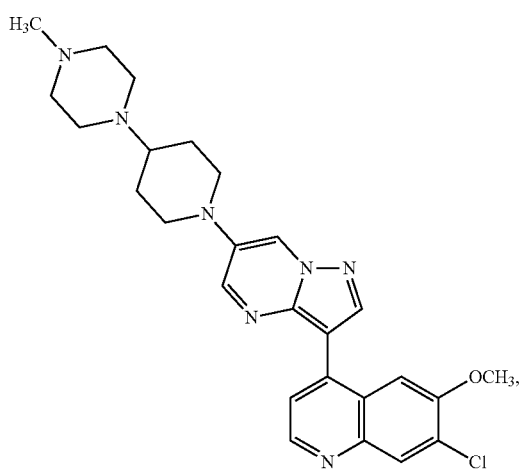
356
-continued
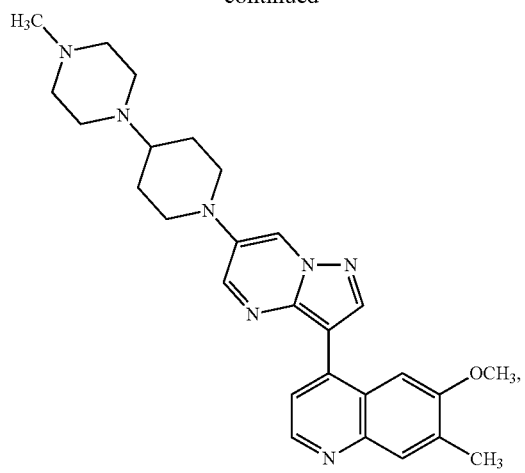
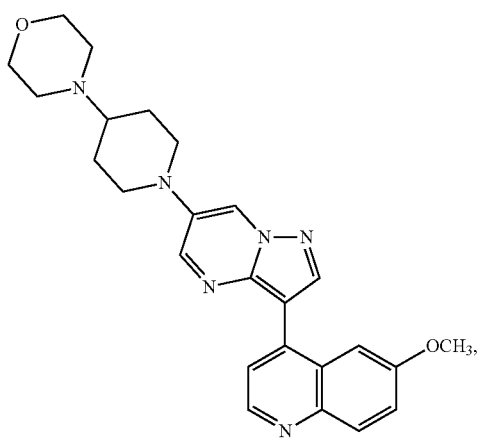
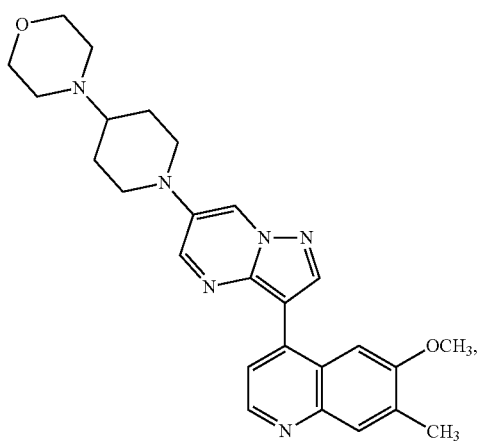

357
-continued
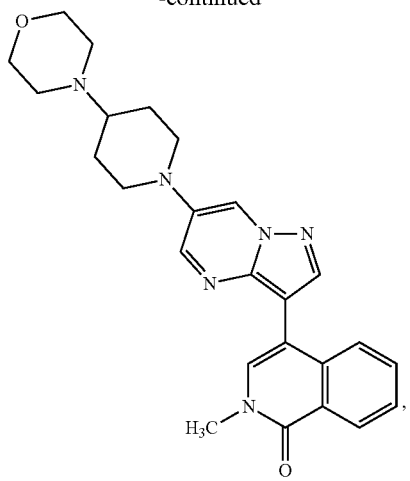
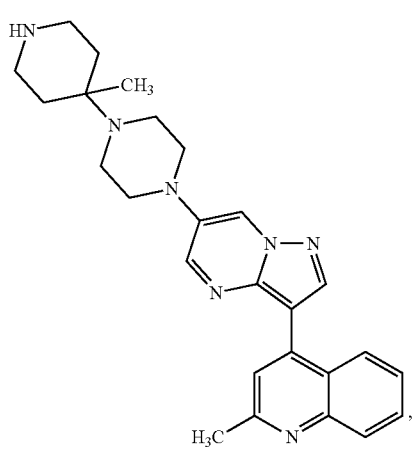
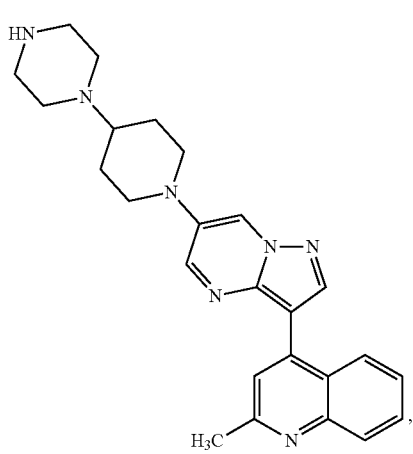
358
-continued
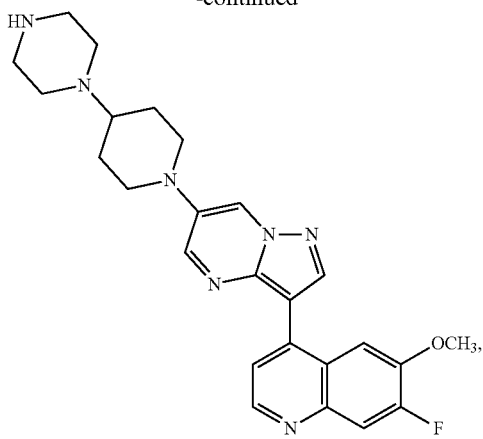
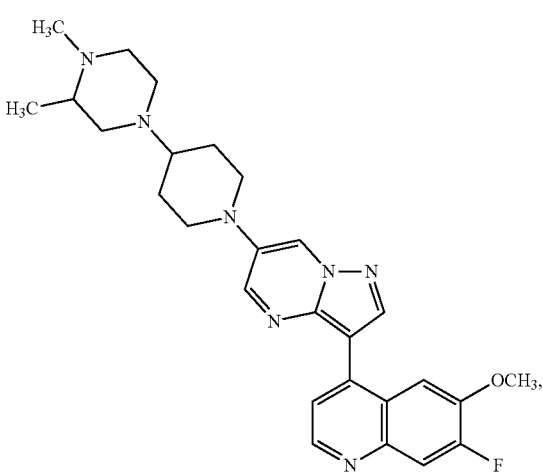

359
-continued
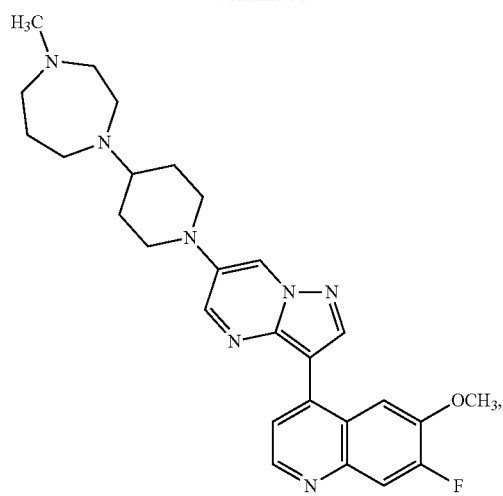
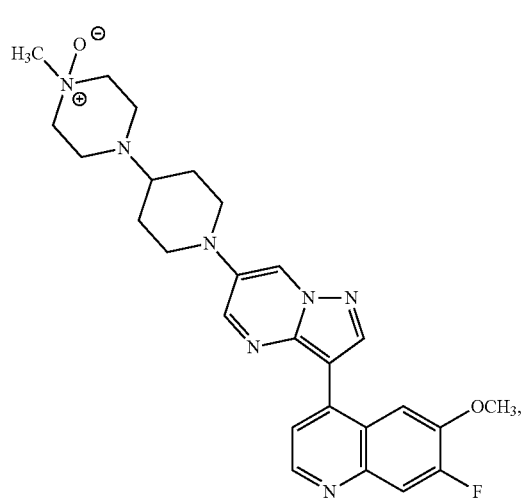
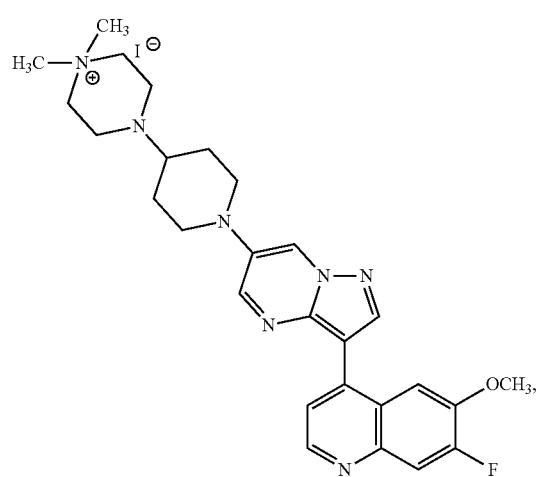
360
-continued
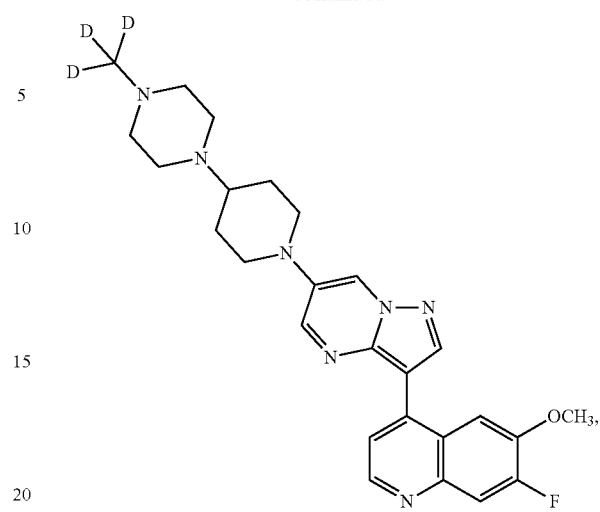
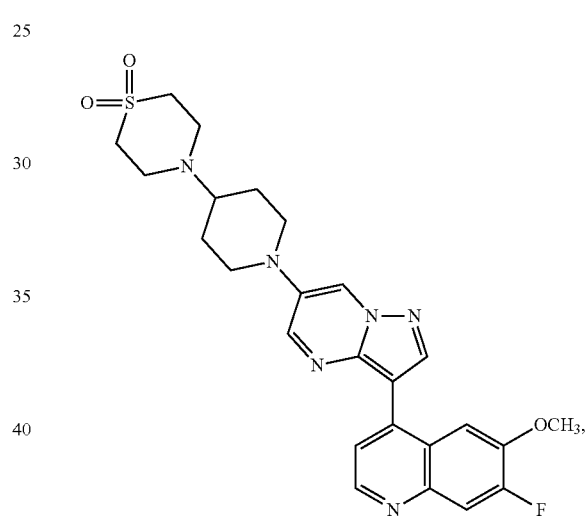
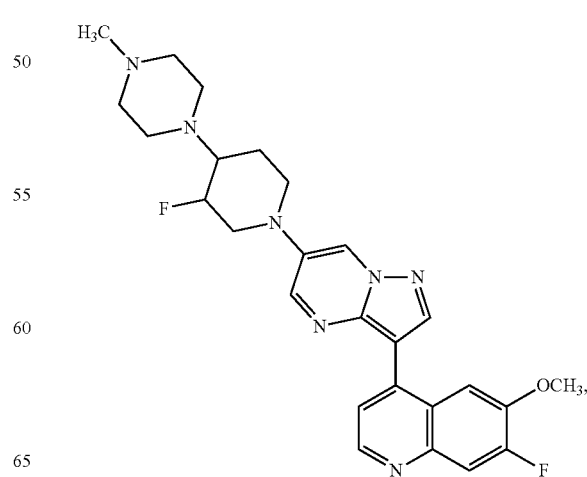

361
-continued
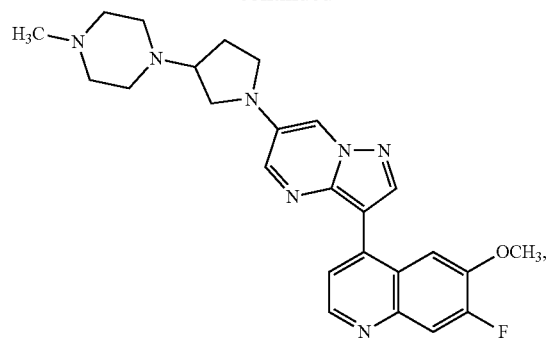
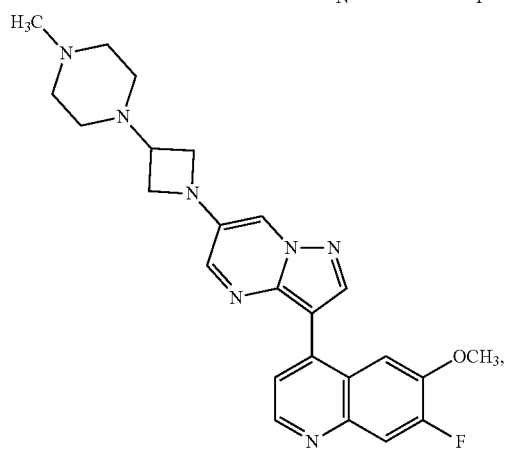
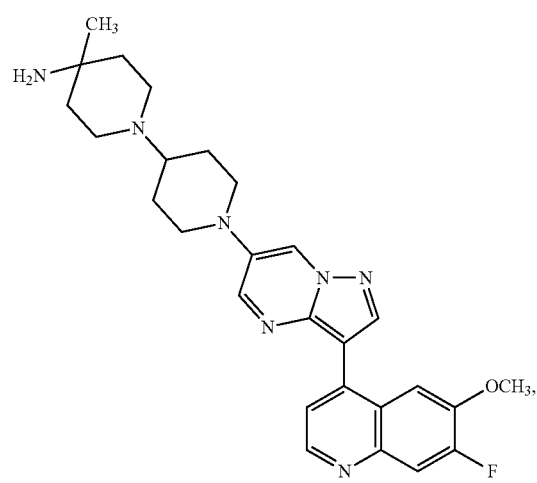
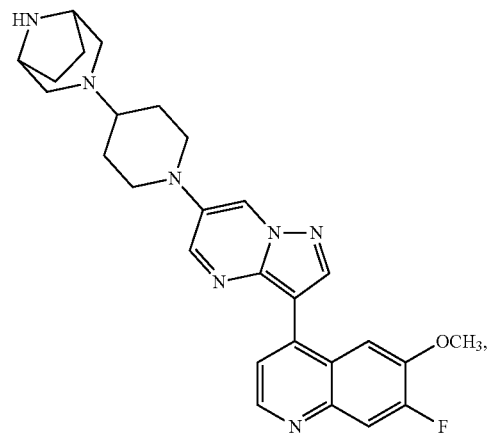
362
-continued
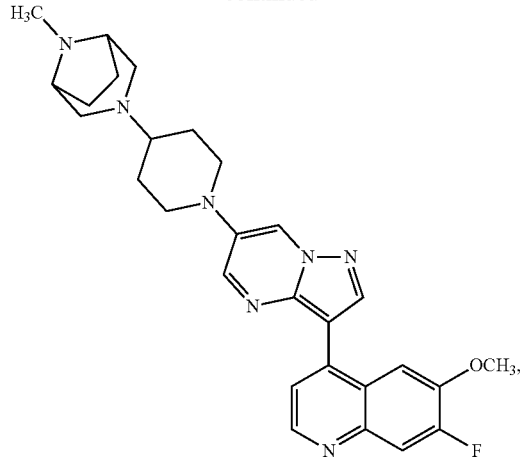
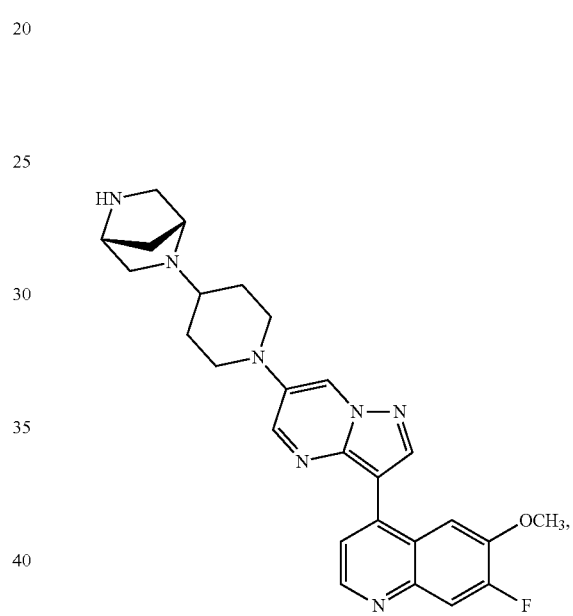
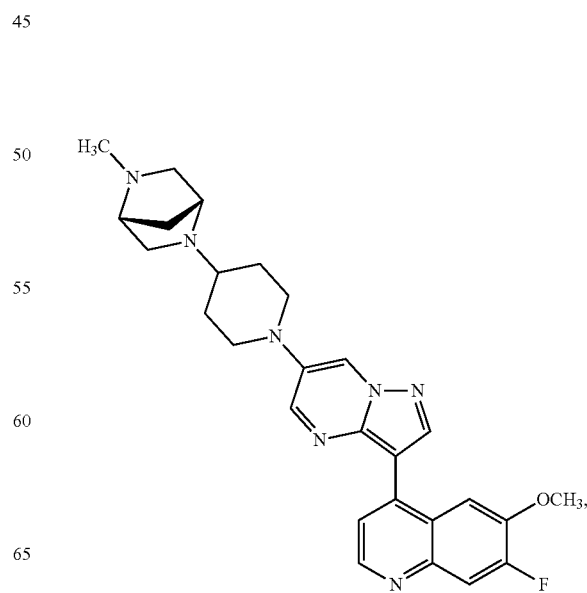

363
-continued
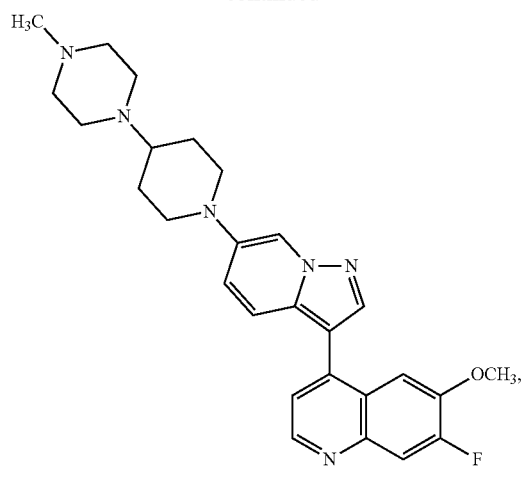
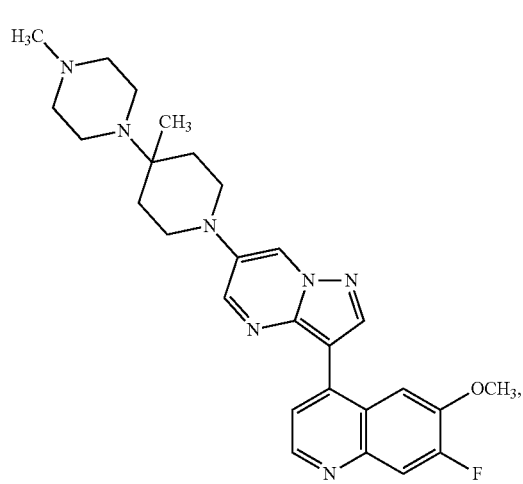
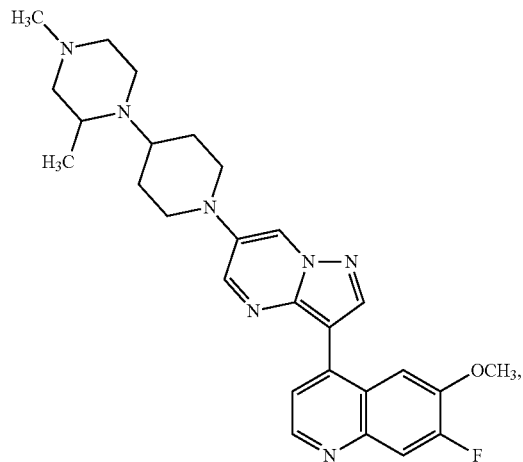
364
-continued
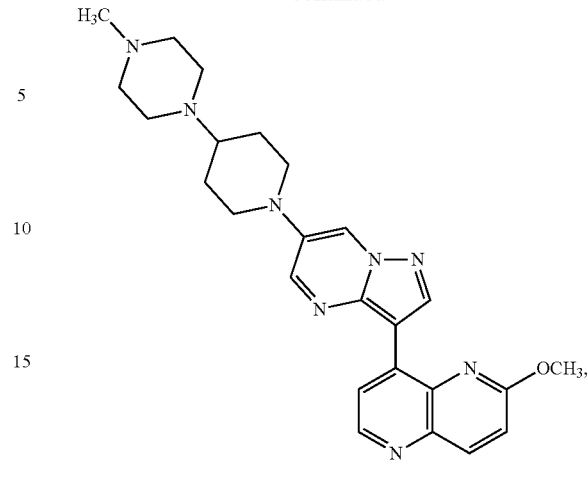
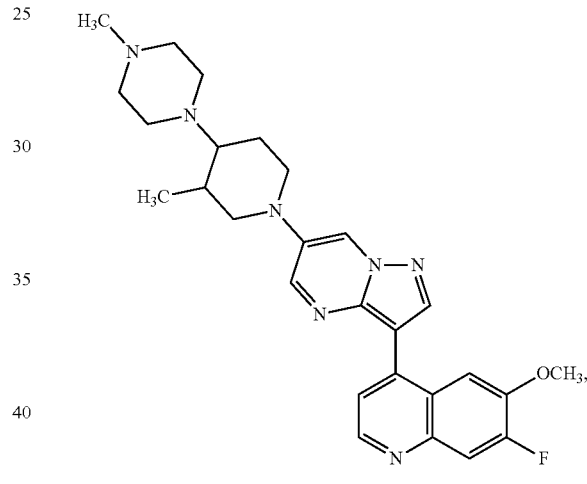
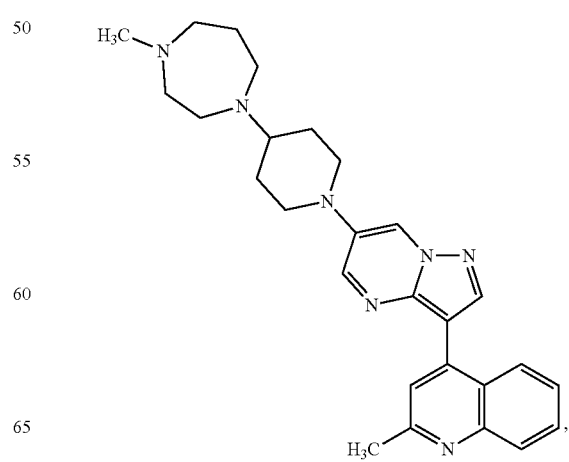

365
-continued
366
-continued
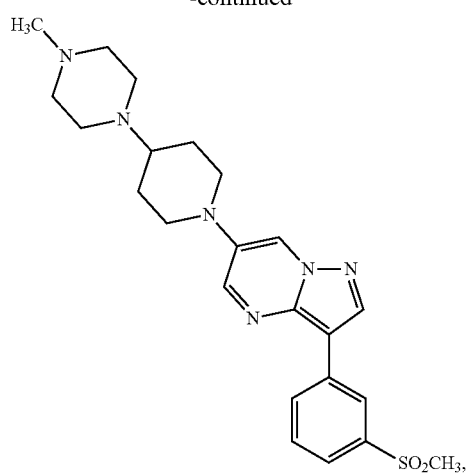
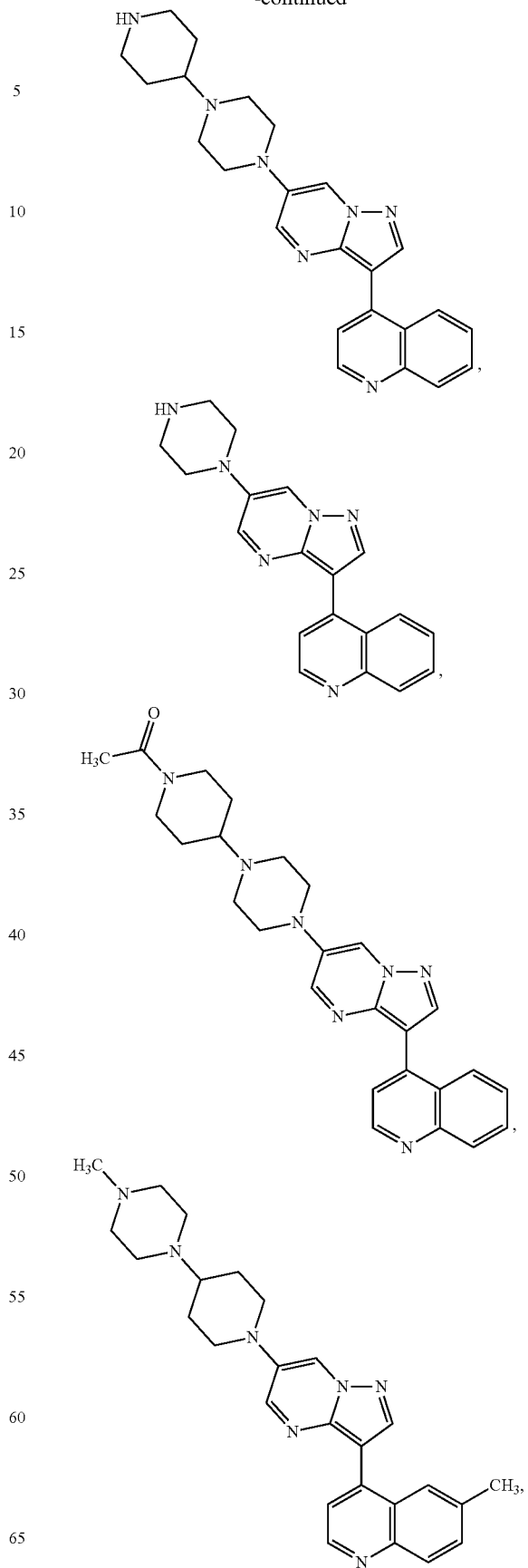

367
-continued
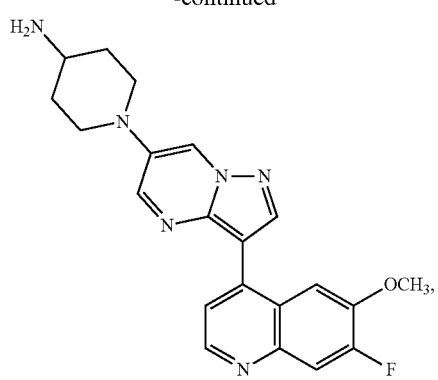
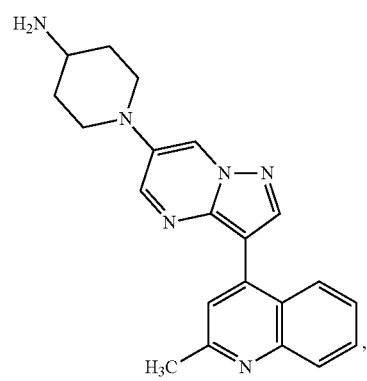
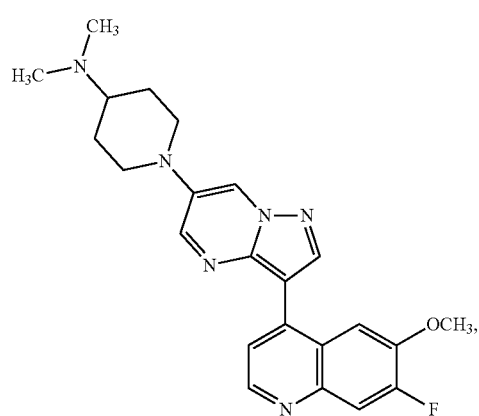
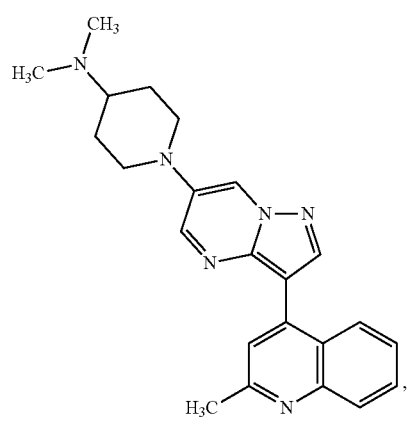
368
-continued
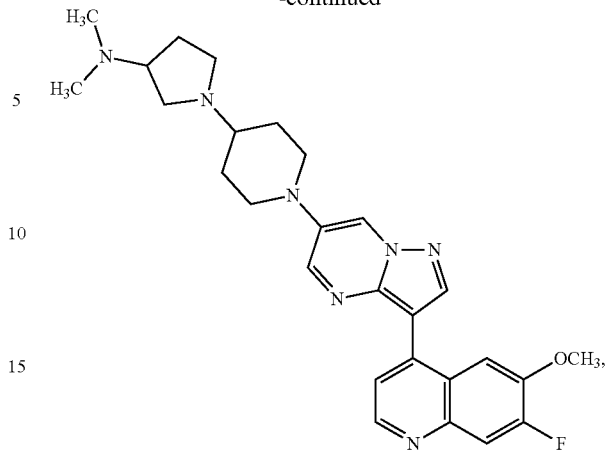
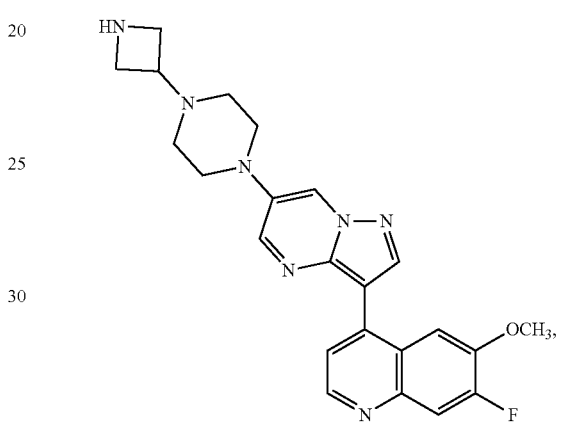
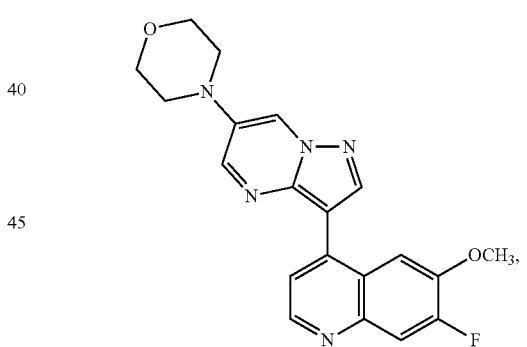
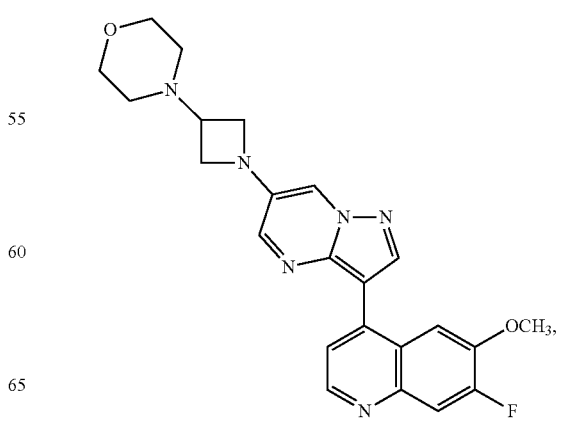

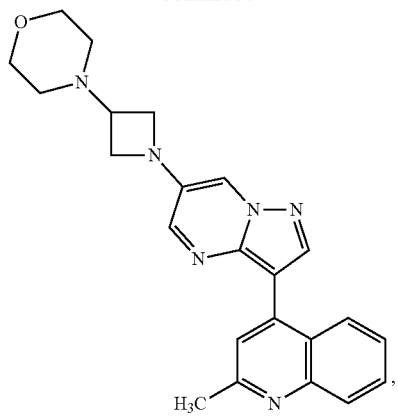
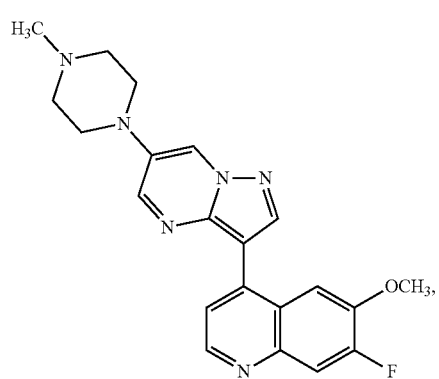
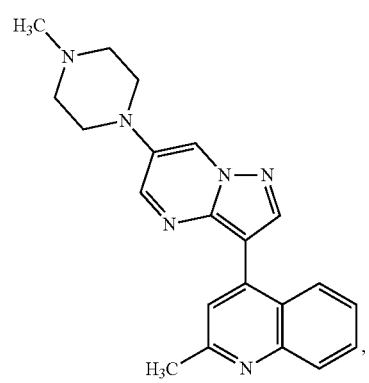
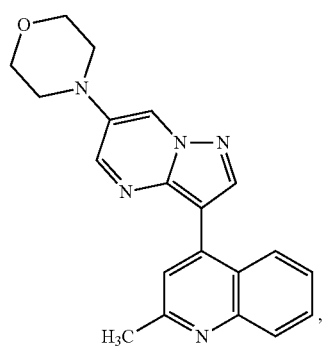
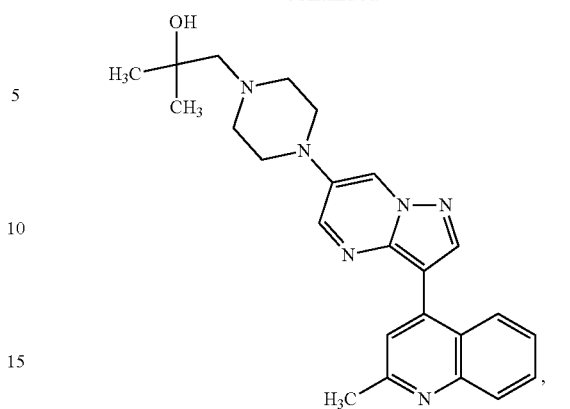
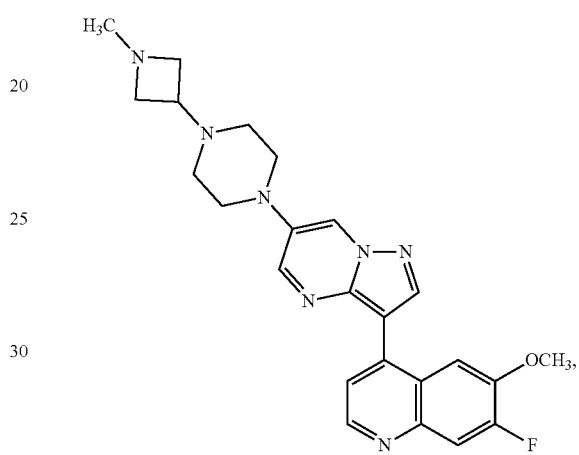
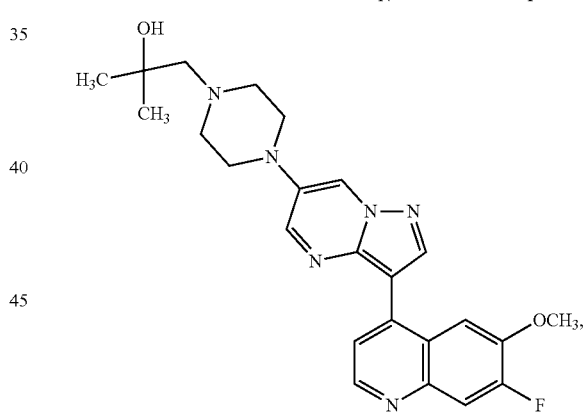
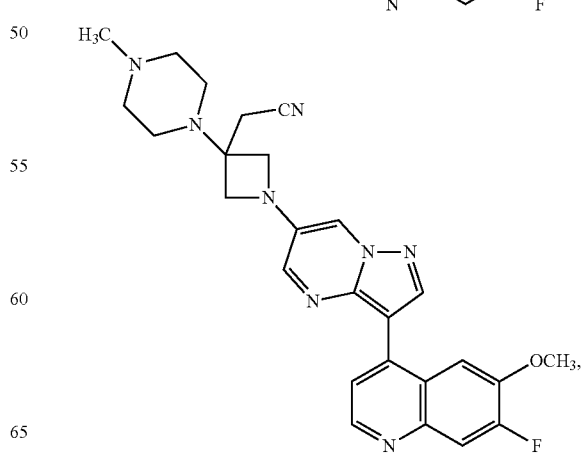

371
-continued
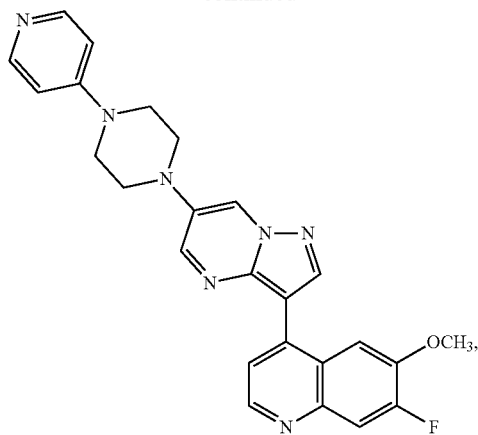
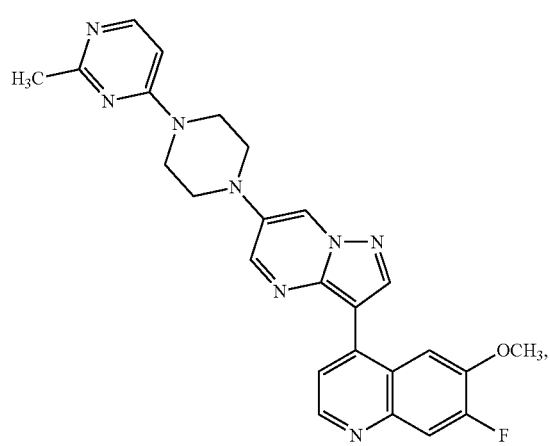
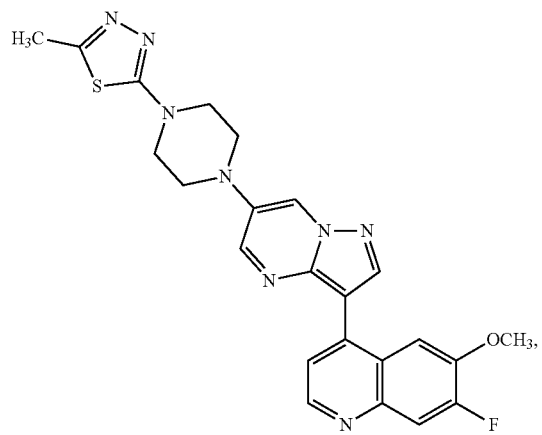
372
-continued
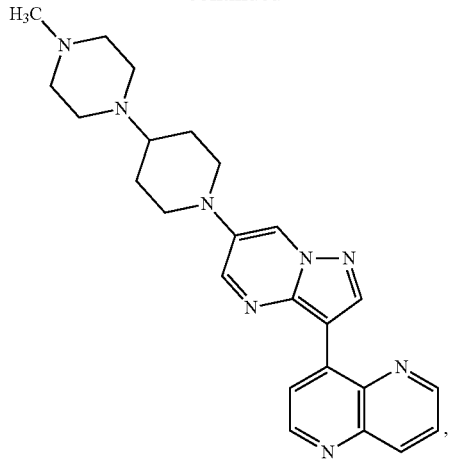
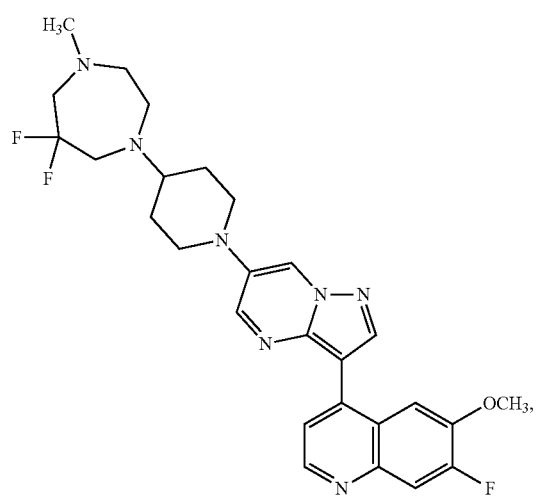
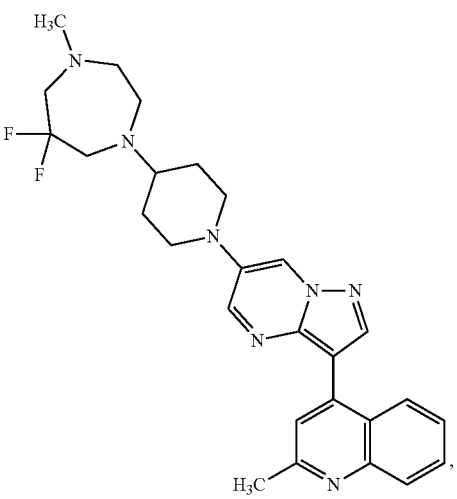

-continued
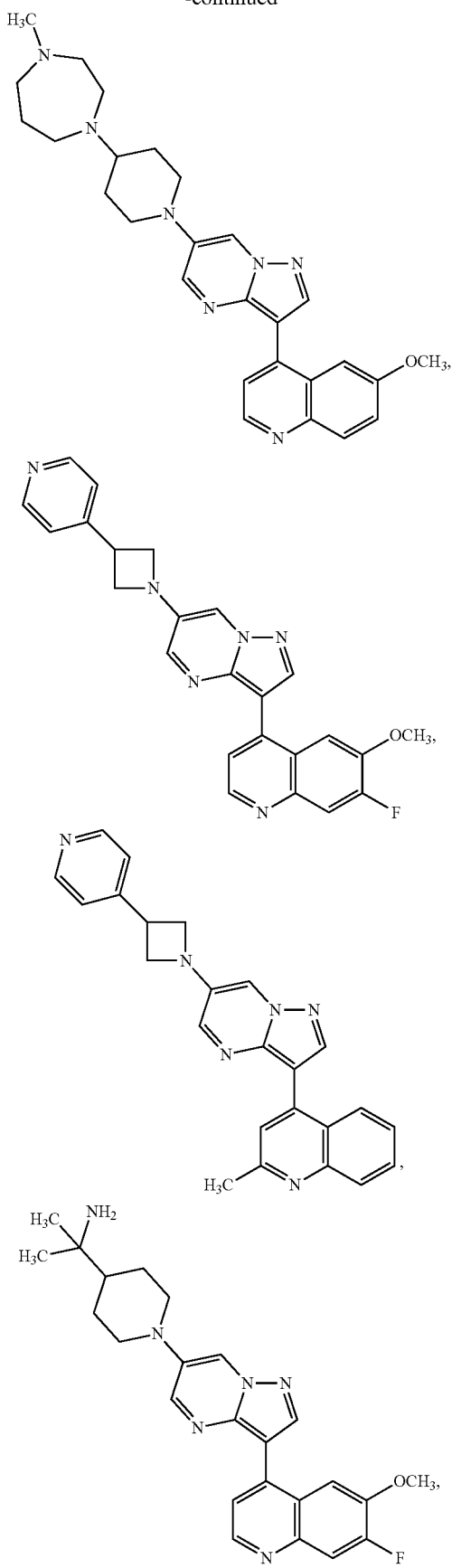
-continued
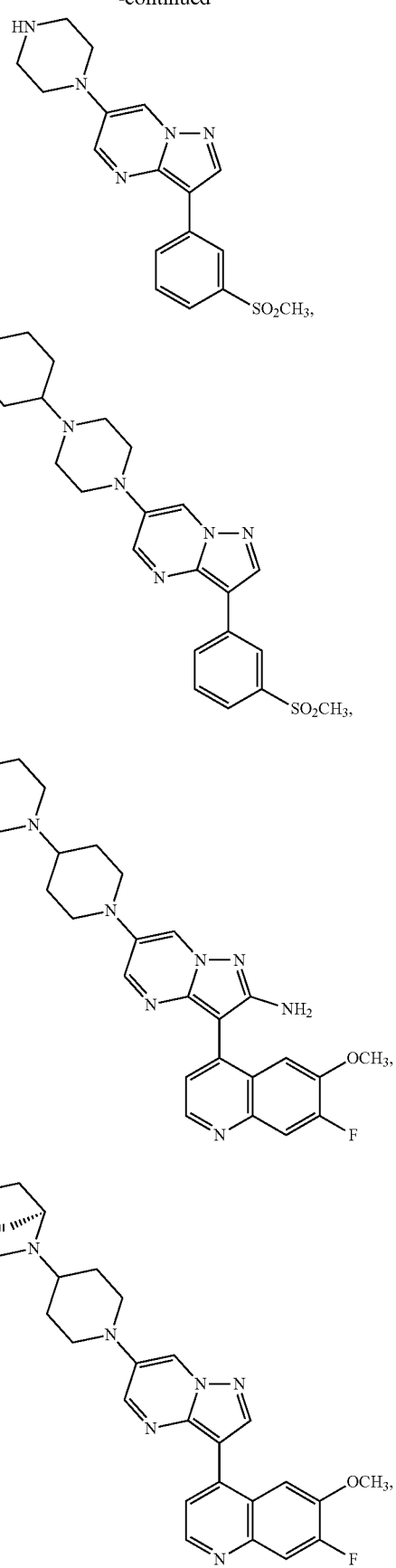

375
-continued
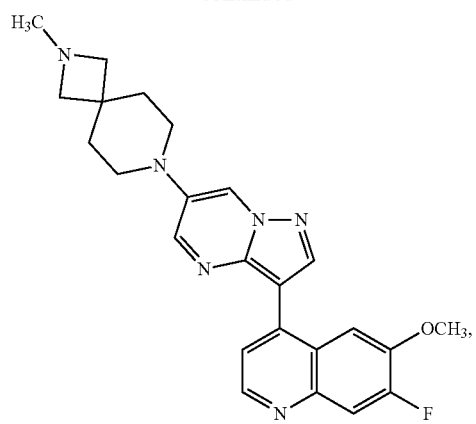
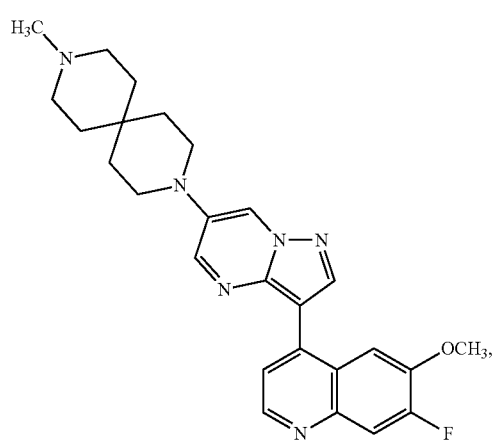
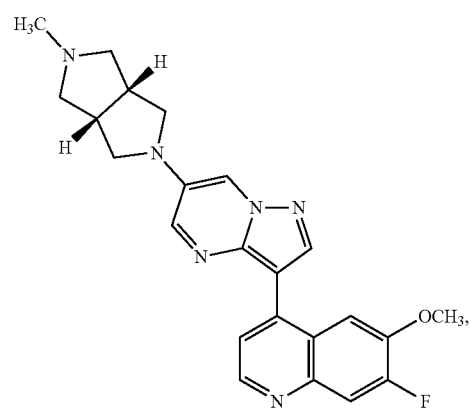
376
-continued
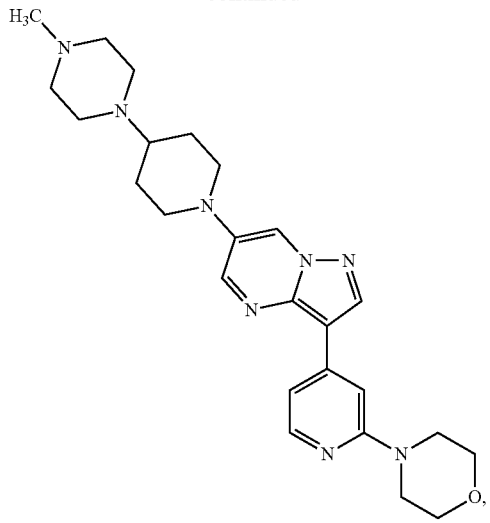
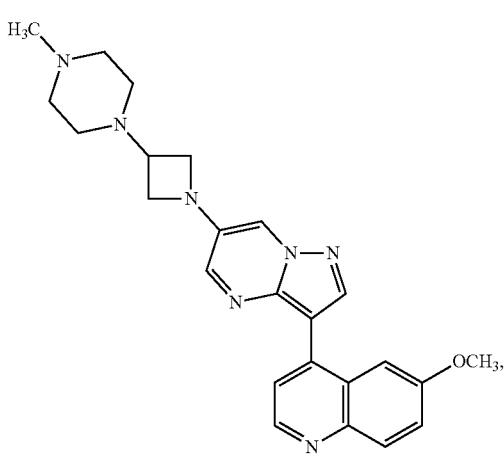

377
-continued
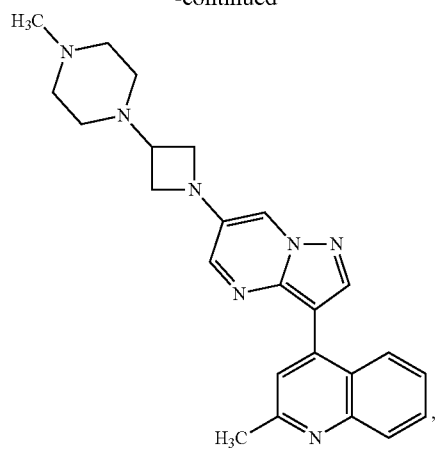
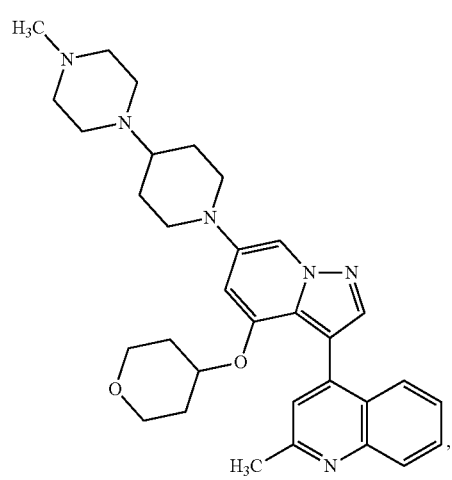
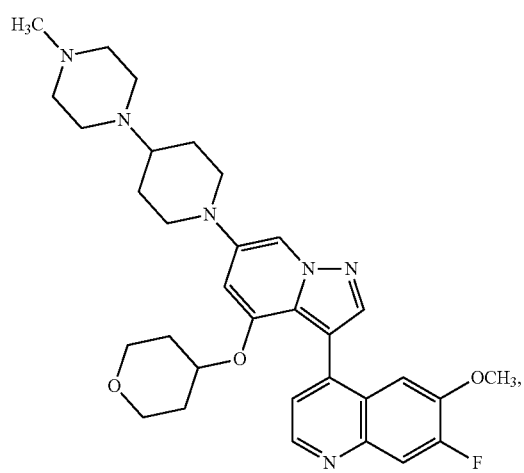
378
-continued
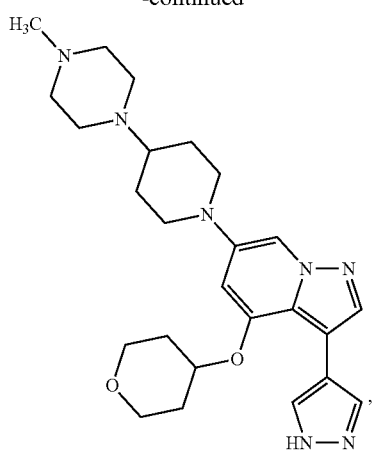
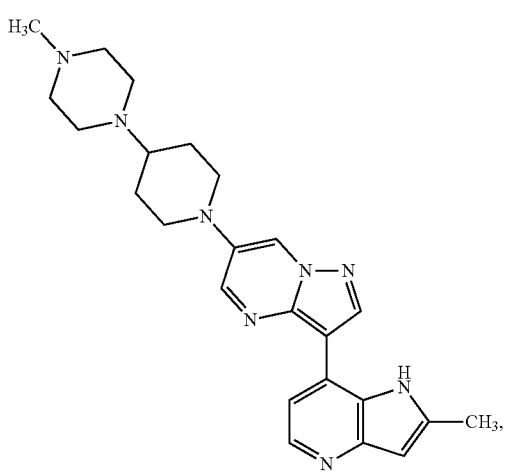

-continued
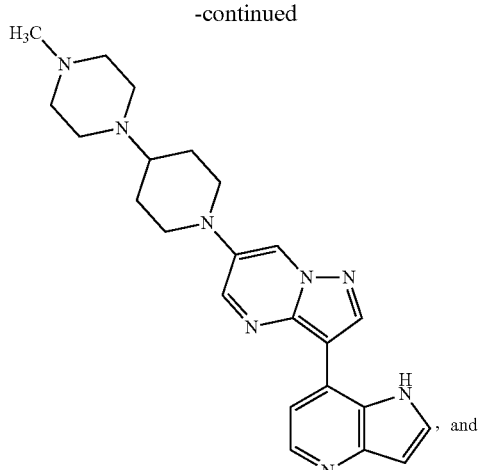
, and
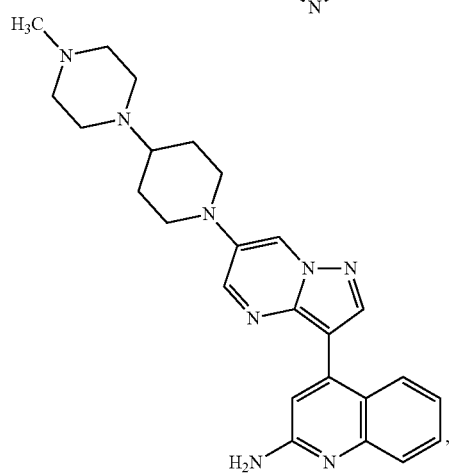
or a pharmaceutically acceptable salt thereof.
7. A compound having a formula selected from:
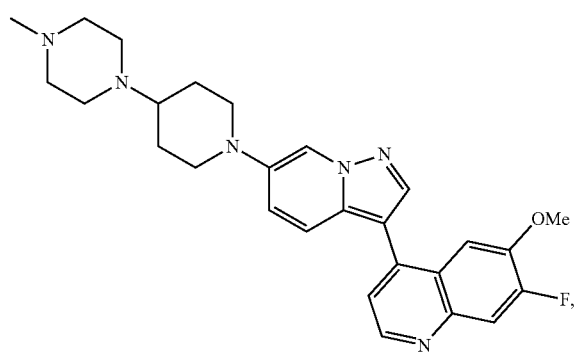
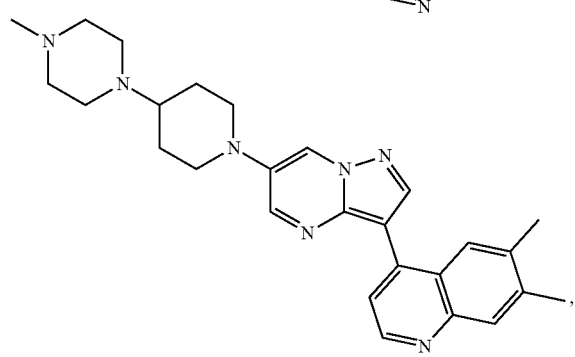
,
-continued
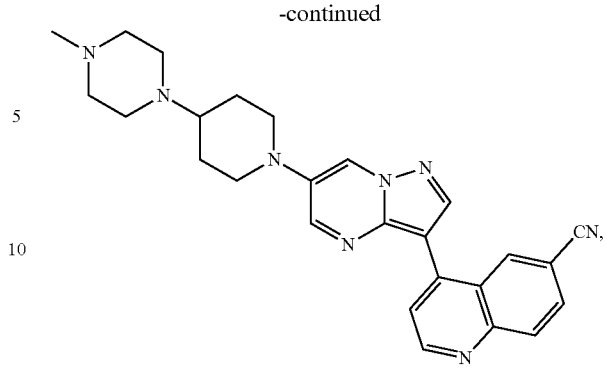
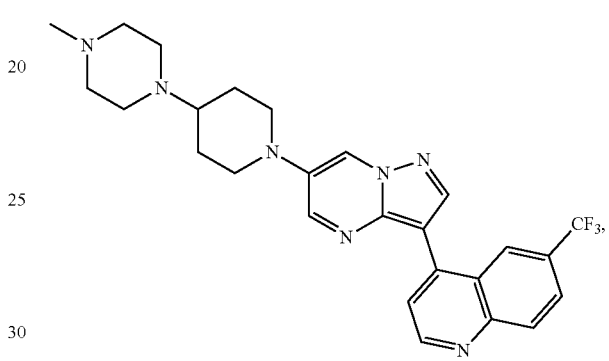
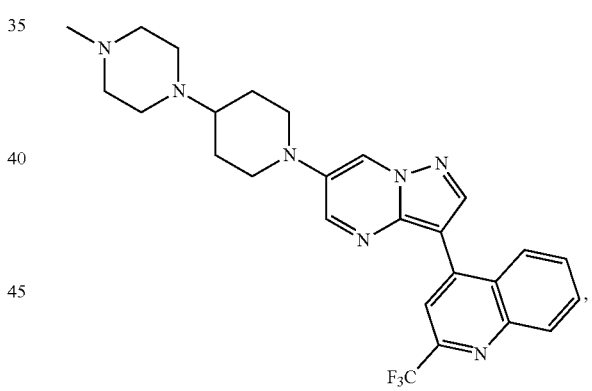
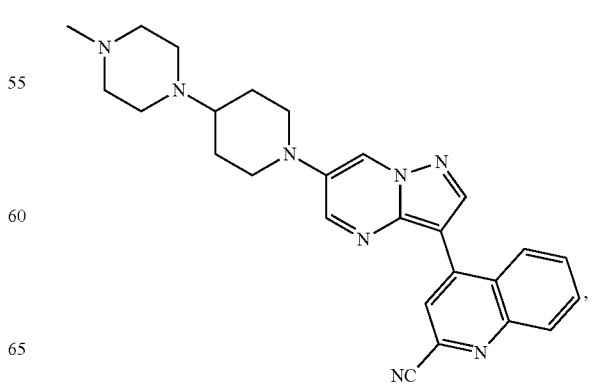

381
-continued
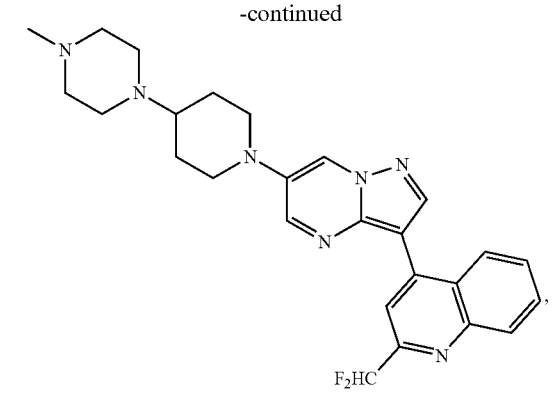
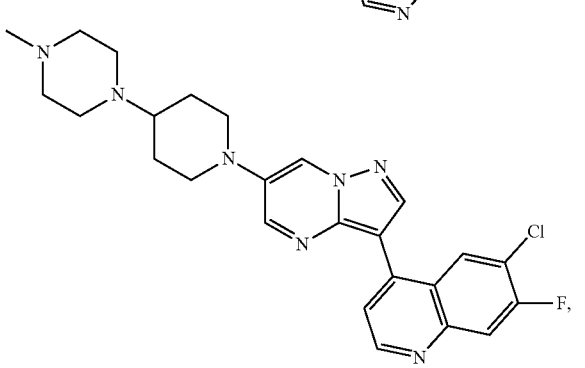
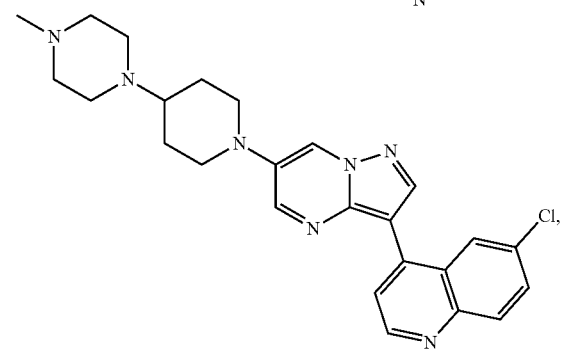
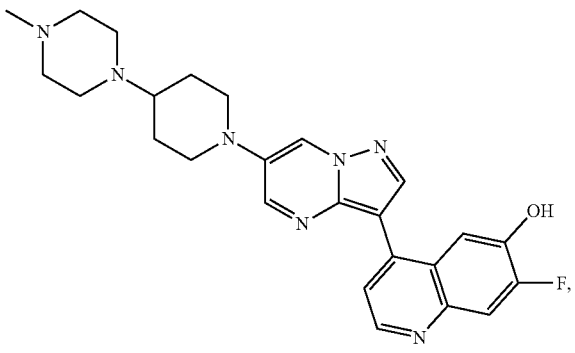
382
-continued
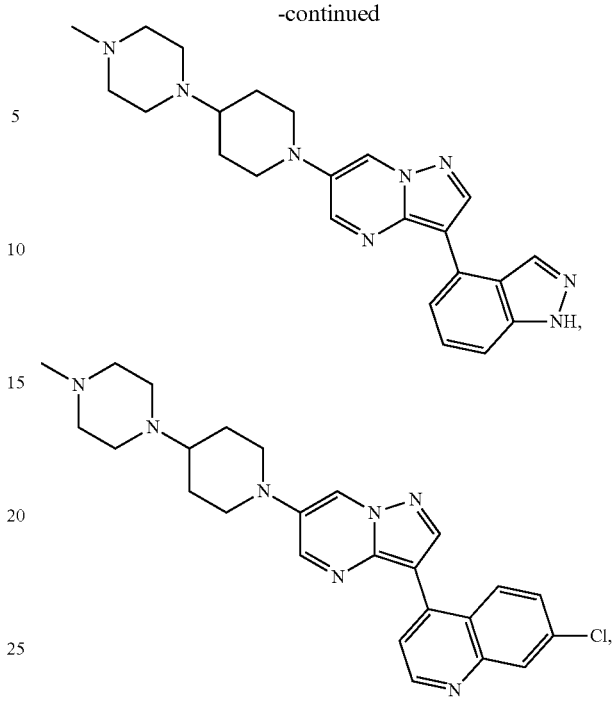
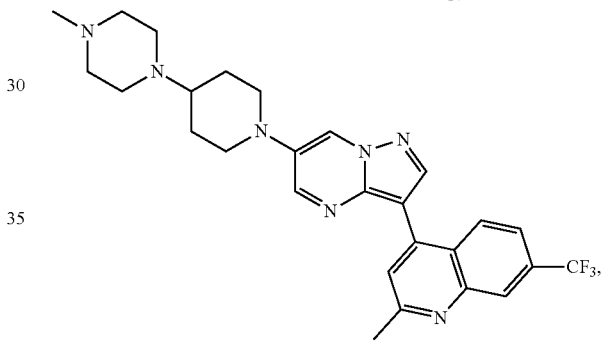
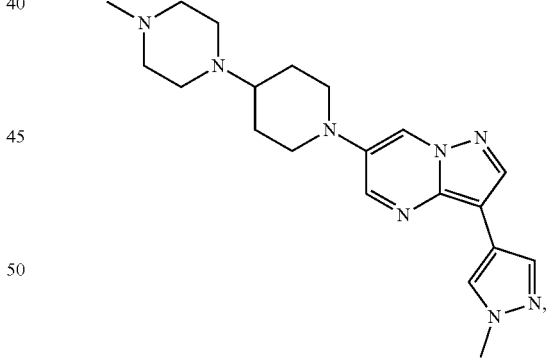
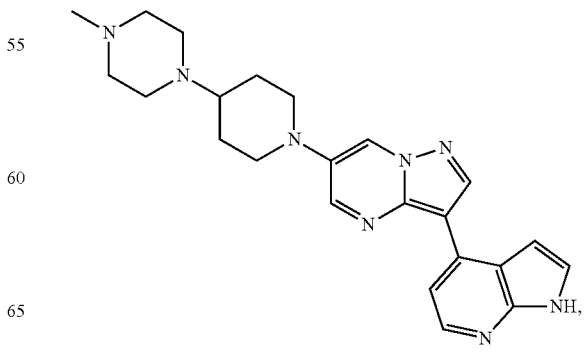

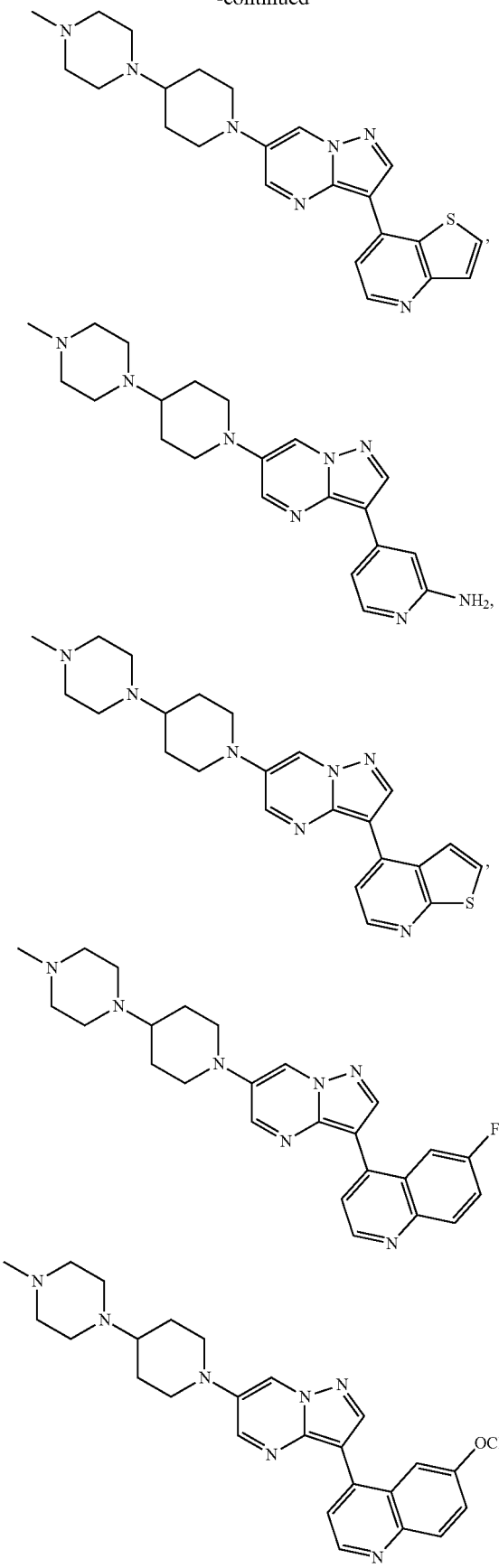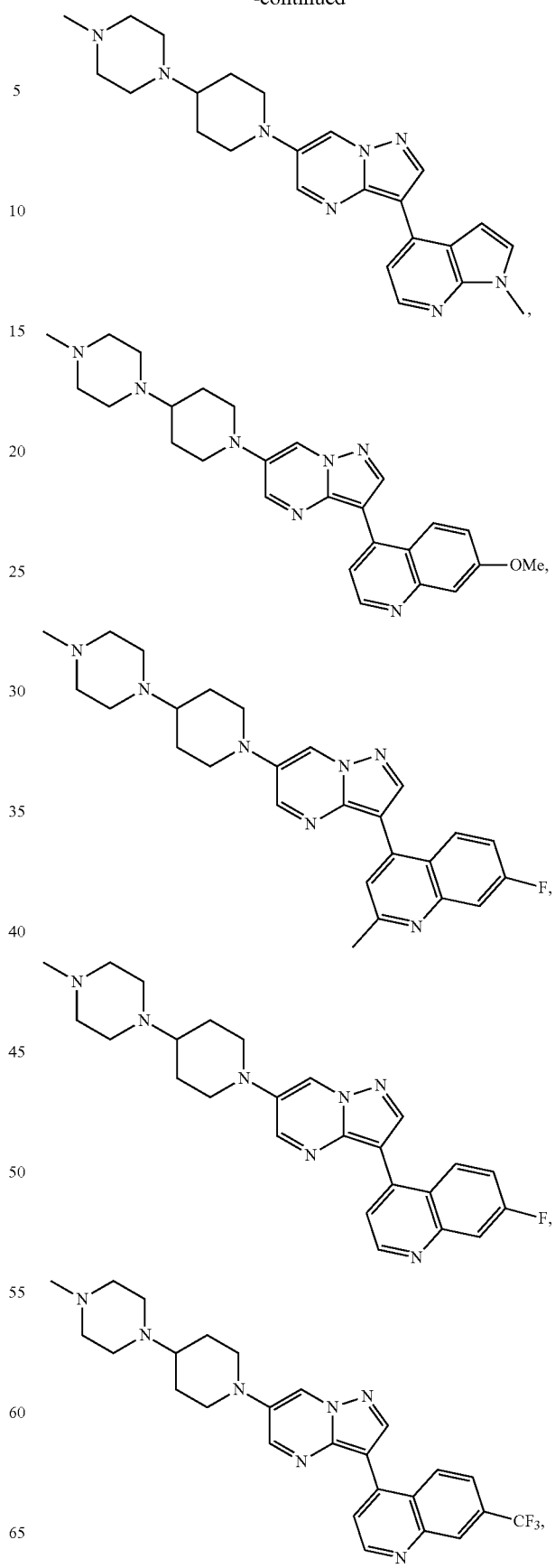

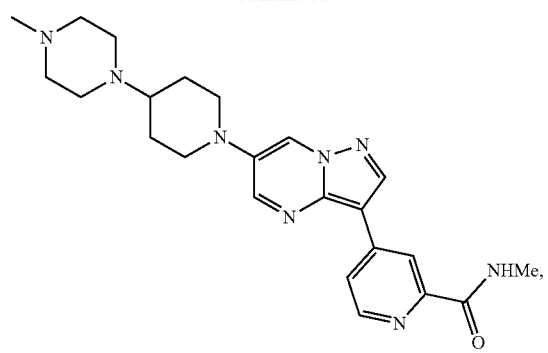
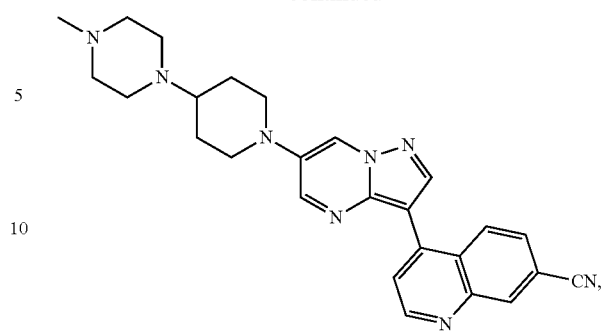
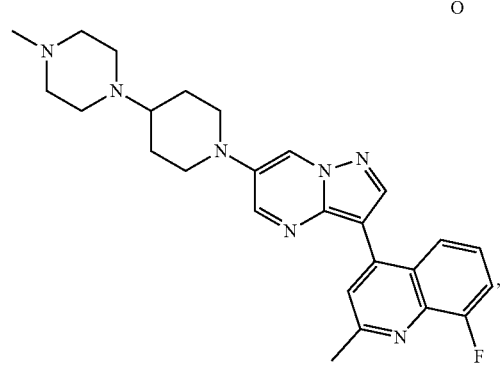
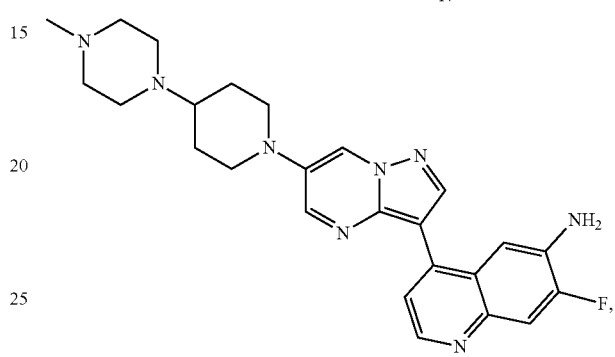
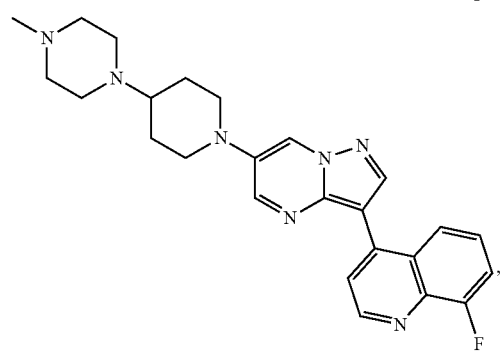
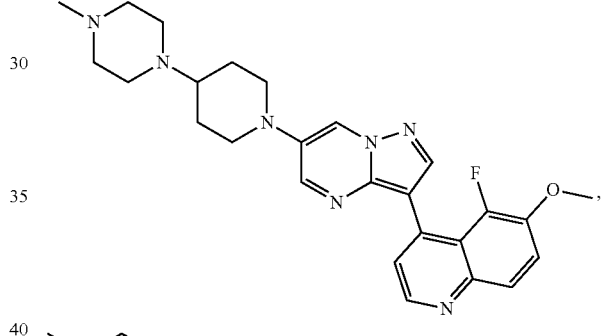
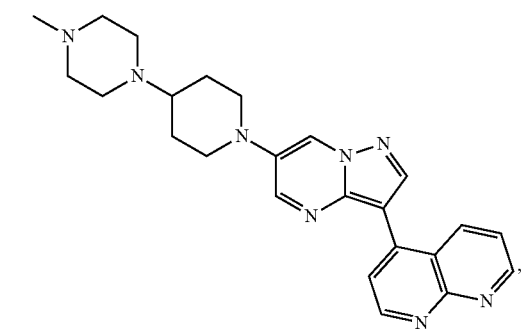
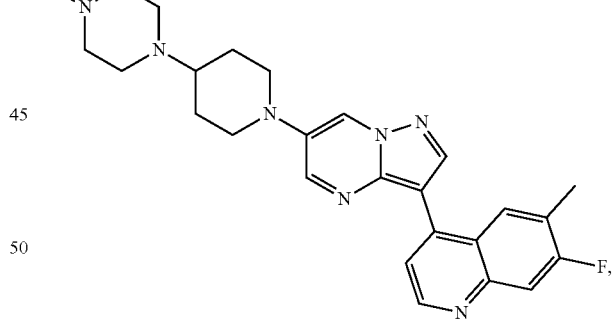
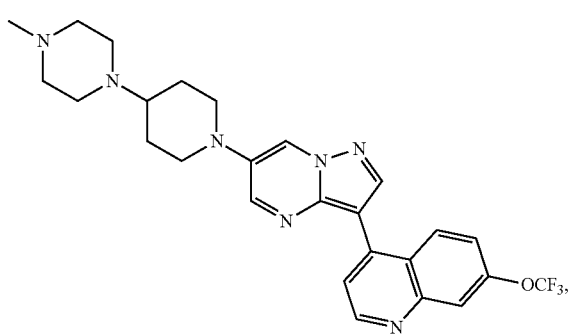

387
-continued
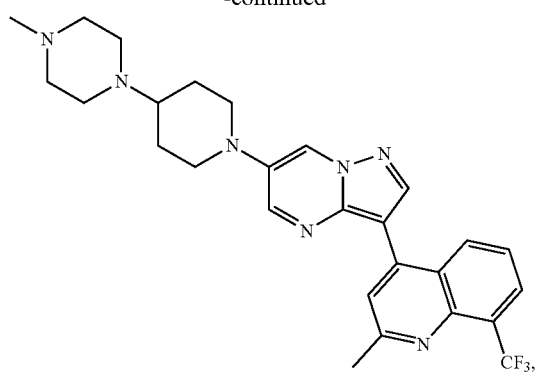
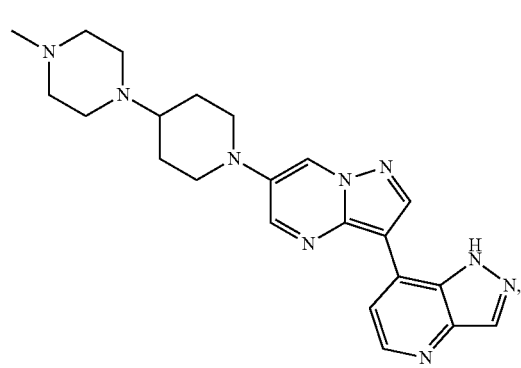
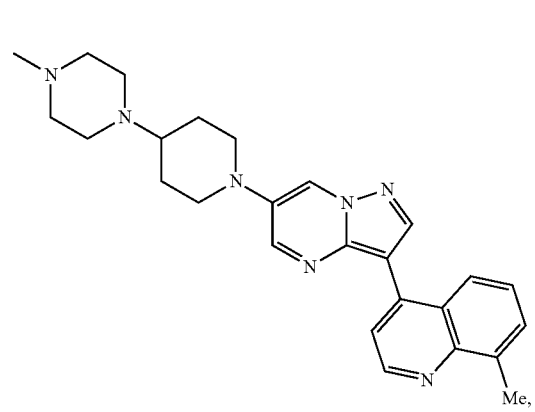
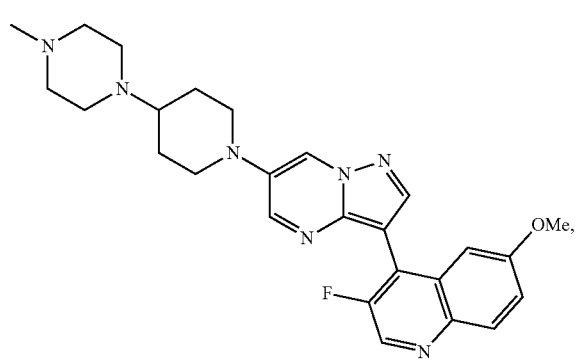
388
-continued
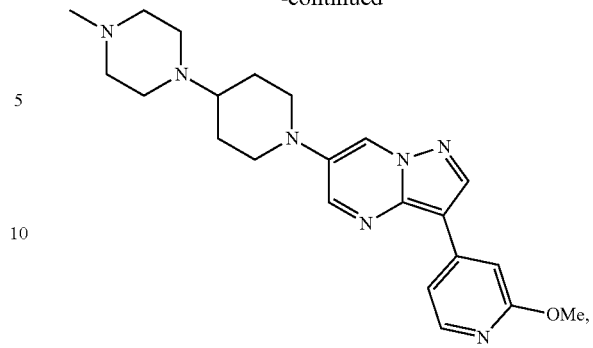
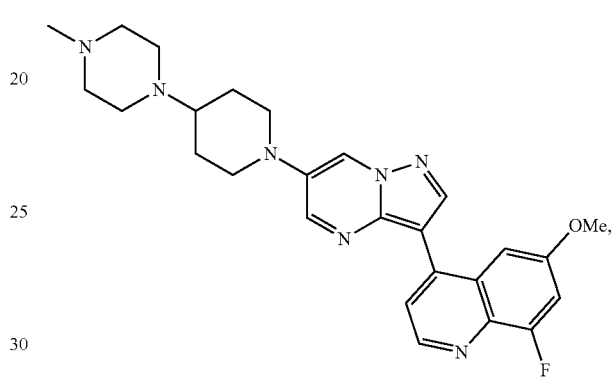
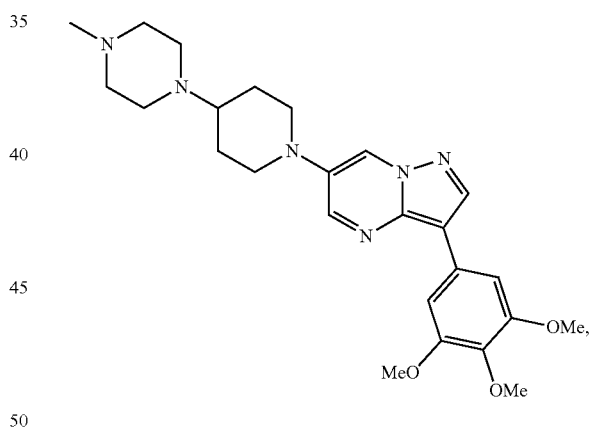
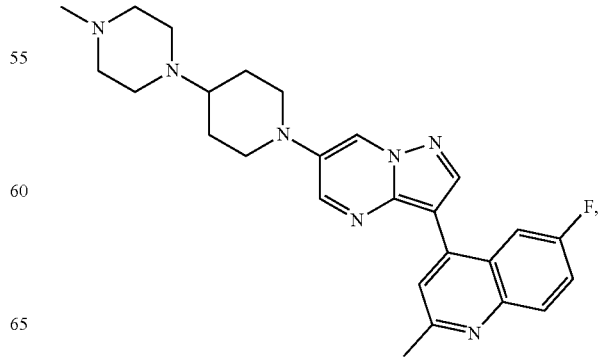

389
-continued
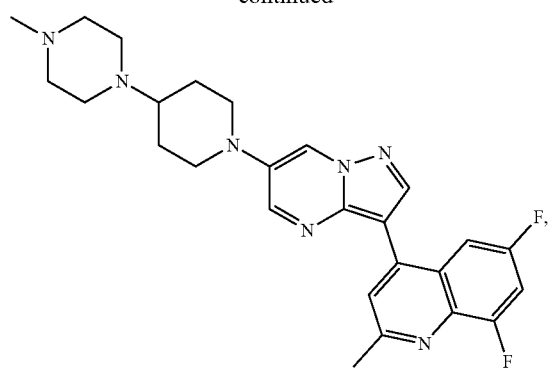
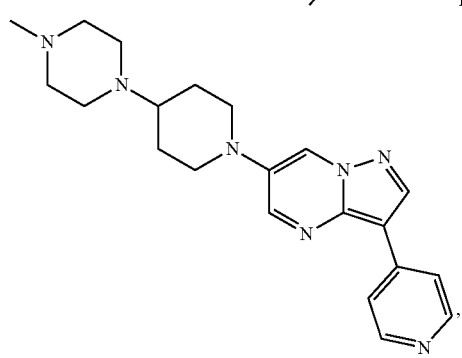
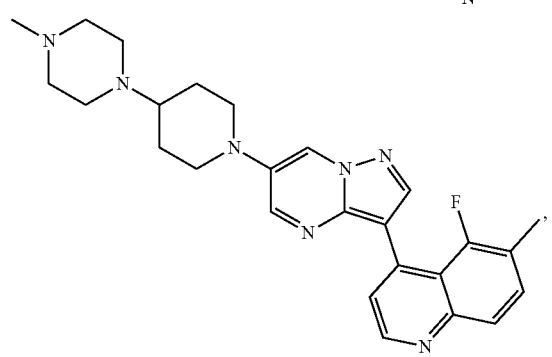
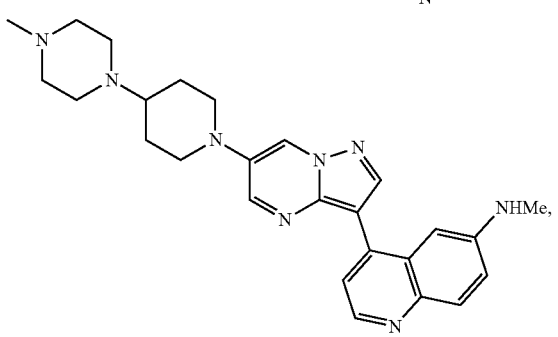
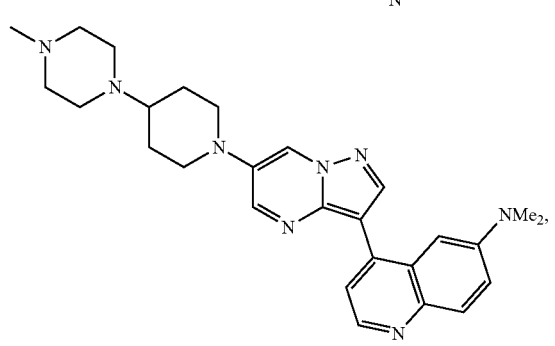
390
-continued
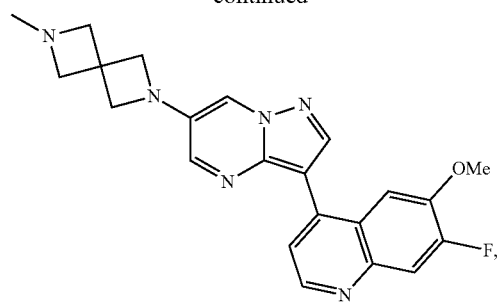
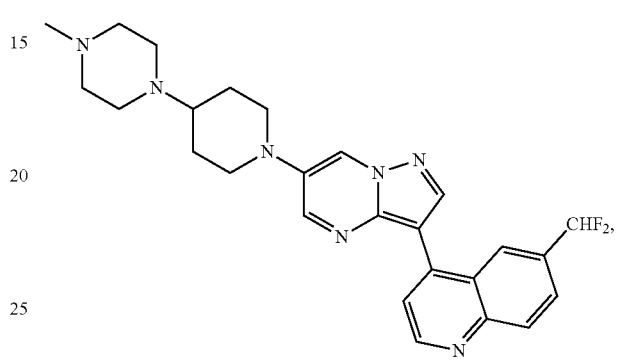
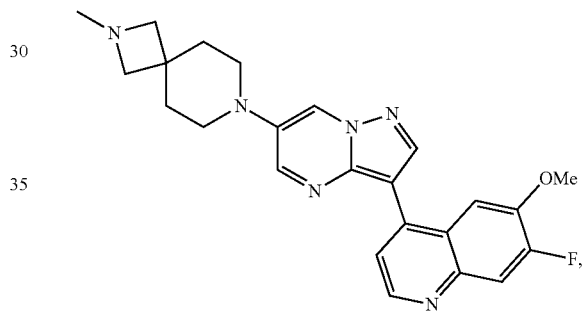
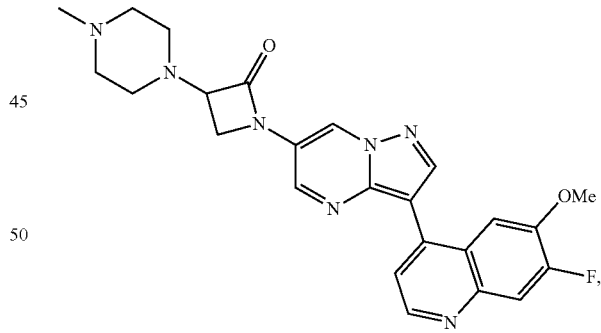
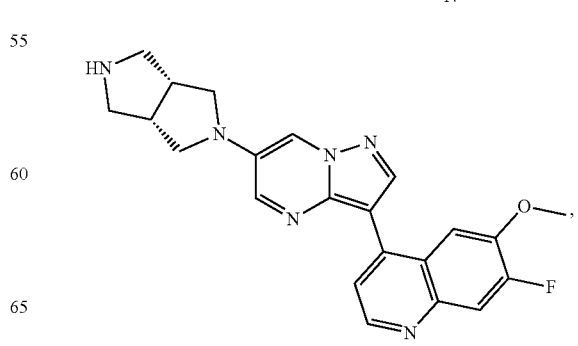

391
-continued
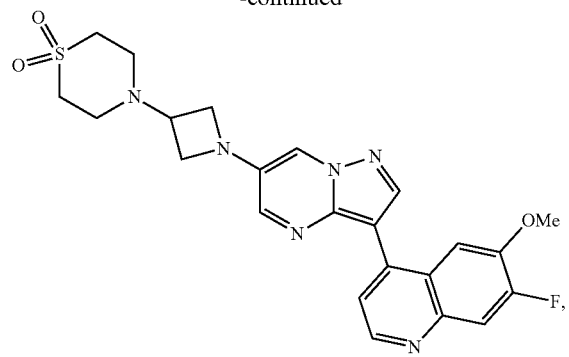
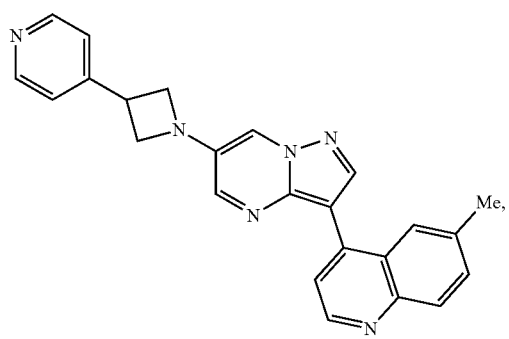
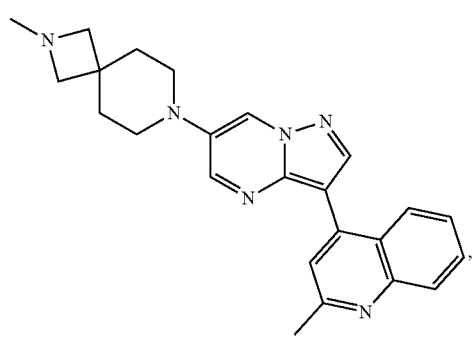
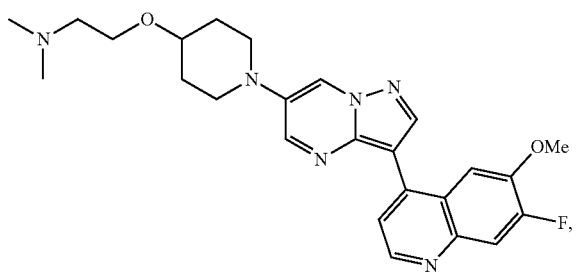
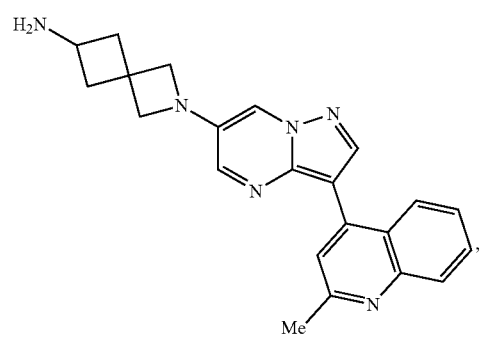
392
-continued
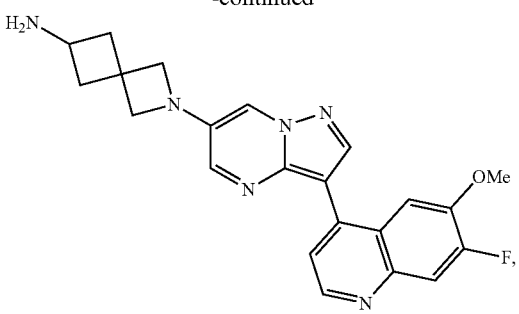
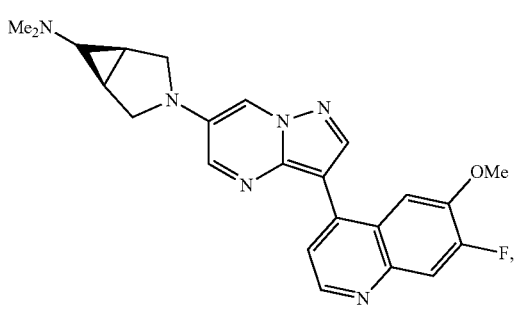
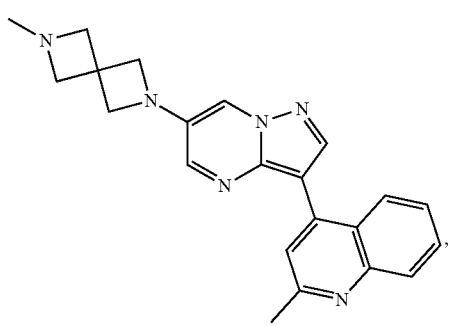
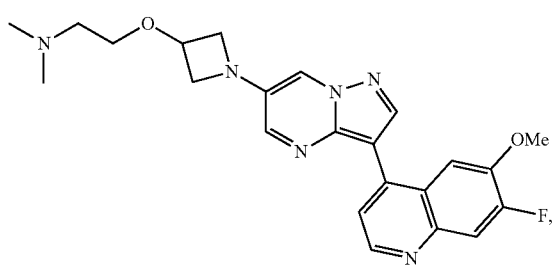
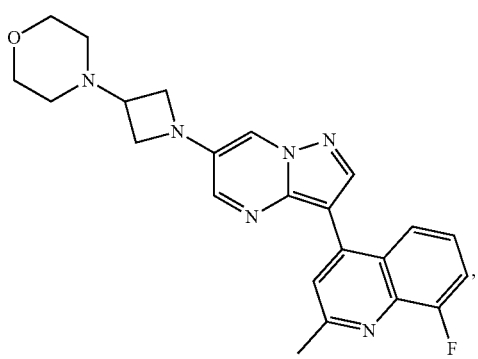

393
-continued
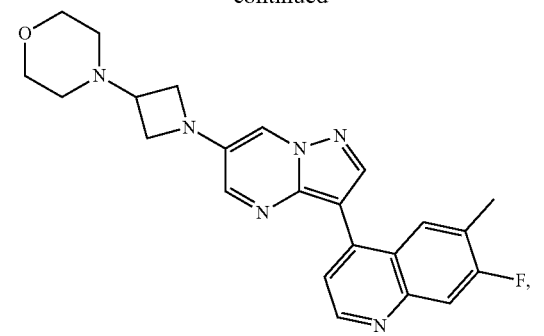
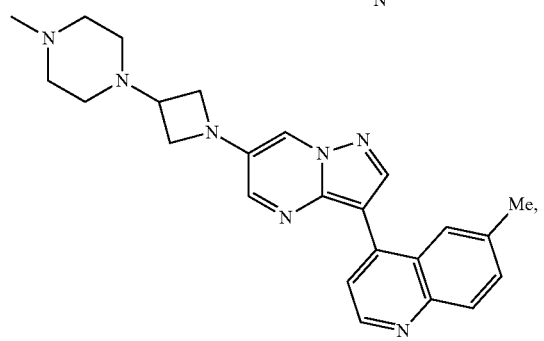
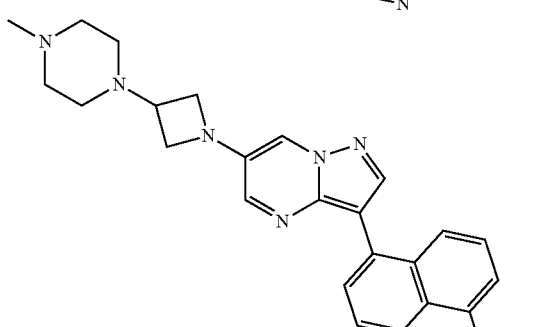
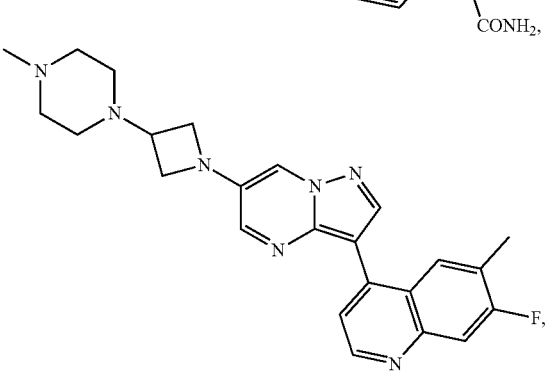
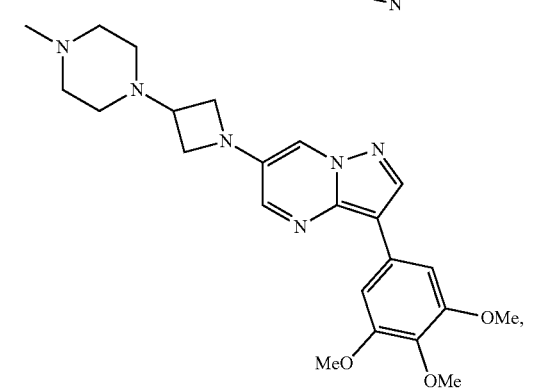
394
-continued
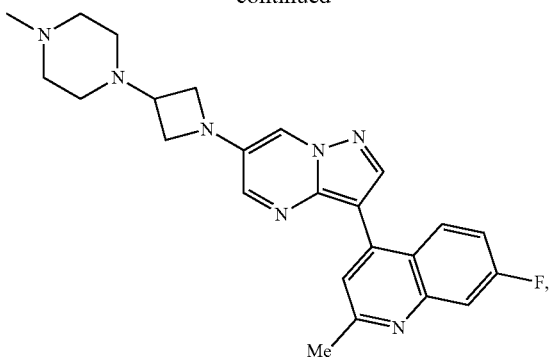
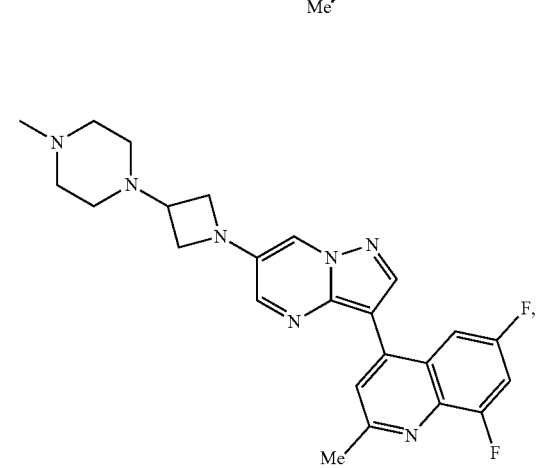
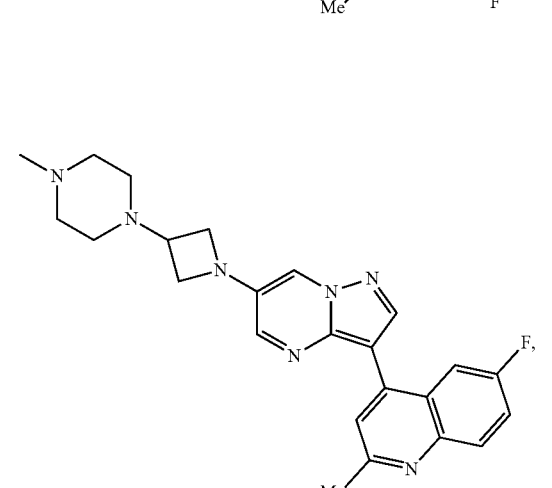
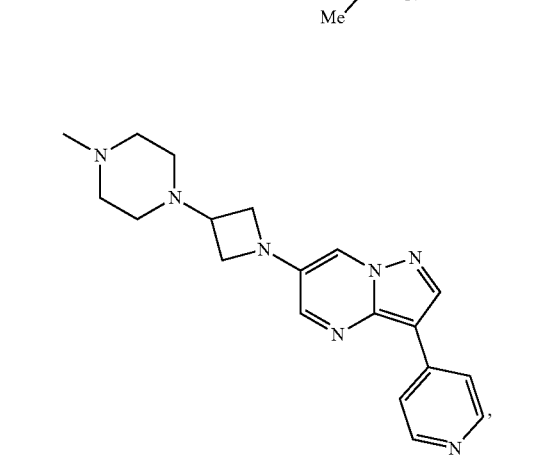

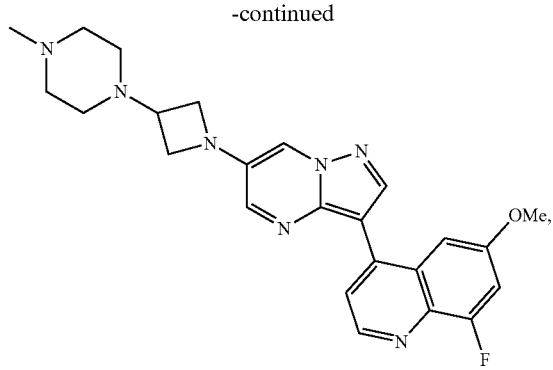
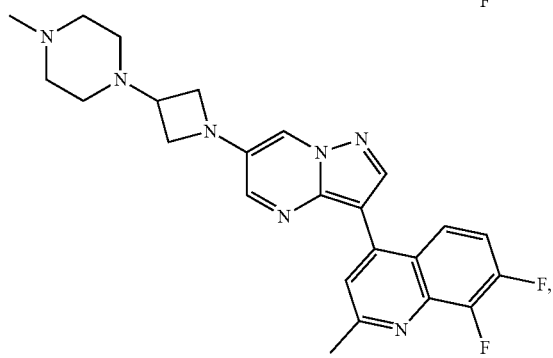
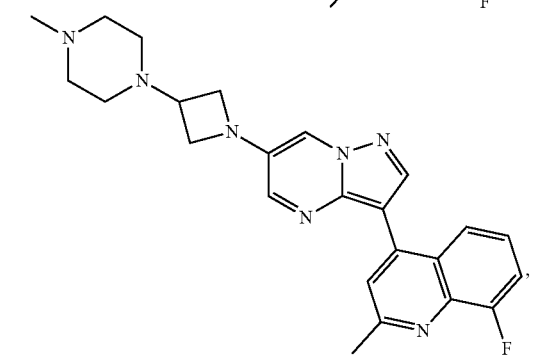
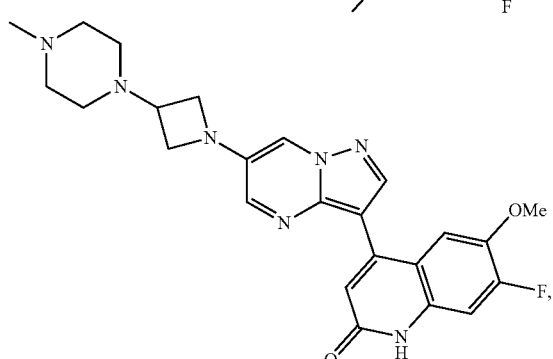
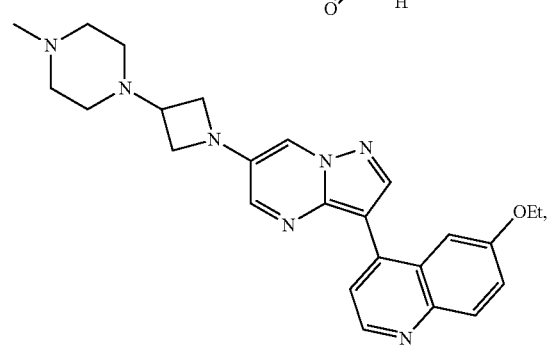
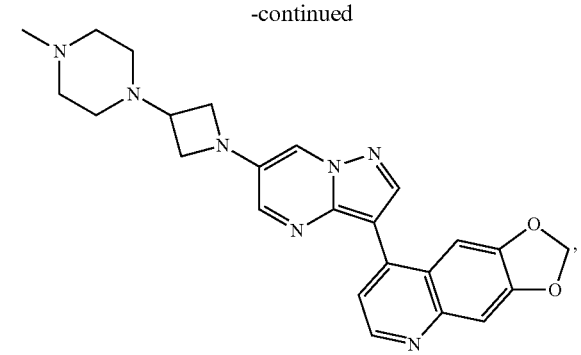
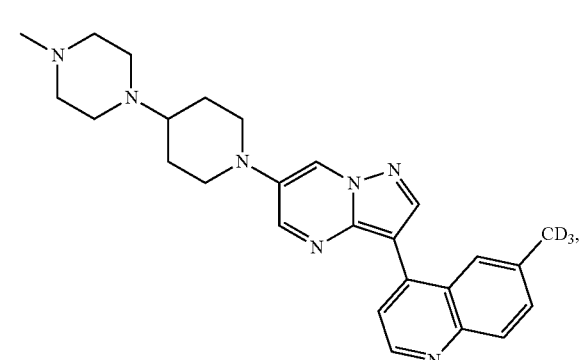
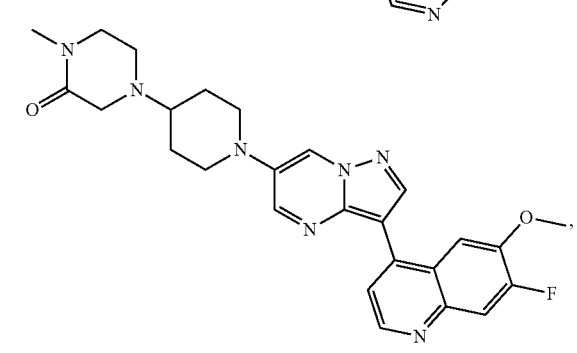
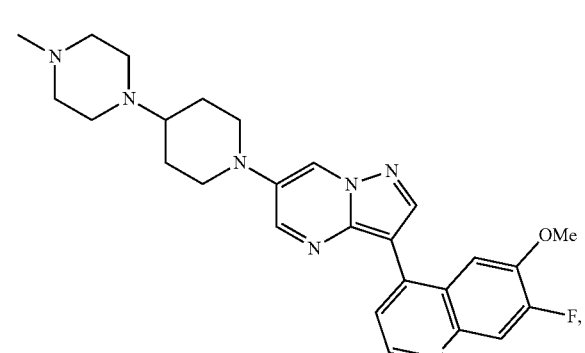
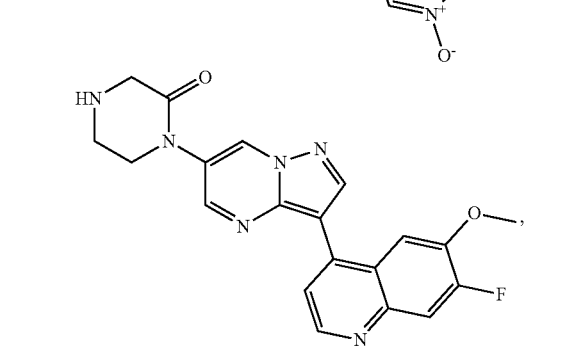

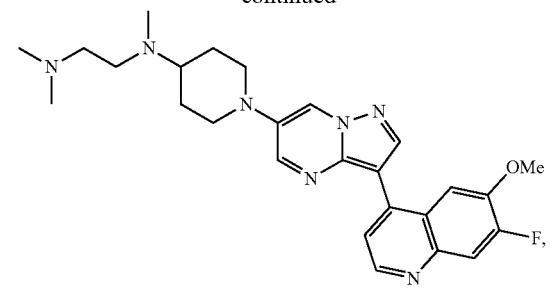
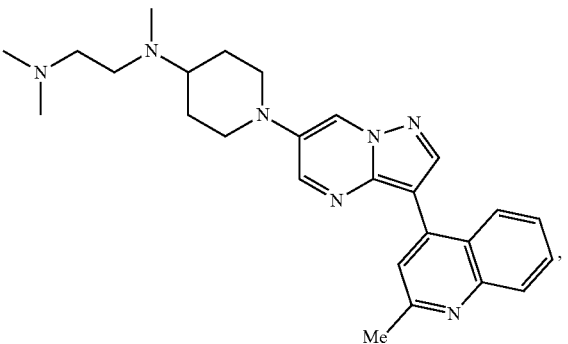
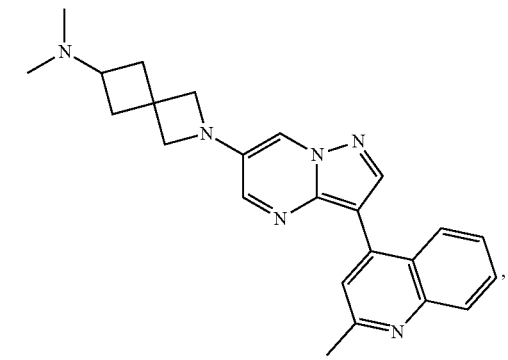
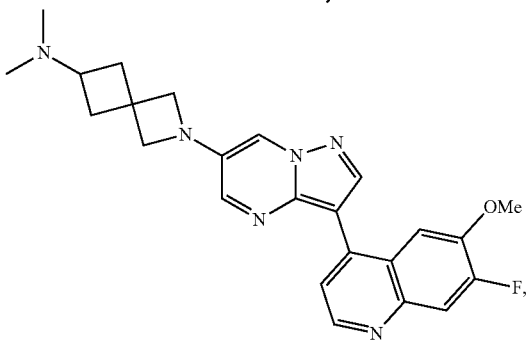
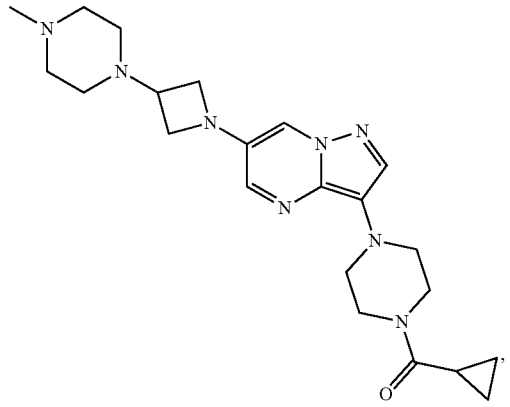
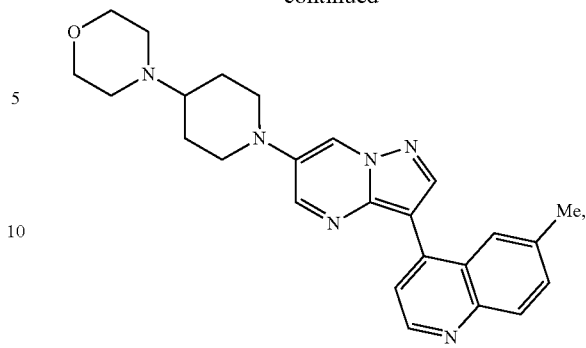
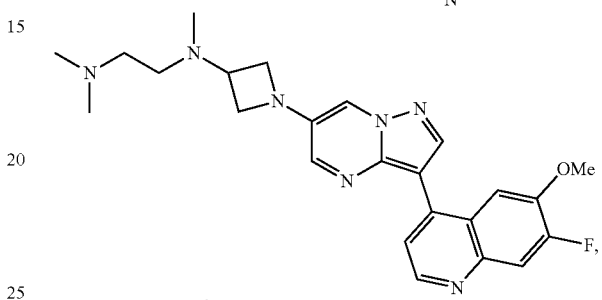
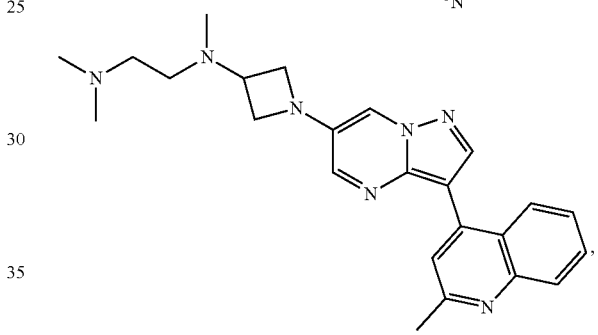
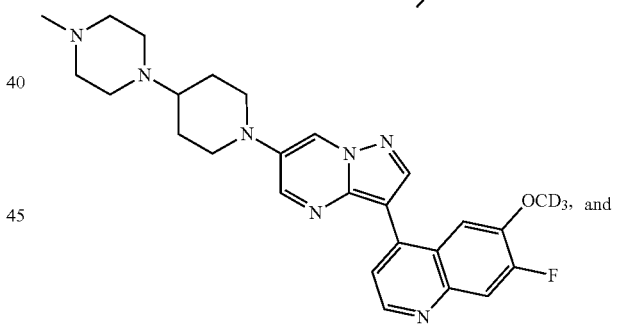
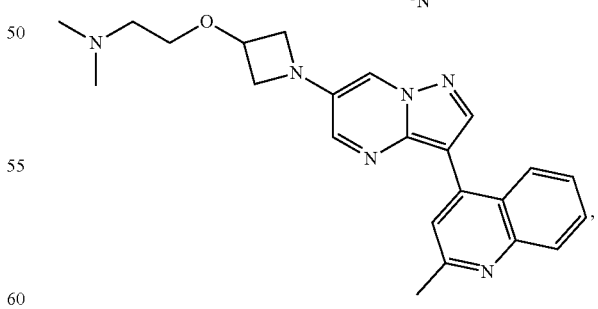
or a pharmaceutically acceptable salt thereof.
8. A pharmaceutical composition comprising a compound according to claim 1, or a pharmaceutically acceptable salt thereof, and one or more pharmaceutically acceptable excipients.

9. A method of treating a subject having anemia, comprising administering to the subject a therapeutically effective amount of a compound according to claim 1, or a pharmaceutically acceptable salt thereof.

10. The method of claim 9, wherein the anemia is iron deficiency anemia or anemia of inflammation.

11. The method of claim 9, wherein the compound is:

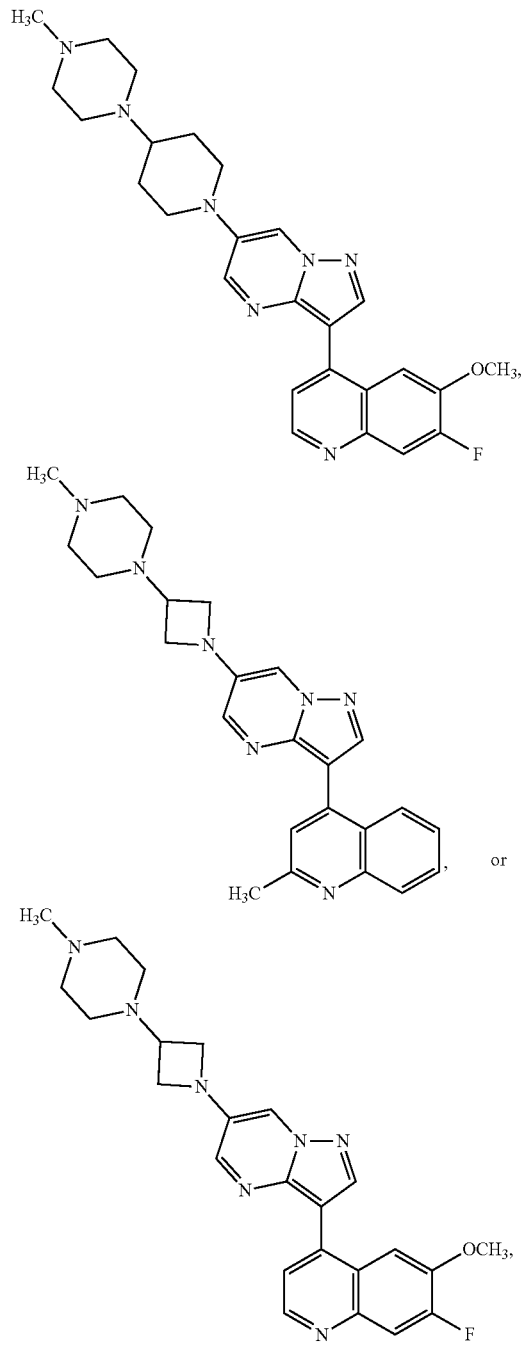

or a pharmaceutically acceptable salt thereof.

12. A method of treating a subject having fibrodysplasia ossificans progressiva, comprising administering to the subject a therapeutically effective amount of a compound according to claim 1, or a pharmaceutically acceptable salt thereof.

13. The method of claim 12, wherein the compound is:

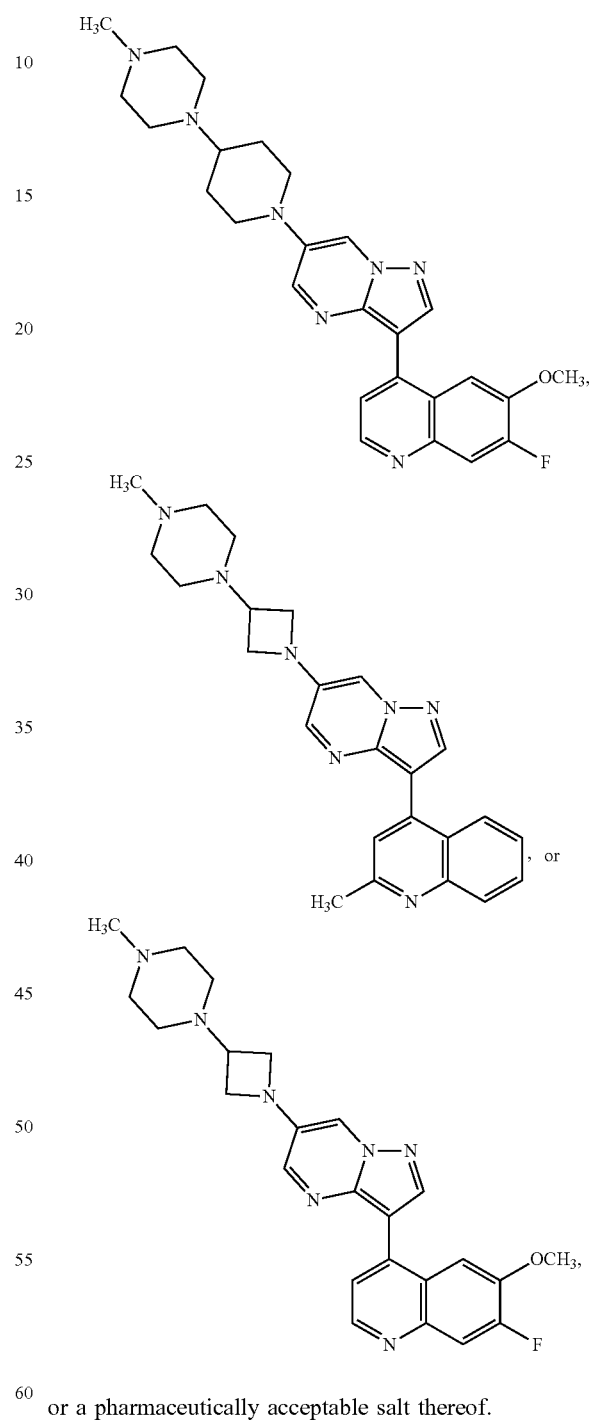

or a pharmaceutically acceptable salt thereof.

* * * * *